United States Patent [19]
Doumaux, Jr. et al.

[11] Patent Number: 5,210,306
[45] Date of Patent: May 11, 1993

[54] PROMOTED AMINES CATALYSIS

[75] Inventors: Arthur R. Doumaux, Jr., Charleston; David J. Schreck, Cross Lanes; Stephen W. King, Scott Depot, all of W. Va.; George A. Skoler, White Plains, N.Y.

[73] Assignee: Union Carbide Chemicals & Plastics Technology Corporation, Danbury, Conn.

[21] Appl. No.: 390,714

[22] Filed: Aug. 8, 1989

[51] Int. Cl.$^5$ .................. C07C 209/16; C07C 209/64; C07D 295/023; C07D 295/13

[52] U.S. Cl. ...................................... 564/479; 544/352; 544/358; 544/401; 544/402; 544/410; 564/305; 564/346; 564/355; 564/360; 564/367; 564/368; 564/371; 564/372; 564/402; 564/443; 564/470; 564/474; 564/480

[58] Field of Search ............... 564/479, 470, 480, 305, 564/346, 355, 360, 367, 368, 371, 372, 402, 443, 474; 544/401, 402, 358; 502/308, 309

[56] References Cited

U.S. PATENT DOCUMENTS

| | | | |
|---|---|---|---|
| 1,799,722 | 4/1971 | Arnold | 564/479 |
| 2,073,671 | 4/1931 | Andrews | 260/127 |
| 2,389,500 | 11/1945 | Goshorn | 564/480 |
| 2,467,205 | 4/1949 | Gresham et al. | 260/268 |
| 3,092,457 | 6/1963 | Sprague | 23/202 |
| 3,207,808 | 9/1965 | Bajars | 260/680 |
| 3,734,963 | 5/1973 | Langer, Jr. | 260/563 R |
| 4,036,881 | 7/1977 | Brennan et al. | 564/479 |
| 4,044,053 | 8/1977 | Brennan et al. | 260/583 P |
| 4,301,036 | 11/1981 | Childress et al. | 252/458 |
| 4,314,083 | 2/1982 | Ford et al. | 564/479 |
| 4,316,840 | 2/1982 | Ford et al. | 260/239 BC |
| 4,316,841 | 2/1982 | Ford et al. | 260/239 BC |
| 4,324,917 | 4/1982 | McConnell | 564/479 |
| 4,362,886 | 12/1982 | Ford et al. | 564/479 |
| 4,394,524 | 7/1983 | Ford et al. | 564/479 |
| 4,399,308 | 8/1983 | Ford et al. | 564/479 |
| 4,448,997 | 5/1984 | Brennan | 564/479 |
| 4,463,193 | 7/1984 | Johnson et al. | 564/479 |

(List continued on next page.)

FOREIGN PATENT DOCUMENTS

| | | |
|---|---|---|
| 0069322 | 1/1983 | European Pat. Off. . |
| 0115138 | 8/1984 | European Pat. Off. . |
| 0146508 | 6/1985 | European Pat. Off. . |
| 0150558 | 8/1985 | European Pat. Off. . |
| 0163253 | 12/1985 | European Pat. Off. . |
| 0228898 | 7/1987 | European Pat. Off. . |
| 0230776 | 8/1987 | European Pat. Off. . |
| 0261773 | 3/1988 | European Pat. Off. . |
| 0290960 | 11/1988 | European Pat. Off. . |
| 0312253 | 4/1989 | European Pat. Off. . |
| 0315189 | 5/1989 | European Pat. Off. . |
| 0328101 | 8/1989 | European Pat. Off. . |
| 0331396 | 9/1989 | European Pat. Off. . |
| 0345995 | 12/1989 | European Pat. Off. . |
| 0375257 | 6/1990 | European Pat. Off. . |
| 375355 | 6/1990 | European Pat. Off. . |
| 4896475 | 12/1973 | Japan . |
| 0171441 | 10/1982 | Japan . |
| 78945 | 5/1985 | Japan . |
| 236752 | 10/1986 | Japan . |
| 236753 | 10/1986 | Japan . |
| 303964 | 12/1988 | Japan . |
| 1439838 | 6/1976 | United Kingdom . |
| 2147896A | 5/1985 | United Kingdom . |
| 9003963 | 4/1990 | World Int. Prop. O. . |

OTHER PUBLICATIONS

Patent Abstracts of Japan, vol. 11, No. 3 (C-395) [2450], Jan. 7th, 1987.

Primary Examiner—Glennon H. Hollrah
Assistant Examiner—Peter G. O'Sullivan
Attorney, Agent, or Firm—R. M. Allen

[57] ABSTRACT

This invention relates to a process for making amines by condensing an amino compound in the presence of a condensation catalyst and a condensation catalyst promoter, wherein said condensation catalyst promoter is present in an amount sufficient to promote the condensation catalyst. This invention also relates to an alkyleneamines producers composition rich in triethylenetetramine (TETA), tetraethylenepentamine (TEPA) and pentaethylenehexamine (PEHA).

39 Claims, No Drawings

U.S. PATENT DOCUMENTS

| | | | |
|---|---|---|---|
| 4,503,253 | 3/1985 | Ford et al. | 564/479 |
| 4,521,600 | 6/1985 | Wells et al. | 544/352 |
| 4,524,143 | 6/1985 | Vanderpool | 502/208 |
| 4,540,822 | 9/1985 | Vanderpool | 564/479 |
| 4,547,591 | 10/1985 | Brennan et al. | 564/479 |
| 4,550,209 | 10/1985 | Unvert et al. | 564/479 |
| 4,552,961 | 11/1985 | Herdle | 544/402 |
| 4,555,582 | 11/1985 | Vanderpool | 564/479 |
| 4,560,798 | 12/1985 | Ford et al. | 564/503 |
| 4,578,517 | 3/1986 | Johnson et al. | 564/479 |
| 4,578,518 | 3/1986 | Vanderpool et al. | 564/479 |
| 4,578,519 | 3/1986 | Larken et al. | 564/479 |
| 4,584,405 | 4/1986 | Vanderpool | 564/479 |
| 4,584,406 | 4/1986 | Vanderpool et al. | 564/479 |
| 4,588,842 | 5/1986 | Vanderpool | 564/479 |
| 4,605,770 | 8/1986 | Ford et al. | 564/479 |
| 4,609,761 | 9/1986 | Watts, Jr. et al. | 564/479 |
| 4,612,397 | 9/1986 | Renken | 564/479 |
| 4,617,418 | 10/1986 | Ford et al. | 564/479 |
| 4,625,030 | 11/1986 | Best | 544/358 |
| 4,683,335 | 7/1987 | Knifton et al. | 564/480 |
| 4,698,427 | 10/1987 | Vanderpool | 544/404 |
| 4,720,588 | 1/1988 | Turcotte et al. | 564/479 |
| 4,774,218 | 9/1988 | Shimasaki et al. | 502/202 |
| 4,806,517 | 2/1989 | Vanderpool et al. | 502/208 |
| 4,822,925 | 4/1989 | Briggs et al. | 568/853 |
| 4,833,248 | 5/1989 | Shimasaki et al. | 546/184 |
| 4,841,061 | 6/1989 | Shimasaki et al. | 546/184 |
| 4,922,024 | 5/1990 | Bowman et al. | 564/480 |
| 4,973,692 | 11/1990 | Burgess et al. | 564/479 |
| 4,983,736 | 1/1991 | Doumany, Jr. et al. | 564/479 |
| 4,996,363 | 2/1991 | Bowman et al. | 564/470 |
| 5,030,740 | 7/1991 | Bowman et al. | 544/357 |

PROMOTED AMINES CATALYSIS

RELATED APPLICATIONS

U.S. patent application Ser. No. 136,615, filed Dec. 22, 1987, commonly assigned.

The following are related, commonly assigned applications, filed on an even date herewith: U.S. patent application Ser. No. 390,829; U.S. Pat. No. 4,986,736; U.S. patent application Ser. No. 390,706; U.S. Pat. No. 5,101,074; and U.S. patent application Ser. No. 390,708; (now abandoned in favor of Ser. No. 742,731, filed Aug. 16, 1991, which in turn has been abandoned in favor of Ser. No. 934,901, filed Aug. 26, 1992). all incorporated herein by reference.

BRIEF SUMMARY OF THE INVENTION

1. Technical Field

This invention relates to a process for making amines by condensing an amino compound in the presence of a condensation catalyst and a condensation catalyst promoter.

This invention also relates to an alkyleneamines producers composition rich in higher polyalkylene polyamines such as triethylenetetramine (TETA), tetraethylenepentamine (TEPA) and pentaethylenehexamine (PEHA).

2. Background of the Invention

There is a substantial body of literature directed to the use of various acid catalysts to effect intramolecular and intermolecular condensation of amino compounds. U.S. Pat. No. 2,073,671 and U.S. Pat. No. 2,467,205 constitute early prior work on the use of acid condensation catalysts to condense amino compounds. U.S. Pat. No. 2,073,671 discusses, in a general fashion, the catalytic intermolecular condensation of alcohols and amines or ammonia using the same phosphate catalysts later favored by U.S. Pat. No. 2,467,205 for the intramolecular condensation of amines. The two patents are not in harmony over the use of other materials as catalysts. To illustrate this point, U.S. Pat. No. 2,073,671 states:

"Alumina, thoria, blue oxide of tungsten, titania, chromic oxide, blue oxide of molybdenum and zirconia have been mentioned in the literature for use as catalysts in carrying out these reactions but their effectiveness is so low that no practical application has been made of their use."

whereas U.S. Pat. No. 2,467,205 in describing the self condensation of ethylenediamine (EDA) under vapor phase conditions, to initially produce ethyleneamines, but after recycle, eventually generates piperazine through multistep condensation reactions, followed by deamination, recommends "dehydration catalysts" which are thereafter characterized as "silica gel, titania gel, alumina, thoria, boron phosphate, aluminum phosphate, and the like."

U.S. Pat. No 2,073,671 describes the condensation catalyst in the following terms:

". . . a heated catalyst or contact mass containing phosphorus and especially one or more of the oxygen acids of phosphorus, their anhydrides, their polymers, and their salts; for example, orthophosphoric acid, metaphosphoric acid, pyrophosphoric acid, phosphorous pentoxide, dimetaphosphoric acid, trimetaphosphoric acid, primary ammonium phosphate, secondary ammonium phosphate, normal ammonium phosphate, ammonium metaphosphate, secondary ammonium pyrophosphate, normal ammonium pyrophosphate, aluminum phosphate, aluminum acid phosphate and mixtures of two or more of such materials."

whereas U.S. Pat. No. 2,467,205 describes one of the preferred catalysts as "basic aluminum phosphate".

U.S. Pat. No. 2,454,404 describes the "catalytic deamination of alkylene polyamines" by reacting diethylenetriamine (DETA) vapor over solid catalysts such as activated alumina, bauxite, certain aluminum silicates such as kaolin and oxides of thorium, titanium and zirconium.

U.S. Pat. Nos. 2,073,671 and 2,467,205 demonstrate a common experience in using aluminum phosphate as a condensation catalyst to produce aliphatic amines, and U.S. Pat. Nos. 2,454,404 and 2,467,205 contemplate the other solid catalysts for deamination of amines to make heterocyclic noncyclic amines. In general, the reaction conditions under which deamination to effect cyclization occurs are more severe than those employed for condensation to generate noncyclic molecules, all other factors being comparable.

U.S. Pat. Nos. 4,540,822, 4,584,406 and 4,588,842 depict the use of Group IVB metal oxides as supports for phosphorus catalysts used to effect the condensation of amino compounds with alkanolamines.

U.S. Pat. No. 4,683,335 describes the use of tungstophosphoric acid, molybdophosphoric acid or mixtures deposited on titania as catalysts for the condensation of amines and alkanolamines to make polyalkylenepolyamines.

U.S. Pat. Nos. 4,314,083, 4,316,840, 4,362,886 and 4,394,524 disclose the use of certain metal sulfates as useful catalysts for the condensation of alkanolamine and an amino compound. No distinction is made between the sulfur compounds in respect to catalytic efficacy. Sulfuric acid is as good as any metal sulfate, and all metal sulfates are treated as equivalents. At column 8 of U.S. Pat. No. 4,314,083, it is noted that boron sulfate "gave extremely high selectivity at a low level" of EDA. However, selectivity in general was shown to increase with an increase of EDA relative to MEA in the feed. The only specific metal surfaces disclosed in the patents are antimony sulfate, beryllium sulfate, iron sulfate and aluminum sulfate.

In the typical case of the manufacture of alkyleneamines, mixtures with other alkyleneamines (including a variety of polyalkylenepolyamines and cyclic alkylenepolyamines) are formed. The same holds true when the object of the process is to produce polyalkylenepolyamines whether acyclic or cyclic, in that a variety of amino compounds are also formed each of these cyclic and acyclic alkyleneamines can be isolated from the mixture.

The acid catalyzed condensation reaction involving the reaction of an alkanolamine with an amino compound in the presence of an acidic catalyst is believed to proceed through the mechanism of esterifying free surface hydroxyl groups on the acid catalyst with the alkanolamine and/or by protonating the alkanolamine in the presence of the acid catalyst, followed by loss of water and amine condensation of the ester or the hydrated species, as the case may be, to form the alkyleneamine. Illustrative prior art directed primarily to the cyclic polyalkylenepolyamines (heterocyclic polyamines), but not necessarily limited to the aforementioned acid condensation reaction, are: U.S. Pat. Nos. 2,937,176, 2,977,363, 2,977,364, 2,985,658, 3,056,788, 3,231,573, 3,167,555, 3,242,183, 3,297,701, 3,172,891, 3,369,019, 3,342,820, 3,956,329, 4,017,494, 4,092,316, 4,182,864, 4,405,784 and 4,514,567; European Patent Applications 0 069 322, 0 111 928 and 0 158 319; East German Patent No. 206,896; Japanese Paten Publication No. 51-141895; and French Patent No. 1,381,243. The evolution of the art to the use of the acid catalyzed condensation reaction to generate acyclic alkyleneamines, particularly acyclic polyalkylenepolyamines, as the predominant products stemmed from the initial disclosure in U.S. Pat. No. 4,036,881, though earlier patent literature fairly well characterized such an effect without labeling it so, see U.S. Pat. No 2,467,205, supra. The acid catalysts are phosphorus compounds and the reaction is carried out in the liquid phase. The trend in this catalyst direction was early set as demonstrated by U.S. Pat. Nos. 2,073,671 and 2,467,205, supra. A modification of this route includes the addition of ammonia to the reaction, see, for example, U.S. Pat. No. 4,394,524 and U.S. Pat. No. 4,463,193 for the purpose of converting alkanolamine such as MEA in situ to alkylene amine such as EDA by reaction with ammonia, and the EDA is in situ reacted with MEA according to the process of U.S. Pat. No. 4,036,881 to form alkyleneamines.

A summary of the prior art employing acid catalysts for making alkyleneamines is set forth in Table 1 below.

TABLE 1

| CITATION | CATALYST TYPE | REACTANTS |
|---|---|---|
| U.S. 2,467,205 | Silica gel, titania gel, alumina, thoria, aluminum phosphate. Preferred catalyst is basic aluminum phosphate. | Vapor phase condensation of EDA over a fixed bed of the catalyst, multipass process shifts from polyethylenepolyamines with the first few cycles. |
| U.S. 4,036,881 | Phosphorus containing substances selected from the group consisting of acidic metal phosphates, phosphoric acid compounds and their anhydrides, phosphorus acid comounds and their anhydrides, alkyl or aryl phosphate esters, alkyl or aryl phosphite esters, alkyl or aryl substituted phosphorous and phosphoric acids wherein said alkyl groups have from 1 to about 8 carbon atoms and said aryl groups have from 6 to about 20 carbon atoms, alkali metal monosalts of phosphoric acid, the thioanalogs of the foregoing, and mixtures of the above. | Alkanolamine and alkyleneamine in liquid phase reaction. |
| U.S. 4,044,053 | Phosphorus containing substances selected from the group consisting of acidic metal phosphates, phosphoric acid compounds and their anhydrides phosphorus acid compounds and their anhydrides, alkyl or aryl phosphate esters, alkyl or aryl phosphite esters, alkyl or aryl substituted phosphorous acids and phosphoric acids wherein said alkyl groups have from 1 to about 8 carbon atoms and said aryl groups have from 6 to about 20 carbon atoms, alkali metal monosalts of phosphoric acid and mixtures of the above. | Alkanepolyols and alkyleneamine in liquid phase reaction. |
| U.S. 4,314,083 | Salt of a nitrogen or sulfur containing substance or the corresponding acid. | Alkanolamine and an alkyleneamine in liquid phase reaction. |
| U.S. 4,316,840 | Metal nitrates and sulfates including zirconium sulfate. | Reforming linear polyamines. |
| U.S. 4,316,841 | Phosphate, preferably boron phosphate. | Reforming linear polyamines. |
| U.S. 4,324,917 | Phosphorus-containing cation exchange resin. | Alkanolamine and an alkyleneamine in liquid phase reaction. |
| U.S. 4,362,886 | Arsenic, antimony or bismuth containing compounds. Antimony sulfate specifically disclosed. | Alkanolamie and an alkyleneamine in liquid phase reaction. |
| U.S. 4,399,308 | Lewis acid halide. | Alkanolamine and an alkyleneamine in liquid phase reaction. |
| U.S. 4,394,524 | Phosphorus-containing substance or salt of a sulfur-containing substance, or the corresponding acid. | Ammonia, alkanolamine and an alkyleneamine in liquid phase reaction. |
| U.S. 4,448,997 | Reacts alumina with phosphoric acid, adds ammonium hydroxide. | EDA with MEA. |
| U.S. 4,463,193 | Group IIIB metal acid phosphate. | Ammonia, alkanolamine and |

TABLE 1-continued

| CITATION | CATALYST TYPE | REACTANTS |
| --- | --- | --- |
| | | an alkyleneamine. |
| U.S. 4,503,253 | Supported phosphoric acid. | Ammonia, alkanolamine and an alkyleneamine. |
| U.S. 4,521,600 | Select hydrogen phosphates and pyrophosphates. | Alkanolamine and an alkyleneamine. |
| U.S. 4,524,143 | Phosphorus impregnated onto zirconium silicate support. | Alkanolamine and an alkyleneamine. |
| U.S. 4,540,822 | Phosphorus compound deposited on a Group IVB metal oxide support. | Alkanolamine and an alkyleneamine, regenerates the catalyst with $O_2$-containing gas. |
| U.S. 4,547,591 | Silica-alumina alone or in combination with an acidic phosphorus cocatalyst. | An ethyleneamine and an alkanolamine; ethyleneamines; or ammonia and an alkanolamine. |
| U.S. 4,550,209 | An intercalatively catalytically active tetravalent zirconium polymeric reaction product of an organo phosphonic acid or an ester thereof with a compound of tetravalent zirconium reactive therewith. | EDA and MEA. |
| U.S. 4,552,961 | Phosphorus amide compound. | Alkyleneamine and alkanolamine and/or alkylene glycol. |
| U.S. 4,555,582 | Phosphorus chemically bonded to a zirconium silicate support. | MEA and EDA. |
| U.S. 4,60,798 | Rare earth metal or strontium acid phosphate. | MEA. |
| U.S. 4,578,517 | Group IIIB metal acid phosphate. | Ammonia or p-/s-amine and alkanolamine. |
| U.S. 4,578,518 | Thermally activated, calcined, pelleted titania containing titanium triphosphate, "...the titania that was used was... anatase." (Col. 9, lines 18-19). | MEA and EDA. |
| U.S. 4,578,519 | Thermally activated, calcined, pelleted titania with chemically bonded phosphorus derived from polyphosphoric acid. | MEA and EDA with optional recycle of DETA. |
| U.S. 4,584,405 | Activated carbon, optionally treated to incorporate phosphorus. Activated carbon may be washed with strong mineral acid to remove impurities followed by water wash. Optional treatment follows. | MEA and EDA. |
| U.S. 4,584,406 | Pelleted Group IVB metal oxide with chemically bonded phosphorus derived from phosphoryl chloride or bromide | MEA and EDA. |
| U.S. 4,588,842 | Thermally activated pelleted Group IVB metal oxide with chemically bonded phosphorus. | MEA and EDA. |
| U.S. 4,605,770 | Group IIA or IIIB metal acid phosphate. | Alkanolamine and an alkyleneamine "in liquid phase". |
| U.S. 4,609,761 | Thermally activated pelleted titania with chemically bonded phosphorus. | MEA and EDA. |
| U.S. 4,612,397 | Thermally activated pelleted titania with chemically bonded phosphorus. | MEA and EDA. |
| U.S. 4,617,418 | Acid catalysts, mentions "beryllium sulfate". | Ammonia, alkanolamine and an alkylenamine "under vapor phase contitions". |
| Japanese Patent Application #1983-185,871, Publication #1985-78,945 | Variety of phosphorus and metal phosphates including Group IVB phosphates. | Ammonia, alkanolamine and ethyleneamine, with ammonia/ alkanolamine molar ratio greater than 11. |
| U.S. 4,683,335 | Tungstophosphoric acid, molybdophosphoric acid or mixtures deposited on titania. Examples 2-7 characterize titania surface areas of 51, 60 and 120 $m^2/gm$. | Claims reaction of MEA and EDA, but discloses self-condensation reaction of EDA and DETA |
| Japanese Patent Application #1985-078,391, Publication #1986-236,752 | Group IVB metal oxide with bonded phosphorus. | Ammonia and MEA. |
| Japanese Patent | Group IVB metal oxide with | Ammonia and MEA. |

TABLE 1-continued

| CITATION | CATALYST TYPE | REACTANTS |
| --- | --- | --- |
| Application #1985-078,392, Publication #1986-236,753 | bonded phosphorus. | |
| U.S. 4,698,427 | Titania having phosphorus thermally chemically bonded to the surface thereof in the form of phosphate bonds. | Diethanolamine and/or hydroxyethyldiethylene-triamine in EDA. |
| U.S. 4,806,517 | Pelleted Group IVB metal oxide with phosphorus thermally chemically bonded to the surface thereof. | MEA and EDA. |

The market demand for higher polyalkylene polyamines such as TETA, TEPA and PEHA has been progressively increasing in recent years. These higher polyalkylene polyamines are desirable co-products with DETA. It would be desirable to satisfy the existing demand from a cost standpoint by modifying slightly the commercial processes directed to the manufacture of DETA from the reaction of MEA and EDA or other suitable starting raw materials such as DETA and AEEA, to the production of TETA, TEPA and PEHA as major products.

It would be desirable to have continuously produced compositions, generated by the reaction of MEA and EDA or other suitable starting raw materials such as DETA and AEEA over a fixed bed of a condensation catalyst under commercial conditions, that are rich in TETA, TEPA and PEHA, and that are not disproporationately high in PIP and other cyclics.

It would be very beneficial to have a process which increases one's ability to generate the manufacture of desirable higher polyalkylene polyamine products such as TETA, TEPA and PEHA without generating large amounts of cyclic alkylenepolyamine products. In addition, it would also be desirable to have a process with raw material flexibility which provides the potential to control congener distribution, linear to cyclic selectivity and linear to branched selectivity of the higher polyalkylene polyamines products. As used herein, congener distribution refers to polyalkylene polyamines containing the same number of nitrogen atoms but not necessarily having the same molecular weight or structure.

The above features are provided by this invention.

SUMMARY OF THE INVENTION

This invention relates in general to a process of making amines which comprises condensing an amino compound in the presence of a condensation catalyst and a condensation catalyst promoter, wherein said condensation catalyst promoter is present in an amount sufficient to promote the condensation catalyst. The condensation catalysts and promoters used herein contain sufficient residual bound hydroxyl groups or other groupings which renders catalyst formation possible by loss of water or its chemical equivalent such as ammonium hydroxide.

More particularly, this invention relates to a process of making amines by the (i) intramolecular condensation of an amino compound to an amine having a lower molecular weight or (ii) the intermolecular condensation of an amino compound with one or more of another amino compound or a compound containing an alcoholic hydroxyl group using a condensation catalyst and a condensation catalyst promoter. A preferred process involves the manufacture of alkyleneamines, most desirably higher polyalkylene polyamines, by such condensation reactions utilizing a Group IVB metal oxide, sodium dihydrogen phosphate, disodium dihydrogen pyrophosphate or sodium trimetaphosphate as the condensation catalyst and a metal oxide as the condensation catalyst promoter.

The invention further relates to a continuously generated alkyleneamines producers composition comprising, based on 100 percent of the weight of the composition and exclusive of any water and/or ammonia present, a) greater than about 3.0 weight percent of the combination of TETA and TEPA,
b) greater than about 0.1 weight percent of TEPA,
c) greater than about 3.0 weight percent of TETA,
d) less than about 90.0 weight percent of DETA and/or EDA,
e) less than about 90.0 weight percent of MEA and/or AEEA,
f) less than about 12.5 weight percent of the combination of PIP and AEP,
g) less than about 15.0 weight percent of other polyalkylene polyamines,
h) a TETA+TAEA to PIP+AEP+PEEDA+DAEP+DPE weight ratio of greater than about 0.5,
i) a TEPA+AETAEA to PIP+AEP+PEEDA+DAEP+DPE+AEPEEDA+iAEPEEDA+AEDAEP+AEDPE+BPEA weight ratio of greater than about 0.5,
j) a TETA to TAEA weight ratio of greater than about 2 0, and
k) a TEPA to AETAEA weight ratio of greater than about 1.0.

As used herein, the term "amino compound" embraces ammonia and any compound containing nitrogen to which is bonded an active hydrogen. Also, as used herein, the term "oxide" embraces oxides, hydroxides and/or mixtures thereof.

For purposes of this invention, the chemical elements are identified in accordance with the Periodic Table of the Elements, CAS version, Handbook of Chemistry and Physics, 67th Ed., 1986–87, inside cover. Also, for purposes of this invention, Group IIIB metal oxides embraces the lanthanides and actinides.

DETAILED DESCRIPTION

The higher polyalkylene polyamines such as TETA, TEPA and PEHA are very useful commercial products for a variety of applications including fuel oil additives, corrosion inhibitors, fabric softeners, fungicides and others. As indicated above, there is lacking a commercial process for the manufacture of enhanced quantities of TETA, TEPA and PEHA especially as significant products of reaction. There is thus a need for the ability to commercially generate larger production quantities of TETA, TEPA and PEHA and that is the direction of this invention. The process of this invention provides for the reaction of MEA and DETA or other suitable starting raw materials such as EDA and AEEA to produce in a continuous manner a reaction product mixture, termed herein an "alkyleneamines producers composition", in which TETA, TEPA and PEHA are principal products of the reaction.

The process of this invention is distinctive insofar as it achieves the generation of high concentrations of TETA, TEPA and PEHA in a manner which can be suitably employed in a commercial process, particularly a continuous process, for the manufacture of alkyleneamines. In particular, the process of this invention allows the production of TETA, TEPA and PEHA in relatively high yields without generating large amounts of cyclic polyalkylene polyamine products. The process of this invention provides starting raw material flexibility thereby allowing the potential to control congener distribution, linear to cyclic selectivity and linear to branched selectivity of the higher polyalkylene polyamine products.

As indicated above, this invention relates to a process of making amines which comprises condensing an amino compound in the presence of a catalytically effective amount of a condensation catalyst and a condensation catalyst promoter, wherein said condensation catalyst promoter is present in an amount sufficient to promote the condensation catalyst.

As also indicated above, this invention relates to a continuously generated alkyleneamines producers composition comprising, based on 100 percent of the weight of the composition and exclusive of any water and/or ammonia present, a) greater than about 3.0 weight percent of the combination of TETA and TEPA,
b) greater than about 0.1 weight percent of TEPA,
c) greater than about 3.0 weight percent of TETA,
d) less than about 90.0 weight percent of DETA and/or EDA,
e) less than about 90.0 weight and/or AEEA,
f) less than about 12.5 weight percent of the combination of PIP and AEP,
g) less than about 15.0 weight percent of other polyalkylene polyamines,
h) a TETA+TAEA to PIP+AEP+PEEDA+DAEP+DPE weight ratio of greater than about 0.5,
i) a TEPA+AETAEA to PIP+AEP+PEEDA+DAEP+DPE+AEPEEDA+iAEPEEDA+AEDAEP+AEDPE+BPEA weight ratio of greater than about 0.5,
j) a TETA to TAEA weight ratio of greater than about 2.0, and
k) a TEPA to AETAEA weight ratio of greater than about 1.0.

The alkyleneamines producers composition of this invention can be subjected to conventional separations techniques for recovering the individual components of the composition. Such techniques are well known in the art and include, for example, distillation.

This invention contemplates the catalyzed condensation by (i) intramolecular condensation of an amino compound to an amine having a lower molecular weight, and (ii) intermolecular condensation of an amino compound with one or more of another amino compound or a compound containing an alcohol hydroxyl group to an amine having a lower, same or higher molecular weight than the reactants, in the presence of a condensation catalyst and a condensation catalyst promoter.

A wide variety of condensation catalysts can be used in this invention. Suitable condensation catalysts should be capable of being promoted by a condensation catalyst promoter described below. For purposes of this invention, the promotion effect can relate to catalytic activity, product selectivity and/or catalyst stability (mechanical or dimensional strength of the catalyst). Illustrative of suitable condensation catalysts for use in this invention include, for example, Group IVB metal oxides, metallic phosphates which may or may not have a cyclic structure, metallic polyphosphates which may or may not have a condensed structure, Group VIB metal containing substances and conventional condensation catalysts known in the art.

The Group IVB metal oxide condensation catalysts are preferred catalysts for use in this invention. Suitable Group IVB metal oxide condensation catalysts a-re disclosed in U.S. patent application Ser. No. 390,829), filed on an even date herewith and incorporated herein by reference. Illustrative of Group IVB metal oxide condensation catalysts include, for example, titanium oxide and zirconium oxide, preferably titanium dioxide and zirconium dioxide including mixtures thereof.

The metallic phosphate and polyphosphate condensation catalysts are also preferred catalysts for use in this invention. The metallic phosphate and polyphosphate condensation catalysts may or may not have a cyclic structure and may or may not have a condensed structure. Suitable metallic phosphate condensation catalysts having a cyclic structure or an acyclic structure are disclosed in U.S. patent application Ser. No 390,706), filed on an even date herewith and incorporated herein by reference. Suitable metallic polyphosphate condensation catalysts having a condensed structure are disclosed in U.S. Pat. No. 4,983,736, filed on an even date herewith and incorporated herein by reference. Illustrative of metallic phosphate and polyphosphate condensation catalysts include, for example, metallic orthophosphates ($PO_4^{-3}$), metallic pyrophosphates ($P_2O_7^{-4}$), metallic polyphosphates (including tripolyphosphates ($P_3O_{10}^{-5}$), tetrapolyphosphates ($P_4O_{13}^{-6}$), pentapolyphosphates ($P_5O_{16}^{-7}$) and higher polyphosphates), metallic metaphosphates (including trimetaphosphates ($P_3O_9^{-3}$), tetrametaphosphates ($P_4O_{12}^{-4}$) and other lower and higher metaphosphates) and metallic ultraphosphates (condensed phosphates containing more $P_2O_5$ than corresponds to the metaphosphate structure). Corresponding metallic metaphosphimates, metallic phosphoramidates and metallic amido and imidophosphates of the above may also be used as condensation catalysts in accordance with this invention. Suitable metals which can be incorporated into the metallic phosphate and polyphosphate condensation catalysts include, for example, Group IA metals, Group IIA metals, Group IIIB metals, Group IVB metals, Group VB metals, Group VIB metals, Group VIIB metals, Group VIII metals, Group IB metals, Group IIB metals, Group IIIA metals, Group IVA metals, Group VA metals, Group VIA metals and mixtures thereof.

Illustrative of metallic orthophosphate catalysts which may be utilized in this invention include, for example, $NaH_2PO_4$, $KH_2PO_4$, $RbH_2PO_4$, $LiH_2PO_4$, $CsH_2PO_4$, $MgHPO_4$, $CaHPOO_4$, $YPO_4$, $CePO_4$, $LaPO_4$, $ThPO_4$, $MnPO_4$, $FePO_4$, $BPO_4$, $AlPO_4$, $BiPO_4$, $Mg(H_2PO_4)_2$, $Ba(H_2PO_4)_2$, $Mg(NH_4)_2PO_4$, Ca(H-

$_2PO_4)_2$, $La(H_2PO_4)_3$ and the like. Illustrative of metallic pyrophosphate catalysts which may be utilized in this invention include, for example, $Na_2H_2P_2O_7$, $K_2H_2P_2O_7$, $Ca_2P_2O_7$, $Mg_2P_2O_7$, $KMnP_2O_7$, $AgMnP_2O_7$, $BaMnP_2O_7$, $NaMnP_2O_7$, $KCrP_2O_7$, $NaCrP_2O_7$, $Na_4P_2O_7$, $K_4P_2O_7$, $Na_3HP_2O_7$, $NaH_3P_2O_7$, $SiP_2O_7$, $Na_6Fe_2(P_2O_7)_3$, $Na_8Fe_4(P_2O_7)_5$, $Na_6Cu(P_2O_7)_2$, $Na_{32}Cu_{14}(P_2O_7)_{15}$, $Na_4Cu_{18}(P_2O_7)_5$, $Na(NH_4)_2P_2O_7$, $Ca(NH_4)_2P_2O_7$, $MgH_2P_2O_7$, $Mg(NH_4)_2P_2O_7$) and the like. Illustrative of metallic polyphosphate catalysts which may be utilized in this invention include, for example, $NaSr_2P_3O_{10}$, $NaCa_2P_3O_{10}$, $NaNi_2P_3O_{13}$, $Na_5P_3O_{10}$, $K_5P_3O_{10}$, $Na_3MgP_3O_{10}$, $Na_3CuP_3O_{10}$, $Cu_5(P_3O_{10})_2$, $Na_3ZnP_3O_{10}$, $Na_3CdP_3O_{10}$, $Na_6Pb(P_3O_{10})_2$, $Na_3CoP_3O_{10}$, $K_3CoP_3O_{10}$, $Na_3NiP_3O_{10}$, $K_2(NH_4)_3P_3O_{10}$, $Ca(NH_4)_2P_3O_{10}$, $La(NH_4)_3P_3O_{10}$, $NaMgH_2P_3O_{10}$ and the like. Illustrative of metallic metaphosphate catalysts which may be utilized in this invention include, for example, $Na_3P_3O_9$, $K_3P_3O_9$, $Ag_3P_3O_9$, $Na_4P_4O_{12}$, $K_4P_4O_{12}$, $Na_2HP_3O_9$, $Na_4Mg(P_3O_9)_2$, $NaSrP_3O_9$, $NaCaP_3O_9$, $NaBaP_3O_9$, $KBaP_3O_9$, $Ca_3(P_3O_9)_2$, $Ba(P_3O_9)_2$, $Na_2Ni_2(P_3O_9)_2$, $Na_4Ni(P_3O_9)_2$, $Na_4Co(P_3O_9)_2$, $Na_4Cd(P_3O_9)_2$ and the like. Illustrative of metallic ultraphosphate catalysts which may be utilized in this invention include, for example, $CaP_4O_{11}$, $Ca_2P_6O_{17}$, $Na_8P_{10}O_{29}$, $Na_6P_8O_{23}$, $Na_2CaP_6O_{17}$, $Na_2P_4O_{11}$, $NaBaP_7O_{18}$, $Na_2P_8O_{21}$, $K_4P_6O_{17}$ and the like. The preferred metallic phosphate and polyphosphate condensation catalysts for use in this invention include Group IA metal dihydrogen orthophosphates, Group IA metal metaphosphates and Group IA metal dihydrogen pyrophosphates, more preferably $NaH_2PO_4$, $Na_3P_3O_9$ and $Na_2H_2P_2O_7$. Other suitable metallic phosphate and polyphosphate condensation catalysts having a condensed structure which are embraced within the scope of this invention are disclosed by Van Wazer, J. R., Phosphorus and Its Compounds, Vol. 1, Interscience Publishers, Inc., N.Y. (1958).

The metallic phosphate and polyphosphate condensation catalysts can be prepared by conventional methods known in the art. Sodium is believed to be one of a small group of cations effective for stabilizing six-membered cyclic metaphosphates at their temperatures of fusion (about 625° C.) without decomposition to linear and/or other condensed phosphates including mixtures. The formation of cyclic and acyclic metallic phosphate and polyphosphate structures appears to depend on the cation ionic size, the coordination number of the cation and the ionic or covalent nature of the metal-oxygen bond.

While not wishing to be bound to any particular theory, it is believed that those metallic phosphates and polyphosphates encompassed within the scope of this invention having a cyclic structure and possessing ionic character and/or ion exchange capacity exhibit desired catalytic activity and provide desired product selectivity in association with a condensation catalyst promoter. While the reaction mixture may initially include one or more metallic phosphates and/or metallic polyphosphates other than metallic phosphates and polyphosphates having a cyclic structure and possessing ionic character and/or ion exchange capacity, it is believed to be desirable that such metallic phosphates and polyphosphates having a cyclic structure and possessing ionic character and/or ion exchange capacity be formed in situ in association with a condensation catalyst promoter in order to provide desired catalytic activity and product selectivity. In such instances, the catalyst preparation conditions or reaction conditions should allow for the formation of metallic phosphates and polyphosphates having a cyclic structure and possessing ionic character and/or ion exchange capacity in association with a condensation catalyst promoter. Mixtures of metallic phosphates and polyphosphates having a cyclic structure and possessing ionic character and/or ion exchange capacity with metallic phosphates and polyphosphates having other than a cyclic structure and other than ionic character and/or ion exchange capacity are believed to exhibit desired catalytic activity and provide desired product selectivity in association with a condensation catalyst promoter.

The Group VIB metal containing condensation catalysts are preferred catalysts for use in this invention. Suitable Group VIB metal containing condensation catalysts are disclosed in U.S. patent application Ser. No. 390,708, filed on an even date herewith and incorporated herein by reference (now abandoned in favor of Ser. No. 742,731, filed Aug. 16, 1991, which in turn has been abandoned in favor of Ser. No. 934,901, filed Aug. 26, 1992). Illustrative of Group VIB metal-containing condensation catalysts include, for example, one or more oxides of tungsten, chromium, molybdenum or mixtures thereof.

A variety of conventional condensation catalysts may be suitable for use in this invention. As indicated above, the conventional condensation catalysts should be capable of being promoted by a condensation catalyst promoter. Illustrative of conventional condensation catalysts may include, for example, those disclosed in U.S. Pat. No. 4,036,881, U.S. Pat. No. 4,806,517, U.S. Pat. No. 4,617,418, U.S. Pat. No. 4,720,588, U.S. Pat. No. 4,394,524, U.S. Pat. No. 4,540,822, U.S. Pat. No. 4,588,842, U.S. Pat. No. 4,605,770, U.S. Pat. No. 4,683,335, U.S. Pat. No. 4,316,841, U.S. Pat. No. 4,463,193, U.S. Pat. No. 4,503,253, U.S. Pat. No. 4,560,798 and U.S. Pat. No. 4,578,517.

Suitable conventional catalysts which can be employed in this invention include phosphorus containing substances such as acidic metal phosphates, phosphoric acid compounds and their anhydrides, phosphorous acid compounds and their anhydrides, alkyl or aryl phosphate esters, alkyl or aryl phosphite esters, alkyl or aryl substituted phosphorous acids and phosphoric acids, alkali metal monosalts of phosphoric acid, the thioanalogs of the foregoing, and mixtures of any of the above.

This invention also embraces the use of promoted vicinal di(hetero)alkylene organometalates in the preparation of amines. Suitable vicinal di(hetero)alkylene organometalates are disclosed in U.S. Pat. No. 5,101,074, filed on an even date herewith and incorporated herein by reference.

The level of activity of the promoted condensation catalysts of the invention is that level which of itself makes the catalysts at least as active in the condensation of amines as, for example, is phosphoric acid on an equivalent basis. Preferably, the promoted condensation catalysts on a support should have a surface area greater than about 70 $m^2/gm$ to as high as about 260 $m^2/gm$ or greater depending upon which metal oxide described below that is employed. In the case of titanium oxides, the surface area should be greater than about 140 $m^2/gm$ to as high as about 260 $m^2/gm$, more preferably, greater than about 160 $m^2/gm$ to as high as about 260 $m^2/gm$, determined according to the single point $N_2$ method. In the case of zirconia oxides, the surface area should be greater than about 70 $m^2/gm$ to as high as about 150 m²/gm, more preferably, greater than about 90 m²/gm to as high as about 135 m²/gm, determined according to the single point $N_2$ method. It is appreciated that the metal oxide promoters described below which can be used in association with the condensation catalyst and the other condensation catalyst promoters described below can affect the surface area of the condensation catalyst. While surface areas described above may be preferred, for purposes of this invention, the surface area of the promoted condensation catalyst should be sufficient to contribute to product selectivity, catalytic activity and/or mechanical or dimensional strength of the catalyst.

Though the condensation catalyst of the invention provides sufficient activity to effect the condensation reaction, certain combinations of reactants and/or product formation can be benefited by employing a condensation catalyst promoter with the condensation catalyst. Condensation catalyst promoters can be used to promote the performance of catalysts in areas of selectivity to certain products. A range of suitable materials may impact the condensation catalysts of this invention in the variety of reaction products. The condensation catalyst promoter may be any material which impacts the condensation catalyst's selection of reaction products or which changes the proportion of any one or more of the reaction products which the condensation catalyst generates at comparable processing conditions. In addition to contributing to product selectivity, the condensation catalyst promoter may be any material which contributes to catalytic activity and/or catalyst stability (mechanical or dimensional strength).

The condensation catalyst promoter for use in this invention should be capable of promoting the condensation catalyst. As indicated above, the promoting effect can relate to catalytic activity, product selectivity and/or catalyst stability (mechanical or dimensional strength of the catalyst). Illustrative of condensation catalyst promoters for use in this invention can include, for example, one or more metal oxides, one or more metallic phosphates which may or may not have a cyclic structure, one or more metallic polyphosphates which may or may not have a condensed structure, one or more Group VIB metal containing substances and one or more conventional materials such as mineral acids or compounds derived from mineral acids. Mixtures of condensation catalyst promoters may also be employed in this invention. For purposes of this invention, the condensation catalyst promoter should be different from the condensation catalyst.

Illustrative of metal oxides which may be utilized as condensation catalyst promoters in association with the condensation catalyst include, for example, one or more of the following: Group IA metal oxides, Group IIA metal oxides, Group IIIB metal oxides (including lanthanides and actinides), Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides and Group IVB metal oxides or mixtures thereof. Certain of these metal oxides may also be used as condensation catalysts in accordance with this invention such as Group IVA and IVB metal oxides. Preferred metal oxides are amphoteric or slightly acidic or slightly basic. Preferred metal oxides which may be utilized in association with the condensation catalyst include, for example, one or more oxides of beryllium, scandium, yttrium, terbium, dysprosium, holmium, erbium, thulium, ytterbium, lutetium, titanium, zirconium, hafnium, vanadium, niobium, tantalum, tungsten, iron, cobalt, zinc, silver, aluminum, gallium, indium, silicon, germanium, tin, lead, arsenic, antimony and bismuth.

Group IVB metal oxides such as titanium dioxide and zirconium dioxide and Group IVA metal oxides such as silica are preferred for use in this invention. For mixed metal oxides in which at least one of the metals is titanium, suitable metals in association with titanium may include, for example, one or more of the following: Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IIIA metals such as boron, aluminum, gallium and indium, Group IVA metals such as silicon, germanium, tin and lead, Group VA metals such as arsenic, antimony and bismuth, and Group IVB metals such as zirconium and hafnium. For mixed metal oxides in which at least one of the metals is zirconium, suitable metals in association with zirconium may include, for example, one or more of the following: Group IVA metals such as silicon, germanium, tin and lead, Group VB metals such as niobium and tantalum, and Group VIB metals such as chromium, molybdenum and tungsten. Certain of these metal oxides may also be effective as condensation catalysts for use in this invention.

Illustrative of mixed metal oxides which may be used as condensation catalyst promoters in association with the condensation catalyst include, for example, $TiO_2$—$SiO_2$, $TiO_2$—$Al_2O_3$, $TiO_2$—$CdO$, $TiO_2$—$Bi_2O_3$, $TiO_2$—$Sb_2O_5$, $TiO_2$—$SnO_2$, $TiO_2$—$ZrO_2$, $TiO_2$—$BeO$, $TiO_2$—$MgO$, $TiO_2$—$CaO$, $TiO_2$—$SrO$, $TiO_2$—$ZnO$, $TiO_2$—$Ga_2O_3$, $TiO_2$—$Y_2O_3$, $TiO_2$—$La_2O_3$, $TiO_2$—$MoO_3$, $TiO_2$—$Mn_2O_3$, $TiO_2$—$Fe_2O_3$, $TiO_2$—$Co_3O_4$, $TiO_2$—$WO_3$, $TiO_2$—$BaO$, $TiO_2$—$Cr_2O_3$, $TiO_2$—$ThO_2$, $TiO_2$—$Na_2O$, $TiO_2$—$BaO$, $TiO_2$—$CaO$, $TiO_2$—$HfO_2$, $TiO_2$—$Li_2O$, $TiO_2$—$Nb_2O_5$, $TiO_2$—$Ta_2O_5$, $TiO_2$—$PbO$, $TiO_2$—$Lu_2O_3$, $TiO_2$—$Yb_2O_3$, $TiO_2$—$CeO_2$, $TiO_2$—$Sc_2O_3$, $TiO_2$—$PbO$, $TiO_2$—$NiO$, $TiO_2$—$CuO$, $TiO_2$—$CoO$, $TiO_2$—$B_2O_3$, $ZrO_2$—$SiO_2$, $ZrO_2$—$Al_2O_3$, $ZrO_2$ $SnO$, $ZrO_2$—$PbO$, $ZrO_2$—$ZrO_2$—$Ta_2O_5$, $ZrO_2$ $Cr_2O_3$, $ZrO_2$—$MoO_3$, $ZrO_2$—$WO_3$, $ZrO_2$—$TiO_2$, $ZrO_2$ $HfO_2$, $TiO_2$—$SiO_2$—$Al_2O_3$, $TiO_2$—$SiO_2$—$ZnO$, $TiO_2$—$SiO_2$—$ZrO_2$, $TiO_2$—$SiO_2$—$CuO$, $TiO_2$—$SiO_2$ $MgO$, $TiO_2$—$SiO$ $TiO_2$—$SiO_2$—$B_2O_3$, $TiO_2$—$SiO_2$—$WO_3$, $TiO_2$—$SiO$ $TiO_2$—$SiO_2$—$MgO$, $TiO_2$—$SiO_2$—$La_2O_3$, $TiO_2$—$SiO$ $TiO_2$—$SiO_2$—$Mn_2O_3$, $TiO_2$—$SiO_2$—$Co_3O_4$, $TiO_2$—$SiO_2$ $NiO$, $TiO_2$—$SiO_2$ $PbO$, $TiO_2$—$SiO_2$ $Bi_2O_3$, $TiO_2$—$Al_2O_3$—$ZnO$, $TiO_2$—$Al_2O_3$—$ZrO_2$, $TiO_2$—$Al_2O_3$—$Fe_2O_3$, $TiO_2$—$Al_2O_3$—$WO_3$, $TiO_2$—$Al_2O_3$—$La_2O_3$, $TiO_2$—$Al_2O_3$—$Co_3O_4$, $ZrO_2$—$SiO_2$—$Al_2O_3$, $ZrO_2$—$SiO_2$—$SnO$, $ZrO_2$—$SiO_2$—$Nb_2O_5$, $ZrO_2$—$SiO_2$—$WO_3$, $ZrO_2$—$SiO_2$—$TiO_2$, $ZrO_2$—$SiO_2$—$MoO_3$, $ZrO_2$—$SiO_2$—$HfO_2$, $ZrO_2$—$SiO_2$—$Ta_2O_5$, $ZrO_2$—$Al_2O_3$—$SiO_2$, $ZrO_2$—$Al_2O_3$—$PbO$, $ZrO_2$—$Al_2O_3$—$Nb_2O_5$, $ZrO_2$—$Al_2O_3$—$WO_3$, $ZrO_2$—$Al_2O_3$—$TiO_2$, $ZrO_2$—$Al_2O_3$—$MoO_3$, $ZrO_2$—$HfO_2$—$Al_2O_3$, $ZrO_2$—$HfO_2$—$TiO_2$, and the like. Other suitable mixed metal oxide promoters embraced within the scope of this invention are disclosed by Tanabe et al., Bulletin of the Chemical Society of Japan, Vol. 47(5). pp. 1064–1066 (1974).

The metal oxides described herein which can be used as condensation catalyst promoters in association with the condensation catalyst may contribute to product selectivity and/or catalytic activity of the reaction and/or stability of the catalyst. The catalyst structure can comprise from about 0 to about 90 percent or greater by weight of the metal oxide, preferably from about 0 to about 75 percent by weight of the metal oxide, and more preferably from about 0 to about 50 percent by weight of the metal oxide, the remainder being the weight of the condensation catalyst. For mixed metal oxides containing titania, higher concentrations of titania can provide very desirable product selectivities including acyclic to cyclic selectivities and linear to branched selectivities of higher polyalkylene polyamine products. As discussed hereinafter, the condensation catalyst of this invention may also contain support(s), binding agent(s) or other additives to stabilize or otherwise help in the manufacture of the catalyst.

Illustrative of metallic phosphates which may or may not have a cyclic structure and metallic polyphosphates which may or may not have a condensed structure which can be utilized as condensation catalyst promoters in association with the condensation catalyst are described hereinabove. Corresponding metallic metaphosphimates, metallic phosphoramidates and metallic amido- and imidophosphates of the above may also be used as condensation catalyst promoters in accordance with this invention. Such metallic phosphates and polyphosphates can contribute to product selectivity, catalytic activity and/or catalyst stability (mechanical or dimensional strength of the catalyst.) Certain of these metallic phosphates and polyphosphates may also be effective as condensation catalysts for use in this invention.

Illustrative of Group VIB metal-containing substances which can be utilized as condensation catalyst promoters in association with the condensation catalyst are described hereinabove. Such Group VIB metal containing substances can contribute to product selectivity, catalytic activity and/or catalyst stability (mechanical or dimensional strength of the catalyst). Certain of these Group VIB metal-containing substances may also be effective as condensation catalysts for use in this invention.

Illustrative of conventional materials which can be utilized as condensation catalyst promoters in association with the condensation catalyst include a mineral acid or a compound derived from a mineral acid. Suitable for use as condensation catalyst promoters are one or more phosphoric acid or a salt of phosphoric acid, hydrogen fluoride, hydrofluoric acid or a fluoride salt, sulfuric acid or a salt of sulfuric acid, and the like. The promoter may also be organic esters of phosphoric acid or a salt of phosphoric acid, hydrogen fluoride organic complexes, hydrofluoric acid organic complexes or a fluoride salt organic complexes, organic esters of sulfuric acid or a salt of sulfuric acid, and the like. Suitable salts of phosphoric acid include sodium dihydrogen phosphate, disodium hydrogen phosphate, sodium phosphate and the like.

The amount of the condensation catalyst promoter of the mineral acid type used with the condensation catalyst of the invention is not narrowly critical. Generally, the amount does not exceed 25 weight percent of the weight of the catalyst. As a rule, it is desirable to use at least 0.01 weight percent of the weight of the catalyst. Preferably, the amount of condensation catalyst promoter will range from about 0.2 to about 10 weight percent of the weight of the catalyst. Most preferably, the amount of condensation promoter will range from about 0.5 to about 5 weight percent of the weight of the catalyst.

The amount of condensation catalyst promoter other than the mineral acid type used with the condensation catalyst is not narrowly critical. Generally, the amount does not exceed 90 weight percent of the weight of the catalyst. The amount of condensation catalyst promoter can range from about 0 to about 90 or greater weight percent of the weight of the catalyst, preferably from about 0 to about 75 weight percent of the weight of the catalyst, and more preferably from about 0 to about 50 weight percent of the weight of the catalyst. Most preferably, the amount of condensation catalyst promoter will range from about 0.5 to about 25 weight percent of the weight of the catalyst.

The condensation catalyst promoter can be provided to the condensation catalyst by conventional procedures known in the art. For example, the promoter can be provided to the catalyst by impregnating particles or monolithic structures comprising the catalyst with liquid comprising the promoter. This is a well known procedure in the art for incorporating additives to a solid support material. The condensation catalyst of the invention may be utilized as solid powders or as fused, bonded or compressed solid pellets, or larger structures in association with the one or more metal oxides, or as coated, fused, bonded or compressed solid pellets, or larger structures, composited with one or more support materials, in association with one or more metal oxides. These solid structures may be treated with the promoter by mixing a liquid body of the promoter with the solid structure. For example, the condensation catalyst solids may be slurried in the promoter, drained, washed and suctioned to remove excess promoter and then dried with heat to remove any volatiles accompanying the promoter. The drying temperature chosen will depend on the nature of the volatiles to be removed. Usually, the time/temperature for effecting drying will be below the conditions for effecting dehydration to remove bound water from the metal oxide in association with the condensation catalyst. Normally the drying temperature will be greater than about 120° C. and below about 600° C. depending on the thermal stability of the catalyst. The drying time will generally go down as the drying temperature rises and vice versus, and may extend from 5 seconds to about 24 hours.

Alternatively, the condensation catalyst promoter can be provided to the condensation catalyst at the time of preparing the catalyst in association with one or more metal oxides. For example, one or more metal oxides may be condensed from their respective hydrolyzable monomers to the desired oxides to form oxide powders which can thereafter be blended and compressed with the catalyst to form pellets and larger structures of the metal oxide-containing condensation catalyst of this invention. The one or more metal oxides which can be used in association with the catalyst in accordance with this invention can be provided from metal salts which can be heated to form the metal oxide. It is appreciated that the promoter can be incorporated into the molecular bonding configuration of the metal oxide containing condensation catalyst by conventional procedures known in the art.

The condensation catalysts in association with one or more metal oxides prior to the treatment of the promoter may be prepared in a wide variety of ways. For example, one or more metal oxides may be provided as a partial condensate on a support, such as a silica or alpha, beta or gamma alumina, silicon carbide, and the like, and then condensed by heating to effect polymerization to the desired oxide form. The metal oxide(s) may be condensed from hydrolyzable monomers to the desired oxide, indeed, to form an oxide powder which can thereafter be compressed in the presence of a condensation catalyst to form pellets and larger structures of the metal oxide containing condensation catalyst of the invention. A blend of the powder and condensation catalyst can be made into a shapeable paste which can be extruded and cut into pellets according to conventional procedures. The extrudate may thereafter be fired to cure the condensation catalyst and fix the structure. The cut extrudate may be blended with a support material such as those characterized above, and the blend fired to fuse the metal oxide-containing catalyst to the support.

In a preferred embodiment of this invention, a high surface area silica or titania can be slurried with an aqueous solution of sodium dihydrogen phosphate, disodium dihydrogen pyrophosphate or sodium trimetaphosphate, extruded, and calcined at a temperature of about 400° C.

A preferred promoted catalyst structure comprises sodium dihydrogen phosphate, disodium dihydrogen pyrophosphate or sodium trimetaphosphate in association with a Group IVA or IVB metal oxide having a surface area of at least a 140 m$^2$/gm which may or may not be bonded to a support material. The term "support," as used herein and in the claims, means a solid structure which does not adversely affect the catalytic properties of the promoted catalyst and is at least as stable as the promoted catalyst to the reaction medium. The support can function as an amine condensation catalyst independent of the condensation catalyst used herein, although it may have lower catalytic activity to the reaction. The support may act in concert with the promoted catalyst to moderate the reaction. Some supports may contribute to the selectivity of the reaction. The promoted catalyst structure can comprise from about 2 to about 60 percent by weight or greater of the support, more preferably from about 10 to about 50 percent by weight of the support, the remainder being the weight of the metal oxide(s) and condensation catalyst. Included in the weight of the support is the weight of any binding agent such as phosphates, sulfates, silicates, fluorides, and the like, and any other additive provided to stabilize or otherwise help in the manufacture of the promoted catalyst. The support may be particles as large or larger than the catalyst component and "glued" to the condensation catalyst and/or metal oxide by virtue of a binding medium.

The support may constitute a separate phase in the process of extruding the catalytic structure. In this embodiment, the support forming material, preferably as a paste is blended with a paste of the condensation catalyst and one or more metal oxides or a partial condensate thereof. The paste may comprise the oxide forms of the support and the condensation catalyst, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the metal oxide containing condensation catalyst.

The use of supports for the condensation catalyst provides a number of significant advantages. It has been determined that some of the promoted condensation catalysts are not as stable in the amines reaction media when utilized over an extended period of time. When the reaction is effected as a batch reaction, this matter is not a problem. However, when the reaction is effected with the promoted condensation catalyst as part of a fixed bed in a tubular reactor, the preferred procedure for carrying out the invention, it is desirable to have the promoted catalyst be more stable. When the promoted catalyst is combined with the support, it has greater stability for the reaction medium, and therefore, it is better able to be used in a fixed bed of a continuous reactor. The supported catalysts suffer from none of the leaching problems that the promoted catalyst per se may have or the problems that are associated with the prior art catalysts, such as acidic phosphorus compounds on silica.

The reactants used in the condensation process of the invention may be ammonia or organic compound containing —NH— and any compound possessing an alcoholic hydroxyl group, subject to the following: the intramolecular condensation of an amino compound produces an amine having a lower molecular weight, and the intermolecular condensation of an amino compound with one or more of another amino compound or a compound containing an alcoholic hydroxyl group produces an amine having a lower, same or higher molecular weight than the reactants.

Illustrative of suitable reactants in effecting the process of the invention, include by way of example:

Ammonia

MEA—monoethanolamine
EDA—ethylenediamine
MeEDA—methylethylenediamine
EtEDA—ethylethylenediamine
AEEA—N-(2-aminoethyl)ethanolamine
HEP—N-(2-hydroxyethyl)piperazine
DETA—diethylenetriamine
AEP—N-(2-aminoethyl)piperazine
TAEA—trisaminoethylamine
TETA—triethylenetetramine
TEPA—tetraethylenepentamine
PEHA—pentaethylenehexamine TETA Isomers TAEA—trisaminoethylamine
TETA—triethylenetetramine
DPE—dipiperazinoethane
DAEP—diaminoethylpiperazine
PEEDA—piperazinoethylethylenediamine TEPA Isomers AETAEA—aminoethyltrisaminoethylamine
TEPA—tetraethylenepentamine
AEDAEP—aminoethyldiaminoethylpiperazine
AEPEEDA—aminoethylpiperazinoethylethylenediamine
iAEPEEDA—isoaminoethylpiperazinoethylethylenediamine
BPEA—bispiperazinoethylamine The foregoing also can represent the products of the reaction. For example, ammonia and MEA are frequently employed to produce EDA along with a variety of other amines, most of which are set forth above.

Glycol compounds can also be employed in the preparation of amines in accordance with this invention. For purposes of this invention, glycol compounds embrace diols and polyols. Illustrative of suitable glycol compounds include alkylene glycols such as ethylene glycol, propylene glycol, 1,3-propane diol or mixtures thereof The process may be effected in the liquid or vapor or supercritical liquid states or mixtures thereof though the actual reaction is believed to occur on the catalyst s solid surface in the absorbed state. In this context, the vapor phase reaction is intended to refer to the general vapor state of the reactants. Though the reaction conditions may range from subatmospheric to superatmospheric conditions, it is desirable to run the reaction from about 50 psig to about 3,000 psig, preferably from about 200 psig to about 2,000 psig The temperature of the reaction may be as low as about 125° C. to about 400° C. Preferably, the reaction temperature ranges from about 150° C. to about 350° C., and most preferably from about 225° C. to about 325° C.

The reaction may be effected by the incremental addition of one of the reactants to the other or by the joint addition of the reactants to the promoted catalyst. The preferred process effects the reaction in a continuous manner over a fixed bed of the promoted condensation catalyst in a tubular reactor. However, the reactor may be carried out by slurrying the promoted catalyst in the reactants or in a batch mode in an autoclave. An inert such as nitrogen, methane and the like can be used in the reaction process.

The preferred process involves the formation of alkyleneamines from the intermolecular condensation of alkanolamines and alkyleneamines or the intramolecular condensation of alkyleneamines or alkanolamines. Illustrative of such reactions are the following reactant combinations:

| REACTANT | REACTANT | PRODUCTS |
| --- | --- | --- |
| Ammonia | Methanol | Monomethylamine Dimethylamine Trimethylamine |
| Ammonia | MEA | EDA, DETA, AEEA, TETA, TEPA, PIP |
| Ammonia | AEEA | DETA, PIP |
| MEA, Ammonia | EDA | EDA, AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| MEA | EDA | AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| EDA | AEEA | HEP, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| DETA | AEEA | TEPA Isomers, AEP |
| EDA | EDA | DETA, TETA AND TEPA Isomers |

The process of the invention provides the ability to generate the manufacture of desirable higher polyalkylene polyamine products such as TETA, TEPA and PEHA without generating large amounts of cyclic alkylenepolyamine products such as PIP, AEP and HEP. The alkyleneamines producers composition of this invention has a TETA+TAEA to PIP+AEP+-PEEDA+DAEP+DPE weight ratio of greater than about 0.5 and a TETA to TAEA weight ratio of greater than about 2.0. The process of this invention provides the potential to control congener distribution, linear to cyclic selectivity and linear to branched selectivity of the higher polyalkylene polyamines.

It is appreciated that the condensation catalysts and condensation catalyst promoters of this invention may also be useful in the production of alkylamines. For example, an alcohol and at least one of ammonia, a primary amine, a secondary amine or a tertiary amine may be contacted in the presence of a condensation catalyst and a condensation catalyst promoter under conditions effective to produce alkylamines.

This invention is further illustrated by certain of the following examples:

EXAMPLES

In the examples set forth in Tables I-XXIV and XLV-LXXI below, the catalyst of choice was placed in a tubular reactor having an outside diameter of 1 inch and an overall length of 30 inches. The catalyst portion of the reactor comprised a length of 24 inches, accommodating 150 cubic centimeters of catalyst. The reactor was made of 316 stainless steel. In the examples set forth in Tables XXV-XLIV and LXXII-CXXXV, the catalyst of choice was placed in one of 3 tubular reactors, each having an outside diameter of 1 inch, and heated by a sand bath. The catalyst portion of the reactor comprised a length of 24 inches, accommodating 100 cubic centimeters of catalyst. As used herein, AB1 refers to a material obtained from Norton Company, Akron, Ohio, which is a mixture of sodium trimetaphosphate and sodium tripolyphosphate. As used in certain of the tables below, acyclic (N4)/cyclic (<=N4) refers to the weight ratio of TETA+TAEA to PIP+AEP+-PEEDA+DAEP+DPE, and acyclic (N5)/cyclic (<=N5) refers to the weight ratio of TEPA+A-ETAEA to PIP+AEP+PEEDA+DAEP+-DPE+AEPEEDA+iAEPEEDA+AEDAEP+A-EDPE+BPEA. The catalysts and promoters employed are identified as follows:

| DESIGNATION | COMPOSITION | PHYSICAL PROPERTIES |
| --- | --- | --- |
| A | Titanium dioxide (anatase), 2% sulfur (presumed to be —OSO$_3$H) content | Particle size: 1/16" cylindrical extrudates; Surface area: 188.4 m$^2$/gm; Pore vol. Hg, cc/gm: |

-continued

| DESIGNATION | COMPOSITION | PHYSICAL PROPERTIES |
|---|---|---|
| | | 0.274; Med. Pore Diam., 0.0092; Crush strength, FPCS, LBS.: 10.8. |
| B | $TiO_2$ (anatase)-$\gamma$-$Al_2O_3$ | Particle size: 1/16" cylindrical extrudates $TiO_2$-$\gamma$-$Al_2O_3$; Catalyst surface area: 162.8 $m_2$/gm.; Pore vol. $N_2$, cc/gm.: 0.338. |
| C | $TiO_2$ (anatase)-$SiO_2$ | Particle size: 1/16: cylindrical extrudates; $TiO_2$—$SiO_2$; Catalyst surface area: 210.9 $m^2$/gm.; Pore vol. $N_2$, cc/gm.: 0.334. |
| D | Catalyst B/small amount of $H_3PO_4$ from diammonium hydrogen phosphate | Particle size: 1/16" cylindrical extrudates $TiO_2$-$\gamma$-$Al_2O_3$; Catalyst surface area: 162.8 $m_2$/gm.; Pore vol. $N_2$, cc/gm.: 0.338. |
| E | Catalyst C/small amount of $H_3PO_4$ from diammonium hydrogen phosphate | Particle size: 1/16" cylindrical extrudates $TiO_2$—$SiO_2$; Catalyst surface area: 210.9 $m^2$/gm.; Pore vol. $N_2$, cc/gm.: 0.334. |
| F | Catalyst B/small amount of HF from $NH_4F$ | Particle size: 1/16" cylindrical extrudates $TiO_2$-$\gamma$-$Al_2O_3$; Catalyst surface area: 162.8 $m_2$/gm.; Pore vol. $N_2$, cc/gm.: 0.338. |
| G | Catalyst B/small amount of $H_2SO_4$ from $(NH_4)_2SO_4$ | Particle size: 1/16" cylindrical extrudates $TiO_2$-$\gamma$-$Al_2O_3$; Catalyst surface area: 162.8 $m_2$/gm.; Pore vol. $N_2$, cc/gm.: 0.338. |
| H | Catalyst C/small amount of HF from $NH_4F$ | Particle size: 1/16: cylindrical extrudates; $TiO_2$—$SiO_2$; Catalyst surface area: 210.9 $m^2$/gm.; Pore vol. $N_2$, cc/gm.: 0.334. |
| I | Catalyst C/small amount of $H_2SO_4$ from $(NH_4)_2SO_4$ | Particle size: 1/16: cylindrical extrudates; $TiO_2$—$SiO_2$; Catalyst surface area: 210.9 $m^2$/gm.; Pore vol. $N_2$, cc/gm.: 0.334. |
| J | $TiO_2$ (anatase)/$Al_2O_3$/ SnO | Particle size: 1/16 inch cylindrical extrudates; Catalyst surface area: 125.0 $m^2$/gm. |
| K | $TiO_2$ (anatase)/$SiO_2$/ $H_3BO_3$ | Particle size: 1/16 inch cylindrical extrudates; Catalyst surface area: 154.0 $m^2$/gm. |
| L | $TiO_2$ (anatase)/$Al_2O_3$/ $Nb_2O_5$/$H_3VO_4$ | Particle size: 1/16 inch cylindrical extrudates; Catalyst surface area: 111.0 $m^2$/gm. |
| M | $TiO_2$ (anatase)/$SiO_2$/ $La_2O_3$/$H_3PO_4$ | Particle size: 1/16 inch cylindrical extrudates; Catalyst surface area 136.0 $m^2$/gm. |
| N | $TiO_2$ (anatase)/$SiO_2$/ $La_2O_3$ | Particle size: 1/16 inch cylindrical extrudates; Catalyst surface area: 136.0 $m^2$/gm. |
| O | $TiO_2$ (anatase)/$Al_2O_3$/ $Nb_2O_5$/$H_3BO_3$ | Particle size: 1/16 inch cylindrical extrudates; Catalyst surface area: 111.0 $m^2$/gm. |
| P | $TiO_2$ (anatase)/$SiO_2$/ $H_3VO_4$ | Particle size: 1/16 inch cylindrical extrudates; Catalyst surface area: 149 $m^2$/gm. |
| Q | $TiO_2$ (anatase)/$Al_2O_3$/ SnO/$H_3PO_4$ | Particle size: 1/16 inch cylindrical extrudates; Catalyst surface area: 125 $m^2$/gm. |
| R | $TiO_2$ (anatase)/$Al_2O_3$ | Particle size: 1/16 inch cylindrical extrudates; Catalyst surface area: 185 $m^2$/gm. |
| S | $TiO_2$ (anatase)/$SiO_2$/ SnO/$H_3BO_3$ | Particle size: 1/16 inch cylindrical extrudates; Catalyst surface area: 141 $m^2$/gm. |
| T | $TiO_2$ (anatase)/$Al_2O_3$/ $La_2O_3$/$H_3VO_4$ | Particle size: 1/16 inch cylindrical extrudates; Catalyst surface area: 148 $m^2$/gm. |
| U | $TiO_2$ (anatase)/$SiO_2$/ $Nb_2O_5$/$H_3PO_4$ | Particle size: 1/16 inch cylindrical extrudates; Catalyst surface area: 129 $m^2$/gm. |
| V | $TiO_2$ (anatase)/$SiO_2$/ $Nb_2O_5$ | Particle size: 1/16 inch cylindrical extrudates; Catalyst surface area: 146 $m^2$/gm. |
| W | $TiO_2$ (anatase)/$Al_2O_3$/ $La_2O_3$/$H_3BO_3$ | Particle size: 1/16 inch cylindrical extrudates; Catalyst surface area: 135 $m^2$gm. |

-continued

| DESIGNATION | COMPOSITION | PHYSICAL PROPERTIES |
|---|---|---|
| X | $TiO_2$ (anatase)/$SiO_2$/ $SnO$/$H_3VO_4$ | Particle size: 1/16 inch cylindrical extrudates; Catalyst surface area: 143 $m^2$/gm. |
| Y | $TiO_2$ (anatase)/$Al_2O_3$/ $H_3PO_4$ | Particle size: 1/16 inch cylindrical extrudates; Catalyst surface area: 150 $m^2$/gm. |
| Z | $TiO_2$ (anatase)/$Al_2O_3$/ $La_2O_3$/$H_3PO_4$ | Particle size: 1/16 inch cylindrical extrudates; Catalyst surface area: 139 $m^2$/gm. |
| AA | $TiO_2$ (anatase)/$SiO_2$/ $Na_2B_4O_7$ | Particle size: 1/16 inch cylindrical extrudates; Catalyst surface area: 99 $m^2$/gm. |
| BB | $TiO_2$ (anatase)/$SiO_2$/ $Na_2SnO_6$ | Particle size: 1/16 inch cylindrical extrudates; Catalyst surface area: 112 $m^2$/gm. |
| CC | $ZrO_2$/$SiO_2$ | Particle size: 1/16 inch cylindrical extrudates; Catalyst surface area: 127 $m^2$/gm. |
| DD | $ZrO_2$/$SiO_2$/ $Nb_2O_5$ | Particle size: 1/16 inch cylindrical extrudates; Catalyst surface area: 126 $m^2$/gm. |
| EE | $ZrO_2$/$SiO_2$/ $H_3BO_3$ | Particle size: 1/16 inch cylindrical extrudates; Catalyst surface area: 126 $m^2$/gm. |
| FF | $ZrO_2$/$SiO_2$/ $NH_4VO_3$ (2 wt. % as $V_2O_5$) | Particle size: 1/16 inch cylindrical extrudates; Catalyst surface area: 169 $m^2$/gm. |
| GG | $TiO_2$ (anatase)/$SiO_2$ | Particle size: 1/16 inch cylindrical extrudates; Catalyst surface area: 169 $m^2$/gm. |
| HH | $TiO_2$ (anatase)/$SiO_2$/ $Al_2O_3$ | Particle size: 1/16 inch cylindrical extrudates; Catalyst surface area: 204 $m^2$/gm. |
| II | $TiO_2$ (anatase)/$SiO_2$/ $B_2O_3$ | Particle size: 1/16 inch cylindrical extrudates; Catalyst surface area: 219 $m^2$/gm. |
| JJ | $TiO_2$ (anatase)/$SiO_2$/ $NH_4HB_2O_7$ (2 wt. % as $B_2O_3$) | Particle size: 1/16 inch cylindrical extrudates; Catalyst surface area: 146 $m^2$/gm. |
| KK | $TiO_2$ (anatase)/$SiO_2$/ $NH_4HB_4O_7$/$WO_3$ | Particle size: 1/16 inch cylindrical extrudates; Catalyst surface area: 148 $m^2$/gm. |
| LL | $TiO_2$ (anatase)/$SiO_2$/ $NH_4HB_4O_7$/$NH_4VO_3$ | Particle size: 1/16 inch cylindrical extrudates; Catalyst surface area: 142 $m^2$/gm. |
| MM | $TiO_2$ (anatase)/$SiO_2$/ $NH_4HB_4O_7$/$NH_4VO_3$ | Particle size: 1/16 inch cylindrical extrudates; Catalyst surface area: 144 $m^2$/gm. |
| NN | $TiO_2$ (anatase)/$SiO_2$/ $NH_4HB_4O_7$/$NaVO_3$ | Particle size: 1/16 inch cylindrical extrudates; Catalyst surface area: 110 $m^2$/gm. |
| OO | $TiO_2$ (anatase)/$SiO_2$/ $(NH_4)_5W_{12}O_{41}$ | Particle size: 1/16 inch cylindrical extrudates; Catalyst surface area: 141 $m^2$/gm. |
| PP | $TiO_2$ (anatase)/$SiO_2$/ $(NH_4)_6H_2W_{12}O_{41}$ (8 wt. %) | Particle size: 1/16 inch cylindrical extrudates; Catalyst surface area: 156 $m^2$/gm. |
| QQ | $TiO_2$ (anatase)/$SiO_2$/ $Na_2WO_4.9WO_3$ (2 wt. % as $WO_3$) | Particle size: 1/16 inch cylindrical extrudates; Catalyst surface area: 145 $m^2$/gm. |
| RR | $TiO_2$ (anatase)/$SiO_2$/ $V_2O_5$ | Particle size: 1/16 inch cylindrical extrudates; Catalyst surface area: 127 $m^2$/gm. |
| SS | $TiO_2$ (anatase)/$SiO_2$/ $NaVO_3$ (2 wt. %) | Particle size: 1/16 inch cylindrical extrudates; Catalyst surface area: 83 $m^2$/gm. |
| TT | $TiO_2$ (anatase)/$SiO_2$/ $La_2O_3$/$B_2O_5$/$WO_3$ | Particle size: 1/16 inch cylindrical extrudates; Catalyst surface area: 152 $m^2$/gm. |
| UU | $ZrO_2$/$SiO_2$/$TiO_2$ | Particle size: 1/16 inch cylindrical extrudates; Catalyst surface area: 127 $m^2$/gm. |
| VV | $ZrO_2$/$SiO_2$/ $(NH_4)_6H_2W_{12}O_{40}$ (2 wt. % as $WO_3$) | Particle size: 1/16 inch cylindrical extrudates; Catalyst surface area: 120 $m^2$/gm. |
| WW | $TiO_2$ (anatase)/ $(NH_4)_2HPO_4$ | Particle size: 1/16 inch cylindrical extrudates; Catalyst surface area: 100 $m^2$/gm. |
| XX | $TiO_2$ (rutile)/ $(NH_4)_2HPO_4$ | Particle size: 1/16 inch cylindrical extrudates; Catalyst surface area: 0.34 $m^2$/gm. |

-continued

| DESIGNATION | COMPOSITION | PHYSICAL PROPERTIES |
|---|---|---|
| YY | $TiO_2$ (rutile)/ $H_3PO_4$ | Particle size: 1/16 inch cylindrical extrudates; Catalyst surface area: 1.08 $m^2$/gm. |
| ZZ | $TiO_2$ (anatase) | Particle size: 1/16 inch cylindrical extrudates; Catalyst surface area: 188.4 $m^2$/gm. |
| AAA | $TiO_2$ (anatase)/$SiO_2$ | Particle size: 1/16 inch cylindrical extrudates; Catalyst surface area: 186 $m^2$/gm. |
| BBB | $TiO_2$ (anatase)/$SiO_2$/ $H_3BO_3$ | Particle size: 1/16 inch cylindrical extrudates; Catalyst surface area: 154 $m^2$/gm. |
| CCC | $TiO_2$ (anatase)/$SiO_2$/ $H_3VO_4$ | Particle size: 1/16 inch cylindrical extrudates; Catalyst surface area: 146 $m^2$/gm. |
| DDD | $TiO_2$ (anatase)/$SiO_2$/ $NH_4BF_4$/$H_3PO_4$ | Particle size: 1/16 inch cylindrical extrudates; Catalyst surface area: 94 $m^2$/gm. |
| EEE | $TiO_2$ (anatase)/$SiO_2$/ $NaBF_4$ | Particle size: 1/16 inch cylindrical extrudates; Catalyst surface area: 107 $m^2$/gm. |
| FFF | $TiO_2$ (anatase)/$SiO_2$/ $H_2B_4O_7$/$H_3PO_4$ | Particle size: 1/16 inch cylindrical extrudates; Catalyst surface area: 142 $m^2$/gm. |
| GGG | $TiO_2$ (anatase)/$SiO_2$/ $Nb_2O_5$ | Particle size: 1/16 inch cylindrical extrudates; Catalyst surface area: 151 $m^2$/gm. |
| HHH | $TiO_2$ (anatase)/$SiO_2$/ $ZrO_2$ | Particle size: 1/16 inch cylindrical extrudates; Catalyst surface area: 151 $m^2$/gm. |
| III | $TiO_2$ (anatase)/$SiO_2$/ $Fe_2O_3$ | Particle size: 1/16 inch cylindrical extrudates; Catalyst surface area: 142 $m^2$/gm. |
| JJJ | $TiO_2$ (anatase)/$SiO_2$/ SnO | Particle size: 1/16 inch cylindrical extrudates; Catalyst surface area: 253 $m^2$/gm. |
| KKK | $TiO_2$ (anatase)/$SiO_2$/ $H_3BO_3$/$H_3VO_4$ | Particle size: 1/16 inch cylindrical extrudates; Catalyst surface area: 152 $m^2$/gm. |
| LLL | $TiO_2$ (anatase)/$SiO_2$/ $Na_2O$ | Particle size: 1/16 inch cylindrical extrudates; Catalyst surface area: 151 $m^2$/gm. |
| MMM | $TiO_2$ (anatase)/$SiO_2$/ ZnO | Particle size: 1/16 inch cylindrical extrudates; Catalyst surface area: 137 $m^2$/gm. |
| NNN | $TiO_2$ (anatase)/$SiO_2$/ $La_2O_3$ | Particle size: 1/16 inch cylindrical extrudates; Catalyst surface area: 134 $m^2$/gm. |
| OOO | $TiO_2$ (anatase)/$SiO_2$/ $Li_2O$ | Particle size: 1/16 inch cylindrical extrudates; Catalyst surface area: 127 $m^2$/gm. |
| PPP | $TiO_2$ (anatase)/$Al_2O_3$ | Particle size: 1/16 inch cylindrical extrudates; Catalyst surface area: 185 $m^2$/gm. |
| QQQ | $TiO_2$ (anatase)/$Al_2O_3$/ $Na_2O$ | Particle size: 1/16 inch cylindrical extrudates; Catalyst surface area: 117 $m^2$/gm. |
| RRR | $TiO_2$ (anatase)/$Al_2O_3$/ $La_2O_3$ | Particle size: 1/16 inch cylindrical extrudates; Catalyst surface area: 142 $m^2$/gm. |
| SSS | $TiO_2$ (anatase)/$Al_2O_3$/ $La_2O_3$/$H_3PO_4$ | Particle size: 1/16 inch cylindrical extrudates; Catalyst surface area: 115 $m^2$/gm. |
| TTT | $TiO_2$ (anatase)/$Al_2O_3$/ MgO | Particle size: 1/16 inch cylindrical extrudates; Catalyst surface area: 137 $m^2$/gm. |
| UUU | $TiO_2$ (anatase)/$Al_2O_3$/ $Li_2O$ | Particle size: 1/16 inch cylindrical extrudates; Catalyst surface area: 105 $m^2$/gm. |
| VVV | $TiO_2$ (anatase)/$Al_2O_3$/ $NaBF_4$ | Particle size: 1/16 inch cylindrical extrudates; Catalyst surface area: 138 $m^2$/gm. |
| WWW | $TiO_2$ (anatase)/$Al_2O_3$/ SrO | Particle size: 1/16 inch cylindrical extrudates; Catalyst surface area: 141 $m^2$/gm. |
| XXX | $TiO_2$ (anatase)/$Al_2O_3$/ $H_3BO_3$ | Particle size: 1/16 inch cylindrical extrudates; Catalyst surface area: 159 $m^2$/gm. |
| YYY | $TiO_2$ (anatase)/$Al_2O_3$/ ZnO | Particle size: 1/16 inch cylindrical extrudates; Catalyst surface area: 141 $m^2$/gm. |

-continued

| DESIGNATION | COMPOSITION | PHYSICAL PROPERTIES |
|---|---|---|
| ZZZ | $TiO_2$ (anatase)/$Al_2O_3$/SnO | Particle size: 1/16 inch cylindrical extrudates; Catalyst surface area: 125 $m^2$/gm. |
| AAAA | $TiO_2$ (anatase)/$Al_2O_3$/$Fe_2O_3$ | Particle size: 1/16 inch cylindrical extrudates; Catalyst surface area: 147 $m^2$/gm. |
| BBBB | Titanium dioxide (anatase)/sodium trimetaphosphate; Ti:P atom ratio = 5.7:1 | Particle size: 1/16 inch cylindrical extrudates; Catalyst surface area: 133.3 $m^2$/gm; Pore volume $N_2$: 0.344 cc/gm; Pore area: 83.5 $m^2$/gm; Bulk density: 1.55 gm/cc. |
| CCCC | Titanium dioxide (anatase)/sodium tripolyphosphate; Ti:P atom ratio = 5.7:1 | Particle size: 1/16 inch cylindrical extrudates; Catalyst surface area: 80.3 $m^2$/gm; Pore volume $N_2$: 0.236 cc/gm; Pore area: 54.2 $m^2$/gm; Bulk density: 1.72 gm/cc. |
| DDDD | Titanium dioxide (anatase)/ABl; Ti:P atom ratio = 5.7:1 | Particle size: 1/16 inch cylindrical extrudates; Catalyst surface area: 115.0 $m^2$gm; Pore volume $N_2$: 0.429 cc/gm; Pore area: 87.4 $m^2$/gm; Bulk density: 1/39 gm/cc. |
| EEEE | Titanium dioxide (anatase)/sodium pyrophosphate; Ti:P atom ratio = 5.7:1 | Particle size: 1/16 inch cylindrical extrudates; Catalyst surface area: 78.6 $m^2$/gm; Pore volume $N_2$: 0.339 cc/gm; Pore area 72.1 $m^2$/gm; Bulk density: 1.59 gm/cc. |
| FFFF | Titanium dioxide (anatase)/ABl/boric acid (2 wt. %) | Particle size: 1/16 inch cylindrical extrudates; Catalyst surface area: 97.1 $m^2$/gm; Pore volume $N_2$: 0.440 cc/gm; Pore area: 84.2 $m^2$/gm; Bulk density: 1.32 gm/cc. |
| GGGG | Titanium dioxide (anatase)/ABl/ammonium tetra-fluoroborate (2 wt. %) | Particle size: 1/16 inch cylindrical extrudates; Catalyst surface area: 39.6 $m^2$/gm; Pore volume $N_2$: 0.442 cc/gm; Pore area: 66.7 $m^2$/gm; Bulk density: 1.34 gm/cc. |
| HHHH | Titanium dioxide (anatase)/ABl/sodium tetra-fluoroborate (8 wt. %) | Particle size: 1/16 inch cylindrical extrudates; Catalyst surface area: 44.1 $m^2$/gm; Pore volume $N_2$: 0.432 cc/gm; Pore area: 69.1 $m^2$/gm; Bulk density: 1.35 gm/cc. |
| IIII | Titanium dioxide (anatase)/ABl/sodium tetra-fluoroborate (8 wt. %) | Particle size: 1/16 inch cylindrical extrudates; Catalyst surface area: 23.0 $m^2$/gm; Pore volume $N_2$: 0.373 cc/gm; Pore area: 36.6 $m^2$/gm; Bulk density: 1.57 gm/cc. |
| JJJJ | Titanium dioxide (anatase)/ABl/sodium metatungstate (1 wt. %) | Particle size: 1/16 inch cylindrical extrudates; Catalyst surface area: 91.3 $m^2$/gm; Pore volume $N_2$: 0.414 cc/gm; Pore area: 75.7 $m^2$/gm; Bulk density: 1.40 gm/cc. |
| KKKK | Titanium dioxide (anatase)/ABl/sodium metatungstate (2 wt. %) | Particle size: 1/16 inch cylindrical extrudates; Catalyst surface area: 101.2 $m^2$/gm; Pore volume $N_2$: 0.442 cc/gm; Pore area: 94.2 $m^2$/gm; Bulk density: 1.38 gm/cc. |
| LLLL | Titanium dioxide (anatase)/ABl/sodium metatungstate (4 wt. %) | Particle size: 1/16 inch cylindrical extrudates: Catalyst surface area: 100.2 $m^2$/gm; Pore volume $N_2$: 0.429 cc/gm; Pore area: 90.0 $m^2$/gm; Bulk density: 1.43 gm/cc. |
| MMMM | Titanium dioxide (anatase)/ABl/ammonium metatungstate (2 wt. % as $WO_3$) | Particle size: 1/16 inch cylindrical extrudates; Catalyst surface area: 97.9 $m^2$/gm; Pore volume $N_2$: 0.431 cc/gm; Pore area: 79.4 $m^2$/gm; Bulk density: 1.43 gm/cc. |
| NNNN | Titanium dioxide (anatase)/ABl/ammonium metatungstate | Particle size: 1/16 inch cylindrical extrudates; Catalyst surface area: 91.8 |

-continued

| DESIGNATION | COMPOSITION | PHYSICAL PROPERTIES |
|---|---|---|
| | (4 wt. % as $WO_3$) | $m^2$/gm; Pore volume $N_2$: 0.402 cc/gm; Pore area: 69.2 $m^2$/gm; Bulk density: 1.51 gm/cc. |
| OOOO | Titanium dioxide (anatase)/ABl/ ammonium metatungstate (8 wt. % as $WO_3$) | Particle size: 1/16 inch cylindrical extrudates; Catalyst surface area: 78.1 $m^2$/gm; Pore volume $N_2$: 0.403 cc/gm; Pore area: 74.0 $m^2$/gm; Bulk density: 1.47 gm/cc. |
| PPPP | Titanium dioxide (anatase)/ABl/ lanthanum oxide (2 wt. %) | Particle size: 1/16 inch cylindrical extrudates; Catalyst surface area: 102.8 $m^2$/gm; Pore volume $N_2$: 0.409 cc/gm; Pore area: 65.3 $m^2$/gm; Bulk density: 1.49 gm/cc. |
| QQQQ | Titanium dioxide (anatase)/ABl/ lanthanum oxide (4 wt. %) | Particle size: 1/16 inch cylindrical extrudates; Catalyst surface area: 102.6 $m^2$/gm; Pore volume $N_2$: 0.418 cc/gm; Pore area: 85.4 $m^2$/gm; Bulk density: 1.41 gm/cc. |
| RRRR | Titanium dioxide (anatase)/ABl/ niobium oxide (2 wt. %) | Particle size: 1/16 inch cylindrical extrudates; Catalyst surface area: 102.8 $m^2$/gm; Pore volume $N_2$: 0.435 cc/gm; Pore area: 85.5 $m^2$/gm; Bulk density: 1.35 gm/cc. |
| SSSS | Titanium dioxide (anatase)/ABl/ sodium bicarbonate (2 wt. %) | Particle size: 1/16 inch cylindrical extrudates; Catalyst surface area: 99.5 $m^2$/gm; Pore volume $N_2$: 0.417 cc/gm; Pore area: 76.4 $m^2$/gm; Bulk density: 1.41 gm/cc. |
| TTTT | Titanium dioxide (anatase)/ABl/ vanadium oxide (2 wt. %) | Particle size: 1/16 inch cylindrical extrudates; Catalyst surface area: 88.7 $m^2$/gm; Pore volume $N_2$: 0.411 cc/gm; Pore area: 63.9 $m^2$/gm; Bulk density: 1.44 gm/cc. |
| UUUU | Titanium dioxide (anatase)/$SiO_2$/ $Al_2O_3$/sodium trimetaphosphate (10 wt. %) | Particle size: 1/16 inch cylindrical extrudates; Catalyst surface area: 129.9 $m^2$/gm; Pore volume $N_2$: 0.321 cc/gm; Pore area: 163 $m^2$/gm; Bulk density: 1.59 gm/cc. |
| VVVV | Titanium dioxide (anatase)/$SiO_2$/ $B_2O_3$/sodium trimetaphosphate (10 wt. %) | Particle size: 1/16 inch cylindrical extrudates; Catalyst surface area: 159.5 $m^2$/gm; Pore volume $N_2$: 0.312 cc/gm; Pore area: 129.8 $m^2$/gm; Bulk density: 1.54 gm/cc. |
| WWWW | Titanium dioxide (anatase)/$SiO_2$/ sodium trimetaphosphate (10 wt. %) | Particle size: 1/16 inch cylindrical extrudates; Catalyst surface area: 136.5 $m^2$/gm; Pore volume $N_2$: 0.399 cc/gm; Pore area: 162.5 $m^2$/gm; Bulk density: 1.48 gm/cc. |
| XXXX | Titanium dioxide/ABl | Particle size: 1/16 inch cylindrical extrudates; Catalyst surface area: 4.40 $m^2$/gm; Pore volume $N_2$: 0.184 cc/gm; Pore area: 19.2 $m^2$/gm; Bulk density: 2.10 gm/cc. |
| YYYY | Titanium dioxide (anatase)/ABl | Particle size: 1/16 inch cylindrical extrudates; Catalyst surface area: 102.0 $m^2$/gm; Pore volume $N_2$: 0.406 cc/gm; Pore area: 68.6 $m^2$/gm; Bulk density: 1.43 gm/cc. |
| ZZZZ | Magnesium oxide/ABl | Particle size: 1/16 inch cylindrical extrudates; Catalyst surface area: 18.1 $m^2$/gm; Pore volume $N_2$: 0.298 cc/gm; Pore area: 52.9 $m^2$/gm; Bulk density: 1.78 gm/cc. |
| AAAAA | Silicon dioxide/ABl | Particle size: 1/16 inch cylindrical extrudates; Catalyst surface area: 33.7 $m^2$/gm; Pore volume $N_2$: 0.496 cc/gm; Pore area: 81.0 $m^2$/gm; Bulk density: 1.06 gm/cc. |

-continued

| DESIGNATION | COMPOSITION | PHYSICAL PROPERTIES |
|---|---|---|
| BBBBB | Aluminum oxide/ lanthanum metaphosphate | Particle size: 1/16 inch cylindrical extrudates; Catalyst surface area: 86.0 m$^2$/gm; Pore volume N$_2$: 0.327 cc/gm; Pore area: 129.5 m$^2$/gm; Bulk density: 1.57 gm/cc. |
| CCCCC | Silicon dioxide/ lanthanum metaphosphate | Particle size: 1/16 inch cylindrical extrudates; Catalyst surface area: 38.7 m$^2$/gm; Pore volume N$_2$: 0.656 cc/gm; Pore area: 90.5 m$^2$/gm; Bulk density: 0.99 gm/cc. |
| DDDDD | Titanium dioxide (anatase)/ABl/ZnO (2 wt. %) | Particle size: 1/16 inch cylindrical extrudates; Catalyst surface area: 90.4 m$^2$/gm; Pore volume N$_2$: 0.427 cc/gm; Pore area: 74.5 m$^2$/gm; Bulk density: 1.49 gm/cc. |
| EEEEE | Titanium dioxide (anatase)/ABl/ZnO (4 wt. %) | Particle size: 1/16 inch cylindrical extrudates; Catalyst surface area: 78.3 m$^2$/gm; Pore volume N$_2$: 0.412 cc/gm; Pore area: 75.1 m$^2$/gm; Bulk density: 1.42 gm/cc. |
| FFFFF | Titanium dioxide (anatase)/ABl/ Nb$_2$O$_5$ (4 wt. %) | Particle size: 1/16 inch cylindrical extrudates; Catalyst surface area: 102.2 m$^2$/gm; Pore volume N$_2$: 0.407 cc/gm; Pore area: 75.4 m$^2$/gm; Bulk density: 1.44 gm/cc. |
| GGGGG | Titanium dioxide (anatase)/ABl/ NaBF$_4$ (8 wt. %) | Particle size: 1/16 inch cylindrical extrudates; Catalyst surface area: 22.5 m$^2$/gm; Pore volume N$_2$: 0.421 cc/gm; Pore area: 55.8 m$^2$/gm; Bulk density: 1.38 gm/cc. |
| HHHHH | Titanium dioxide (anatase)/sodium dihydrogen phosphate; Ti:P atom ratio = 5.7:1 | Particle size: 1/16 inch cylindrical extrudates; Catalyst surface area: 117.1 m$^2$/gm; Pore volume N$_2$: 0.321 cc/gm; Pore area: 85.7 m$^2$/gm; Bulk density: 1.64 gm/cc. |
| IIIII | Titanium dioxide (anatase)/disodium dihydrogen pyrophosphate; Ti:P atom ratio = 5.7:1 | Particle size: 1/16 inch cylindrical extrudates; Catalyst surface area: 133.5 m$^2$/gm; Pore N$_2$: 0.291 cc/gm; Pore area: 89.6 m$^2$/gm; Bulk density: 1.66 gm/cc. |
| JJJJJ | Titanium dioxide (anatase)/disodium hydrogen phosphate; Ti:P atom ratio = 5.7:1 | Particle size: 1/16 inch cylindrical extrudates; Catalyst surface area: 117/4 m$^2$/gm; Pore volume N$_2$: 0.346 cc/gm; Pore area 86.5 m$^2$/gm; Bulk density: 1.53 gm/cc. |
| KKKKK | Titanium dioxide (anatase)/sodium phosphate; Ti:P atom ratio = 5.7:1 | Particle size: 1/16 inch cylindrical extrudates; Catalyst surface area: 88.4 m$^2$/gm; Pore volume N$_2$: 0.365 cc/gm; Pore area: 76.90 m$^2$/gm; Bulk density: 1.48 gm/cc. |
| LLLLL | TiO$_2$ (anatase)/ (NH$_4$)$_6$H$_6$W$_{12}$O$_{40}$ (15 wt. % W). | Particle size: 1/16 inch cylindrical extrudates; TiO$_2$ surface area: 200 m$^2$/gm. |
| MMMMM | TiO$_2$ (anatase)/SiO$_2$/ (NH$_4$)$_6$H$_6$W$_{12}$O$_{40}$ (15 wt. % W); TiO$_2$/SiO$_2$ wt. ratio = 88/12. | Particle size: 1/16 inch cylindrical extrudates; TiO$_2$—SiO$_2$ surface area: 175 m$^2$/gm. |
| NNNNN | ZrO$_2$/SiO$_2$/ (NH$_4$)$_6$H$_6$W$_{12}$O$_{40}$ (15 wt. % W). | Particle size: 1/16 inch cylindrical extrudates; ZrO$_2$—SiO$_2$ surface area: 127 m$^2$/gm. |
| OOOOO | TiO$_2$ (anatase)/SiO$_2$ (NH$_4$)$_6$H$_6$W$_{12}$O$_{40}$ (7.5 wt. % W); TiO$_2$/SiO$_2$ wt. ratio = 88/12. | Particle size: 1/16 inch cylindrical extrudates; TiO$_2$—SiO$_2$ surface area: 175 m$^2$/gm. |
| PPPPP | TiO$_2$ (anatase)/SiO$_2$/ | Particle size: 1/16 |

| DESIGNATION | COMPOSITION | PHYSICAL PROPERTIES |
|---|---|---|
| | $(NH_4)_6H_6W_{12}O_{40}$ (15 wt. % W)/$La_2O_3$ (1 wt. % La); $TiO_2/SiO_2$ wt. ratio = 88/12. | inch cylindrical extrudates; $TiO_2$—$SiO_2$ surface area: 175 $m^2$/gm. |
| QQQQQ | $TiO_2$ (anatase)/$SiO_2$/ $(NH_4)_6H_6W_{12}O_{40}$ (7.5 wt. % W)/$La_2O_3$ (0.5 wt. % La); $TiO_2/SiO_2$ wt. ratio = 88/12. | Particle size: 1/16 inch cylindrical extrudates; $TiO_2$—$SiO_2$ surface area: 175 $m^2$/gm. |
| RRRRR | $ZrO_2/SiO_2$/ $(NH_4)_6H_6W_{12}O_{40}$ (15 wt. % W)/ $La_2O_3$ (1.0 wt. % La). | Particle size: 1/16 inch cylindrical extrudates; $ZrO_2$—$SiO_2$ surface area: 127 $m^2$/gm. |
| SSSSS | $TiO_2$ (anatase)/$SiO_2/WO_3$ (3.0 wt. % $WO_3$) | Particle size: 1/16 inch cylindrical extrudates; Catalyst surface area: 234 $m^2$/gm. |
| TTTTT | $TiO_2$ (anatase)/$SiO_2/WO_3$/ $(NH_4)_6H_6W_{12}O_{40}$ (7.5 wt. % W) | Particle size: 1/16 inch cylindrical extrudates; $TiO_2$—$SiO_2$—$WO_3$ surface area: 234 $m^2$/gm. |
| UUUUU | $TiO_2$ (anatase)/$SiO_2/SiO_2$ 12 $WO_3$. 26 $H_2O$ (7.5 wt. % W). | Particle size: 1/16 inch cylindrical extrudates; $TiO_2$—$SiO_2$ surface area: 175 $m^2$/gm. |
| VVVVV | $TiO_2$ (anatase)/$SiO_2/Al_2O_3$/ $(NH_4)_6H_6W_{12}O_{40}$ (7.5 wt. % W). | Particle size: 1/16 inch cylindrical extrudates; $TiO_2$—$SiO_2$—$Al_2O_3$ surface area: 175 $m^2$/gm. |
| WWWWW | $TiO_2$ (anatase)/$Al_2O_3/SiO_2$/ $(NH_4)_6H_6W_{12}O_{40}$ (7.5 wt. % W). | Particle size: 1/16 inch cylindrical extrudates; $TiO_2$—$Al_2O_3$—$SiO_2$ surface area: 175 $m^2$/gm. |
| XXXXX | $TiO_2$ (anatase)/$SiO_2$/ $(NH_4)_6H_6W_{12}O_{40}$ (7.5 wt. % W); $TiO_2/SiO_2$ wt. ratio = 70/30. | Particle size: 1/16 inch cylindrical extrudates; $TiO_2$—$SiO_2$ surface area: 195 $m^2$/gm. |
| YYYYY | $TiO_2$ (anatase). | Particle size: 1/16 inch cylindrical extrudates; Catalyst surface area: 200 $m^2$/gm. |
| ZZZZZ | $TiO_2$ (anatase)/$SiO_2$; $TiO_2/SiO_2$ wt. ratio = 70/30. | Particle size: 1/16 inch cylindrical extrudates; Catalyst surface area: 195 $m^2$/gm. |
| AAAAAA | $TiO_2$ (anatase)/$SiO_2$; $TiO_2/SiO_2$ wt. ratio = 88/12. | Particle size: 1/16 inch cylindrical extrudates; Catalyst surface area: 175 $m^2$/gm. |
| BBBBBB | $ZrO_2/SiO_2$. | Particle size: 1/16 inch cylindrical extrudates; Catalyst surface area: 127 $m^2$/gm. |
| CCCCCC | $\gamma$-$Al_2O_3/(NH_4)_6H_6W_{12}O_{40}$ (7.5 wt. % W). | Particle size: 1/16 inch cylindrical extrudates; $\gamma$-$Al_2O_3$ surface area: 105 $m^2$/gm. |
| DDDDDD | $TiO_2$ (anatase)/$SiO_2$/ $(NH_4)_6H_6W_{12}O_{40}$ (7.5 wt. % W); $TiO_2/SiO_2$ wt. ratio = 70/30. | Particle size: 1/16 inch cylindrical extrudates; $TiO_2$—$SiO_2$ surface area: 195 $m^2$/gm. |
| EEEEEE | $TiO_2$ (anatase)/$SiO_2/WO_3$ (7 wt. % $WO_3$). | Particle size: 1/16 inch cylindrical extrudates; Catalyst surface area: 224 $m^2$/gm. |
| FFFFFF | $TiO_2$ (anatase)/$SiO_2$/ | Particle size: 1/16 |

-continued

| DESIGNATION | COMPOSITION | PHYSICAL PROPERTIES |
|---|---|---|
| | $(NH_4)_6H_6W_{12}O_{40}$ (7.5 wt. % W)/ $B_2O_3$ (1.0 wt. % B). | inch cylindrical extrudates; $TiO_2$—$SiO_2$ surface area: 195 m$^2$/gm. |
| GGGGGG | $TiO_2$ (anatase)/$SiO_2$/ $(NH_4)_6H_6W_{12}O_{40}$ (7.5 wt. % W)/ ZnO (1.0 wt. % Zn); $TiO_2$/$SiO_2$ wt. ratio = 70/30. | Particle size: 1/16 inch cylindrical extrudates; $TiO_2$—$SiO_2$ surface area: 195 m$^2$/gm. |
| HHHHHH | $TiO_2$ (anatase)/$SiO_2$/ $(NH_4)_6H_6W_{12}O_{40}$ (7.5 wt. % W)/ $ThO_2$ (1.0 wt. % Th); $TiO_2$/$SiO_2$ wt. ratio = 70/30. | Particle size: 1/16 inch cylindrical extrudates; $TiO_2$—$SiO_2$ surface area: 195 m$^2$/gm. |
| IIIIII | $TiO_2$ (anatase)/$SiO_2$/ $(NH_4)_6H_6W_{12}O_{40}$ (7.5 wt. % W)/ $NH_4F$—HF (1.0 wt. % F); $TiO_2$/$SiO_2$ wt. ratio = 70/30. | Particle size: 1/16 inch cylindrical extrudates; $TiO_2$—$SiO_2$ surface area: 195 m$^2$/gm. |
| JJJJJJ | $TiO_2$ (anatase)/$SiO_2$/ $(NH_4)_6H_6W_{12}O_{40}$ (7.5 wt. % W)/ $CeO_2$ (1.0 wt. % Ce); $TiO_2$/$SiO_2$ wt. ratio = 70/30. | Particle size: 1/16 inch cylindrical extrudates; $TiO_2$—$SiO_2$ surface area: 195 m$^2$/gm. |
| KKKKKK | $TiO_2$ (anatase)/$WO_3$ (10 wt. % $WO_3$). | Particle size: 1/16 inch cylindrical extrudates; Catalyst surface area: 253 m$^2$/gm. |
| LLLLLL | $SiO_2$/$WO_3$ (10 wt. % $WO_3$). | Particle size: 1/16 inch cylindrical extrudates; Catalyst surface area: 144 m$^2$/gm. |
| MMMMMM | $TiO_2$ (anatase)/$SiO_2$; $TiO_2$/$SiO_2$ wt. ratio = 40/60 | Particle size: 1/16 inch cylindrical extrudates; Catalyst surface area: 201 m$^2$/gm. |

For each run in Tables I-XXIV and XLV-LXXI, the tubular reaction system was brought up to the desiqnated conditions. The ammonia feed was established first, then the EDA-MEA, DETA-AEEA or DETA MEA feed, as appropriate. After a sufficient line out period, a two hour timed run was conducted, then the experiment was run overnight and sampled. The feed was changed to another reactant set and the above procedure was repeated for each of the examples in Tables I-XXIV and XLV-LXXI.

For each run in Tables XXV-XLIV and LXXII--CXXXV, the tubular reaction system was brought up to the designated conditions. The premixed ammonia-DETA feed was established first, then the DETA-MEA feed. After a sufficient line out period, a two hour timed run was conducted and a sample taken. The temperature was then adjusted for the next experiment. This procedure was repeated for each of the examples in Tables XXV-XLIV and LXXII-CXXXV.

The catalysts employed in the examples hereinafter were prepared as follows:

Diammonium hydrogen phosphate preparation to provide a performance moderator: Catalyst pellets (150 cc) were added to a saturated solution of diammonium hydrogen phosphate in water. Enough solution was added to completely immerse the pellets. The slurry was allowed to stand at a temperature of 55°-60° C. for a period of 8 hours. The catalyst was filtered, washed with water until the wash water was neutral, dried at a temperature of 100° C., and then calcined at a temperature of 600° C. for a period of 6-8 hours.

Hydrogen fluoride preparation to provide a performance moderator: Catalyst pellets (150 cc) were added to a saturated solution of ammonium fluoride in water. Enough solution was added to completely immerse the pellets. The slurry was allowed to stand at a temperature of 55°-60° C. for a period of 8 hours. The catalyst was filtered, washed with water until the wash water was neutral, dried at a temperature of 100° C., and then calcined at a temperature of 600° C. for a period of 6-8 hours.

Sulfuric acid preparation to provide a performance moderator: Catalyst pellets (150 cc) were added to a saturated solution of ammonium sulphate in water. Enough solution was added to completely immerse the pellets. The slurry was allowed to stand at a temperature of 55°-60° C. for a period of 8 hours. The catalyst was filtered, washed with water until the wash water was neutral, dried at a temperature of 100° C., and then calcined at a temperature of 600° C. for a period of 6-8 hours.

Catalyst J Preparation: Tin (II) ethylene glycoxide (9.88 grams) was dissolved in 150 milliliters of monoethanolamine. The resulting solution was diluted with isopropanol (80 milliliters) and the $TiO_2Al_2O_3$ support (280 grams) was impregnated. The support turned yellow. After a period of 1 hour, the catalyst was filtered and washed with excess isopropanol, dried and then calcined at a temperature of 600° C. for a period of 16 hours. The catalyst was divided into 2 equal parts—one part was used to make Catalyst Q.

Catalyst K Preparation: Boric acid (2.86 grams) was dissolved in just enough water to impregnate the $TiO_2$/$SiO_2$ support (140 grams). The catalyst was dried at a temperature of 100° C. and then calcined at a temperature of 400° C. for a period of 16 hours.

Catalyst L Preparation: The TiO$_2$/Al$_2$O$_3$ support (280 grams) was impregnated with niobium pentoxide-toluene solution (13.68 grams of niobium pentoxide). Excess toluene was removed under reduced pressure on a Buchi rotary evaporator. The catalyst was dried at a temperature of 100° C. and then calcined at a temperature of 400° C. for a period of 16 hours. The catalyst was divided into 2 equal parts. One part was impregnated with ammonium vanadate (2.83 grams) dissolved in water. This catalyst was dried at a temperature of 100° C. and then calcined at a temperature of 400° C. for a period of 16 hours. The second part was used to make Catalyst O described below.

Catalyst M Preparation: The TiO$_2$/SiO$_2$ support (280 grams) was impregnated with lanthanum nitrate (7.59 grams) in sufficient water to wet all of the support. The wet catalyst was dried at a temperature of 100° C. and then calcined at a temperature of 400° C. for a period of 16 hours. The catalyst (140 grams) was then soaked in 85% phosphoric acid for a period of 1 hour and washed with water until neutral. The catalyst was dried at a temperature of 100° C. and then calcined at a temperature of 400° C. for a period of 16 hours.

Catalyst N Preparation: The TiO$_2$/SiO$_2$ support (280 grams) was impregnated with lanthanum nitrate (7.59 grams) in sufficient water to wet all of the support. The wet catalyst was dried at a temperature of 100° C. and then calcined at a 78mperature of 400° C. for a period of 16 hours.

Catalyst O Preparation: The second part of Catalyst L greenware was impregnated with boric acid (2.86 grams) in sufficient water to wet the support The catalyst was dried at a temperature of 100° C. and then calcined at a temperature of 400° C. for a period of 16 hours.

Catalyst P Preparation: Ammonium vanadate (2.83 grams) was dissolved in sufficient water to impregnate the TiO$_2$/SiO$_2$ support (140 grams). The wet catalyst was dried at a temperature of 100° C. and then calcined at a temperature of 400° C. for a period of 16 hours.

Catalyst Q Preparation: The second part of Catalyst J greenware was impregnated with 85% phosphoric acid for a period of 1 hour and then washed with water until neutral. The catalyst was dried at a temperature of 100° C. and then calcined at a temperature of 400° C. for a period of 16 hours.

Catalyst R Preparation: The TiO$_2$Al$_2$O$_3$ support was used without further treatment.

Catalyst S Preparation: Tin (II) ethylene glycoxide (9.88 grams) was dissolved in 150 milliliters of monoethanolamine and the TiO$_2$/SiO$_2$ support (280 grams) was impregnated therewith. The TiO$_2$/SiO$_2$ support turned yellow. After a period of 1 hour, the catalyst was filtered and washed with excess isopropanol to remove excess monoethanolamine. The catalyst was dried at a temperature of 100° C. and then calcined at a temperature of 400° C. for a period of 16 hours The catalyst was divided into 2 equal parts. One part was impregnated with boric acid (2.86 grams) dissolved in sufficient water to wet the support. This catalyst was dried at a temperature of 100° C. and then calcined at a temperature of 400° C. for a period of 16 hours. The second part was used to make Catalyst X described below.

Catalyst T Preparation: The TiO$_2$/Al$_2$O$_3$ support (280 grams) was impregnated with lanthanum nitrate (7.59 grams) in sufficient water to wet the support. The catalyst was dried at a temperature of 100° C. and then calcined at a temperature of 400° C. for a period of 16 hours. The catalyst was then impregnated with ammonium vanadate (2.83 grams) in sufficient water to wet the support. The catalyst was dried at a temperature of 100° C. and then calcined at a temperature of 400° C. for a period of 16 hours.

Catalyst U Preparation: The TiO$_2$/SiO$_2$ support (280 grams) was impregnated with niobium pentoxide in toluene (13.68 grams). Excess toluene was removed under reduced pressure on a Buchi rotary evaporator. The catalyst was dried at a temperature of 100° C. and then calcined at a temperature of 400° C. for a period of 16 hours. The catalyst was divided into 2 equal parts. One portion was impregnated with 85% phosphoric acid for a period of 1 hour and then washed with water until neutral. The wet catalyst was dried at a temperature of 100° C. and then calcined at a temperature of 400° C. for a period of 16 hours. The second part was used as Catalyst V described below.

Catalyst V Preparation: The second part of Catalyst U prior to impregnation with phosphoric acid was used without further treatment.

Catalyst W Preparation: The TiO$_2$Al$_2$O$_3$ support (280 grams) was impregnated with lanthanum nitrate (7.59 grams) in sufficient water to wet the support. The catalyst was dried at a temperature of 100° C. and then calcined at a temperature of 400° C. for a period of 16 hours. The catalyst was then impregnated with boric acid (2.86 grams) in sufficient water to wet the support. The catalyst was dried at a temperature of 100° C. and then calcined at a temperature of 400° C. for a period of 16 hours.

Catalyst X Preparation: The second part of Catalyst S greenware was impregnated with ammonium vanadate (2.83 grams) in sufficient water to wet the support. The catalyst was dried at a temperature of 100° C. and then calcined at a temperature of 400° C. for a period of 16 hours.

Catalyst Y Preparation: The TiO$_2$/Al$_2$O$_3$ support (140 grams) was impregnated with 85% phosphoric acid for a period of 1 hour and then washed with water until neutral. The wet catalyst was dried at a temperature of 100° C. and then calcined at a temperature of 400° C. for a period of 16 hours.

Catalyst Z Preparation: The TiO$_2$/Al$_2$O$_3$ support (280 grams) was impregnated with lanthanum nitrate (7.59 grams) in sufficient water to wet all of the support. The wet catalyst was dried at a temperature of 100° C. and then calcined at a temperature of 400° C. for a period of 16 hours. The catalyst (140 grams) was then soaked in 85% phosphoric acid for a period of 1 hour and washed with water until neutral. The catalyst was dried at a temperature of 100° C. and then calcined at a temperature of 400° C. for a period of 16 hours Catalyst AA Preparation: Sodium tetraborate (21 grams) was dissolved in water (112 grams) and used to impregnate the TiO$_2$/SiO$_2$ support (140 grams). After a period of 1 hour, excess liquid was decanted and the material dried at a temperature of 100° C. for a period of 1 hour. The catalyst was then calcined at a temperature of 400° C. for a period of 16 hours.

Catalyst BB Preparation: Sodium stannate (21 grams) was dissolved in just enough water (56.4 grams) to impregnate the TiO$_2$/SiO$_2$ support (140 grams). After a period of 1 hour, the catalyst was calcined at a temperature of 400° C. for a period of 16 hours.

Catalyst CC Preparation: The ZrO$_2$/SiO$_2$ support was used without further treatment.

Catalyst DD Preparation: A solution of niobium pentethoxide (25.28 grams) in toluene (84.18 grams) was prepared. The ZrO$_2$/SiO$_2$ support (140 grams) was slurried with toluene (75 milliliters) and then the niobium pentethoxide solution (29.6 grams) was added. Excess toluene was removed under reduced pressure and the catalyst was dried at a temperature of 100° C. for a period of 1 hour. The catalyst was then calcined at a temperature of 400° C. for a period of 16 hours.

Catalyst EE Preparation: Boric acid (2.86 grams) was dissolved in methanol (75 milliliters) and the ZrO$_2$/SiO$_2$ support (140 grams) was impregnated with this solution. The catalyst was dried at a temperature of 100° C. for a period of 1 hour and then calcined at a temperature of 400° C. for a period of 16 hours.

Catalyst FF Preparation: Ammonium metavanadate (2.86 grams) was dissolved in water (75 milliliters) and the ZrO$_2$/SiO$_2$ support (140 grams) was impregnated with this solution. The catalyst was dried at a temperature of 100° C. for a period of 1 hour and then calcined at a temperature of 400° C. for a period of 16 hours.

Catalyst GG Preparation: The TiO$_2$/SiO$_2$ support was used without further treatment.

Catalyst HH Preparation: The TiO$_2$/SiO$_2$Al$_2$O$_3$ support was used without further treatment.

Catalyst II Preparation: Boric acid (2.86 grams) was dissolved in just enough water to impregnate the TiO$_2$/SiO$_2$ support (140 grams). The catalyst was dried at a temperature of 100° C. for a period of 1 hour and the calcined at a temperature of 400° C. for a period of 16 hours.

Catalyst JJ Preparation: Ammonium hydrogentetraborate (4.19 grams) was dissolved in water (104.3 grams) to wet the TiO$_2$/SiO$_2$ support (140 grams). After an impregnation period of 1 hour, the catalyst was dried at a temperature of 100° C. for a period of 1 hour and then calcined at a temperature of 400° C. for a period of 16 hours.

Catalyst KK Preparation: Ammonium hydrogentetraborate (4.19 grams) and ammonium tungstate (5.89 grams) were dissolved in sufficient water (95.45 grams) to wet the TiO$_2$/SiO$_2$ support (140 grams). After an impregnation period of 1 hour at room temperature, the catalyst was dried at a temperature of 100° C. for a period of 1 hour and then calcined at a temperature of 400° C. for a period of 16 hours.

Catalyst LL Preparation: Ammonium hydrogentetraborate (4.19 grams) and ammonium vanadate (5.62 grams) were dissolved in sufficient water (170.2 grams) to dissolve the inorganic salts. The TiO$_2$/SiO$_2$ support (140 grams) was immersed in this solution for a period of 1 hour. Excess liquid was decanted and the catalyst was dried at a temperature of 100° C. for a period of 1 hour. The catalyst was then calcined at a temperature of 600° C. for a period of 16 hours.

Catalyst MM Preparation: Ammonium hydrogentetraborate (4.19 grams) and ammonium vanadate (5.62 grams) were dissolved in sufficient hot water (176 grams). The TiO$_2$/SiO$_2$ support (140 grams) was added to the hot solution, stirred well and then allowed to cool to room temperature The catalyst slurry was transferred to a round bottom flask and stripped under reduced pressure using a Buchi evaporator. The catalyst was dried at a temperature of 100° C. for a period of 1 hour and then calcined at a temperature of 400° C. for a period of 16 hours.

Catalyst NN Preparation: Ammonium hydrogentetraborate (4.19 grams) was dissolved in sufficient water (94 grams) to wet the TiO$_2$/SiO$_2$ support (140 grams). After an impregnation period of 1 hour, the catalyst was dried at a temperature of 100° C. and then calcined at a temperature of 400° C. for a period of 16 hours. Sodium vanadate (5.85 grams) was dissolved in water (94 grams) sufficient to wet the calcined material. After an impregnation period of 1 hour, the catalyst was redried at a temperature of 100° C. and calcined at a temperature of 400° C. for a period of 16 hours.

Catalyst OO Preparation: Ammonium metatungstate (3.12 grams) was dissolved in a sufficient amount of water (103 grams) to wet the TiO$_2$/SiO$_2$ support (140 grams). The catalyst was dried at a temperature of 100° C. for a period of 1 hour and then calcined at a temperature of 400° C. for a period of 16 hours.

Catalyst PP Preparation: Ammonium metatungstate (12.26 grams) was dissolved in a sufficient amount of water (94 grams) to wet the TiO$_2$/SiO$_2$ support (140 grams) The catalyst was dried at a temperature of 100° C. for a period of 1 hour and then calcined at a temperature of 400° C. for a period of 16 hours.

Catalyst QQ Preparation: Sodium metatungstate (2.86 grams) was dissolved in sufficient water (88.4 grams) to wet the TiO$_2$/SiO$_2$ support (140 grams). After an impregnation period of 1 hour at room temperature, the catalyst was dried at a temperature of 100° C. for a period of 1 hour and then calcined at a temperature of 400° C. for a period of 16 hours.

Catalyst RR Preparation: A solution of vanadium triisopropoxide (7.60) grams in toluene (76.85 grams) was prepared and added to the TiO$_2$/SiO$_2$ support (140 grams) in a round bottom flask on a Buchi evaporator. After mixing for a period of 1 hour, excess toluene was removed under reduced pressure and the catalyst was calcined at a temperature of 400° C. for a period of 16 hours.

Catalyst SS Preparation: Sodium vanadate (21 grams) was dissolved in water (84.3 grams). A small amount (2.55 grams) did not dissolve and this was removed by filtration. The solution was poured over the TiO$_2$/SiO$_2$ support with stirring. Excess liquid (14.85 grams) was removed and the catalyst was calcined at a temperature of 400° C. for a period of 16 hours.

Catalyst TT Preparation: Boric acid (2.97 grams), lanthanum nitrate (10.39 grams) and ammonium tungstate (6 13 grams) were dissolved in water (94 grams) and the TiO$_2$/SiO$_2$ support (140 grams) was impregnated with the solution. The catalyst was dried at a temperature of 100° C. for a period of 1 hour and then calcined at a temperature of 400° C. for a period of 16 hours.

Catalyst UU Preparation: Titanium isopropoxide (10 25 grams) was dissolved in toluene (45.44 grams). This solution was used to impregnate the ZrO$_2$/SiO$_2$ support (140 grams). Excess toluene was removed under reduced pressure. The catalyst was dried at a temperature of 100° C. for a period of 1 hour and then calcined at a temperature of 400° C. for a period of 16 hours.

Catalyst VV Preparation: Ammonium tunqstate (3.12 grams) was dissolved in a sufficient amount of water (63.24 grams) to wet the ZrO$_2$/SiO$_2$ support (140 grams). After impregnation for a period of 1 hour at room temperature, the catalyst was dried at a temperature of 100° C. for a period of 1 hour and then calcined at a temperature of 400° C. for a period of 16 hours.

Catalyst WW Preparation: Diammonium hydrogen phosphate (65 grams) was dissolved in water (50 grams) in a round bottom flask and anatase TiO$_2$ (150 cubic centimeters) was added to the flask. The flask was rotated on a Buchi rotary evaporator under reduced pressure for a period of 2 hours. The resulting slurry was filtered, washed with water (100 milliliters) and dried at a temperature of 100° C. for a period of 1 hour and then at a temperature of 250° C. for overnight.

Catalyst XX Preparation: Diammonium hydrogen phosphate (65 grams) was dissolved in water (50 grams) in a round bottom flask and rutile TiO$_2$ (150 cubic centimeters) was added to the flask. The flask was rotated on a Buchi rotary evaporator under reduced pressure for a period of 2 hours. The resulting slurry was filtered, washed with water (100 milliliters) and dried at a temperature of 100° C. for a period of 1 hour and then at a temperature of 250° C. for overnight.

Catalyst YY Preparation: Orthophosphoric acid (52 grams), water (50 grams) and TiO$_2$ (171.11 grams) were placed in a flask on a Buchi rotary evaporator at a pressure of 210 millimeters Hg for a period of 2 hours. The catalyst was filtered and washed with distilled water (2500 milliliters) to pH 6, dried at a temperature of 100° C. for a period of 1 hour and then at a temperature of 250° C. for a period of 16 hours. The resulting catalyst (171.11 grams) was slurried with phosphoric acid (52.37 grams) and water (50.05 grams) for a period of 2 hours on a Buchi rotary evaporator at a pressure of 310 mm Hg, filtered, washed with water (100 milliliters), evaporated dry and heated at a temperature of 100° C. for a period of 1 hour and then at a temperature of 250° C. for a period of 16 hours.

Catalyst ZZ Preparation: The TiO$_2$ support was used without further treatment.

Catalyst AAA Preparation: Obtained from Norton Company, Akron, Ohio.

Catalyst BBB Preparation: Boric acid (1.81 grams) was mixed in sufficient water to wet the TiO$_2$/SiO$_2$ support (100 grams). After an impregnation period of 1 hour, the catalyst was calcined at a temperature of 400° C. for a period of 16 hours.

Catalyst CCC Preparation: Ammonium vanadate (2.63 grams) was mixed in sufficient water to wet the TiO$_2$/SiO$_2$ support (140 grams). After an impregnation period of 1 hour at room temperature, the catalyst was calcined at a temperature of 400° C. for a period of 16 hours.

Catalyst DDD Preparation: Ammonium tetrafluoroborate (8.39 grams) and diammonium hydroqen phosphate (10.52 grams) were dissolved in sufficient water to wet the TiO$_2$/SiO$_2$ support (140 grams). After an impregnation period of 1 hour at room temperature, the catalyst was dried at a temperature of 100° C. for a period of 1 hour and then calcined at a temperature of 400° C. for a period of 16 hours.

Catalyst EEE Preparation: Sodium tetrafluoroborate (2.86 grams) was dissolved in sufficient water to wet the TiO$_2$/SiO$_2$ support (140 grams). After an impregnation period of 1 hour, the catalyst was calcined at a temperature of 400° C. for a period of 16 hours.

Catalyst FFF Preparation: Ammonium hydrogen tetraborate (4.18 grams) and diammonium hydrogen phosphate (10.52 grams) were dissolved in sufficient water to wet the TiO$_2$/SiO$_2$ support (140 grams). After an impregnation period of 1 hour at room temperature, the catalyst was dried at a temperature of 100° C. for a period of 8 hours and then calcined at a temperature of 400° C. for a period of 16 hours.

Catalyst GGG Preparation: Niobium pentoxide (13.67 grams) dissolved in toluene (approximately 200 milliliters) was used to wet the TiO$_2$/SiO$_2$ support (280 grams). After an impregnation period of 15 minutes at room temperature, toluene was removed under reduced pressure and the catalyst was dried at a temperature of 100° C. for a period of 8 hours and then calcined at a temperature of 400° C. for a period of 16 hours.

Catalyst HHH Preparation: Zirconium n-propoxide (7.59 grams) dissolved in toluene (62 grams) was used to wet the TiO$_2$/SiO$_2$ support (140 grams). After standing overnight under a cover at room temperature, the catalyst was stripped under reduced pressure and then calcined at a temperature of 400° C. for a period of 16 hours.

Catalyst III Preparation: Ferric nitrate 9H$_2$O (7.21 grams) was dissolved in sufficient water to wet the TiO$_2$/SiO$_2$ support (140 grams). After an impregnation period of 1 hour, the catalyst was calcined at a temperature of 400° C. for a period of 16 hours.

Catalyst JJJ Preparation: Tin (II) acetate (95%) (4.42 grams) was dissolved in sufficient water to wet the TiO$_2$/SiO$_2$ support (140 grams). After an impregnation period of 1 hour, the catalyst was calcined at a temperature of 400° C. for a period of 16 hours.

Catalyst KKK Preparation: Ammonium hydroqen borate (2.53 grams) and ammonium vanadate (5.62 grams) were dissolved at a temperature of 75° C. in excess water to wet the TiO$_2$/SiO$_2$ support (140 grams). The excess water was then evaporated. After an impregnation period of 1 hour, the catalyst was calcined at a temperature of 400° C. for a period of 16 hours.

Catalyst LLL Preparation: Sodium bicarbonate (4.15 grams) was dissolved in sufficient water to wet the TiO$_2$/SiO$_2$ support (100 grams). After an impregnation period of 1 hour at room temperature, the catalyst was calcined at a temperature of 400° C. for a period of 16 hours.

Catalyst MMM Preparation: Zinc nitrate hexahydrate (10 44 grams) was dissolved in sufficient water to wet the TiO$_2$/SiO$_2$ support (140 grams). After an impregnation period of 1 hour at room temperature, the catalyst was calcined at a temperature of 400° C. for a period of 16 hours.

Catalyst NNN Preparation: Lanthanum nitrate hexahydrate (3.79 grams) was dissolved in sufficient water to wet the TiO$_2$/SiO$_2$ support (140 grams). After an impregnation period of 1 hour at room temperature, the catalyst was calcined at a temperature of 400° C. for a period of 16 hours.

Catalyst OOO Preparation: Lithium acetate dihydrate (9.74 grams) was dissolved in sufficient water to wet the TiO$_2$/SiO$_2$ support (140 grams). After an impregnation period of 1 hour at room temperature, the catalyst was calcined at a temperature of 400° C. for a period of 16 hours.

Catalyst PPP Preparation: Obtained from Norton Company, Akron, Ohio.

Catalyst QQQ Preparation: Sodium bicarbonate (4.15 grams) was dissolved in sufficient water to wet the TiO$_2$/Al$_2$O$_3$ support (100 rams). After an impregnation period of 1 hour at room temperature, the catalyst was calcined at a temperature of 400° C. for a period of 16 hours.

Catalyst RRR Preparation: Lanthanum nitrate hexahydrate (3.79 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst SSS Preparation: Lanthanum nitrate hexahydrate (4.29 grams) was dissolved in sufficient water to wet the TiO$_2$/Al$_2$O$_3$ support (160 grams). After an impregnation period of 1 hour at room temperature, the catalyst was calcined at a temperature of 400° C. for a period of 16 hours. This material (140 grams) was slurried with 85% phosphoric acid (90 milliliters) for a period of 1 hour, filtered, washed with water until pH of 6.5 and then calcined at a temperature of 400° C. for a period of 16 hours.

Catalyst TTT Preparation: Magnesium nitrate hexahydrate (18.17 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst UUU Preparation: Lithium acetate dihydrate (9.74 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst VVV Preparation: Sodium tetrafluoroborate (2.86 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst WWW Preparation: Strontium nitrate (5.84 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst XXX Preparation: Boric acid (1.81 grams) was dissolved in sufficient water to wet the TiO$_2$/Al$_2$O$_3$ support (100 grams). After an impregnation period of 1 hour at room temperature, the catalyst was calcined at a temperature of 400° C. for a period of 16 hours.

Catalyst YYY Preparation: Zinc nitrate hexahydrate (10.44 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst ZZZ Preparation: Stannous acetate (95%) (4.42 grams) was dissolved in hot monoethanolamine, diluted with isopropanol (30 grams) and slurried with the TiO$_2$/Al$_2$O$_3$ support (140 grams). After an impregnation period of 1 hour at room temperature, the catalyst was dried at a temperature of 100° C. for a period of 1 hour. Excess liquid was then drained off. The catalyst was washed with isopropanol and then calcined at a temperature of 400° C. for a period of 16 hours.

Catalyst AAAA Preparation: Ferric nitrate 9H$_2$O (7.21 grams) was dissolved in sufficient water to wet the TiO$_2$/Al$_2$O$_3$ support (140 grams). After an impregnation period of 1 hour at room temperature, the catalyst was calcined at a temperature of 400° C. for a period of 16 hours.

Catalyst BBBB: Obtained from Norton Company, Akron, Ohio.

Catalyst CCCC: Obtained from Norton Company, Akron, Ohio.

Catalyst DDDD: Obtained from Norton Company, Akron, Ohio.

Catalyst EEEE: Obtained from Norton Company, Akron, Ohio.

Catalyst FFFF: Catalyst DDDD pellets (140 grams) were added to a solution of boric acid (5.07 grams) in methanol (94.2 grams). The methanol was removed using a Buchi rotary evaporator. The catalyst was dried at a temperature of 100° C. for a period of 1 hour and then calcined at a temperature of 400° C. for a period of 16 hours.

Catalyst GGGG: Catalyst DDDD pellets (140 grams) were added to a solution of ammonium tetrafluoroborate (2.86 grams) in water. Enough solution was prepared to completely wet the pellets. The resulting slurry was allowed to stand for a period of 1 hour at room temperature. The catalyst was dried at a temperature of 100° C. for a period of 1 hour and then calcined at a temperature of 400° C. for a period of 16 hours.

Catalyst HHHH: Catalyst DDDD pellets (140.1 grams) were added to a solution of sodium tetrafluoroborate (8.58 grams) in sufficient water to completely wet the pellets. The catalyst was dried at a temperature of 100° C. for a period of 1 hour and then calcined at a temperature of 400° C. for a period of 16 hours.

Catalyst IIII: Catalyst DDDD pellets (140.1 grams) were added to a solution of sodium tetrafluoroborate (8.58 grams) in sufficient water to completely wet the pellets. The catalyst was dried at a temperature of 100° C. for a period of 1 hour and then calcined at a temperature of 400° C. for a period of 16 hours.

Catalyst JJJJ: Catalyst DDDD pellets (140.2 grams) were added to a solution of sodium metatungstate (1.43 grams) in sufficient water to completely wet the pellets. The catalyst was dried at a temperature of 100° C. for a period of 1 hour and then calcined at a temperature of 400° C. for a period of 16 hours.

Catalyst KKKK: Catalyst DDDD pellets (140.2 grams) were added to a solution of sodium metatungstate (2.86 grams) in sufficient water to completely wet the pellets. The catalyst was dried at a temperature of 100° C. for a period of 1 hour and then calcined at a temperature of 400° C. for a period of 16 hours.

Catalyst LLLL: Catalyst DDDD pellets (140.1 grams) were added to a solution of sodium metatungstate (5.71 grams) in sufficient water to completely wet the pellets. The catalyst was dried at a temperature of 100° C. for a period of 1 hour and then calcined at a temperature of 400° C. for a period of 16 hours.

Catalyst MMMM: Catalyst DDDD pellets (140.1 grams) were added to a solution of ammonium metatungstate (3 12 grams) in sufficient water to completely wet the pellets. The catalyst was dried at a temperature of 100° C. for a period of 1 hour and then calcined at a temperature of 400° C. for a period of 16 hours.

Catalyst NNNN: Catalyst DDDD pellets (140 grams) were added to a solution of ammonium metatungstate (6.24 grams) in sufficient water to completely wet the pellets. The catalyst was dried at a temperature of 100° C. for a period of 1 hour and then calcined at a temperature of 400° C. for a period of 16 hours.

Catalyst OOOO: Catalyst DDDD pellets (140.1 grams) were added to a solution of ammonium metatungstate (12.48 grams) in sufficient water to completely wet the pellets. The catalyst was dried at a temperature of 100° C. for a period of 1 hour and then calcined at a temperature of 400° C. for a period of 16 hours.

Catalyst PPPP: Catalyst DDDD pellets (140.1 grams) were added to a solution of lanthanum nitrate hexahydrate (7.59 grams) in sufficient water to completely wet the pellets. The catalyst was dried at a temperature of 100° C. for a period of 1 hour and then calcined at a temperature of 400° C. for a period of 16 hours.

Catalyst QQQQ: Catalyst DDDD pellets (143.1 grams) were added to a solution of lanthanum nitrate hexahydrate (15.18 grams) in sufficient water to completely wet the pellets. The catalyst was dried at a temperature of 100° C. for a period of 1 hour and then calcined at a temperature of 400° C. for a period of 16 hours.

Catalyst RRRR: Catalyst DDDD pellets (140 grams) were added to a solution of niobium pentethoxide (6.84 grams) in toluene (66 grams). Enough solution was added to completely immerse the pellets. The resulting slurry was stripped on a Buchi rotary evaporator The catalyst was then calcined at a temperature of 400° C. for a period of 16 hours.

Catalyst SSSS: Catalyst DDDD pellets (140.4 grams) were added to a solution of sodium bicarbonate (3.87 grams) in sufficient water to completely wet the pellets. The catalyst was dried at a temperature of 100° C. for a period of 1 hour and then calcined at a temperature of 400° C. for a period of 16 hours.

Catalyst TTTT: Catalyst DDDD pellets (143.5 grams) were added to a solution of vanadium triisopropoxide (7.63 grams) in toluene (66.74 grams). Enough solution was added to completely wet the pellets. The resulting slurry was stripped under reduced pressure. The catalyst was then calcined at a temperature of 400° C. for a period of 16 hours.

Catalyst UUUU: Sodium trimetaphosphate (14.0 grams) was dissolved in a sufficient amount of water (82.7 grams) to wet the $TiO_2/SiO_2/Al_2O_3$ support (140 grams). After impregnation for a period of 1 hour at room temperature, the catalyst was dried at a temperature of 100° C. for a period of 1 hour and then calcined at a temperature of 400° C. for a period of 16 hours.

Catalyst VVVV: Sodium trimetaphosphate (14.13 grams) were dissolved in water (56.0 grams) and isopropanol (87.0 grams). The $TiO_2/SiO_2$ support (140 grams) was impregnated with the solution. The catalyst was dried at a temperature of 100° C. for a period of 1 hour and then calcined at a temperature of 400° C. for a period of 16 hours.

Catalyst WWWW: Sodium trimetaphosphate (14.05 grams) was dissolved in a sufficient amount of water (85.92 grams) to wet the $TiO_2/SiO_2$ support (140 grams). After impregnation for a period of 1 hour at room temperature, the catalyst was dried at a temperature of 100° C. for a period of 1 hour and then calcined at a temperature of 400° C for a period of 16 hours.

Catalyst XXXX: Obtained from Norton Company, Akron, Ohio.

Catalyst YYYY: Obtained from Norton Company, Akron, Ohio.

Catalyst ZZZZ: Obtained from Norton Company, Akron, Ohio.

Catalyst AAAAA: Obtained from Norton Company, Akron, Oh.:o.

Catalyst BBBBB: Obtained from Norton Company, Akron, Ohio.

Catalyst CCCCC: Obtained from Norton Company, Akron, Ohio.

Catalyst DDDDD: Catalyst DDDD pellets (140.5 grams) were added to a solution of zinc nitrate hexahydrate (10.45 grams) in sufficient water to completely wet the pellets. The catalyst was dried at a temperature of 100° C. for a period of 1 hour and then calcined at a temperature of 400° C. for a period of 16 hours.

Catalyst EEEEE: Catalyst DDDD pellets (140.78 grams) were added to a solution of zinc nitrate hexahydrate (20.88 grams) in sufficient water to completely wet the pellets The catalyst was dried at a temperature of 100° C. for a period of 1 hour and then calcined at a temperature of 400° C. for a period of 16 hours.

Catalyst FFFFF: Catalyst DDDD pellets (140.1 grams) were added to a solution of niobium pentethoxide (13.68 grams) in toluene (66.2 grams). Enough solution was added to completely wet the pellets. The resulting slurry was allowed to stand for a period of 1 hour. The catalyst was dried at a temperature of 100° C. for a period of 1 hour and then calcined at a temperature of 400° C. for a period of 16 hours.

Catalyst GGGGG: Catalyst DDDD pellets (140.15 grams) were added to a solution of sodium tetrafluoroborate (8.58 grams) in sufficient water to completely wet the pellets. The catalyst was dried at a temperature of 100° C. for a period of 1 hour and then calcined at a temperature of 400° C. for a period of 16 hours.

Catalyst HHHHH: Obtained from Norton Company, Akron, Ohio.

Catalyst IIIII: Obtained from Norton Company, Akron, Ohio.

Catalyst JJJJJ: Obtained from Norton Company, Akron, Ohio.

Catalyst KKKKK: Obtained from Norton Company, Akron, Ohio.

Catalyst LLLLL Preparation: Ammonium metatungstate (12.14 grams) was dissolved in water (60 grams) and an aliquot sufficient to wet the $TiO_2$ support (140 grams) was used. After wetting, the catalyst was calcined at a temperature of 350° C. for a period of 1 hour. The impregnation and calcination steps were repeated twice more to give the catalyst.

Catalyst MMMMM Preparation: Ammonium metatungstate (12.14 grams) was dissolved in water (48 grams) and an aliquot sufficient to wet the $TiO_2/SiO_2$ support (55 grams) was used. After wetting, the catalyst was calcined at a temperature of 350° C. for a period of 1 hour. The impregnation and calcination steps were repeated twice more to give the catalyst.

Catalyst NNNNN Preparation: Ammonium metatungstate (12.14 grams) was dissolved in water (48 grams) and an aliquot sufficient to wet the $ZrO_2/SiO_2$ support (55 grams) was used. After wetting, the catalyst was calcined at a temperature of 350° C. for a period of 1 hour. The impregnation and calcination steps were repeated twice more to give the catalyst.

Catalyst OOOOO Preparation: Ammonium metatungstate (6.07 grams) was dissolved in water (45 grams) and an aliquot sufficient to wet the $TiO_2/SiO_2$ support (55 grams) was used. After wetting, the catalyst was calcined at a temperature of 350° C. for a period of 1 hour. The impregnation and calcination steps were repeated twice more to give the catalyst.

Catalyst PPPPP Preparation: Ammonium metatungstate (12.14 grams) and lanthanum nitrate (5.0 grams) were dissolved in water (45 grams) and an aliquot sufficient to wet the $TiO_2/SiO_2$ support (55 grams) was used. After wetting, the catalyst was calcined at a temperature of 350° C. for a period of 1 hour. The impregnation and calcination steps were repeated twice more to give the catalyst.

Catalyst QQQQQ Preparation: Ammonium metatungstate (6.07 grams) and lanthanum nitrate (2.5 grams) were dissolved in water (45 grams) and an aliquot sufficient to wet the TiO$_2$/SiO$_2$ support (55 grams) was used. After wetting, the catalyst was calcined at a temperature of 350° C. for a period of 1 hour. The impregnation and calcination steps were repeated twice more to give the catalyst.

Catalyst RRRRR Preparation: Ammonium metatungstate (12.14 grams) and lanthanum nitrate (5.0 grams) were dissolved in water (45 grams) and an aliquot sufficient to wet the ZrO$_2$/SiO$_2$ support (55 grams) was used. After wetting, the catalyst was calcined at a temperature of 350° C. for a period of 1 hour. The impregnation and calcination steps were repeated twice more to give the catalyst.

Catalyst SSSSS Preparation: Obtained from Norton Company, Akron, Ohio.

Catalyst TTTTT Preparation: Ammonium metatungstate (6.07 grams) was dissolved in water (35 grams) and an aliquot sufficient to wet the TiO$_2$/SiO$_2$/WO$_3$ support (55 grams) was used. After wetting, the catalyst was calcined at a temperature of 350° C. for a period of 1 hour. The impregnation and calcination steps were repeated twice more to give the catalyst.

Catalyst UUUUU Preparation: Silicotungstic acid (6 8 grams) was dissolved in water (40 grams) and an aliquot sufficient to wet the TiO$_2$/SiO$_2$ support (55 grams) was used. After wetting, the catalyst was calcined at a temperature of 350° C. for a period of 1 hour. The impregnation and calcination steps were repeated twice more to give the catalyst.

Catalyst VVVVV Preparation: Ammonium metatungstate (6.07 grams) was dissolved in water (40 grams) and an aliquot sufficient to wet the TiO$_2$/SiO$_2$/Al$_2$O$_3$ support (55 grams) was used. After wetting, the catalyst was calcined at a temperature of 350° C. for a period of 1 hour. The impregnation and calcination steps were repeated twice more to give the catalyst.

Catalyst WWWWW Preparation: Ammonium metatungstate (6.07 grams) was dissolved in water (40 grams) and an aliquot sufficient to wet the TiO$_2$/Al$_2$O$_3$/SiO$_2$ support was used. After wetting, the catalyst was calcined at a temperature of 350° C. for a period of 1 hour. The impregnation and calcination steps were repeated twice more to give the catalyst.

Catalyst XXXXX Preparation: Ammonium metatungstate (6.07 grams) was dissolved in water (40 grams) and an aliquot sufficient to wet the TiO$_2$/SiO$_2$ support (55 grams) was used. After wetting, the catalyst was calcined at a temperature of 350° C. for a period of 1 hour. The impregnation and calcination steps were repeated twice more to give the catalyst.

Catalyst YYYYY Preparation: Obtained from LaRoche Chemical Company, Cleveland, Ohio.

Catalyst ZZZZZ Preparation: Obtained from Norton Company, Akron, Ohio.

Catalyst AAAAAA Preparation: Obtained from Norton Company, Akron, Ohio.

Catalyst BBBBBB Preparation: Obtained from Norton Company, Akron, Ohio.

Catalyst CCCCCC Preparation: Ammonium metatungstate (11.42 grams) was dissolved in water (45 grams) and an aliquot sufficient to wet the γ-Al$_2$O$_3$ support (52 grams) was used. After wetting, the catalyst was calcined at a temperature of 350° C. for a period of 1 hour. The impregnation and calcination steps were repeated twice more to give the catalyst.

Catalyst DDDDDD Preparation: Ammonium metatungstate (6.07 grams) was dissolved in water (40 grams) and an aliquot sufficient to wet the TiO$_2$/SiO$_2$ support (55 grams) was used. After wetting, the catalyst was calcined at a temperature of 350° C. for a period of 1 hour. The impregnation and calcination steps were repeated twice more to give the catalyst.

Catalyst EEEEEE Preparation: Obtained from Norton Company, Akron, Ohio.

Catalyst FFFFFF Preparation: Ammonium metatungstate (6.07 grams) and boric acid (3.14 grams) were dissolved in water (30 grams) and an aliquot sufficient to wet the TiO$_2$/SiO$_2$ support (55 grams) was used. After wetting, the catalyst was calcined at a temperature of 350° C. for a period of 1 hour The impregnation and calcination steps were repeated twice more to give the catalyst.

Catalyst GGGGGG Preparation: Ammonium metatungstate (6.07 grams) and zinc nitrate (1.6 grams) were dissolved in water (30 grams) and an aliquot sufficient to wet the TiO$_2$/SiO$_2$ support (55 grams) was used. After wetting, the catalyst was calcined at a temperature of 350° C. for a period of 1 hour. The impregnation and calcination steps were repeated twice more to give the catalyst.

Catalyst HHHHHH Preparation: Ammonium metatungstate (6.07 grams) and thorium nitrate (1.31 grams) were dissolved in water (35 grams) and an aliquot sufficient to wet the TiO$_2$/SiO$_2$ support (55 grams) was used. After wetting, the catalyst was calcined at a temperature of 350° C. for a period of 1 hour. The impregnation and calcination steps were repeated twice more to give the catalyst.

Catalyst IIIIII Preparation: Ammonium metatungstate (6.07 grams) and ammonium bifluoride (0.82 grams) were dissolved in water (35 grams) and an aliquot sufficient to wet the TiO$_2$/SiO$_2$ support (55 grams) was used. After wetting, the catalyst was calcined at a temperature of 350°C. for a period of 1 hour. The impregnation and calcination steps were repeated twice more to give the catalyst.

Catalyst JJJJJJ Preparation: Ammonium metatungstate (6.07 grams) and cerium nitrate (1.71 grams) were dissolved in water (35 grams) and an aliquot sufficient to wet the TiO$_2$/SiO$_2$ support (55 grams) was used. After wetting, the catalyst was calcined at a temperature of 350° C. for a period of 1 hour. The impregnation and calcination steps were repeated twice more to give the catalyst.

Catalyst KKKKKK Preparation: Obtained from Norton Company, Akron, Ohio.

Catalyst LLLLLL Preparation: Obtained from Norton Company, Akron, Ohio.

Catalyst MMMMMM Preparation: Obtained from Norton Company, Akron, Ohio.

TABLE I

| Example No. | 1 | 2 | 3 | 4 | 5 | 6 | 7 | 8 | 9 |
|---|---|---|---|---|---|---|---|---|---|
| Catalyst Type | A | A | A | A | A | A | A | A | A |
| TEMP., °C.; ave. | 228 | 241 | 290 | 294 | 268 | 242 | 247 | 295 | 270 |

TABLE I-continued

| PRES., psia | 1172.7 | 1214.7 | 1214.7 | 1214.7 | 914.7 | 1214.7 | 1214.7 | 414.7 | 614.7 |
|---|---|---|---|---|---|---|---|---|---|
| AEEA SV;M/kg cat/hr. | 1.61 | 1.44 | 1.5 | 1.56 | 0.9 | 0.57 | 0.69 | 1.18 | 2.21 |
| EDA/AEEA Mole Ratio | 1.5 | 1.5 | 2 | 2 | 5 | 8 | 8 | 2 | 0.8 |
| NH₃/AEEA Mole Ratio | 24.2 | 45.83 | 34.9 | 36.33 | 55.94 | 107.9 | 91.22 | 66.88 | 30.36 |
| H₂O/AEEA Mole Ratio | 0.86 | 0.86 | 0.66 | 1.38 | 1.18 | 3.61 | 3.61 | 0.66 | 0.44 |
| Wt % H₂O | 7.4 | 7.4 | 5 | 10 | 5 | 10 | 10 | 5 | 5 |
| % Conversion AEEA | 70.4 | 73.2 | 97 | 61.8 | 97.3 | 43.3 | 23.3 | 98.6 | 27 |
| ANALYTICAL, area % | | | | | | | | | |
| EDA | 62.81 | 65.97 | 60.95 | 62.65 | 77.39 | 87.72 | 84.11 | 60.49 | 43.42 |
| MEA | 0.92 | 0.41 | 0.12 | 0.13 | 0 | 0 | 0 | 0 | 0 |
| PIP | 5.52 | 5.84 | 9.66 | 6.36 | 5.23 | 0.68 | 0.64 | 11.37 | 3.72 |
| DETA | 2.33 | 2.58 | 3.68 | 1.24 | 3.49 | 0 | 0.13 | 4.03 | 0 |
| AEEA | 15.51 | 14.19 | 1.36 | 17.33 | 0.7 | 9.96 | 13.57 | 0.63 | 49.49 |
| AEP | 0.89 | 1.03 | 2.13 | 0.35 | 2.49 | 0.06 | 0.05 | 3.82 | 0.06 |
| HEP | 0.17 | 0.13 | 0.1 | 0.14 | 0.04 | 0 | 0.01 | 0.1 | 0.06 |
| TETA | 5.1 | 4.45 | 4.47 | 1.78 | 4.64 | 0.40 | 0.46 | 3.36 | 0.20 |
| DAEP | 1.70 | 1.77 | 4.42 | 3.10 | 2.00 | 0.16 | 0.16 | 5.78 | 1.52 |
| PEEDA | 1.99 | 2.11 | 5.00 | 3.02 | 2.15 | 0.12 | 0.10 | 5.09 | 1.01 |
| DPE | 0 | 0.56 | 0.14 | 0.19 | 0.07 | 0 | 0 | 0.32 | — |
| Total TETAS | 8.79 | 8.38 | 14.02 | 8.08 | 8.91 | 0.68 | 0.71 | 14.26 | 2.72 |
| Total TEPAS | 0.87 | 0.77 | 2.01 | 0.29 | 0.96 | 0.22 | 0.14 | 1.62 | 0.04 |
| Total Byproducts | 2.18 | 0.72 | 5.98 | 3.43 | 0.79 | 0.68 | 0.64 | 3.67 | 0.49 |
| % Water | 16.68 | 21.18 | 13.75 | 13.94 | 10.66 | 12 | 9.97 | 17.34 | 12.18 |

| Example No. | 10 | 11 | 12 | 13 | 14 |
|---|---|---|---|---|---|
| Catalyst Type | F | G | D | D | B |
| Temp. °C. | 172 | 178 | 258 | 261 | 284 |
| Press. psig | 614 | 614.7 | 614.7 | 614.7 | 614.7 |
| Space velocity gmol/kg-cat/hr | 2.2 | 2.4 | 2.2 | 3.3 | 2 |
| Feed Comp. | EDA/AEEA/NH₃ | EDA/AEEA/NH₃ | EDA/AEEA/NH₃ | DETA/MEA/NH₃ | DETA/MEA/NH₃ |
| Feed Mole Ratio | 2/1/37 | 2/1/12.5 | 2/1/10.8 | 2/1/11.9 | 2/1/10.7 |
| % water; feed | 5 | 0 | 5 | 5 | 5 |
| % Conv. | 40.4 | 40.7 | 41.5 | 34.5(DETA) | 66.7 |
| Rₓ Outlet Comp. Area % GG | | | | | |
| EDA | 32.94 | 46.98 | 39.1 | 1.63 | 1.45 |
| MEA | 0.38 | 0 | 0.66 | 24.16 | 7.75 |
| PIP | 0.03 | 0 | 8.95 | 0.93 | 0.77 |
| DETA | 8.03 | 24.37 | 1.3 | 50.93 | 75.48 |
| AEEA | 57.53 | 27.91 | 27.01 | 2.22 | 0.19 |
| AEP | 0.98 | 0.72 | 0.85 | 7.76 | 1.54 |
| nc-TETA[2] | 0.02 | 0 | 7.96 | | |
| nc-TETA | | | | 8.21 | 9.67 |
| c-TETA[3] | | 0 | 6.68 | | |
| c-TETA | | | | 0.89 | 0.55 |
| TEPA's | 0.02 | 0 | 1.73 | 1.88 | 1.13 |
| HPA/UNKNOWNS | 0.06 | 0.02 | 5.55 | 1.35 | 1.45 |

| Example No. | 15 | 16 | 17 | 18 | 19 |
|---|---|---|---|---|---|
| Catalyst Type | H | E | E | C | C |
| Temp. °C. | 180 | 268 | 266 | 257 | 279 |
| Press. psig | 614.7 | 614.7 | 614.7 | 614.7 | 614.7 |
| Space velocity gmol/kg-cat/hr | 3.3 | 2.4 | 2.1 | 2.4 | 2.3 |
| Feed Comp. | EDA/AEEA/NH₃ | EDA/AEEA/NH₃ | DETA/MEA/NH₃ | DETA/MEA/NH₃ | DETA/MEA/NH₃ |
| Feed Mole Ratio | 2/1/9.5 | 2/1/18.5 | 2/1/16.2 | 2/1/11.7 | 2/1/13.2 |
| % water; feed | 0 | 0 | 0 | 0 | 0 |
| % Conv. | 23.5 | 96.2 | 42.9 | 45.3 | 75 |
| Rₓ Outlet Comp. Area % GG | | | | | |
| EDA | 58.46 | 43.41 | 2.32 | .56 | 1.02 |
| MEA | 0.03 | 0.14 | 13.14 | 12.7 | 5.71 |
| PIP | 0.05 | 16.67 | 2.28 | 0.47 | 1.32 |
| DETA | 6.12 | 5.16 | 42.38 | 80.17 | 78.73 |
| AEEA | 35.27 | 1.74 | 0.96 | 0.35 | 0 |
| AEP | 0 | 2.17 | 8.87 | 0.84 | 1.77 |
| nc-TETA[2] | 0 | 8.3 | 14.84 | 3.95 | 6.43 |
| c-TETA[3] | 0 | 12.17 | 3.46 | 0.17 | 0.55 |
| TEPA's | 0 | 2.61 | 7.08 | 0.34 | 0.93 |
| HPA/UNKNOWNS | 0.07 | 7.55 | 4.48 | 0.4 | 3.04 |

| Example No. | 20 | 21 | 22 |
|---|---|---|---|
| Catalyst Type | B | I | C |
| Temp. °C. | 259 | 179 | 274 |
| Press. psig | 614.7 | 614.7 | 614.7 |
| Space velocity | 2.1 | 2.4 | 4.7 |

TABLE I-continued

| gmol/kg-cat/hr Feed Comp. | EDA/AEEA/NH$_3$ | EDA/AEEA/NH$_3$ | EDA/MEA/NH$_3$ |
|---|---|---|---|
| Feed Mole Ratio | 2/1/10.0 | 2/1/11.1 | 1/1/5.3 |
| % water; feed | 5 | 0 | 0 |
| % Conv. | 21.8 | 42.3 | 42 |
| R$_x$ Outlet Comp. Area % GG | | | |
| EDA | 44.38 | 61.7 | 56.03 |
| MEA | 0 | 0 | 29.12 |
| PIP | 2.25 | 0 | 1.83 |
| DETA | 8.92 | 10.43 | 4.58 |
| AEEA | 37.01 | 25.84 | 1.44 |
| AEP | 0.21 | 0.5 | 1.92 |
| nc-TETA[2] | 5.64 | | |
| nc-TETA | | 0 | 1.00 |
| c-TETA[3] | 0.58 | | |
| c-TETA | | 0 | 0.99 |
| TEPA's | 0.45 | 0 | 0.53 |
| HPA/UNKNOWNS | 0.47 | 1.53 | 2.54 |

[2] nc = noncyclics
[3] c = cyclics

TABLE II

| Example No. | 23 | 24 | 25 | 26 | 27 | 28 | 29 | 30 | 31 |
|---|---|---|---|---|---|---|---|---|---|
| Catalyst Type | J | J | J | J | J | J | J | J | J |
| Catalyst weight, gm | 81.0 | 81.0 | 81.0 | 81.0 | 81.0 | 81.0 | 81.0 | 81.0 | 81.0 |
| Pressure, psig | 600 | 600 | 600 | 600 | 600 | 600 | 600 | 600 | 600 |
| Temperature, °C. | 269.7 | 269.5 | 280.7 | 260.2 | 270.9 | 258.8 | 279.7 | 268.7 | 268.9 |
| Time on organics, hrs. | 25.0 | 27.0 | 30.0 | 47.5 | 53.0 | 72.5 | 78.5 | 96.0 | 104.0 |
| Duration of run, hrs. | 2 | 2 | 2 | 2 | 2 | 2 | 2 | 2 | 2 |
| MEA SV, gmol/hr/kgcat | 4.65 | 4.99 | 5.19 | 4.45 | 4.75 | 3.91 | 4.36 | 4.43 | 4.87 |
| NH$_3$ feedrate, gm/hr | 40.6 | 43.8 | 46.3 | 36.7 | 38.6 | 30.9 | 35.8 | 38.5 | 42.3 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.06 | 0.96 | 1.65 | 0.58 | 0.93 | 0.44 | 1.29 | 0.76 | 0.71 |
| MeEDA | 0 | 0 | 0 | 0 | 0 | 0 | 0 | 0 | 0 |
| MEA | 27.97 | 29.69 | 25.97 | 33.84 | 31.26 | 33.34 | 25.75 | 31.85 | 32.53 |
| EtEDA | 0 | 0 | 0 | 0 | 0 | 0 | 0 | 0 | 0 |
| PIP | 0.41 | 0.35 | 0.65 | 0.13 | 0.26 | 0.09 | 0.38 | 0.15 | 0.12 |
| DETA | 48.20 | 49.21 | 45.95 | 52.63 | 51.53 | 56.05 | 49.30 | 52.04 | 53.16 |
| AEEA | 3.81 | 4.35 | 3.82 | 3.19 | 4.30 | 2.48 | 4.17 | 3.47 | 3.39 |
| AEP | 0.47 | 0.36 | 0.67 | 0.22 | 0.30 | 0.17 | 0.47 | 0.26 | 0.25 |
| HEP | 0 | 0 | 0 | 0 | 0 | 0 | 0 | 0 | 0 |
| TETA's | 10.10 | 8.61 | 10.77 | 5.04 | 7.01 | 3.88 | 9.98 | 5.75 | 4.72 |
| TEPA's | 3.39 | 1.88 | 3.55 | 0.11 | 0.82 | 0 | 2.63 | 0.63 | 0.44 |
| MEA Conversion % | 22.93 | 17.73 | 26.84 | 5.52 | 13.89 | 7.65 | 28.09 | 10.64 | 8.96 |
| Acyclic (N4)/cyclic (< = N4), weight ratio | 43.8 | 46.8 | 41.4 | 100 | 119 | AL | 32.1 | 80.5 | AL |
| Acyclic (N5)/cyclic (< = N5), weight ratio | 19.5 | AL | AL | — | AL | 0.2 | AC | | |
| Σ(N5)/Σ(N4), weight ratio | 0.26 | 0.17 | 0.25 | 0.02 | 0.09 | 0 | 0.20 | 0.08 | 0.07 |

AL = All linear
AC = All cyclic

TABLE III

| Example No. | 32 | 33 | 34 | 35 | 36 | 37 | 38 | 39 | 40 | 41 | 42 | 43 |
|---|---|---|---|---|---|---|---|---|---|---|---|---|
| Catalyst Type | K | K | K | K | K | K | K | K | K | K | K | K |
| Catalyst weight, gm | 69.8 | 69.8 | 69.8 | 69.8 | 69.8 | 69.8 | 69.8 | 69.8 | 69.8 | 69.8 | 69.8 | 69.8 |
| Pressure, psig | 600 | 600 | 600 | 600 | 600 | 600 | 600 | 600 | 600 | 600 | 600 | 600 |
| Temperature, °C. | 269.0 | 269.9 | 270.1 | 269.8 | 280.3 | 280.8 | 260.0 | 270.4 | 260.6 | 280.7 | 270.0 | 270.5 |
| Time on organics, hrs. | 7.0 | 25.0 | 28.2 | 27.0 | 32.0 | 30.0 | 51.0 | 55.5 | 76.0 | 80.0 | 98.0 | 100.0 |
| Duration of run, hrs. | 2 | 2 | 2.2 | 2 | 2 | 2 | 2 | 2 | 1 | 1 | 2 | 2 |
| MEA SV, gmol/hr/kgcat | 6.58 | 4.13 | 5.83 | 4.39 | 6.7 | 3.45 | 5.23 | 1.85 | 5.05 | 5.44 | 5.46 | 5.60 |
| NH$_3$ feedrate, gm/hr | 57.2 | 38.4 | 52.1 | 41.1 | 48.5 | 32.7 | 40.3 | 15.1 | 19.8 | 21.6 | 44.6 | 46.2 |
| Liquid feed composition, wt. % | | | | | | | | | | | | |
| DETA | 62.81 | 62.81 | 62.81 | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 | 37.19 | 37.19 | 37.19 |
| Liquid product composition, wt. % | | | | | | | | | | | | |
| EDA | 1.24 | 1.60 | 0.95 | 1.21 | 1.43 | 1.80 | 0.74 | 0.74 | 0.74 | 1.34 | 0.74 | 0.87 |
| MeEDA | 0 | 0 | 0 | 0 | 0 | 0 | 0 | 0 | 0 | 0 | 0 | 0 |
| MEA | 19.67 | 22.54 | 26.20 | 25.34 | 19.49 | 20.13 | 29.73 | 29.73 | 29.73 | 23.12 | 28.77 | 29.57 |

TABLE III-continued

| Example No. | 32 | 33 | 34 | 35 | 36 | 37 | 38 | 39 | 40 | 41 | 42 | 43 |
|---|---|---|---|---|---|---|---|---|---|---|---|---|
| EtEDA | 0 | 0 | 0 | 0 | 0 | 0 | 0 | 0 | 0 | 0 | 0 | 0 |
| PIP | 0.65 | 1.03 | 0.53 | 0.72 | 0.93 | 1.19 | 0.38 | 0.38 | 0.38 | 0.86 | 0.40 | 0.44 |
| DETA | 55.44 | 45.02 | 50.44 | 47.30 | 46.80 | 44.02 | 51.65 | 51.65 | 51.65 | 48.33 | 52.65 | 50.62 |
| AEEA | 2.25 | 3.72 | 4.05 | 4.52 | 2.91 | 3.70 | 3.10 | 3.10 | 3.10 | 2.98 | 3.53 | 3.82 |
| AEP | 0.70 | 1.12 | 0.49 | 0.69 | 1.01 | 1.09 | 0.37 | 0.37 | 0.37 | 0.82 | 0.34 | 0.38 |
| HEP | 0 | 0 | 0 | 0 | 0 | 0 | 0 | 0 | 0 | 0 | 0 | 0 |
| TETA's | 9.65 | 11.96 | 9.66 | 10.63 | 12.87 | 13.06 | 6.39 | 6.39 | 6.39 | 11.07 | 7.31 | 6.58 |
| TEPA's | 4.85 | 6.85 | 2.52 | 3.79 | 7.21 | 6.64 | 1.70 | 1.70 | 1.70 | 5.04 | 0.69 | 1.22 |
| MEA Conversion % | 46.11 | 37.81 | 27.53 | 29.68 | 45.85 | 43.35 | 16.29 | 16.29 | 16.29 | 35.76 | 19.42 | 16.21 |
| Acyclic (N4)/cyclic (< = N4), weight ratio | 27.7 | 12.2 | 32.7 | 35.6 | 21.4 | 23.5 | 29.0 | 29.0 | 54.2 | 21.4 | 24.9 | 26.3 |
| Acyclic (N5)/cyclic (< = N5), weight ratio | 24.3 | 16.4 | AL | 42.8 | 14.0 | 17.2 | AL | AL | 1.0 | 22.0 | 1.2 | 4.0 |
| Σ(N5)/Σ(N4), weight ratio | 0.39 | 0.44 | 0.20 | 0.28 | 0.43 | 0.39 | 0.21 | 0.21 | 0.21 | 0.35 | 0.07 | 0.14 |

AL = All linear

TABLE IV

| Example No. | 44 | 45 | 46 | 47 | 48 | 49 | 50 | 51 | 52 |
|---|---|---|---|---|---|---|---|---|---|
| Catalyst Type | L | L | L | L | L | L | L | L | L |
| Catalyst weight, gm | 81.0 | 81.0 | 81.0 | 81.0 | 81.0 | 81.0 | 81.0 | 81.0 | 81.0 |
| Pressure, psig | 600 | 600 | 600 | 600 | 600 | 600 | 600 | 600 | 600 |
| Temperature, °C. | 270.0 | 280.0 | 260.0 | 270.0 | 261.1 | 281.0 | 270.0 | 271.1 | 280.8 |
| Time on organics, hrs. | 5.5 | 8.5 | 25.5 | 30.5 | 49.0 | 55.0 | 63.0 | 65.0 | 83.5 |
| Duration of run, hrs. | 1 | 2 | 2 | 2 | 2 | 2 | 2 | 2 | 2 |
| MEA SV, gmol/hr/kgcat | 4.82 | 2.44 | 5.36 | 5.37 | 5.39 | 5.95 | 5.42 | 5.82 | 5.02 |
| NH3 feedrate, gm/hr | 21.8 | 22.1 | 55.8 | 54.8 | 55.0 | 69.9 | 57.3 | 61.5 | 56.6 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 2.69 | 2.69 | 1.29 | 1.35 | 1.28 | 3.69 | 2.47 | 2.35 | 4.26 |
| MeEDA | 0 | 0 | 0 | 0 | 0 | 0 | 0 | 0 | 0 |
| MEA | 26.60 | 26.60 | 35.62 | 32.63 | 34.35 | 25.96 | 31.23 | 30.52 | 27.27 |
| EtEDA | 0 | 0 | 0 | 0 | 0 | 0 | 0 | 0 | 0 |
| PIP | 0.37 | 0.37 | 0.08 | 0.14 | 0.05 | 0.19 | 0.09 | 0.08 | 0.14 |
| DETA | 47.58 | 47.58 | 53.88 | 52.05 | 56.50 | 53.83 | 57.32 | 55.41 | 53.05 |
| AEEA | 2.60 | 2.60 | 1.47 | 1.73 | 1.17 | 1.43 | 1.35 | 1.26 | 1.21 |
| AEP | 0.43 | 0.43 | 0.20 | 0.26 | 0.19 | 0.38 | 0.27 | 0.27 | 0.44 |
| HEP | 0 | 0 | 0 | 0 | 0 | 0 | 0 | 0 | 0 |
| TETA's | 10.73 | 10.73 | 3.22 | 5.26 | 1.92 | 6.33 | 1.69 | 2.44 | 3.03 |
| TEPA's | 1.91 | 1.91 | 0 | 0.28 | 0 | 0.67 | 0 | 1.71 | 1.16 |
| MEA Conversion % | 24.56 | 24.56 | 0.03 | 6.94 | 3.40 | 25.65 | 11.47 | 13.43 | 19.76 |
| Acyclic (N4)/cyclic (< =N4), weight ratio | 151.7 | 21.9 | 14.4 | 19.4 | 7.9 | 25.5 | 3.0 | 5.5 | 4.7 |
| Acyclic (N5)/cyclic (< =N5), weight ratio | 4.0 | 7.9 | — | 2.1 | — | 1.2 | — | 1.4 | 1.6 |
| Σ(N5)/Σ(N4), weight ratio | 0.14 | 0.13 | 0 | 0.04 | 0 | 0.08 | 0 | 0.54 | 0.30 |

TABLE V

| Example No. | 53 | 54 | 55 | 56 | 57 | 58 | 59 | 60 | 61 |
|---|---|---|---|---|---|---|---|---|---|
| Catalyst Type | M | M | M | M | M | M | M | M | M |
| Catalyst weight, gm | 85.2 | 85.2 | 85.2 | 85.2 | 85.2 | 85.2 | 85.2 | 85.2 | 85.2 |
| Pressure, psig | 600 | 600 | 600 | 600 | 600 | 600 | 600 | 600 | 600 |
| Temperature, °C. | 270.0 | 280.0 | 260.0 | 270.0 | 260.8 | 280.5 | 270.0 | 271.1 | 280.3 |
| Time on organics, hrs. | 5.5 | 8.5 | 25.5 | 30.5 | 49.0 | 55.0 | 63.0 | 65.0 | 83.5 |
| Duration of run, hrs. | 1 | 2 | 2 | 2 | 2 | 2 | 2 | 2 | 2 |
| MEA SV, gmol/hr/kgcat | 5.28 | 5.07 | 5.48 | 5.84 | 5.52 | 6.52 | 5.81 | 6.13 | 5.44 |
| NH3 feedrate, gm/hr | 24.7 | 48.6 | 56.6 | 61.3 | 58.5 | 58.5 | 62.6 | 66.0 | 62.2 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.32 | 2.15 | 0.85 | 1.26 | 0.90 | 2.02 | 1.37 | 1.38 | 2.33 |
| MeEDA | 0 | 0 | 0 | 0 | 0 | 0 | 0 | 0 | 0 |
| MEA | 15.57 | 10.16 | 24.66 | 18.69 | 22.60 | 8.57 | 15.60 | 15.52 | 7.94 |
| EtEDA | 0 | 0 | 0 | 0 | 0 | 0 | 0 | 0 | 0 |
| PIP | 1.21 | 1.79 | 0.67 | 1.08 | 0.67 | 1.48 | 1.10 | 1.14 | 1.74 |
| DETA | 41.58 | 39.29 | 46.91 | 43.53 | 49.14 | 40.82 | 44.78 | 45.27 | 38.44 |
| AEEA | 2.20 | 1.15 | 2.85 | 2.14 | 2.98 | 0.66 | 1.62 | 1.56 | 0.56 |

TABLE V-continued

| Example No. | 53 | 54 | 55 | 56 | 57 | 58 | 59 | 60 | 61 |
|---|---|---|---|---|---|---|---|---|---|
| AEP | 1.22 | 1.98 | 0.54 | 1.04 | 0.61 | 1.67 | 1.07 | 1.11 | 1.93 |
| HEP | 0 | 0 | 0 | 0 | 0 | 0 | 0 | 0 | 0 |
| TETA's | 16.72 | 18.77 | 11.96 | 15.23 | 12.45 | 17.75 | 16.10 | 16.16 | 17.53 |
| TEPA's | 11.40 | 12.43 | 4.91 | 8.93 | 4.19 | 15.36 | 10.78 | 10.47 | 17.18 |
| MEA Conversion % | 56.69 | 71.01 | 31.16 | 47.92 | 37.24 | 75.81 | 57.10 | 57.41 | 77.50 |
| Acyclic (N4)/cyclic ($\leq$N4), weight ratio | 28.1 | 10.7 | 39.8 | 27.5 | 58.3 | 10.0 | 28.4 | 20.2 | 7.7 |
| Acyclic (N5)/cyclic ($\leq$N5), weight ratio | 17.8 | 11.1 | AL | 28.1 | AL | 9.6 | 20.8 | 20.2 | 7.7 |
| $\Sigma$(N5)/$\Sigma$(N4), weight ratio | 0.53 | 0.51 | 0.32 | 0.45 | 0.26 | 0.67 | 0.52 | 0.50 | 0.76 |

AL = All linear

TABLE VI

| Example No. | 62 | 63 | 64 | 65 | 66 | 67 | 68 | 69 | 70 |
|---|---|---|---|---|---|---|---|---|---|
| Catalyst Type | N | N | N | N | N | N | N | N | N |
| Catalyst weight, gm | 77.8 | 77.8 | 77.8 | 77.8 | 77.8 | 77.8 | 77.8 | 77.8 | 77.8 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.0 | 270.0 |
| Time on organics, hrs. | 5.7 | 24.0 | 29.9 | 46.7 | 50.7 | 70.0 | 73.2 | 94.5 | 96.2 |
| Duration of run, hrs. | 1 | 2 | 2 | 2 | 2 | 2 | 1 | 1.5 | 1.5 |
| AEEA SV, gmol/hr/kgcat | 6.67 | 4.63 | 4.91 | 3.59 | 2.96 | 2.58 | 3.91 | 3.41 | 3.48 |
| NH3 feedrate, gm/hr | 21.8 | 50.0 | 46.9 | 32.5 | 28.0 | 23.2 | 18.2 | 22.2 | 22.7 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 0.44 | 0.39 | 0.77 | 0.24 | 0.48 | 0.24 | 0.87 | 0.49 | 0.48 |
| MeEDA | 0 | 0 | 0 | 0 | 0 | 0 | 0 | 0 | 0 |
| MEA | 0.09 | 0 | 0.08 | 0 | 0 | 0 | 0.07 | 0.08 | 0.08 |
| EtEDA | 0 | 0 | 0 | 0 | 0 | 0 | 0 | 0 | 0 |
| PIP | 4.44 | 4.13 | 5.87 | 3.20 | 4.67 | 3.53 | 6.10 | 4.40 | 4.40 |
| DETA | 43.18 | 42.76 | 43.32 | 44.28 | 43.52 | 42.38 | 42.49 | 42.87 | 42.71 |
| AEEA | 26.48 | 26.78 | 16.71 | 37.36 | 26.70 | 34.34 | 16.74 | 27.84 | 28.30 |
| AEP | 0.39 | 0.35 | 0.55 | 0.17 | 0.36 | 0.18 | 0.54 | 0.34 | 0.32 |
| HEP | 0 | 0 | 0 | 0 | 0 | 0 | 0 | 0 | 0 |
| TETA's | 3.69 | 4.01 | 5.95 | 1.76 | 3.48 | 2.16 | 5.38 | 3.50 | 3.11 |
| TEPA's | 15.71 | 15.98 | 19.62 | 9.10 | 14.81 | 12.31 | 18.59 | 13.57 | 13.51 |
| AEEA Conversion % | 45.75 | 45.11 | 65.52 | 23.95 | 45.05 | 29.69 | 64.66 | 42.02 | 40.92 |
| Acyclic (N4)/cyclic ($\leq$N4), weight ratio | 0.1 | 0.1 | 0.1 | 0.1 | 0.1 | 0.1 | 0.1 | 0.1 | 0.1 |
| Acyclic (N5)/cyclic ($\leq$N5), | 34.1 | 27.3 | 26.5 | 28.9 | 32.0 | 5.2 | 31.0 | 31.9 | 38.4 |
| $\Sigma$(N5)/$\Sigma$(N4), weight ratio | 4.3 | 4.0 | 3.3 | 5.2 | 4.3 | 5.7 | 3.5 | 3.9 | 4.3 |

TABLE VII

| Example No. | 71 | 72 | 73 | 74 | 75 | 76 | 77 | 78 | 79 |
|---|---|---|---|---|---|---|---|---|---|
| Catalyst Type | O | O | O | O | O | O | O | O | O |
| Catalyst weight, gm | 79.2 | 79.2 | 79.2 | 79.2 | 79.2 | 79.2 | 79.2 | 79.2 | 79.2 |
| Pressure, psig | 600 | 600 | 600 | 600 | 600 | 600 | 600 | 600 | 600 |
| Temperature, °C. | 270.0 | 270.0 | 283.0 | 258.0 | 270.9 | 260.0 | 280.8 | 270.3 | 270.9 |
| Time on organics, hrs. | 5.5 | 24.0 | 29.5 | 48.2 | 54.0 | 72.0 | 77.0 | 96.0 | 98.0 |
| Duration of run, hrs. | 2 | 2 | 1 | 2.2 | 2 | 2 | 2 | 2 | 2 |
| AEEA SV, gmol/hr/kgcat | — | — | — | — | — | — | — | — | — |
| NH3 feedrate, gm/hr | 23.9 | 44.4 | 23.5 | 60.7 | 63.0 | 38.0 | 50.5 | 43.3 | 42.4 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 0.72 | 0.52 | 1.19 | 0.21 | 0.27 | 0 | 0.86 | 0.49 | 0.45 |
| MeEDA | 0 | 0 | 0 | 0 | 0 | 0 | 0 | 0 | 0 |
| MEA | 0.18 | 0 | 0.10 | 0 | 0 | 0 | 0.12 | 0.07 | 0.08 |
| EtEDA | 0 | 0 | 0 | 0 | 0 | 0 | 0 | 0 | 0 |
| PIP | 3.26 | 3.37 | 5.01 | 1.95 | 2.53 | 1.91 | 4.25 | 3.00 | 2.84 |
| DETA | 44.51 | 41.52 | 43.07 | 43.76 | 42.61 | 42.89 | 43.51 | 44.61 | 43.96 |
| AEEA | 21.05 | 28.04 | 18.66 | 41.43 | 34.60 | 41.04 | 22.86 | 32.99 | 33.50 |
| AEP | 0.51 | 0.40 | 0.69 | 0.17 | 0.30 | 0.17 | 0.46 | 0.30 | 0.30 |
| HEP | 0 | 0 | 0 | 0 | 0 | 0 | 0 | 0 | 0 |
| TETA's | 4.12 | 3.89 | 5.55 | 1.56 | 2.66 | 1.64 | 4.87 | 2.56 | 2.65 |
| TEPA's | 16.72 | 15.50 | 16.20 | 6.95 | 11.77 | 8.80 | 15.08 | 9.19 | 10.75 |
| AEEA Conversion % | 55.29 | 41.70 | 60.26 | 15.17 | 28.72 | 16.50 | 51.95 | 30.81 | 30.79 |
| Acyclic (N4)/cyclic ($\leq$N4), weight ratio | 0.1 | 0.2 | 0.2 | 0.2 | 0.1 | 0.2 | 0.2 | 0.1 | 0.1 |

TABLE VII-continued

| Example No. | 71 | 72 | 73 | 74 | 75 | 76 | 77 | 78 | 79 |
|---|---|---|---|---|---|---|---|---|---|
| Acyclic (N5)/cyclic (<=N5), weight ratio | 21.9 | 28.0 | 18.9 | 18.8 | 35.8 | 32.4 | 25.2 | 26.1 | 16.9 |
| $\Sigma$(N5)/$\Sigma$(N4), weight ratio | 4.1 | 4.0 | 2.9 | 4.5 | 4.4 | 3.1 | 3.1 | 3.6 | 4.1 |

TABLE VIII

| Example No. | 80 | 81 | 82 | 83 | 84 | 85 | 86 | 87 | 88 |
|---|---|---|---|---|---|---|---|---|---|
| Catalyst Type | P | P | P | P | P | P | P | P | P |
| Catalyst weight, gm | 70.3 | 70.3 | 70.3 | 70.3 | 70.3 | 70.3 | 70.3 | 70.3 | 70.3 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.6 | 269.0 |
| Time on organics, hrs. | 5.5 | 22.5 | 29.0 | 52.0 | 54.5 | 72.2 | 78.0 | 96.5 | 98.5 |
| Duration of run, hrs. | 2 | 1 | 2 | 1 | 1 | 2 | 2 | 2 | 2 |
| AEEA SV, gmol/hr/kgcat | — | — | — | — | — | — | — | — | — |
| NH3 feedrate, gm/hr | 21.6 | 14.3 | 32.8 | 30.7 | 29.8 | 50.4 | 43.6 | 38.0 | 38.9 |
| Liquid feed composition, wt. %, | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 2.46 | 1.29 | 1.46 | 0.41 | 0.59 | 0.36 | 0.24 | 0.75 | 0.70 |
| MeEDA | 0 | 0 | 0 | 0 | 0 | 0 | 0 | 0 | 0 |
| MEA | 1.52 | 0.91 | 0.77 | 0.43 | 0.40 | 0.21 | 0.22 | 0.23 | 0.17 |
| EtEDA | 0 | 0 | 0 | 0 | 0 | 0 | 0 | 0 | 0 |
| PIP | 4.80 | 3.83 | 4.36 | 2.11 | 2.78 | 2.01 | 4.12 | 3.40 | 3.25 |
| DETA | 37.58 | 41.15 | 42.68 | 44.21 | 41.99 | 43.58 | 39.66 | 43.51 | 41.45 |
| AEEA | 16.78 | 26.05 | 23.62 | 42.66 | 33.98 | 43.20 | 23.91 | 34.37 | 33.86 |
| AEP | 1.48 | 0.54 | 0.55 | 0.14 | 0.31 | 0.14 | 0.42 | 0.29 | 0.20 |
| HEP | 0 | 0 | 0 | 0 | 0 | 0 | 0 | 0 | 0 |
| TETA's | 7.37 | 3.99 | 3.66 | 0.85 | 2.68 | 1.01 | 4.52 | 2.37 | 2.61 |
| TEPA's | 16.17 | 14.01 | 13.88 | 5.45 | 10.84 | 5.68 | 18.03 | 9.38 | 10.95 |
| AEEA Conversion % | 63.30 | 44.80 | 49.70 | 12.60 | 29.00 | 11.50 | 49.67 | 28.70 | 29.10 |
| Acyclic (N4)/cyclic (<=N4), weight ratio | 0.9 | 0.3 | 0.1 | 0.1 | 0.1 | 0.3 | 0.1 | 0.1 | 0.1 |
| Acyclic (N5)/cyclic (<=N5), weight ratio | 11.8 | 20.5 | 23.8 | 22.6 | 22.9 | 24.2 | 13.2 | 30.5 | 18.2 |
| $\Sigma$(N5)/$\Sigma$(N4), weight ratio | 2.2 | 3.5 | 3.8 | 6.4 | 4.0 | 5.6 | 4.0 | 4.0 | 4.2 |

TABLE IX

| Example No. | 89 | 90 | 91 | 92 | 93 | 94 | 95 | 96 | 97 |
|---|---|---|---|---|---|---|---|---|---|
| Catalyst Type | Q | Q | Q | Q | Q | Q | Q | Q | Q |
| Catalyst weight, gm | 92.4 | 92.4 | 92.4 | 92.4 | 92.4 | 92.4 | 92.4 | 92.4 | 92.4 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.0 | 270.0 |
| Time on organics, hrs. | 5.7 | 24.0 | 29.0 | 46.7 | 50.7 | 70.0 | 73.2 | 94.5 | 96.2 |
| Duration of run, hrs. | 1 | 2 | 2 | 2 | 2 | 2 | 1 | 1.5 | 1.5 |
| AEEA SV, gmol/hr/kgcat | — | — | — | — | — | — | — | — | — |
| NH3 feedrate, gm/hr | 20.7 | 54.6 | 46.1 | 39.5 | 43.8 | 36.2 | 19.9 | 23.6 | 24.5 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 0.62 | 0.77 | 1.43 | 0.35 | 0.65 | 0.34 | 1.54 | 0.85 | 0.85 |
| MeEDA | 0 | 0 | 0 | 0 | 0 | 0 | 0 | 0 | 0 |
| MEA | 0.05 | 0.05 | 0.12 | 0 | 0 | 0 | 0.12 | 0.05 | 0.05 |
| EtEDA | 0 | 0 | 0 | 0 | 0 | 0 | 0 | 0 | 0 |
| PIP | 5.03 | 5.21 | 6.86 | 3.37 | 4.62 | 3.56 | 6.78 | 5 | 4.91 |
| DETA | 41.13 | 41.09 | 41.25 | 41.84 | 41.18 | 42.24 | 40.18 | 40.78 | 40.48 |
| AEEA | 22.03 | 21.43 | 12.01 | 33.20 | 23.91 | 32.48 | 12.42 | 22.88 | 23.37 |
| AEP | 0.50 | 0.51 | 1.00 | 0.32 | 0.47 | 0.32 | 0.94 | 0.49 | 0.47 |
| HEP | 0 | 0 | 0 | 0 | 0 | 0 | 0 | 0 | 0 |
| TETA's | 4.09 | 4.42 | 6.08 | 2.05 | 3.98 | 1.87 | 4.49 | 3.99 | 3.92 |
| TEPA's | 20.24 | 20.45 | 22.65 | 14.14 | 19.44 | 13.37 | 20.88 | 18.77 | 18.49 |
| AEEA Conversion % | 54.80 | 56.17 | 74.97 | 32.22 | 51.14 | 32.91 | 72.86 | 52.54 | 51.35 |
| Acyclic (N4)/cyclic (<=N4), weight ratio | 0.2 | 0.2 | 0.2 | 0.2 | 0.2 | 0.2 | 0.3 | 0.2 | 0.2 |
| Acyclic (N5)/cyclic (<=N5), weight ratio | 37.8 | 37.9 | 37.9 | 28.4 | 39.5 | 22.2 | 22.3 | 40.8 | 36.2 |
| $\Sigma$(N5)/$\Sigma$(N4), weight ratio | 5.0 | 4.6 | 4.6 | 6.9 | 4.9 | 7.2 | 4.7 | 4.7 | 4.7 |

TABLE X

| Example No. | 98 | 99 | 100 | 101 | 102 | 103 | 104 | 105 | 106 |
|---|---|---|---|---|---|---|---|---|---|
| Catalyst Type | R | R | R | R | R | R | R | R | R |
| Catalyst weight, gm | 83.0 | 83.0 | 83.0 | 83.0 | 83.0 | 83.0 | 83.0 | 83.0 | 83.0 |
| Pressure, psig | 600 | 600 | 600 | 600 | 600 | 600 | 600 | 600 | 600 |
| Temperature, °C. | 269.3 | 269.2 | 280.3 | 260.0 | 270.7 | 258.8 | 279.4 | 268.6 | 268.9 |
| Time on organics, hrs. | 25.0 | 27.0 | 30.0 | 47.5 | 53.0 | 72.5 | 78.5 | 96.0 | 104.0 |
| Duration of run, hrs. | 2 | 2 | 2 | 2 | 2 | 2 | 2 | 2 | 2 |
| MEA SV, gmol/hr/kgcat | 4.36 | 5.83 | 4.87 | 4.24 | 4.63 | 4.25 | 4.23 | 4.49 | 4.84 |
| $NH_3$ feedrate, gm/hr | 3.93 | 42.6 | 44.5 | 35.7 | 38.8 | 34.3 | 35.5 | 39.3 | 42.8 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.48 | 1.57 | 2.02 | 0.69 | 1.06 | 0.53 | 1.45 | 0.83 | 0.78 |
| MeEDA | 0 | 0 | 0 | 0 | 0 | 0 | 0 | 0 | 0 |
| MEA | 22.85 | 29.24 | 17.65 | 29.77 | 25.97 | 31.82 | 20.10 | 27.71 | 29.07 |
| EtEDA | 0 | 0 | 0 | 0 | 0 | 0 | 0 | 0 | 0 |
| PIP | 0.64 | 0.66 | 0.94 | 0.22 | 0.41 | 0.15 | 0.60 | 0.26 | 0.23 |
| DETA | 45.36 | 55.10 | 42.59 | 50.64 | 49.02 | 53.67 | 45.37 | 50.33 | 50.69 |
| AEEA | 4.02 | 5.66 | 3.65 | 4.36 | 4.97 | 3.75 | 4.15 | 4.75 | 4.55 |
| AEP | 0.79 | 0.77 | 1.15 | 0.28 | 0.45 | 0.23 | 0.79 | 0.79 | 0.30 |
| HEP | 0 | 0 | 0 | 0 | 0 | 0 | 0 | 0 | 0 |
| TETA's | 12.73 | 15.31 | 14.61 | 7.65 | 9.90 | 5.99 | 13.50 | 8.57 | 7.66 |
| TEPA's | 5.73 | 6.96 | 8.41 | 1.55 | 2.93 | 0.37 | 6.56 | 2.11 | 1.74 |
| MEA Conversion % | 36.63 | 34.01 | 50.31 | 17.19 | 28.09 | 12.29 | 43.92 | 23.51 | 19.12 |
| Acyclic (N4)/cyclic (<=N4), weight ratio | 26.3 | 37 | 19.1 | 59.2 | 49.2 | 73.5 | 30.6 | 56.3 | 91.8 |
| Acyclic (N5)/cyclic (<=N5), weight ratio | 16.6 | 26.7 | 17.3 | AL | AL | Al | 16.1 | AL | AL |
| Σ(N5)/Σ(N4), weight ratio | 0.35 | 0.35 | 0.44 | 0.16 | 0.23 | 0.05 | 0.38 | 0.19 | 0.18 |

AL = All linear

TABLE XI

| Example No. | 107 | 108 | 109 | 110 | 111 | 112 | 113 | 114 | 115 |
|---|---|---|---|---|---|---|---|---|---|
| Catalyst Type | S | S | S | S | S | S | S | S | S |
| Catalyst weight, gm | 87.0 | 87.0 | 87.0 | 87.0 | 87.0 | 87.0 | 87.0 | 87.0 | 87.0 |
| Pressure, psig | 600 | 600 | 600 | 600 | 600 | 600 | 600 | 600 | 600 |
| Temperature, °C. | 270.0 | 280.0 | 260.0 | 270.0 | 260.0 | 280.2 | 270.0 | 270.8 | 279.6 |
| Time on organics, hrs. | 5.5 | 8.5 | 25.5 | 30.5 | 49.0 | 55.0 | 63.0 | 65.0 | 83.5 |
| Duration of run, hrs. | 1 | 2 | 2 | 2 | 2 | 2 | 2 | 2 | 2 |
| MEA SV, gmol/hr/kgcat | 4.98 | 3.19 | 5.17 | 5.40 | 4.94 | 5.17 | 2.91 | 3.20 | 2.01 |
| $NH_3$ feedrate, gm/hr | 23.8 | 22.8 | 28.4 | 28.8 | 26.7 | 31.6 | 16.1 | 17.5 | 11.7 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.41 | 2.05 | 0.56 | 0.87 | 0.58 | 1.66 | 1.73 | 1.61 | 3.20 |
| MeEDA | 0 | 0 | 0 | 0 | 0 | 0 | 0 | 0 | 0 |
| MEA | 19.33 | 14.89 | 32.59 | 28.88 | 30.91 | 19.92 | 22.47 | 22.59 | 14.36 |
| EtEDA | 0 | 0 | 0 | 0 | 0 | 0 | 0 | 0 | 0 |
| PIP | 0.90 | 1.42 | 0.34 | 0.61 | 0.30 | 1.17 | 1.29 | 1.22 | 2.55 |
| DETA | 52.52 | 49.03 | 53.57 | 50.73 | 55.21 | 50.05 | 49.40 | 49.57 | 40.30 |
| AEEA | 3.10 | 2.24 | 2.82 | 3.11 | 2.59 | 2.54 | 2.81 | 2.84 | 1.84 |
| AEP | 0.85 | 1.56 | 0.26 | 0.44 | 0.23 | 1.07 | 0.95 | 0.90 | 2.16 |
| HEP | 0 | 0 | 0 | 0 | 0 | 0 | 0 | 0 | 0 |
| TETA's | 9.47 | 11.11 | 5.40 | 8.10 | 5.43 | 11.41 | 10.18 | 10.98 | 13.32 |
| TEPA's | 5.10 | 7.91 | 0.97 | 2.28 | 0.46 | 5.29 | 4.71 | 5.15 | 11.87 |
| MEA Conversion % | 46.07 | 57.87 | 10.12 | 19.83 | 14.19 | 44.75 | 37.61 | 38.21 | 59.43 |
| Acyclic (N4)/cyclic (<=N4), weight ratio | 27.7 | 11.6 | 29.1 | 31.2 | 29.4 | 19.7 | 18.6 | 24.8 | 5.9 |
| Acyclic (N5)/cyclic (<=N5), weight ratio | 24.3 | 7.9 | 3.8 | AL | 0.5 | 12.4 | 13.9 | 20.6 | 8.8 |
| Σ(N5)/Σ(N4), weight ratio | 0.42 | 0.55 | 0.14 | 0.22 | 0.07 | 0.36 | 0.36 | 0.36 | 0.69 |

AL = All linear

TABLE XII

| Example No. | 116 | 117 | 118 | 119 | 120 | 121 | 122 | 123 | 124 |
|---|---|---|---|---|---|---|---|---|---|
| Catalyst Type | T | T | T | T | T | T | T | T | T |
| Catalyst weight, gm | 70.3 | 70.3 | 70.3 | 70.3 | 70.3 | 70.3 | 70.3 | 70.3 | 70.3 |
| Pressure, psig | 600 | 600 | 600 | 600 | 600 | 600 | 600 | 600 | 600 |
| Temperature, °C. | 269.6 | 269.8 | 280.0 | 260.0 | 269.9 | 259.9 | 280.0 | 270.0 | 269.8 |
| Time on organics, hrs. | 7.0 | 28.2 | 32.0 | 51.0 | 55.5 | 76.0 | 80.0 | 98.0 | 100.0 |

TABLE XII-continued

| Example No. | 116 | 117 | 118 | 119 | 120 | 121 | 122 | 123 | 124 |
|---|---|---|---|---|---|---|---|---|---|
| Duration of run, hrs. | 2 | 2.2 | 2 | 2 | 2 | 1 | 1 | 2 | 2 |
| MEA SV, gmol/hr/kgcat | 6.41 | 5.47 | 5.54 | 5.55 | 5.99 | 4.94 | 4.87 | 5.13 | 5.09 |
| $NH_3$ feedrate, gm/hr | 57.0 | 50.0 | 47.4 | 42.9 | 51.0 | 19.5 | 20.2 | 42.8 | 42.6 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.76 | 1.72 | 2.79 | 1.20 | 1.54 | 1.03 | 3.28 | 1.62 | 1.77 |
| MeEDA | 0 | 0 | 0 | 0 | 0 | 0 | 0 | 0 | 0 |
| MEA | 28.93 | 31.18 | 25.30 | 34.17 | 32.94 | 36.96 | 29.76 | 34.70 | 34.76 |
| EtEDA | 0 | 0 | 0 | 0 | 0 | 0 | 0 | 0 | 0 |
| PIP | 0.31 | 0.20 | 0.35 | 0.11 | 0.13 | 0.05 | 0.26 | 0.08 | 0.08 |
| DETA | 51.86 | 51.84 | 47.27 | 52.54 | 50.53 | 55.52 | 49.86 | 54.14 | 52.26 |
| AEEA | 2.46 | 2.38 | 2.35 | 1.71 | 1.94 | 1.39 | 2.21 | 1.69 | 1.72 |
| AEP | 0.34 | 0.26 | 0.43 | 0.27 | 0.22 | 0.18 | 0.37 | 0.23 | 0.23 |
| HEP | 0 | 0 | 0 | 0 | 0 | 0 | 0 | 0 | 0 |
| TETA's | 8.21 | 6.88 | 8.88 | 4.83 | 4.02 | 0.75 | 6.01 | 1.23 | 2.76 |
| TEPA's | 1.20 | 0.40 | 1.93 | 0.61 | 0.28 | 0 | 0.77 | 0.75 | 0.69 |
| MEA Conversion % | 19.48 | 12.50 | 25.30 | 4.19 | 3.61 | 3.96 | 14.28 | 1.23 | 0.93 |
| Acyclic (N4)/cyclic ($<=$N4), weight ratio | 61.5 | 34.2 | 29.6 | 8.2 | 10.8 | 5.2 | 15.9 | 5.1 | 10.0 |
| Acyclic (N5)/cyclic ($<=$N5), weight ratio | 8.7 | 2.5 | 6.9 | 3.1 | 1.0 | — | 1.6 | 0.8 | 0.9 |
| $\Sigma(N5)/\Sigma(N4)$, weight ratio | 0.11 | 0.04 | 0.18 | 0.10 | 0.05 | 0.00 | 0.10 | 0.47 | 0.19 |

TABLE XIII

| Example No. | 125 | 126 | 127 | 128 | 129 | 130 | 131 | 132 | 133 |
|---|---|---|---|---|---|---|---|---|---|
| Catalyst Type | U | U | U | U | U | U | U | U | U |
| Catalyst weight, gm | 80.0 | 80.0 | 80.0 | 80.0 | 80.0 | 80.0 | 80.0 | 80.0 | 80.0 |
| Pressure, psig | 600 | 600 | 600 | 600 | 600 | 600 | 600 | 600 | 600 |
| Temperature, °C. | 269.2 | 270.6 | 280.0 | 260.0 | 270.6 | 260.3 | 280.3 | 270.0 | 270.4 |
| Time on organics, hrs. | 7.0 | 28.2 | 32.0 | 51.0 | 55.5 | 76.0 | 80.0 | 98.0 | 100.0 |
| Duration of run, hrs. | 2 | 2.2 | 2 | 2 | 2 | 1 | 1 | 2 | 2 |
| MEA SV, gmol/hr/kgcat | 5.80 | 5.38 | 5.30 | 5.18 | 5.59 | 4.76 | 4.64 | 4.77 | 4.93 |
| $NH_3$ feedrate, gm/hr | 58.1 | 55.5 | 50.5 | 45.4 | 52.8 | 21.4 | 21.7 | 44.7 | 46.5 |
| Liquid feed composition, wt. % | | | | | | | | | |
| DETA | 62.81 | 62.81 | 62.81 | 62.81 | 62.81 | 62.81 | 62.81 | 62.81 | 62.81 |
| MEA | 37.19 | 37.19 | 37.19 | 37.19 | 37.19 | 37.19 | 37.19 | 37.19 | 37.19 |
| Liquid product composition, wt. % | | | | | | | | | |
| EDA | 1.49 | 1.58 | 2.41 | 1.49 | 1.60 | 1.33 | 3.12 | 1.81 | 1.94 |
| MeEDA | 0 | 0 | 0 | 0 | 0 | 0 | 0 | 0 | 0 |
| MEA | 15.80 | 15.60 | 7.88 | 21.06 | 16.72 | 23.31 | 8.72 | 16.63 | 16.40 |
| EtEDA | 0 | 0 | 0 | 0 | 0 | 0 | 0 | 0 | 0 |
| PIP | 1.24 | 1.29 | 1.79 | 1.18 | 1.30 | 1.03 | 2.25 | 1.45 | 1.52 |
| DETA | 43.99 | 41.88 | 35.04 | 44.83 | 41.24 | 45.12 | 38.12 | 42.49 | 42.23 |
| AEEA | 1.68 | 1.76 | 0.69 | 2.11 | 1.79 | 2.59 | 0.65 | 1.94 | 1.78 |
| AEP | 1.28 | 1.32 | 2.09 | 1.44 | 1.21 | 0.82 | 2.32 | 1.36 | 1.42 |
| HEP | 0 | 0 | 0 | 0 | 0 | 0 | 0 | 0 | 0 |
| TETA's | 16.06 | 16.67 | 18.12 | 12.97 | 15.56 | 12.51 | 17.44 | 15.73 | 15.55 |
| TEPA's | 10.63 | 11.12 | 17.85 | 7.24 | 9.80 | 5.36 | 14.78 | 9.38 | 9.35 |
| MEA Conversion % | 56.44 | 56.59 | 77.25 | 41.21 | 52.29 | 34.25 | 75.14 | 53.32 | 53.67 |
| Acyclic (N4)/cyclic ($<=$N4), weight ratio | 45.2 | 22.5 | 7.5 | 21.2 | 22.4 | 34.8 | 8.8 | 23.5 | 22.7 |
| Acyclic (N5)/cyclic ($<=$N5), weight ratio | 22.8 | 18.1 | 7.8 | 16.0 | 18.1 | 30.1 | 9.5 | 16.3 | 16.1 |
| $\Sigma(N5)/\Sigma(N4)$, weight ratio | 0.51 | 0.52 | 0.76 | 0.43 | 0.48 | 0.33 | 0.65 | 0.46 | 0.46 |

TABLE XIV

| Example No. | 134 | 135 | 136 | 137 | 138 | 139 | 140 | 141 | 142 |
|---|---|---|---|---|---|---|---|---|---|
| Catalyst Type | V | V | V | V | V | V | V | V | V |
| Catalyst weight, gm | 73.7 | 73.7 | 73.7 | 73.7 | 73.7 | 73.7 | 73.7 | 73.7 | 73.7 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.7 | 270.0 |
| Time on organics, hrs. | 5.5 | 22.5 | 29.0 | 52.0 | 54.5 | 72.2 | 78.0 | 96.5 | 98.5 |
| Duration of run, hrs. | 2 | 1 | 2 | 1 | 1 | 2 | 2 | 2 | 2 |
| AEEA SV, gmol/hr/kgcat | 6.67 | 4.63 | 4.91 | 3.59 | 2.96 | 2.58 | 3.91 | 3.41 | 3.48 |
| $NH_3$ feedrate, gm/hr | 23.9 | 9.9 | 48.8 | 23.5 | 28.5 | 31.0 | 25.0 | 26.9 | 26.3 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, | | | | | | | | | |

TABLE XIV-continued

| Example No. | 134 | 135 | 136 | 137 | 138 | 139 | 140 | 141 | 142 |
|---|---|---|---|---|---|---|---|---|---|
| wt. % | | | | | | | | | |
| EDA | 1.79 | 1.51 | 1.41 | 0.34 | 0.50 | 0.35 | 1.70 | 0.78 | 0.74 |
| MeEDA | 0 | 0 | 0 | 0 | 0 | 0 | 0 | 0 | 0 |
| MEA | 1.07 | 1.17 | 0.74 | 0.25 | 0.33 | 0.24 | 0.04 | 0.16 | 0.15 |
| EtEDA | 0 | 0 | 0 | 0 | 0 | 0 | 0 | 0 | 0 |
| PIP | 5.52 | 3.76 | 5.76 | 2.81 | 3.63 | 3.64 | 6.92 | 5.05 | 4.86 |
| DETA | 35.90 | 41.93 | 41.57 | 41.16 | 41.76 | 42.48 | 39.49 | 41.16 | 39.75 |
| AEEA | 12.93 | 27.03 | 18.11 | 36.99 | 28.20 | 33.45 | 13.29 | 23.75 | 23.90 |
| AEP | 1.55 | 0.45 | 0.89 | 0.18 | 0.37 | 0.30 | 0.97 | 0.44 | 0.40 |
| HEP | 0 | 0 | 0 | 0 | 0 | 0 | 0 | 0 | 0 |
| TETA's | 8.53 | 3.5 | 6.04 | 2.12 | 3.43 | 2.57 | 7.05 | 4.24 | 3.96 |
| TEPA's | 20.89 | 12.30 | 16.43 | 11.31 | 14.45 | 12.09 | 20.16 | 16.39 | 16.70 |
| AEEA Conversion % | 71.98 | 42.53 | 61.68 | 24.04 | 40.94 | 31.50 | 71.70 | 50.18 | 49.03 |
| Acyclic (N4)/cyclic ($<=$N4), weight ratio | 0.6 | 0.3 | 0.3 | 0.1 | 0.1 | 0.1 | 0.2 | 0.1 | 0.1 |
| Acyclic (N5)/cyclic ($<=$N5), weight ratio | 11.5 | 23.0 | 21.5 | 29.0 | 36.6 | 40.9 | 21.5 | 38.7 | 40.6 |
| $\Sigma$(N5)/$\Sigma$(N4), weight ratio | 2.4 | 3.5 | 2.7 | 5.3 | 4.2 | 4.7 | 2.9 | 3.9 | 4.2 |

TABLE XV

| Example No. | 143 | 144 | 145 | 146 | 147 | 148 | 149 | 150 | 151 |
|---|---|---|---|---|---|---|---|---|---|
| Catalyst Type | W | W | W | W | W | W | W | W | W |
| Catalyst weight, gm | 73.4 | 73.4 | 73.4 | 73.4 | 73.4 | 73.4 | 73.4 | 73.4 | 73.4 |
| Pressure, psig | 600 | 600 | 600 | 600 | 600 | 600 | 600 | 600 | 600 |
| Temperature, °C. | 270.0 | 270.0 | 283.0 | 258.0 | 270.9 | 260.0 | 280.8 | 270.3 | 270.9 |
| Time on organics, hrs. | 6.0 | 24.0 | 29.5 | 48.2 | 54.0 | 72.0 | 77.0 | 96.0 | 98.0 |
| Duration of run, hrs. | 2 | 2 | 1 | 2.2 | 2 | 2 | 2 | 2 | 2 |
| AEEA SV, gmol/hr/kgcat | — | — | — | — | — | — | — | — | — |
| NH3 feedrate, gm/hr | 49.4 | 47.0 | 25.3 | 63.8 | 66.2 | 40.9 | 55.0 | 45.8 | 45.5 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 0.59 | 0.51 | 1.22 | 0.19 | 0.25 | 0.17 | 0.76 | 0.44 | 0.45 |
| MeEDA | 0 | 0 | 0 | 0 | 0 | 0 | 0 | 0 | 0 |
| MEA | 0.20 | 0.07 | 0.09 | 0 | 0 | 0 | 0.12 | 0.07 | 0.07 |
| EtEDA | 0 | 0 | 0 | 0 | 0 | 0 | 0 | 0 | 0 |
| PIP | 2.85 | 3.05 | 4.72 | 1.66 | 2.14 | 1.61 | 3.58 | 2.65 | 2.63 |
| DETA | 45.65 | 41.32 | 44.05 | 44.34 | 42.13 | 42.52 | 43.04 | 44.85 | 44.90 |
| AEEA | 24.65 | 30.56 | 20.44 | 43.92 | 36.81 | 42.99 | 25.69 | 25.38 | 36.09 |
| AEP | 0.44 | 0.40 | 0.82 | 0.17 | 0.31 | 0.16 | 0.51 | 0.32 | 0.31 |
| HEP | 0 | 0 | 0 | 0 | 0 | 0 | 0 | 0 | 0 |
| TETA's | 3.12 | 2.96 | 4.96 | 0.73 | 1.76 | 0.98 | 4.05 | 1.48 | 1.46 |
| TEPA's | 14.38 | 15.11 | 15.08 | 6.05 | 11.07 | 7.67 | 15.97 | 8.80 | 8.72 |
| AEEA Conversion % | 47.86 | 36.83 | 56.81 | 10.83 | 23.78 | 12.00 | 46.91 | 40.95 | 25.27 |
| Acyclic (N4)/cyclic ($<=$N4), weight ratio | 0.2 | 0.2 | 0.3 | 0.1 | 0.1 | 0.2 | 0.2 | 0.1 | 0.1 |
| Acyclic (N5)/cyclic ($<=$N5), weight ratio | 29.2 | 29.9 | 16.2 | 33.1 | 34.6 | 30.5 | 23.6 | 23.1 | 24.5 |
| $\Sigma$(N5)/$\Sigma$(N4), weight ratio | 4.6 | 5.1 | 3.0 | 8.3 | 6.3 | 7.8 | 3.9 | 6.0 | 6.0 |

TABLE XVI

| Example No. | 152 | 153 | 154 | 155 | 156 | 157 | 158 | 159 | 160 |
|---|---|---|---|---|---|---|---|---|---|
| Catalyst Type | X | X | X | X | X | X | X | X | X |
| Catalyst weight, gm | 84.4 | 84.4 | 84.4 | 84.4 | 84.4 | 84.4 | 84.4 | 84.4 | 84.4 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.6 | 270.0 |
| Time on organics, hrs. | 5.5 | 22.5 | 29.0 | 52.0 | 54.5 | 72.2 | 78.0 | 96.5 | 98.5 |
| Duration of run, hrs. | 2 | 1 | 2 | 1 | 1 | 2 | 2 | 2 | 2 |
| AEEA SV, gmol/hr/kgcat | — | — | — | — | — | — | — | — | — |
| NH3 feedrate, gm/hr | 22.1 | 22.5 | 49.2 | 28.0 | 28.5 | 49.7 | 46.8 | 44.6 | 47.7 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 2.27 | 4.55 | 1.74 | 0.58 | 0.94 | 0.50 | 1.87 | 1.19 | 0.98 |
| MeEDA | 0 | 0 | 0 | 0 | 0 | 0 | 0 | 0 | 0 |
| MEA | 1.91 | 0.49 | 0.96 | 0.60 | 0.48 | 0.27 | 0.22 | 0.28 | 0.28 |
| EtEDA | 0 | 0 | 0 | 0 | 0 | 0 | 0 | 0 | 0 |
| PIP | 4.38 | 8.82 | 4.05 | 1.76 | 2.73 | 1.76 | 4.35 | 3.33 | 3.06 |
| DETA | 38.78 | 30.56 | 43.07 | 43.47 | 43.02 | 41.40 | 40.62 | 43.07 | 43.67 |

TABLE XVI-continued

| Example No. | 152 | 153 | 154 | 155 | 156 | 157 | 158 | 159 | 160 |
|---|---|---|---|---|---|---|---|---|---|
| AEEA | 18.03 | 6.55 | 25.13 | 44.40 | 34.37 | 41.62 | 22.92 | 33.81 | 36.22 |
| AEP | 1.04 | 3.42 | 0.47 | 0.13 | 0.29 | 0.13 | 0.45 | 0.29 | 0.20 |
| HEP | 0 | 0 | 0 | 0 | 0 | 0 | 0 | 0 | 0 |
| TETA's | 6.08 | 12.34 | 3.31 | 0.97 | 2.18 | 1.33 | 4.49 | 1.70 | 2.15 |
| TEPA's | 15.92 | 19.32 | 12.10 | 4.88 | 8.78 | 6.37 | 13.97 | 9.45 | 8.66 |
| AEEA Conversion % | 60.54 | 85.60 | 46.11 | 9.39 | 27.39 | 12.20 | 50.03 | 28.95 | 25.46 |
| Acyclic (N4)/cyclic ($\leq$ N4), weight ratio | 0.6 | 0.4 | 0.1 | 0.5 | 0.3 | 0.4 | 0.1 | 0.4 | 0.3 |
| Acyclic (N5)/cyclic ($\leq$ N5), weight ratio | 11.7 | 4.9 | 20.9 | 19.5 | 28.4 | 21.5 | 8.5 | 25.7 | 24.0 |
| $\Sigma$(N5)/$\Sigma$(N4), weight ratio | 2.6 | 1.6 | 3.7 | 5.0 | 4.0 | 4.8 | 3.1 | 3.1 | 4.0 |

TABLE XVII

| Example No. | 161 | 162 | 163 | 164 | 165 | 166 | 167 | 168 | 169 |
|---|---|---|---|---|---|---|---|---|---|
| Catalyst Type | Y | Y | Y | Y | Y | Y | Y | Y | Y |
| Catalyst weight, gm | 78.3 | 78.3 | 78.3 | 78.3 | 78.3 | 78.3 | 78.3 | 78.3 | 78.3 |
| Pressure, psig | 600 | 600 | 600 | 600 | 600 | 600 | 600 | 600 | 600 |
| Temperature, °C. | 270.0 | 270.0 | 283.0 | 258.0 | 270.9 | 260.0 | 280.8 | 270.3 | 270.9 |
| Time on organics, hrs. | 6.0 | 24.0 | 29.5 | 48.2 | 54.0 | 72.0 | 77.0 | 96.0 | 98.0 |
| Duration of run, hrs. | 2 | 2 | 1 | 2.2 | 2 | 2 | 2 | 2 | 2 |
| AEEA SV, gmol/hr/kgcat | — | — | — | — | — | — | — | — | — |
| NH$_3$ feedrate, gm/hr | 47.8 | 42.9 | 23.8 | 60.8 | 63.8 | 38.3 | 51.1 | 44.1 | 43.5 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 1.79 | 0.84 | 2.05 | 0.26 | 0.49 | 0.27 | 1.47 | 0.88 | 0.81 |
| MeEDA | 0 | 0 | 0 | 0 | 0 | 0 | 0 | 0 | 0 |
| MEA | 0.07 | 0.08 | 0.15 | 0 | 0 | 0 | 0.13 | 0.12 | 0.12 |
| EtEDA | 0 | 0 | 0 | 0 | 0 | 0 | 0 | 0 | 0 |
| PIP | 5.48 | 5.20 | 7.62 | 3.16 | 4.17 | 3.14 | 6.53 | 5.51 | 5.21 |
| DETA | 40.75 | 39.06 | 40.46 | 42.44 | 41.21 | 41.62 | 39.57 | 44.13 | 42.64 |
| AEEA | 21.03 | 20.82 | 10.49 | 34.11 | 26.14 | 34.43 | 12.94 | 23.33 | 23.17 |
| AEP | 0.61 | 0.59 | 1.43 | 0.32 | 0.45 | 0.31 | 1.03 | 0.58 | 0.53 |
| HEP | 0 | 0 | 0 | 0 | 0 | 0 | 0 | 0 | 0 |
| TETA's | 4.60 | 5.02 | 7.77 | 1.84 | 3.81 | 2.33 | 7.05 | 3.48 | 3.34 |
| TEPA's | 19.42 | 20.43 | 18.20 | 12.67 | 16.32 | 13.13 | 21.97 | 15.04 | 14.97 |
| AEEA Conversion % | 56.84 | 56.59 | 77.33 | 29.89 | 45.43 | 29.60 | 72.79 | 51.60 | 50.71 |
| Acyclic (N4)/cyclic ($\leq$ N4), weight ratio | 0.2 | 0.2 | 0.3 | 0.1 | 0.2 | 0.2 | 0.3 | 0.1 | 0.1 |
| Acyclic (N5)/cyclic ($\leq$ N5), weight ratio | 30.5 | 30.6 | 14.2 | 41.1 | 35.1 | 47.8 | 18.1 | 25.1 | 25.8 |
| $\Sigma$(N5)/$\Sigma$(N4), weight ratio | 4.2 | 4.1 | 2.3 | 6.9 | 4.3 | 5.6 | 3.1 | 4.3 | 4.5 |

TABLE XVIII

| Example No. | 170 | 171 | 172 | 173 | 174 | 175 | 176 | 177 | 178 |
|---|---|---|---|---|---|---|---|---|---|
| Catalyst Type | Z | Z | Z | Z | Z | Z | Z | Z | Z |
| Catalyst weight, gm | 84.8 | 84.8 | 84.8 | 84.8 | 84.8 | 84.8 | 84.8 | 84.8 | 84.8 |
| Pressure, psig | 600 | 600 | 600 | 600 | 600 | 600 | 600 | 600 | 600 |
| Temperature, °C. | 270.0 | 270.0 | 280.0 | 260.0 | 270.0 | 260.0 | 280.0 | 270.0 | 270.0 |
| Time on organics, hrs. | 5.7 | 24.0 | 29.0 | 46.7 | 50.7 | 70.0 | 73.2 | 94.5 | 96.2 |
| Duration of run, hrs. | 1 | 2 | 2 | 2 | 2 | 2 | 1 | 1.5 | 1.5 |
| AEEA SV, gmol/hr/kgcat | — | — | — | — | — | — | — | — | — |
| NH$_3$ feedrate, gm/hr | 23.3 | 50.0 | 45.6 | 37.3 | 41.3 | 34.5 | 19.1 | 23.4 | 23.3 |
| Liquid feed composition, wt. % | | | | | | | | | |
| DETA | 49.76 | 49.76 | 49.76 | 49.76 | 49.76 | 49.76 | 49.76 | 49.76 | 49.76 |
| AEEA | 50.24 | 50.24 | 50.24 | 50.24 | 50.24 | 50.24 | 50.24 | 50.24 | 50.24 |
| Liquid product composition, wt. % | | | | | | | | | |
| EDA | 0.46 | 0.56 | 1.34 | 0.26 | 0.50 | 0.25 | 1.36 | 0.64 | 0.65 |
| MeEDA | 0 | 0 | 0 | 0 | 0 | 0 | 0 | 0 | 0 |
| MEA | 0 | 0.09 | 0.11 | 0 | 0 | 0 | 0.09 | 0 | 0 |
| EtEDA | 0 | 0 | 0 | 0 | 0 | 0 | 0 | 0 | 0 |
| PIP | 4.46 | 4.64 | 6.90 | 3.48 | 4.69 | 3.53 | 8.83 | 4.93 | 4.96 |
| DETA | 38.35 | 39.67 | 40.51 | 42.49 | 41.05 | 41.84 | 39.34 | 40.20 | 40.66 |
| AEEA | 21.70 | 22.16 | 12.36 | 33.12 | 23.84 | 32.81 | 12.26 | 22.74 | 23.22 |
| AEP | 0.54 | 0.54 | 1.08 | 0.35 | 0.51 | 0.36 | 1.06 | 0.54 | 0.53 |
| HEP | 0 | 0 | 0 | 0 | 0 | 0 | 0 | 0 | 0 |
| TETA's | 4.66 | 4.54 | 5.86 | 1.96 | 4.12 | 1.95 | 6.78 | 4.09 | 3.94 |
| TEPA's | 22.98 | 21.35 | 22.56 | 13.30 | 18.84 | 13.34 | 21.88 | 19.39 | 18.23 |
| AEEA Conversion % | 55.33 | 54.49 | 74.05 | 32.14 | 50.92 | 32.17 | 74.60 | 52.73 | 51.51 |
| Acyclic (N4)/cyclic ($\leq$ N4), | 0.2 | 0.2 | 0 | 0.2 | 0.2 | 0.1 | 0.2 | 0.2 | 0.2 |

TABLE XVIII-continued

| Example No. | 170 | 171 | 172 | 173 | 174 | 175 | 176 | 177 | 178 |
|---|---|---|---|---|---|---|---|---|---|
| weight ratio | | | | | | | | | |
| Acyclic (N5)/cyclic (<=N5), weight ratio | 33.9 | 27.1 | 19.1 | 18.8 | 36.7 | 14.2 | 18.5 | 32.2 | 36.5 |
| Σ(N5)/Σ(N4), weight ratio | 4.9 | 4.7 | 3.9 | 4.5 | 4.6 | 6.8 | 3.2 | 4.7 | 4.6 |

TABLE XIX

| Example No. | 179 | 180 | 181 | 182 | 183 | 184 | 185 | 186 |
|---|---|---|---|---|---|---|---|---|
| Catalyst Type | AA | AA | AA | AA | AA | AA | AA | AA |
| Catalyst weight, gm | 127.9 | 127.9 | 127.9 | 127.9 | 127.9 | 127.9 | 127.9 | 127.9 |
| Pressure, psig | 600 | 600 | 600 | 600 | 600 | 600 | 600 | 600 |
| Temperature, °C. | 252.8 | 252.5 | 252.8 | 273.3 | 271.5 | 274.3 | 273.8 | 273.3 |
| Time on organics, hrs. | 3.5 | 18.0 | 20.0 | 42.0 | 44.5 | 51.5 | 66.4 | 68.5 |
| Duration of run, hrs. | 2 | 14.5 | 2 | 16.5 | 2.5 | 2 | 14.8 | 2.1 |
| MEA SV, gmol/hr/kgcat | 1.82 | 1.81 | 1.82 | 1.75 | 1.79 | 1.39 | 1.52 | 1.63 |
| NH3 feedrate, gm/hr | 49.0 | 59.9 | 59.9 | 50.7 | 48.4 | 55.0 | 48.0 | 67.5 |
| Liquid feed composition, wt. % | | | | | | | | |
| DETA | 77.16 | 77.16 | 77.16 | 77.16 | 77.16 | 66.46 | 66.46 | 66.46 |
| MEA | 22.84 | 22.84 | 22.84 | 22.84 | 22.84 | — | — | — |
| AEEA | — | — | — | — | — | 33.54 | 33.54 | 33.54 |
| Liquid product composition, wt. % | | | | | | | | |
| EDA | 0.44 | 0 | 0 | 0.57 | 0.56 | 0.53 | 0.55 | 0.64 |
| MeEDA | 0 | 0 | 0 | 0 | 0 | 0 | 0 | 0 |
| MEA | 19.06 | 20.36 | 20.38 | 16.79 | 17.14 | 1.82 | 0 | 0 |
| EtEDA | 0 | 0 | 0 | 0 | 0 | 0 | 0 | 0 |
| PIP | 0.35 | 0.17 | 0.13 | 0.55 | 0.56 | 5.29 | 5.83 | 6.16 |
| DETA | 73.70 | 76.19 | 77.06 | 74.38 | 74.02 | 70.73 | 66.69 | 69.84 |
| AEEA | 0 | 0 | 0 | 0 | 0 | 5.43 | 8.01 | 8.11 |
| AEP | 0.35 | 0.27 | 0.25 | 0.62 | 0.63 | 0.79 | 0.58 | 0.60 |
| HEP | 0 | 0 | 0 | 0 | 0 | 0 | 0 | 0 |
| TETA's | 3.10 | 3.40 | 1.18 | 3.97 | 3.94 | 3.94 | 4.98 | 4.71 |
| TEPA's | 0.75 | 0 | 0 | 0.92 | 0.97 | 6.54 | 8.17 | 8.30 |
| ROH Conversion % | 15.38 | 11.83 | 10.33 | 25.88 | 24.31 | 83.30 | 75.45 | 76.02 |
| Acyclic (N4)/cyclic (<=N4), weight ratio | AL | AL | AL | 23.21 | 23.20 | 0.32 | 0.11 | 0.12 |
| Acyclic (N5)/cyclic (<=N5), weight ratio | AL | — | — | AL | AL | 12.43 | 18.50 | 41.50 |
| Σ(N5)/Σ(N4), weight ratio | 0.24 | 0 | 0 | 0.23 | 0.24 | — | — | — |

AL = All linear

TABLE XX

| Example No. | 187 | 188 | 189 | 190 | 191 | 192 | 193 | 194 |
|---|---|---|---|---|---|---|---|---|
| Catalyst Type | BB | BB | BB | BB | BB | BB | BB | BB |
| Catalyst weight, gm | 125.7 | 125.7 | 125.7 | 125.7 | 125.7 | 125.7 | 125.7 | 125.7 |
| Pressure, psig | 600 | 600 | 600 | 600 | 600 | 600 | 600 | 600 |
| Temperature, °C. | 260.8 | 260.0 | 280.5 | 280.5 | 281.5 | 281.3 | 279.8 | 260.5 |
| Time on organics, hrs. | 16.7 | 18.7 | 24.1 | 41.1 | 48.1 | 64.8 | 66.8 | |
| Duration of run, hrs. | 15.7 | 2 | 2 | 16.7 | 2 | 15.8 | 2 | 15.7 |
| MEA SV, gmol/hr/kgcat | 1.77 | 2.02 | 1.77 | 1.76 | 1.77 | 1.63 | 1.62 | 1.60 |
| NH3 feedrate, gm/hr | 58.2 | 55.5 | 49.0 | 52.7 | 49.0 | 52.5 | 54.5 | 60.0 |
| Liquid feed composition, wt. % | | | | | | | | |
| DETA | 77.16 | 77.16 | 77.16 | 77.16 | 77.16 | 66.46 | 66.46 | 77.16 |
| MEA | 22.84 | 22.84 | 22.84 | 22.84 | 22.84 | — | — | 22.84 |
| AEEA | — | — | — | — | — | 33.54 | 33.54 | — |
| Liquid product composition, wt. % | | | | | | | | |
| EDA | 0 | 0 | 1.64 | 1.13 | 1.40 | 2.21 | 2.12 | 0 |
| MeEDA | 0 | 0 | 0 | 0 | 0 | 0 | 0 | 0 |
| MEA | 24.27 | 24.79 | 18.55 | 15.91 | 20.12 | 0 | 0 | 29.98 |
| EtEDA | 0 | 0 | 0 | 0 | 0 | 0 | 0 | 0 |
| PIP | 0.48 | 0.31 | 1.35 | 1.37 | 1.20 | 7.44 | 6.49 | 0.49 |
| DETA | 71.40 | 72.05 | 67.88 | 71.46 | 67.32 | 70.71 | 71.20 | 66.77 |
| AEEA | 0 | 0 | 0 | 0 | 0 | 0 | 0 | 0 |
| AEP | 0.34 | 0.32 | 1.14 | 1.08 | 0.98 | 1.10 | 1.08 | 0.25 |
| HEP | 0 | 0 | 0 | 0 | 0 | 0 | 0 | 0 |
| TETA's | 2.39 | 2.45 | 5.92 | 5.54 | 5.28 | 6.49 | 5.66 | 0.44 |
| TEPA's | 0.93 | 0 | 2.51 | 2.18 | 2.79 | 11.91 | 12.44 | 0.99 |
| ROH Conversion % | 6.29 | 8.67 | 19.20 | 30.97 | 12.19 | 100.00 | 100.00 | 0 |
| Acyclic (N4)/cyclic (<=N4), weight ratio | AL | AL | 8.42 | 8.58 | 8.53 | 0.23 | 0.25 | 3.97 |
| Acyclic (N5)/cyclic (<=N5), weight ratio | AL | — | 4.53 | AL | 6.19 | 10.77 | 11.11 | AL |
| Σ(N5)/Σ(N4), | 0.39 | 0 | 0.42 | 0.39 | 0.53 | — | — | 2.25 |

TABLE XX-continued

| Example No. | 187 | 188 | 189 | 190 | 191 | 192 | 193 | 194 |
|---|---|---|---|---|---|---|---|---|
| weight ratio | | | | | | | | |

AL = All linear

TABLE XXI

| Example No. | 195 | 196 | 197 | 198 | 199 |
|---|---|---|---|---|---|
| Catalyst Type | CC | CC | CC | CC | CC |
| Catalyst weight, gm | 132.3 | 132.3 | 132.3 | 132.3 | 132.3 |
| Pressure, psig | 600 | 600 | 600 | 600 | 600 |
| Temperature, °C. | 255.5 | 253.5 | 253.3 | 277.3 | 276.3 |
| Time on organics, hrs. | 5.5 | 22.2 | 24.2 | 29.7 | 46.5 |
| Duration of run, hrs. | 2 | 15.4 | 2 | 1.2 | 16 |
| MEA SV, gmol/hr/kgcat | 1.76 | 1.79 | 1.80 | 3.05 | 1.80 |
| $NH_3$ feedrate, gm/hr | 56 | 53 | 58 | 80 | 57.9 |
| Liquid feed composition, wt. % | | | | | |
| DETA | 77.16 | 77.16 | 77.16 | 77.16 | 77.16 |
| MEA | 22.84 | 22.84 | 22.84 | 22.84 | 22.84 |
| Liquid product composition, wt. % | | | | | |
| EDA | 0.72 | 0.57 | 0.61 | 4.72 | 5.56 |
| MeEDA | 0 | 0 | 0 | 0 | 0 |
| MEA | 19.39 | 18.82 | 18.97 | 10.58 | 10.88 |
| EtEDA | 0 | 0 | 0 | 0 | 0 |
| PIP | 0.58 | 0.75 | 0.78 | 4.57 | 5.28 |
| DETA | 74.48 | 72.48 | 73.22 | 60.61 | 57.25 |
| AEEA | 1.14 | 0.55 | 0 | 0 | 0 |
| AEP | 0.59 | 0.73 | 0.75 | 4.56 | 5.02 |
| HEP | 0 | 0 | 0 | 0 | 0 |
| TETA's | 3.51 | 4.43 | 4.30 | 8.20 | 8.44 |
| TEPA's | 0.74 | 1.50 | 1.20 | 4.98 | 5.47 |
| ROH Conversion % | 16.90 | 18.49 | 17.80 | 54.71 | 53.33 |
| Acyclic (N4)/cyclic (< =N4), weight ratio | AL | 14.38 | 14.15 | 1.84 | 1.69 |
| Acyclic (N5)/cyclic (< =N5), weight ratio | AL | AL | AL | 1.17 | 1.13 |
| $\Sigma(N5)/\Sigma(N4)$, weight ratio | — | — | — | — | — |

AL = All linear
AC = All cyclic

TABLE XXII

| Example No. | 200 | 201 | 202 | 203 | 204 | 205 | 206 | 207 | 208 | 209 | 210 | 211 |
|---|---|---|---|---|---|---|---|---|---|---|---|---|
| Catalyst Type | DD | DD | DD | DD | DD | DD | DD | DD | DD | DD | DD | DD |
| Catalyst weight, gm | 119.0 | 119.0 | 119.0 | 119.0 | 119.0 | 119.0 | 119.0 | 119.0 | 119.0 | 119.0 | 119.0 | 119.0 |
| Pressure, psig | 600 | 600 | 600 | 600 | 600 | 600 | 600 | 600 | 600 | 600 | 600 | 600 |
| Temperature, °C. | 256.8 | 262.3 | 258.5 | 277.3 | 280.8 | 280.8 | 280.8 | 255.8 | 274.8 | 280.3 | 280.0 | 259.0 |
| Time on organics, hrs. | 4.5 | 20.5 | 22.5 | 27.5 | 35.5 | 57.0 | 59.0 | 80.5 | 87.5 | 104.5 | 106.5 | 111.5 |
| Duration of run, hrs. | 2 | 16 | 2 | 2 | 1.5 | 21 | 2 | 20.7 | 2 | 16 | 2 | 2 |
| MEA SV, gmol/hr/kgcat | 1.77 | 1.92 | 1.93 | 1.93 | 1.92 | 1.67 | 1.60 | 1.71 | 1.64 | 1.66 | 1.72 | 1.90 |
| $NH_3$ feedrate, gm/hr | 70.0 | 65.8 | 53.0 | 61.5 | 50.6 | 55.5 | 51.0 | 55.1 | 57 | 56.1 | 58 | 74.5 |
| Liquid feed composition, wt. % | | | | | | | | | | | | |
| DETA | 77.16 | 77.16 | 77.16 | 77.16 | 77.16 | 66.46 | 66.46 | 66.46 | 66.46 | 66.46 | 66.46 | 66.46 |
| MEA | 22.84 | 22.84 | 22.84 | 22.84 | 22.84 | — | — | — | — | — | — | — |
| AEEA | — | — | — | — | — | 33.54 | 33.54 | 33.54 | 33.54 | 33.54 | 33.54 | 33.54 |
| Liquid product composition, wt. % | | | | | | | | | | | | |
| EDA | 0.44 | 0.46 | 0.48 | 2.39 | 5.14 | 4.62 | 4.73 | 0.69 | 3.82 | 4.27 | 4.42 | 0.75 |
| MeEDA | 0 | 0 | 0 | 0 | 0 | 0 | 0 | 0 | 0 | 0 | 0 | 0 |
| MEA | 17.17 | 16.69 | 16.56 | 11.29 | 8.13 | 0.93 | 0 | 0.35 | 0 | 0 | 0 | 18.51 |
| EtEDA | 0 | 0 | 0 | 0 | 0 | 0 | 0 | 0 | 0 | 0 | 0 | 0 |
| PIP | 0.62 | 0.74 | 0.75 | 2.63 | 4.42 | 9.83 | 10.45 | 5.60 | 9.71 | 10.22 | 10.06 | 1.17 |
| DETA | 71.04 | 70.74 | 70.92 | 64.82 | 58.99 | 58.30 | 57.95 | 64.75 | 60.92 | 58.93 | 58.24 | 68.48 |
| AEEA | 0.48 | 0.48 | 0.48 | 0.48 | 0.48 | 0.48 | 0.48 | 9.57 | 0 | 0 | 0 | 0.52 |
| AEP | 0.60 | 0.70 | 0.71 | 2.82 | 4.88 | 3.71 | 3.66 | 0.61 | 3.10 | 3.40 | 3.52 | 0.94 |
| HEP | 0 | 0 | 0 | 0 | 0 | 0 | 0 | 0 | 0 | 0 | 0 | 0 |
| TETA's | 5.44 | 5.34 | 6.10 | 9.66 | 10.38 | 9.60 | 9.73 | 4.33 | 9.27 | 10.07 | 10.19 | 6.01 |
| TEPA's | 1.89 | 2.14 | 2.19 | 4.62 | 5.30 | 8.66 | 9.12 | 11.34 | 8.91 | 8.88 | 9.52 | 3.26 |
| ROH Conversion % | 24.22 | 26.1# | 27.45 | 51.68 | 65.20 | 100.00 | 98.57 | 71.43 | 100.00 | 100.00 | 100.00 | 20.00 |
| Acyclic (N4)/cyclic (< =N4), weight ratio | AL | 20.27 | 18.61 | 2.93 | 2.23 | 0.39 | 0.33 | 0.13 | 0.30 | 0.33 | 0.38 | 9.99 |
| Acyclic (N5)/cyclic (< =N5), weight ratio | AL | AL | AL | 2.51 | 1.23 | 1.67 | 1.62 | 27.57 | 1.85 | 1.65 | 1.72 | 4.18 |
| $\Sigma(N5)/\Sigma(N4)$, | — | — | — | — | — | — | — | — | — | — | — | — |

TABLE XXII-continued

| Example No. | 200 | 201 | 202 | 203 | 204 | 205 | 206 | 207 | 208 | 209 | 210 | 211 |
|---|---|---|---|---|---|---|---|---|---|---|---|---|
| weight ratio | | | | | | | | | | | | |

TABLE XXIII

| Example No. | 212 | 213 | 214 | 215 | 216 | 217 | 218 | 219 | 220 | 221 |
|---|---|---|---|---|---|---|---|---|---|---|
| Catalyst Type | EE | EE | EE | EE | EE | EE | EE | EE | EE | EE |
| Catalyst weight, gm | 117.0 | 117.0 | 117.0 | 117.0 | 117.0 | 117.0 | 117.0 | 117.0 | 117.0 | 117.0 |
| Pressure, psig | 600 | 600 | 600 | 600 | 600 | 600 | 600 | 600 | 600 | 600 |
| Temperature, °C. | 263.3 | 264.5 | 264.5 | 282.3 | 283.0 | 283.8 | 283.3 | 277.5 | 282.8 | 262.8 |
| Time on organics, hrs. | 15 | 17 | 17 | 23 | 39 | 41 | 45 | 63.5 | 65.5 | 70.5 |
| Duration of run, hrs. | 14 | 2 | 2 | 2 | 15 | 2 | 2 | 17.5 | 2 | 2 |
| MEA SV, gmol/hr/kgcat | 1.80 | 1.87 | 1.68 | 1.74 | 1.82 | 1.76 | 1.60 | 1.57 | 1.58 | 1.66 |
| $NH_3$ feedrate, gm/hr | 69.3 | 61.0 | 61.0 | 107.5 | 66.8 | 61.5 | 62.0 | 53.2 | 60.5 | 70 |
| Liquid feed composition, wt. % | | | | | | | | | | |
| DETA | 77.16 | 77.16 | 77.16 | 77.16 | 77.16 | 77.16 | 66.46 | 66.46 | 66.46 | 66.46 |
| MEA | 22.84 | 22.84 | 22.84 | 22.84 | 22.84 | 22.84 | — | — | — | — |
| AEEA | — | — | — | — | — | — | 33.54 | 33.54 | 33.54 | 33.54 |
| Liquid product composition, wt. % | | | | | | | | | | |
| EDA | 0.34 | 0.33 | 0.31 | 1.45 | 1.71 | 1.75 | 2.27 | 2.48 | 2.68 | 0.50 |
| MeEDA | 0 | 0 | 0 | 0 | 0 | 0 | 0 | 0 | 0 | 0 |
| MEA | 19.00 | 19.14 | 18.85 | 13.73 | 13.66 | 13.73 | 1.37 | 0.78 | 0.82 | 0.68 |
| EtEDA | 0 | 0 | 0 | 0 | 0 | 0 | 0 | 0 | 0 | 0 |
| PIP | 0.45 | 0.45 | 0.44 | 1.77 | 2.06 | 2.14 | 6.70 | 6.85 | 7.15 | 3.16 |
| DETA | 74.32 | 74.61 | 74.55 | 69.65 | 68.47 | 68.83 | 64.69 | 61.15 | 60.88 | 66.11 |
| AEEA | 0.76 | 0.67 | 0.71 | 0.35 | 0.33 | 0.29 | 2.61 | 2.71 | 2.64 | 15.68 |
| AEP | 0.51 | 0.49 | 0.51 | 2.02 | 2.23 | 2.30 | 2.23 | 2.42 | 2.52 | 0.46 |
| HEP | 0 | 0 | 0 | 0 | 0 | 0 | 0.09 | 0.10 | 0.11 | 0.10 |
| TETA's | 3.45 | 3.22 | 3.39 | 6.74 | 6.78 | 6.65 | 7.65 | 8.09 | 8.08 | 5.03 |
| TEPA's | 1.05 | 0.96 | 1.09 | 3.63 | 3.95 | 3.89 | 9.99 | 10.75 | 10.78 | 7.59 |
| ROH Conversion % | 17.59 | 16.93 | 18.24 | 41.12 | 41.39 | 41.33 | 92.30 | 91.79 | 92.00 | 53.98 |
| Acyclic (N4)/cyclic (<=N4), weight ratio | 30.61 | 34.71 | 19.41 | 20.90 | 3.06 | 3.12 | 0.32 | 0.29 | 0.31 | 0.60 |
| Acyclic (N5)/cyclic (<=N5), weight ratio | AL | AL | AL | 1.83 | 1.60 | 1.53 | 1.98 | 1.79 | 1.77 | 19.83 |
| Σ(N5)/Σ(N4), weight ratio | 0.30 | 0.30 | 0.32 | 0.54 | 0.58 | 0.50 | — | — | — | — |

AL = All linear

TABLE XXIV

| Example No. | 222 | 223 | 224 | 225 | 226 | 227 | 228 | 229 | 230 | 231 |
|---|---|---|---|---|---|---|---|---|---|---|
| Catalyst Type | FF | FF | FF | FF | FF | FF | FF | FF | FF | FF |
| Catalyst weight, gm | 119.4 | 119.4 | 119.4 | 119.4 | 119.4 | 119.4 | 119.4 | 119.4 | 119.4 | 119.4 |
| Pressure, psig | 600 | 600 | 600 | 600 | 600 | 600 | 600 | 600 | 600 | 600 |
| Temperature, °C. | 232.8 | 230.0 | 231.8 | 248.5 | 244.0 | 247.3 | 248.8 | 250.5 | 249.5 | 230.3 |
| Time on organics, hrs. | 4.0 | 19.7 | 22.2 | 27.1 | 43.7 | 45.7 | 51.0 | 68.0 | 70 | 93 |
| Duration of run, hrs. | 2 | 15.7 | 2.6 | 2.2 | 15.7 | 2 | 2 | 16 | 2 | 21 |
| MEA SV, gmol/hr/kgcat | 1.95 | 1.85 | 1.96 | 1.68 | 1.71 | 1.79 | 1.54 | 1.49 | 1.64 | 1.63 |
| $NH_3$ feedrate, gm/hr | 59.0 | 52.1 | 74.8 | 63.8 | 54.2 | 65.5 | 54.0 | 55.6 | 59 | 73 |
| Liquid feed composition, wt. % | | | | | | | | | | |
| DETA | 77.16 | 77.16 | 77.16 | 77.16 | 77.16 | 77.16 | 66.46 | 66.46 | 66.46 | 66.46 |
| MEA | 22.84 | 22.84 | 22.84 | 22.84 | 22.84 | 22.84 | — | — | — | — |
| AEEA | — | — | — | — | — | — | 33.54 | 33.54 | 33.54 | 33.54 |
| Liquid product composition, wt. % | | | | | | | | | | |
| EDA | 1.32 | 1.44 | 1.38 | 4.97 | 4.71 | 4.33 | 3.75 | 4.12 | 4.10 | 0.88 |
| MeEDA | 0 | 0 | 0 | 0 | 0 | 0 | 0 | 0 | 0 | 0 |
| MEA | 22.49 | 22.38 | 23.57 | 16.24 | 15.26 | 16.13 | 0.96 | 0.79 | 0.89 | 0.46 |
| EtEDA | 0 | 0 | 0 | 0 | 0 | 0 | 0 | 0 | 0 | 0 |
| PIP | 0.15 | 0.16 | 0.15 | 0.66 | 0.70 | 0.68 | 4.48 | 4.55 | 4.47 | 1.85 |
| DETA | 71.90 | 71.93 | 72.75 | 66.24 | 65.86 | 67.79 | 65.70 | 65.25 | 63.53 | 66.74 |
| AEEA | 0 | 0 | 0 | 0 | 0 | 0 | 7.29 | 6.78 | 7.30 | 23.94 |
| AEP | 0.30 | 0.29 | 0.28 | 0.71 | 0.71 | 0.73 | 0.85 | 1.01 | 0.83 | 0.27 |
| HEP | 0 | 0 | 0 | 0 | 0 | 0 | 0 | 0 | 0 | 0 |
| TETA's | 1.74 | 1.84 | 1.76 | 4.20 | 4.28 | 4.17 | 4.03 | 4.23 | 4.21 | 1.31 |
| TEPA's | 0 | 0 | 0 | 1.02 | 1.00 | 1.02 | 5.49 | 5.53 | 6.01 | 3.03 |
| ROH Conversion % | 0.60 | 0.05 | 3.44 | 24.99 | 28.48 | 26.24 | 76.87 | 78.43 | | |
| MEA Conversion % | | | | | | | | | 76.53 | 28.00 |
| Acyclic (N4)/cyclic (<=N4), weight ratio | AL | AL | AL | 9.42 | 10.16 | 9.87 | 0.41 | 0.41 | 0.40 | 0.49 |
| Acyclic (N5)/cyclic (<=N5), weight ratio | — | — | — | 3.61 | 3.28 | 3.95 | 11.99 | 12.16 | 7.62 | AL |

TABLE XXIV-continued

| Example No. | 222 | 223 | 224 | 225 | 226 | 227 | 228 | 229 | 230 | 231 |
|---|---|---|---|---|---|---|---|---|---|---|
| Σ(N5)/Σ(N4), weight ratio | 0 | 0 | 0 | 0.24 | 0.23 | 0.24 | — | — | — | — |

AL = All linear

TABLE XXV

| Example No. | 232 | 233 | 234 | 235 | 236 | 237 | 238 | 239 | 240 |
|---|---|---|---|---|---|---|---|---|---|
| Catalyst Type | GG | GG | GG | GG | GG | GG | GG | GG | GG |
| Catalyst weight, gm | 71.7 | 71.7 | 71.7 | 71.7 | 71.7 | 71.7 | 71.7 | 71.7 | 71.7 |
| Pressure, psig | 600 | 600 | 600 | 600 | 600 | 600 | 600 | 600 | 600 |
| Temperature, °C. | 270 | 270 | 280 | 260 | 270 | 260 | 280 | 270 | 269.4 |
| Time on organics, hrs. | 5.5 | 24.0 | 29.5 | 48.5 | 53.5 | 72.0 | 77.5 | 93.0 | 94.0 |
| Duration of run, hrs. | 2 | 2 | 2 | 2 | 2 | 2 | 2 | 1 | 1 |
| MEA SV, gmol/hr/kgcat | 4.14 | 4.46 | 4.36 | 5.52 | 4.51 | 4.41 | 4.26 | 4.15 | 4.18 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.411 | 2.048 | 2.803 | 0.721 | 0.985 | 0.509 | 2.082 | 1.210 | 1.044 |
| MEA | 16.945 | 15.112 | 10.441 | 24.560 | 21.874 | 32.907 | 18.277 | 27.514 | 28.346 |
| PIP | 1.144 | 1.466 | 1.969 | 0.566 | 0.916 | 0.444 | 1.962 | 1.108 | 1.004 |
| DETA | 51.236 | 51.808 | 51.005 | 56.963 | 56.336 | 50.564 | 48.639 | 48.512 | 49.317 |
| AEEA | 1.633 | 0.750 | 0.471 | 2.854 | 1.334 | 3.313 | 0.761 | 3.022 | 2.993 |
| AEP | 1.408 | 1.792 | 2.383 | 0.570 | 0.907 | 0.527 | 2.313 | 1.179 | 1.053 |
| HEP | 0.000 | 0.000 | 0.000 | 0.000 | 0.000 | 0.000 | 0.000 | 0.000 | 0.000 |
| TAEA | 0.906 | 1.541 | 1.048 | 0.803 | 0.704 | 0.531 | 0.684 | 0.714 | 0.712 |
| 1-TETA | 10.823 | 10.188 | 9.970 | 6.179 | 6.720 | 4.624 | 7.721 | 6.104 | 5.767 |
| DAEP | 0.338 | 0.535 | 0.797 | 0.105 | 0.195 | 0.111 | 0.723 | 0.309 | 0.262 |
| PEEDA | 0.223 | 0.461 | 0.644 | 0.087 | 0.173 | 0.000 | 0.675 | 0.341 | 0.227 |
| DPE | 0.000 | 0.000 | 0.111 | 0.000 | 0.000 | 0.000 | 0.110 | 0.067 | 0.000 |
| AE-TAEA | 1.379 | 1.180 | 1.543 | 0.441 | 0.741 | 0.374 | 1.397 | 0.543 | 0.462 |
| 1-TEPA | 4.588 | 3.926 | 4.570 | 1.388 | 1.867 | 0.952 | 3.120 | 1.724 | 1.606 |
| AE-DAEP | 0.244 | 0.289 | 0.620 | 0.000 | 0.100 | 0.000 | 0.570 | 0.111 | 0.092 |
| AE-PEEDA | 0.105 | 0.109 | 0.209 | 0.000 | 0.00 | 0.00 | 0.260 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.173 | 0.272 | 0.386 | 0.000 | 0.073 | 0.000 | 0.000 | 0.121 | 0.081 |
| Others | 0.204 | 1.075 | 1.532 | 0.612 | 0.554 | 0.444 | 1.746 | 1.371 | 1.233 |
| MEA Conversion, % | 53.39 | 58.54 | 71.07 | 33.10 | 39.32 | 8.35 | 48.80 | 23.43 | 21.10 |
| DETA Conversion, % | 16.24 | 15.52 | 16.01 | 7.78 | 7.12 | 16.31 | 19.02 | 19.77 | 18.42 |
| Acyclic(N4), % | 95.43 | 92.18 | 87.66 | 97.32 | 95.28 | 97.90 | 84.79 | 90.50 | 92.98 |
| Acyclic(N5), % | 91.95 | 88.40 | 83.42 | 100.00 | 93.78 | 100.00 | 84.48 | 90.71 | 92.29 |
| Σ(N5)/Σ(N4), weight ratio | 0.53 | 0.45 | 0.58 | 0.25 | 0.36 | 0.25 | 0.54 | 0.33 | 0.32 |
| Acyclic(N4)/cyclic (<=N4), weight ratio | 3.77 | 2.76 | 1.87 | 5.26 | 3.39 | 4.77 | 1.45 | 2.27 | 2.54 |

TABLE XXVI

| Example No. | 241 | 242 | 243 | 244 | 245 | 246 | 247 | 248 | 249 |
|---|---|---|---|---|---|---|---|---|---|
| Catalyst Type | HH | HH | HH | HH | HH | HH | HH | HH | HH |
| Catalyst weight, gm | 73 | 73 | 73 | 73 | 73 | 73 | 73 | 73 | 73 |
| Pressure, psig | 600 | 600 | 600 | 600 | 600 | 600 | 600 | 600 | 600 |
| Temperature, °C. | 267.3 | 271.6 | 280.3 | 269.1 | 261.9 | 278.4 | 268.9 | 268.5 | |
| Time on organics, hrs. | 6.5 | 25.5 | 30.5 | 49.5 | 54.5 | 73.5 | 78.5 | 97.0 | 99.2 |
| Duration of run, hrs. | 2 | 2 | 2 | 2 | 2 | 2 | 2 | 2 | 2 |
| MEA SV, gmol/hr/kgcat | 3.79 | 3.55 | 3.59 | 3.31 | 3.30 | 3.15 | 3.16 | 2.93 | 3.01 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.819 | 1.510 | 2.684 | 0.504 | 1.224 | 0.583 | 2.338 | 1.353 | 1.183 |
| MEA | 19.544 | 21.769 | 15.677 | 27.977 | 25.881 | 29.371 | 18.842 | 24.539 | 25.072 |
| PIP | 2.131 | 1.958 | 2.907 | 0.791 | 1.591 | 0.810 | 2.955 | 1.830 | 1.645 |
| DETA | 50.736 | 54.179 | 44.864 | 59.947 | 57.394 | 60.159 | 52.360 | 57.664 | 58.300 |
| AEEA | 1.308 | 1.561 | 0.890 | 1.790 | 1.759 | 1.755 | 1.156 | 1.824 | 1.888 |
| AEP | 2.087 | 1.610 | 2.837 | 0.614 | 0.959 | 0.559 | 2.442 | 1.151 | 1.012 |
| HEP | 0.000 | 0.000 | 0.000 | 0.000 | 0.000 | 0.000 | 0.000 | 0.000 | 0.000 |
| TAEA | 0.474 | 0.468 | 0.382 | 0.280 | 0.349 | 0.222 | 0.415 | 0.272 | 0.294 |
| 1-TETA | 7.326 | 7.199 | 7.828 | 4.424 | 5.292 | 3.705 | 7.135 | 5.363 | 5.018 |
| DAEP | 0.724 | 0.483 | 1.000 | 0.210 | 0.231 | 0.161 | 0.542 | 0.359 | 9.292 |
| PEEDA | 0.625 | 0.332 | 1.108 | 0.086 | 0.180 | 0.101 | 0.599 | 0.000 | 0.173 |
| DPE | 0.419 | 0.000 | 0.165 | 0.000 | 0.000 | 0.000 | 0.000 | 0.161 | 0.000 |
| AE-TAEA | 0.941 | 0.687 | 1.356 | 0.000 | 0.305 | 0.000 | 0.786 | 1.117 | 0.287 |
| 1-TEPA | 3.854 | 2.896 | 4.945 | 0.160 | 0.979 | 0.000 | 3.242 | 0.000 | 0.839 |
| AE-DAEP | 0.454 | 0.209 | 0.781 | 0.000 | 0.000 | 0.000 | 0.386 | 0.000 | 0.000 |
| AE-PEEDA | 0.243 | 0.101 | 1.082 | 0.000 | 0.000 | 0.000 | 0.209 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.138 | 0.000 | 0.372 | 0.000 | 0.000 | 0.000 | 0.000 | 0.000 | 0.000 |

TABLE XXVI-continued

| Example No. | 241 | 242 | 243 | 244 | 245 | 246 | 247 | 248 | 249 |
|---|---|---|---|---|---|---|---|---|---|
| BPEA | 0.000 | 0.000 | 0.648 | 0.000 | 0.000 | 0.000 | 0.000 | 0.656 | 0.000 |
| Others | 1.377 | 0.788 | 3.906 | 0.418 | 0.685 | 0.294 | 1.783 | 0.000 | 0.667 |
| MEA Conversion, % | 47.04 | 41.40 | 57.92 | 24.31 | 30.19 | 20.72 | 49.47 | 33.74 | 32.35 |
| DETA Conversion, % | 18.29 | 13.32 | 28.42 | 3.61 | 7.99 | 3.49 | 16.55 | 7.46 | 6.51 |
| Acyclic(N4), % | 81.52 | 90.39 | 78.32 | 94.08 | 93.21 | 93.74 | 86.87 | 91.55 | 91.94 |
| Acyclic(N5), % | 85.16 | 92.04 | 68.62 | 100.00 | 100.00 | 0.00 | 87.13 | 62.99 | 100.00 |
| $\Sigma(N5)/\Sigma(N4)$, weight ratio | 0.59 | 0.46 | 0.88 | 0.03 | 0.21 | 0.00 | 0.53 | 0.29 | 0.19 |
| Acyclic(N4)/cyclic ($<=$N4), weight ratio | 1.30 | 1.75 | 1.02 | 2.77 | 1.91 | 2.41 | 1.15 | 1.61 | 1.70 |

TABLE XXVII

| Example No. | 250 | 251 | 252 | 253 | 254 | 255 | 256 | 257 | 258 |
|---|---|---|---|---|---|---|---|---|---|
| Catalyst Type | II | II | II | II | II | II | II | II | II |
| Catalyst weight, gm | 81.2 | 81.2 | 81.2 | 81.2 | 81.2 | 81.2 | 81.2 | 81.2 | 81.2 |
| Pressure, psig | 600 | 600 | 600 | 600 | 600 | 600 | 600 | 600 | 600 |
| Temperature, °C. | 274.4 | 274.4 | 280.9 | 259.8 | 270.6 | 259.9 | 281.6 | 270.4 | 270.4 |
| Time on organics, hrs. | 22.0 | 26.0 | 45.5 | 50.5 | 69.0 | 74.5 | 95.0 | 119.0 | 120.0 |
| Duration of run, hrs. | 2 | 2 | 2 | 2 | 2 | 2 | 2 | 1 | 1 |
| MEA SV, gmol/hr/kgcat | 2.91 | 2.63 | 2.50 | 2.66 | 2.59 | 2.54 | 1.88 | 5.74 | 2.90 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.736 | 1.042 | 2.004 | 0.059 | 0.914 | 0.285 | 2.016 | 0.695 | 0.525 |
| MEA | 21.698 | 25.193 | 18.576 | 29.894 | 25.669 | 27.372 | 16.604 | 25.555 | 23.517 |
| PIP | 0.596 | 0.702 | 1.478 | 0.343 | 0.603 | 0.232 | 1.461 | 0.441 | 0.380 |
| DETA | 56.344 | 55.631 | 51.168 | 57.632 | 56.035 | 63.408 | 49.886 | 55.967 | 57.620 |
| AEEA | 3.232 | 3.031 | 2.286 | 2.679 | 3.151 | 1.296 | 2.181 | 2.896 | 3.070 |
| AEP | 0.919 | 0.802 | 1.485 | 0.437 | 0.730 | 0.367 | 1.549 | 0.662 | 0.582 |
| HEP | 0.000 | 0.000 | 0.000 | 0.000 | 0.000 | 0.000 | 0.000 | 0.000 | 0.000 |
| TAEA | 1.205 | 1.108 | 1.349 | 0.407 | 0.739 | 0.402 | 1.529 | 0.684 | 0.604 |
| 1-TETA | 7.587 | 6.573 | 10.443 | 4.085 | 6.496 | 2.782 | 9.613 | 6.122 | 6.727 |
| DAEP | 0.164 | 0.130 | 0.275 | 0.056 | 0.100 | 0.000 | 0.490 | 0.102 | 0.089 |
| PEEDA | 0.116 | 0.097 | 0.252 | 0.036 | 0.072 | 0.138 | 0.496 | 0.074 | 0.057 |
| DPE | 0.000 | 0.000 | 0.000 | 0.000 | 0.030 | 0.101 | 0.040 | 0.044 | 0.066 |
| AE-TAEA | 0.283 | 0.253 | 0.369 | 0.000 | 0.132 | 0.000 | 0.958 | 0.123 | 0.173 |
| 1-TEPA | 0.935 | 0.989 | 2.771 | 0.078 | 0.737 | 0.000 | 3.253 | 0.664 | 0.581 |
| AE-DAEP | 0.000 | 0.000 | 0.161 | 0.000 | 0.000 | 0.000 | 0.196 | 0.075 | 0.000 |
| AE-PEEDA | 0.000 | 0.000 | 0.125 | 0.000 | 0.000 | 0.000 | 0.156 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 0.666 | 0.639 | 1.229 | 1.336 | 0.741 | 0.467 | 2.672 | 0.616 | 0.819 |
| MEA Conversion, % | 39.80 | 31.57 | 49.29 | 18.66 | 30.14 | 25.57 | 54.52 | 29.35 | 35.28 |
| DETA Conversion, % | 8.23 | 10.19 | 16.98 | 6.80 | 9.36 | 2.48 | 18.80 | 8.04 | 5.76 |
| Acyclic(N4), % | 96.92 | 97.13 | 95.72 | 98.01 | 97.29 | 93.00 | 91.57 | 96.87 | 97.18 |
| Acyclic(N5), % | 100.00 | 100.00 | 91.66 | 100.00 | 100.00 | 0.00 | 92.28 | 91.26 | 100.00 |
| $\Sigma(N5)/\Sigma(N4)$, weight ratio | 0.13 | 0.16 | 0.28 | 0.02 | 0.12 | 0.00 | 0.38 | 0.12 | 0.10 |
| Acyclic(N4)/cyclic ($<=$N4), weight ratio | 4.90 | 4.44 | 3.38 | 5.16 | 4.71 | 3.80 | 2.76 | 5.14 | 6.24 |

TABLE XXVIII

| Example No. | 259 | 260 | 261 | 262 | 263 | 264 | 265 | 266 | 267 |
|---|---|---|---|---|---|---|---|---|---|
| Catalyst Type | JJ | JJ | JJ | JJ | JJ | JJ | JJ | JJ | JJ |
| Catalyst weight, gm | 70.6 | 70.6 | 70.6 | 70.6 | 70.6 | 70.6 | 70.6 | 70.6 | 70.6 |
| Pressure, psig | 600 | 600 | 600 | 600 | 600 | 600 | 600 | 600 | 600 |
| Temperature, °C. | 267.9 | 267.8 | 277.8 | 259.9 | 270.1 | 259.9 | 280.1 | 269.6 | 269 |
| Time on organics, hrs. | 5.0 | 7.5 | 26.0 | 31.5 | 50.0 | 55.5 | 74.0 | 78.0 | 80.0 |
| Duration of run, hrs. | 1 | 1 | 2 | 2 | 2 | 2 | 2 | 2 | 1.5 |
| MEA SV, gmol/hr/kgcat | 7.43 | 7.71 | 3.35 | 3.61 | 3.27 | 3.62 | 3.67 | 3.54 | 3.54 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.791 | 0.623 | 1.276 | 0.399 | 0.923 | 0.398 | 1.559 | 0.813 | 0.864 |
| MEA | 26.509 | 30.058 | 23.663 | 33.991 | 28.444 | 31.796 | 22.071 | 26.996 | 27.146 |
| PIP | 1.147 | 0.517 | 1.058 | 0.224 | 0.638 | 0.217 | 1.106 | 0.510 | 0.513 |
| DETA | 47.682 | 54.106 | 51.834 | 56.779 | 55.100 | 57.812 | 53.839 | 55.907 | 56.086 |
| AEEA | 0.876 | 3.177 | 3.108 | 1.987 | 3.003 | 2.067 | 1.970 | 2.801 | 2.726 |
| AEP | 1.015 | 0.506 | 1.073 | 0.246 | 0.586 | 0.243 | 0.935 | 0.458 | 0.457 |
| HEP | 0.000 | 0.000 | 0.000 | 0.000 | 0.000 | 0.000 | 0.000 | 0.000 | 0.000 |
| TAEA | 1.944 | 0.557 | 0.833 | 0.309 | 0.576 | 0.340 | 0.831 | 0.577 | 0.572 |
| 1-TETA | 9.028 | 4.870 | 7.412 | 2.839 | 4.781 | 2.784 | 7.153 | 4.597 | 4.540 |
| DAEP | 0.183 | 0.000 | 0.187 | 0.000 | 0.086 | 0.000 | 0.082 | 0.095 | 0.087 |
| PEEDA | 0.136 | 0.000 | 0.165 | 0.000 | 0.000 | 0.000 | 0.169 | 0.000 | 0.069 |

TABLE XXVIII-continued

| Example No. | 259 | 260 | 261 | 262 | 263 | 264 | 265 | 266 | 267 |
|---|---|---|---|---|---|---|---|---|---|
| DPE | 0.000 | 0.000 | 0.000 | 0.000 | 0.000 | 0.000 | 0.000 | 0.000 | 0.000 |
| AE-TAEA | 1.392 | 0.209 | 0.543 | 0.000 | 0.357 | 0.119 | 0.545 | 0.238 | 0.228 |
| 1-TEPA | 2.723 | 0.634 | 2.000 | 0.109 | 0.910 | 0.179 | 1.995 | 0.719 | 0.686 |
| AE-DAEP | 0.000 | 0.000 | 0.000 | 0.000 | 0.000 | 0.000 | 0.000 | 0.000 | 0.000 |
| AE-PEEDA | 0.000 | 0.000 | 0.000 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.194 | 0.000 | 0.000 |
| Others | 0.293 | 0.493 | 0.939 | 0.196 | 0.758 | 0.426 | 1.662 | 0.989 | 1.025 |
| MEA Conversion, % | 26.38 | 17.06 | 34.61 | 6.67 | 22.13 | 12.36 | 39.22 | 25.04 | 24.86 |
| DETA Conversion, % | 21.30 | 11.27 | 14.88 | 7.35 | 10.35 | 5.30 | 11.85 | 7.74 | 7.73 |
| Acyclic(N4), % | 97.18 | 100.00 | 95.91 | 100.00 | 98.42 | 100.00 | 96.96 | 98.19 | 97.83 |
| Acyclic(N5), % | 100.00 | 100.00 | 100.00 | 100.00 | 100.00 | 100.00 | 92.92 | 100.00 | 100.00 |
| Σ(N5)/Σ(N4), weight ratio | 0.36 | 0.16 | 0.30 | 0.03 | 0.23 | 0.10 | 0.33 | 0.18 | 0.17 |
| Acyclic(N4)/cyclic (<=N4), weight ratio | 4.42 | 5.30 | 3.32 | 6.42 | 4.09 | 6.79 | 3.48 | 4.87 | 4.54 |

TABLE XXIX

| Example No. | 268 | 269 | 270 | 271 | 272 | 273 | 274 | 275 | 276 |
|---|---|---|---|---|---|---|---|---|---|
| Catalyst Type | KK | KK | KK | KK | KK | KK | KK | KK | KK |
| Catalyst weight, gm | 75.7 | 75.7 | 75.7 | 75.7 | 75.7 | 75.7 | 75.7 | 75.7 | 75.7 |
| Pressure, psig | 600 | 600 | 600 | 600 | 600 | 600 | 600 | 600 | 600 |
| Temperature, °C. | 269.6 | 272.7 | 279.9 | 260.3 | 268.3 | 261.4 | 278.9 | 270.6 | 271.7 |
| Time on organics, hrs. | 7.5 | 26.0 | 31.0 | 47.0 | 53.0 | 58.5 | 73.0 | 78.0 | 80.0 |
| Duration of run, hrs. | 2 | 2 | 2 | 2 | 2 | 2.5 | 2 | 2 | 2 |
| MEA SV, gmol/hr/kgcat | 3.78 | 3.60 | 4.14 | 2.88 | 4.21 | 4.57 | 4.11 | 4.29 | 4.20 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.512 | 2.957 | 2.611 | 0.873 | 1.230 | 0.581 | 2.105 | 1.136 | 1.147 |
| MEA | 19.636 | 15.858 | 13.674 | 24.751 | 22.713 | 28.289 | 17.328 | 24.549 | 24.295 |
| PIP | 0.850 | 1.545 | 1.281 | 0.362 | 0.559 | 0.213 | 0.983 | 0.499 | 0.466 |
| DETA | 53.823 | 48.802 | 49.039 | 57.674 | 55.152 | 58.393 | 51.571 | 56.716 | 56.142 |
| AEEA | 1.077 | 0.809 | 1.020 | 2.059 | 1.793 | 1.783 | 1.230 | 1.886 | 1.876 |
| AEP | 0.980 | 2.034 | 1.569 | 0.409 | 0.641 | 0.321 | 1.189 | 0.550 | 0.582 |
| HEP | 0.000 | 0.000 | 0.000 | 0.000 | 0.000 | 0.000 | 0.000 | 0.000 | 0.000 |
| TAEA | 1.511 | 1.463 | 1.689 | 0.877 | 1.037 | 0.668 | 1.665 | 0.917 | 0.952 |
| 1-TETA | 9.931 | 10.166 | 10.473 | 6.953 | 8.198 | 5.375 | 10.489 | 7.020 | 7.339 |
| DAEP | 0.209 | 0.694 | 0.560 | 0.075 | 0.134 | 0.000 | 0.248 | 0.095 | 0.105 |
| PEEDA | 0.118 | 0.559 | 0.497 | 0.000 | 0.091 | 0.000 | 0.182 | 0.000 | 0.067 |
| DPE | 0.000 | 0.157 | 0.076 | 0.000 | 0.000 | 0.000 | 0.068 | 0.000 | 0.000 |
| AE-TAEA | 1.152 | 1.307 | 1.509 | 0.447 | 0.967 | 0.273 | 1.060 | 0.599 | 0.651 |
| 1-TEPA | 2.758 | 3.629 | 3.880 | 0.863 | 1.812 | 0.388 | 3.088 | 0.995 | 1.169 |
| AE-DAEP | 0.000 | 0.343 | 0.336 | 0.000 | 0.000 | 0.000 | 0.222 | 0.000 | 0.000 |
| AE-PEEDA | 0.000 | 0.145 | 0.157 | 0.000 | 0.000 | 0.000 | 0.112 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.334 | 0.000 | 0.000 | 0.000 | 0.000 | 0.000 | 0.000 |
| BPEA | 0.000 | 0.099 | 0.291 | 0.000 | 0.000 | 0.000 | 0.106 | 0.000 | 0.000 |
| Others | 1.043 | 2.132 | 3.402 | 0.377 | 0.694 | 0.316 | 1.555 | 0.738 | 0.659 |
| MEA Conversion, % | 46.54 | 56.52 | 62.58 | 32.37 | 37.89 | 22.83 | 52.40 | 32.99 | 33.57 |
| DETA Conversion, % | 12.92 | 20.49 | 20.25 | 6.35 | 10.36 | 5.33 | 15.81 | 7.99 | 8.76 |
| Acyclic(N4), % | 97.22 | 89.18 | 91.48 | 99.05 | 97.62 | 100.00 | 96.06 | 98.82 | 97.97 |
| Acyclic(N5), % | 100.00 | 89.36 | 82.82 | 100.00 | 100.00 | 100.00 | 90.40 | 100.00 | 100.00 |
| Σ(N5)/Σ(N4), weight ratio | 0.33 | 0.42 | 0.49 | 0.17 | 0.29 | 0.11 | 0.36 | 0.20 | 0.22 |
| Acyclic(N4)/cyclic (<=N4), weight ratio | 5.31 | 2.33 | 3.05 | 9.26 | 6.48 | 11.31 | 4.55 | 6.94 | 6.80 |

TABLE XXX

| Example No. | 277 | 278 | 279 | 280 | 281 | 282 | 283 | 284 | 285 |
|---|---|---|---|---|---|---|---|---|---|
| Catalyst Type | LL | LL | LL | LL | LL | LL | LL | LL | LL |
| Catalyst weight, gm | 70.6 | 70.6 | 70.6 | 70.6 | 70.6 | 70.6 | 70.6 | 70.6 | 70.6 |
| Pressure, psig | 590 | 600 | 600 | 600 | 600 | 600 | 600 | 600 | 600 |
| Temperature, °C. | 267.9 | 267.8 | 277.8 | 259.9 | 270.1 | 259.9 | 280.1 | 269.6 | 269 |
| Time on organics, hrs. | 5.0 | 7.5 | 26.0 | 31.5 | 50.0 | 55.5 | 74.0 | 78.0 | 80.0 |
| Duration of run, hrs. | 1 | 1 | 2 | 2 | 2 | 2 | 2 | 2 | 1.5 |
| MEA SV, gmol/hr/kgcat | 0.39 | 8.50 | 4.10 | 4.26 | 3.89 | 4.41 | 4.10 | 4.07 | 4.13 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.167 | 2.266 | 4.396 | 1.162 | 2.491 | 1.273 | 4.640 | 2.530 | 2.433 |
| MEA | 28.978 | 28.688 | 26.446 | 33.928 | 28.222 | 33.924 | 23.574 | 29.868 | 29.121 |
| PIP | 0.494 | 0.372 | 0.461 | 0.092 | 0.207 | 0.083 | 0.544 | 0.212 | 0.203 |
| DETA | 48.084 | 52.021 | 51.406 | 57.383 | 55.479 | 56.855 | 50.221 | 53.418 | 55.210 |

TABLE XXX-continued

| Example No. | 277 | 278 | 279 | 280 | 281 | 282 | 283 | 284 | 285 |
|---|---|---|---|---|---|---|---|---|---|
| AEEA | 1.425 | 1.525 | 1.038 | 1.006 | 1.321 | 1.043 | 1.027 | 1.313 | 1.296 |
| AEP | 0.568 | 0.441 | 0.564 | 0.230 | 0.352 | 0.215 | 0.561 | 0.299 | 0.305 |
| HEP | 0.000 | 0.000 | 0.000 | 0.000 | 0.000 | 0.000 | 0.000 | 0.000 | 0.000 |
| TAEA | 0.506 | 0.561 | 0.265 | 0.113 | 0.219 | 0.139 | 0.375 | 0.264 | 0.266 |
| 1-TETA | 7.871 | 6.131 | 3.828 | 1.714 | 4.080 | 1.741 | 5.218 | 3.019 | 3.221 |
| DAEP | 0.101 | 0.000 | 0.095 | 0.124 | 0.000 | 0.000 | 0.085 | 0.000 | 0.000 |
| PEEDA | 0.100 | 0.080 | 0.203 | 0.117 | 0.000 | 0.093 | 0.111 | 0.114 | 0.072 |
| DPE | 0.117 | 0.000 | 0.254 | 0.107 | 0.132 | 0.000 | 0.309 | 0.118 | 0.097 |
| AE-TAEA | 0.530 | 0.252 | 0.150 | 0.000 | 0.133 | 0.000 | 0.191 | 0.000 | 0.000 |
| 1-TEPA | 1.837 | 0.607 | 0.160 | 0.000 | 0.131 | 0.000 | 0.719 | 0.000 | 0.000 |
| AE-DAEP | 0.100 | 0.000 | 0.000 | 0.000 | 0.000 | 0.000 | 0.112 | 0.000 | 0.000 |
| AE-PEEDA | 0.000 | 0.157 | 0.147 | 0.000 | 0.000 | 0.000 | 0.178 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.101 | 0.093 |
| BPEA | 0.000 | 0.000 | 0.000 | 0.000 | 0.000 | 0.000 | 0.000 | 0.000 | 0.000 |
| Others | 2.103 | 1.740 | 5.237 | 1.773 | 2.532 | 1.674 | 5.777 | 2.917 | 2.755 |
| MEA Conversion, % | 19.77 | 20.18 | 26.43 | 7.46 | 21.73 | 6.67 | 34.14 | 15.86 | 18.88 |
| DETA Conversion, % | 20.89 | 13.97 | 15.01 | 6.98 | 8.55 | 7.04 | 16.62 | 10.56 | 8.60 |
| Acyclic(N4), % | 96.35 | 98.82 | 88.13 | 84.00 | 97.03 | 95.30 | 91.72 | 93.42 | 95.39 |
| Acyclic(N5), % | 95.93 | 84.54 | 67.84 | 0.00 | 100.00 | 0.00 | 75.87 | 0.00 | 0.00 |
| Σ(N5)/Σ(N4), weight ratio | 0.28 | 0.15 | 0.10 | 0.00 | 0.06 | 0.00 | 0.20 | 0.03 | 0.03 |
| Acyclic(N4)/cyclic (<=N4), weight ratio | 6.07 | 7.50 | 2.60 | 2.72 | 6.22 | 4.81 | 3.47 | 4.42 | 5.16 |

TABLE XXXI

| Example No. | 286 | 287 | 288 | 289 | 290 | 291 | 292 | 293 | 294 |
|---|---|---|---|---|---|---|---|---|---|
| Catalyst Type | MM | MM | MM | MM | MM | MM | MM | MM | MM |
| Catalyst weight, gm | 80.1 | 80.1 | 80.1 | 80.1 | 80.1 | 80.1 | 80.1 | 80.1 | 80.1 |
| Pressure, psig | 600 | 600 | 600 | 600 | 600 | 600 | 600 | 600 | 600 |
| Temperature, °C. | 270.1 | 270 | 280.2 | 259.7 | 270.1 | 259.6 | 280 | 270 | 270 |
| Time on organics, hrs. | 5.0 | 7.5 | 26.5 | 31.5 | 49.7 | 54.0 | 74.0 | 77.5 | 80.0 |
| Duration of run, hrs. | 2 | 2 | 2 | 2 | 2 | 2 | 2 | 2 | 2 |
| MEA SV, gmol/hr/kgcat | 3.81 | 3.85 | 3.23 | 4.01 | 3.93 | 4.12 | 3.71 | 3.87 | 3.79 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.935 | 2.148 | 4.938 | 0.907 | 1.895 | 0.879 | 4.006 | 2.166 | 1.951 |
| MEA | 18.750 | 21.318 | 20.112 | 30.534 | 28.213 | 31.731 | 24.388 | 29.089 | 28.221 |
| PIP | 0.553 | 0.373 | 0.726 | 0.053 | 0.150 | 0.043 | 0.410 | 0.190 | 0.179 |
| DETA | 59.396 | 52.368 | 51.336 | 60.802 | 57.134 | 60.506 | 53.455 | 57.017 | 58.930 |
| AEEA | 0.561 | 0.915 | 0.707 | 0.796 | 1.023 | 0.782 | 0.908 | 1.152 | 1.167 |
| AEP | 0.744 | 0.572 | 0.748 | 0.309 | 0.383 | 0.307 | 0.625 | 0.384 | 0.410 |
| HEP | 0.000 | 0.000 | 0.000 | 0.000 | 0.000 | 0.000 | 0.000 | 0.000 | 0.000 |
| TAEA | 1.214 | 1.199 | 0.429 | 0.429 | 0.192 | 0.365 | 0.366 | 0.265 | 0.266 |
| 1-TETA | 9.307 | 8.213 | 5.708 | 1.341 | 2.861 | 1.182 | 4.049 | 2.751 | 2.937 |
| DAEP | 0.134 | 0.098 | 0.388 | 0.083 | 0.164 | 0.000 | 0.099 | 0.107 | 0.177 |
| PEEDA | 0.113 | 0.091 | 0.487 | 0.000 | 0.168 | 0.097 | 0.310 | 0.113 | 0.134 |
| DPE | 0.111 | 0.074 | 0.489 | 0.000 | 0.145 | 0.000 | 0.313 | 0.141 | 0.126 |
| AE-TAEA | 0.592 | 0.135 | 0.282 | 0.140 | 0.151 | 0.000 | 0.279 | 0.118 | 0.152 |
| 1-TEPA | 2.145 | 1.256 | 0.907 | 0.000 | 0.116 | 0.111 | 0.000 | | |
| AE-DAEP | 0.105 | 0.097 | 0.165 | 0.000 | 0.000 | 0.000 | 0.000 | 0.000 | 0.000 |
| AE-PEEDA | 0.221 | 0.227 | 0.312 | 0.000 | 0.000 | 0.000 | 0.129 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 7.869 | 5.765 | 6.160 | 1.656 | 2.354 | 1.509 | 5.848 | 2.786 | 2.669 |
| MEA Conversion, % | 49.20 | 41.78 | 44.57 | 16.55 | 21.53 | 13.41 | 32.99 | 20.19 | 23.49 |
| DETA Conversion, % | 18.85 | 15.01 | 15.92 | 1.24 | 5.56 | 1.86 | 12.71 | 7.03 | 5.05 |
| Acyclic(N4), % | 96.71 | 97.29 | 81.81 | 95.55 | 86.50 | 94.12 | 85.94 | 89.31 | 88.02 |
| Acyclic(N5), % | 89.37 | 81.10 | 67.94 | 100.00 | 100.00 | 0.00 | 75.42 | 100.00 | 100.00 |
| Σ(N5)/Σ(N4), weight ratio | 0.28 | 0.18 | 0.23 | 0.08 | 0.08 | 0.00 | 0.10 | 0.07 | 0.04 |
| Acyclic(N4)/cyclic (<=N4), weight ratio | 6.36 | 7.80 | 2.16 | 3.98 | 3.03 | 3.47 | 2.51 | 3.23 | 3.12 |

TABLE XXXII

| Example No. | 295 | 296 | 297 | 298 | 299 | 300 | 301 | 302 | 303 |
|---|---|---|---|---|---|---|---|---|---|
| Catalyst Type | NN | NN | NN | NN | NN | NN | NN | NN | NN |
| Catalyst weight, gm | 81.2 | 81.2 | 81.2 | 81.2 | 81.2 | 81.2 | 81.2 | 81.2 | 81.2 |
| Pressure, psig | 600 | 600 | 600 | 600 | 600 | 600 | 600 | 600 | 600 |
| Temperature, °C. | 269.9 | 272.7 | 279.9 | 260.3 | 268.3 | 261.4 | 278.9 | 270.6 | 271.7 |
| Time on organics, hrs. | 7.5 | 26.0 | 31.0 | 47.0 | 53.0 | 58.5 | 73.0 | 78.0 | 80.0 |
| Duration of run, hrs. | 2 | 2 | 2 | 2 | 2 | 2.5 | 2 | 2 | 2 |
| MEA SV, gmol/hr/kgcat | 3.80 | 3.43 | 3.59 | 3.68 | 3.75 | 4.01 | 3.56 | 3.87 | 3.87 |
| DETA/MEA mole ratio | 1.00 | 1.00 | 1.00 | 1.00 | 1.00 | 1.00 | 1.00 | 1.00 | 1.00 |

TABLE XXXII-continued

| Example No. | 295 | 296 | 297 | 298 | 299 | 300 | 301 | 302 | 303 |
|---|---|---|---|---|---|---|---|---|---|
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.775 | 2.809 | 2.208 | 1.431 | 2.058 | 0.987 | 4.151 | 1.948 | 1.942 |
| MEA | 28.020 | 25.978 | 11.404 | 32.207 | 28.431 | 31.510 | 25.905 | 30.029 | 29.693 |
| PIP | 0.108 | 0.150 | 0.000 | 0.069 | 0.120 | 0.040 | 0.254 | 0.118 | 0.112 |
| DETA | 59.798 | 58.058 | 46.899 | 58.424 | 57.923 | 59.289 | 52.433 | 57.883 | 58.062 |
| AEEA | 0.541 | 0.675 | 1.138 | 0.696 | 0.890 | 0.677 | 0.840 | 0.882 | 0.858 |
| AEP | 0.313 | 0.348 | 1.766 | 0.248 | 0.320 | 0.252 | 0.449 | 0.311 | 0.322 |
| HEP | 0.000 | 0.000 | 0.000 | 0.000 | 0.000 | 0.000 | 0.000 | 0.000 | 0.000 |
| TAEA | 0.092 | 0.169 | 1.615 | 0.393 | 0.129 | 0.398 | 0.234 | 0.129 | 0.128 |
| 1-TETA | 3.144 | 3.193 | 10.766 | 1.341 | 2.981 | 1.076 | 3.031 | 2.141 | 2.296 |
| DAEP | 0.168 | 0.096 | 0.685 | 0.064 | 0.076 | 0.099 | 0.109 | 0.146 | 0.166 |
| PEEDA | 0.243 | 0.153 | 0.635 | 0.058 | 0.167 | 0.147 | 0.177 | 0.113 | 0.141 |
| DPE | 0.184 | 0.207 | 0.122 | 0.098 | 0.172 | 0.095 | 0.253 | 0.136 | 0.160 |
| AE-TAEA | 0.203 | 0.120 | 2.095 | 0.000 | 0.159 | 0.000 | 0.298 | 0.115 | 0.142 |
| 1-TEPA | 0.216 | 0.000 | 5.688 | 0.179 | 0.000 | 0.121 | 0.099 | 0.000 | 0.000 |
| AE-DAEP | 0.000 | 0.000 | 0.571 | 0.000 | 0.000 | 0.000 | 0.000 | 0.000 | 0.000 |
| AE-PEEDA | 0.000 | 0.000 | 0.651 | 0.000 | 0.000 | 0.000 | 0.098 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.469 | 0.000 | 0.000 | 0.000 | 0.000 | 0.000 | 0.000 |
| BPEA | 0.000 | 0.000 | 0.532 | 0.000 | 0.000 | 0.000 | 0.000 | 0.000 | 0.000 |
| Others | 2.095 | 3.752 | 4.778 | 2.591 | 3.333 | 2.170 | 6.088 | 2.749 | 2.847 |
| MEA Conversion, % | 23.74 | 28.57 | 68.94 | 12.45 | 22.42 | 13.61 | 27.80 | 17.72 | 18.86 |
| DETA Conversion, % | 3.28 | 5.12 | 24.09 | 5.62 | 6.07 | 3.39 | 13.14 | 5.74 | 5.71 |
| Acyclic(N4), % | 84.47 | 88.05 | 89.57 | 88.73 | 88.23 | 81.18 | 85.84 | 85.16 | 83.84 |
| Acyclic(N5), % | 100.00 | 100.00 | 77.78 | 100.00 | 100.00 | 100.00 | 80.24 | 100.00 | 100.00 |
| Σ(N5)/Σ(N4), weight ratio | 0.11 | 0.03 | 0.72 | 0.09 | 0.05 | 0.07 | 0.13 | 0.04 | 0.05 |
| Acyclic(N4)/cyclic (<=N4), weight ratio | 3.19 | 3.52 | 3.86 | 3.23 | 3.64 | 2.33 | 2.63 | 2.75 | 2.69 |

TABLE XXXIII

| Example No. | 304 | 305 | 306 | 307 | 308 | 309 | 310 | 311 | 312 |
|---|---|---|---|---|---|---|---|---|---|
| Catalyst Type | OO | OO | OO | OO | OO | OO | OO | OO | OO |
| Catalyst weight, gm | 76.3 | 76.3 | 76.3 | 76.3 | 76.3 | 76.3 | 76.3 | 76.3 | 76.3 |
| Pressure, psig | 600 | 600 | 600 | 600 | 600 | 600 | 600 | 600 | 600 |
| Temperature, °C. | 269.9 | 272.7 | 279.9 | 260.3 | 268.3 | 261.4 | 278.9 | 270.6 | 271.7 |
| Time on organics, hrs. | 7.5 | 26.0 | 31.0 | 47.0 | 53.0 | 58.5 | 73.0 | 78.0 | 80.0 |
| Duration of run, hrs. | 2 | 2 | 2 | 2 | 2 | 2.5 | 2 | 2 | 2 |
| MEA SV, gmol/hr/kgcat | 3.99 | 3.68 | 4.09 | 2.65 | 1.23 | 0.96 | 3.38 | 3.80 | 3.31 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.574 | 1.791 | 4.858 | 0.968 | 2.024 | 2.100 | 2.080 | 0.921 | 0.937 |
| MEA | 18.061 | 16.725 | 23.777 | 24.322 | 13.187 | 16.037 | 16.072 | 23.937 | 22.805 |
| PIP | 1.056 | 0.060 | 0.323 | 0.500 | 1.357 | 1.136 | 1.291 | 0.528 | 0.587 |
| DETA | 52.716 | 51.336 | 50.891 | 55.597 | 51.804 | 51.667 | 51.643 | 57.189 | 56.650 |
| AEEA | 1.515 | 1.794 | 0.774 | 3.457 | 3.008 | 2.269 | 1.717 | 2.377 | 3.256 |
| AEP | 1.413 | 1.302 | 0.469 | 0.517 | 1.435 | 1.300 | 1.360 | 0.518 | 0.660 |
| HEP | 0.000 | 0.000 | 0.000 | 0.000 | 0.000 | 0.000 | 0.000 | 0.000 | 0.000 |
| TAEA | 1.676 | 1.719 | 0.290 | 0.781 | 1.672 | 1.529 | 1.523 | 0.820 | 0.879 |
| 1-TETA | 11.477 | 11.388 | 3.548 | 6.608 | 11.810 | 11.030 | 10.185 | 6.667 | 7.190 |
| DAEP | 0.280 | 0.282 | 0.141 | 0.080 | 0.263 | 0.294 | 0.263 | 0.097 | 0.107 |
| PEEDA | 0.193 | 0.215 | 0.257 | 0.000 | 0.192 | 0.203 | 0.206 | 0.000 | 0.067 |
| DPE | 0.000 | 0.000 | 0.366 | 0.000 | 0.000 | 0.072 | 0.000 | 0.000 | 0.000 |
| AE-TAEA | 0.773 | 0.861 | 0.327 | 0.406 | 0.810 | 0.775 | 0.789 | 0.456 | 0.513 |
| 1-TEPA | 3.017 | 3.327 | 0.123 | 0.963 | 3.541 | 3.449 | 2.992 | 1.036 | 1.135 |
| AE-DAEP | 0.088 | 0.115 | 0.110 | 0.000 | 0.227 | 0.177 | 0.222 | 0.000 | 0.000 |
| AE-PEEDA | 0.000 | 0.000 | 0.176 | 0.000 | 0.115 | 0.135 | 0.110 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.094 | 0.000 | 0.000 | 0.072 | 0.098 | 0.058 | 0.000 | 0.000 |
| Others | 0.509 | 0.841 | 7.550 | 0.461 | 1.103 | 0.677 | 1.461 | 0.555 | 0.534 |
| MEA Conversion, % | 50.94 | 53.95 | 33.72 | 32.83 | 63.87 | 55.94 | 55.35 | 34.29 | 37.73 |
| DETA Conversion, % | 14.90 | 15.99 | 15.70 | 8.75 | 15.64 | 15.63 | 14.74 | 6.69 | 8.06 |
| Acyclic(N4), % | 96.53 | 96.35 | 83.41 | 98.93 | 96.73 | 95.66 | 96.15 | 98.72 | 97.88 |
| Acyclic(N5), % | 97.72 | 95.24 | 61.11 | 100.00 | 91.31 | 91.12 | 90.64 | 100.00 | 100.00 |
| Σ(N5)/Σ(N4), weight ratio | 0.28 | 0.32 | 0.16 | 0.18 | 0.34 | 0.35 | 0.34 | 0.20 | 0.20 |
| Acyclic(N4)/cyclic (<=N4), weight ratio | 4.47 | 4.59 | 2.47 | 6.74 | 4.15 | 4.18 | 3.75 | 6.55 | 5.67 |

TABLE XXXIV

| Example No. | 313 | 314 | 315 | 316 | 317 | 318 | 319 | 320 | 321 |
|---|---|---|---|---|---|---|---|---|---|
| Catalyst Type | PP | PP | PP | PP | PP | PP | PP | PP | PP |

TABLE XXXIV-continued

| Example No. | 313 | 314 | 315 | 316 | 317 | 318 | 319 | 320 | 321 |
|---|---|---|---|---|---|---|---|---|---|
| Catalyst weight, gm | 76.1 | 76.1 | 76.1 | 76.1 | 76.1 | 76.1 | 76.1 | 76.1 | 76.1 |
| Pressure, psig | 600 | 600 | 600 | 600 | 600 | 600 | 600 | 600 | 600 |
| Temperature, °C. | 270 | 270 | 280 | 260 | 270 | 260 | 280 | 270 | 269.4 |
| Time on organics, hrs. | 5.5 | 24.0 | 29.5 | 48.5 | 53.5 | 72.0 | 77.5 | 93.0 | 94.0 |
| Duration of run, hrs. | 2 | 2 | 2 | 2 | 2 | 2 | 2 | 1 | 1 |
| MEA SV, gmol/hr/kgcat | 4.03 | 3.42 | 4.57 | 5.42 | 4.80 | 4.26 | 4.14 | 4.21 | 1.91 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.718 | 0.000 | 3.456 | 1.014 | 1.450 | 0.805 | 3.050 | 1.886 | 1.860 |
| MEA | 13.198 | 13.705 | 10.445 | 24.724 | 21.688 | 32.394 | 18.370 | 26.238 | 25.429 |
| PIP | 1.176 | 1.217 | 1.276 | 0.318 | 0.501 | 0.279 | 1.161 | 0.667 | 0.651 |
| DETA | 44.099 | 47.849 | 45.082 | 54.434 | 53.648 | 46.319 | 42.468 | 43.338 | 42.572 |
| AEEA | 1.298 | 1.149 | 0.783 | 1.841 | 1.512 | 2.946 | 1.159 | 2.722 | 2.762 |
| AEP | 1.774 | 1.847 | 1.906 | 0.410 | 0.649 | 0.391 | 1.624 | 0.861 | 0.848 |
| HEP | 0.000 | 0.000 | 0.000 | 0.000 | 0.000 | 0.000 | 0.000 | 0.000 | 0.000 |
| TAEA | 1.744 | 1.923 | 1.704 | 1.507 | 1.720 | 1.323 | 1.037 | 1.629 | 1.656 |
| 1-TETA | 12.612 | 12.764 | 11.841 | 8.466 | 10.127 | 7.262 | 9.928 | 9.641 | 10.039 |
| DAEP | 0.762 | 0.661 | 0.856 | 0.081 | 0.169 | 0.072 | 0.671 | 0.224 | 0.201 |
| PEEDA | 0.511 | 0.477 | 0.625 | 0.000 | 0.110 | 0.000 | 0.510 | 0.153 | 0.129 |
| DPE | 0.135 | 0.166 | 0.089 | 0.000 | 0.000 | 0.000 | 0.101 | 0.076 | 0.000 |
| AE-TAEA | 2.518 | 1.883 | 2.119 | 0.797 | 1.392 | 0.705 | 1.873 | 1.397 | 1.507 |
| 1-TEPA | 6.017 | 4.679 | 5.227 | 1.495 | 2.798 | 1.149 | 4.035 | 2.862 | 3.120 |
| AE-DAEP | 0.397 | 0.354 | 0.577 | 0.000 | 0.000 | 0.000 | 0.486 | 0.102 | 0.214 |
| AE-PEEDA | 0.098 | 0.000 | 0.207 | 0.000 | 0.000 | 0.000 | 0.102 | 0.000 | 0.103 |
| iAE-PEEDA | 0.000 | 0.000 | 0.000 | 0.000 | 0.000 | 0.000 | 0.000 | 0.000 | 0.000 |
| AE-DPE | 0.180 | 0.219 | 0.363 | 0.000 | 0.000 | 0.000 | 0.246 | 0.303 | 0.151 |
| BPEA | 0.182 | 0.198 | 0.325 | 0.000 | 0.000 | 0.000 | 0.200 | 0.174 | 0.113 |
| Others | 1.581 | 2.529 | 4.320 | 0.513 | 0.856 | 0.383 | 4.070 | 1.426 | 1.246 |
| MEA Conversion, % | 63.48 | 62.41 | 71.33 | 32.51 | 41.96 | 8.72 | 48.56 | 27.14 | 28.62 |
| DETA Conversion, % | 27.47 | 22.01 | 26.47 | 11.69 | 14.67 | 22.43 | 29.33 | 28.48 | 28.98 |
| Acyclic(N4), % | 91.07 | 91.84 | 89.61 | 99.19 | 97.70 | 99.17 | 89.54 | 96.14 | 97.25 |
| Acyclic(N5), % | 90.88 | 89.49 | 83.31 | 100.00 | 100.00 | 100.00 | 85.10 | 88.03 | 88.85 |
| $\Sigma(N5)/\Sigma(N4)$, weight ratio | 0.60 | 0.46 | 0.58 | 0.23 | 0.35 | 0.21 | 0.57 | 0.41 | 0.43 |
| Acyclic(N4)/cyclic (<=N4), weight ratio | 3.29 | 3.36 | 2.85 | 12.33 | 8.29 | 11.56 | 2.70 | 5.69 | 6.40 |

TABLE XXXV

| Example No. | 322 | 323 | 324 | 325 | 326 | 327 | 328 | 329 | 330 |
|---|---|---|---|---|---|---|---|---|---|
| Catalyst Type | QQ | QQ | QQ | QQ | QQ | QQ | QQ | QQ | QQ |
| Catalyst weight, gm | 78.5 | 78.5 | 78.5 | 78.5 | 78.5 | 78.5 | 78.5 | 78.5 | 78.5 |
| Pressure, psig | 600 | 600 | 600 | 600 | 600 | 600 | 600 | 600 | 600 |
| Temperature, °C. | 270.3 | 270.8 | 280.9 | 259.5 | 270.8 | 261.4 | 282.6 | 273.4 | 270.8 |
| Time on organics, hrs. | 4.0 | 7.0 | 26.0 | 31.0 | 50.0 | 55.0 | 74.0 | 79.0 | 99.5 |
| Duration of run, hrs. | 2 | 2 | 2 | 2 | 2 | 2 | 2 | 2 | 2 |
| MEA SV, gmol/hr/kgcat | 3.42 | 3.32 | 3.47 | 3.50 | 3.64 | 3.76 | 3.58 | 3.51 | 3.64 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.064 | 1.889 | 2.436 | 0.860 | 0.798 | 0.344 | 1.077 | 0.453 | 0.663 |
| MEA | 14.084 | 15.810 | 12.462 | 36.060 | 25.744 | 30.392 | 15.607 | 22.241 | 25.522 |
| PIP | 1.454 | 1.307 | 1.613 | 0.473 | 0.583 | 0.199 | 0.827 | 0.380 | 0.467 |
| DETA | 51.792 | 51.235 | 52.756 | 54.948 | 56.753 | 59.500 | 53.106 | 59.354 | 60.415 |
| AEEA | 0.857 | 1.123 | 0.758 | 1.393 | 0.172 | 1.675 | 1.251 | 1.785 | 0.264 |
| AEP | 2.286 | 1.884 | 2.151 | 0.372 | 0.645 | 0.390 | 1.366 | 0.626 | 0.647 |
| HEP | 0.000 | 0.000 | 0.000 | 0.000 | 0.000 | 0.000 | 0.000 | 0.000 | 0.000 |
| TAEA | 1.116 | 0.989 | 1.006 | 0.279 | 0.629 | 0.401 | 1.612 | 0.804 | 0.629 |
| 1-TETA | 12.082 | 10.881 | 10.297 | 2.687 | 6.508 | 4.381 | 11.880 | 6.933 | 5.481 |
| DAEP | 0.742 | 0.738 | 0.685 | 0.000 | 0.135 | 0.000 | 0.271 | 0.099 | 0.151 |
| PEEDA | 0.468 | 0.513 | 0.507 | 0.000 | 0.071 | 0.000 | 0.256 | 0.087 | 0.127 |
| DPE | 0.000 | 0.133 | 0.000 | 0.000 | 0.000 | 0.000 | 0.000 | 0.000 | 0.000 |
| AE-TAEA | 1.823 | 1.579 | 1.601 | 0.000 | 0.441 | 0.000 | 0.202 | 0.000 | 0.380 |
| 1-TEPA | 5.194 | 4.155 | 4.031 | 0.000 | 0.624 | 0.000 | 3.427 | 0.617 | 0.349 |
| AE-DAEP | 0.472 | 0.373 | 0.373 | 0.000 | 0.000 | 0.000 | 0.230 | 0.000 | 0.000 |
| AE-PEEDA | 0.179 | 0.155 | 0.159 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.109 | 0.154 | 0.117 | 0.000 | 0.000 | 0.000 | 0.186 | 0.000 | 0.000 |
| BPEA | 0.000 | 0.000 | 0.000 | 0.000 | 0.000 | 0.000 | 0.000 | 0.000 | 0.000 |
| Others | 0.428 | 0.801 | 1.358 | 0.429 | 2.397 | 0.417 | 2.141 | 1.419 | 2.054 |
| MEA Conversion, % | 62.62 | 57.18 | 65.91 | 1.08 | 29.53 | 17.71 | 57.46 | 38.96 | 31.32 |
| DETA Conversion, % | 18.31 | 17.53 | 14.23 | 7.67 | 10.42 | 4.25 | 13.98 | 3.19 | 3.37 |
| Acyclic(N4), % | 91.61 | 89.56 | 90.46 | 100.00 | 97.20 | 100.00 | 96.24 | 97.65 | 95.65 |
| Acyclic(N5), % | 90.22 | 89.36 | 89.68 | 0.00 | 100.00 | 0.00 | 89.72 | 100.00 | 100.00 |
| $\Sigma(N5)/\Sigma(N4)$, weight ratio | 0.54 | 0.48 | 0.50 | 0.00 | 0.14 | 0.00 | 0.29 | 0.08 | 0.11 |
| Acyclic(N4)/cyclic | 2.67 | 2.59 | 2.28 | 3.51 | 4.98 | 8.11 | 4.96 | 6.49 | 4.39 |

TABLE XXXV-continued

| Example No. | 322 | 323 | 324 | 325 | 326 | 327 | 328 | 329 | 330 |
|---|---|---|---|---|---|---|---|---|---|
| (<=N4), weight ratio | | | | | | | | | |

TABLE XXXVI

| Example No. | 331 | 332 | 333 | 334 | 335 | 336 | 337 | 338 | 339 |
|---|---|---|---|---|---|---|---|---|---|
| Catalyst Type | RR | RR | RR | RR | RR | RR | RR | RR | RR |
| Catalyst weight, gm | 74.5 | 74.5 | 74.5 | 74.5 | 74.5 | 74.5 | 74.5 | 74.5 | 74.5 |
| Pressure, psig | 600 | 600 | 600 | 600 | 600 | 600 | 600 | 600 | 600 |
| Temperature, °C. | 267.3 | 271.6 | 280.4 | 260.3 | 269.1 | 261.9 | 278.4 | 268.9 | 268.5 |
| Time on organics, hrs. | 6.5 | 25.5 | 30.5 | 49.5 | 54.5 | 73.5 | 78.5 | 97.0 | 99.2 |
| Duration of run, hrs. | 2 | 2 | 2 | 2 | 2 | 2 | 2 | 2 | 2 |
| MEA SV, gmol/hr/kgcat | 4.48 | 4.16 | 4.21 | 3.93 | 3.96 | 3.98 | 4.08 | 3.40 | 3.96 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.181 | 1.202 | 2.220 | 0.541 | 0.922 | 0.455 | 1.851 | 1.236 | 0.863 |
| MEA | 24.149 | 27.125 | 24.297 | 32.485 | 29.621 | 31.003 | 24.872 | 30.577 | 28.781 |
| PIP | 0.405 | 0.291 | 0.859 | 0.101 | 0.203 | 0.079 | 0.464 | 0.261 | 0.228 |
| DETA | 57.182 | 59.913 | 55.802 | 60.897 | 60.714 | 62.348 | 54.893 | 58.708 | 61.316 |
| AEEA | 0.929 | 1.479 | 1.151 | 1.074 | 1.180 | 0.920 | 1.384 | 1.342 | 1.371 |
| AEP | 0.649 | 0.503 | 0.740 | 0.341 | 0.427 | 0.349 | 0.703 | 0.474 | 0.446 |
| HEP | 0.000 | 0.000 | 0.000 | 0.000 | 0.000 | 0.000 | 0.000 | 0.000 | 0.000 |
| TAEA | 0.720 | 0.473 | 0.644 | 0.321 | 0.303 | 0.320 | 0.553 | 0.276 | 0.291 |
| 1-TETA | 7.014 | 4.341 | 6.500 | 1.844 | 3.136 | 1.875 | 6.108 | 2.942 | 3.059 |
| DAEP | 0.113 | 0.000 | 0.109 | 0.000 | 0.098 | 0.000 | 0.348 | 0.090 | 0.090 |
| PEEDA | 0.098 | 0.000 | 0.111 | 0.000 | 0.000 | 0.000 | 0.583 | 0.000 | 0.000 |
| DPE | 0.000 | 0.000 | 0.083 | 0.000 | 0.000 | 0.000 | 0.182 | 0.000 | 0.000 |
| AE-TAEA | 0.438 | 0.224 | 0.288 | 0.000 | 0.000 | 0.000 | 0.826 | 0.000 | 0.000 |
| 1-TEPA | 1.158 | 0.139 | 0.695 | 0.000 | 0.000 | 0.000 | 1.081 | 0.000 | 0.000 |
| AE-DAEP | 0.000 | 0.000 | 0.000 | 0.000 | 0.000 | 0.000 | 0.000 | 0.000 | 0.000 |
| AE-PEEDA | 0.105 | 0.000 | 0.000 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 1.839 | 1.060 | 2.010 | 0.836 | 1.046 | 0.930 | 2.604 | 0.915 | 0.887 |
| MEA Conversion, % | 34.39 | 26.20 | 33.56 | 12.26 | 19.77 | 16.34 | 32.77 | 16.26 | 21.89 |
| DETA Conversion, % | 7.68 | 3.12 | 9.31 | 2.25 | 2.27 | 0.01 | 11.81 | 4.45 | 1.10 |
| Acyclic(N4), % | 97.35 | 100.00 | 95.92 | 100.00 | 97.24 | 100.00 | 85.69 | 97.27 | 97.40 |
| Acyclic(N5), % | 93.82 | 100.00 | 100.00 | 0.00 | 0.00 | 0.00 | 100.00 | 0.00 | 0.00 |
| Σ(N5)/Σ(N4), weight ratio | 0.21 | 0.08 | 0.13 | 0.00 | 0.00 | 0.00 | 0.25 | 0.00 | 0.00 |
| Acyclic(N4)/cyclic (<=N4), weight ratio | 6.12 | 6.06 | 3.75 | 4.89 | 4.73 | 5.13 | 2.92 | 3.90 | 4.39 |

TABLE XXXVII

| Example No. | 340 | 341 | 342 | 343 | 344 | 345 | 346 | 347 | 348 |
|---|---|---|---|---|---|---|---|---|---|
| Catalyst Type | SS | SS | SS | SS | SS | SS | SS | SS | SS |
| Catalyst weight, gm | 84 | 84 | 84 | 84 | 84 | 84 | 84 | 84 | 84 |
| Pressure, psig | 600 | 600 | 600 | 600 | 600 | 600 | 600 | 600 | 600 |
| Temperature, °C. | 270 | 270 | 280 | 260 | 270 | 260 | 280 | 270 | 270 |
| Time on organics, hrs. | 6.5 | 24.0 | 29.5 | 48.0 | 53.7 | 71.0 | 74.0 | 98.0 | 99.0 |
| Duration of run, hrs. | 2 | 2 | 2 | 2 | 2 | 2 | 1 | 2 | 1 |
| MEA SV, gmol/hr/kgcat | 2.92 | 2.94 | 2.91 | 3.00 | 3.21 | 2.85 | 3.69 | 3.28 | 3.38 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 3.143 | 3.522 | 6.151 | 1.751 | 3.148 | 1.874 | 5.153 | 2.734 | 2.608 |
| MEA | 30.100 | 29.982 | 26.771 | 32.968 | 30.586 | 32.904 | 26.314 | 31.293 | 31.488 |
| PIP | 0.084 | 0.091 | 0.154 | 0.000 | 0.064 | 0.042 | 0.115 | 0.055 | 0.064 |
| DETA | 55.305 | 54.533 | 48.236 | 58.522 | 54.943 | 55.103 | 47.403 | 53.775 | 53.754 |
| AEEA | 0.153 | 0.233 | 0.160 | 0.091 | 0.000 | 0.090 | 0.176 | 0.171 | 0.152 |
| AEP | 0.295 | 0.276 | 0.352 | 0.223 | 0.245 | 0.200 | 0.308 | 0.227 | 0.225 |
| HEP | 0.000 | 0.000 | 0.000 | 0.000 | 0.000 | 0.000 | 0.000 | 0.000 | 0.000 |
| TAEA | 0.380 | 0.387 | 0.555 | 0.226 | 1.227 | 0.630 | 0.434 | 0.277 | 0.290 |
| 1-TETA | 1.422 | 1.462 | 1.967 | 0.594 | 0.634 | 0.365 | 1.619 | 0.287 | 0.240 |
| DAEP | 0.097 | 0.089 | 0.101 | 0.117 | 0.081 | 0.068 | 0.090 | 0.088 | 0.095 |
| PEEDA | 0.084 | 0.081 | 0.215 | 0.150 | 0.109 | 0.121 | 0.166 | 0.158 | 0.167 |
| DPE | 0.181 | 0.185 | 0.356 | 0.110 | 0.150 | 0.062 | 0.241 | 0.134 | 0.129 |
| AE-TAEA | 0.000 | 0.000 | 0.184 | 0.000 | 0.000 | 0.000 | 0.122 | 0.000 | 0.000 |
| 1-TEPA | 0.133 | 0.000 | 0.123 | 0.000 | 0.148 | 0.103 | 0.000 | 0.000 | 0.000 |
| AE-DAEP | 0.000 | 0.000 | 0.000 | 0.000 | 0.132 | 0.000 | 0.000 | 0.000 | 0.000 |
| AE-PEEDA | 0.000 | 0.000 | 0.104 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 4.933 | 5.408 | 9.890 | 3.207 | 4.813 | 2.118 | 8.097 | 5.003 | 4.889 |

TABLE XXXVII-continued

| Example No. | 340 | 341 | 342 | 343 | 344 | 345 | 346 | 347 | 348 |
|---|---|---|---|---|---|---|---|---|---|
| MEA Conversion, % | 17.10 | 17.35 | 25.92 | 10.37 | 15.66 | 6.14 | 22.88 | 11.56 | 10.89 |
| DETA Conversion, % | 9.47 | 10.66 | 20.67 | 5.44 | 9.96 | 6.58 | 17.43 | 9.67 | 9.59 |
| Acyclic(N4), % | 83.24 | 83.89 | 78.95 | 68.51 | 84.54 | 79.89 | 80.51 | 59.78 | 57.54 |
| Acyclic(N5), % | 100.00 | 0.00 | 74.66 | 0.00 | 52.87 | 100.00 | 100.00 | 0.00 | 0.00 |
| $\Sigma(N5)/\Sigma(N4)$, weight ratio | 0.06 | 0.00 | 0.13 | 0.00 | 0.13 | 0.08 | 0.05 | 0.00 | 0.00 |
| Acyclic(N4)/cyclic (<=N4), weight ratio | 2.43 | 2.56 | 2.14 | 1.37 | 2.87 | 2.02 | 2.23 | 0.85 | 0.78 |

TABLE XXXVIII

| Example No. | 349 | 350 | 351 | 352 | 353 | 354 | 355 | 356 | 357 |
|---|---|---|---|---|---|---|---|---|---|
| Catalyst Type | TT | TT | TT | TT | TT | TT | TT | TT | TT |
| Catalyst weight, gm | 80.7 | 80.7 | 80.7 | 80.7 | 80.7 | 80.7 | 80.7 | 80.7 | 80.7 |
| Pressure, psig | 600 | 600 | 600 | 600 | 600 | 600 | 600 | 600 | 600 |
| Temperature, °C. | 269.6 | 269.6 | 279.5 | 260.0 | 269.8 | 259.2 | 280.0 | 271.4 | 269.4 |
| Time on organics, hrs. | 20.5 | 24.5 | 44.0 | 49.0 | 68.0 | 73.0 | 92.0 | 97.0 | 116.5 |
| Duration of run, hrs. | 2 | 2 | 2 | 2 | 2 | 2 | 2 | 2 | 2 |
| MEA SV, gmol/hr/kgcat | 3.55 | 3.63 | 3.60 | 3.78 | 3.52 | 3.53 | 3.01 | 3.34 | 3.20 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.354 | 1.094 | 2.246 | 0.648 | 1.032 | 0.457 | 2.918 | 1.351 | 1.546 |
| MEA | 18.152 | 18.204 | 13.314 | 28.101 | 23.557 | 28.629 | 14.287 | 21.618 | 21.329 |
| PIP | 0.850 | 0.723 | 1.703 | 0.353 | 0.902 | 0.303 | 2.036 | 0.844 | 1.106 |
| DETA | 49.396 | 53.187 | 48.982 | 57.642 | 58.104 | 58.959 | 49.804 | 54.426 | 52.827 |
| AEEA | 1.115 | 1.255 | 0.534 | 1.459 | 0.788 | 1.073 | 0.483 | 0.249 | 0.256 |
| AEP | 1.250 | 0.946 | 2.103 | 0.528 | 0.967 | 0.526 | 2.138 | 1.089 | 1.122 |
| HEP | 0.000 | 0.000 | 0.000 | 0.000 | 0.000 | 0.000 | 0.000 | 0.000 | 0.000 |
| TAEA | 0.869 | 1.413 | 1.083 | 0.729 | 0.404 | 0.462 | 0.770 | 1.319 | 1.258 |
| l-TETA | 12.723 | 11.602 | 11.826 | 6.274 | 7.800 | 5.369 | 10.228 | 9.582 | 9.770 |
| DAEP | 0.209 | 0.196 | 0.731 | 0.061 | 0.485 | 0.286 | 0.654 | 0.151 | 0.165 |
| PEEDA | 0.152 | 0.141 | 0.630 | 0.000 | 0.281 | 0.137 | 0.454 | 0.114 | 0.115 |
| DPE | 0.000 | 0.000 | 0.064 | 0.000 | 0.000 | 0.000 | 0.062 | 0.000 | 0.000 |
| AE-TAEA | 0.956 | 1.039 | 2.383 | 0.000 | 0.000 | 0.000 | 1.590 | 0.000 | 0.000 |
| l-TEPA | 3.937 | 3.244 | 5.190 | 0.326 | 0.168 | 0.000 | 3.399 | 0.708 | 0.786 |
| AE-DAEP | 0.509 | 0.284 | 0.454 | 0.000 | 0.000 | 0.000 | 0.085 | 0.000 | 0.000 |
| AE-PEEDA | 0.534 | 0.100 | 0.131 | 0.000 | 0.000 | 0.000 | 0.201 | 0.087 | 0.108 |
| iAE-PEEDA | 0.000 | 0.000 | 0.000 | 0.000 | 0.000 | 0.000 | 0.000 | 0.000 | 0.000 |
| AE-DPE | 1.412 | 0.293 | 0.271 | 0.000 | 0.000 | 0.000 | 0.168 | 0.099 | 0.371 |
| BPEA | 0.000 | 0.000 | 0.000 | 0.000 | 0.000 | 0.000 | 0.000 | 0.000 | 0.000 |
| Others | 1.363 | 1.228 | 2.694 | 1.129 | 0.741 | 0.607 | 2.400 | 3.254 | 3.290 |
| MEA Conversion, % | 51.28 | 50.92 | 64.50 | 24.02 | 35.62 | 22.13 | 60.51 | 41.07 | 41.44 |
| DETA Conversion, % | 21.21 | 14.77 | 22.37 | 7.37 | 5.63 | 4.69 | 18.19 | 11.82 | 13.80 |
| Acyclic(N4), % | 97.41 | 97.47 | 90.05 | 99.13 | 91.45 | 93.23 | 90.38 | 97.63 | 97.53 |
| Acyclic(N5), % | 66.59 | 86.35 | 89.84 | 100.00 | 100.00 | 0.00 | 91.65 | 79.22 | 62.13 |
| $\Sigma(N5)/\Sigma(N4)$, weight ratio | 0.53 | 0.37 | 0.59 | 0.05 | 0.02 | 0.00 | 0.45 | 0.08 | 0.11 |
| Acyclic(N4)/cyclic (<=N4), weight ratio | 5.52 | 6.49 | 2.47 | 7.44 | 3.11 | 4.66 | 2.06 | 4.96 | 4.40 |

TABLE XXXIX

| Example No. | 358 | 359 | 360 | 361 | 362 | 363 | 364 | 365 | 366 |
|---|---|---|---|---|---|---|---|---|---|
| Catalyst Type | UU | UU | UU | UU | UU | UU | UU | UU | UU |
| Catalyst weight, gm | 89 | 89 | 89 | 89 | 89 | 89 | 89 | 89 | 89 |
| Pressure, psig | 600 | 600 | 600 | 600 | 600 | 600 | 600 | 600 | 600 |
| Temperature, °C. | 270 | 270 | 280 | 260 | 270 | 260 | 270 | 270 | 270 |
| Time on organics, hrs. | 6.5 | 24.0 | 29.5 | 48.0 | 53.7 | 71.0 | 24.0 | 98.0 | 99.0 |
| Duration of run, hrs. | 2 | 2 | 2 | 2 | 2 | 2 | 2 | 2 | 1 |
| MEA SV, gmol/hr/kgcat | 2.91 | 2.74 | 2.97 | 2.84 | 3.12 | 2.66 | 2.76 | 2.88 | 3.02 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.718 | 0.645 | 1.457 | 0.333 | 0.542 | 0.310 | 1.234 | 0.585 | 0.539 |
| MEA | 27.595 | 26.525 | 25.356 | 30.520 | 27.336 | 29.634 | 25.529 | 26.745 | 28.074 |
| PIP | 1.107 | 1.105 | 2.119 | 0.588 | 1.024 | 0.549 | 1.947 | 0.000 | 0.917 |
| DETA | 57.184 | 57.402 | 53.992 | 60.160 | 55.509 | 55.391 | 54.113 | 54.836 | 55.562 |
| AEEA | 1.254 | 1.122 | 0.744 | 1.059 | 0.901 | 0.959 | 0.906 | 1.108 | 1.108 |
| AEP | 0.828 | 0.865 | 1.760 | 0.408 | 0.730 | 0.375 | 1.646 | 0.736 | 0.672 |
| HEP | 0.000 | 0.000 | 0.000 | 0.000 | 0.000 | 0.000 | 0.000 | 0.000 | 0.000 |
| TAEA | 0.643 | 0.674 | 0.525 | 0.429 | 0.414 | 0.344 | 0.605 | 0.489 | 0.512 |
| l-TETA | 5.227 | 5.572 | 5.376 | 3.427 | 4.632 | 2.912 | 6.015 | 5.284 | 4.209 |
| DAEP | 0.127 | 0.144 | 0.312 | 0.000 | 0.117 | 0.000 | 0.350 | 0.115 | 0.094 |
| PEEDA | 0.140 | 0.173 | 0.363 | 0.000 | 0.128 | 0.000 | 0.428 | 0.126 | 0.099 |
| DPE | 0.000 | 0.000 | 0.000 | 0.000 | 0.000 | 0.000 | 0.000 | 0.000 | 0.000 |
| AE-TAEA | 0.366 | 0.492 | 0.490 | 0.169 | 0.040 | 0.124 | 0.669 | 0.166 | 0.274 |

TABLE XXXIX-continued

| Example No. | 358 | 359 | 360 | 361 | 362 | 363 | 364 | 365 | 366 |
|---|---|---|---|---|---|---|---|---|---|
| 1-TEPA | 1.413 | 1.833 | 1.908 | 0.515 | 1.633 | 0.351 | 2.473 | 1.458 | 1.032 |
| AE-DAEP | 0.000 | 0.000 | 0.150 | 0.000 | 0.000 | 0.000 | 0.136 | 0.098 | 0.000 |
| AE-PEEDA | 0.000 | 0.000 | 0.131 | 0.000 | 0.000 | 0.000 | 0.136 | 0.079 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.112 | 0.000 | 0.000 |
| Others | 0.277 | 0.238 | 0.707 | 0.082 | 0.575 | 0.000 | 0.491 | 0.374 | 0.208 |
| MEA Conversion, % | 25.36 | 28.39 | 30.94 | 17.40 | 23.34 | 13.63 | 31.57 | 23.79 | 20.82 |
| DETA Conversion, % | 8.07 | 7.90 | 12.61 | 3.24 | 7.49 | 4.05 | 13.80 | 7.13 | 6.87 |
| Acyclic(N4), % | 95.65 | 95.17 | 89.74 | 100.00 | 95.38 | 100.00 | 89.49 | 95.99 | 96.08 |
| Acyclic(N5), % | 100.00 | 100.00 | 89.50 | 100.00 | 100.00 | 100.00 | 89.11 | 90.17 | 100.00 |
| Σ(N5)/Σ(N4), weight ratio | 0.29 | 0.35 | 0.41 | 0.18 | 0.32 | 0.15 | 0.48 | 0.30 | 0.27 |
| Acyclic(N4)/cyclic (<=N4). weight ratio | 2.67 | 2.73 | 1.30 | 3.87 | 2.52 | 3.52 | 1.51 | 5.90 | 2.65 |

TABLE XL

| Example No. | 367 | 368 | 369 | 370 | 371 | 372 | 373 | 374 |
|---|---|---|---|---|---|---|---|---|
| Catalyst Type | VV | VV | VV | VV | VV | VV | VV | VV |
| Catalyst weight, gm | 89 | 89 | 89 | 89 | 89 | 89 | 89 | 89 |
| Pressure, psig | 600 | 600 | 600 | 600 | 600 | 600 | 600 | 600 |
| Temperature, °C. | 270 | 280 | 260 | 270 | 260 | 260 | 270 | 270 |
| Time on organics, hrs. | 6.5 | 29.5 | 48.0 | 53.7 | 71.0 | 74.0 | 98.0 | 99.0 |
| Duration of run, hrs. | 2 | 2 | 2 | 2 | 2 | 1 | 2 | 1 |
| MEA SV, gmol/hr/kgcat | 3.60 | 4.04 | 3.87 | 3.77 | 3.63 | 3.82 | 3.80 | 4.14 |
| DETA/MEA mole ratio | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 |
| Crude product composition, wt. % | | | | | | | | |
| EDA | 0.213 | 0.589 | 0.063 | 0.237 | 0.132 | 0.597 | 0.268 | 0.221 |
| MEA | 28.924 | 28.276 | 32.679 | 29.051 | 31.767 | 26.401 | 29.867 | 31.406 |
| PIP | 0.577 | 1.302 | 0.331 | 0.637 | 0.305 | 1.250 | 0.636 | 0.606 |
| DETA | 60.693 | 59.604 | 61.967 | 55.284 | 57.693 | 54.502 | 57.225 | 57.491 |
| AEEA | 1.337 | 0.873 | 0.904 | 0.882 | 0.873 | 1.072 | 1.112 | 1.076 |
| AEP | 0.468 | 1.015 | 0.268 | 0.432 | 0.237 | 0.913 | 0.463 | 0.406 |
| HEP | 0.000 | 0.000 | 0.000 | 0.000 | 0.000 | 0.000 | 0.000 | 0.000 |
| TAEA | 0.446 | 0.369 | 0.216 | 0.202 | 0.171 | 0.391 | 0.328 | 0.287 |
| 1-TETA | 3.783 | 3.779 | 1.991 | 2.687 | 1.723 | 4.061 | 2.922 | 2.612 |
| DAEP | 0.000 | 0.182 | 0.000 | 0.064 | 0.000 | 0.133 | 0.000 | 0.000 |
| PEEDA | 0.000 | 0.236 | 0.000 | 0.000 | 0.000 | 0.175 | 0.000 | 0.000 |
| DPE | 0.000 | 0.000 | 0.000 | 0.000 | 0.000 | 0.000 | 0.000 | 0.000 |
| AE-TAEA | 0.194 | 0.224 | 0.000 | 0.000 | 0.000 | 0.289 | 0.138 | 0.000 |
| 1-TEPA | 0.663 | 0.879 | 0.000 | 0.296 | 0.000 | 1.049 | 0.455 | 0.350 |
| AE-DAEP | 0.000 | 0.000 | 0.000 | 0.000 | 0.000 | 0.000 | 0.000 | 0.000 |
| AE-PEEDA | 0.000 | 0.000 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 |
| Others | 0.102 | 0.321 | 0.081 | 0.079 | 0.000 | 0.307 | 0.187 | 0.194 |
| MEA Conversion, % | 21.74 | 24.03 | 11.82 | 14.35 | 8.93 | 24.03 | 15.55 | 11.95 |
| DETA Conversion, % | 2.40 | 4.83 | 0.62 | 3.13 | 1.70 | 6.80 | 3.84 | 4.21 |
| Acyclic(N4), % | 100.00 | 90.85 | 100.00 | 97.82 | 100.00 | 93.54 | 100.00 | 100.00 |
| Acyclic(N5), % | 100.00 | 100.00 | 0.00 | 100.00 | 0.00 | 100.00 | 100.00 | 100.00 |
| Σ(N5)/Σ(N4), weight ratio | 0.20 | 0.24 | 0.00 | 0.10 | 0.00 | 0.28 | 0.18 | 0.12 |
| Acyclic(N4)/cyclic (<=N4), weight ratio | 4.04 | 1.52 | 3.69 | 2.55 | 3.50 | 1.80 | 2.96 | 2.86 |

TABLE XLI

| Example No. | 375 | 376 | 377 | 378 | 379 | 380 | 381 | 382 | 383 |
|---|---|---|---|---|---|---|---|---|---|
| Catalyst Type | WW | WW | WW | WW | WW | WW | WW | WW | WW |
| Catalyst weight, gm | 109.3 | 109.3 | 109.3 | 109.3 | 109.3 | 109.3 | 109.3 | 109.3 | 109.3 |
| Pressure, psig | 600 | 600 | 600 | 600 | 600 | 600 | 600 | 600 | 600 |
| Temperature, °C. | 272.8 | 272.4 | 281.4 | 261.6 | 271.6 | 261.2 | 281.1 | 271.8 | 271.8 |
| Time on organics, hrs. | 4.5 | 25.5 | 30.5 | 49.5 | 54.5 | 73.5 | 78.5 | 96.5 | 98.0 |
| Duration of run, hrs. | 2 | 2 | 2 | 2 | 2 | 2 | 2 | 1 | 1 |
| MEA SV, gmol/hr/kgcat | 2.41 | 2.58 | 2.54 | 2.56 | 2.62 | 2.46 | 2.37 | 2.35 | 2.01 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.497 | 6.772 | 12.561 | 3.271 | 5.650 | 3.027 | 8.398 | 6.989 | 6.342 |
| MEA | 11.926 | 3.136 | 0.306 | 9.052 | 3.533 | 8.556 | 0.344 | 2.253 | 2.052 |
| PIP | 1.508 | 3.617 | 5.688 | 2.203 | 3.219 | 2.114 | 3.924 | 3.679 | 3.432 |
| DETA | 43.663 | 34.939 | 27.007 | 40.944 | 37.212 | 42.204 | 28.868 | 34.736 | 33.388 |
| AEEA | 0.175 | 0.056 | 0.056 | 0.424 | 0.046 | 0.430 | 0.068 | 0.054 | 0.052 |
| AEP | 2.674 | 6.800 | 10.087 | 3.163 | 5.751 | 2.837 | 8.269 | 5.679 | 5.546 |

TABLE XLI-continued

| Example No. | 375 | 376 | 377 | 378 | 379 | 380 | 381 | 382 | 383 |
|---|---|---|---|---|---|---|---|---|---|
| HEP | 0.000 | 0.000 | 0.000 | 0.000 | 0.000 | 0.000 | 0.000 | 0.000 | 0.000 |
| TAEA | 5.276 | 2.471 | 0.713 | 3.624 | 2.701 | 3.372 | 1.567 | 2.339 | 2.387 |
| 1-TETA | 13.602 | 13.192 | 7.877 | 15.395 | 13.650 | 14.959 | 10.350 | 13.399 | 13.817 |
| DAEP | 0.031 | 3.410 | 4.966 | 0.050 | 2.804 | 1.167 | 5.005 | 2.753 | 2.852 |
| PEEDA | 0.402 | 1.586 | 3.460 | 0.670 | 1.378 | 0.689 | 3.719 | 1.712 | 1.642 |
| DPE | 0.164 | 0.126 | 0.173 | 0.124 | 0.130 | 0.189 | 0.296 | 0.208 | 0.214 |
| AE-TAEA | 4.114 | 2.399 | 0.888 | 3.396 | 2.480 | 3.259 | 1.667 | 2.421 | 2.684 |
| 1-TEPA | 4.558 | 5.996 | 3.503 | 6.285 | 6.269 | 6.192 | 5.083 | 6.762 | 7.401 |
| AE-DAEP | 0.056 | 1.150 | 2.203 | 0.395 | 0.981 | 0.321 | 2.619 | 1.146 | 1.196 |
| AE-PEEDA | 0.000 | 0.368 | 0.656 | 0.172 | 0.301 | 0.143 | 0.777 | 0.355 | 0.371 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.202 | 0.000 | 0.000 | 0.000 | 0.230 | 0.000 | 0.049 |
| BPEA | 0.019 | 0.170 | 0.043 | 0.198 | 0.142 | 0.105 | 0.056 | 0.133 | 0.249 |
| Others | 2.325 | 4.721 | 8.340 | 3.395 | 3.331 | 1.197 | 7.221 | 4.133 | 4.304 |
| MEA Conversion, % | 67.86 | 91.64 | 99.18 | 75.79 | 90.41 | 76.63 | 99.08 | 93.85 | 94.36 |
| DETA Conversion, % | 30.07 | 44.67 | 56.74 | 34.91 | 39.97 | 31.48 | 53.83 | 43.61 | 45.49 |
| Acyclic(N4), % | 96.93 | 75.36 | 49.97 | 95.75 | 79.13 | 89.96 | 56.92 | 77.11 | 77.49 |
| Acyclic(N5), % | 99.14 | 83.26 | 58.59 | 92.68 | 86.00 | 94.33 | 64.70 | 84.90 | 84.39 |
| Σ(N5)/Σ(N4), weight ratio | 0.45 | 0.49 | 0.44 | 0.53 | 0.49 | 0.49 | 0.50 | 0.53 | 0.57 |
| Acyclic(N4)/cyclic (<=N4), weight ratio | 3.95 | 1.01 | 0.35 | 3.06 | 1.23 | 2.62 | 0.56 | 1.12 | 1.18 |

TABLE XLII

| Example No. | 384 | 385 | 386 | 387 | 388 | 389 | 390 | 391 | 392 |
|---|---|---|---|---|---|---|---|---|---|
| Catalyst Type | XX | XX | XX | XX | XX | XX | XX | XX | XX |
| Catalyst weight, gm | 117 | 117 | 117 | 117 | 117 | 117 | 117 | 117 | 117 |
| Pressure, psig | 600 | 600 | 600 | 600 | 600 | 600 | 600 | 600 | 600 |
| Temperature, °C. | 269.3 | 269.2 | 279.4 | 258.8 | 269.2 | 259.4 | 279.2 | 268.9 | 269.6 |
| Time on organics, hrs. | 23.5 | 27.5 | 47.0 | 52.0 | 71.0 | 76.0 | 95.0 | 100.0 | 120.0 |
| Duration of run, hrs. | 2 | 2 | 2 | 2 | 2 | 2 | 2 | 2 | 2 |
| MEA SV, gmol/hr/kgcat | 2.58 | 2.36 | 2.57 | 2.67 | 2.50 | 2.45 | 1.13 | 0.81 | 1.98 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 3.709 | 3.837 | 8.600 | 2.804 | 3.721 | 0.488 | 9.601 | 7.741 | 3.411 |
| MEA | 9.936 | 9.370 | 5.731 | 16.450 | 9.968 | 25.695 | 3.708 | 7.550 | 16.344 |
| PIP | 2.708 | 2.524 | 4.204 | 1.433 | 2.717 | 0.842 | 4.962 | 3.887 | 2.182 |
| DETA | 38.446 | 38.390 | 33.775 | 45.291 | 38.571 | 55.220 | 34.097 | 37.900 | 43.567 |
| AEEA | 0.291 | 0.324 | 0.317 | 0.339 | 0.292 | 0.367 | 0.388 | 0.526 | 0.391 |
| AEP | 4.686 | 4.502 | 7.284 | 1.974 | 4.702 | 0.717 | 8.582 | 5.708 | 2.836 |
| HEP | 0.000 | 0.000 | 0.000 | 0.000 | 0.000 | 0.000 | 0.000 | 0.000 | 0.000 |
| TAEA | 3.835 | 4.377 | 2.941 | 4.188 | 3.848 | 1.310 | 2.846 | 3.803 | 3.747 |
| 1-TETA | 8.969 | 9.950 | 7.471 | 9.662 | 8.998 | 6.251 | 8.150 | 9.402 | 9.633 |
| DAEP | 1.874 | 1.752 | 2.889 | 0.521 | 1.880 | 0.065 | 2.947 | 1.720 | 0.876 |
| PEEDA | 0.861 | 0.698 | 1.317 | 0.180 | 0.864 | 0.000 | 1.373 | 0.837 | 0.409 |
| DPE | 0.078 | 0.000 | 0.059 | 0.000 | 0.078 | 0.000 | 0.000 | 0.000 | 0.000 |
| AE-TAEA | 0.228 | 0.307 | 0.306 | 0.270 | 0.229 | 0.199 | 0.000 | 0.000 | 0.000 |
| 1-TEPA | 4.090 | 4.452 | 0.103 | 3.018 | 4.103 | 0.000 | 2.329 | 3.192 | 2.764 |
| AE-DAEP | 0.690 | 0.464 | 0.318 | 0.583 | 0.692 | 0.000 | 0.787 | 0.451 | 0.000 |
| AE-PEEDA | 0.231 | 0.161 | 0.259 | 0.301 | 0.232 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.068 | 0.115 | 0.462 | 1.425 | 0.068 | 0.000 | 0.359 | 0.000 | 0.257 |
| BPEA | 0.160 | 0.349 | 0.515 | 0.765 | 0.161 | 0.000 | 0.358 | 0.278 | 0.000 |
| Others | 8.818 | 8.017 | 13.158 | 2.876 | 8.846 | 1.176 | 7.923 | 4.755 | 2.383 |
| MEA Conversion, % | 72.57 | 74.10 | 84.35 | 54.81 | 72.57 | 27.13 | 89.78 | 78.65 | 53.20 |
| DETA Conversion, % | 36.91 | 36.95 | 45.17 | 26.06 | 36.91 | 6.93 | 44.14 | 36.31 | 25.86 |
| Acyclic(N4), % | 81.99 | 85.39 | 70.94 | 95.19 | 81.99 | 99.14 | 71.79 | 83.78 | 91.24 |
| Acyclic(N5), % | 78.98 | 81.38 | 20.83 | 51.69 | 78.98 | 100.00 | 60.77 | 81.41 | 91.50 |
| Σ(N5)/Σ(N4), weight ratio | 0.35 | 0.35 | 0.13 | 0.44 | 0.35 | 0.03 | 0.25 | 0.25 | 0.21 |
| Acyclic(N4)/cyclic (<=N4), weight ratio | 1.25 | 1.51 | 0.66 | 3.37 | 1.25 | 4.66 | 0.62 | 1.09 | 2.12 |

TABLE XLIII

| Example No. | 393 | 394 | 395 | 396 | 397 | 398 | 399 | 400 | 401 |
|---|---|---|---|---|---|---|---|---|---|
| Catalyst Type | YY | YY | YY | YY | YY | YY | YY | YY | YY |
| Catalyst weight, gm | 109.7 | 109.7 | 109.7 | 109.7 | 109.7 | 109.7 | 109.7 | 109.7 | 109.7 |
| Pressure, psig | 600 | 600 | 600 | 600 | 600 | 600 | 600 | 600 | 600 |
| Temperature, °C. | 272.8 | 272.4 | 281.4 | 261.6 | 271.6 | 261.2 | 281.1 | 271.8 | 271.8 |
| Time on organics, hrs. | 4.5 | 25.5 | 30.5 | 49.5 | 54.5 | 73.5 | 78.5 | 96.5 | 98.0 |
| Duration of run, hrs. | 2 | 2 | 2 | 2 | 2 | 2 | 2 | 1 | 1 |
| MEA SV, gmol/hr/kgcat | 2.30 | 2.46 | 2.44 | 2.27 | 2.30 | 2.79 | 2.53 | 3.81 | 2.50 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |

TABLE XLIII-continued

| Example No. | 393 | 394 | 395 | 396 | 397 | 398 | 399 | 400 | 401 |
|---|---|---|---|---|---|---|---|---|---|
| Crude product composition, wt. % | | | | | | | | | |
| EDA | 2.261 | 1.959 | 2.786 | 1.241 | 1.755 | 1.003 | 1.824 | 1.913 | 1.114 |
| MEA | 11.820 | 15.971 | 11.138 | 22.601 | 18.976 | 22.986 | 18.586 | 22.750 | 22.718 |
| PIP | 1.520 | 1.200 | 1.593 | 0.719 | 1.121 | 0.694 | 1.109 | 1.280 | 0.748 |
| DETA | 45.153 | 45.959 | 41.322 | 50.852 | 47.133 | 52.385 | 47.720 | 47.166 | 49.655 |
| AEEA | 0.011 | 0.410 | 0.153 | 0.999 | 0.569 | 0.740 | 0.269 | 0.266 | 0.465 |
| AEP | 2.740 | 1.799 | 2.738 | 1.065 | 1.366 | 0.830 | 1.702 | 2.957 | 1.051 |
| HEP | 0.000 | 0.000 | 0.000 | 0.000 | 0.000 | 0.000 | 0.000 | 0.000 | 0.000 |
| TAEA | 4.881 | 4.991 | 5.095 | 4.056 | 4.454 | 3.564 | 3.729 | 2.475 | 3.404 |
| 1-TETA | 14.240 | 13.568 | 13.497 | 10.800 | 11.889 | 10.434 | 10.309 | 7.038 | 9.572 |
| DAEP | 0.016 | 0.382 | 1.089 | 0.163 | 0.254 | 0.130 | 0.690 | 1.198 | 0.295 |
| PEEDA | 0.211 | 0.138 | 0.463 | 0.071 | 0.110 | 0.061 | 0.347 | 0.648 | 0.149 |
| DPE | 0.149 | 0.000 | 0.194 | 0.034 | 0.000 | 0.066 | 0.208 | 0.175 | 0.058 |
| AE-TAEA | 3.624 | 3.300 | 4.229 | 1.833 | 2.595 | 1.438 | 2.605 | 1.218 | 2.163 |
| 1-TEPA | 4.655 | 3.616 | 5.175 | 2.182 | 2.918 | -1.629 | 3.169 | 1.628 | 2.578 |
| AE-DAEP | 0.025 | 0.000 | 0.194 | 0.047 | 0.000 | 0.000 | 0.138 | 0.331 | 0.250 |
| AE-PEEDA | 0.000 | 0.000 | 0.091 | 0.000 | 0.000 | 0.000 | 0.071 | 0.087 | 0.071 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.044 | 0.000 | 0.126 | 0.000 | 0.000 | 0.000 | 0.000 | 0.000 | 0.000 |
| Others | 1.451 | 0.368 | 1.796 | 0.219 | 0.402 | 0.081 | 0.814 | 2.102 | 0.506 |
| MEA Conversion, % | 68.07 | 57.17 | 69.70 | 39.78 | 48.09 | 38.05 | 49.16 | 37.30 | 38.16 |
| DETA Conversion, % | 27.50 | 25.91 | 33.19 | 19.47 | 23.36 | 16.10 | 22.42 | 22.74 | 19.67 |
| Acyclic(N4), % | 98.07 | 97.27 | 91.41 | 98.23 | 97.82 | 98.20 | 91.85 | 82.48 | 96.27 |
| Acyclic(N5), % | 99.18 | 100.00 | 95.81 | 98.83 | 100.00 | 100.00 | 96.51 | 87.21 | 93.66 |
| Σ(N5)/Σ(N4), weight ratio | 0.43 | 0.36 | 0.48 | 0.27 | 0.33 | 0.22 | 0.39 | 0.28 | 0.38 |
| Acyclic(N4)/cyclic (<=N4), weight ratio | 4.12 | 5.27 | 3.06 | 7.24 | 5.73 | 7.86 | 3.46 | 1.52 | 5.64 |

TABLE XLIV

| Example No. | 402 | 403 | 404 | 405 |
|---|---|---|---|---|
| Catalyst Type | ZZ | ZZ | ZZ | ZZ |
| Catalyst weight, gm | 91.33 | 91.33 | 91.33 | 91.33 |
| Pressure, psig | 597 | 597 | 596 | 596 |
| Temperature, °C. | 270 | 284 | 258 | 272 |
| Time on organics, hrs. | 20.5 | 25.5 | 44.5 | 49.5 |
| Duration of run, hrs. | 2 | 2 | 2 | 2 |
| MEA SV, gmol/hr/kgcat | 2.39 | 2.58 | 2.52 | 2.54 |
| DETA/MEA mole ratio | 1.00 | 1.00 | 1.00 | 1.00 |
| NH$_3$/MEA mole ratio | 5.97 | 5.97 | 5.97 | 5.97 |
| Crude product composition, wt. % | | | | |
| EDA | 4.834 | 8.303 | 4.455 | 3.149 |
| MEA | 5.992 | 2.084 | 9.647 | 10.990 |
| PIP | 2.283 | 3.699 | 1.702 | 1.505 |
| DETA | 24.621 | 19.876 | 30.406 | 33.928 |
| AEEA | 1.216 | 0.261 | 1.338 | 2.268 |
| AEP | 3.659 | 6.379 | 2.728 | 2.013 |
| HEP | 0.000 | 0.000 | 0.000 | 0.000 |
| TAEA | 1.286 | 0.698 | 1.273 | 1.595 |
| TETA | 12.156 | 7.714 | 10.112 | 12.504 |
| DAEP | 2.494 | 4.084 | 1.904 | 1.055 |
| PEEDA | 1.717 | 3.007 | 0.160 | 0.699 |
| DPE | 0.254 | 0.161 | 0.302 | 0.234 |
| AE-TAEA | 2.896 | 1.747 | 2.455 | 2.914 |
| 1-TEPA | 10.186 | 6.866 | 8.071 | 8.571 |
| AE-DAEP | 1.858 | 3.439 | 1.934 | 0.777 |
| AE-PEEDA | 0.718 | 0.938 | 0.748 | 0.439 |
| iAE-PEEDA | 0.000 | 0.000 | 0.000 | 0.000 |
| AE-DPE | 0.091 | 0.255 | 0.169 | 0.039 |
| BPEA | 0.403 | 0.377 | 0.505 | 0.558 |
| Others | 14.617 | 19.011 | 15.441 | 9.062 |
| MEA Conversion, % | 84.09 | 94.41 | 74.56 | 70.46 |
| DETA Conversion, % | 61.16 | 68.33 | 52.34 | 45.81 |
| Acyclic(N4), % | 75.07 | 53.70 | 82.79 | 87.64 |
| Acyclic(N5), % | 80.99 | 63.23 | 75.82 | 86.37 |
| Σ(N5)/Σ(N4), weight ratio | 0.90 | 0.87 | 1.01 | 0.83 |
| Acyclic(N4)/cyclic (<=N4), weight ratio | 1.29 | 0.49 | 1.68 | 2.56 |

TABLE XLV

| Example No. | 406 | 407 | 408 | 409 | 410 | 411 |
|---|---|---|---|---|---|---|
| Catalyst Type | AAA | AAA | AAA | AAA | AAA | AAA |
| Catalyst weight, gm | 107 | 107 | 107 | 107 | 107 | 107 |
| Pressure, psig | 600 | 600 | 600 | 600 | 600 | 600 |
| Temperature, °C. | 277 | 277 | 277 | 313 | 314 | 314 |
| Time on organics, hrs. | 3.0 | 18.7 | 20.7 | 26.0 | 42.7 | 44.7 |
| Duration of run, hrs. | 1 | 16 | 2 | 2 | 16 | 2 |
| MEA SV, gmol/hr/kgcat | 2.26 | 2.24 | 2.27 | 2.10 | 2.08 | 2.11 |
| NH$_3$ feedrate, gm/hr | 59 | 59 | 56 | 59 | 59 | 59 |
| Liquid feed composition, wt. % | | | | | | |
| DETA | 77.16 | 77.16 | 77.16 | 77.16 | 77.16 | 77.16 |
| MEA | 22.84 | 22.84 | 22.84 | 22.84 | 22.84 | 22.84 |
| EDA | — | — | — | — | — | — |
| Liquid product composition, wt. % | | | | | | |
| EDA | 1.69 | 1.53 | 1.11 | 5.98 | 5.97 | 6.14 |
| MeEDA | 0.00 | 0.00 | 0.00 | 0.00 | 0.00 | 0.00 |
| MEA | 10.19 | 7.13 | 8.50 | 1.44 | 1.75 | 1.70 |
| EtEDA | 0.00 | 0.00 | 0.00 | 0.00 | 0.00 | 0.00 |
| PIP | 1.17 | 1.29 | 1.08 | 4.26 | 4.38 | 4.67 |
| DETA | 63.75 | 67.41 | 69.62 | 56.36 | 56.78 | 56.34 |
| AEEA | 1.16 | 0.51 | 0.78 | 0.78 | 0.78 | 0.78 |

TABLE XLV-continued

| Example No. | 406 | 407 | 408 | 409 | 410 | 411 |
|---|---|---|---|---|---|---|
| AEP | 1.48 | 1.64 | 1.20 | 5.91 | 5.77 | 5.86 |
| HEP | 0.00 | 0.00 | 0.00 | 0.07 | 0.09 | 0.07 |
| TETA's | 13.90 | 13.58 | 11.94 | 14.21 | 13.22 | 13.20 |
| TEPA's | 4.76 | 4.63 | 3.90 | 5.29 | 3.76 | 3.77 |
| ROH Conversion % | 56.11 | 69.33 | 63.43 | 93.70 | 92.18 | 92.41 |
| Acyclic (N4)/cyclic (<=N4), weight ratio | 16.2 | 13.3 | 20.9 | 2.2 | 2.0 | 2.0 |
| Acyclic (N5)/cyclic (<=N5), weight ratio | 11.6 | 10.9 | 16.1 | 1.2 | 2.2 | 2.4 |
| Σ(N5)/Σ(N4), weight ratio | — | — | — | — | — | — |

TABLE XLVI

| Example No. | 412 | 413 | 414 | 415 | 416 | 417 | 418 | 419 | 420 | 421 |
|---|---|---|---|---|---|---|---|---|---|---|
| Catalyst Type | BBB | BBB | BBB | BBB | BBB | BBB | BBB | BBB | BBB | BBB |
| Catalyst weight, gm | 123.7 | 123.7 | 123.7 | 123.7 | 123.7 | 123.7 | 123.7 | 123.7 | 123.7 | 123.7 |
| Pressure, psig | 600 | 600 | 600 | 600 | 600 | 600 | 600 | 600 | 600 | 600 |
| Temperature, °C. | 266 | 272 | 271 | 270 | 298 | 300 | 300 | 299 | 303 | 302 |
| Time on organics, hrs. | 10.5 | 15.5 | 32.5 | 34.5 | 40.5 | 55.5 | 57.5 | 63.0 | 81.5 | 129.5 |
| Duration of run, hrs. | 10 | 2 | 16 | 2 | 2 | 15 | 15 | 2 | 2 | 2 |
| MEA SV, gmol/hr/kgcat | 1.94 | 1.72 | 1.97 | 1.97 | 2.02 | 1.94 | 0.26 | 1.88 | 1.97 | 1.89 |
| NH3 feedrate, gm/hr | 38.4 | 56.0 | 57.0 | 63.0 | 59.0 | 60.2 | 57.5 | 57.0 | 58.5 | 46.5 |
| Liquid feed composition, wt. % | | | | | | | | | | |
| DETA | 77.16 | 77.16 | 77.16 | 77.16 | 77.16 | 77.16 | 77.16 | 77.16 | 77.16 | 77.16 |
| MEA | 22.84 | 22.84 | 22.84 | 22.84 | 22.84 | 22.84 | 22.84 | 22.84 | 22.84 | 22.84 |
| Liquid product composition, wt. % | | | | | | | | | | |
| EDA | 0.97 | 1.21 | 1.01 | 0.94 | 3.46 | 2.86 | 2.63 | 2.72 | 2.46 | 2.44 |
| MeEDA | 0.00 | 0.00 | 0.00 | 0.00 | 0.00 | 0.00 | 0.00 | 0.00 | 0.00 | 0.00 |
| MEA | 13.53 | 11.37 | 11.57 | 12.57 | 4.80 | 6.56 | 7.31 | 7.23 | 8.08 | 7.91 |
| EtEDA | 0.00 | 0.00 | 0.00 | 0.00 | 0.00 | 0.00 | 0.00 | 0.00 | 0.00 | 0.00 |
| PIP | 0.63 | 0.72 | 0.58 | 0.58 | 2.14 | 1.81 | 1.37 | 1.78 | 1.56 | 1.61 |
| DETA | 74.34 | 73.54 | 74.39 | 75.32 | 69.81 | 71.72 | 73.83 | 72.52 | 73.94 | 73.16 |
| AEEA | 0.91 | 0.72 | 0.86 | 0.86 | 0.34 | 0.32 | 0.28 | 0.39 | 0.52 | 0.47 |
| AEP | 0.59 | 0.81 | 0.71 | 0.63 | 2.42 | 1.93 | 1.74 | 1.74 | 1.55 | 1.59 |
| HEP | 0.00 | 0.00 | 0.00 | 0.00 | 0.00 | 0.00 | 0.00 | 0.00 | 0.00 | 0.00 |
| TETA's | 7.74 | 9.46 | 8.96 | 7.68 | 12.10 | 10.11 | 8.91 | 9.43 | 8.16 | 7.76 |
| TEPA's | 1.07 | 1.81 | 1.48 | 1.17 | 2.94 | 2.34 | 1.88 | 2.12 | 1.79 | 1.93 |
| ROH Conversion % | 41.89 | 51.36 | 50.41 | 46.08 | 79.45 | 71.67 | 68.42 | 68.80 | 65.08 | 65.40 |
| Acyclic (N4)/cyclic (<=N4), weight ratio | 100.0 | 73.1 | 38.5 | 74.8 | 8.1 | 8.9 | 10.6 | 9.9 | 10.1 | 9.4 |
| Acyclic (N5)/cyclic (<=N5), weight ratio | — | — | — | — | — | 5.1 | 5.5 | 8.0 | 8.2 | 5.2 |
| Σ(N5)/Σ(N4), weight ratio | — | — | — | — | — | — | — | — | — | — |

TABLE XLVII

| Example No. | 422 | 423 | 424 | 425 | 426 | 427 | 428 | 429 | 430 |
|---|---|---|---|---|---|---|---|---|---|
| Catalyst Type | CCC | CCC | CCC | CCC | CCC | CCC | CCC | CCC | CCC |
| Catalyst weight, gm | 105.7 | 105.7 | 105.7 | 105.7 | 105.7 | 105.7 | 105.7 | 105.7 | 105.7 |
| Pressure, psig | 600 | 600 | 600 | 600 | 600 | 600 | 600 | 600 | 600 |
| Temperature, °C. | 268 | 281 | 275 | 302 | 304 | 304 | 303 | 302 | 302 |
| Time on organics, hrs. | 4.7 | 19.7 | 21.7 | 26.7 | 43.7 | 45.7 | 51.2 | 66.7 | 68.7 |
| Duration of run, hrs. | 2 | 15 | 2 | 2 | 17 | 2 | 2 | 14 | 2 |
| MEA SV, gmol/hr/kgcat | 2.09 | 2.13 | 2.20 | 2.06 | 2.14 | 2.09 | 1.90 | 2.02 | 1.91 |
| NH3 feedrate, gm/hr | 49.5 | 42.8 | 54.5 | 47.5 | 51.0 | 41.5 | 54.5 | 58.8 | 53.0 |
| Liquid feed composition, wt. % | | | | | | | | | |
| DETA | 77.16 | 77.16 | 77.16 | 77.16 | 77.16 | 77.16 | 66.46 | 66.46 | 66.46 |
| MEA | 22.84 | 22.84 | 22.84 | 22.84 | 22.84 | 22.84 | — | — | — |
| AEEA | — | — | — | — | — | — | 33.54 | 33.54 | 33.54 |
| Liquid product composition, wt. % | | | | | | | | | |
| EDA | 2.25 | 1.42 | 1.17 | 4.33 | 4.33 | 4.06 | 2.41 | 2.32 | 2.62 |
| MeEDA | 0.00 | 0.00 | 0.00 | 0.00 | 0.00 | 0.00 | 0.00 | 0.00 | 0.00 |
| MEA | 8.59 | 11.37 | 12.86 | 5.60 | 6.05 | 5.73 | 0.00 | 0.00 | 0.00 |
| EtEDA | 0.00 | 0.00 | 0.00 | 0.00 | 0.00 | 0.00 | 0.00 | 0.00 | 0.00 |
| PIP | 1.36 | 0.68 | 0.49 | 1.69 | 1.70 | 1.69 | 9.19 | 9.15 | 9.13 |
| DETA | 70.30 | 74.76 | 76.82 | 71.05 | 71.22 | 71.97 | 68.27 | 68.90 | 70.40 |
| AEEA | 0.80 | 0.97 | 0.85 | 0.31 | 0.40 | 0.00 | 1.15 | 1.10 | 0.53 |
| AEP | 1.27 | 0.69 | 0.53 | 1.68 | 1.67 | 1.61 | 1.32 | 1.33 | 1.51 |
| HEP | 0.00 | 0.00 | 0.00 | 0.00 | 0.00 | 0.00 | 0.00 | 0.00 | 0.00 |

TABLE XLVII-continued

| Example No. | 422 | 423 | 424 | 425 | 426 | 427 | 428 | 429 | 430 |
|---|---|---|---|---|---|---|---|---|---|
| TETA's | 10.97 | 8.09 | 5.52 | 9.47 | 8.65 | 7.79 | 6.49 | 6.41 | 6.60 |
| TEPA's | 2.93 | 1.60 | 0.93 | 2.07 | 1.87 | 1.65 | 7.25 | 7.27 | 5.87 |
| ROH Conversion % | 63.07 | 51.25 | 44.36 | 75.40 | 73.30 | 74.34 | 96.50 | 96.70 | 98.40 |
| Acyclic (N4)/cyclic ($\leq$N4), weight ratio | 9.09 | 72.20 | 100.00 | 8.90 | 8.70 | 7.90 | 0.30 | 0.30 | 0.30 |
| Acyclic (N5)/cyclic ($\leq$N5), weight ratio | 28.90 | 100.00 | 100.00 | 15.10 | 10.60 | 9.60 | 13.10 | 13.60 | 9.50 |
| $\Sigma$(N5)/$\Sigma$(N4), weight ratio | — | — | — | — | — | — | 1.10 | 1.10 | 0.90 |

TABLE XLVIII

| Example No. | 431 | 432 | 433 | 434 | 435 | 436 | 437 | 438 | 439 | 440 | 441 |
|---|---|---|---|---|---|---|---|---|---|---|---|
| Catalyst Type | DDD | DDD | DDD | DDD | DDD | DDD | DDD | DDD | DDD | DDD | DDD |
| Catalyst weight, gm | 121 | 121 | 121 | 121 | 121 | 121 | 121 | 121 | 121 | 121 | 121 |
| Pressure, psig | 600 | 600 | 600 | 600 | 600 | 600 | 600 | 600 | 600 | 600 | 600 |
| Temperature, °C. | 279 | 270 | 270 | 269 | 269 | 275 | 270 | 272 | 274 | 272 | 258 |
| Time on organics, hrs. | 4.5 | 18.5 | 35.5 | 37.5 | 43.5 | 54.5 | 62.5 | 66.0 | 82.0 | 84.0 | 90.7 |
| Duration of run, hrs. | 2 | 2 | 16 | 2 | 2 | 2 | 2 | 2 | 15 | 2 | 2 |
| MEA SV, gmol/hr/kgcat | 2.00 | 1.98 | 1.98 | 2.03 | 2.03 | 2.01 | 1.97 | 1.68 | 1.70 | 1.69 | 1.33 |
| NH₃ feedrate, gm/hr | 67.2 | 72.0 | 48.1 | 46.0 | 44.5 | 41.1 | 47.5 | 48.0 | 45.1 | 49.0 | 86.5 |
| Liquid feed composition, wt. % | | | | | | | | | | | |
| DETA | 77.16 | 77.16 | 77.16 | 77.16 | 77.16 | 77.16 | 77.16 | 66.46 | 66.46 | 66.46 | 66.46 |
| MEA | 22.84 | 22.84 | 22.84 | 22.84 | 22.84 | 22.84 | 22.84 | — | — | — | — |
| AEEA | — | — | — | — | — | — | — | 33.54 | 33.54 | 33.54 | 33.54 |
| Liquid product composition, wt. % | | | | | | | | | | | |
| EDA | 5.79 | 1.61 | 1.48 | 1.43 | 1.18 | 1.34 | 1.37 | 1.05 | 1.04 | 1.08 | 0.48 |
| MeEDA | 0.00 | 0.00 | 0.00 | 0.00 | 0.00 | 0.00 | 0.00 | 0.00 | 0.00 | 0.00 | 0.00 |
| MEA | 2.74 | 6.67 | 7.72 | 7.67 | 7.39 | 6.27 | 6.43 | 0.31 | 0.11 | 0.12 | 0.15 |
| EtEDA | 0.00 | 0.00 | 0.00 | 0.00 | 0.00 | 0.00 | 0.00 | 0.00 | 0.00 | 0.00 | 0.00 |
| PIP | 4.65 | 1.25 | 1.17 | 1.16 | 0.99 | 1.15 | 1.21 | 10.37 | 10.57 | 10.55 | 7.06 |
| DETA | 61.98 | 71.25 | 73.17 | 73.07 | 69.92 | 68.69 | 68.71 | 58.64 | 58.83 | 59.53 | 67.06 |
| AEEA | 0.00 | 0.16 | 0.22 | 0.24 | 0.45 | 0.42 | 0.37 | 5.96 | 6.64 | 6.72 | 15.36 |
| AEP | 5.74 | 1.29 | 0.94 | 0.93 | 0.97 | 1.13 | 1.18 | 1.35 | 1.26 | 1.20 | 0.59 |
| HEP | 0.00 | 0.00 | 0.00 | 0.00 | 0.00 | 0.00 | 0.00 | 0.00 | 0.00 | 0.00 | 0.00 |
| TETA's | 13.80 | 14.03 | 12.81 | 12.89 | 14.92 | 16.23 | 15.76 | 8.51 | 8.04 | 7.49 | 3.04 |
| TEPA's | 3.53 | 2.45 | 1.96 | 2.10 | 3.18 | 3.62 | 3.71 | 10.70 | 11.09 | 10.99 | 6.08 |
| ROH Conversion % | 88.45 | 71.55 | 67.20 | 67.43 | 68.55 | 73.37 | 72.65 | 82.40 | 80.50 | 80.30 | 55.20 |
| Acyclic (N4)/cyclic ($\leq$N4), weight ratio | 3.69 | 8.70 | 46.60 | 49.50 | 44.30 | 38.60 | 34.50 | 0.25 | 0.17 | 0.18 | 0.12 |
| Acyclic (N5)/cyclic ($\leq$N5), weight ratio | 2.70 | 100.00 | 100.00 | 100.00 | 100.00 | 100.00 | 100.00 | 34.00 | 38.70 | 44.00 | 100.00 |
| $\Sigma$(N5)/$\Sigma$(N4), weight ratio | — | — | — | — | — | — | — | 1.30 | 1.40 | 1.50 | 2.00 |

TABLE XLIX

| Example No. | 442 | 443 | 444 | 445 | 446 | 447 | 448 | 449 | 450 |
|---|---|---|---|---|---|---|---|---|---|
| Catalyst Type | EEE | EEE | EEE | EEE | EEE | EEE | EEE | EEE | EEE |
| Catalyst weight, gm | 118.7 | 118.7 | 118.7 | 118.7 | 118.7 | 118.7 | 118.7 | 118.7 | 118.7 |
| Pressure, psig | 600 | 600 | 600 | 600 | 600 | 600 | 600 | 600 | 600 |
| Temperature, °C. | 267 | 268 | 267 | 289 | 284 | 301 | 291 | 298 | 260 |
| Time on organics, hrs. | 8.5 | 19.0 | 21.0 | 25.0 | 28.0 | 32.0 | 35.0 | 39.0 | 43.0 |
| Duration of run, hrs. | 2 | 10 | 2 | 2 | 2 | 2 | 2 | 2 | 2 |
| MEA SV, gmol/hr/kgcat | 2.01 | 2.04 | 2.11 | 2.00 | 1.94 | 1.58 | 1.65 | 1.57 | 1.68 |
| NH₃ feedrate, gm/hr | 45.2 | 47.4 | 47.5 | 54.0 | 51.0 | 46.0 | 43.0 | 30.0 | 46.0 |
| Liquid feed composition, wt. % | | | | | | | | | |
| DETA | 77.16 | 77.16 | 77.16 | 77.16 | 77.16 | 66.46 | 66.46 | 66.46 | 66.46 |
| MEA | 22.84 | 22.84 | 22.84 | 22.84 | 22.84 | — | — | — | — |
| AEEA | — | — | — | — | — | 33.54 | 33.54 | 33.54 | 33.54 |
| Liquid product composition, wt. % | | | | | | | | | |
| EDA | 1.12 | 0.95 | 0.83 | 2.89 | 2.86 | 2.46 | 1.69 | 2.41 | 0.31 |
| MeEDA | 0.00 | 0.00 | 0.00 | 0.00 | 0.00 | 0.00 | 0.00 | 0.00 | 0.00 |
| MEA | 11.83 | 12.17 | 12.64 | 6.50 | 6.93 | 0.45 | 0.52 | 0.34 | 0.45 |
| EtEDA | 0.00 | 0.00 | 0.00 | 0.00 | 0.00 | 0.00 | 0.00 | 0.00 | 0.00 |
| PIP | 0.94 | 0.63 | 0.49 | 1.87 | 1.84 | 11.04 | 10.33 | 11.22 | 3.39 |
| DETA | 76.42 | 79.20 | 76.28 | 68.84 | 71.08 | 57.52 | 61.86 | 67.91 | 75.51 |
| AEEA | 0.36 | 0.28 | 0.54 | 0.17 | 0.17 | 0.90 | 2.98 | 0.97 | 17.00 |
| AEP | 0.63 | 0.39 | 0.41 | 1.88 | 1.71 | 2.52 | 1.37 | 1.71 | 0.27 |
| HEP | 0.00 | 0.00 | 0.00 | 0.00 | 0.00 | 0.00 | 0.00 | 0.00 | 0.00 |
| TETA's | 7.47 | 5.50 | 7.52 | 11.98 | 10.95 | 11.25 | 8.74 | 6.93 | 1.01 |
| TEPA's | 1.02 | 0.54 | 0.97 | 3.35 | 2.49 | 8.61 | 9.41 | 5.34 | 2.07 |
| ROH Conversion % | 49.35 | 47.67 | 45.70 | 71.94 | 70.17 | 97.30 | 91.10 | 97.10 | 49.80 |

TABLE XLIX-continued

| Example No. | 442 | 443 | 444 | 445 | 446 | 447 | 448 | 449 | 450 |
|---|---|---|---|---|---|---|---|---|---|
| Acyclic (N4)/cyclic (<=N4), weight ratio | 100.00 | 100.00 | 100.00 | 10.60 | 13.70 | 0.30 | 0.20 | 0.20 | 0.20 |
| Acyclic (N5)/cyclic (<=N5), weight ratio | 100.00 | 100.00 | 100.00 | 5.78 | 8.20 | 4.40 | 22.80 | 100.00 | 100.00 |
| Σ(N5)/Σ(N4), weight ratio | — | — | — | — | — | 0.80 | 1.10 | 0.80 | 2.00 |

TABLE L

| Example No. | 451 | 452 | 453 | 454 | 455 | 456 | 457 | 458 | 459 | 460 | 461 | 462 |
|---|---|---|---|---|---|---|---|---|---|---|---|---|
| Catalyst Type | FFF | FFF | FFF | FFF | FFF | FFF | FFF | FFF | FFF | FFF | FFF | FFF |
| Catalyst weight, gm | 123.6 | 123.6 | 123.6 | 123.6 | 123.6 | 123.6 | 123.6 | 123.6 | 123.6 | 123.6 | 123.6 | 123.6 |
| Pressure, psig | 600 | 600 | 600 | 600 | 600 | 600 | 600 | 600 | 600 | 600 | 600 | 600 |
| Temperature, °C. | 279 | 277 | 276 | 260 | 263 | 264 | 261 | 262 | 263 | 274 | 277 | 276 |
| Time on organics, hrs. | 4.7 | 22.0 | 24.0 | 29.0 | 45.0 | 47.0 | 52.5 | 69.0 | 71.0 | 76.5 | 93.5 | 95.0 |
| Duration of run, hrs. | 2 | 17 | 2 | 2 | 16 | 2 | 2 | 16 | 2 | 16 | 16 | 1 |
| MEA SV, gmol/hr/kgcat | 1.92 | 1.96 | 1.93 | 1.96 | 1.97 | 1.99 | 1.73 | 1.70 | 1.74 | 1.65 | 1.66 | 1.73 |
| NH3 feedrate, gm/hr | 53.0 | 48.4 | 55.0 | 52.0 | 49.3 | 49.5 | 47.0 | 47.3 | 46.5 | 49.0 | 49.9 | 54.6 |
| Liquid feed composition, wt. % | | | | | | | | | | | | |
| PIP | — | — | — | — | — | — | — | — | — | — | — | — |
| DETA | 77.16 | 77.16 | 77.16 | 77.16 | 77.16 | 77.16 | 66.46 | 66.46 | 66.46 | 66.46 | 66.46 | 66.46 |
| MEA | 22.84 | 22.84 | 22.84 | 22.84 | 22.84 | 22.84 | — | — | — | — | — | — |
| AEEA | — | — | — | — | — | — | 33.54 | 33.54 | 33.54 | 33.54 | 33.54 | 33.54 |
| Liquid product composition, wt. % | | | | | | | | | | | | |
| EDA | 3.96 | 3.55 | 3.17 | 1.21 | 1.14 | 1.30 | 0.77 | 0.77 | 0.67 | 1.58 | 1.88 | 1.60 |
| MeEDA | 0.00 | 0.00 | 0.00 | 0.00 | 0.00 | 0.00 | 0.00 | 0.00 | 0.00 | 0.00 | 0.00 | 0.00 |
| MEA | 2.91 | 2.56 | 2.50 | 7.40 | 7.44 | 7.38 | 0.18 | 0.00 | 0.00 | 0.00 | 0.00 | 0.00 |
| EtEDA | 0.00 | 0.00 | 0.00 | 0.00 | 0.00 | 0.00 | 0.00 | 0.00 | 0.00 | 0.00 | 0.00 | 0.00 |
| PIP | 3.12 | 2.46 | 2.21 | 1.06 | 1.05 | 1.15 | 8.23 | 8.70 | 8.57 | 10.86 | 10.76 | 10.60 |
| DETA | 61.14 | 63.82 | 60.32 | 71.24 | 72.08 | 68.84 | 65.43 | 66.94 | 69.33 | 65.27 | 62.85 | 65.63 |
| AEEA | 0.00 | 0.00 | 0.00 | 0.00 | 0.00 | 0.29 | 3.28 | 3.21 | 3.00 | 0.42 | 0.35 | 0.00 |
| AEP | 4.38 | 3.42 | 3.06 | 1.06 | 0.99 | 1.07 | 0.00 | 0.91 | 0.88 | 1.66 | 1.77 | 1.70 |
| HEP | 0.00 | 0.00 | 0.00 | 0.00 | 0.00 | 0.00 | 0.00 | 0.00 | 0.00 | 0.00 | 0.00 | 0.00 |
| TETA's | 17.74 | 18.49 | 18.86 | 15.11 | 14.78 | 15.71 | 6.46 | 5.73 | 5.20 | 7.71 | 8.60 | 7.54 |
| TEPA's | 4.05 | 4.67 | 5.70 | 2.73 | 2.32 | 3.70 | 14.12 | 13.23 | 12.12 | 11.71 | 11.80 | 11.62 |
| ROH Conversion % | 87.61 | 89.27 | 89.19 | 68.76 | 68.57 | 68.77 | 90.40 | 90.70 | 91.30 | 99.80 | 99.00 | 100.00 |
| Acyclic (N4)/cyclic (<=N4), weight ratio | 7.20 | 11.20 | 11.20 | 80.70 | 100.00 | 46.90 | 0.30 | 0.20 | 0.10 | 0.20 | 0.30 | 0.20 |
| Acyclic (N5)/cyclic (<=N5), weight ratio | 100.00 | 18.00 | 17.30 | 100.00 | 100.00 | 100.00 | 85.10 | 94.20 | 100.00 | 35.10 | 26.40 | 30.80 |
| Σ(N5)/Σ(N4), weight ratio | — | — | — | — | — | — | 2.20 | 2.30 | 2.30 | 1.50 | 1.40 | 1.50 |

TABLE LI

| Example No. | 463 | 464 | 465 | 466 | 467 | 468 | 469 | 470 | 471 | 472 | 473 |
|---|---|---|---|---|---|---|---|---|---|---|---|
| Catalyst Type | GGG | GGG | GGG | GGG | GGG | GGG | GGG | GGG | GGG | GGG | GGG |
| Catalyst weight, gm | 116.6 | 116.6 | 116.6 | 116.6 | 116.6 | 116.6 | 116.6 | 116.6 | 116.6 | 116.6 | 116.6 |
| Pressure, psig | 600 | 600 | 600 | 600 | 600 | 600 | 600 | 600 | 600 | 600 | 600 |
| Temperature, °C. | 277 | 284 | 272 | 272 | 277 | 266 | 267 | 266 | 282 | 282 | 281 |
| Time on organics, hrs. | 4.5 | 20.0 | 22.0 | 27.5 | 44.5 | 52.5 | 69.5 | 71.5 | 76.5 | 94.5 | 96.5 |
| Duration of run, hrs. | 2 | 15 | 2 | 2 | 15 | 2 | 15 | 2 | 2 | 16 | 2 |
| MEA SV, gmol/hr/kgcat | 2.02 | 2.05 | 2.13 | 2.03 | 2.02 | 1.76 | 1.80 | 1.79 | 1.72 | 2.04 | 2.06 |
| NH3 feedrate, gm/hr | 60.5 | 54.7 | 57.0 | 54.5 | 43.5 | 68.5 | 53.1 | 45.5 | 66.0 | 60.6 | 56.0 |
| Liquid feed composition, wt. % | | | | | | | | | | | |
| DETA | 77.16 | 77.16 | 77.16 | 77.16 | 77.16 | 66.46 | 66.46 | 66.46 | 66.46 | 77.16 | 77.16 |
| MEA | 22.84 | 22.84 | 22.84 | 22.84 | 22.84 | — | — | — | — | 22.84 | 22.84 |
| AEEA | — | — | — | — | — | 33.54 | 33.54 | 33.54 | 33.54 | — | — |
| Liquid product composition, wt. % | | | | | | | | | | | |
| EDA | 2.05 | 2.24 | 1.23 | 0.78 | 0.73 | 0.38 | 0.32 | 0.39 | 1.58 | 2.16 | 2.07 |
| MeEDA | 0.00 | 0.00 | 0.00 | 0.00 | 0.00 | 0.00 | 0.00 | 0.00 | 0.00 | 0.00 | 0.00 |
| MEA | 5.90 | 3.75 | 6.68 | 8.22 | 8.34 | 0.26 | 0.00 | 0.19 | 0.00 | 4.77 | 4.91 |
| EtEDA | 0.00 | 0.00 | 0.00 | 0.00 | 0.00 | 0.00 | 0.00 | 0.00 | 0.00 | 0.00 | 0.00 |
| PIP | 2.21 | 2.48 | 1.56 | 1.14 | 1.10 | 6.66 | 6.97 | 6.77 | 9.99 | 2.49 | 2.37 |
| DETA | 74.52 | 75.33 | 75.56 | 79.77 | 81.46 | 72.66 | 76.76 | 73.28 | 65.22 | 73.27 | 75.76 |
| AEEA | 0.00 | 0.00 | 0.00 | 0.00 | 0.00 | 6.14 | 5.08 | 6.32 | 0.00 | 0.00 | 0.00 |
| AEP | 2.09 | 2.54 | 1.56 | 1.05 | 1.06 | 0.64 | 0.61 | 0.59 | 1.90 | 2.48 | 2.38 |
| HEP | 0.00 | 0.00 | 0.00 | 0.00 | 0.00 | 0.00 | 0.00 | 0.00 | 0.00 | 0.00 | 0.00 |
| TETA's | 11.24 | 11.94 | 11.23 | 8.09 | 6.69 | 5.09 | 4.22 | 4.81 | 9.47 | 10.79 | 10.14 |
| TEPA's | 1.89 | 1.67 | 2.03 | 0.92 | 0.62 | 7.62 | 5.92 | 7.17 | 9.26 | 3.34 | 2.36 |
| ROH Conversion % | 75.18 | 84.30 | 71.82 | 65.14 | 64.60 | 82.00 | 85.20 | 81.60 | 100.00 | 79.85 | 79.41 |
| Acyclic (N4)/cyclic (<=N4), | 15.00 | 12.40 | 17.20 | 100.00 | 100.00 | 0.11 | 0.00 | 0.10 | 0.20 | 7.30 | 8.40 |

TABLE LI-continued

| Example No. | 463 | 464 | 465 | 466 | 467 | 468 | 469 | 470 | 471 | 472 | 473 |
|---|---|---|---|---|---|---|---|---|---|---|---|
| weight ratio | | | | | | | | | | | |
| Acyclic (N5)/cyclic (<=N5), weight ratio | 100.00 | 100.00 | 100.00 | 100.00 | 100.00 | 62.00 | 100.00 | 70.20 | 7.21 | 2.50 | 7.40 |
| Σ(N5)/Σ(N4), weight ratio | — | — | — | — | — | 1.30 | 1.40 | 1.50 | 1.00 | — | — |

TABLE LII

| Example No. | 474 | 475 | 476 | 477 | 478 | 479 | 480 | 481 | 482 | 483 | 484 | 485 |
|---|---|---|---|---|---|---|---|---|---|---|---|---|
| Catalyst Type | HHH | HHH | HHH | HHH | HHH | HHH | HHH | HHH | HHH | HHH | HHH | HHH |
| Catalyst weight, gm | 118.4 | 118.4 | 118.4 | 118.4 | 118.4 | 118.4 | 118.4 | 118.4 | 118.4 | 118.4 | 118.4 | 118.4 |
| Pressure, psig | 600 | 600 | 600 | 600 | 600 | 600 | 600 | 600 | 600 | 600 | 600 | 600 |
| Temperature, °C. | 267 | 276 | 276 | 295 | 296 | 296 | 298 | 270 | 271 | 266 | 267 | 268 |
| Time on organics, hrs. | 8.0 | 21.0 | 23.0 | 29.0 | 45.0 | 47.0 | 53.0 | 69.0 | 71.0 | 77.0 | 93.0 | 95.0 |
| Duration of run, hrs. | 2 | 13 | 2 | 2 | 16 | 2 | 2 | 16 | 2 | 2 | 16 | 2 |
| MEA SV, gmol/hr/kgcat | 1.96 | 2.00 | 2.06 | 2.01 | 1.99 | 2.01 | 1.68 | 1.72 | 1.71 | 1.98 | 2.00 | 2.01 |
| NH3 feedrate, gm/hr | 65.5 | 57.4 | 53.5 | 59.0 | 46.6 | 36.0 | 64.0 | 49.5 | 51.5 | 51.0 | 49.3 | 49.5 |
| Liquid feed composition, wt. % | | | | | | | | | | | | |
| DETA | 77.16 | 77.16 | 77.16 | 77.16 | 77.16 | 77.16 | 66.46 | 66.46 | 66.46 | 77.16 | 77.16 | 77.16 |
| MEA | 22.84 | 22.84 | 22.84 | 22.84 | 22.84 | 22.84 | — | — | — | 22.84 | 22.84 | 22.84 |
| AEEA | — | — | — | — | — | — | 33.54 | 33.54 | 33.54 | — | — | — |
| Liquid product composition, wt. % | | | | | | | | | | | | |
| EDA | 0.81 | 0.99 | 1.00 | 3.45 | 3.60 | 3.29 | 2.33 | 0.00 | 0.37 | 0.27 | 0.48 | 0.51 |
| MeEDA | 0.00 | 0.00 | 0.00 | 0.00 | 0.00 | 0.00 | 0.00 | 0.00 | 0.00 | 0.00 | 0.00 | 0.00 |
| MEA | 8.16 | 6.51 | 7.10 | 1.45 | 2.25 | 2.43 | 0.00 | 0.00 | 0.00 | 10.27 | 10.50 | 10.46 |
| EtEDA | 0.00 | 0.00 | 0.00 | 0.00 | 0.00 | 0.00 | 0.00 | 0.00 | 0.00 | 0.00 | 0.00 | 0.00 |
| PIP | 1.03 | 1.41 | 1.44 | 3.95 | 4.17 | 4.13 | 12.33 | 6.69 | 6.85 | 0.80 | 0.75 | 0.77 |
| DETA | 77.87 | 78.14 | 74.65 | 76.12 | 72.14 | 74.46 | 69.31 | 82.62 | 77.14 | 84.56 | 84.28 | 84.63 |
| AEEA | 0.00 | 0.00 | 0.00 | 0.00 | 0.00 | 0.00 | 0.00 | 4.62 | 6.65 | 0.00 | 0.00 | 0.00 |
| AEP | 1.04 | 1.43 | 1.38 | 4.56 | 4.28 | 4.25 | 3.27 | 0.72 | 0.61 | 0.74 | 0.72 | 0.71 |
| HEP | 0.00 | 0.00 | 0.00 | 0.00 | 0.00 | 0.00 | 0.00 | 0.00 | 0.00 | 0.00 | 0.00 | 0.00 |
| TETA's | 9.61 | 9.93 | 11.80 | 9.39 | 10.88 | 9.44 | 8.73 | 2.75 | 3.71 | 2.87 | 2.89 | 2.61 |
| TEPA's | 1.49 | 1.59 | 2.63 | 1.08 | 2.34 | 1.86 | 3.29 | 2.60 | 4.50 | 0.49 | 0.39 | 0.00 |
| ROH Conversion % | 65.45 | 72.55 | 70.09 | 93.97 | 90.62 | 89.88 | 100.00 | 86.50 | 80.60 | 56.14 | 55.12 | 55.13 |
| Acyclic (N4)/cyclic (<=N4), weight ratio | 53.30 | 37.90 | 23.80 | 4.10 | 4.40 | 4.10 | 0.20 | 0.00 | 0.00 | 100.00 | 100.00 | 100.00 |
| Acyclic (N5)/cyclic (<=N5), weight ratio | 100.00 | 100.00 | 100.00 | 1.90 | 2.10 | 2.00 | 5.40 | 100.00 | 100.00 | 100.00 | 100.00 | 100.00 |
| Σ(N5)/Σ(N4), weight ratio | — | — | — | — | — | — | 0.40 | 1.00 | 1.20 | — | — | — |

TABLE LIII

| Example No. | 486 | 487 | 488 | 489 | 490 | 491 | 492 | 493 | 494 | 495 | 496 | 497 |
|---|---|---|---|---|---|---|---|---|---|---|---|---|
| Catalyst Type | III | III | III | III | III | III | III | III | III | III | III | III |
| Catalyst weight, gm | 118.2 | 118.2 | 118.2 | 118.2 | 118.2 | 118.2 | 118.2 | 118.2 | 118.2 | 118.2 | 118.2 | 118.2 |
| Pressure, psig | 600 | 600 | 600 | 600 | 600 | 600 | 600 | 600 | 600 | 600 | 600 | 600 |
| Temperature, °C. | 272 | 271 | 273 | 299 | 301 | 300 | 302 | 302 | 273 | 270 | 272 | 272 |
| Time on organics, hrs. | 4.0 | 17.0 | 19.0 | 25.0 | 42.5 | 44.5 | 50.5 | 59.0 | 62.0 | 72.7 | 82.0 | 84.0 |
| Duration of run, hrs. | 2 | 13 | 2 | 2 | 17 | 2 | 8 | 8 | 2 | 2 | 9 | 2 |
| MEA SV, gmol/hr/kgcat | 1.98 | 1.99 | 1.98 | 1.98 | 1.96 | 2.02 | 1.69 | 1.68 | 1.67 | 1.99 | 2.08 | 2.01 |
| NH3 feedrate, gm/hr | 69.0 | 70.7 | 59.0 | 55.5 | 49.9 | 65.5 | 48.0 | 47.8 | 57.5 | 45.0 | 44.0 | 41.0 |
| Liquid feed composition, wt. % | | | | | | | | | | | | |
| DETA | 77.16 | 77.16 | 77.16 | 77.16 | 77.16 | 77.16 | 66.46 | 66.46 | 66.46 | 77.16 | 77.16 | 77.16 |
| MEA | 22.84 | 22.84 | 22.84 | 22.84 | 22.84 | 22.84 | — | — | — | 22.84 | 22.84 | 22.84 |
| AEEA | — | — | — | — | — | — | 33.54 | 33.54 | 33.54 | — | — | — |
| Liquid product composition, wt. % | | | | | | | | | | | | |
| EDA | 0.74 | 0.72 | 0.58 | 2.88 | 2.15 | 2.01 | 1.65 | 1.44 | 0.00 | 0.21 | 0.22 | 0.00 |
| MeEDA | 0.00 | 0.00 | 0.00 | 0.00 | 0.00 | 0.00 | 0.00 | 0.00 | 0.00 | 0.00 | 0.00 | 0.00 |
| MEA | 7.89 | 7.63 | 8.40 | 1.99 | 3.10 | 3.86 | 0.00 | 0.00 | 0.19 | 11.14 | 11.57 | 11.60 |
| EtEDA | 0.00 | 0.00 | 0.00 | 0.00 | 0.00 | 0.00 | 0.00 | 0.00 | 0.00 | 0.00 | 0.00 | 0.00 |
| PIP | 1.28 | 1.11 | 0.93 | 3.30 | 3.03 | 2.79 | 12.61 | 12.29 | 7.23 | 0.82 | 0.77 | 0.77 |
| DETA | 79.77 | 73.47 | 73.54 | 76.57 | 79.28 | 79.79 | 71.48 | 70.87 | 78.08 | 84.83 | 84.22 | 85.08 |
| AEEA | 0.23 | 0.50 | 0.70 | 0.00 | 0.00 | 0.00 | 0.00 | 0.00 | 7.36 | 0.00 | 0.00 | 0.00 |
| AEP | 0.78 | 1.01 | 0.88 | 2.61 | 2.05 | 1.80 | 1.93 | 1.71 | 0.19 | 0.29 | 0.25 | 0.21 |
| HEP | 0.00 | 0.00 | 0.00 | 0.00 | 0.00 | 0.00 | 0.00 | 0.00 | 0.00 | 0.00 | 0.00 | 0.00 |
| TETA's | 7.63 | 11.54 | 11.52 | 8.85 | 6.88 | 7.59 | 5.61 | 6.10 | 2.44 | 1.85 | 2.29 | 1.69 |
| TEPA's | 1.03 | 2.90 | 2.71 | 1.72 | 1.36 | 1.22 | 3.11 | 4.22 | 3.46 | 0.37 | 0.26 | 0.19 |
| ROH Conversion % | 66.33 | 67.44 | 64.22 | 91.52 | 86.72 | 83.64 | 100.00 | 100.00 | 78.20 | 52.05 | 50.20 | 50.04 |
| Acyclic (N4)/cyclic (<=N4), weight ratio | 22.50 | 26.60 | 14.70 | 14.70 | 5.70 | 2.30 | 0.20 | 0.20 | 0.10 | 100.00 | 100.00 | 100.00 |

TABLE LIII-continued

| Example No. | 486 | 487 | 488 | 489 | 490 | 491 | 492 | 493 | 494 | 495 | 496 | 497 |
|---|---|---|---|---|---|---|---|---|---|---|---|---|
| Acyclic (N5)/cyclic (<=N5), weight ratio | 100.00 | 33.50 | 100.00 | 100.00 | 4.50 | 1.90 | 1.90 | 2.90 | 14.00 | 100.00 | 100.00 | 100.00 |
| Σ(N5)/Σ(N4), weight ratio | — | — | — | — | — | — | 0.60 | 0.70 | 1.40 | — | — | — |

TABLE LIV

| Example No. | 498 | 499 | 500 | 501 | 502 | 503 | 504 | 505 | 506 | 507 | 508 | 509 |
|---|---|---|---|---|---|---|---|---|---|---|---|---|
| Catalyst Type | JJJ | JJJ | JJJ | JJJ | JJJ | JJJ | JJJ | JJJ | JJJ | JJJ | JJJ | JJJ |
| Catalyst weight, gm | 118.3 | 118.3 | 118.3 | 118.3 | 118.3 | 118.3 | 118.3 | 118.3 | 118.3 | 118.3 | 118.3 | 118.3 |
| Pressure, psig | 600 | 600 | 600 | 600 | 600 | 600 | 600 | 600 | 600 | 600 | 600 | 600 |
| Temperature, °C. | 272 | 271 | 272 | 300 | 302 | 302 | 301 | 274 | 275 | 275 | 276 | 276 |
| Time on organics, hrs. | 4.0 | 17.5 | 19.5 | 25.0 | 41.0 | 43.0 | 48.0 | 65.0 | 67.0 | 72.0 | 85.0 | 87.0 |
| Duration of run, hrs. | 2 | 13 | 2 | 2 | 16 | 2 | 2 | 16 | 2 | 2 | 15 | 2 |
| MEA SV, gmol/hr/kgcat | 1.94 | 1.98 | 1.91 | 1.92 | 1.90 | 1.89 | 3.34 | 3.38 | 3.37 | 2.03 | 1.96 | 1.97 |
| NH3 feedrate, gm/hr | 45.0 | 45.9 | 48.5 | 46.0 | 58.4 | 55.0 | 55.5 | 53.0 | 50.5 | 52.5 | 51.0 | 49.5 |
| Liquid feed composition, wt. % | | | | | | | | | | | | |
| DETA | 77.16 | 77.16 | 77.16 | 77.16 | 77.16 | 77.16 | 66.46 | 66.46 | 66.46 | 77.16 | 77.16 | 77.16 |
| MEA | 22.84 | 22.84 | 22.84 | 22.84 | 22.84 | 22.84 | — | — | — | 22.84 | 22.84 | 22.84 |
| AEEA | — | — | — | — | — | — | 33.54 | 33.54 | 33.54 | — | — | — |
| Liquid product composition, wt. % | | | | | | | | | | | | |
| EDA | 0.48 | 0.50 | 0.45 | 2.70 | 2.96 | 2.83 | 2.44 | 0.36 | 0.40 | 0.51 | 0.50 | 0.59 |
| MeEDA | 0.00 | 0.00 | 0.00 | 0.00 | 0.00 | 0.00 | 0.00 | 0.00 | 0.00 | 0.00 | 0.00 | 0.00 |
| MEA | 9.18 | 9.77 | 9.84 | 2.44 | 2.92 | 2.93 | 0.00 | 0.30 | 0.29 | 10.04 | 10.18 | 10.47 |
| EtEDA | 0.00 | 0.00 | 0.00 | 0.00 | 0.00 | 0.00 | 0.00 | 0.00 | 0.00 | 0.00 | 0.00 | 0.00 |
| PIP | 1.10 | 1.10 | 1.07 | 3.88 | 3.86 | 3.85 | 11.79 | 7.03 | 7.40 | 1.33 | 1.23 | 1.21 |
| DETA | 77.40 | 77.67 | 78.15 | 68.03 | 67.03 | 66.76 | 61.93 | 69.26 | 69.84 | 76.33 | 78.33 | 77.59 |
| AEEA | 0.64 | 0.63 | 0.64 | 0.00 | 0.07 | 0.08 | 0.00 | 7.10 | 6.01 | 0.69 | 0.48 | 0.51 |
| AEP | 0.85 | 0.84 | 0.82 | 3.78 | 3.70 | 3.69 | 2.60 | 0.76 | 0.77 | 0.99 | 0.91 | 0.90 |
| HEP | 0.00 | 0.00 | 0.00 | 0.00 | 0.00 | 0.00 | 0.00 | 0.00 | 0.10 | 0.00 | 0.00 | 0.00 |
| TETA's | 7.04 | 6.84 | 6.47 | 11.12 | 10.94 | 11.03 | 9.81 | 5.55 | 5.66 | 7.02 | 6.22 | 6.15 |
| TEPA's | 60.31 | 57.98 | 57.64 | 89.42 | 87.25 | 87.18 | 100.00 | 78.90 | 82.20 | 56.92 | 56.32 | 54.87 |
| ROH Conversion % | | | | | | | | | | | | |
| Acyclic (N4)/cyclic (<=N4), weight ratio | 22.40 | 22.90 | 21.20 | 4.00 | 4.10 | 4.00 | 0.30 | 0.10 | 0.10 | 13.50 | 21.40 | 20.40 |
| Acyclic (N5)/cyclic (<=N5), weight ratio | 100.00 | 100.00 | 100.00 | 2.30 | 2.30 | 2.20 | 2.10 | 19.10 | 20.10 | 9.40 | 100.00 | 100.00 |
| Σ(N5)/Σ(N4), weight ratio | — | — | — | — | — | — | 0.70 | 1.30 | 1.30 | — | — | — |

TABLE LV

| Example No. | 510 | 511 | 512 | 513 | 514 | 515 | 516 | 517 | 518 |
|---|---|---|---|---|---|---|---|---|---|
| Catalys Type | KKK | KKK | KKK | KKK | KKK | KKK | KKK | KKK | KKK |
| Catalyst weight, gm | 116.2 | 116.2 | 116.2 | 116.2 | 116.2 | 11.62 | 116.2 | 116.2 | 116.2 |
| Pressure, psig | 600 | 600 | 600 | 600 | 600 | 600 | 600 | 600 | 600 |
| Temperature, °C. | 281 | 289 | 255 | 253 | 308 | 300 | 297 | 272 | 268 |
| Time on organics, hrs. | 8.5 | 17.5 | 65.0 | 67.0 | 73.0 | 88.5 | 90.5 | 96.7 | 114.5 |
| Duration of run, hrs. | 2 | 9 | 10 | 2 | 2 | 15 | 2 | 2 | 2 |
| MEA SV, gmol/hr/kgcat | 1.95 | 1.92 | 1.68 | 1.73 | 1.62 | 1.74 | 1.71 | 1.68 | 1.72 |
| NH3 feedrate, gm/hr | 47.2 | 45.6 | 46.8 | 45.0 | 44.0 | 43.3 | 47.0 | 43.0 | 46.5 |
| Liquid feed composition, wt. % | | | | | | | | | |
| DETA | 77.16 | 77.16 | 66.46 | 66.46 | 77.16 | 77.16 | 77.16 | 66.46 | 66.46 |
| MEA | 22.84 | 22.84 | — | — | 22.84 | 22.84 | 22.84 | — | — |
| AEEA | — | — | 33.54 | 33.54 | — | — | — | 33.54 | 33.54 |
| Liquid product composition, wt. % | | | | | | | | | |
| EDA | 2.23 | 1.99 | 0.37 | 0.35 | 9.13 | 5.71 | 5.98 | 1.22 | 1.22 |
| MeEDA | 0.00 | 0.00 | 0.00 | 0.00 | 0.00 | 0.00 | 0.00 | 0.00 | 0.00 |
| MEA | 9.36 | 10.47 | 0.39 | 0.36 | 4.75 | 8.86 | 8.41 | 0.45 | 0.45 |
| EtEDA | 0.00 | 0.00 | 0.00 | 0.00 | 0.00 | 0.00 | 0.00 | 0.00 | 0.00 |
| PIP | 0.65 | 0.44 | 1.26 | 1.29 | 1.40 | 0.90 | 0.92 | 3.43 | 3.43 |
| DETA | 75.37 | 77.92 | 74.89 | 76.09 | 63.34 | 69.29 | 67.65 | 74.85 | 84.85 |
| AEEA | 0.45 | 0.44 | 20.42 | 19.29 | 0.21 | 0.22 | 0.32 | 11.31 | 11.31 |
| AEP | 0.71 | 0.52 | 0.00 | 0.00 | 1.52 | 1.00 | 1.05 | 0.45 | 0.45 |
| HEP | 0.00 | 0.00 | 0.00 | 0.00 | 0.00 | 0.00 | 0.00 | 0.00 | 0.00 |
| TETA's | 6.89 | 4.55 | 0.22 | 0.21 | 6.49 | 5.50 | 6.02 | 2.05 | 2.05 |
| TEPA's | 1.28 | 0.49 | 0.96 | 0.89 | 0.99 | 0.57 | 0.79 | 3.05 | 3.05 |
| ROH Conversion % | 58.81 | 53.66 | 38.60 | 41.80 | 76.90 | 58.71 | 60.45 | 65.60 | 65.60 |
| Acyclic (N4)/cyclic (<=N4), weight ratio | 20.00 | 41.60 | 0.00 | 0.00 | 4.70 | 7.80 | 8.10 | 0.30 | 0.20 |
| Acyclic (N5)/cyclic (<=N5), weight ratio | 100.00 | 100.00 | 100.00 | 100.00 | 2.50 | 100.00 | 100.00 | 100.00 | 100.00 |
| Σ(N5)/Σ(N4), | — | — | 4.40 | 4.20 | — | — | — | 1.50 | 1.50 |

TABLE LV-continued

| Example No. | 510 | 511 | 512 | 513 | 514 | 515 | 516 | 517 | 518 |
|---|---|---|---|---|---|---|---|---|---|
| weight ratio | | | | | | | | | |

TABLE LVI

| Example No. | 519 | 520 | 521 | 522 | 523 | 524 | 525 | 526 | 527 | 528 | 529 |
|---|---|---|---|---|---|---|---|---|---|---|---|
| Catalyst Type | LLL | LLL | LLL | LLL | LLL | LLL | LLL | LLL | LLL | LLL | LLL |
| Catalyst weight, gm | 131.5 | 131.5 | 131.5 | 131.5 | 131.5 | 131.5 | 131.5 | 131.5 | 131.5 | 131.5 | 131.5 |
| Pressure, psig | 600 | 600 | 600 | 600 | 600 | 600 | 600 | 600 | 600 | 600 | 600 |
| Temperature, °C. | 273 | 277 | 277 | 305 | 300 | 300 | 300 | 303 | 301 | 278 | 276 |
| Time on organics, hrs. | 5.0 | 21.7 | 23.7 | 29.0 | 45.0 | 47.0 | 53.0 | 70.0 | 72.0 | 76.0 | 80.0 |
| Duration of run, hrs. | 2 | 15 | 2 | 1 | 16 | 2 | 2 | 16 | 2 | 2 | 2 |
| MEA SV, gmol/hr/kgcat | 1.86 | 1.78 | 1.86 | 1.39 | 1.71 | 1.52 | 1.54 | 1.50 | 1.57 | 1.54 | 1.75 |
| NH3 feedrate, gm/hr | 53.0 | 48.6 | 45.0 | 49.0 | 45.0 | 50.5 | 54.5 | 48.0 | 53.0 | 50.0 | 47.0 |
| Liquid feed composition, wt. % | | | | | | | | | | | |
| DETA | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | — | — | — | — | 22.84 |
| AEEA | — | — | — | — | — | — | 33.54 | 33.54 | 33.54 | 33.54 | — |
| Liquid product composition, wt. % | | | | | | | | | | | |
| EDA | 0.39 | 0.41 | 0.44 | 4.14 | 1.93 | 1.70 | 1.17 | 1.32 | 1.32 | 0.35 | 0.48 |
| MeEDA | 0.00 | 0.00 | 0.00 | 0.00 | 0.00 | 0.00 | 0.00 | 0.00 | 0.00 | 0.00 | 0.00 |
| MEA | 12.44 | 11.40 | 11.03 | 1.91 | 5.20 | 5.43 | 0.00 | 0.00 | 0.00 | 0.00 | 10.23 |
| EtEDA | 0.00 | 0.00 | 0.00 | 0.00 | 0.00 | 0.00 | 0.00 | 0.00 | 0.00 | 0.00 | 0.00 |
| PIP | 1.04 | 1.00 | 0.97 | 4.80 | 2.81 | 2.65 | 9.73 | 9.94 | 10.69 | 7.37 | 1.48 |
| DETA | 77.93 | 79.28 | 78.81 | 69.34 | 71.17 | 73.05 | 72.15 | 68.24 | 72.00 | 76.09 | 78.06 |
| AEEA | 0.76 | 0.54 | 0.58 | 0.00 | 0.00 | 0.00 | 0.00 | 0.00 | 0.00 | 3.28 | 0.50 |
| AEP | 0.86 | 0.88 | 0.85 | 5.19 | 2.82 | 2.57 | 2.10 | 2.26 | 2.37 | 0.74 | 1.14 |
| HEP | 0.00 | 0.00 | 0.00 | 0.00 | 0.00 | 0.00 | 0.00 | 0.00 | 0.00 | 0.00 | 0.00 |
| TETA's | 5.36 | 5.49 | 5.87 | 10.35 | 10.83 | 10.10 | 7.69 | 8.66 | 7.72 | 5.03 | 5.65 |
| TEPA's | 0.88 | 0.66 | 0.82 | 1.52 | 2.87 | 2.53 | 5.44 | 6.42 | 4.62 | 6.46 | 1.98 |
| ROH Conversion % | 46.63 | 51.16 | 52.65 | 91.86 | 77.72 | 76.79 | 100.00 | 100.00 | 100.00 | 90.40 | 56.31 |
| Acyclic (N4)/cyclic (<=N4), weight ratio | 20.20 | 25.50 | 22.70 | 3.20 | 6.60 | 7.30 | 0.20 | 0.20 | 0.20 | 0.10 | 5.90 |
| Acyclic (N5)/cyclic (<=N5), weight ratio | 100.00 | 100.00 | 100.00 | 1.70 | 6.80 | 8.20 | 11.40 | 7.50 | 8.30 | 52.40 | 18.50 |
| Σ(N5)/Σ(N4), weight ratio | — | — | — | — | — | — | 0.70 | 0.70 | 0.60 | 1.30 | — |

TABLE LVII

| Example No. | 530 | 531 | 532 | 533 | 534 | 535 | 536 | 537 |
|---|---|---|---|---|---|---|---|---|
| Catalyst Type | MMM | MMM | MMM | MMM | MMM | MMM | MMM | MMM |
| Catalyst weight, gm | 120.5 | 120.5 | 120.5 | 120.5 | 120.5 | 120.5 | 120.5 | 120.5 |
| Pressure, psig | 600 | 600 | 600 | 600 | 600 | 600 | 600 | 600 |
| Temperature, °C. | 268 | 273 | 300 | 301 | 302 | 301 | 302 | 301 |
| Time on organics, hrs. | 2 | 16 | 2 | 15 | 2 | 2 | 13 | 3 |
| Duration of run, hrs. | 2 | 16 | 2 | 15 | 2 | 2 | 13 | 3 |
| MEA SV, gmol/hr/kgcat | 1.93 | 2.17 | 1.86 | 1.93 | 1.92 | 1.65 | 1.68 | 1.72 |
| NH3 feedrate, gm/hr | 77.0 | 57.7 | 51.5 | 53.0 | 51.5 | 51.5 | 46.4 | 48.7 |
| Liquid feed composition, wt. % | | | | | | | | |
| DETA | 77.16 | 77.16 | 77.16 | 77.16 | 77.16 | 66.46 | 66.46 | 66.46 |
| MEA | 22.84 | 22.84 | 22.84 | 22.84 | 22.84 | — | — | — |
| AEEA | — | — | — | — | — | 33.54 | 33.54 | 33.54 |
| Liquid product composition, wt. % | | | | | | | | |
| EDA | 0.46 | 0.36 | 1.97 | 1.71 | 1.80 | 1.01 | 1.10 | 1.04 |
| MeEDA | 0.00 | 0.00 | 0.00 | 0.00 | 0.00 | 0.00 | 0.00 | 0.00 |
| MEA | 8.19 | 8.94 | 3.30 | 4.02 | 4.32 | 0.00 | 0.00 | 0.00 |
| EtEDA | 0.00 | 0.00 | 0.00 | 0.00 | 0.00 | 0.00 | 0.00 | 0.00 |
| PIP | 0.71 | 0.58 | 1.70 | 1.53 | 1.45 | 8.12 | 8.21 | 8.14 |
| DETA | 81.58 | 82.37 | 80.61 | 82.51 | 85.17 | 78.02 | 81.61 | 78.10 |
| AEEA | 0.00 | 0.00 | 0.00 | 0.00 | 0.00 | 0.00 | 0.00 | 0.00 |
| AEP | 0.77 | 0.66 | 1.96 | 1.66 | 1.50 | 1.16 | 1.11 | 1.10 |
| HEP | 0.00 | 0.00 | 0.00 | 0.00 | 0.00 | 0.00 | 0.00 | 0.00 |
| TETA's | 7.44 | 0.49 | 0.59 | 0.26 | 0.00 | 5.01 | 3.31 | 4.78 |
| ROH Conversion % | 65.18 | 61.92 | 86.01 | 82.82 | 81.58 | 100.00 | 100.00 | 100.00 |
| Acyclic (N4)/cyclic (<=N4), weight ratio | 100.00 | 100.00 | 12.60 | 15.50 | 100.00 | 0.10 | 0.00 | 0.10 |
| Acyclic (N5)/cyclic (<=N5), weight ratio | 100.00 | 100.00 | 100.00 | 100.00 | — | 25.20 | 100.00 | 20.90 |
| Σ(N5)/Σ(N4), weight ratio | — | — | — | — | — | 0.90 | 0.80 | 0.86 |

TABLE LVIII

| Example No. | 538 | 539 | 540 | 541 | 542 | 543 | 544 | 545 | 546 | 547 | 548 | 549 |
|---|---|---|---|---|---|---|---|---|---|---|---|---|
| Catalyst Type | NNN | NNN | NNN | NNN | NNN | NNN | NNN | NNN | NNN | NNN | NNN | NNN |
| Catalyst weight, gm | 119.6 | 119.6 | 119.6 | 119.6 | 119.6 | 119.6 | 119.6 | 119.6 | 119.6 | 119.6 | 119.6 | 119.6 |
| Pressure, psig | 600 | 600 | 600 | 600 | 600 | 600 | 600 | 600 | 600 | 600 | 600 | 600 |
| Temperature, °C. | 272 | 274 | 273 | 299 | 301 | 300 | 273 | 300 | 298 | 299 | 272 | 275 |
| Time on organics, hrs. | 4.0 | 20.0 | 22.0 | 27.0 | 44.0 | 46.0 | 49.0 | 66.0 | 68.0 | 70.0 | 74.0 | 86.0 |
| Duration of run, hrs. | 2 | 16 | 2 | 2 | 16 | 2 | 2 | 16 | 2 | 2 | 3 | 3 |
| MEA SV, gmol/hr/kgcat | 2.01 | 2.16 | 2.02 | 1.93 | 1.94 | 2.01 | 1.99 | 1.71 | 1.73 | 1.65 | 1.71 | 1.15 |
| NH3 feedrate, gm/hr | 47.0 | 46.5 | 53.5 | 44.0 | 60.8 | 50.5 | 59.0 | 45.2 | 56.5 | 56.5 | 64.0 | 59.4 |
| Liquid feed composition, wt. % | | | | | | | | | | | | |
| DETA | 77.16 | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | 22.84 | — | — | — | — | 22.84 |
| AEEA | — | — | — | — | — | — | — | 33.54 | 33.54 | 33.54 | 33.54 | — |
| Liquid product composition, wt. % | | | | | | | | | | | | |
| EDA | 0.00 | 0.00 | 0.00 | 2.00 | 1.82 | 1.80 | 0.00 | 1.63 | 1.66 | 1.44 | 0.00 | 0.00 |
| MeEDA | 0.00 | 0.00 | 0.00 | 0.00 | 0.00 | 0.00 | 0.00 | 0.00 | 0.00 | 0.00 | 0.00 | 0.00 |
| MEA | 6.84 | 7.07 | 7.00 | 2.75 | 2.63 | 2.57 | 8.52 | 0.00 | 0.00 | 0.00 | 0.00 | 9.35 |
| EtEDA | 0.00 | 0.00 | 0.00 | 0.00 | 0.00 | 0.00 | 0.00 | 0.00 | 0.00 | 0.00 | 0.00 | 0.00 |
| PIP | 1.21 | 0.85 | 0.69 | 1.96 | 2.02 | 2.11 | 0.58 | 9.79 | 10.05 | 10.16 | 6.52 | 0.72 |
| DETA | 83.64 | 87.98 | 88.48 | 83.40 | 82.22 | 81.77 | 87.13 | 75.36 | 72.92 | 72.45 | 80.94 | 83.87 |
| AEEA | 0.00 | 0.00 | 0.00 | 0.00 | 0.00 | 0.00 | 0.00 | 0.00 | 0.00 | 0.00 | 3.47 | 0.00 |
| AEP | 1.32 | 0.82 | 0.72 | 2.56 | 2.51 | 2.55 | 0.69 | 1.93 | 1.98 | 1.88 | 0.57 | 0.69 |
| HEP | 0.00 | 0.00 | 0.00 | 0.00 | 0.00 | 0.00 | 0.00 | 0.00 | 0.00 | 0.00 | 0.00 | 0.00 |
| TETA's | 6.59 | 3.27 | 3.11 | 6.33 | 7.56 | 7.85 | 3.08 | 7.07 | 7.66 | 7.60 | 3.57 | 4.14 |
| TEPA's | 0.41 | 0.00 | 0.00 | 0.00 | 0.56 | 0.71 | 0.00 | 3.95 | 4.60 | 5.08 | 4.74 | 0.51 |
| ROH Conversion % | 71.08 | 69.97 | 70.25 | 88.33 | 88.90 | 89.16 | 63.70 | 100.00 | 100.00 | 100.00 | 89.80 | 59.87 |
| Acyclic (N4)/cyclic (<=N4), weight ratio | 100.00 | 100.00 | 100.00 | 14.10 | 7.74 | 7.62 | 100.00 | 0.00 | 0.18 | 0.17 | 0.00 | 0.00 |
| Acyclic (N5)/cyclic (<=N5), weight ratio | 100.00 | 0.00 | 00.00 | 0.00 | 0.00 | 0.00 | 0.00 | 11.00 | 9.80 | 11.09 | 100.00 | 100.00 |
| Σ(N5)/Σ(N4), weight ratio | — | — | — | — | — | — | — | 0.60 | 0.60 | 0.70 | 1.30 | — |

TABLE LIX

| Example No. | 550 | 551 | 552 | 553 | 554 | 555 | 556 | 557 | 558 | 559 | 560 |
|---|---|---|---|---|---|---|---|---|---|---|---|
| Catalyst Type | OOO | OOO | OOO | OOO | OOO | OOO | OOO | OOO | OOO | OOO | OOO |
| Catalyst weight, gm | 119.0 | 119.0 | 119.0 | 119.0 | 119.0 | 119.0 | 119.0 | 119.0 | 119.0 | 119.0 | 119.0 |
| Pressure, psig | 600 | 600 | 600 | 600 | 600 | 600 | 600 | 600 | 600 | 600 | 600 |
| Temperature, °C. | 272 | 271 | 272 | 293 | 293 | 293 | 293 | 290 | 292 | 270 | 270 |
| Time on organics, hrs. | 6.0 | 22.0 | 24.0 | 29.0 | 46.0 | 48.0 | 53.0 | 69.5 | 71.5 | 76.5 | 93.0 |
| Duration of run, hrs. | 2 | 16 | 2 | 2 | 16 | 2 | 2 | 15 | 2 | 2 | 16 |
| MEA SV, gmol/hr/kgcat | 1.91 | 1.91 | 1.92 | 1.87 | 1.87 | 1.92 | 1.56 | 1.58 | 1.50 | 1.66 | 1.69 |
| NH3 feedrate, gm/hr | 50.0 | 45.0 | 51.0 | 61.0 | 52.0 | 63.5 | 65.0 | 47.8 | 50.5 | 45.0 | 68.6 |
| Liquid feed composition, wt. % | | | | | | | | | | | |
| DETA | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | — | — | — | — | 22.84 |
| AEEA | — | — | — | — | — | — | 33.54 | 33.54 | 33.54 | 33.54 | — |
| Liquid product composition, wt. % | | | | | | | | | | | |
| EDA | 0.63 | 0.69 | 0.72 | 2.72 | 3.02 | 2.99 | 2.68 | 3.21 | 3.67 | 0.60 | 0.78 |
| MeEDA | 0.00 | 0.00 | 0.00 | 0.00 | 0.00 | 0.00 | 0.00 | 0.00 | 0.00 | 0.00 | 0.00 |
| MEA | 15.06 | 14.67 | 14.70 | 7.20 | 6.66 | 6.83 | 0.37 | 0.24 | 0.24 | 0.45 | 14.81 |
| EtEDA | 0.00 | 0.00 | 0.00 | 0.00 | 0.00 | 0.00 | 0.00 | 0.00 | 0.00 | 0.00 | 0.00 |
| PIP | 0.51 | 0.58 | 0.59 | 1.88 | 2.08 | 2.11 | 6.78 | 7.42 | 7.73 | 4.42 | 1.25 |
| DETA | 76.49 | 75.73 | 75.87 | 69.26 | 69.03 | 67.89 | 61.99 | 60.81 | 59.19 | 65.18 | 71.26 |
| AEEA | 0.75 | 0.79 | 0.78 | 0.17 | 0.00 | 0.21 | 0.24 | 0.16 | 0.00 | 10.62 | 1.89 |
| AEP | 0.53 | 0.59 | 0.60 | 2.19 | 2.37 | 2.41 | 2.12 | 2.49 | 2.81 | 0.51 | 0.71 |
| HEP | 0.00 | 0.00 | 0.00 | 0.00 | 0.00 | 0.00 | 0.00 | 0.00 | 0.00 | 0.00 | 0.00 |
| TETA's | 4.07 | 4.50 | 4.48 | 9.01 | 9.15 | 8.99 | 8.99 | 9.15 | 9.40 | 4.16 | 5.02 |
| TEPA's | 1.66 | 1.99 | 1.94 | 5.81 | 5.97 | 6.10 | 12.71 | 11.71 | 12.96 | 12.13 | 3.62 |
| ROH Conversion % | 35.01 | 36.68 | 36.63 | 69.16 | 71.53 | 70.57 | 99.30 | 99.50 | 100.00 | 68.50 | 36.13 |
| Acyclic (N4)/cyclic (<=N4), weight ratio | 100.00 | 40.70 | 32.30 | 4.40 | 4.00 | 4.20 | 0.67 | 0.30 | 0.30 | 0.10 | 5.00 |
| Acyclic (N5)/cyclic (<=N5), weight ratio | 100.00 | 100.00 | 100.00 | 2.90 | 2.40 | 2.50 | 2.50 | 1.90 | 1.10 | 21.70 | 100.00 |
| Σ(N4)/Σ(N5), weight ratio | — | — | — | — | — | — | 1.40 | 1.30 | 1.40 | 2.90 | — |

TABLE LX

| Example No. | 561 | 562 | 563 | 564 | 565 | 566 | 567 | 568 |
|---|---|---|---|---|---|---|---|---|
| Catalyst Type | PPP | PPP | PPP | PPP | PPP | PPP | PPP | PPP |
| Catalyst weight, gm | 113.7 | 113.7 | 113.7 | 113.7 | 113.7 | 113.7 | 113.7 | 113.7 |
| Pressure, psig | 600 | 600 | 600 | 600 | 600 | 600 | 600 | 600 |
| Temperature, °C. | 274 | 274 | 299 | 29 | 303 | 294 | 297 | 293 |
| Time on organics, hrs. | 18.0 | 20.0 | 25.0 | 41.7 | 43.4 | 49.0 | 65.5 | 67.4 |

TABLE LX-continued

| | | | | | | | | |
|---|---|---|---|---|---|---|---|---|
| Duration of run, hrs. | 16 | 2 | 2 | 16 | 2 | 2 | 16 | 2 |
| MEA SV, gmol/hr/kgcat | 2.15 | 2.19 | 2.20 | 2.10 | 2.19 | 2.11 | 2.14 | 2.06 |
| $NH_3$ feedrate, gm/hr | 55.6 | 43.0 | 52.0 | 55.0 | 38.0 | 84.0 | 52.0 | 54.0 |
| Liquid feed composition, wt. % | | | | | | | | |
| DETA | 77.16 | 77.16 | 77.16 | 77.16 | 77.16 | 73.30 | 73.30 | 73.30 |
| MEA | 22.84 | 22.84 | 22.84 | 22.84 | 22.84 | 21.70 | 21.70 | 21.70 |
| EDA | — | — | — | — | — | — | — | — |
| $H_2O$ | — | — | — | — | — | 5.00 | 5.00 | 5.00 |
| Liquid product composition, wt. % | | | | | | | | |
| EDA | 0.85 | 0.69 | 2.50 | 1.60 | 1.42 | 1.28 | 1.24 | 1.16 |
| MeEDA | 0.00 | 0.00 | 0.00 | 0.00 | 0.00 | 0.00 | 0.00 | 0.00 |
| MEA | 11.05 | 11.08 | 3.45 | 6.52 | 7.59 | 10.77 | 11.01 | 11.46 |
| EtEDA | 0.00 | 0.00 | 0.00 | 0.00 | 0.00 | 0.00 | 0.00 | 0.00 |
| PIP | 0.46 | 0.37 | 1.22 | 0.77 | 0.70 | 0.53 | 0.50 | 0.46 |
| DETA | 71.01 | 72.32 | 65.63 | 70.92 | 72.86 | 73.67 | 73.65 | 74.18 |
| AEEA | 1.08 | 1.21 | 0.25 | 0.59 | 0.78 | 0.94 | 1.06 | 1.07 |
| AEP | 0.69 | 0.56 | 2.04 | 1.27 | 1.14 | 0.99 | 0.93 | 0.88 |
| HEP | 0.00 | 0.00 | 0.00 | 0.00 | 0.00 | 0.00 | 0.00 | 0.00 |
| TETA's | 11.09 | 10.78 | 15.98 | 11.82 | 10.35 | 8.14 | 8.13 | 7.51 |
| TEPA's | 2.74 | 2.32 | 5.41 | 3.35 | 2.60 | 1.92 | 1.81 | 1.57 |
| ROH Conversion % | 52.50 | 52.51 | 85.08 | 71.61 | 67.04 | 53.28 | 52.25 | 50.21 |
| Acyclic (N4)/cyclic (<=N4), weight ratio | 30.30 | 100.00 | 9.50 | 13.90 | 13.00 | 17.80 | 19.80 | 21.10 |
| Acyclic (N5)/cyclic (<=N5), weight ratio | 31.60 | 100.00 | 6.70 | 10.00 | 13.40 | 12.90 | 31.20 | 14.90 |
| Σ(N5)/Σ(N4), weight ratio | 14.70 | 10.50 | 5.30 | 7.10 | 7.60 | 8.00 | 8.70 | 9.00 |

| Example No. | 569 | 570 | 571 | 572 | 573 | 574 |
|---|---|---|---|---|---|---|
| Catalyst Type | PPP | PPP | PPP | PPP | PPP | PPP |
| Catalyst weight, gm | 113.7 | 113.7 | 113.7 | 113.7 | 113.7 | 113.7 |
| Pressure, psig | 600 | 600 | 600 | 600 | 600 | 600 |
| Temperature, °C. | 299 | 298 | 297 | 300 | 298 | 298 |
| Time on organics, hrs. | 72.4 | 89.5 | 91.5 | 112.2 | 114.2 | 149.2 |
| Duration of run, hrs. | 2 | 16 | 2 | 15 | 2 | 2 |
| MEA SV, gmol/hr/kgcat | 2.09 | 2.07 | 2.08 | 3.06 | 3.17 | 11.03 |
| $NH_3$ feedrate, gm/hr | 47.0 | 67.0 | 49.5 | 57.0 | 54.0 | 47.0 |
| Liquid feed composition, wt. % | | | | | | |
| DETA | 77.16 | 77.16 | 77.16 | — | — | — |
| MEA | 22.84 | 22.84 | 22.84 | 33.70 | 33.70 | 100.00 |
| EDA | — | — | — | 66.30 | 66.30 | — |
| $H_2O$ | — | — | — | — | — | — |
| Liquid product composition, wt. % | | | | | | |
| EDA | 1.17 | 1.09 | 1.06 | 69.42 | 67.49 | 1.37 |
| MeEDA | 0.00 | 0.00 | 0.00 | 0.00 | 0.00 | 0.00 |
| MEA | 9.15 | 10.15 | 10.62 | 20.41 | 20.60 | 85.05 |
| EtEDA | 0.00 | 0.00 | 0.00 | 0.00 | 0.00 | 0.00 |
| PIP | 0.52 | 0.44 | 0.40 | 0.54 | 0.53 | 0.51 |
| DETA | 72.91 | 74.49 | 75.62 | 4.65 | 6.35 | 1.42 |
| AEEA | 1.21 | 1.18 | 1.20 | 2.23 | 2.29 | 8.02 |
| AEP | 0.90 | 0.83 | 0.80 | 0.62 | 0.62 | 0.58 |
| HEP | 0.06 | 0.00 | 0.00 | 0.00 | 0.00 | 0.39 |
| TETA's | 8.79 | 7.76 | 6.81 | 1.00 | 1.04 | 0.51 |
| TEPA's | 2.10 | 1.50 | 1.19 | 0.11 | 0.82 | 0.00 |
| ROH Conversion % | | | | | | |
| Acyclic (N4)/cyclic (<=N4), weight ratio | 14.70 | 15.60 | 18.70 | — | — | — |
| Acyclic (N5)/cyclic (<=N5), weight ratio | 21.40 | 100.00 | 100.00 | — | — | — |
| Σ(N5)/Σ(N4), weight ratio | 7.60 | 8.10 | 8.70 | — | — | — |

TABLE LXI

| Example No. | 575 | 576 | 577 | 578 | 579 | 580 | 581 |
|---|---|---|---|---|---|---|---|
| Catalyst Type | QQQ | QQQ | QQQ | QQQ | QQQ | QQQ | QQQ |
| Catalyst weight, gm | 123.1 | 123.1 | 123.1 | 123.1 | 123.1 | 123.1 | 123.1 |
| Pressure, psig | 600 | 600 | 600 | 600 | 600 | 600 | 600 |
| Temperature, °C. | 278 | 280 | 279 | 308 | 306 | 305 | 305 |
| Time on organics, hrs. | 31.2 | 19.5 | 21.5 | 26.2 | 32.2 | 49.2 | 51.2 |
| Duration of run, hrs. | 1 | 16 | 2 | 2 | 2 | 16 | 2 |
| MEA SV, gmol/hr/kgcat | 2.14 | 1.96 | 1.95 | 1.93 | 1.91 | 1.64 | 1.65 |
| $NH_3$ feedrate, gm/hr | 80.0 | 53.0 | 53.5 | 58.5 | 59.5 | 56.0 | 47.0 |
| Liquid feed composition, wt. % | | | | | | | |
| DETA | 77.16 | 77.16 | 77.16 | 77.16 | 77.16 | 66.46 | 66.46 |
| MEA | 22.84 | 22.84 | 22.84 | 22.84 | 22.84 | — | — |
| AEEA | — | — | — | — | — | 33.54 | 33.54 |
| Liquid product composition, | | | | | | | |

TABLE LXI-continued

| Example No. | 575 | 576 | 577 | 578 | 579 | 580 | 581 |
|---|---|---|---|---|---|---|---|
| wt. % | | | | | | | |
| EDA | 0.93 | 0.49 | 0.46 | 1.74 | 1.34 | 1.17 | 1.12 |
| MeEDA | 0.00 | 0.00 | 0.00 | 0.00 | 0.00 | 0.00 | 0.00 |
| MEA | 15.52 | 14.20 | 14.55 | 7.82 | 10.95 | 0.58 | 0.25 |
| EtEDA | 0.00 | 0.00 | 0.00 | 0.00 | 0.00 | 0.00 | 0.00 |
| PIP | 0.08 | 0.13 | 0.11 | 0.66 | 0.36 | 4.33 | 4.26 |
| DETA | 79.78 | 80.09 | 80.45 | 79.71 | 78.22 | 72.69 | 71.85 |
| AEEA | 0.63 | 0.82 | 0.84 | 0.58 | 0.97 | 4.41 | 5.88 |
| AEP | 0.38 | 0.42 | 0.39 | 1.19 | 0.85 | 0.97 | 0.80 |
| HEP | 0.00 | 0.00 | 0.00 | 0.00 | 0.12 | 0.15 | 0.08 |
| TETA's | 2.32 | 3.12 | 2.68 | 6.54 | 3.78 | 8.89 | 8.53 |
| TEPA's | 0.00 | 0.22 | 0.16 | 1.09 | 0.55 | 4.30 | 4.08 |
| ROH Conversion % | 32.65 | 38.51 | 37.03 | 65.50 | 51.72 | 86.80 | 82.30 |
| Acyclic (N4)/cyclic ($\leq$N4), weight ratio | — | — | 100.00 | 11.57 | 12.90 | 7.79 | 10.00 |
| Acyclic (N5)/cyclic ($\leq$N5), weight ratio | — | — | — | — | — | 0.10 | 0.10 |
| $\Sigma$(N5)/$\Sigma$(N4), weight ratio | — | — | — | — | — | 0.50 | 0.50 |

TABLE LXII

| Example No. | 582 | 583 | 584 | 585 | 586 | 587 | 588 | 589 |
|---|---|---|---|---|---|---|---|---|
| Catalyst Type | RRR | RRR | RRR | RRR | RRR | RRR | RRR | RRR |
| Catalyst weight, gm | 116.4 | 116.4 | 116.4 | 116.4 | 116.4 | 116.4 | 116.4 | 116.4 |
| Pressure, psig | 600 | 600 | 600 | 600 | 600 | 600 | 600 | 600 |
| Temperature, °C. | 274 | 274 | 274 | 303 | 301 | 303 | 301 | 301 |
| Time on organics, hrs. | 3.0 | 18.8 | 20.8 | 26.5 | 43.0 | 45.0 | 50.4 | 55.1 |
| Duration of run, hrs. | 1 | 16 | 2 | 2 | 16 | 2 | 2 | 2 |
| MEA SV, gmol/hr/kgcat | 2.05 | 2.07 | 2.11 | 2.03 | 2.02 | 1.97 | 3.24 | 3.26 |
| NH$_3$ feedrate, gm/hr | 70.0 | 60.3 | 53.5 | 93.0 | 60.8 | 61.0 | 53.0 | 78.5 |
| Liquid feed composition, wt. % | | | | | | | | |
| DETA | 77.16 | 77.16 | 77.16 | 77.16 | 77.16 | 77.16 | 62.81 | 62.81 |
| MEA | 22.84 | 22.84 | 22.84 | 22.84 | 22.84 | 22.84 | 37.19 | 37.19 |
| Liquid product composition, wt. % | | | | | | | | |
| EDA | 1.07 | 1.05 | 0.86 | 3.00 | 2.27 | 1.97 | 2.25 | 1.86 |
| MeEDA | 0.00 | 0.00 | 0.00 | 0.00 | 0.00 | 0.00 | 0.00 | 0.00 |
| MEA | 10.34 | 10.06 | 11.47 | 3.86 | 6.06 | 7.28 | 15.71 | 21.10 |
| EtEDA | 0.00 | 0.00 | 0.00 | 0.00 | 0.00 | 0.00 | 0.00 | 0.00 |
| PIP | 1.07 | 0.69 | 0.44 | 1.4 | 1.06 | 0.87 | 1.14 | 0.71 |
| DETA | 71.40 | 71.74 | 74.72 | 68.70 | 70.45 | 72.29 | 62.19 | 63.50 |
| AEEA | 2.14 | 1.02 | 1.02 | 0.29 | 0.47 | 0.62 | 1.27 | 1.68 |
| AEP | 1.05 | 0.89 | 0.63 | 2.17 | 1.54 | 1.30 | 1.61 | 1.01 |
| HEP | 0.00 | 0.00 | 0.00 | 0.00 | 0.00 | 0.00 | 0.00 | 0.00 |
| TETA's | 8.90 | 10.65 | 8.62 | 13.51 | 11.60 | 10.01 | 9.86 | 5.67 |
| TEPA's | 3.00 | 2.71 | 1.52 | 3.58 | 2.99 | 2.10 | 2.09 | 1.32 |
| ROH Conversion % | 55.63 | 56.77 | 50.69 | 83.26 | 73.52 | 68.05 | 57.95 | 43.18 |
| Acyclic (N4)/cyclic ($\leq$N4), weight ratio | 14.20 | 26.00 | 40.00 | 7.30 | 9.40 | 11.10 | 8.40 | 13.00 |
| Acyclic (N5)/cyclic ($\leq$N5), weight ratio | 21.70 | 25.90 | 100.00 | 3.90 | 5.60 | 26.00 | 13.70 | 2.97 |
| $\Sigma$(N5)/$\Sigma$(N4), weight ratio | 5.00 | 9.50 | 13.00 | 3.90 | — | — | 4.00 | 4.70 |

TABLE LXIII

| Example No. | 590 | 591 | 592 | 593 | 594 | 595 | 596 | 597 | 598 | 599 | 600 | 601 |
|---|---|---|---|---|---|---|---|---|---|---|---|---|
| Catalyst Type | SSS | SSS | SSS | SSS | SSS | SSS | SSS | SSS | SSS | SSS | SSS | SSS |
| Catalyst weight, gm | 105.1 | 105.1 | 105.1 | 105.1 | 105.1 | 105.1 | 105.1 | 105.1 | 105.1 | 105.1 | 105.1 | 105.1 |
| Pressure, psig | 600 | 600 | 600 | 600 | 600 | 600 | 600 | 600 | 600 | 600 | 600 | 600 |
| Temperature, °C. | 284 | 286 | 284 | 304 | 303 | 276 | 276 | 280 | 306 | 311 | 311 | 311 |
| Time on organics, hrs. | 3.0 | 19.0 | 20.0 | 41.6 | 43.6 | 49.0 | 65.0 | 67.0 | 71.0 | 78.0 | 92.0 | 94.0 |
| Duration of run, hrs. | 1 | 16 | 2 | 16 | 2 | 2 | 15 | 2 | 2 | 2 | 16 | 2 |
| MEA SV, gmol/hr/kgcat | 2.30 | 2.34 | 2.35 | 2.26 | 2.29 | 2.00 | 1.97 | 1.94 | 1.96 | 1.84 | 1.90 | 1.98 |
| NH$_3$ feedrate, gm/hr | 60.5 | 59.0 | 52.5 | 53.4 | 56.5 | 54.5 | 61.5 | 54.0 | 48.0 | 63.0 | 45.0 | 53.0 |
| Liquid feed composition, wt. % | | | | | | | | | | | | |
| EDA | — | — | — | — | — | — | — | — | — | 18.29 | 18.29 | 18.29 |
| DETA | 77.16 | 77.16 | 77.16 | 77.16 | 77.16 | 66.46 | 66.46 | 66.46 | 66.46 | 31.41 | 31.41 | 31.41 |
| MEA | 22.84 | 22.84 | 22.84 | 22.84 | 22.84 | — | — | — | — | 18.59 | 18.59 | 18.59 |
| AEEA | — | — | — | — | — | 33.54 | 33.54 | 33.54 | 33.54 | 31.71 | 31.71 | 31.71 |
| Liquid product composition, wt. % | | | | | | | | | | | | |
| EDA | 1.42 | 1.51 | 1.58 | 4.01 | 4.05 | 0.68 | 0.62 | 0.57 | 3.04 | 27.12 | 23.79 | 25.27 |
| MeEDA | 0.00 | 0.00 | 0.00 | 0.00 | 0.00 | 0.00 | 0.00 | 0.00 | 0.00 | 0.00 | 0.00 | 0.00 |
| MEA | 9.68 | 8.49 | 9.09 | 3.41 | 3.82 | 0.36 | 0.19 | 0.16 | 0.00 | 3.52 | 3.25 | 3.40 |
| EtEDA | 0.00 | 0.00 | 0.00 | 0.00 | 0.00 | 0.00 | 0.00 | 0.00 | 0.00 | 0.00 | 0.00 | 0.00 |

TABLE LXIII-continued

| Example No. | 590 | 591 | 592 | 593 | 594 | 595 | 596 | 597 | 598 | 599 | 600 | 601 |
|---|---|---|---|---|---|---|---|---|---|---|---|---|
| PIP | 1.16 | 1.29 | 1.28 | 2.99 | 2.95 | 6.65 | 6.30 | 5.94 | 9.68 | 10.98 | 9.83 | 10.11 |
| DETA | 71.42 | 70.10 | 71.52 | 65.54 | 64.54 | 71.47 | 69.54 | 69.17 | 57.76 | 28.16 | 27.11 | 27.67 |
| AEEA | 0.59 | 0.59 | 0.55 | 0.23 | 0.18 | 8.21 | 9.71 | 10.06 | 0.27 | 0.42 | 0.37 | 0.33 |
| AEP | 1.08 | 1.25 | 1.22 | 3.33 | 3.12 | 0.89 | 0.75 | 0.73 | 3.14 | 6.78 | 7.24 | 6.99 |
| HEP | 0.00 | 0.00 | 0.00 | 0.00 | 0.00 | 0.00 | 0.00 | 0.00 | 0.00 | 0.00 | 0.00 | 0.00 |
| TETA's | 11.29 | 12.78 | 11.42 | 13.94 | 14.12 | 4.16 | 3.83 | 3.84 | 11.05 | 12.22 | 14.47 | 13.61 |
| TEPA's | 2.65 | 3.21 | 2.53 | 3.96 | 4.53 | 6.84 | 8.00 | 8.60 | 10.52 | 6.38 | 7.75 | 7.53 |
| ROH Conversion % | 58.68 | 63.87 | 61.20 | 85.42 | 83.62 | 75.90 | 71.50 | 70.50 | 99.20 | 81.42 | 82.82 | 81.99 |
| Acyclic (N4)/cyclic (<=N4), weight ratio | 28.50 | 26.30 | 26.00 | 6.70 | 6.80 | 0.40 | 0.30 | 0.30 | 0.50 | 0.90 | 0.90 | 0.90 |
| Acyclic (N5)/cyclic (<=N5), weight ratio | — | — | 100.00 | 4.10 | 4.00 | 61.00 | 79.00 | 28.20 | 4.10 | 0.70 | 0.80 | 0.80 |
| Σ(N5)/Σ(N4), weight ratio | — | — | — | — | — | 1.64 | 2.10 | 2.20 | 1.00 | — | — | — |

TABLE LXIV

| | Example No. | | | | | | | | | | |
|---|---|---|---|---|---|---|---|---|---|---|---|
| | 602 | 603 | 604 | 605 | 606 | 607 | 608 | 609 | 610 | 611 | 612 |
| Catalyst Type | TTT | TTT | TTT | TTT | TTT | TTT | TTT | TTT | TTT | TTT | TTT |
| Catalyst weight, gm | 117.9 | 117.9 | 117.9 | 117.9 | 117.9 | 117.9 | 117.9 | 117.9 | 117.9 | 117.9 | 117.9 |
| Pressure, psig | 600 | 600 | 600 | 600 | 600 | 600 | 600 | 600 | 600 | 600 | 600 |
| Temperature, °C. | 278 | 277 | 301 | 302 | 301 | 300 | 300 | 303 | 301 | 302 | 302 |
| Time on organics, hrs. | 18.0 | 20.0 | 25.0 | 40.0 | 42.0 | 47.5 | 65.5 | 87.0 | 88.5 | 109.0 | 111.0 |
| Duration of run, hrs. | 16 | 2 | 2 | 14 | 2 | 2 | 2 | 19 | 2 | 20 | 2 |
| MEA SV, gmol/hr/kgcat | 2.03 | 2.06 | 1.98 | 2.00 | 2.11 | 1.74 | 1.32 | 3.51 | 3.79 | 3.30 | 3.45 |
| NH₃ feedrate, gm/hr | 56.0 | 54.0 | 54.0 | 63.0 | 61.0 | 60.0 | 10.0 | 67.8 | 54.0 | 67.9 | 48.5 |
| Liquid feed composition, wt. % | | | | | | | | | | | |
| DETA | 77.16 | 77.16 | 77.16 | 77.16 | 77.16 | 66.46 | 66.46 | 62.81 | 62.81 | 62.81 | 62.81 |
| MEA | 22.84 | 22.84 | 22.84 | 22.84 | 22.84 | — | — | 37.19 | 37.19 | 37.19 | 37.19 |
| AEEA | — | — | — | — | — | 33.54 | 33.54 | — | — | — | — |
| Liquid product composition, wt. % | | | | | | | | | | | |
| EDA | 1.02 | 0.88 | 3.46 | 2.84 | 2.51 | 1.46 | 2.23 | 2.44 | 2.31 | 2.15 | 2.01 |
| MeEDA | 0.00 | 0.00 | 0.00 | 0.00 | 0.00 | 0.00 | 0.00 | 0.00 | 0.00 | 0.00 | 0.00 |
| MEA | 12.18 | 11.85 | 5.47 | 5.76 | 6.66 | 0.35 | 0.15 | 15.93 | 16.51 | 17.85 | 18.61 |
| EtEDA | 0.00 | 0.00 | 0.00 | 0.00 | 0.00 | 0.00 | 0.00 | 0.00 | 0.00 | 0.00 | 0.00 |
| PIP | 0.50 | 0.49 | 1.74 | 1.49 | 1.27 | 5.41 | 5.82 | 1.39 | 1.23 | 1.13 | 1.02 |
| DETA | 74.13 | 74.56 | 70.50 | 71.81 | 70.37 | 70.92 | 61.30 | 60.00 | 61.02 | 61.91 | 62.27 |
| AEEA | 1.14 | 1.11 | 0.39 | 0.48 | 0.56 | 3.78 | 4.31 | 1.92 | 1.89 | 2.00 | 2.10 |
| AEP | 0.64 | 0.64 | 2.16 | 1.91 | 1.65 | 1.24 | 2.04 | 1.64 | 1.58 | 1.42 | 1.26 |
| HEP | 0.00 | 0.00 | 0.00 | 0.00 | 0.00 | 0.00 | 0.00 | 0.00 | 0.00 | 0.00 | 0.00 |
| TETA's | 7.19 | 7.69 | 10.84 | 10.30 | 10.16 | 6.34 | 7.31 | 9.54 | 9.36 | 8.29 | 8.01 |
| TEPA's | 2.28 | 1.79 | 2.96 | 2.74 | 3.47 | 8.47 | 12.87 | 3.31 | 2.80 | 2.39 | 2.35 |
| ROH Conversion % | 47.45 | 48.87 | 76.39 | 75.07 | 70.93 | 88.80 | 87.00 | 57.42 | 56.04 | 52.52 | 50.66 |
| Acyclic (N4)/cyclic (<=N4), weight ratio | 30.70 | 29.40 | 6.40 | 7.90 | 8.10 | 0.30 | 0.50 | 6.70 | 6.40 | 8.40 | 9.20 |
| Acyclic (N5)/cyclic (<=N5), weight ratio | 2.70 | 100.00 | 3.50 | 4.40 | 5.20 | 11.70 | 12.20 | 4.70 | 3.90 | 4.80 | 5.10 |
| Σ(N5)/Σ(N4), weight ratio | — | — | — | — | — | 1.30 | 1.80 | — | — | — | — |

TABLE LXV

| Example No. | 613 | 614 | 615 | 616 | 617 | 618 | 619 | 620 | 621 |
|---|---|---|---|---|---|---|---|---|---|
| Catalyst Type | UUU | UUU | UUU | UUU | UUU | UUU | UUU | UUU | UUU |
| Catalyst weight, gm | 116.4 | 116.4 | 116.4 | 116.4 | 116.4 | 116.4 | 116.4 | 116.4 | 116.4 |
| Pressure, psig | 600 | 600 | 600 | 600 | 600 | 600 | 600 | 600 | 600 |
| Temperature, °C. | 278 | 291 | 278 | 304 | 307 | 306 | 301 | 302 | 302 |
| Time on organics, hrs. | 18.0 | 20.2 | 22.2 | 28.0 | 44.5 | 46.5 | 55.5 | 68.5 | 70.5 |
| Duration of run, hrs. | 16 | 16 | 2 | 2 | 16 | 2 | 2 | 13 | 2 |
| MEA SV, gmol/hr/kgcat | 2.03 | 2.05 | 2.06 | 2.07 | 2.00 | 2.02 | 1.73 | 1.72 | 1.78 |
| NH₃ feedrate, gm/hr | 56.0 | 51.2 | 51.5 | 56.0 | 56.0 | 53.5 | 64.0 | 59.7 | 59.7 |
| Liquid feed composition, wt. % | | | | | | | | | |
| DETA | 77.16 | 77.16 | 77.16 | 77.16 | 77.16 | 77.16 | 66.46 | 66.46 | 66.46 |
| MEA | 22.84 | 22.84 | 22.84 | 22.84 | 22.84 | 22.84 | — | — | — |
| AEEA | — | — | — | — | — | — | 33.54 | 33.54 | 33.54 |
| Liquid product composition, wt. % | | | | | | | | | |
| EDA | 1.02 | 1.12 | 0.70 | 2.22 | 2.31 | 2.54 | 1.67 | 1.70 | 1.86 |
| MeEDA | 0.00 | 0.00 | 0.00 | 0.00 | 0.00 | 0.00 | 0.00 | 0.00 | 0.00 |
| MEA | 12.18 | 10.60 | 11.71 | 6.34 | 6.10 | 6.24 | 0.21 | 0.00 | 0.20 |
| EtEDA | 0.00 | 0.00 | 0.00 | 0.00 | 0.00 | 0.00 | 0.00 | 0.00 | 0.00 |
| PIP | 0.50 | 0.56 | 0.35 | 1.18 | 1.19 | 1.22 | 7.01 | 6.71 | 7.26 |
| DETA | 74.13 | 76.35 | 76.18 | 74.45 | 74.51 | 74.81 | 73.57 | 73.53 | 73.22 |
| AEEA | 1.14 | 0.90 | 1.00 | 0.49 | 0.42 | 0.43 | 1.39 | 1.52 | 1.41 |
| AEP | 0.64 | 0.79 | 0.61 | 1.53 | 1.60 | 1.58 | 1.22 | 1.17 | 1.15 |
| HEP | 0.00 | 0.00 | 0.00 | 0.00 | 0.00 | 0.00 | 0.10 | 0.00 | 0.09 |
| TETA's | 7.19 | 7.58 | 7.18 | 9.57 | 8.76 | 8.18 | 7.33 | 7.38 | 7.12 |

TABLE LXV-continued

| Example No. | 613 | 614 | 615 | 616 | 617 | 618 | 619 | 620 | 621 |
|---|---|---|---|---|---|---|---|---|---|
| TEPA's | 2.28 | 1.36 | 1.47 | 1.86 | 3.57 | 1.80 | 4.61 | 5.25 | 4.68 |
| ROH Conversion % | 47.45 | 54.45 | 49.55 | 72.57 | 73.87 | 72.74 | 95.90 | 95.50 | 95.80 |
| Acyclic (N4)/cyclic (<=N4), weight ratio | 30.70 | 24.30 | 30.50 | 11.20 | 10.20 | 8.90 | 0.20 | 0.10 | 0.10 |
| Acyclic (N5)/cyclic (<=N5), weight ratio | 2.70 | 100.00 | 100.00 | 10.00 | 5.80 | 7.40 | 11.80 | 9.80 | 11.00 |
| $\Sigma$(N5)/$\Sigma$(N4), weight ratio | — | — | — | — | — | — | 0.60 | 0.70 | 0.70 |

TABLE LXVI

| Example No. | 622 | 623 | 624 | 625 | 626 | 627 | 628 | 629 |
|---|---|---|---|---|---|---|---|---|
| Catalyst Type | VVV | VV | VVV | VVV | VVV | VVV | VVV | VVV |
| Catalyst weight, gm | 117.2 | 117.2 | 117.2 | 117.2 | 117.2 | 117.2 | 117.2 | 117.2 |
| Pressure, psig | 600 | 600 | 600 | 600 | 600 | 600 | 600 | 600 |
| Temperature, °C. | 276 | 277 | 275 | 299 | 290 | 302 | 300 | 308 |
| Time on organics, hrs. | 4.0 | 11.0 | 20.0 | 26.0 | 36.0 | 40.0 | 45.0 | 57.0 |
| Duration of run, hrs. | 2 | 2 | 2 | 2 | 10 | 2 | 2 | 2 |
| MEA SV, gmol/hr/kgcat | 1.76 | 2.31 | 2.08 | 2.00 | 2.03 | 1.95 | 1.81 | 1.69 |
| NH$_3$ feedrate, gm/hr | 29.0 | 37.5 | 58.0 | 55.0 | 55.0 | 52.0 | 59.0 | 49.5 |
| Liquid feed composition, wt. % | | | | | | | | |
| DETA | 77.16 | 77.16 | 77.16 | 77.16 | 77.16 | 77.16 | 66.46 | 66.46 |
| MEA | 22.84 | 22.84 | 22.84 | 22.84 | 22.84 | 22.84 | — | — |
| AEEA | — | — | — | — | — | — | 33.54 | 33.54 |
| Liquid product composition, wt. % | | | | | | | | |
| EDA | 1.54 | 1.38 | 1.38 | 2.84 | 2.73 | 3.56 | 1.85 | 2.20 |
| MeEDA | 0.00 | 0.00 | 0.00 | 0.00 | 0.00 | 0.00 | 0.00 | 0.00 |
| MEA | 8.33 | 7.66 | 13.37 | 5.58 | 5.61 | 6.07 | 0.33 | 0.00 |
| EtEDA | 0.00 | 0.00 | 0.00 | 0.00 | 0.00 | 0.00 | 0.00 | 0.00 |
| PIP | 1.26 | 1.16 | 0.29 | 1.49 | 1.48 | 1.46 | 7.47 | 6.84 |
| DETA | 74.34 | 74.58 | 80.12 | 74.81 | 70.27 | 70.19 | 71.84 | 71.91 |
| AEEA | 1.27 | 0.89 | 0.00 | 0.00 | 0.00 | 0.13 | 1.65 | 1.10 |
| AEP | 0.64 | 1.29 | 0.54 | 1.97 | 1.90 | 1.84 | 1.31 | 1.68 |
| HEP | 0.00 | 0.00 | 0.00 | 0.00 | 0.00 | 0.00 | 0.00 | 0.00 |
| TETA's | 10.00 | 10.98 | 4.25 | 10.18 | 11.99 | 10.45 | 5.91 | 6.40 |
| TEPA's | 2.07 | 1.86 | 0.00 | 1.74 | 3.50 | 2.98 | 7.79 | 6.50 |
| ROH Conversion % | 64.49 | 67.56 | 42.44 | 76.15 | 75.80 | 73.51 | 95.10 | 96.70 |
| Acyclic (N4)/cyclic (<=N4), weight ratio | 17.80 | 20.40 | 20.40 | 9.50 | 11.40 | 9.80 | 0.20 | 0.30 |
| Acyclic (N5)/cyclic (<=N5), weight ratio | — | — | — | 5.30 | 7.30 | — | 22.60 | 11.20 |
| $\Sigma$(N5)/$\Sigma$(N4), weight ratio | — | — | — | — | — | — | 1.30 | 1.00 |

TABLE LXVII

| Example No. | 630 | 631 | 632 | 633 | 634 | 635 | 636 | 637 |
|---|---|---|---|---|---|---|---|---|
| Catalyst Type | WWW | WWW | WWW | WWW | WWW | WWW | WWW | WWW |
| Catalyst weight, gm | 107.3 | 107.3 | 107.3 | 107.3 | 107.3 | 107.3 | 107.3 | 107.3 |
| Pressure, psig | 600 | 600 | 600 | 600 | 600 | 600 | 600 | 600 |
| Temperature, °C. | 276 | 275 | 276 | 300 | 301 | 300 | 301 | 301 |
| Time on organics, hrs. | 4.0 | 14.0 | 16.0 | 21.0 | 37.5 | 39.5 | 47.5 | 44.0 |
| Duration of run, hrs. | 2 | 10 | 2 | 2 | 16 | 2 | 2 | 2 |
| MEA SV, gmol/hr/kgcat | 2.22 | 2.22 | 2.28 | 2.18 | 2.06 | 1.92 | 1.90 | 1.82 |
| NH$_3$ feedrate, gm/hr | 49.0 | 53.7 | 51.0 | 49.0 | 52.3 | 60.0 | 61.0 | 49.5 |
| Liquid feed composition, wt. % | | | | | | | | |
| DETA | 77.16 | 77.16 | 77.16 | 77.16 | 77.16 | 66.46 | 66.46 | 66.46 |
| MEA | 22.84 | 22.84 | 22.84 | 22.84 | 22.84 | — | — | — |
| AEEA | — | — | — | — | — | 33.54 | 33.54 | 33.54 |
| Liquid product composition, wt. % | | | | | | | | |
| EDA | 0.59 | 0.48 | 0.42 | 1.39 | 1.39 | 1.17 | 1.18 | 1.35 |
| MeEDA | 0.00 | 0.00 | 0.00 | 0.00 | 0.00 | 0.00 | 0.00 | 0.00 |
| MEA | 11.78 | 12.64 | 12.69 | 7.30 | 8.85 | 0.48 | 0.00 | 8.79 |
| EtEDA | 0.00 | 0.00 | 0.00 | 0.00 | 0.00 | 0.00 | 0.00 | 0.00 |
| PIP | 0.32 | 0.18 | 0.14 | 0.65 | 0.57 | 5.50 | 5.68 | 0.57 |
| DETA | 81.41 | 81.70 | 81.91 | 81.16 | 82.83 | 79.81 | 81.98 | 84.88 |
| AEEA | 1.12 | 0.89 | 0.89 | 0.00 | 0.00 | 2.01 | 1.94 | 1.08 |
| AEP | 0.57 | 0.50 | 0.48 | 1.17 | 1.08 | 1.14 | 1.08 | 0.00 |
| HEP | 0.00 | 0.00 | 0.00 | 0.00 | 0.00 | 0.00 | 0.00 | 0.00 |
| TETA's | 3.71 | 3.08 | 2.89 | 5.97 | 3.52 | 6.18 | 5.18 | 1.83 |
| TEPA's | 0.00 | 0.00 | 0.00 | 0.65 | 0.00 | 1.97 | 1.34 | 0.00 |
| ROH Conversion % | 49.22 | 45.39 | 45.13 | 68.46 | 61.55 | 94.00 | 94.20 | 96.70 |
| Acyclic (N4)/cyclic (<=N4), weight ratio | 100.00 | 100.00 | 100.00 | 25.40 | 18.40 | 100.00 | 100.00 | 100.00 |
| Acyclic (N5)/cyclic (<=N5), weight ratio | — | — | — | 100.00 | — | 0.00 | 0.00 | — |
| $\Sigma$(N5)/$\Sigma$(N4), | — | — | — | — | — | 0.30 | 0.30 | — |

TABLE LXVII-continued

| Example No. | 630 | 631 | 632 | 633 | 634 | 635 | 636 | 637 |
|---|---|---|---|---|---|---|---|---|
| weight ratio | | | | | | | | |

TABLE LXVIII

| Example No. | 638 | 639 | 640 | 641 | 642 | 643 | 644 | 645 |
|---|---|---|---|---|---|---|---|---|
| Catalyst Type | XXX | XXX | XXX | XXX | XXX | XXX | XXX | XXX |
| Catalyst weight, gm | 126.9 | 126.9 | 126.9 | 126.9 | 126.9 | 126.9 | 126.9 | 126.9 |
| Pressure, psig | 600 | 600 | 600 | 600 | 600 | 600 | 600 | 600 |
| Temperature, °C. | 282 | 264 | 269 | 296 | 283 | 290 | 299 | 272 |
| Time on organics, hrs. | 4.0 | 24.0 | 27.0 | 48.0 | 50.0 | 67.5 | 69.5 | 75.0 |
| Duration of run, hrs. | 2 | 2 | 2 | 2 | 2 | 15 | 2 | 2 |
| MEA SV, gmol/hr/kgcat | 1.87 | 1.84 | 1.86 | 1.71 | 1.87 | 1.63 | 1.67 | 1.64 |
| NH$_3$ feedrate, gm/hr | 53.5 | 54.0 | 51.0 | 55.0 | 50.0 | 45.0 | 41.0 | 51.0 |
| Liquid feed composition, wt. % | | | | | | | | |
| DETA | 77.16 | 77.16 | 77.16 | 77.16 | 77.16 | 66.46 | 66.46 | 66.46 |
| MEA | 22.84 | 22.84 | 22.84 | 22.84 | 22.84 | — | — | — |
| AEEA | — | — | — | — | — | 33.54 | 33.54 | 33.54 |
| Liquid product composition, wt. % | | | | | | | | |
| EDA | 2.60 | 1.08 | 0.73 | 2.34 | 1.57 | 1.64 | 1.62 | 0.00 |
| MeEDA | 0.00 | 0.00 | 0.00 | 0.00 | 0.00 | 0.00 | 0.00 | 0.00 |
| MEA | 2.38 | 8.61 | 10.46 | 5.48 | 7.30 | 0.00 | 0.00 | 0.00 |
| EtEDA | 0.00 | 0.00 | 0.00 | 0.00 | 0.00 | 0.00 | 0.00 | 0.00 |
| PIP | 2.30 | 0.91 | 0.71 | 2.12 | 1.59 | 11.97 | 12.36 | 6.27 |
| DETA | 72.97 | 78.50 | 79.50 | 76.30 | 78.68 | 68.16 | 71.0 | 77.31 |
| AEEA | 0.00 | 0.00 | 0.00 | 0.00 | 0.00 | 1.42 | 1.38 | 14.18 |
| AEP | 3.04 | 1.12 | 0.68 | 2.28 | 1.55 | 1.79 | 1.72 | 0.47 |
| HEP | 0.00 | 0.00 | 0.00 | 0.00 | 0.00 | 0.00 | 0.00 | 0.00 |
| TETA's | 13.55 | 7.63 | 6.79 | 7.81 | 7.22 | 8.73 | 7.12 | 1.57 |
| TEPA's | 3.04 | 1.60 | 0.92 | 1.88 | 1.11 | 4.32 | 3.21 | 0.00 |
| ROH Conversion % | 90.08 | 63.26 | 55.30 | 76.51 | 68.80 | 95.90 | 96.00 | 58.30 |
| Acyclic (N4)/cyclic (<=N4), weight ratio | 7.10 | 10.50 | 100.00 | 5.40 | 9.90 | 0.10 | 0.00 | 0.00 |
| Acyclic (N5)/cyclic (<=N5), weight ratio | 7.80 | 100.00 | 100.00 | 2.90 | 100.00 | 10.50 | 100.00 | 100.00 |
| $\Sigma$(N5)/$\Sigma$(N4), weight ratio | — | — | — | — | — | 0.50 | 0.50 | — |

TABLE LXIX

| Example No. | 646 | 647 | 648 | 649 | 650 | 651 | 652 | 653 | 654 | 655 | 656 |
|---|---|---|---|---|---|---|---|---|---|---|---|
| Catalyst Type | YYY | YYY | YYY | YYY | YYY | YYY | YYY | YYY | YYY | YYY | YYY |
| Catalyst weight, gm | 120.2 | 120.2 | 120.2 | 120.2 | 120.2 | 120.2 | 120.2 | 120.2 | 120.2 | 120.2 | 120.2 |
| Pressure, psig | 600 | 600 | 600 | 600 | 600 | 600 | 600 | 600 | 600 | 600 | 600 |
| Temperature, °C. | 272 | 273 | 273 | 289 | 300 | 299 | 297 | 300 | 299 | 272 | 272 |
| Time on organics, hrs. | 3.5 | 19.5 | 21.5 | 27.5 | 43.5 | 45.5 | 50.5 | 66.5 | 68.5 | 70.5 | 73.5 |
| Duration of run, hrs. | 2 | 16 | 2 | 2 | 16 | 2 | 2 | 16 | 2 | 2 | 1 |
| MEA SV, gmol/hr/kgcat | 1.92 | 1.95 | 2.06 | 2.09 | 1.94 | 1.99 | 1.56 | 1.58 | 1.55 | 1.66 | 2.03 |
| NH$_3$ feedrate, gm/hr | 111.0 | 50.9 | 66.0 | 80.0 | 58.0 | 55.0 | 68.0 | 64.5 | 84.8 | 67.0 | 49.0 |
| Liquid feed composition, wt. % | | | | | | | | | | | |
| DETA | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | — | — | — | — | 22.84 |
| AEEA | — | — | — | — | — | — | 33.54 | 33.54 | 33.54 | 33.54 | — |
| Liquid product composition, wt. % | | | | | | | | | | | |
| EDA | 0.00 | 0.00 | 0.00 | 0.00 | 1.08 | 0.00 | 0.00 | 0.00 | 0.00 | 0.00 | 0.00 |
| MeEDA | 0.00 | 0.00 | 0.00 | 0.00 | 0.00 | 0.00 | 0.00 | 0.00 | 0.00 | 0.00 | 0.00 |
| MEA | 8.22 | 8.33 | 7.82 | 2.98 | 3.36 | 3.69 | 1.08 | 1.14 | 0.00 | 0.00 | 9.79 |
| EtEDA | 0.00 | 0.00 | 0.00 | 0.00 | 0.00 | 0.00 | 0.00 | 0.00 | 0.00 | 0.00 | 0.00 |
| PIP | 0.00 | 0.00 | 0.00 | 0.91 | 0.73 | 0.71 | 5.156 | 4.86 | 4.64 | 3.87 | 0.43 |
| DETA | 88.30 | 87.01 | 88.01 | 84.49 | 81.52 | 83.00 | 83.96 | 79.07 | 83.12 | 84.96 | 87.16 |
| AEEA | 0.00 | 0.00 | 0.00 | 0.00 | 0.00 | 0.00 | 0.00 | 0.65 | 0.73 | 5.72 | 0.00 |
| AEP | 0.37 | 0.38 | 0.38 | 1.42 | 1.30 | 1.22 | 1.35 | 1.06 | 1.01 | 0.43 | 0.49 |
| HEP | 0.00 | 0.00 | 0.00 | 0.00 | 0.00 | 0.00 | 0.00 | 0.00 | 0.00 | 0.00 | 0.00 |
| TETA's | 3.10 | 4.29 | 3.79 | 8.95 | 10.19 | 8.57 | 4.93 | 6.53 | 5.81 | 2.15 | 2.13 |
| TEPA's | 0.00 | 0.00 | 0.00 | 0.75 | 1.14 | 0.79 | 2.69 | 5.45 | 4.13 | 2.87 | 0.00 |
| ROH Conversion % | 64.92 | 64.48 | 66.67 | 87.43 | 85.77 | 84.16 | 99.30 | 99.50 | 100.00 | 68.50 | 58.15 |
| Acyclic (N4)/cyclic (<=N4), weight ratio | 100.00 | 100.00 | 100.00 | 26.20 | 17.50 | 17.80 | 0.31 | 0.10 | 0.06 | 0.00 | 100.00 |
| Acyclic (N5)/cyclic (<=N5), weight ratio | — | — | — | 100.00 | 100.00 | 100.00 | 100.00 | 22.20 | 100.00 | 100.00 | — |
| $\Sigma$(N5)/$\Sigma$(N4), weight ratio | — | — | — | — | — | — | — | — | — | — | — |

TABLE LXX

| Example No. | 657 | 658 | 659 | 660 | 661 | 662 | 663 | 664 | 665 | 666 | 667 |
|---|---|---|---|---|---|---|---|---|---|---|---|
| Catalyst Type | ZZZ | ZZZ | ZZZ | ZZZ | ZZZ | ZZZ | ZZZ | ZZZ | ZZZ | ZZZ | ZZZ |
| Catalyst weight, gm | 116.3 | 116.3 | 116.3 | 116.3 | 116.3 | 116.3 | 116.3 | 116.3 | 116.3 | 116.3 | 116.3 |
| Pressure, psig | 600 | 600 | 600 | 600 | 600 | 600 | 600 | 600 | 600 | 600 | 600 |
| Temperature, °C. | 275 | 275 | 275 | 300 | 303 | 300 | 299 | 299 | 300 | 274 | 275 |
| Time on organics, hrs. | 6.0 | 23.0 | 25.0 | 29.0 | 47.0 | 49.0 | 54.0 | 71.0 | 73.0 | 78.0 | 95.0 |
| Duration of run, hrs. | 2 | 16 | 2 | 2 | 16 | 2 | 2 | 17 | 2 | 2 | 16 |
| MEA SV, gmol/hr/kgcat | 1.92 | 2.00 | 2.03 | 1.96 | 1.96 | 1.95 | 1.74 | 1.51 | 1.60 | 1.78 | 1.99 |
| NH3 feedrate, gm/hr | 70.0 | 61.1 | 57.5 | 49.5 | 51.3 | 52.0 | 55.5 | 48.8 | 50.5 | 55.0 | 48.3 |
| Liquid feed composition, wt. % | | | | | | | | | | | |
| DETA | 77.16 | 77.16 | 77.16 | 77.16 | 77.16 | 77.16 | 66.46 | 66.46 | 66.46 | 66.46 | 77.16 |
| MEA | 22.84 | 22.84 | 22.84 | 22.84 | 22.84 | 22.84 | — | — | — | — | 22.84 |
| AEEA | — | — | — | — | — | — | 33.54 | 33.54 | 33.54 | 33.54 | — |
| Liquid feed composition, wt. % | | | | | | | | | | | |
| EDA | 1.09 | 0.80 | 0.74 | 1.86 | 1.69 | 1.60 | 1.45 | 1.55 | 1.62 | 0.58 | 0.58 |
| MeEDA | 0.00 | 0.00 | 0.00 | 0.00 | 0.00 | 0.00 | 0.00 | 0.00 | 0.00 | 0.00 | 0.00 |
| MEA | 13.57 | 15.03 | 15.47 | 8.52 | 10.49 | 11.24 | 0.62 | 0.38 | 0.38 | 0.46 | 16.94 |
| EtEDA | 0.00 | 0.00 | 0.00 | 0.00 | 0.00 | 0.00 | 0.00 | 0.00 | 0.00 | 0.00 | 0.00 |
| PIP | 0.34 | 0.20 | 0.18 | 0.56 | 0.47 | 0.42 | 3.49 | 3.53 | 3.46 | 1.39 | 0.14 |
| DETA | 71.01 | 74.43 | 74.82 | 71.47 | 73.78 | 74.30 | 72.62 | 70.62 | 71.21 | 69.66 | 76.98 |
| AEEA | 1.11 | 1.21 | 1.24 | 0.65 | 0.87 | 0.99 | 4.29 | 4.09 | 4.36 | 20.93 | 2.65 |
| AEP | 0.51 | 0.33 | 0.31 | 0.91 | 0.77 | 0.73 | 0.76 | 0.68 | 0.67 | 0.22 | 0.25 |
| HEP | 0.00 | 0.00 | 0.00 | 0.00 | 0.00 | 0.00 | 0.00 | 0.00 | 0.00 | 0.00 | 0.00 |
| TETA's | 7.40 | 5.81 | 5.25 | 8.79 | 6.82 | 5.83 | 6.63 | 6.99 | 6.60 | 1.40 | 1.67 |
| TEPA's | 3.76 | 1.88 | 1.60 | 4.50 | 2.87 | 2.23 | 8.06 | 8.11 | 7.70 | 4.25 | 0.37 |
| ROH Conversion % | 41.20 | 35.13 | 33.09 | 62.86 | 54.23 | 50.62 | 87.20 | 87.50 | 86.70 | 37.40 | 26.29 |
| Acyclic (N4)/cyclic (<=N4), weight ratio | 24.50 | 100.00 | 100.00 | 12.00 | 12.80 | 11.60 | 0.12 | 0.10 | 0.10 | 0.10 | 100.00 |
| Acyclic (N5)/cyclic (<=N5), weight ratio | 96.0 | 100.00 | 100.00 | 5.90 | 8.70 | 17.10 | 10.20 | 11.50 | 12.70 | 100.00 | 100.00 |
| Σ(N5)/Σ(N4), weight ratio | — | — | — | — | — | — | 1.20 | 1.20 | 1.20 | 3.00 | — |

TABLE LXXI

| Example No. | 668 | 669 | 670 | 671 | 672 | 673 | 674 | 675 | 676 | 677 | 678 |
|---|---|---|---|---|---|---|---|---|---|---|---|
| Catalyst Type | AAAA | AAAA | AAAA | AAAA | AAAA | AAAA | AAAA | AAAA | AAAA | AAAA | AAAA |
| Catalyst weight, gm | 117.7 | 117.7 | 117.7 | 117.7 | 117.7 | 117.7 | 117.7 | 117.7 | 117.7 | 117.7 | 117.7 |
| Pressure, psig | 600 | 600 | 600 | 600 | 600 | 600 | 600 | 600 | 600 | 600 | 600 |
| Temperature, °C. | 275 | 275 | 277 | 303 | 302 | 302 | 273 | 301 | 301 | 274 | 274 |
| Time on organics, hrs. | 6.0 | 22.0 | 24.0 | 29.0 | 45.6 | 47.6 | 52.6 | 69.7 | 71.7 | 76.7 | 93.7 |
| Duration of run, hrs. | 2 | 16 | 2 | 2 | 16 | 2 | 2 | 16 | 2 | 2 | 16 |
| MEA SV, gmol/hr/kgcat | 1.98 | 1.99 | 2.03 | 1.99 | 1.99 | 2.03 | 2.00 | 1.58 | 1.70 | 1.75 | 1.98 |
| NH3 feedrate, gm/hr | 68.0 | 54.3 | 50.5 | 5.5 | 47.8 | 48.5 | 79.0 | 68.3 | 72.5 | 79.5 | 68.1 |
| Liquid feed composition, wt. % | | | | | | | | | | | |
| DETA | 77.16 | 77.16 | 77.16 | 77.16 | 77.16 | 77.16 | 77.16 | 66.46 | 66.46 | 66.46 | 77.16 |
| MEA | 22.84 | 22.84 | 22.84 | 22.84 | 22.84 | 22.84 | 22.84 | — | — | — | 22.84 |
| AEEA | — | — | — | — | — | — | — | 33.54 | 33.54 | 33.54 | — |
| Liquid product composition, wt. % | | | | | | | | | | | |
| EDA | 0.97 | 0.91 | 0.90 | 2.63 | 2.07 | 1.73 | 0.53 | 1.35 | 1.32 | 0.42 | 0.48 |
| MeEDA | 0.00 | 0.00 | 0.00 | 0.00 | 0.00 | 0.00 | 0.00 | 0.00 | 0.00 | 0.00 | 0.00 |
| MEA | 11.59 | 11.42 | 11.61 | 3.72 | 5.41 | 7.22 | 15.50 | 0.39 | 0.26 | 0.39 | 15.13 |
| EtEDA | 0.00 | 0.00 | 0.00 | 0.00 | 0.00 | 0.00 | 0.00 | 0.00 | 0.00 | 0.00 | 0.00 |
| PIP | 0.35 | 0.33 | 0.31 | 0.84 | 0.64 | 0.53 | 0.12 | 3.59 | 3.54 | 1.45 | 0.22 |
| DETA | 71.40 | 70.89 | 71.27 | 67.56 | 69.33 | 71.24 | 76.04 | 68.79 | 68.37 | 66.67 | 74.89 |
| AEEA | 1.15 | 1.26 | 1.28 | 0.23 | 0.44 | 0.85 | 1.39 | 2.48 | 3.15 | 20.08 | 3.01 |
| AEP | 0.52 | 0.49 | 0.47 | 1.53 | 1.12 | 0.91 | 0.30 | 0.81 | 0.69 | 0.23 | 0.29 |
| HEP | 0.00 | 0.00 | 0.00 | 0.00 | 0.00 | 0.00 | 0.00 | 0.00 | 0.00 | 0.00 | 0.00 |
| TETA's | 9.08 | 9.52 | 9.30 | 12.67 | 11.55 | 9.77 | 4.68 | 6.58 | 6.06 | 1.62 | 3.65 |
| TEPA's | 4.20 | 4.41 | 4.17 | 7.89 | 6.69 | 5.30 | 1.17 | 13.35 | 12.33 | 7.56 | 1.63 |
| ROH Conversion % | 50.26 | 51.01 | 50.20 | 83.98 | 76.63 | 68.73 | 33.00 | 92.60 | 90.40 | 39.90 | 34.34 |
| Acyclic (N4)/cyclic (<=N4), weight ratio | 38.80 | 46.80 | 50.10 | 9.60 | 13.90 | 17.20 | 100.00 | 0.30 | 0.20 | 0.20 | 15.70 |
| Acyclic (N5)/cyclic (<=N5), weight ratio | 21.00 | 24.40 | 22.90 | 4.10 | 6.10 | 8.90 | 100.00 | 13.50 | 16.00 | 100.00 | 8.20 |
| Σ(N5)/Σ(N4), weight ratio | — | — | — | — | — | — | — | 2.00 | 12.00 | 4.70 | — |

TABLE LXXII

| Example No. | 679 | 680 | 681 | 682 | 683 | 684 | 685 | 686 | 687 |
|---|---|---|---|---|---|---|---|---|---|
| Catalyst Type | BBBB | BBBB | BBBB | BBBB | BBBB | BBBB | BBBB | BBBB | BBBB |
| Catalyst weight, gm | 78.74 | 78.74 | 78.74 | 78.74 | 78.74 | 78.74 | 78.74 | 78.74 | 78.74 |
| Pressure, psig | 606 | 603 | 603 | 602 | 603 | 603 | 603 | 598 | 603 |
| Temperature, °C. | 270 | 270 | 280 | 269 | 259 | 280 | 280 | 270.1 | 270 |
| Time on organics, hrs. | 4.5 | 4.5 | 28.5 | 51.5 | 71.5 | 76.5 | 100.5 | 120 | 167.5 |
| Duration of run, hrs. | 2 | 2 | 2 | 2 | 2 | 2 | 2 | 2 | 2 |
| MEA SV, gmol/hr/kgcat | 3.46 | 3.84 | 3.94 | 3.87 | 3.77 | 3.63 | 3.78 | 3.83 | 3.81 |

TABLE LXXII-continued

| | | | | | | | | | |
|---|---|---|---|---|---|---|---|---|---|
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.874 | 1.232 | 1.585 | 0.847 | 0.433 | 1.400 | 1.565 | 0.773 | 0.551 |
| MEA | 12.473 | 11.945 | 7.517 | 13.370 | 17.877 | 6.436 | 7.199 | 12.823 | 16.111 |
| PIP | 0.965 | 1.116 | 1.414 | 1.070 | 0.651 | 1.400 | 1.451 | 1.028 | 0.807 |
| DETA | 39.228 | 39.867 | 35.453 | 41.854 | 47.014 | 35.668 | 35.534 | 41.213 | 44.005 |
| AEEA | 1.227 | 1.108 | 0.479 | 1.371 | 2.399 | 0.486 | 0.502 | 1.388 | 1.922 |
| AEP | 1.183 | 1.533 | 1.814 | 1.158 | 0.708 | 1.977 | 1.886 | 1.126 | 0.824 |
| HEP | 0.000 | 0.000 | 0.000 | 0.000 | 0.000 | 0.000 | 0.000 | 0.000 | 0.000 |
| TAEA | 2.760 | 2.694 | 2.611 | 2.646 | 2.564 | 2.683 | 2.567 | 2.662 | 2.560 |
| 1-TETA | 12.867 | 13.297 | 13.364 | 12.613 | 12.062 | 14.170 | 13.658 | 12.943 | 12.257 |
| DAEP | 0.519 | 0.744 | 0.968 | 0.425 | 0.180 | 1.018 | 0.985 | 0.432 | 0.232 |
| PEEDA | 0.110 | 0.111 | 0.154 | 0.082 | 0.152 | 0.059 | 0.710 | 0.336 | 0.206 |
| DPE | 0.118 | 0.120 | 0.127 | 0.085 | 0.097 | 0.087 | 0.322 | 0.227 | 0.120 |
| AE-TAEA | 4.110 | 3.926 | 4.516 | 3.704 | 2.640 | 4.497 | 4.572 | 3.788 | 3.014 |
| 1-TEAP | 7.436 | 7.679 | 8.979 | 7.093 | 5.411 | 8.403 | 9.298 | 7.467 | 6.239 |
| AE-DAEP | 0.140 | 0.117 | 0.182 | 0.100 | 0.097 | 0.000 | 0.808 | 0.390 | 0.275 |
| AE-PEEDA | 0.099 | 0.100 | 0.129 | 0.096 | 0.000 | 0.720 | 0.173 | 0.127 | 0.099 |
| iAE-PEEDA | 0.000 | 0.000 | 0.000 | 0.000 | 0.000 | 0.000 | 0.000 | 0.000 | 0.000 |
| AE-DPE | 0.304 | 0.169 | 0.301 | 0.160 | 0.065 | 0.160 | 1.020 | 0.739 | 0.467 |
| BPEA | 0.639 | 0.578 | 0.844 | 0.573 | 0.045 | 0.211 | 1.060 | 0.835 | 0.435 |
| Others | 8.068 | 6.841 | 11.264 | 5.414 | 2.775 | 11.735 | 8.190 | 6.222 | 3.695 |
| MEA Conversion, % | 66.60 | 68.06 | 79.87 | 63.84 | 52.17 | 82.68 | 80.79 | 66.20 | 56.64 |
| DETA Conversion, % | 37.56 | 36.64 | 43.59 | 32.72 | 25.25 | 42.94 | 43.64 | 35.44 | 29.62 |
| Acyclic(N4), wt. % | 95.43 | 94.25 | 92.75 | 96.27 | 97.15 | 93.54 | 88.94 | 94.00 | 96.37 |
| Acyclic(N5), wt. % | 90.71 | 92.25 | 90.26 | 92.08 | 97.50 | 92.20 | 81.92 | 84.33 | 87.88 |
| Σ(N5)/Σ(N4), weight ratio | 0.78 | 0.74 | 0.87 | 0.74 | 0.55 | 0.78 | 0.93 | 0.80 | 0.68 |
| Acyclic(N4)/cyclic(<=N4), weight ratio | 5.40 | 4.41 | 3.57 | 5.41 | 8.18 | 3.71 | 3.03 | 4.96 | 6.77 |

| Example No. | 688 | 689 | 690 | 691 | 692 | 693 | 694 | 695 | 696 |
|---|---|---|---|---|---|---|---|---|---|
| Catalyst Type | BBBB | BBBB | BBBB | BBBB | BBBB | BBBB | BBBB | BBBB | BBBB |
| Catalyst weight, gm | 78.74 | 78.74 | 78.74 | 78.74 | 78.74 | 78.74 | 78.74 | 78.74 | 78.74 |
| Pressure, psig | 603 | 604 | 603 | 604 | 603 | 603 | 603 | 604 | 604 |
| Temperature, °C. | 280 | 259 | 269 | 260 | 280 | 270 | 280 | 270 | 270 |
| Time on organics, hrs. | 172.5 | 191.5 | 196.5 | 214.5 | 219.5 | 238.5 | 243.5 | 262.5 | 266 |
| Duration of run, hrs. | 2 | 2 | 2 | 2 | 2 | 2 | 2 | 2 | 2 |
| MEA SV, gmol/hr/kgcat | 3.71 | 3.89 | 3.89 | 3.81 | 3.78 | 3.79 | 3.51 | 3.51 | 3.71 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.445 | 0.461 | 0.791 | 0.658 | 1.456 | 0.910 | 1.122 | 1.072 | 1.017 |
| MEA | 5.976 | 18.787 | 12.858 | 18.141 | 6.956 | 13.064 | 13.239 | 11.990 | 12.608 |
| PIP | 1.387 | 0.691 | 1.023 | 0.811 | 1.416 | 1.148 | 1.024 | 1.234 | 1.186 |
| DETA | 33.430 | 47.586 | 40.957 | 45.580 | 35.955 | 41.603 | 42.624 | 40.482 | 40.928 |
| AEEA | 0.443 | 2.282 | 1.404 | 1.879 | 0.493 | 1.322 | 1.350 | 1.216 | 1.269 |
| AEP | 1.827 | 0.682 | 1.103 | 0.881 | 1.832 | 1.184 | 1.192 | 1.267 | 1.191 |
| HEP | 0.000 | 0.000 | 0.000 | 0.000 | 0.000 | 0.000 | 0.000 | 0.000 | 0.000 |
| TAEA | 2.553 | 2.310 | 2.681 | 2.359 | 2.571 | 2.654 | 2.361 | 2.647 | 2.627 |
| 1-TETA | 13.506 | 10.647 | 12.732 | 10.997 | 13.341 | 12.720 | 11.438 | 12.833 | 12.755 |
| DAEP | 1.004 | 0.173 | 0.386 | 0.275 | 0.888 | 0.410 | 0.490 | 0.472 | 0.422 |
| EEDA | 0.710 | 0.146 | 0.310 | 0.222 | 0.654 | 0.36 | 0.382 | 0.369 | 0.339 |
| DPE | 0.335 | 0.085 | 0.184 | 0.086 | 0.309 | 0.196 | 0.271 | 0.070 | 0.135 |
| AE-TAEA | 4.645 | 2.372 | 3.629 | 2.706 | 4.368 | 3.735 | 3.951 | 3.951 | 3.751 |
| 1-TEPA | 9.538 | 4.500 | 6.990 | 5.378 | 8.945 | 7.412 | 6.576 | 7.610 | 7.246 |
| AE-DAEP | 0.848 | 0.213 | 0.276 | 0.183 | 0.700 | 0.300 | 0.385 | 0.331 | 0.291 |
| AE-PEEDA | 0.185 | 0.000 | 0.057 | 0.056 | 0.084 | 0.065 | 0.085 | 0.035 | 0.028 |
| iAE-PEEDA | 0.000 | 0.000 | 0.000 | 0.000 | 0.000 | 0.000 | 0.000 | 0.000 | 0.000 |
| AE-DPE | 1.089 | 0.315 | 0.667 | 0.434 | 1.016 | 0.698 | 0.091 | 0.064 | 0.062 |
| BPEA | 1.026 | 0.247 | 0.634 | 0.403 | 0.932 | 0.638 | 0.093 | 0.594 | 0.053 |
| Others | 9.232 | 1.904 | 3.598 | 2.311 | 6.162 | 3.686 | 6.348 | 5.045 | 5.231 |
| MEA conversion, % | 83.70 | 48.64 | 64.40 | 50.59 | 80.69 | 64.55 | 64.31 | 67.22 | 65.36 |
| DETA conversion, % | 45.82 | 22.68 | 32.60 | 26.22 | 40.67 | 32.91 | 31.71 | 34.22 | 33.16 |
| Acyclic(N4), wt. % | 88.68 | 96.56 | 94.60 | 95.81 | 89.58 | 94.23 | 92.35 | 94.45 | 94.49 |
| Acyclic(N5), wt. % | 81.83 | 89.87 | 86.66 | 88.25 | 82.97 | 86.76 | 94.15 | 91.86 | 96.21 |
| Acyclic(N4)/cyclic(<=N4), weight ratio | 3.05 | 7.29 | 5.13 | 5.86 | 3.12 | 4.70 | 4.11 | 4.54 | 4.70 |

TABLE LXXIII

| Example No. | 697 | 698 | 699 | 700 | 701 | 702 | 703 | 704 | 705 |
|---|---|---|---|---|---|---|---|---|---|
| Catalyst Type | CCCC | CCCC | CCCC | CCCC | CCCC | CCCC | CCCC | CCCC | CCCC |
| Catalyst weight, gm | 84.66 | 84.66 | 84.66 | 84.66 | 84.66 | 84.66 | 84.66 | 84.66 | 84.66 |
| Pressure, psig | 598 | 598 | 598 | 598 | 598 | 599 | 599 | 598 | 603 |
| Temperature, °C. | 270 | 270 | 280 | 259 | 269 | 259 | 280 | 280 | 270.1 |
| Time on organics, hrs. | 4.5 | 23.5 | 28.5 | 47.5 | 51.5 | 71.5 | 76.5 | 100.5 | 120 |
| Duration of run, hrs. | 2 | 2 | 2 | 2 | 2 | 2 | 2 | 2 | 2 |
| MEA SV, gmol/hr/kgcat | 2.95 | 2.82 | 2.91 | 2.90 | 2.89 | 2.81 | 2.72 | 2.85 | 2.92 |
| DETA/MEA mole ratio | 1.00 | 1.00 | 1.00 | 1.00 | 1.00 | 1.00 | 1.00 | 1.00 | 1.00 |

TABLE LXXIII-continued

| NH₃/MEA mole ratio | 5.97 | 5.97 | 5.97 | 5.97 | 5.97 | 5.97 | 5.97 | 5.97 | 5.97 |
|---|---|---|---|---|---|---|---|---|---|
| Crude product composition, wt. % | | | | | | | | | |
| EDA | 0.387 | 0.451 | 0.942 | 0.263 | 0.472 | 0.251 | 0.768 | 0.805 | 0.481 |
| MEA | 18.211 | 18.550 | 12.561 | 24.117 | 18.908 | 22.270 | 11.181 | 11.851 | 17.815 |
| PIP | 0.711 | 0.768 | 1.105 | 0.411 | 0.731 | 0.450 | 1.013 | 1.082 | 0.763 |
| DETA | 45.762 | 47.529 | 39.025 | 52.023 | 46.902 | 51.519 | 38.122 | 38.925 | 46.516 |
| AEEA | 1.902 | 2.077 | 1.192 | 2.582 | 2.111 | 2.804 | 1.247 | 1.088 | 2.005 |
| AEP | 0.846 | 0.787 | 1.214 | 0.446 | 0.718 | 0.519 | 1.229 | 1.254 | 0.767 |
| HEP | 0.000 | 0.000 | 0.000 | 0.000 | 0.000 | 0.000 | 0.000 | 0.000 | 0.000 |
| TAEA | 2.031 | 2.252 | 2.423 | 1.674 | 2.273 | 2.036 | 2.764 | 2.429 | 2.345 |
| 1-TETA | 10.921 | 11.106 | 12.012 | 8.125 | 11.140 | 9.812 | 13.613 | 12.691 | 11.657 |
| DAEP | 0.186 | 0.202 | 0.477 | 0.080 | 0.175 | 0.097 | 0.523 | 0.523 | 0.191 |
| PEEDA | 0.159 | 0.178 | 0.147 | 0.057 | 0.157 | 0.084 | 0.424 | 0.443 | 0.174 |
| DPE | 0.084 | 0.096 | 0.095 | 0.052 | 0.114 | 0.086 | 0.094 | 0.303 | 0.105 |
| AE-TAEA | 2.341 | 2.390 | 3.575 | 1.205 | 2.444 | 1.558 | 4.042 | 3.853 | 2.650 |
| 1-TEPA | 3.918 | 5.171 | 7.286 | 2.186 | 6.082 | 3.822 | 8.123 | 8.109 | 6.868 |
| AE-DAEP | 0.366 | 0.189 | 0.131 | 0.129 | 0.081 | 0.000 | 0.417 | 0.508 | 0.093 |
| AE-PEEDA | 0.080 | 0.079 | 0.101 | 0.068 | 0.000 | 0.000 | 0.113 | 0.139 | 0.000 |
| iAE-PEEDA | 0.000 | 0.000 | 0.000 | 0.000 | 0.000 | 0.000 | 0.000 | 0.000 | 0.000 |
| AE-DPE | 0.403 | 0.061 | 0.264 | 0.051 | 0.078 | 0.066 | 0.220 | 0.797 | 0.055 |
| BPEA | 0.328 | 0.276 | 0.649 | 0.076 | 0.291 | 0.128 | 0.215 | 0.930 | 0.371 |
| Others | 6.126 | 2.669 | 9.532 | 1.845 | 2.513 | 1.388 | 8.524 | 7.390 | 2.594 |
| MEA conversion, % | 51.16 | 50.15 | 66.20 | 34.36 | 49.36 | 40.71 | 70.01 | 68.44 | 52.59 |
| DETA conversion, % | 27.06 | 24.09 | 37.59 | 15.85 | 25.35 | 18.49 | 39.22 | 38.40 | 26.43 |
| Acyclic(N4), wt. % | 96.80 | 96.56 | 95.26 | 98.11 | 96.78 | 97.79 | 94.03 | 92.26 | 96.75 |
| Acyclic(N5), wt. % | 84.17 | 92.59 | 90.47 | 91.27 | 94.99 | 96.53 | 92.65 | 83.44 | 94.83 |
| Σ(N5)/Σ(N4), weight ratio | 0.56 | 0.59 | 0.79 | 0.37 | 0.65 | 0.46 | 0.75 | 0.87 | 0.69 |
| Acyclic(N4)/cyclic(<=N4), weight ratio | 6.52 | 6.58 | 4.75 | 9.37 | 7.08 | 9.58 | 4.99 | 4.20 | 7.00 |

| Example No. | 706 | 707 | 708 | 709 | 710 | 711 | 712 | 713 | 714 | 715 |
|---|---|---|---|---|---|---|---|---|---|---|
| Catalyst Type | CCCC | CCCC | CCCC | CCCC | CCCC | CCCC | CCCC | CCCC | CCCC | CCCC |
| Catalyst weight, gm | 84.66 | 84.66 | 84.66 | 84.66 | 84.66 | 84.66 | 84.66 | 84.66 | 84.66 | 84.66 |
| Pressure, psig | 598 | 598 | 598 | 598 | 598 | 599 | 599 | 604 | 604 | 604 |
| Temperature, °C. | 270 | 280 | 259 | 269 | 260 | 280 | 270 | 280 | 270 | 270 |
| Time on organics, hrs. | 167.5 | 172.5 | 191.5 | 196.5 | 214.5 | 219.5 | 238.5 | 243.5 | 262.5 | 266 |
| Duration of run, hrs. | 2 | 2 | 2 | 2 | 2 | 2 | 2 | 2 | 2 | 2 |
| MEA SV, gmol/hr/kgcat | 2.92 | 2.51 | 2.94 | 2.91 | 3.37 | 2.82 | 2.90 | 2.83 | 2.69 | 2.83 |
| DETA/MEA mole ratio | 1.00 | 1.00 | 1.00 | 1.00 | 1.00 | 1.00 | 1.00 | 1.00 | 1.00 | 1.00 |
| NH₃/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 0.768 | 0.935 | 0.259 | 0.554 | 0.303 | 0.984 | 0.731 | 1.166 | 0.772 | 0.727 |
| MEA | 11.617 | 9.895 | 22.5045 | 16.654 | 25.518 | 10.278 | 15.594 | 9.688 | 14.486 | 15.223 |
| PIP | 1.012 | 1.112 | 0.501 | 0.801 | 0.351 | 1.163 | 0.969 | 1.258 | 0.984 | 0.967 |
| DETA | 38.660 | 37.291 | 50.906 | 4.882 | 53.431 | 38.532 | 43.211 | 37.652 | 42.240 | 43.621 |
| AEEA | 1.321 | 0.909 | 2.608 | 1.955 | 2.502 | 0.852 | 1.707 | 0.755 | 1.601 | 1.652 |
| AEP | 1.097 | 1.308 | 0.480 | 0.827 | 0.406 | 1.361 | 1.004 | 1.440 | 1.010 | 0.980 |
| HEP | 0.000 | 0.000 | 0.000 | 0.000 | 0.000 | 0.000 | 0.000 | 0.000 | 0.000 | 0.000 |
| TAEA | 2.638 | 2.623 | 2.028 | 2.607 | 1.424 | 2.641 | 2.659 | 2.671 | 2.744 | 2.666 |
| 1-TETA | 12.643 | 12.534 | 9.067 | 11.734 | 6.423 | 12.393 | 11.936 | 12.701 | 12.439 | 12.081 |
| DAEP | 0.461 | 0.560 | 0.119 | 0.241 | 0.079 | 0.538 | 0.298 | 0.622 | 0.320 | 0.282 |
| PEEDA | 0.353 | 0.455 | 0.081 | 0.211 | 0.068 | 0.431 | 0.263 | 0.498 | 0.276 | 0.248 |
| DPE | 0.353 | 0.332 | 0.103 | 0.133 | 0.127 | 0.308 | 0.161 | 0.109 | 0.118 | 0.100 |
| AE-TAEA | 3.971 | 4.248 | 1.719 | 2.992 | 1.105 | 4.215 | 3.423 | 4.647 | 3.605 | 3.411 |
| 1-TEPA | 8.051 | 8.471 | 3.147 | 5.870 | 1.995 | 8.144 | 6.726 | 8.696 | 6.609 | 6.249 |
| AE-DAEP | 0.479 | 0.536 | 0.073 | 0.161 | 0.074 | 0.499 | 0.236 | 0.581 | 0.204 | 0.181 |
| AE-PEEDA | 0.163 | 0.150 | 0.064 | 0.000 | 0.053 | 0.132 | 0.054 | 0.123 | 0.034 | 0.030 |
| iAE-PEEDA | 0.000 | 0.000 | 0.000 | 0.000 | 0.000 | 0.000 | 0.000 | 0.000 | 0.000 | 0.000 |
| AE-DPE | 0.793 | 0.918 | 0.151 | 0.456 | 0.092 | 0.892 | 0.536 | 0.306 | 0.061 | 0.063 |
| BPEA | 0.949 | 1.033 | 0.115 | 0.459 | 0.108 | 0.885 | 0.576 | 0.724 | 0.059 | 0.402 |
| Others | 7.450 | 7.630 | 1.713 | 2.553 | 2.042 | 6.020 | 3.491 | 7.953 | 4.671 | 3.839 |
| MEA conversion, % | 68.95 | 73.17 | 39.26 | 54.71 | 30.82 | 71.85 | 58.06 | 73.87 | 60.45 | 58.58 |
| DETA conversion, % | 38.60 | 39.91 | 18.34 | 27.46 | 13.91 | 37.28 | 30.93 | 39.64 | 31.46 | 29.46 |
| Acyclic(N4), wt. % | 92.90 | 91.84 | 97.34 | 96.08 | 96.64 | 92.17 | 95.29 | 92.60 | 95.51 | 95.90 |
| Acyclic(N5), wt. % | 83.45 | 82.83 | 92.34 | 89.17 | 90.46 | 83.69 | 87.90 | 88.50 | 96.63 | 93.47 |
| Σ(N5)/Σ(N4), weight ratio | 0.88 | 0.93 | 0.46 | 0.67 | 0.42 | 0.91 | 0.76 | 0.91 | 0.67 | 0.67 |
| Acyclic(N4)/cyclic(<=N4), weight ratio | 4.66 | 4.02 | 8.64 | 6.48 | 7.62 | 3.95 | 5.42 | 3.91 | 5.61 | 5.72 |

TABLE LXXIV

| | Example No. | | | | | | | | |
|---|---|---|---|---|---|---|---|---|---|
| | 716 | 717 | 718 | 719 | 720 | 721 | 722 | 723 | 724 |
| Catalyst Type | DDDD | DDDD | DDDD | DDDD | DDDD | DDDD | DDDD | DDDD | DDDD |
| Catalyst weight, gm | 75 | 75 | 75 | 75 | 75 | 75 | 75 | 75 | 75 |
| Pressure, psig | 607.5 | 600 | 600 | 600 | 600 | 600 | 600 | 600 | 600 |
| Temperature, °C. | 267.9 | 267.8 | 277.8 | 259.9 | 270.1 | 259.9 | 280.9 | 269.6 | 269 |
| Time on organics, hrs. | 5 | 7.5 | 26 | 31.5 | 50 | 55.5 | 74 | 78 | 80 |
| Duration of run, hrs. | 1 | 1 | 2 | 2 | 2 | 2 | 2 | 2 | 1.5 |
| MEA SV, gmol/hr/kgcat | 8.48 | 8.57 | 4.17 | 3.96 | 3.90 | 4.22 | 4.15 | 4.01 | 3.97 |

TABLE LXXIV-continued

| | Example No. | | | | | | | | |
|---|---|---|---|---|---|---|---|---|---|
| | 716 | 717 | 718 | 719 | 720 | 721 | 722 | 723 | 724 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.673 | 0.822 | 1.742 | 0.612 | 1.367 | 0.688 | 2.430 | 1.370 | 1.341 |
| MEA | 33.641 | 24.246 | 13.234 | 26.804 | 16.396 | 24.443 | 8.046 | 15.672 | 15.462 |
| PIP | 0.585 | 1.113 | 0.000 | 0.823 | 1.584 | 0.886 | 1.994 | 1.506 | 1.484 |
| DETA | 51.838 | 49.325 | 40.936 | 52.117 | 49.168 | 51.098 | 40.046 | 47.408 | 47.941 |
| AEEA | 2.205 | 0.926 | 0.312 | 1.512 | 0.754 | 1.506 | 0.202 | 0.925 | 0.850 |
| AEP | 0.502 | 0.953 | 1.969 | 0.613 | 1.431 | 0.666 | 2.287 | 1.330 | 1.326 |
| HEP | 0.000 | 0.000 | 0.000 | 0.000 | 0.000 | 0.000 | 0.000 | 0.000 | 0.000 |
| TAEA | 0.488 | 2.104 | 2.220 | 1.660 | 2.270 | 1.751 | 2.342 | 2.219 | 2.195 |
| 1-TETA | 4.586 | 9.252 | 11.293 | 7.569 | 10.817 | 7.792 | 12.031 | 10.555 | 10.356 |
| DAEP | 0.000 | 0.167 | 0.922 | 0.114 | 0.307 | 0.112 | 1.101 | 0.290 | 0.271 |
| PEEDA | 0.000 | 0.113 | 0.678 | 0.000 | 0.217 | 0.075 | 0.791 | 0.209 | 0.196 |
| DPE | 0.000 | 0.000 | 0.205 | 0.000 | 0.000 | 0.000 | 0.096 | 0.000 | 0.000 |
| AE-TAEA | 0.234 | 1.259 | 3.575 | 0.885 | 2.431 | 1.011 | 3.561 | 2.057 | 2.019 |
| 1-TEPA | 0.541 | 2.471 | 6.977 | 1.667 | 5.274 | 1.895 | 7.683 | 4.176 | 3.991 |
| AE-DAEP | 0.000 | 0.000 | 0.676 | 0.000 | 0.134 | 0.000 | 0.783 | 0.149 | 0.124 |
| AE-PEEDA | 0.000 | 0.000 | 0.710 | 0.000 | 0.089 | 0.000 | 0.718 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.882 | 0.000 | 0.270 | 0.091 | 1.072 | 0.423 | 0.395 |
| BPEA | 0.000 | 0.000 | 0.729 | 0.000 | 0.340 | 0.077 | 0.874 | 0.385 | 0.362 |
| Others | 0.455 | 0.399 | 3.890 | 0.125 | 1.112 | 0.488 | 5.301 | 1.685 | 1.506 |
| MEA conversion, % | 6.59 | 32.47 | 63.69 | 25.82 | 54.29 | 31.29 | 78.37 | 56.01 | 56.32 |
| DETA conversion, % | 14.45 | 18.36 | 33.25 | 14.28 | 23.51 | 14.64 | 36.03 | 20.92 | 19.52 |
| Acyclic(N4), wt. % | 100.00 | 97.59 | 88.22 | 98.78 | 96.15 | 98.08 | 87.85 | 96.23 | 96.41 |
| Acyclic(N5), wt. % | 100.00 | 100.00 | 77.88 | 100.00 | 90.24 | 94.53 | 76.53 | 86.69 | 87.22 |
| Σ(N5)/Σ(N4), weight ratio | 0.15 | 0.32 | 0.88 | 0.27 | 0.63 | 0.32 | 0.90 | 0.54 | 0.53 |
| Acyclic(N4)/cyclic(<=N4), weight ratio | 4.67 | 4.84 | 3.58 | 5.96 | 3.70 | 5.49 | 2.29 | 3.83 | 3.83 |

TABLE LXXV

| | Example No. | | | | | | | | |
|---|---|---|---|---|---|---|---|---|---|
| | 725 | 726 | 727 | 728 | 729 | 730 | 731 | 732 | 733 |
| Catalyst Type | EEEE | EEEE | EEEE | EEEE | EEEE | EEEE | EEEE | EEEE | EEEE |
| Catalyst weight, gm | 68.38 | 68.38 | 68.38 | 68.38 | 68.38 | 68.38 | 68.38 | 68.38 | 68.38 |
| Pressure, psig | 602 | 602 | 602 | 602 | 602 | 603 | 603 | 602 | 602 |
| Temperature, °C. | 270 | 270 | 280 | 259 | 269 | 259 | 280 | 280 | 270.1 |
| Time on organics, hrs. | 4.5 | 23.5 | 28.5 | 47.5 | 51.5 | 71.5 | 76.5 | 100.5 | 120 |
| Duration of run, hrs. | 2 | 2 | 2 | 2 | 2 | 2 | 2 | 2 | 2 |
| MEA SV, gmol/hr/kgcat | 3.96 | 3.87 | 4.09 | 3.96 | 3.90 | 3.87 | 3.92 | 3.90 | 4.03 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.223 | 0.361 | 0.675 | 0.212 | 0.396 | 0.180 | 0.730 | 0.795 | 0.461 |
| MEA | 24.445 | 22.069 | 16.449 | 26.799 | 21.362 | 24.727 | 13.740 | 14.037 | 20.260 |
| PIP | 0.470 | 0.526 | 0.892 | 0.297 | 0.553 | 0.298 | 0.888 | 0.897 | 0.585 |
| DETA | 53.878 | 51.806 | 46.950 | 56.278 | 50.889 | 55.710 | 44.046 | 42.839 | 49.907 |
| AEEA | 2.281 | 2.479 | 1.818 | 2.578 | 2.565 | 2.914 | 1.871 | 1.449 | 2.318 |
| AEP | 0.515 | 0.624 | 1.064 | 0.387 | 0.663 | 0.447 | 1.193 | 1.137 | 0.672 |
| HEP | 0.000 | 0.000 | 0.000 | 0.000 | 0.000 | 0.000 | 0.000 | 0.000 | 0.000 |
| TAEA | 1.420 | 1.640 | 2.118 | 1.210 | 1.747 | 1.411 | 2.465 | 2.237 | 1.931 |
| 1-TETA | 7.238 | 7.768 | 10.879 | 5.638 | 8.217 | 6.704 | 12.235 | 11.091 | 9.032 |
| DAEP | 0.092 | 0.160 | 0.324 | 0.058 | 0.188 | 0.079 | 0.480 | 0.476 | 0.204 |
| PEEDA | 0.097 | 0.137 | 0.289 | 0.053 | 0.154 | 0.073 | 0.398 | 0.393 | 0.166 |
| DPE | 0.075 | 0.095 | 0.046 | 0.052 | 0.063 | 0.100 | 0.355 | 0.333 | 0.191 |
| AE-TAEA | 1.219 | 1.522 | 2.583 | 0.752 | 1.679 | 0.945 | 3.598 | 3.115 | 2.003 |
| 1-TEPA | 2.039 | 2.628 | 5.427 | 1.366 | 3.512 | 1.934 | 6.530 | 6.472 | 4.096 |
| AE-DAEP | 0.173 | 0.187 | 0.318 | 0.000 | 0.179 | 0.087 | 0.390 | 0.491 | 0.208 |
| AE-PEEDA | 0.066 | 0.063 | 0.068 | 0.000 | 0.071 | 0.080 | 0.096 | 0.129 | 0.079 |
| iAE-PEEDA | 0.000 | 0.000 | 0.000 | 0.000 | 0.000 | 0.000 | 0.000 | 0.000 | 0.000 |
| AE-DPE | 0.141 | 0.121 | 0.160 | 0.073 | 0.175 | 0.115 | 0.175 | 0.301 | 0.139 |
| BPEA | 0.101 | 0.141 | 0.381 | 0.047 | 0.197 | 0.060 | 0.186 | 0.732 | 0.292 |
| Others | 2.821 | 3.594 | 4.790 | 1.260 | 3.582 | 1.974 | 6.576 | 7.895 | 3.856 |
| MEA conversion, % | 34.76 | 40.66 | 56.27 | 27.73 | 42.89 | 34.28 | 64.11 | 62.93 | 46.18 |
| DETA conversion, % | 14.55 | 17.21 | 25.83 | 9.80 | 19.14 | 12.00 | 31.61 | 32.77 | 21.21 |
| Acyclic(N4), wt. % | 97.05 | 96.00 | 95.18 | 97.67 | 96.10 | 96.98 | 92.27 | 91.72 | 95.13 |
| Acyclic(N5), wt. % | 87.14 | 89.01 | 89.63 | 94.66 | 89.31 | 89.37 | 92.28 | 85.30 | 89.48 |
| Σ(N5)/Σ(N4), weight ratio | 0.42 | 0.48 | 0.65 | 0.32 | 0.56 | 0.38 | 0.69 | 0.77 | 0.59 |
| Acyclic(N4)/cyclic(<=N4), weight ratio | 7.31 | 6.11 | 4.97 | 8.08 | 6.15 | 8.14 | 4.44 | 4.12 | 6.03 |

| | Example No. | | | | | | | | | |
|---|---|---|---|---|---|---|---|---|---|---|
| | 734 | 735 | 736 | 737 | 738 | 739 | 740 | 741 | 742 | 743 |
| Catalyst Type | EEEE | EEEE | EEEE | EEEE | EEEE | EEEE | EEEE | EEEE | EEEE | EEEE |

TABLE LXXV-continued

| | | | | | | | | | | |
|---|---|---|---|---|---|---|---|---|---|---|
| Catalyst weight, gm | 68.38 | 68.38 | 68.38 | 68.38 | 68.38 | 68.38 | 68.38 | 68.38 | 68.38 | 68.38 |
| Pressure, psig | 602 | 602 | 603 | 602 | 603 | 603 | 602 | 603 | 603 | 603 |
| Temperature, °C. | 270 | 280 | 259 | 269 | 260 | 280 | 270 | 280 | 270 | 270 |
| Time on organics, hrs. | 167.5 | 172.5 | 191.5 | 196.5 | 214.5 | 219.5 | 238.5 | 243.5 | 262.5 | 266 |
| Duration of run, hrs. | 2 | 2 | 2 | 2 | 2 | 2 | 2 | 2 | 2 | 2 |
| MEA SV, gmol/hr/kgcat | 3.92 | 3.98 | 4.05 | 4.06 | 3.59 | 4.00 | 3.95 | 4.40 | 3.76 | 3.89 |
| DETA/MEA mole ratio | 1.00 | 1.00 | 1.00 | 1.00 | 1.00 | 1.00 | 1.00 | 1.00 | 1.00 | 1.00 |
| NH$_3$/MEA | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 0.516 | 0.878 | 0.251 | 0.489 | 0.337 | 0.945 | 0.600 | 1.593 | 0.706 | 0.676 |
| MEA | 18.745 | 12.739 | 24.769 | 19.980 | 21.647 | 14.371 | 19.473 | 6.716 | 18.311 | 19.235 |
| PIP | 0.611 | 0.931 | 0.340 | 0.589 | 0.483 | 0.985 | 0.679 | 1.480 | 0.743 | 0.731 |
| DETA | 47.493 | 41.921 | 53.539 | 49.348 | 49.438 | 44.879 | 48.790 | 36.170 | 47.421 | 48.217 |
| AEEA | 2.331 | 1.424 | 2.555 | 2.352 | 2.505 | 1.539 | 2.260 | 0.475 | 2.170 | 2.155 |
| AEP | 0.691 | 1.141 | 0.402 | 0.686 | 0.479 | 1.175 | 0.770 | 1.905 | 0.803 | 0.752 |
| HEP | 0.000 | 0.000 | 0.000 | 0.000 | 0.000 | 0.000 | 0.000 | 0.000 | 0.000 | 0.000 |
| TAEA | 2.040 | 2.361 | 1.480 | 1.962 | 2.037 | 2.311 | 2.070 | 2.556 | 2.174 | 1.990 |
| 1-TETA | 9.416 | 11.410 | 6.735 | 8.956 | 8.928 | 10.980 | 9.466 | 13.448 | 10.036 | 9.225 |
| DAEP | 0.223 | 0.454 | 0.082 | 0.179 | 0.113 | 0.411 | 0.216 | 0.992 | 0.260 | 0.214 |
| PEEDA | 0.181 | 0.371 | 0.072 | 0.153 | 0.087 | 0.337 | 0.181 | 0.685 | 0.205 | 0.176 |
| DPE | 0.211 | 0.323 | 0.103 | 0.188 | 0.090 | 0.336 | 0.229 | 0.084 | 0.151 | 0.130 |
| AE-TAEA | 2.229 | 3.445 | 1.148 | 1.988 | 1.704 | 3.208 | 2.190 | 4.698 | 2.609 | 2.255 |
| 1-TEPA | 4.517 | 6.679 | 2.110 | 3.632 | 3.226 | 6.048 | 4.274 | 8.949 | 4.512 | 4.130 |
| AE-DAEP | 0.250 | 0.419 | 0.072 | 0.068 | 0.065 | 0.302 | 0.149 | 0.729 | 0.156 | 0.129 |
| AE-PEEDA | 0.091 | 0.113 | 0.055 | 0.000 | 0.051 | 0.055 | 0.000 | 0.083 | 0.027 | 0.026 |
| iAE-PEEDA | 0.000 | 0.000 | 0.000 | 0.000 | 0.000 | 0.000 | 0.000 | 0.000 | 0.000 | 0.000 |
| AE-DPE | 0.100 | 0.642 | 0.059 | 0.074 | 0.169 | 0.596 | 0.296 | 0.104 | 0.073 | 0.070 |
| BPEA | 0.316 | 0.649 | 0.081 | 0.221 | 0.152 | 0.558 | 0.257 | 0.781 | 0.053 | 0.056 |
| Others | 4.550 | 5.879 | 1.898 | 3.066 | 1.779 | 4.582 | 3.140 | 7.552 | 4.192 | 3.803 |
| MEA conversion, % | 49.40 | 65.33 | 32.69 | 45.43 | 40.15 | 61.44 | 47.63 | 81.50 | 50.64 | 47.61 |
| DETA conversion, % | 23.81 | 32.19 | 13.53 | 19.90 | 18.77 | 28.43 | 22.01 | 40.80 | 24.03 | 21.95 |
| Acyclic(N4), wt. % | 94.90 | 92.30 | 96.97 | 95.46 | 97.43 | 92.46 | 94.85 | 90.08 | 95.20 | 95.57 |
| Acyclic(N5), wt. % | 89.91 | 84.74 | 92.45 | 93.93 | 91.87 | 85.96 | 90.20 | 88.94 | 95.85 | 95.78 |
| Σ(N5)/Σ(N4), weight ratio | 0.62 | 0.80 | 0.42 | 0.52 | 0.48 | 0.75 | 0.59 | 0.86 | 0.58 | 0.57 |
| Acyclic(N4)/cyclic(<=N4), weight ratio | 5.98 | 4.28 | 8.23 | 6.09 | 8.76 | 4.10 | 5.56 | 3.11 | 5.65 | 5.60 |

TABLE LXXVI

| | Example No. | | | | | | | | |
|---|---|---|---|---|---|---|---|---|---|
| | 744 | 745 | 746 | 747 | 748 | 749 | 750 | 751 | 752 |
| Catalyst Type | FFFF | FFFF | FFFF | FFFF | FFFF | FFFF | FFFF | FFFF | FFFF |
| Catalyst weight, gm | 73.5 | 73.5 | 73.5 | 73.5 | 73.5 | 73.5 | 73.5 | 73.5 | 73.5 |
| Pressure, psig | 600 | 600 | 600 | 600 | 600 | 600 | 600 | 600 | 600 |
| Temperature, °C. | 271.8 | 270 | 280.2 | 260.9 | 270.6 | 261.2 | 281.5 | 270 | 270 |
| Time on organics, hrs. | 5 | 8.5 | 25 | 30 | 34 | 49 | 55 | 76 | 78 |
| Duration of run, hrs. | 2 | 2 | 2 | 2 | 2 | 2 | 2 | 2 | 2 |
| MEA SV, gmol/hr/kgcat | 4.58 | 4.68 | 4.69 | 4.82 | 4.64 | 4.33 | 4.30 | 4.25 | 4.63 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition wt. % | | | | | | | | | |
| EDA | 1.589 | 2.650 | 2.164 | 0.505 | 0.958 | 0.544 | 2.028 | 0.834 | 1.373 |
| MEA | 12.185 | 10.223 | 10.619 | 22.868 | 16.851 | 21.648 | 7.865 | 11.872 | 15.153 |
| PIP | 1.766 | 1.979 | 2.007 | 0.826 | 1.277 | 0.872 | 2.020 | 1.302 | 1.673 |
| DETA | 50.183 | 46.166 | 46.617 | 54.246 | 49.991 | 54.106 | 39.033 | 47.518 | 46.832 |
| AEEA | 0.119 | 0.000 | 0.000 | 0.956 | 0.608 | 1.198 | 0.102 | 0.526 | 0.540 |
| AEP | 2.179 | 2.940 | 2.249 | 0.787 | 1.410 | 0.884 | 2.331 | 1.655 | 1.577 |
| HEP | 0.000 | 0.000 | 0.000 | 0.000 | 0.000 | 0.000 | 0.000 | 0.000 | 0.000 |
| TAEA | 2.287 | 2.018 | 2.378 | 1.970 | 2.298 | 2.027 | 2.600 | 2.786 | 2.092 |
| 1-TETA | 11.888 | 11.231 | 12.228 | 9.216 | 11.514 | 9.474 | 13.657 | 14.189 | 11.667 |
| DAEP | 0.650 | 1.480 | 0.908 | 0.125 | 0.263 | 0.142 | 0.136 | 0.460 | 0.271 |
| PEEDA | 0.395 | 0.990 | 0.562 | 0.087 | 0.186 | 0.092 | 0.793 | 0.320 | 0.185 |
| DPE | 0.000 | 0.079 | 0.082 | 0.000 | 0.000 | 0.000 | 0.063 | 0.000 | 0.000 |
| AE-TAEA | 2.483 | 2.485 | 2.951 | 1.171 | 2.213 | 1.284 | 3.723 | 3.229 | 2.178 |
| 1-TEPA | 5.189 | 5.996 | 6.225 | 2.266 | 4.333 | 2.454 | 8.413 | 6.752 | 4.536 |
| AE-DAEP | 0.456 | 1.010 | 0.453 | 0.000 | 0.214 | 0.000 | 0.650 | 0.175 | 0.435 |
| AE-PEEDA | 0.128 | 0.369 | 0.129 | 0.000 | 0.181 | 0.000 | 0.200 | 0.000 | 0.419 |
| iAE-PEEDA | 0.000 | 0.000 | 0.000 | 0.000 | 0.000 | 0.000 | 0.000 | 0.000 | 0.000 |
| AE-DPE | 0.131 | 0.143 | 0.206 | 0.000 | 0.132 | 0.000 | 0.735 | 0.194 | 0.412 |
| BPEA | 0.097 | 0.158 | 0.137 | 0.000 | 0.160 | 0.000 | 0.654 | 0.211 | 0.541 |
| Others | 0.955 | 2.634 | 1.884 | 0.416 | 0.810 | 0.314 | 3.399 | 0.747 | 2.735 |
| MEA conversion, % | 67.00 | 72.55 | 71.14 | 37.96 | 54.14 | 41.18 | 78.38 | 67.95 | 58.74 |
| DETA conversion, % | 19.21 | 26.33 | 24.71 | 12.54 | 19.15 | 12.63 | 36.23 | 23.77 | 24.21 |
| Acyclic(N4), wt. % | 93.14 | 83.87 | 90.40 | 98.14 | 96.85 | 98.00 | 89.08 | 95.60 | 96.79 |
| Acyclic(N5), wt. % | 90.43 | 83.47 | 90.84 | 100.00 | 90.50 | 100.00 | 84.43 | 94.51 | 78.79 |
| Σ(N5)/Σ(N4), weight ratio | 0.56 | 0.64 | 0.63 | 0.30 | 0.51 | 0.32 | 0.79 | 0.59 | 0.60 |
| Acyclic(N4)/cyclic(<=N4), | 2.84 | 1.77 | 2.51 | 6.13 | 4.40 | 5.78 | 2.57 | 4.54 | 3.71 |

TABLE LXXVI-continued

| | Example No. | | | | | | | | |
|---|---|---|---|---|---|---|---|---|---|
| | 744 | 745 | 746 | 747 | 748 | 749 | 750 | 751 | 752 |
| weight ratio | | | | | | | | | |

TABLE LXXVII

| | Example No. | | | | | | | | |
|---|---|---|---|---|---|---|---|---|---|
| | 753 | 754 | 755 | 756 | 757 | 758 | 759 | 760 | 761 |
| Catalyst Type | GGGG | GGGG | GGGG | GGGG | GGGG | GGGG | GGGG | GGGG | GGGG |
| Catalyst weight, gm | 76.8 | 76.8 | 76.8 | 76.8 | 76.8 | 76.8 | 76.8 | 76.8 | 76.8 |
| Pressure, psig | 600 | 600 | 600 | 600 | 600 | 600 | 600 | 600 | 600 |
| Temperature, °C. | 271.8 | 270 | 280.2 | 260.9 | 270.6 | 261.2 | 281.5 | 270 | 270 |
| Time on organics, hrs. | 5 | 8.5 | 25 | 30 | 34 | 49 | 55 | 76 | 78 |
| Duration of run, hrs. | 2 | 2 | 2 | 2 | 2 | 2 | 2 | 2 | 2 |
| MEA SV, gmol/hr/kgcat | 4.12 | 4.24 | 4.01 | 4.36 | 4.32 | 4.20 | 4.12 | 4.07 | 4.24 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.668 | 1.225 | 4.618 | 0.557 | 0.985 | 0.575 | 1.947 | 0.795 | 1.103 |
| MEA | 20.080 | 14.935 | 10.851 | 24.320 | 17.690 | 22.023 | 6.480 | 10.724 | 12.429 |
| PIP | 0.842 | 1.211 | 3.467 | 0.742 | 1.218 | 0.827 | 1.830 | 1.251 | 1.391 |
| DETA | 54.453 | 48.042 | 42.353 | 55.896 | 51.741 | 52.738 | 44.334 | 45.995 | 43.281 |
| AFEA | 0.451 | 0.313 | 0.139 | 1.169 | 0.760 | 1.449 | 0.113 | 0.560 | 0.651 |
| AEP | 0.974 | 1.563 | 4.537 | 0.688 | 1.325 | 0.757 | 2.402 | 1.604 | 1.454 |
| HEP | 0.000 | 0.000 | 0.000 | 0.000 | 0.000 | 0.000 | 0.000 | 0.000 | 0.000 |
| TAEA | 2.048 | 2.361 | 1.079 | 1.584 | 2.048 | 1.917 | 2.309 | 2.717 | 2.272 |
| 1-TETA | 10.507 | 12.537 | 9.182 | 8.077 | 10.742 | 9.822 | 13.034 | 15.283 | 13.463 |
| DAEP | 0.193 | 0.511 | 1.628 | 0.101 | 0.256 | 0.153 | 0.989 | 0.531 | 0.365 |
| PEEDA | 0.122 | 0.327 | 1.082 | 0.000 | 0.173 | 0.087 | 0.592 | 0.336 | 0.226 |
| DPE | 0.000 | 0.000 | 0.152 | 0.000 | 0.000 | 0.000 | 0.071 | 0.000 | 0.000 |
| AE-TAEA | 1.448 | 2.895 | 1.930 | 0.722 | 1.679 | 1.331 | 3.231 | 3.219 | 2.996 |
| 1-TEPA | 2.807 | 6.158 | 3.803 | 1.591 | 3.499 | 2.971 | 7.631 | 7.644 | 6.601 |
| AE-DAEP | 0.000 | 0.383 | 1.217 | 0.000 | 0.082 | 0.000 | 0.605 | 0.208 | 0.516 |
| AE-PEEDA | 0.000 | 0.091 | 0.346 | 0.000 | 0.000 | 0.000 | 0.174 | 0.000 | 0.418 |
| iAE-PEEDA | 0.000 | 0.000 | 0.000 | 0.000 | 0.000 | 0.000 | 0.000 | 0.000 | 0.000 |
| AE-DPE | 0.000 | 0.211 | 0.255 | 0.000 | 0.095 | 0.000 | 0.622 | 0.212 | 0.696 |
| BPEA | 0.000 | 0.119 | 0.152 | 0.000 | 0.089 | 0.000 | 0.573 | 0.168 | 0.136 |
| Others | 0.356 | 1.079 | 3.709 | 0.353 | 0.618 | 0.261 | 2.961 | 0.934 | 4.252 |
| MEA conversion, % | 45.60 | 59.89 | 70.22 | 33.93 | 51.41 | 40.05 | 82.26 | 70.97 | 66.33 |
| DETA conversion, % | 12.33 | 23.33 | 30.92 | 9.75 | 15.54 | 14.68 | 27.88 | 26.01 | 30.31 |
| Acyclic(N4), wt. % | 97.56 | 94.68 | 78.19 | 98.96 | 96.75 | 97.99 | 90.27 | 95.40 | 96.38 |
| Acyclic(N5), wt. % | 100.00 | 91.84 | 74.42 | 100.00 | 95.12 | 100.00 | 84.62 | 94.86 | 84.46 |
| Σ(N5)/Σ(N4), weight ratio | 0.33 | 0.63 | 0.59 | 0.24 | 0.41 | 0.36 | 0.76 | 0.61 | 0.70 |
| Acyclic(N4)/cyclic(< =N4), weight ratio | 5.89 | 4.12 | 0.94 | 6.31 | 4.30 | 6.43 | 2.61 | 4.84 | 4.58 |

TABLE LXXVIII

| | Example No. | | | | | | | |
|---|---|---|---|---|---|---|---|---|
| | 762 | 763 | 764 | 765 | 766 | 767 | 768 | 769 |
| Catalyst Type | HHHH | HHHH | HHHH | HHHH | HHHH | HHHH | HHHH | HHHH |
| Catalyst weight, gm | 76.9 | 76.9 | 76.9 | 76.9 | 76.9 | 76.9 | 76.9 | 76.9 |
| Pressure, psig | 600 | 600 | 600 | 600 | 600 | 600 | 600 | 600 |
| Temperature, °C. | 274.4 | 274.4 | 280.9 | 259.8 | 270.6 | 259.9 | 281.6 | 270.4 |
| Time on organics, hrs. | 22 | 26 | 45.5 | 50.5 | 69 | 74.5 | 95 | 119 |
| Duration of run, hrs. | 2 | 2 | 2 | 2 | 2 | 2 | 2 | 2 |
| MEA SV, gmol/hr/kgcat | 3.43 | 3.31 | 2.85 | 3.38 | 3.41 | 3.28 | 3.10 | 3.37 |
| DETA/MEA mole ratio | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 |
| Crude product composition, wt. % | | | | | | | | |
| EDA | 1.637 | 1.752 | 6.215 | 1.030 | 1.705 | 0.900 | 2.931 | 2.193 |
| MEA | 11.346 | 11.171 | 3.117 | 18.167 | 8.987 | 15.534 | 1.812 | 8.349 |
| PIP | 0.000 | 1.648 | 4.753 | 1.076 | 1.772 | 1.117 | 2.704 | 1.830 |
| DETA | 46.167 | 45.574 | 31.042 | 48.855 | 44.146 | 47.263 | 56.512 | 40.724 |
| AEEA | 0.707 | 0.779 | 0.145 | 2.493 | 0.622 | 2.337 | 0.000 | 0.571 |
| AEP | 1.861 | 1.810 | 7.515 | 1.125 | 2.031 | 1.205 | 4.394 | 2.315 |
| HEP | 0.000 | 0.000 | 0.000 | 0.000 | 0.000 | 0.000 | 0.000 | 0.000 |
| TAEA | 2.681 | 2.785 | 1.354 | 2.334 | 2.745 | 2.609 | 1.349 | 2.559 |
| 1-TETA | 14.827 | 14.769 | 9.178 | 13.329 | 15.519 | 14.514 | 14.115 | 14.634 |
| DAEP | 0.707 | 0.684 | 3.204 | 0.266 | 0.862 | 0.288 | 1.482 | 1.224 |
| PEEDA | 0.445 | 0.480 | 2.063 | 0.161 | 0.535 | 0.170 | 0.741 | 0.805 |
| DPE | 0.104 | 0.070 | 0.140 | 0.000 | 0.097 | 0.000 | 0.000 | 0.048 |
| AE-TAEA | 2.754 | 2.700 | 1.519 | 1.536 | 2.882 | 1.909 | 0.548 | 2.624 |
| 1-TEPA | 6.335 | 6.366 | 3.932 | 3.904 | 7.086 | 4.851 | 1.430 | 7.214 |
| AE-DAEP | 0.241 | 0.242 | 1.881 | 0.138 | 0.283 | 0.068 | 0.260 | 0.638 |
| AE-PEEDA | 0.079 | 0.075 | 0.401 | 0.000 | 0.087 | 0.000 | 0.000 | 0.188 |
| iAE-PEEDA | 0.000 | 0.000 | 0.000 | 0.000 | 0.000 | 0.000 | 0.000 | 0.000 |
| AE-DPE | 0.000 | 0.000 | 0.420 | 0.000 | 0.205 | 0.042 | 0.000 | 0.216 |

TABLE LXXVIII-continued

| | Example No. | | | | | | | |
|---|---|---|---|---|---|---|---|---|
| | 762 | 763 | 764 | 765 | 766 | 767 | 768 | 769 |
| BPEA | 0.223 | 0.231 | 0.079 | 0.000 | 0.239 | 0.045 | 0.000 | 0.261 |
| Others | 1.726 | 1.594 | 11.423 | 0.487 | 1.637 | 0.517 | 0.425 | 2.538 |
| MEA conversion, % | 69.01 | 69.88 | 91.52 | 51.10 | 75.61 | 57.80 | 94.97 | 76.78 |
| DETA conversion, % | 25.06 | 26.98 | 49.81 | 21.84 | 28.79 | 23.70 | 6.73 | 32.70 |
| Acyclic(N4), wt. % | 93.31 | 93.43 | 66.08 | 97.35 | 92.43 | 97.40 | 87.43 | 89.22 |
| Acyclic(N5), wt. % | 94.36 | 94.30 | 66.22 | 97.52 | 92.46 | 97.75 | 88.40 | 88.31 |
| Σ(N5)/Σ(N4), weight ratio | 0.51 | 0.51 | 0.52 | 0.35 | 0.55 | 0.39 | 0.13 | 0.58 |
| Acyclic(N4)/cyclic(<=N4), weight ratio | 5.62 | 3.74 | 0.60 | 5.96 | 3.45 | 6.16 | 1.66 | 2.76 |

TABLE LXXIX

| | Example No. | | | | | | |
|---|---|---|---|---|---|---|---|
| | 770 | 771 | 772 | 773 | 774 | 775 | 776 |
| Catalyst Type | IIII | IIII | IIII | IIII | IIII | IIII | IIII |
| Catalyst weight, gm | 79.56 | 79.56 | 79.56 | 79.56 | 79.56 | 79.56 | 79.56 |
| Pressure, psig | 602 | 602 | 603 | 602 | 602 | 603 | 603 |
| Temperature, °C. | 268.2 | 270 | 280 | 258 | 270 | 279.6 | 269.3 |
| Time on organics, hrs. | 24 | 4.5 | 29 | 48 | 72 | 77 | 96.25 |
| Duration of run, hrs. | 2 | 2 | 2 | 2 | 2 | 2 | 2 |
| MEA SV, gmol/hr/kgcat | 1.40 | 2.14 | 0.94 | 0.90 | 2.37 | 1.20 | 0.78 |
| DETA/MEA mole ratio | 1.00 | 1.00 | 1.00 | 1.00 | 1.00 | 1.00 | 1.00 |
| NH₃/MEA mole ratio | 5.97 | 5.97 | 5.97 | 5.97 | 5.97 | 5.97 | 5.97 |
| Crude product composition, wt. % | | | | | | | |
| EDA | 1.357 | 2.006 | 4.277 | 2.306 | 1.090 | 3.199 | 2.846 |
| MEA | 3.284 | 1.883 | 0.923 | 5.261 | 9.399 | 1.511 | 0.959 |
| PIP | 1.251 | 1.346 | 2.162 | 1.382 | 0.869 | 1.861 | 1.707 |
| DETA | 35.076 | 34.162 | 23.951 | 32.591 | 36.463 | 29.869 | 26.799 |
| AEEA | 0.000 | 0.000 | 0.254 | 1.603 | 1.807 | 0.455 | 0.394 |
| AEP | 2.193 | 2.794 | 3.951 | 1.914 | 1.135 | 3.122 | 2.893 |
| HEP | 0.000 | 0.000 | 0.000 | 0.000 | 0.000 | 0.000 | 0.000 |
| TAEA | 2.772 | 3.324 | 1.853 | 2.782 | 2.789 | 2.443 | 2.434 |
| 1-TETA | 17.464 | 21.229 | 13.658 | 16.596 | 14.933 | 15.761 | 14.689 |
| DAEP | 1.240 | 1.560 | 2.447 | 0.995 | 0.521 | 1.740 | 1.700 |
| PEEDA | 0.891 | 1.074 | 0.289 | 0.699 | 0.388 | 0.125 | 0.247 |
| DPE | 0.000 | 0.000 | 0.355 | 0.262 | 0.143 | 0.157 | 0.291 |
| AE-TAEA | 4.199 | 5.092 | 0.220 | 4.454 | 4.587 | 4.487 | 4.743 |
| 1-TEPA | 9.456 | 11.417 | 10.338 | 9.746 | 8.931 | 11.169 | 10.912 |
| AE-DAEP | 0.765 | 0.809 | 0.324 | 0.167 | 0.134 | 0.189 | 0.259 |
| AE-PEEDA | 0.060 | 0.064 | 0.193 | 0.141 | 0.097 | 0.112 | 0.175 |
| iAE-PEEDA | 0.278 | 0.000 | 0.000 | 0.000 | 0.000 | 0.000 | 0.000 |
| AE-DPE | 0.000 | 0.242 | 0.496 | 0.187 | 0.158 | 0.174 | 0.433 |
| BPEA | 0.000 | 0.000 | 0.734 | 0.667 | 0.692 | 0.754 | 0.232 |
| Others | 6.124 | 6.280 | 20.326 | 8.645 | 7.394 | 10.911 | 15.928 |
| MEA conversion, % | 90.76 | 95.12 | 97.45 | 85.78 | 74.59 | 95.86 | 97.37 |
| DETA conversion, % | 41.33 | 47.41 | 60.62 | 47.66 | 41.42 | 51.33 | 56.29 |
| Acyclic(N4), wt. % | 90.47 | 90.31 | 83.39 | 90.83 | 94.39 | 90.00 | 88.44 |
| Acyclic(N5), wt. % | 92.53 | 93.67 | 85.81 | 92.43 | 92.59 | 92.72 | 93.44 |
| Σ(N5)/Σ(N4), weight ratio | 0.66 | 0.65 | 0.66 | 0.72 | 0.78 | 0.83 | 0.87 |
| Acyclic(N4)/cyclic(<=N4), weight ratio | 3.63 | 3.62 | 1.69 | 3.69 | 5.80 | 2.60 | 2.50 |

TABLE LXXX

| | Example No. | | | | | | | |
|---|---|---|---|---|---|---|---|---|
| | 777 | 778 | 779 | 780 | 781 | 782 | 783 | 784 |
| Catalyst Type | JJJJ | JJJJ | JJJJ | JJJJ | JJJJ | JJJJ | JJJJ | JJJJ |
| Catalyst weight, gm | 78.44 | 78.44 | 78.44 | 78.44 | 78.44 | 78.44 | 78.44 | 78.44 |
| Pressure, psig | 598 | 598 | 598 | 598 | 598 | 598 | 598 | 598 |
| Temperature, °C. | 268.2 | 270 | 280 | 258 | 268 | 270 | 279.6 | 269.3 |
| Time on organics, hrs. | 24 | 4 | 29 | 48 | 53 | 72 | 77 | 96.25 |
| Duration of run, hrs. | 2 | 2 | 2 | 2 | 2 | 2 | 2 | 2 |
| MEA SV, gmol/hr/kgcat | 2.38 | 3.12 | 3.09 | 3.01 | 3.06 | 2.97 | 2.39 | 3.07 |
| DETA/MEA mole ratio | 1.00 | 1.00 | 1.00 | 1.00 | 1.00 | 1.00 | 1.00 | 1.00 |
| NH₃/MEA mole ratio | 5.97 | 5.97 | 5.97 | 5.97 | 5.97 | 5.97 | 5.97 | 5.97 |
| Crude product composition, wt. % | | | | | | | | |
| EDA | 1.113 | 0.976 | 1.860 | 0.782 | 1.043 | 1.302 | 1.824 | 0.980 |
| MEA | 10.615 | 12.327 | 5.220 | 14.139 | 10.320 | 9.098 | 6.092 | 8.653 |
| PIP | 1.129 | 1.005 | 1.496 | 0.859 | 1.132 | 1.320 | 1.611 | 1.111 |
| DETA | 36.799 | 37.931 | 31.746 | 39.773 | 37.334 | 36.528 | 34.990 | 34.182 |
| AEEA | 1.033 | 1.258 | 0.344 | 1.844 | 1.311 | 1.136 | 0.541 | 1.124 |
| AEP | 1.305 | 1.132 | 2.067 | 0.979 | 1.353 | 1.472 | 2.104 | 1.379 |
| HEP | 0.000 | 0.000 | 0.000 | 0.000 | 0.000 | 0.000 | 0.000 | 0.000 |
| TAEA | 2.615 | 2.470 | 2.365 | 2.433 | 2.657 | 2.733 | 2.577 | 2.612 |
| 1-TETA | 14.292 | 13.515 | 14.587 | 14.440 | 14.597 | 14.582 | 14.930 | 13.465 |
| DAEP | 0.594 | 0.489 | 1.269 | 0.296 | 0.595 | 0.603 | 1.041 | 0.647 |

TABLE LXXX-continued

| | Example No. | | | | | | | |
|---|---|---|---|---|---|---|---|---|
| | 777 | 778 | 779 | 780 | 781 | 782 | 783 | 784 |
| PEEDA | 0.435 | 0.400 | 0.866 | 0.242 | 0.463 | 0.496 | 0.064 | 0.168 |
| DPE | 0.131 | 0.135 | 0.159 | 0.052 | 0.133 | 0.092 | 0.091 | 0.150 |
| AE-TAEA | 3.929 | 3.799 | 4.211 | 3.918 | 4.621 | 4.393 | 4.377 | 4.357 |
| 1-TEPA | 8.291 | 7.823 | 9.865 | 6.776 | 8.516 | 8.862 | 9.611 | 8.767 |
| AE-DAEP | 0.503 | 0.527 | 1.032 | 0.400 | 0.502 | 0.089 | 0.121 | 0.177 |
| AE-PEEDA | 0.099 | 0.115 | 0.175 | 0.082 | 0.088 | 0.060 | 0.083 | 0.122 |
| iAE-PEEDA | 0.000 | 0.000 | 0.000 | 0.000 | 0.000 | 0.000 | 0.000 | 0.000 |
| AE-DPE | 0.163 | 0.228 | 0.356 | 0.253 | 0.153 | 0.091 | 0.117 | 0.297 |
| BPEA | 0.610 | 0.599 | 0.845 | 0.412 | 0.618 | 0.748 | 0.798 | 0.729 |
| Others | 7.223 | 7.030 | 12.137 | 4.048 | 6.784 | 6.715 | 8.479 | 10.461 |
| MEA conversion, % | 71.04 | 66.53 | 86.00 | 61.31 | 72.29 | 75.11 | 83.32 | 76.14 |
| DETA conversion, % | 40.33 | 38.80 | 49.40 | 35.32 | 40.42 | 40.60 | 43.06 | 43.99 |
| Acyclic(N4), wt. % | 93.58 | 93.98 | 88.08 | 96.62 | 93.54 | 93.56 | 93.61 | 94.34 |
| Acyclic(N5), wt. % | 89.89 | 88.77 | 85.39 | 90.32 | 90.62 | 93.07 | 92.60 | 90.83 |
| Σ(N5)/Σ(N4), weight ratio | 0.75 | 0.77 | 0.86 | 0.68 | 0.79 | 0.77 | 0.81 | 0.85 |
| Acyclic(N4)/cyclic(<=N4), weight ratio | 4.70 | 5.06 | 2.89 | 6.95 | 4.69 | 4.35 | 3.57 | 4.66 |

TABLE LXXXI

| | Example No. | | | | | | | | |
|---|---|---|---|---|---|---|---|---|---|
| | 785 | 786 | 787 | 788 | 789 | 790 | 791 | 792 | 793 |
| Catalyst Type | KKKK | KKKK | KKKK | KKKK | KKKK | KKKK | KKKK | KKKK | KKKK |
| Catalyst weight, gm | 73.3 | 73.3 | 73.3 | 73.3 | 73.3 | 73.3 | 73.3 | 73.3 | 73.3 |
| Pressure, psig | 598 | 603 | 603 | 605 | 604 | 604.9 | 604 | 604 | 604 |
| Temperature, °C. | 274.8 | 274.2 | 280.3 | 261.2 | 271.4 | 261.8 | 180.2 | 269.7 | 269.6 |
| Time on organics, hrs. | 6 | 8 | 26 | 33 | 50 | 54.5 | 74 | 98.5 | 100 |
| Duration of run, hrs. | 2 | 2 | 2 | 2 | 2 | 2 | 2 | 2 | 2 |
| MEA SV, gmol/hr/kgcat | 4.27 | 4.14 | 3.79 | 3.77 | 3.97 | 3.92 | 3.80 | 4.20 | 4.17 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.429 | 1.424 | 3.172 | 0.868 | 1.570 | 0.800 | 3.025 | 0.882 | 1.051 |
| MEA | 14.429 | 13.943 | 9.322 | 21.725 | 13.285 | 20.998 | 6.949 | 13.400 | 14.889 |
| PIP | 1.355 | 1.300 | 2.261 | 0.868 | 1.478 | 0.814 | 2.234 | 1.030 | 1.176 |
| DETA | 47.230 | 42.295 | 39.568 | 53.087 | 43.212 | 52.672 | 42.607 | 43.225 | 47.069 |
| AEEA | 0.550 | 0.512 | 0.197 | 1.245 | 0.559 | 1.274 | 0.098 | 0.676 | 0.823 |
| AEP | 1.672 | 1.513 | 2.379 | 0.784 | 1.629 | 0.825 | 2.731 | 1.328 | 1.396 |
| HEP | 0.000 | 0.000 | 0.000 | 0.000 | 0.000 | 0.000 | 0.000 | 0.000 | 0.000 |
| TAEA | 2.605 | 2.279 | 2.424 | 2.158 | 2.317 | 2.279 | 2.342 | 2.467 | 2.739 |
| 1-TETA | 13.001 | 12.670 | 12.814 | 9.683 | 12.889 | 10.389 | 12.621 | 13.828 | 13.069 |
| DAEP | 0.431 | 0.360 | 0.995 | 0.154 | 0.368 | 0.187 | 1.128 | 0.319 | 0.360 |
| PEEDA | 0.302 | 0.232 | 0.710 | 0.092 | 0.242 | 0.106 | 0.753 | 0.216 | 0.238 |
| DPE | 0.000 | 0.000 | 0.075 | 0.000 | 0.000 | 0.000 | 0.089 | 0.000 | 0.000 |
| AE-TAEA | 2.986 | 2.963 | 3.398 | 1.553 | 2.893 | 1.804 | 3.351 | 3.239 | 3.092 |
| 1-TEPA | 5.571 | 5.909 | 7.347 | 2.674 | 5.827 | 3.180 | 7.449 | 6.276 | 6.252 |
| AE-DAEP | 0.181 | 0.442 | 0.599 | 0.000 | 0.449 | 0.000 | 0.673 | 0.454 | 0.145 |
| AE-PEEDA | 0.000 | 0.529 | 0.187 | 0.000 | 0.476 | 0.000 | 0.202 | 0.384 | 0.000 |
| iAE-PEEDA | 0.000 | 0.000 | 0.000 | 0.000 | 0.000 | 0.000 | 0.000 | 0.000 | 0.000 |
| AE-DPE | 0.352 | 0.757 | 0.645 | 0.089 | 0.811 | 0.084 | 0.585 | 0.601 | 0.363 |
| BPEA | 0.223 | 0.550 | 0.560 | 0.093 | 0.574 | 0.076 | 0.109 | 0.674 | 0.300 |
| Others | 1.202 | 3.012 | 3.419 | 0.547 | 3.170 | 0.521 | 3.655 | 3.060 | 1.300 |
| MEA conversion, % | 61.11 | 61.45 | 74.39 | 41.37 | 63.75 | 43.71 | 81.09 | 63.56 | 60.17 |
| DETA conversion, % | 24.34 | 30.49 | 35.40 | 14.85 | 29.93 | 16.08 | 31.11 | 30.14 | 25.17 |
| Acyclic(N4), wt. % | 95.51 | 96.19 | 89.54 | 97.97 | 96.15 | 97.74 | 88.37 | 96.82 | 96.36 |
| Acyclic(N5), wt. % | 91.88 | 79.57 | 84.37 | 95.88 | 79.06 | 96.89 | 87.32 | 81.83 | 92.04 |
| Σ(N5)/Σ(N4), weight ratio | 0.57 | 0.72 | 0.75 | 0.36 | 0.70 | 0.40 | 0.73 | 0.69 | 0.62 |
| Acyclic(N4)/cyclic(<=N4), weight ratio | 4.15 | 4.39 | 2.37 | 6.24 | 4.09 | 6.56 | 2.16 | 5.63 | 4.99 |

TABLE LXXXII

| | Example No. | | | | | | | | |
|---|---|---|---|---|---|---|---|---|---|
| | 794 | 795 | 796 | 797 | 798 | 799 | 800 | 801 | 802 |
| Catalyst Type | LLLL | LLLL | LLLL | LLLL | LLLL | LLLL | LLLL | LLLL | LLLL |
| Catalyst weight, gm | 78.4 | 78.4 | 78.4 | 78.4 | 78.4 | 78.4 | 78.4 | 78.4 | 78.4 |
| Pressure, psig | 600 | 600 | 600 | 600 | 600 | 600 | 600 | 600 | 600 |
| Temperature, °C. | 269.3 | 269.2 | 279.4 | 258.8 | 269.2 | 259.4 | 279.2 | 268.9 | 269.6 |
| Time on organics, hrs. | 23.5 | 27.5 | 47 | 52 | 71 | 76 | 95 | 100 | 120 |
| Duration of run, hrs. | 2 | 2 | 2 | 2 | 2 | 2 | 2 | 2 | 2 |
| MEA SV, gmol/hr/kgcat | 3.21 | 3.22 | 3.15 | 3.26 | 3.16 | 3.28 | 2.60 | 3.20 | 2.85 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.011 | 1.726 | 3.400 | 1.045 | 1.704 | 2.927 | 2.694 | 1.875 | 2.016 |
| MEA | 19.645 | 19.830 | 10.922 | 24.936 | 17.747 | 13.549 | 6.399 | 19.549 | 17.740 |

TABLE LXXXII-continued

| | Example No. | | | | | | | | |
|---|---|---|---|---|---|---|---|---|---|
| | 794 | 795 | 796 | 797 | 798 | 799 | 800 | 801 | 802 |
| PIP | 1.597 | 1.489 | 2.412 | 0.797 | 1.531 | 2.082 | 2.206 | 1.710 | 1.570 |
| DETA | 49.999 | 49.815 | 44.929 | 54.559 | 49.660 | 43.523 | 37.413 | 49.063 | 49.599 |
| AEEA | 0.269 | 0.305 | 0.156 | 0.448 | 0.288 | 0.213 | 0.000 | 0.288 | 0.481 |
| AEP | 1.525 | 1.493 | 2.688 | 0.754 | 1.573 | 3.273 | 2.897 | 1.565 | 1.777 |
| HEP | 0.000 | 0.000 | 0.000 | 0.000 | 0.000 | 0.000 | 0.000 | 0.000 | 0.000 |
| TAEA | 2.104 | 2.144 | 2.134 | 1.661 | 2.231 | 4.370 | 1.861 | 2.034 | 2.061 |
| 1-TETA | 9.952 | 10.859 | 11.222 | 7.684 | 10.454 | 11.481 | 11.542 | 9.840 | 10.021 |
| DAEP | 0.081 | 0.238 | 1.038 | 0.095 | 0.470 | 1.096 | 1.664 | 0.680 | 0.442 |
| PEEDA | 0.215 | 0.153 | 0.603 | 0.062 | 0.241 | 0.388 | 1.166 | 0.368 | 0.000 |
| DPE | 0.000 | 0.000 | 0.051 | 0.000 | 0.000 | 0.000 | 0.000 | 0.000 | 0.000 |
| AE-TAEA | 0.000 | 0.000 | 0.000 | 0.000 | 0.000 | 4.286 | 4.233 | 0.000 | 1.883 |
| 1-TEPA | 1.592 | 1.629 | 2.342 | 0.742 | 1.760 | 4.935 | 8.341 | 1.975 | 2.969 |
| AE-DAEP | 0.000 | 0.168 | 0.443 | 0.077 | 0.178 | 0.160 | 1.448 | 0.296 | 0.000 |
| AE-PEEDA | 0.160 | 0.000 | 0.095 | 0.000 | 0.069 | 0.000 | 0.614 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.066 | 0.073 | 0.204 | 0.051 | 0.268 | 0.089 | 0.503 | 0.000 | 0.000 |
| BPEA | 0.000 | 0.000 | 0.076 | 0.000 | 0.000 | 0.496 | 0.000 | 0.000 | 0.000 |
| Others | 3.564 | 3.489 | 6.276 | 2.170 | 3.688 | 1.449 | 6.241 | 2.737 | 0.000 |
| MEA conversion, % | 45.57 | 45.47 | 69.23 | 31.62 | 50.63 | 63.79 | 82.59 | 45.48 | 49.85 |
| DETA conversion, % | 17.68 | 18.59 | 24.77 | 11.08 | 17.90 | 30.86 | 39.50 | 18.68 | 16.68 |
| Acyclic(N4), wt. % | 97.60 | 97.08 | 88.75 | 98.34 | 94.69 | 91.44 | 82.57 | 91.89 | 96.47 |
| Acyclic(N5), wt. % | 87.57 | 87.12 | 74.10 | 85.31 | 77.39 | 97.37 | 80.42 | 86.95 | 100.00 |
| Σ(N5)/Σ(N4), weight ratio | 0.15 | 0.14 | 0.21 | 0.09 | 0.17 | 0.55 | 0.96 | 0.18 | 0.39 |
| Acyclic(N4)/cyclic(<=N4), weight ratio | 3.53 | 3.86 | 1.97 | 5.47 | 3.33 | 2.32 | 1.69 | 2.75 | 3.19 |

TABLE LXXXIII

| | Example No. | | | | | | | | |
|---|---|---|---|---|---|---|---|---|---|
| | 803 | 804 | 805 | 806 | 807 | 808 | 809 | 810 | 811 |
| Catalyst Type | MMMM | MMMM | MMMM | MMMM | MMMM | MMMM | MMMM | MMMM | MMMM |
| Catalyst weight, gm | 73.2 | 73.2 | 73.2 | 73.2 | 73.2 | 73.2 | 73.2 | 73.2 | 73.2 |
| Pressure, psig | 600 | 600 | 600 | 600 | 600 | 600 | 600 | 600 | 600 |
| Temperature, °C. | 270.1 | 270 | 280.2 | 259.7 | 270.1 | 259.6 | 280 | 270 | 270 |
| Time on organics, hrs. | 5 | 7.5 | 26.5 | 31.5 | 49.75 | 54 | 74 | 77.5 | 80 |
| Duration of run, hrs. | 2 | 2 | 2 | 2 | 2 | 2 | 2 | 2 | 2 |
| MEA SV, gmol/hr/kgcat | 4.58 | 4.67 | 4.05 | 4.77 | 4.61 | 4.82 | 4.51 | 4.47 | 4.60 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.979 | 1.000 | 2.216 | 0.524 | 0.877 | 0.472 | 2.124 | 1.229 | 1.025 |
| MEA | 17.990 | 19.335 | 10.087 | 24.701 | 17.662 | 24.119 | 9.596 | 17.400 | 17.389 |
| PIP | 0.989 | 0.964 | 1.718 | 0.593 | 0.993 | 0.590 | 1.696 | 1.203 | 1.145 |
| DETA | 50.172 | 53.162 | 45.219 | 55.645 | 50.697 | 55.944 | 45.259 | 49.313 | 51.748 |
| AEEA | 0.000 | 0.433 | 0.000 | 1.012 | 0.642 | 1.026 | 0.126 | 0.667 | 0.713 |
| AEP | 1.134 | 1.062 | 2.216 | 0.613 | 1.091 | 0.648 | 2.172 | 1.229 | 1.334 |
| TAEA | 2.208 | 2.198 | 2.406 | 1.617 | 2.175 | 1.619 | 2.323 | 2.162 | 2.307 |
| 1-TETA | 9.955 | 10.785 | 12.776 | 7.737 | 10.803 | 7.844 | 12.734 | 10.465 | 11.340 |
| DAEP | 0.232 | 0.218 | 0.936 | 0.103 | 0.249 | 0.110 | 0.896 | 0.273 | 0.300 |
| PEEDA | 0.124 | 0.143 | 0.603 | 0.062 | 0.166 | 0.000 | 0.576 | 0.174 | 0.184 |
| DPE | 0.000 | 0.075 | 0.075 | 0.000 | 0.000 | 0.000 | 0.085 | 0.000 | 0.000 |
| AE-TAEA | 1.588 | 1.180 | 3.177 | 0.735 | 2.054 | 0.826 | 3.277 | 1.942 | 2.255 |
| 1-TEPA | 2.656 | 2.775 | 6.758 | 1.190 | 3.841 | 1.534 | 6.807 | 4.191 | 4.651 |
| AE-DAEP | 0.114 | 0.097 | 0.606 | 0.000 | 0.000 | 0.000 | 0.525 | 0.086 | 0.106 |
| AE-PEEDA | 0.000 | 0.000 | 0.149 | 0.000 | 0.000 | 0.000 | 0.136 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.235 | 0.000 | 0.000 | 0.000 | 0.222 | 0.121 | 0.135 |
| BPEA | 0.000 | 0.000 | 0.112 | 0.000 | 0.000 | 0.000 | 0.109 | 0.000 | 0.128 |
| Others | 6.460 | 0.646 | 1.993 | 0.269 | 0.439 | 0.218 | 1.489 | 0.694 | 0.701 |
| MEA conversion, % | 51.45 | 47.17 | 72.49 | 32.06 | 50.75 | 33.87 | 73.52 | 51.33 | 53.62 |
| DETA conversion, % | 19.53 | 13.67 | 26.69 | 9.04 | 15.98 | 8.83 | 25.77 | 18.02 | 17.97 |
| Acyclic(N4), wt. % | 97.15 | 97.30 | 90.39 | 98.27 | 96.90 | 98.85 | 90.62 | 96.58 | 96.57 |
| Acyclic(N5), wt. % | 97.38 | 97.61 | 90.01 | 100.00 | 100.00 | 100.00 | 91.03 | 95.24 | 94.93 |
| Σ(N5)/Σ(N4), weight ratio | 0.35 | 0.30 | 0.66 | 0.20 | 0.44 | 0.25 | 0.67 | 0.49 | 0.51 |
| Acyclic(N4)/cyclic(<=N4), weight ratio | 4.91 | 5.44 | 2.74 | 6.83 | 5.19 | 7.02 | 2.78 | 4.39 | 4.61 |

TABLE LXXXIV

| Example No. | 812 | 813 | 814 | 815 | 816 | 817 | 818 | 819 | 820 |
|---|---|---|---|---|---|---|---|---|---|
| Catalyst Type | NNNN | NNNN | NNNN | NNNN | NNNN | NNNN | NNNN | NNNN | NNNN |
| Catalyst weight, gm | 76.6 | 76.6 | 76.6 | 76.6 | 76.6 | 76.6 | 76.6 | 76.6 | 76.6 |
| Pressure, psig | 597 | 599 | 594 | 596 | 597 | 598 | 598 | 578 | 592 |
| Temperature, °C. | 274.8 | 274.2 | 280.3 | 261.2 | 271.4 | 261.8 | 280.2 | 269.7 | 269.6 |
| Time on organics, hrs. | 6 | 8 | 26 | 33 | 50 | 54.5 | 74 | 98.5 | 100 |
| Duration of run, hrs. | 2 | 2 | 2 | 2 | 2 | 2 | 2 | 1.5 | 1.5 |

TABLE LXXXIV-continued

| Example No. | 812 | 813 | 814 | 815 | 816 | 817 | 818 | 819 | 820 |
|---|---|---|---|---|---|---|---|---|---|
| MEA SV, gmol/hr/kgcat | 3.47 | 3.41 | 3.15 | 3.08 | 3.28 | 3.12 | 3.05 | 3.41 | 3.47 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.061 | 2.011 | 3.148 | 1.184 | 2.307 | 1.307 | 3.298 | 4.426 | 1.702 |
| MEA | 11.521 | 11.310 | 6.396 | 20.282 | 13.265 | 20.615 | 5.659 | 11.296 | 14.677 |
| PIP | 1.527 | 1.470 | 2.157 | 0.932 | 1.702 | 0.989 | 2.146 | 3.452 | 1.419 |
| DETA | 42.334 | 40.741 | 38.310 | 49.435 | 42.179 | 50.484 | 37.713 | 34.699 | 46.940 |
| AEEA | 0.171 | 0.229 | 0.345 | 1.161 | 0.498 | 1.159 | 0.000 | 0.094 | 0.619 |
| AEP | 2.239 | 2.094 | 3.230 | 0.922 | 1.874 | 0.956 | 3.141 | 5.456 | 1.744 |
| HEP | 0.000 | 0.000 | 0.000 | 0.000 | 0.000 | 0.000 | 0.000 | 0.000 | 0.000 |
| TAEA | 2.485 | 2.769 | 2.228 | 2.289 | 2.411 | 2.243 | 1.952 | 1.031 | 2.473 |
| 1-TETA | 13.469 | 14.759 | 13.494 | 11.956 | 12.180 | 10.324 | 11.730 | 8.626 | 13.276 |
| DAEP | 0.942 | 0.959 | 1.643 | 0.249 | 0.703 | 0.219 | 1.537 | 2.523 | 0.455 |
| PEEDA | 0.758 | 0.783 | 1.241 | 0.150 | 0.500 | 0.132 | 1.082 | 1.975 | 0.332 |
| DPE | 0.099 | 0.097 | 0.135 | 0.000 | 0.076 | 0.000 | 0.130 | 0.128 | 0.000 |
| AE-TAEA | 3.476 | 3.863 | 3.743 | 2.042 | 3.220 | 1.844 | 3.286 | 1.977 | 3.025 |
| 1-TEPA | 6.876 | 7.762 | 8.263 | 3.497 | 6.138 | 3.258 | 7.403 | 4.058 | 5.508 |
| AE-DAEP | 0.571 | 0.509 | 1.049 | 0.000 | 0.355 | 0.000 | 1.086 | 2.356 | 0.367 |
| AE-PEEDA | 0.150 | 0.159 | 0.419 | 0.000 | 0.107 | 0.000 | 0.878 | 0.928 | 0.121 |
| iAE-PEEDA | 0.000 | 0.000 | 0.000 | 0.000 | 0.000 | 0.000 | 0.000 | 0.000 | 0.000 |
| AE-DPE | 0.410 | 0.460 | 0.567 | 0.176 | 0.433 | 0.123 | 0.974 | 0.089 | 0.242 |
| BPEA | 0.370 | 0.402 | 0.445 | 0.148 | 0.335 | 0.123 | 0.797 | 0.129 | 0.142 |
| Others | 3.222 | 3.202 | 4.458 | 0.022 | 2.377 | 0.934 | 5.999 | 8.878 | 1.378 |
| MEA conversion, % | 69.06 | 69.99 | 82.87 | 44.85 | 63.31 | 44.03 | 84.47 | 69.87 | 60.81 |
| DETA conversion, % | 32.44 | 35.75 | 39.01 | 20.11 | 30.67 | 18.54 | 38.47 | 45.00 | 25.51 |
| Acyclic(N4), wt. % | 89.87 | 90.50 | 83.90 | 97.28 | 91.94 | 97.28 | 83.27 | 67.62 | 95.24 |
| Acyclic(N5), wt. % | 87.34 | 88.37 | 82.89 | 94.47 | 88.39 | 95.40 | 74.10 | 63.28 | 90.73 |
| Σ(N5)/Σ(N4), weight ratio | 0.67 | 0.68 | 0.77 | 0.40 | 0.67 | 0.41 | 0.88 | 0.67 | 0.57 |
| Acyclic(N4)/cyclic (<=N4), weight ratio | 2.87 | 3.24 | 1.87 | 6.32 | 3.01 | 5.47 | 1.70 | 0.71 | 3.99 |

TABLE LXXXV

| Example No. | 821 | 822 | 823 | 824 | 825 | 826 | 827 | 828 | 829 |
|---|---|---|---|---|---|---|---|---|---|
| Catalyst Type | OOOO | OOOO | OOOO | OOOO | OOOO | OOOO | OOOO | OOOO | OOOO |
| Catalyst weight, gm | 77.2 | 77.2 | 77.2 | 77.2 | 77.2 | 77.2 | 77.2 | 77.2 | 77.2 |
| Pressure, psig | 606 | 602 | 603 | 599 | 605 | 601.3 | 604 | 605 | 602 |
| Temperature, °C. | 274.8 | 274.2 | 280.3 | 261.2 | 271.4 | 261.8 | 280.2 | 269.7 | 269.6 |
| Time on organics, hrs. | 6 | 8 | 26 | 33 | 50 | 54.5 | 74 | 98.5 | 100 |
| Duration of run, hrs. | 2 | 2 | 2 | 2 | 2 | 2 | 2 | 1.5 | 1.5 |
| MEA SV, gmol/hr/kgcat | 3.66 | 3.28 | 3.32 | 3.12 | 3.38 | 3.23 | 3.28 | 3.68 | 3.71 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 4.605 | 3.886 | 5.431 | 1.582 | 3.133 | 1.518 | 5.888 | 2.090 | 2.159 |
| MEA | 14.165 | 13.840 | 8.988 | 20.796 | 15.163 | 22.247 | 9.341 | 16.165 | 15.935 |
| PIP | 2.743 | 2.486 | 3.003 | 1.044 | 1.960 | 1.001 | 3.051 | 1.333 | 1.433 |
| DETA | 39.645 | 39.381 | 34.406 | 46.873 | 40.571 | 50.785 | 37.693 | 42.241 | 45.956 |
| AEEA | 0.101 | 0.264 | 0.101 | 0.891 | 0.476 | 0.962 | 0.000 | 0.631 | 0.594 |
| AEP | 3.421 | 3.180 | 4.196 | 1.218 | 2.294 | 1.114 | 3.834 | 1.851 | 1.880 |
| HEP | 0.000 | 0.000 | 0.000 | 0.000 | 0.000 | 0.000 | 0.000 | 0.000 | 0.000 |
| TAEA | 1.671 | 1.753 | 1.198 | 1.910 | 2.183 | 2.023 | 1.193 | 2.292 | 2.459 |
| 1-TETA | 10.517 | 11.090 | 10.855 | 9.315 | 11.704 | 9.626 | 10.401 | 11.963 | 12.528 |
| DAEP | 1.223 | 1.224 | 1.875 | 0.287 | 0.898 | 0.251 | 1.503 | 0.631 | 0.765 |
| PEEDA | 1.151 | 1.136 | 1.743 | 0.206 | 0.759 | 0.177 | 1.167 | 0.451 | 0.617 |
| DPE | 0.130 | 0.119 | 0.213 | 0.000 | 0.080 | 0.000 | 0.109 | 0.000 | 0.105 |
| AE-TAEA | 2.230 | 2.468 | 2.555 | 1.718 | 2.775 | 1.629 | 2.507 | 2.873 | 3.183 |
| 1-TEPA | 5.038 | 5.654 | 6.324 | 3.175 | 5.413 | 2.702 | 5.290 | 5.112 | 5.477 |
| AE-DAEP | 0.832 | 0.808 | 1.544 | 0.156 | 0.488 | 0.107 | 1.070 | 0.396 | 0.424 |
| AE-PEEDA | 0.403 | 0.315 | 0.858 | 0.000 | 0.160 | 0.000 | 0.446 | 0.111 | 0.106 |
| iAE-PEEDA | 0.000 | 0.000 | 0.000 | 0.000 | 0.000 | 0.000 | 0.000 | 0.000 | 0.000 |
| AE-DPE | 0.130 | 0.259 | 0.457 | 0.096 | 0.092 | 0.000 | 0.307 | 0.366 | 0.235 |
| BPEA | 0.134 | 0.409 | 0.354 | 0.122 | 0.279 | 0.000 | 0.451 | 0.213 | 0.175 |
| Others | 4.461 | 4.200 | 9.270 | 1.000 | 3.341 | 0.756 | 6.468 | 2.101 | 1.798 |
| MEA conversion, % | 61.68 | 62.60 | 76.38 | 40.76 | 58.41 | 39.45 | 75.52 | 57.13 | 58.04 |
| DETA conversion, % | 36.26 | 36.76 | 46.26 | 20.64 | 33.86 | 17.85 | 38.88 | 26.66 | 28.09 |
| Acyclic(N4), wt. % | 82.96 | 83.82 | 75.88 | 95.80 | 88.88 | 96.46 | 80.67 | 92.94 | 90.97 |
| Acyclic(N5), wt. % | 82.90 | 81.94 | 73.43 | 92.89 | 88.93 | 97.60 | 77.42 | 88.03 | 90.21 |
| Σ(N5)/Σ(N4), weight ratio | 0.60 | 0.65 | 0.76 | 0.45 | 0.59 | 0.37 | 0.70 | 0.59 | 0.58 |
| Acyclic(N4)/cyclic (<=N4), weight ratio | 1.41 | 1.58 | 1.09 | 4.07 | 2.32 | 4.58 | 1.20 | 3.34 | 3.12 |

TABLE LXXXVI

| Example No. | 830 | 831 | 832 | 833 | 834 | 835 | 836 | 837 | 838 |
|---|---|---|---|---|---|---|---|---|---|
| Catalyst Type | PPPP | PPPP | PPPP | PPPP | PPPP | PPPP | PPPP | PPPP | PPPP |
| Catalyst weight, gm | 74.1 | 74.1 | 74.1 | 74.1 | 74.1 | 74.1 | 74.1 | 74.1 | 74.1 |
| Pressure, psig | 600 | 600 | 600 | 600 | 600 | 600 | 600 | 600 | 600 |
| Temperature, °C. | 270.1 | 270 | 280.2 | 259.7 | 270.1 | 259.6 | 280 | 270 | 270 |
| Time on organics, hrs. | 5 | 7.5 | 26.5 | 31.5 | 49.75 | 54 | 74 | 77.5 | 80 |
| Duration of run, hrs. | 2 | 2 | 2 | 2 | 2 | 2 | 2 | 2 | 2 |
| MEA SV, gmol/hr/kgcat | 4.32 | 4.45 | 3.86 | 4.75 | 4.55 | 4.76 | 4.72 | 4.88 | 4.68 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.799 | 0.893 | 2.371 | 0.614 | 1.122 | 0.619 | 1.998 | 0.866 | 1.017 |
| MEA | 16.923 | 18.142 | 8.959 | 23.814 | 16.116 | 25.054 | 10.110 | 16.161 | 17.198 |
| PIP | 1.117 | 1.135 | 0.000 | 0.764 | 1.371 | 0.835 | 1.977 | 1.209 | 1.356 |
| DETA | 50.969 | 52.494 | 43.962 | 55.309 | 48.689 | 54.390 | 47.265 | 50.840 | 51.369 |
| AEEA | 0.000 | 0.655 | 0.113 | 1.240 | 0.695 | 1.219 | 0.126 | 0.812 | 0.802 |
| AEP | 1.445 | 1.273 | 2.405 | 0.656 | 1.488 | 0.655 | 2.444 | 1.326 | 1.362 |
| HEP | 0.000 | 0.000 | 0.000 | 0.000 | 0.000 | 0.000 | 0.000 | 0.000 | 0.000 |
| TAEA | 2.361 | 2.414 | 2.424 | 1.705 | 2.211 | 1.553 | 2.474 | 2.443 | 2.319 |
| 1-TETA | 10.806 | 11.071 | 12.003 | 8.100 | 10.604 | 7.390 | 12.128 | 11.857 | 11.027 |
| DAEP | 0.223 | 0.211 | 1.034 | 0.102 | 0.328 | 0.101 | 0.788 | 0.287 | 0.268 |
| PEEDA | 0.000 | 0.150 | 0.742 | 0.000 | 0.209 | 0.000 | 0.537 | 0.199 | 0.180 |
| DPE | 0.000 | 0.000 | 0.122 | 0.000 | 0.000 | 0.000 | 0.109 | 0.000 | 0.000 |
| AE-TAEA | 1.975 | 1.711 | 2.755 | 0.748 | 2.130 | 0.714 | 2.508 | 2.424 | 1.870 |
| 1-TEPA | 3.599 | 3.260 | 6.223 | 1.444 | 4.940 | 1.373 | 5.742 | 5.006 | 3.901 |
| AE-DAEP | 0.249 | 0.000 | 0.609 | 0.000 | 0.099 | 0.000 | 0.378 | 0.000 | 0.000 |
| AE-PEEDA | 0.508 | 0.000 | 0.659 | 0.000 | 0.000 | 0.000 | 0.116 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.236 | 0.000 | 0.800 | 0.000 | 0.118 | 0.000 | 0.334 | 0.140 | 0.099 |
| BPEA | 0.164 | 0.000 | 0.533 | 0.000 | 0.126 | 0.000 | 0.204 | 0.121 | 0.116 |
| Others | 2.605 | 0.440 | 4.535 | 0.205 | 0.635 | 0.218 | 1.962 | 0.607 | 0.694 |
| MEA conversion, % | 54.25 | 50.54 | 75.37 | 34.57 | 54.94 | 30.55 | 72.30 | 56.49 | 53.15 |
| DETA conversion, % | 18.10 | 14.95 | 28.17 | 9.69 | 19.10 | 10.39 | 23.03 | 18.65 | 16.84 |
| Acyclic(N4), wt. % | 98.33 | 97.39 | 88.38 | 98.97 | 95.98 | 98.88 | 91.06 | 96.71 | 96.75 |
| Acyclic(N5), wt. % | 82.81 | 100.00 | 77.54 | 100.00 | 95.38 | 100.00 | 88.88 | 96.60 | 96.42 |
| Σ(N5)/Σ(N4), weight ratio | 0.50 | 0.36 | 0.71 | 0.22 | 0.56 | 0.23 | 0.58 | 0.52 | 0.43 |
| Acyclic(N4)/cyclic (<=N4), weight ratio | 4.73 | 4.87 | 3.35 | 6.44 | 3.77 | 5.62 | 2.58 | 4.73 | 4.21 |

TABLE LXXXVII

| Example No. | 839 | 840 | 841 | 842 | 843 | 844 | 845 | 846 | 847 |
|---|---|---|---|---|---|---|---|---|---|
| Catalyst Type | QQQQ | QQQQ | QQQQ | QQQQ | QQQQ | QQQQ | QQQQ | QQQQ | QQQQ |
| Catalyst weight, gm | 78.9 | 78.9 | 78.9 | 78.9 | 78.9 | 78.9 | 78.9 | 78.9 | 78.9 |
| Pressure, psig | 600 | 600 | 600 | 600 | 600 | 600 | 600 | 600 | 600 |
| Temperature, °C. | 270.3 | 270.8 | 280.9 | 259.5 | 270.8 | 261.4 | 282.6 | 273.4 | 270.8 |
| Time on organics, hrs. | 4 | 7 | 26 | 31 | 50 | 55 | 74 | 79 | 99.5 |
| Duration of run, hrs. | 2 | 2 | 2 | 2 | 2 | 2 | 2 | 2 | 2 |
| MEA SV, gmol/hr/kgcat | 3.12 | 3.22 | 3.28 | 3.33 | 3.43 | 3.59 | 3.37 | 3.31 | 3.46 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.169 | 1.189 | 2.230 | 1.402 | 1.099 | 0.671 | 1.752 | 0.918 | 1.448 |
| MEA | 15.817 | 15.231 | 6.402 | 28.485 | 16.384 | 22.977 | 5.783 | 12.331 | 15.301 |
| PIP | 1.664 | 1.609 | 2.315 | 1.465 | 1.764 | 1.139 | 2.015 | 1.420 | 1.843 |
| DETA | 52.256 | 51.487 | 43.212 | 53.634 | 51.751 | 53.055 | 43.336 | 47.964 | 50.154 |
| AEEA | 0.283 | 0.283 | 0.000 | 1.094 | 0.153 | 0.886 | 0.000 | 0.400 | 0.339 |
| AEP | 1.915 | 1.855 | 2.978 | 0.777 | 1.978 | 1.094 | 2.884 | 1.762 | 2.059 |
| HEP | 0.000 | 0.000 | 0.000 | 0.000 | 0.000 | 0.000 | 0.000 | 0.000 | 0.000 |
| TAEA | 2.062 | 2.339 | 1.830 | 0.884 | 2.131 | 1.899 | 2.473 | 2.651 | 2.259 |
| 1-TETA | 11.022 | 11.780 | 12.001 | 6.150 | 11.397 | 9.186 | 13.960 | 13.405 | 11.464 |
| DAEP | 0.337 | 0.328 | 1.290 | 0.078 | 0.299 | 0.126 | 1.238 | 0.389 | 0.381 |
| PEEDA | 0.207 | 0.217 | 0.927 | 0.046 | 0.186 | 0.076 | 0.763 | 0.288 | 0.260 |
| DPE | 0.000 | 0.000 | 0.251 | 0.000 | 0.000 | 0.000 | 0.000 | 0.000 | 0.000 |
| AE-TAEA | 1.815 | 1.985 | 2.926 | 0.503 | 1.572 | 1.100 | 3.768 | 3.096 | 1.880 |
| 1-TEPA | 3.691 | 3.831 | 7.181 | 0.912 | 3.369 | 2.347 | 8.080 | 6.384 | 3.990 |
| AE-DAEP | 0.243 | 0.116 | 1.511 | 0.121 | 0.213 | 0.276 | 0.809 | 0.295 | 0.138 |
| AE-PEEDA | 0.000 | 0.000 | 0.928 | 0.000 | 0.000 | 0.000 | 0.238 | 0.136 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 1.302 | 0.000 | 0.106 | 0.156 | 0.212 | 0.000 | 0.537 |
| BPEA | 0.000 | 0.000 | 0.709 | 0.000 | 0.000 | 0.000 | 0.505 | 0.127 | 0.377 |
| Others | 0.459 | 0.872 | 2.746 | 0.399 | 0.607 | 0.361 | 2.423 | 0.974 | 1.252 |
| MEA conversion, % | 56.77 | 58.52 | 82.77 | 22.06 | 55.23 | 37.72 | 84.29 | 66.57 | 58.72 |
| DETA conversion, % | 15.12 | 16.67 | 30.89 | 12.79 | 15.96 | 14.53 | 30.04 | 22.72 | 19.59 |
| Acyclic(N4), wt. % | 96.01 | 96.29 | 84.86 | 98.26 | 96.54 | 98.20 | 89.14 | 95.95 | 95.54 |
| Acyclic(N5), wt. % | 95.76 | 98.04 | 69.43 | 92.12 | 93.94 | 88.86 | 87.04 | 94.45 | 84.81 |
| Σ(N5)/Σ(N4), weight ratio | 0.42 | 0.40 | 0.89 | 0.21 | 0.38 | 0.34 | 0.74 | 0.60 | 0.48 |
| Acyclic(N4)/cyclic (<=N4), | 3.17 | 3.52 | 1.78 | 2.97 | 3.20 | 4.55 | 2.38 | 4.16 | 3.02 |

TABLE LXXXVII-continued

| Example No. | 839 | 840 | 841 | 842 | 843 | 844 | 845 | 846 | 847 |
|---|---|---|---|---|---|---|---|---|---|
| weight ratio | | | | | | | | | |

TABLE LXXXVIII

| Example No. | 848 | 849 | 850 | 851 | 852 | 853 | 854 | 855 | 856 |
|---|---|---|---|---|---|---|---|---|---|
| Catalyst Type | RRRR | RRRR | RRRR | RRRR | RRRR | RRRR | RRRR | RRRR | RRRR |
| Catalyst weight, gm | 75 | 75 | 75 | 75 | 75 | 75 | 75 | 75 | 75 |
| Pressure, psig | 600 | 600 | 600 | 600 | 600 | 600 | 600 | 600 | 600 |
| Temperature, °C. | 271.8 | 270 | 280.2 | 260.9 | 270.6 | 261.2 | 281.5 | 270 | 270 |
| Time on organics, hrs. | 5 | 8.5 | 25 | 30 | 34 | 49 | 55 | 76 | 78 |
| Duration of run, hrs. | 2 | 2 | 2 | 2 | 2 | 2 | 2 | 2 | 2 |
| MEA SV, gmol/hr/kgcat | 4.47 | 4.56 | 4.56 | 4.83 | 4.82 | 4.39 | 4.36 | 4.29 | 4.45 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.810 | 0.695 | 1.728 | 0.496 | 1.051 | 0.606 | 2.250 | 1.081 | 1.235 |
| MEA | 17.286 | 19.405 | 12.726 | 23.941 | 20.602 | 23.930 | 10.050 | 16.058 | 17.476 |
| PIP | 0.000 | 0.893 | 1.726 | 0.691 | 1.246 | 0.771 | 1.912 | 1.336 | 1.440 |
| DETA | 49.596 | 50.668 | 47.269 | 55.529 | 51.649 | 54.615 | 43.590 | 49.568 | 50.015 |
| AEEA | 0.486 | 0.691 | 0.138 | 1.063 | 0.715 | 1.234 | 0.241 | 0.655 | 0.684 |
| AEP | 1.371 | 0.938 | 1.974 | 0.669 | 1.231 | 0.731 | 2.221 | 1.449 | 1.413 |
| HEP | 0.000 | 0.000 | 0.000 | 0.000 | 0.000 | 0.000 | 0.000 | 0.000 | 0.000 |
| TAEA | 2.260 | 2.121 | 2.389 | 1.786 | 2.157 | 1.878 | 2.470 | 2.355 | 2.187 |
| 1-TETA | 12.072 | 9.647 | 11.834 | 8.149 | 10.098 | 8.642 | 12.086 | 11.364 | 11.254 |
| DAEP | 0.252 | 0.179 | 0.649 | 0.097 | 0.211 | 0.112 | 0.851 | 0.313 | 0.251 |
| PEEDA | 0.179 | 0.124 | 0.372 | 0.070 | 0.144 | 0.071 | 0.630 | 0.209 | 0.172 |
| DPE | 0.000 | 0.000 | 0.000 | 0.000 | 0.000 | 0.000 | 0.068 | 0.000 | 0.000 |
| AE-TAEA | 2.502 | 1.504 | 2.751 | 0.826 | 1.555 | 0.937 | 2.780 | 2.257 | 2.015 |
| 1-TEPA | 4.580 | 2.966 | 5.577 | 1.450 | 2.954 | 1.689 | 6.099 | 4.795 | 4.114 |
| AE-DAEP | 0.259 | 0.000 | 0.387 | 0.000 | 0.084 | 0.000 | 0.395 | 0.000 | 0.231 |
| AE-PEEDA | 0.105 | 0.000 | 0.100 | 0.000 | 0.000 | 0.000 | 0.111 | 0.000 | 0.177 |
| iAE-PEEDA | 0.000 | 0.000 | 0.000 | 0.000 | 0.000 | 0.000 | 0.000 | 0.000 | 0.000 |
| AE-DPE | 0.166 | 0.000 | 0.181 | 0.000 | 0.077 | 0.000 | 0.451 | 0.115 | 0.108 |
| BPEA | 0.000 | 0.068 | 0.138 | 0.000 | 0.100 | 0.000 | 0.352 | 0.164 | 0.105 |
| Others | 0.756 | 0.599 | 1.252 | 0.294 | 0.726 | 0.304 | 2.563 | 0.790 | 0.884 |
| MEA conversion, % | 52.45 | 44.86 | 64.94 | 34.49 | 44.04 | 34.90 | 71.93 | 55.92 | 52.53 |
| DETA conversion, % | 18.91 | 14.44 | 22.61 | 9.70 | 16.62 | 11.71 | 27.65 | 19.14 | 19.26 |
| Acyclic(N4), wt. % | 97.08 | 97.48 | 93.30 | 98.35 | 97.19 | 98.29 | 90.39 | 96.33 | 96.95 |
| Acyclic(N5), wt. % | 93.03 | 98.50 | 91.18 | 100.00 | 94.52 | 100.00 | 87.15 | 96.19 | 90.81 |
| Σ(N5)/Σ(N4), weight ratio | 0.52 | 0.38 | 0.60 | 0.23 | 0.38 | 0.25 | 0.63 | 0.51 | 0.49 |
| Acyclic(N4)/cyclic (< =N4), weight ratio | 7.95 | 5.51 | 3.01 | 6.51 | 4.33 | 6.24 | 2.56 | 4.15 | 4.10 |

TABLE LXXXIX

| Example No. | 857 | 858 | 859 | 860 | 861 | 862 | 863 | 864 | 865 |
|---|---|---|---|---|---|---|---|---|---|
| Catalyst Type | SSSS | SSSS | SSSS | SSSS | SSSS | SSSS | SSSS | SSSS | SSSS |
| Catalyst weight, gm | 74.9 | 74.9 | 74.9 | 74.9 | 74.9 | 74.9 | 74.9 | 74.9 | 74.9 |
| Pressure, psig | 600 | 600 | 600 | 600 | 600 | 600 | 600 | 600 | 600 |
| Temperature, °C. | 269.3 | 269.2 | 279.4 | 258.8 | 269.2 | 259.4 | 279.2 | 268.9 | 269.6 |
| Time on organics, hrs. | 23.5 | 27.5 | 47 | 52 | 71 | 76 | 95 | 100 | 120 |
| Duration of run, hrs. | 2 | 2 | 2 | 2 | 2 | 2 | 2 | 2 | 2 |
| MEA SV, gmol/hr/kgcat | 3.93 | 3.73 | 3.63 | 3.84 | 3.64 | 3.67 | 3.53 | 3.56 | 3.35 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.980 | 0.906 | 2.141 | 0.568 | 1.040 | 0.888 | 2.069 | 1.289 | 1.356 |
| MEA | 20.085 | 19.419 | 12.916 | 27.282 | 20.217 | 25.518 | 12.998 | 22.393 | 20.330 |
| PIP | 1.509 | 1.448 | 2.211 | 0.850 | 1.624 | 0.922 | 2.027 | 1.573 | 1.718 |
| DETA | 52.434 | 51.557 | 46.545 | 55.689 | 52.087 | 54.254 | 47.895 | 52.707 | 52.473 |
| AEEA | 0.262 | 0.255 | 0.178 | 0.429 | 0.220 | 0.421 | 0.000 | 0.268 | 0.263 |
| AEP | 1.402 | 1.413 | 2.106 | 0.696 | 1.428 | 0.823 | 2.307 | 1.348 | 1.537 |
| HEP | 0.000 | 0.000 | 0.000 | 0.000 | 0.000 | 0.000 | 0.000 | 0.000 | 0.000 |
| TAEA | 1.988 | 2.084 | 2.094 | 1.374 | 1.867 | 1.680 | 1.920 | 1.733 | 1.944 |
| 1-TETA | 9.493 | 9.950 | 10.311 | 6.413 | 8.947 | 7.890 | 9.728 | 7.823 | 8.760 |
| DAEP | 0.173 | 0.198 | 0.645 | 0.058 | 0.382 | 0.275 | 0.714 | 0.279 | 0.373 |
| PEEDA | 0.127 | 0.146 | 0.460 | 0.052 | 0.150 | 0.192 | 0.328 | 0.000 | 0.000 |
| DPE | 0.000 | 0.000 | 0.056 | 0.000 | 0.000 | 0.000 | 0.000 | 0.000 | 0.000 |
| AE-TAEA | 0.000 | 0.000 | 0.000 | 0.000 | 0.000 | 0.000 | 0.000 | 0.000 | 0.000 |
| 1-TEPA | 1.257 | 1.371 | 2.257 | 0.448 | 1.195 | 0.801 | 2.316 | 0.979 | 1.375 |
| AE-DAEP | 0.000 | 0.292 | 0.334 | 0.000 | 0.091 | 0.104 | 0.624 | 0.000 | 0.000 |
| AE-PEEDA | 0.084 | 0.135 | 0.070 | 0.000 | 0.000 | 0.000 | 0.485 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.208 | 0.779 | 1.181 | 0.000 | 0.365 | 0.281 | 0.490 | 0.000 | 0.365 |
| BPEA | 0.000 | 0.000 | 0.287 | 0.000 | 0.000 | 0.000 | 0.631 | 0.000 | 0.000 |

TABLE LXXXIX-continued

| Example No. | 857 | 858 | 859 | 860 | 861 | 862 | 863 | 864 | 865 |
|---|---|---|---|---|---|---|---|---|---|
| Others | 2.920 | 3.097 | 5.689 | 1.582 | 2.587 | 1.652 | 6.070 | 1.507 | 2.305 |
| MEA conversion, % | 44.42 | 46.57 | 63.21 | 25.08 | 43.62 | 30.56 | 63.95 | 36.84 | 43.63 |
| DETA conversion, % | 13.76 | 15.69 | 21.21 | 9.11 | 13.68 | 12.26 | 21.06 | 11.65 | 13.54 |
| Acyclic(N4), wt. % | 97.46 | 97.22 | 91.45 | 98.61 | 95.31 | 95.35 | 91.79 | 97.16 | 96.64 |
| Acyclic(N5), wt. % | 81.13 | 53.17 | 72.13 | 100.00 | 72.41 | 67.51 | 50.94 | 100.00 | 79.03 |
| Σ(N5)/Σ(N4), weight ratio | 0.13 | 0.21 | 0.23 | 0.06 | 0.15 | 0.12 | 0.36 | 0.10 | 0.16 |
| Acyclic(N4)/cyclic (<=N4), weight ratio | 3.58 | 3.76 | 2.26 | 4.70 | 3.02 | 4.33 | 2.17 | 2.99 | 2.95 |

TABLE XC

| Example No. | 866 | 867 | 868 | 869 | 870 | 871 | 872 | 873 | 874 |
|---|---|---|---|---|---|---|---|---|---|
| Catalyst Type | TTTT | TTTT | TTTT | TTTT | TTTT | TTTT | TTTT | TTTT | TTTT |
| Catalyst weight, gm | 77.1 | 77.1 | 77.1 | 77.1 | 77.1 | 77.1 | 77.1 | 77.1 | 77.1 |
| Pressure, psig | 600 | 600 | 600 | 600 | 600 | 600 | 600 | 600 | 600 |
| Temperature, °C. | 270.3 | 270.8 | 280.9 | 259.5 | 270.8 | 261.4 | 282.6 | 272.4 | 270.8 |
| Time on organics, hrs. | 4 | 7 | 26 | 31 | 50 | 55 | 74 | 79 | 99.5 |
| Duration of run, hrs. | 2 | 2 | 2 | 2 | 2 | 2 | 2 | 2 | 2 |
| MEA SV, gmol/hr/kgcat | 3.57 | 3.84 | 3.80 | 3.90 | 4.07 | 4.29 | 4.00 | 4.02 | 4.09 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.064 | 1.067 | 2.949 | 1.044 | 1.126 | 0.634 | 1.319 | 0.655 | 0.856 |
| MEA | 19.737 | 20.664 | 15.833 | 33.488 | 22.772 | 28.669 | 10.428 | 16.261 | 18.470 |
| PIP | 1.010 | 1.060 | 2.508 | 1.029 | 1.433 | 0.868 | 1.591 | 0.964 | 1.166 |
| DETA | 52.528 | 52.478 | 47.832 | 54.061 | 52.460 | 55.001 | 46.963 | 50.475 | 53.782 |
| AEEA | 0.618 | 0.649 | 0.219 | 0.981 | 0.066 | 1.055 | 0.134 | 0.751 | 0.219 |
| AEP | 1.111 | 1.092 | 2.117 | 0.537 | 1.255 | 0.600 | 2.045 | 1.283 | 1.400 |
| HEP | 0.000 | 0.000 | 0.000 | 0.000 | 0.000 | 0.000 | 0.000 | 0.000 | 0.000 |
| TAEA | 1.982 | 1.964 | 1.306 | 0.527 | 1.836 | 1.309 | 2.590 | 2.505 | 2.082 |
| l-TETA | 10.911 | 10.012 | 8.857 | 4.302 | 9.388 | 6.368 | 13.545 | 12.661 | 10.355 |
| DAEP | 0.183 | 0.172 | 0.652 | 0.031 | 0.165 | 0.065 | 0.739 | 0.233 | 0.193 |
| PEEDA | 0.134 | 0.122 | 0.487 | 0.000 | 0.108 | 0.000 | 0.478 | 0.186 | 0.154 |
| DPE | 0.000 | 0.000 | 0.321 | 0.000 | 0.000 | 0.000 | 0.000 | 0.000 | 0.000 |
| AE-TAEA | 1.065 | 1.592 | 1.529 | 0.149 | 0.830 | 0.433 | 3.290 | 2.387 | 1.478 |
| 1-TEPA | 2.728 | 3.034 | 2.962 | 0.125 | 2.166 | 0.748 | 6.467 | 4.760 | 2.918 |
| AE-DAEP | 0.123 | 0.000 | 0.376 | 0.000 | 0.049 | 0.125 | 0.366 | 0.110 | 0.086 |
| AE-PEEDA | 0.000 | 0.000 | 0.218 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.142 | 0.198 | 0.600 | 0.000 | 0.000 | 0.000 | 0.151 | 0.105 | 0.000 |
| BPEA | 0.000 | 0.000 | 0.310 | 0.000 | 0.000 | 0.000 | 0.157 | 0.065 | 0.000 |
| Others | 0.983 | 0.675 | 2.785 | 0.347 | 1.245 | 0.414 | 1.358 | 0.510 | 1.052 |
| MEA conversion, % | 46.25 | 43.91 | 56.39 | 7.91 | 37.98 | 21.73 | 71.61 | 56.02 | 49.81 |
| DETA conversion, % | 14.98 | 15.34 | 21.70 | 11.65 | 15.09 | 10.85 | 24.02 | 18.86 | 13.13 |
| Acyclic(N4), wt. % | 97.60 | 97.60 | 87.44 | 99.35 | 97.63 | 99.16 | 92.99 | 97.31 | 97.29 |
| Acyclic(N5), wt. % | 93.48 | 95.89 | 74.91 | 100.00 | 98.39 | 90.46 | 93.53 | 96.24 | 98.09 |
| Σ(N5)/Σ(N4), weight ratio | 0.31 | 0.39 | 0.52 | 0.06 | 0.26 | 0.17 | 0.60 | 0.48 | 0.35 |
| Acyclic(N4)/cyclic (<=N4), weight ratio | 5.29 | 4.89 | 1.67 | 3.02 | 3.79 | 5.01 | 3.32 | 5.69 | 4.27 |

TABLE XCI

| Example No. | 875 | 876 | 877 | 878 | 879 | 880 | 881 | 882 | 883 |
|---|---|---|---|---|---|---|---|---|---|
| Catalyst Type | UUUU | UUUU | UUUU | UUUU | UUUU | UUUU | UUUU | UUUU | UUUU |
| Catalyst weight, gm | 89.1 | 89.1 | 89.1 | 89.1 | 89.1 | 89.1 | 89.1 | 89.1 | 89.1 |
| Pressure, psig | 600 | 600 | 600 | 600 | 600 | 600 | 600 | 600 | 600 |
| Temperature, °C. | 274.4 | 274.4 | 280.9 | 259.8 | 270.6 | 259.9 | 281.6 | 270.4 | 270.4 |
| Time on organics, hrs. | 22 | 26 | 45.5 | 50.5 | 69 | 74.5 | 95 | 119 | 120 |
| Duration of run, hrs. | 2 | 2 | 2 | 2 | 2 | 2 | 2 | 1 | 1 |
| MEA SV, gmol/hr/kgcat | 3.54 | 3.49 | 3.26 | 3.62 | 3.67 | 3.54 | 3.50 | 7.34 | 3.64 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.720 | 2.147 | 6.050 | 1.506 | 2.063 | 0.510 | 4.522 | 1.700 | 1.717 |
| MEA | 17.172 | 17.646 | 11.090 | 24.376 | 18.880 | 23.711 | 12.670 | 19.091 | 19.532 |
| PIP | 3.605 | 3.285 | 6.865 | 1.922 | 2.983 | 1.500 | 5.411 | 2.536 | 2.650 |
| DETA | 45.019 | 47.846 | 36.936 | 51.126 | 46.069 | 60.718 | 38.319 | 46.051 | 46.810 |
| AEEA | 1.105 | 0.896 | 0.266 | 2.671 | 1.310 | 1.103 | 0.484 | 1.774 | 1.241 |
| AEP | 2.925 | 2.891 | 6.159 | 1.195 | 2.402 | 1.058 | 4.968 | 2.089 | 2.120 |
| HEP | 0.000 | 0.000 | 0.000 | 0.000 | 0.000 | 0.000 | 0.000 | 0.000 | 0.000 |
| TAEA | 1.209 | 0.424 | 0.376 | 0.813 | 1.233 | 0.599 | 0.517 | 1.195 | 0.782 |
| l-TETA | 10.239 | 10.478 | 8.946 | 8.826 | 10.269 | 6.805 | 9.581 | 9.683 | 9.534 |
| DAEP | 0.772 | 0.760 | 1.868 | 0.178 | 0.640 | 0.127 | 1.531 | 0.559 | 0.548 |
| PEEDA | 0.840 | 0.880 | 2.576 | 0.170 | 0.724 | 0.140 | 2.159 | 0.624 | 0.603 |
| DPE | 0.041 | 0.054 | 0.072 | 0.000 | 0.086 | 0.000 | 0.101 | 0.052 | 0.032 |

TABLE XCI-continued

| Example No. | 875 | 876 | 877 | 878 | 879 | 880 | 881 | 882 | 883 |
|---|---|---|---|---|---|---|---|---|---|
| AE-TAEA | 0.934 | 0.596 | 0.549 | 0.231 | 0.979 | 0.000 | 0.711 | 0.904 | 0.788 |
| 1-TEPA | 4.738 | 4.381 | 4.535 | 2.107 | 4.687 | 0.000 | 5.357 | 4.353 | 4.151 |
| AE-DAEP | 0.398 | 0.278 | 1.152 | 0.049 | 0.262 | 0.000 | 0.969 | 0.257 | 0.237 |
| AE-PEEDA | 0.126 | 0.129 | 0.254 | 0.000 | 0.115 | 0.000 | 0.235 | 0.109 | 0.104 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.047 | 0.000 | 0.000 | 0.000 | 0.000 | 0.000 | 0.000 |
| BPEA | 0.000 | 0.000 | 0.000 | 0.000 | 0.000 | 0.000 | 0.000 | 0.000 | 0.000 |
| Others | 1.657 | 1.439 | 3.878 | 0.448 | 1.598 | 0.000 | 3.154 | 1.704 | 1.370 |
| MEA conversion, % | 53.55 | 52.50 | 70.19 | 33.82 | 49.12 | 35.88 | 65.36 | 47.50 | 45.94 |
| DETA conversion, % | 27.63 | 23.46 | 41.00 | 17.51 | 26.21 | 2.41 | 37.74 | 24.74 | 23.00 |
| Acyclic(N4), % | 87.38 | 86.56 | 67.36 | 96.51 | 88.80 | 96.51 | 72.70 | 89.80 | 89.71 |
| Acyclic(N5), % | 91.53 | 92.44 | 77.77 | 97.93 | 93.75 | 0.00 | 83.44 | 93.50 | 93.54 |
| Σ(N5)/Σ(N4), weight ratio | 0.47 | 0.43 | 0.47 | 0.24 | 0.47 | 0.00 | 0.52 | 0.46 | 0.46 |
| Acyclic(N4)/cyclic (<=N4), weight ratio | 1.40 | 1.39 | 0.53 | 2.78 | 1.68 | 2.61 | 0.71 | 1.86 | 1.73 |

TABLE XCII

| Example No. | 884 | 885 | 886 | 887 | 888 | 889 | 890 | 891 | 892 |
|---|---|---|---|---|---|---|---|---|---|
| Catalyst Type | VVVV | VVVV | VVVV | VVVV | VVVV | VVVV | VVVV | VVVV | VVVV |
| Catalyst weight, gm | 91.7 | 91.7 | 91.7 | 91.7 | 91.7 | 91.7 | 91.7 | 91.7 | 91.7 |
| Pressure, psig | 600 | 600 | 600 | 600 | 600 | 600 | 600 | 600 | 600 |
| Temperature, °C. | 268.6 | 268.9 | 278.6 | 259.1 | 268.3 | 258.2 | 278.9 | 269 | 269.6 |
| Time on organics, hrs. | 3 | 22 | 27 | 51 | 69.5 | 74 | 93 | 99 | 116.5 |
| Duration of run, hrs. | 2 | 2 | 2 | 2 | 2 | 2 | 2 | 2 | 2 |
| MEA SV, gmol/hr/kgcat | 1.87 | 2.59 | 2.79 | 2.74 | 2.82 | 2.85 | 2.58 | 2.74 | 2.59 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.183 | 2.188 | 1.770 | 0.548 | 1.020 | 0.597 | 1.940 | 1.065 | 1.184 |
| MEA | 27.641 | 27.702 | 4.345 | 16.309 | 9.520 | 16.119 | 3.529 | 9.960 | 7.884 |
| PIP | 0.359 | 0.359 | 1.724 | 0.781 | 1.295 | 0.831 | 1.768 | 1.334 | 1.404 |
| DETA | 50.123 | 50.233 | 32.473 | 45.537 | 37.563 | 44.839 | 30.507 | 38.688 | 35.307 |
| AEEA | 1.469 | 1.473 | 0.272 | 2.441 | 0.835 | 2.461 | 0.259 | 0.891 | 0.693 |
| AEP | 0.425 | 0.425 | 2.604 | 0.939 | 1.587 | 0.990 | 2.516 | 1.641 | 1.764 |
| HEP | 0.000 | 0.000 | 0.000 | 0.000 | 0.000 | 0.000 | 0.000 | 0.000 | 0.000 |
| TAEA | 0.540 | 0.541 | 1.884 | 1.758 | 2.057 | 1.894 | 1.864 | 1.979 | 2.025 |
| l-TETA | 5.907 | 5.920 | 14.212 | 13.575 | 13.856 | 13.962 | 13.839 | 13.903 | 13.810 |
| DAEP | 0.000 | 0.000 | 1.323 | 0.221 | 0.725 | 0.221 | 1.371 | 0.816 | 0.894 |
| PEEDA | 0.077 | 0.077 | 1.066 | 0.195 | 0.561 | 0.189 | 1.056 | 0.588 | 0.667 |
| DPE | 0.000 | 0.000 | 0.212 | 0.073 | 0.453 | 0.073 | 0.204 | 0.194 | 0.226 |
| AE-TAEA | 0.243 | 0.243 | 3.128 | 1.661 | 2.763 | 1.921 | 3.001 | 2.711 | 2.954 |
| 1-TEPA | 0.585 | 0.586 | 9.266 | 4.428 | 7.937 | 4.979 | 9.181 | 7.693 | 8.505 |
| AE-DAEP | 0.000 | 0.000 | 1.117 | 0.186 | 0.635 | 0.255 | 1.174 | 0.589 | 0.748 |
| AE-PEEDA | 0.151 | 0.152 | 0.266 | 0.147 | 0.165 | 0.151 | 0.247 | 0.180 | 0.234 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.400 | 0.000 | 0.339 | 0.241 | 0.370 | 0.292 | 0.377 |
| BPEA | 0.000 | 0.000 | 0.692 | 0.194 | 0.581 | 0.058 | 0.692 | 0.473 | 0.620 |
| Others | 1.677 | 1.680 | 14.327 | 2.888 | 11.047 | 4.339 | 13.830 | 8.942 | 12.375 |
| MEA conversion, % | 20.18 | 20.18 | 88.44 | 54.92 | 74.73 | 56.63 | 90.23 | 73.20 | 78.90 |
| DETA conversion, % | 13.97 | 13.97 | 48.67 | 25.19 | 40.75 | 28.30 | 49.82 | 38.12 | 43.84 |
| Acyclic(N4), % | 98.82 | 98.82 | 86.09 | 96.91 | 90.15 | 97.10 | 85.65 | 90.86 | 89.86 |
| Acyclic(N5), % | 84.54 | 84.54 | 83.35 | 92.03 | 86.19 | 90.74 | 83.07 | 87.15 | 85.28 |
| Σ(N5)/Σ(N4), weight ratio | 0.15 | 0.15 | 0.80 | 0.42 | 0.70 | 0.47 | 0.80 | 0.68 | 0.76 |
| Acyclic(N4)/cyclic (<=N4), weight ratio | 7.50 | 7.50 | 2.32 | 6.94 | 3.44 | 6.91 | 2.27 | 3.47 | 3.20 |

TABLE XCIII

| Example No. | 893 | 894 | 895 | 896 | 897 | 898 | 899 | 900 | 901 |
|---|---|---|---|---|---|---|---|---|---|
| Catalyst Type | WWWW | WWWW | WWWW | WWWW | WWWW | WWWW | WWWW | WWWW | WWWW |
| Catalyst weight, gm | 79.6 | 79.6 | 79.6 | 79.6 | 79.6 | 79.6 | 79.6 | 79.6 | 79.6 |
| Pressure, psig | 600 | 600 | 600 | 600 | 600 | 600 | 600 | 600 | 600 |
| Temperature, °C. | 268.6 | 268.9 | 278.6 | 259.1 | 268.3 | 258.2 | 278.9 | 269 | 269.6 |
| Time on organics, hrs. | 3 | 22 | 27 | 51 | 69.5 | 74 | 93 | 99 | 116.5 |
| Duration of run, hrs. | 2 | 2 | 2 | 2 | 2 | 2 | 2 | 2 | 2 |
| MEA SV, gmol/hr/kgcat | 3.34 | 2.66 | 2.48 | 3.46 | 3.32 | 3.85 | 2.73 | 2.84 | 2.42 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.402 | 0.984 | 1.667 | 0.394 | 0.739 | 0.489 | 1.751 | 1.291 | 1.139 |
| MEA | 15.275 | 9.355 | 3.835 | 17.982 | 9.833 | 17.982 | 3.544 | 9.828 | 6.948 |
| PIP | 1.023 | 1.416 | 1.735 | 0.823 | 1.192 | 0.874 | 1.765 | 1.556 | 1.504 |
| DETA | 46.636 | 38.050 | 30.559 | 46.962 | 37.022 | 46.771 | 30.103 | 39.458 | 33.830 |
| AEEA | 0.563 | 0.635 | 0.229 | 2.288 | 0.818 | 2.437 | 0.237 | 0.909 | 0.647 |

TABLE XCIII-continued

| Example No. | 893 | 894 | 895 | 896 | 897 | 898 | 899 | 900 | 901 |
|---|---|---|---|---|---|---|---|---|---|
| AEP | 1.146 | 1.654 | 2.572 | 0.964 | 1.493 | 0.918 | 2.432 | 1.661 | 1.837 |
| HEP | 0.000 | 0.000 | 0.000 | 0.000 | 0.000 | 0.000 | 0.000 | 0.000 | 0.000 |
| TAEA | 1.055 | 1.701 | 1.742 | 1.714 | 1.968 | 1.798 | 1.727 | 1.992 | 1.965 |
| l-TETA | 14.353 | 14.398 | 14.401 | 12.742 | 14.026 | 12.801 | 13.949 | 14.704 | 14.368 |
| DAEP | 0.249 | 0.654 | 1.412 | 0.204 | 0.702 | 0.176 | 1.305 | 0.678 | 0.917 |
| PEEDA | 0.325 | 0.561 | 0.102 | 0.191 | 0.551 | 0.167 | 1.053 | 0.549 | 0.702 |
| DPE | 0.121 | 0.297 | 0.229 | 0.068 | 0.281 | 0.065 | 0.214 | 0.195 | 0.339 |
| AE-TAEA | 1.394 | 2.685 | 2.896 | 1.785 | 2.857 | 2.350 | 2.894 | 2.684 | 2.950 |
| l-TEPA | 5.057 | 7.739 | 9.422 | 4.753 | 8.218 | 4.811 | 9.500 | 7.913 | 9.201 |
| AE-DAEP | 0.509 | 0.622 | 1.153 | 0.165 | 0.574 | 0.183 | 1.120 | 0.446 | 0.733 |
| AE-PEEDA | 0.114 | 0.112 | 0.260 | 0.085 | 0.186 | 0.082 | 0.318 | 0.112 | 0.220 |
| iAE-PEEDA | 0.000 | 0.000 | 0.000 | 0.000 | 0.000 | 0.000 | 0.000 | 0.000 | 0.000 |
| AE-DPE | 0.157 | 0.184 | 0.396 | 0.088 | 0.450 | 0.068 | 0.417 | 0.000 | 0.374 |
| BPEA | 0.332 | 0.572 | 0.676 | 0.225 | 0.581 | 0.214 | 0.673 | 0.443 | 0.631 |
| Others | 4.749 | 7.940 | 13.943 | 2.415 | 10.748 | 2.214 | 13.837 | 6.329 | 12.335 |
| MEA conversion, % | 58.32 | 74.19 | 89.50 | 51.84 | 73.69 | 51.51 | 90.14 | 73.15 | 81.27 |
| DETA conversion, % | 26.00 | 37.61 | 50.21 | 24.08 | 41.13 | 25.04 | 50.22 | 35.93 | 45.79 |
| Acyclic(N4), % | 95.68 | 91.41 | 85.48 | 96.90 | 91.24 | 97.28 | 85.90 | 92.15 | 89.29 |
| Acyclic(N5), % | 85.30 | 87.49 | 83.21 | 92.07 | 86.08 | 92.90 | 83.07 | 91.37 | 86.12 |
| Σ(N5)/Σ(N4), weight ratio | 0.47 | 0.68 | 0.78 | 0.48 | 0.73 | 0.51 | 0.82 | 0.64 | 0.77 |
| Acyclic(N4)/cyclic (<=N4), weight ratio | 5.38 | 3.51 | 2.29 | 6.43 | 3.79 | 6.63 | 2.32 | 3.60 | 3.08 |

TABLE XCIV

| Example No. | 902 | 903 | 904 | 905 | 906 | 907 | 908 | 909 | 910 | 911 |
|---|---|---|---|---|---|---|---|---|---|---|
| Catalyst Type | XXXX | XXXX | XXXX | XXXX | XXXX | XXXX | XXXX | XXXX | XXXX | XXXX |
| Catalyst weight, gm | 87.7 | 87.7 | 87.7 | 87.7 | 87.7 | 87.7 | 87.7 | 87.7 | 87.7 | 87.7 |
| Pressure, psig | 603 | 596 | 606 | 600 | 600 | 600 | 607 | 600 | 590 | 600 |
| Temperature, °C. | 269 | 279 | 260 | 270 | 270 | 259.6 | 279 | 270 | 280 | 270 |
| Time on organics, hrs. | 21 | 28 | 49 | 54 | 73.5 | 97.5 | 116 | 121 | 139 | 144 |
| Duration of run, hrs. | 2 | 2 | 2 | 2 | 2 | 2 | 2 | 2 | 2 | 2 |
| MEA SV, gmol/hr/kgcat | 0.91 | 0.59 | 2.75 | 1.43 | 2.59 | 2.77 | 2.41 | 2.60 | 2.29 | 2.43 |
| DETA/MEA mole ratio | 1.00 | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 2.350 | 1.919 | 0.622 | 0.752 | 0.640 | 0.391 | 1.122 | 0.738 | 1.310 | 1.032 |
| MEA | 23.993 | 22.805 | 29.044 | 27.951 | 26.940 | 30.561 | 23.577 | 28.244 | 22.626 | 14.670 |
| PIP | 0.625 | 0.683 | 0.215 | 0.276 | 0.295 | 0.203 | 0.700 | 0.146 | 0.834 | 1.073 |
| DETA | 52.709 | 52.718 | 55.792 | 52.407 | 51.421 | 56.953 | 49.965 | 55.022 | 49.613 | 43.078 |
| AEEA | 0.839 | 0.906 | 0.676 | 0.848 | 0.865 | 0.965 | 0.936 | 1.077 | 0.953 | 1.870 |
| AEP | 0.670 | 0.712 | 0.316 | 0.322 | 0.328 | 0.257 | 0.586 | 0.387 | 0.639 | 1.002 |
| HEP | 0.000 | 0.000 | 0.000 | 0.000 | 0.000 | 0.000 | 0.000 | 0.000 | 0.000 | 0.000 |
| TAEA | 1.188 | 1.399 | 0.875 | 0.858 | 0.973 | 0.696 | 1.543 | 1.161 | 1.716 | 2.408 |
| l-TETA | 5.320 | 6.386 | 4.275 | 4.119 | 4.573 | 3.717 | 7.655 | 5.591 | 8.550 | 11.687 |
| DAEP | 0.347 | 0.266 | 0.123 | 0.104 | 0.092 | 0.061 | 0.191 | 0.106 | 0.224 | 0.280 |
| PEEDA | 0.057 | 0.170 | 0.083 | 0.060 | 0.058 | 0.038 | 0.023 | 0.067 | 0.028 | 0.239 |
| DPE | 0.083 | 0.083 | 0.030 | 0.034 | 0.035 | 0.027 | 0.067 | 0.045 | 0.075 | 0.094 |
| AE-TAEA | 0.899 | 0.988 | 0.607 | 0.509 | 0.572 | 0.374 | 0.052 | 0.789 | 1.664 | 3.061 |
| l-TEPA | 1.485 | 1.792 | 1.076 | 0.867 | 0.939 | 0.666 | 2.604 | 1.419 | 3.031 | 5.965 |
| AE-DAEP | 0.280 | 0.202 | 0.116 | 0.085 | 0.000 | 0.035 | 0.142 | 0.084 | 0.162 | 0.312 |
| AE-PEEDA | 0.108 | 0.080 | 0.000 | 0.033 | 0.069 | 0.000 | 0.000 | 0.035 | 0.042 | 0.048 |
| iAE-PEEDA | 0.000 | 0.000 | 0.000 | 0.000 | 0.000 | 0.000 | 0.000 | 0.000 | 0.000 | 0.000 |
| AE-DPE | 0.043 | 0.000 | 0.000 | 0.000 | 0.000 | 0.000 | 0.000 | 0.000 | 0.000 | 0.146 |
| BPEA | 0.107 | 0.106 | 0.059 | 0.022 | 0.081 | 0.000 | 0.175 | 0.080 | 0.210 | 0.374 |
| Others | 2.935 | 3.026 | 0.992 | 0.725 | 0.939 | 0.685 | 3.151 | 0.949 | 2.575 | 3.282 |
| MEA Conversion, % | 33.53 | 37.20 | 19.34 | 18.02 | 20.14 | 15.44 | 33.80 | 22.92 | 37.97 | 59.15 |
| DETA Conversion, % | 13.21 | 13.72 | 7.91 | 8.64 | 9.40 | 6.34 | 16.63 | 10.76 | 19.16 | 28.71 |
| Acyclic(N4), % | 93.03 | 93.76 | 95.63 | 96.18 | 96.79 | 97.22 | 97.03 | 96.87 | 96.92 | 95.83 |
| Acyclic(N5), % | 81.55 | 87.74 | 90.59 | 90.79 | 90.93 | 96.73 | 89.33 | 91.76 | 91.91 | 91.11 |
| Σ(N5)/Σ(N4), weight ratio | 0.42 | 0.38 | 0.34 | 0.29 | 0.29 | 0.24 | 0.31 | 0.35 | 0.48 | 0.67 |
| Acyclic(N4)/cyclic | 3.65 | 4.07 | 6.72 | 6.26 | 6.87 | 7.52 | 5.87 | 6.61 | 5.71 | 5.24 |

TABLE XCV

| Example No. | 912 | 913 | 914 | 915 | 916 | 917 | 918 | 919 | 920 | 921 |
|---|---|---|---|---|---|---|---|---|---|---|
| Catalyst Type | YYYY | YYYY | YYYY | YYYY | YYYY | YYYY | YYYY | YYYY | YYYY | YYYY |
| Catalyst weight, gm | 83.01 | 83.01 | 83.01 | 83.01 | 83.01 | 83.01 | 83.01 | 83.01 | 83.01 | 83.01 |
| Pressure, psig | 603 | 596 | 599 | 599 | 601 | 597 | 603 | 603 | 602 | 603 |
| Temperature, °C. | 271 | 278 | 260 | 271 | 260 | 280 | 270 | 280 | 270 | 270 |
| Time on organics, hrs. | 99 | 104 | 123 | 128 | 147 | 152 | 171 | 176 | 195 | 206.75 |
| MEA SV, gmol/hr/kgcat | 3.13 | 3.33 | 3.26 | 3.20 | 3.18 | 3.07 | 2.34 | 2.47 | 2.21 | 2.35 |
| DETA/MEA mole ratio | 1.00 | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 1.984 | 2.995 | 1.212 | 1.766 | 1.149 | 2.885 | 1.710 | 2.748 | 1.423 | 1.500 |
| MEA | 6.383 | 3.073 | 13.003 | 5.647 | 11.598 | 3.611 | 10.193 | 5.664 | 10.816 | 11.721 |

TABLE XCV-continued

| Example No. | 912 | 913 | 914 | 915 | 916 | 917 | 918 | 919 | 920 | 921 |
|---|---|---|---|---|---|---|---|---|---|---|
| PIP | 1.434 | 1.763 | 1.183 | 1.449 | 1.142 | 1.861 | 1.330 | 1.727 | 1.168 | 1.186 |
| DETA | 32.000 | 30.373 | 38.190 | 32.197 | 37.489 | 30.866 | 31.155 | 29.136 | 31.286 | 32.092 |
| AEEA | 0.501 | 0.186 | 1.296 | 0.439 | 1.265 | 0.220 | 0.847 | 0.403 | 0.987 | 1.078 |
| AEP | 1.636 | 2.525 | 1.050 | 1.785 | 1.133 | 2.307 | 1.524 | 2.483 | 1.278 | 1.244 |
| HEP | 0.000 | 0.000 | 0.000 | 0.000 | 0.000 | 0.000 | 0.000 | 0.000 | 0.000 | 0.000 |
| TAEA | 2.376 | 1.934 | 2.312 | 2.434 | 2.613 | 2.044 | 2.151 | 1.797 | 2.071 | 2.140 |
| 1-TETA | 12.940 | 12.003 | 11.840 | 13.576 | 13.452 | 12.217 | 10.663 | 10.795 | 10.563 | 10.796 |
| DAEP | 0.920 | 1.655 | 0.439 | 1.079 | 0.545 | 1.534 | 0.822 | 1.573 | 0.617 | 0.608 |
| PEEDA | 0.665 | 1.233 | 0.355 | 0.842 | 0.415 | 1.110 | 0.628 | 1.133 | 0.479 | 0.498 |
| DPE | 0.287 | 0.120 | 0.230 | 0.316 | 0.181 | 0.104 | 0.063 | 0.089 | 0.229 | 0.044 |
| AE-TAEA | 4.489 | 3.831 | 3.705 | 4.743 | 4.293 | 4.176 | 3.815 | 3.271 | 3.526 | 3.575 |
| 1-TEPA | 9.472 | 9.488 | 7.999 | 10.201 | 8.828 | 9.980 | 8.349 | 8.770 | 7.873 | 7.613 |
| AE-DAEP | 0.811 | 1.698 | 0.463 | 0.927 | 0.392 | 1.458 | 0.759 | 1.596 | 0.624 | 0.664 |
| AE-PEEDA | 0.148 | 0.223 | 0.123 | 0.165 | 0.067 | 0.216 | 0.150 | 0.128 | 0.081 | 0.078 |
| iAE-PEEDA | 0.000 | 0.000 | 0.000 | 0.000 | 0.000 | 0.000 | 0.000 | 0.000 | 0.000 | 0.000 |
| AE-DPE | 0.151 | 0.482 | 0.201 | 0.162 | 0.057 | 0.283 | 0.193 | 0.229 | 0.390 | 0.325 |
| BPEA | 0.149 | 0.853 | 0.178 | 0.215 | 0.057 | 0.232 | 0.082 | 0.655 | 0.601 | 0.569 |
| Others | 9.595 | 14.536 | 7.200 | 10.480 | 6.385 | 12.915 | 9.485 | 10.732 | 7.587 | 7.371 |
| MEA Conversion, % | 81.81 | 91.66 | 64.27 | 84.42 | 68.27 | 90.05 | 69.91 | 83.37 | 67.11 | 64.89 |
| DETA Conversion, % | 45.79 | 51.02 | 37.63 | 47.22 | 39.06 | 49.48 | 45.34 | 49.17 | 43.45 | 42.86 |
| Acyclic(N4), % | 89.11 | 82.25 | 93.25 | 87.74 | 93.37 | 83.84 | 89.43 | 81.83 | 90.51 | 91.84 |
| Acyclic(N5), % | 91.73 | 80.36 | 92.38 | 91.05 | 95.82 | 86.60 | 91.13 | 82.19 | 87.05 | 87.25 |
| $\Sigma(N5)/\Sigma(N4)$, weight ratio | 0.89 | 0.98 | 0.83 | 0.90 | 0.80 | 0.96 | 0.93 | 0.95 | 0.94 | 0.91 |
| Acyclic(N4)/cyclic ($<=$N4), weight ratio | 3.10 | 1.91 | 4.34 | 2.93 | 4.70 | 2.06 | 2.93 | 1.80 | 3.35 | 3.61 |

TABLE XCVI

| Example No. | 922 | 923 | 924 | 925 | 926 | 927 | 928 | 929 | 930 | 931 | 932 |
|---|---|---|---|---|---|---|---|---|---|---|---|
| Catalyst Type | ZZZZ | ZZZZ | ZZZZ | ZZZZ | ZZZZ | ZZZZ | ZZZZ | ZZZZ | ZZZZ | ZZZZ | ZZZZ |
| Catalyst weight, gm | 84.9 | 84.9 | 84.9 | 84.9 | 82.11 | 84.9 | 84.9 | 84.9 | 84.9 | 84.9 | 84.9 |
| Pressure, psig | 604 | 604 | 604 | 604 | 602 | 604 | 602 | 603 | 600 | 600 | 600 |
| Temperature, °C. | 268 | 279 | 258 | 270 | 259 | 278 | 269 | 278 | 279 | 270 | 270 |
| Time on organics, hrs. | 24.5 | 27.75 | 47 | 52 | 71 | 76 | 95 | 99 | 118.5 | 139.8 | 141.5 |
| Duration of run, hrs. | 2 | 2 | 2 | 2 | 2 | 2 | 2 | 2 | 2 | 1 | 1 |
| MEA SV, gmol/hr/kgcat | 2.66 | 2.74 | 2.85 | 3.15 | 3.30 | 3.27 | 3.01 | 3.14 | 2.91 | 2.26 | 3.32 |
| DETA/MEA mole ratio | 1.00 | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 | 5.97 |
| Crude product composition, wt. % | | | | | | | | | | | |
| EDA | 0.261 | 0.356 | 0.244 | 0.282 | 0.226 | 0.267 | 0.193 | 0.300 | 0.276 | 0.137 | 0.175 |
| MEA | 32.096 | 31.884 | 33.649 | 33.262 | 34.748 | 33.604 | 35.331 | 34.218 | 33.615 | 33.551 | 33.298 |
| PIP | 0.012 | 0.017 | 0.009 | 0.013 | 0.000 | 0.013 | 0.000 | 0.014 | 0.015 | 0.021 | 0.015 |
| DETA | 53.034 | 52.823 | 55.550 | 57.167 | 58.160 | 57.340 | 58.631 | 55.561 | 55.690 | 57.452 | 57.445 |
| AEEA | 0.039 | 0.072 | 0.023 | 0.200 | 0.054 | 0.089 | 0.039 | 0.073 | 0.075 | 0.063 | 0.067 |
| AEP | 0.256 | 0.295 | 0.218 | 0.287 | 0.233 | 0.349 | 0.288 | 0.358 | 0.393 | 0.340 | 0.313 |
| HEP | 0.000 | 0.000 | 0.000 | 0.000 | 0.000 | 0.000 | 0.000 | 0.000 | 0.000 | 0.000 | 0.000 |
| TAEA | 0.091 | 0.098 | 0.112 | 0.187 | 0.094 | 0.150 | 0.077 | 0.475 | 0.111 | 0.137 | 0.171 |
| 1-TETA | 0.144 | 0.122 | 0.087 | 0.577 | 0.076 | 0.434 | 0.092 | 0.000 | 0.343 | 0.416 | 0.498 |
| DAEP | 0.024 | 0.031 | 0.016 | 0.056 | 0.000 | 0.021 | 0.000 | 0.067 | 0.044 | 0.030 | 0.027 |
| PEEDA | 0.194 | 0.074 | 0.183 | 0.037 | 0.211 | 0.152 | 0.077 | 0.082 | 0.052 | 0.036 | 0.034 |
| DPE | 0.069 | 0.085 | 0.053 | 0.027 | 0.094 | 0.065 | 0.061 | 0.044 | 0.047 | 0.082 | 0.055 |
| AE-TAEA | 0.000 | 0.037 | 0.000 | 0.045 | 0.000 | 0.085 | 0.052 | 0.000 | 0.000 | 0.000 | 0.000 |
| 1-TEPA | 0.147 | 0.062 | 0.000 | 0.047 | 0.000 | 0.068 | 0.000 | 0.036 | 0.061 | 0.000 | 0.071 |
| AE-DAEP | 0.000 | 0.000 | 0.000 | 0.000 | 0.024 | 0.060 | 0.027 | 0.091 | 0.114 | 0.028 | 0.000 |
| AE-PEEDA | 0.000 | 0.168 | 0.000 | 0.000 | 0.000 | 0.000 | 0.000 | 0.041 | 0.000 | 0.129 | 0.332 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.000 | 0.039 | 0.000 | 0.053 | 0.035 | 0.162 | 0.044 | 0.031 | 0.092 | 0.099 | 0.097 |
| BPEA | 0.344 | 0.000 | 0.000 | 0.000 | 0.000 | 0.038 | 0.000 | 0.000 | 0.000 | 0.000 | 0.066 |
| Others | 1.659 | 2.389 | 1.815 | 2.931 | 1.866 | 3.482 | 2.698 | 3.109 | 3.712 | 2.859 | 2.756 |
| MEA Conversion, % | 3.06 | 3.91 | 2.16 | 6.89 | 3.11 | 7.25 | 3.34 | 3.38 | 5.38 | 6.32 | 7.15 |
| DETA Conversion, % | 4.80 | 5.39 | 4.00 | 4.90 | 3.62 | 5.94 | 4.67 | 6.76 | 6.84 | 4.67 | 4.80 |
| Acyclic(N4), % | 44.95 | 53.51 | 44.02 | 86.49 | 35.80 | 71.03 | 54.99 | 71.17 | 76.09 | 78.86 | 85.22 |
| Acyclic(N5), % | 30.60 | 32.37 | 0.00 | 63.66 | 0.00 | 37.00 | 42.32 | 18.14 | 22.79 | 0.00 | 12.61 |
| $\Sigma(N5)/\Sigma(N4)$, weight ratio | 0.92 | 0.75 | 0.00 | 0.16 | 0.13 | 0.50 | 0.40 | 0.30 | 0.45 | 0.36 | 0.72 |
| Acyclic(N4)/cyclic ($<=$N4), weight ratio | 0.42 | 0.44 | 0.41 | 1.82 | 0.32 | 0.97 | 0.40 | 0.84 | 0.82 | 1.09 | 1.51 |

TABLE XCVII

| Example No. | 933 | 934 | 935 | 936 | 937 | 938 | 939 | 940 | 941 |
|---|---|---|---|---|---|---|---|---|---|
| Catalyst Type | AAAAA | AAAAA | AAAAA | AAAAA | AAAAA | AAAAA | AAAAA | AAAAA | AAAAA |
| Catalyst weight, gm | 45.68 | 45.68 | 45.68 | 45.68 | 45.68 | 45.68 | 45.68 | 45.68 | 45.68 |
| Pressure, psig | 600 | 599 | 607 | 596 | 600 | 600 | 600 | 600 | 604 |
| Temperature, °C. | 269 | 279 | 260 | 270 | 270 | 259.6 | 279 | 270 | 280 |
| Time on organics, hrs. | 21 | 28 | 49 | 54 | 73.5 | 97.5 | 116 | 121 | 139 |
| Duration of run, hrs. | 2 | 2 | 2 | 2 | 2 | 2 | 2 | 2 | 2 |
| MEA SV, gmol/hr/kgcat | 5.74 | 5.87 | 5.23 | 6.08 | 3.67 | 3.99 | 2.29 | 4.68 | 5.77 |
| DETA/MEA mole ratio | 1.00 | 1.00 | 1.00 | 1.00 | 1.00 | 1.00 | 1.00 | 1.00 | 1.00 |

TABLE XCVII-continued

| Example No. | 933 | 934 | 935 | 936 | 937 | 938 | 939 | 940 | 941 |
|---|---|---|---|---|---|---|---|---|---|
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 4.265 | 6.176 | 3.433 | 3.075 | 3.788 | 3.313 | 4.920 | 3.283 | 4.944 |
| MEA | 5.796 | 3.354 | 10.079 | 7.161 | 8.233 | 12.638 | 5.859 | 8.995 | 7.083 |
| PIP | 2.117 | 2.992 | 1.443 | 1.595 | 1.901 | 1.711 | 3.037 | 1.662 | 2.421 |
| DETA | 28.085 | 21.574 | 33.585 | 28.671 | 28.468 | 35.387 | 22.837 | 31.649 | 26.907 |
| AEEA | 0.099 | 0.063 | 0.399 | 0.132 | 0.103 | 0.381 | 0.025 | 0.197 | 0.067 |
| AEP | 4.039 | 6.092 | 2.608 | 3.219 | 3.601 | 3.484 | 6.074 | 3.491 | 5.328 |
| HEP | 0.000 | 0.000 | 0.000 | 0.000 | 0.000 | 0.000 | 0.000 | 0.000 | 0.000 |
| TAEA | 3.229 | 1.766 | 3.587 | 3.434 | 2.819 | 2.812 | 1.936 | 3.537 | 2.241 |
| 1-TETA | 11.677 | 6.932 | 11.244 | 11.553 | 10.261 | 9.480 | 6.501 | 11.947 | 9.241 |
| DAEP | 2.387 | 3.807 | 1.767 | 1.907 | 1.991 | 1.653 | 4.685 | 2.133 | 3.545 |
| PEEDA | 1.116 | 1.889 | 0.855 | 0.890 | 0.958 | 0.844 | 2.020 | 0.989 | 1.785 |
| DPE | 0.174 | 0.405 | 0.101 | 0.132 | 0.139 | 0.113 | 0.580 | 0.315 | 0.262 |
| AE-TAEA | 5.681 | 3.174 | 5.080 | 5.634 | 4.681 | 3.953 | 2.940 | 5.597 | 3.677 |
| 1-TEPA | 8.664 | 6.535 | 6.720 | 7.856 | 6.920 | 5.613 | 3.566 | 7.833 | 6.809 |
| AE-DAEP | 0.935 | 0.738 | 0.803 | 0.708 | 0.722 | 0.579 | 0.757 | 0.823 | 1.937 |
| AE-PEEDA | 0.258 | 1.129 | 0.214 | 0.198 | 0.223 | 0.219 | 0.904 | 0.272 | 0.737 |
| iAE-PEEDA | 0.000 | 0.000 | 0.000 | 0.000 | 0.000 | 0.000 | 0.000 | 0.000 | 0.000 |
| AE-DPE | 0.055 | 0.256 | 0.050 | 0.037 | 0.048 | 0.047 | 0.237 | 0.050 | 0.057 |
| BPEA | 0.975 | 0.822 | 0.665 | 0.847 | 0.688 | 0.813 | 0.350 | 0.801 | 0.858 |
| Others | 8.808 | 15.412 | 6.548 | 7.053 | 6.595 | 5.262 | 19.371 | 7.036 | 12.602 |
| MEA Conversion, % | 84.08 | 90.34 | 72.07 | 79.20 | 75.41 | 64.40 | 83.73 | 75.68 | 81.06 |
| DETA Conversion, % | 54.16 | 63.06 | 44.68 | 50.52 | 49.47 | 40.75 | 62.31 | 49.14 | 57.23 |
| Acyclic(N4), % | 80.21 | 58.78 | 84.49 | 83.65 | 80.90 | 82.49 | 53.67 | 81.83 | 67.25 |
| Acyclic(N5), % | 86.58 | 76.69 | 87.20 | 88.29 | 87.35 | 85.23 | 74.32 | 87.34 | 74.50 |
| Σ(N5)/Σ(N4), weight ratio | 0.89 | 0.86 | 0.77 | 0.85 | 0.82 | 0.75 | 0.56 | 0.81 | 0.82 |
| Acyclic(N4)/cyclic (<=N4), weight ratio | 1.52 | 0.57 | 2.19 | 1.94 | 1.52 | 1.58 | 0.51 | 1.80 | 0.86 |

TABLE XCVIII

| Example No. | 942 | 943 | 944 | 945 | 946 | 947 | 948 | 949 | 950 |
|---|---|---|---|---|---|---|---|---|---|
| Catalyst Type | BBBBB | BBBBB | BBBBB | BBBBB | BBBBB | BBBBB | BBBBB | BBBBB | BBBBB |
| Catalyst weight, gm | 71.9 | 71.9 | 71.9 | 71.9 | 71.9 | 71.9 | 71.9 | 71.9 | 71.9 |
| Pressure, psig | 604 | 604 | 609 | 606 | 600 | 600 | 603 | 602 | 602 |
| Temperature, °C. | 270 | 282 | 258 | 272 | 260 | 280 | 273 | 281 | 272 |
| Time on organics, hrs. | 20.5 | 25.5 | 44.5 | 49.5 | 69.3 | 93.3 | 116.5 | 121.5 | 138.5 |
| Duration of run, hrs. | 2 | 2 | 2 | 2 | 2 | 2 | 2 | 2 | 2 |
| MEA SV, gmol/hr/kgcat | 3.36 | 3.46 | 3.43 | 3.50 | 3.55 | 3.41 | 3.50 | 3.67 | 3.49 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.654 | 1.188 | 0.880 | 0.700 | 0.372 | 1.659 | 0.860 | 1.397 | 0.841 |
| MEA | 26.367 | 22.170 | 24.384 | 27.194 | 29.909 | 21.016 | 27.518 | 23.168 | 26.560 |
| PIP | 0.812 | 1.365 | 0.882 | 0.772 | 0.000 | 1.711 | 0.812 | 1.473 | 0.833 |
| DETA | 51.269 | 45.690 | 48.835 | 51.840 | 55.476 | 43.224 | 51.818 | 46.089 | 52.002 |
| AEEA | 2.016 | 1.702 | 1.570 | 1.900 | 1.779 | 1.481 | 1.827 | 1.619 | 1.976 |
| AEP | 0.692 | 1.168 | 0.882 | 0.598 | 0.374 | 1.439 | 0.624 | 1.193 | 0.678 |
| HEP | 0.000 | 0.000 | 0.000 | 0.000 | 0.000 | 0.000 | 0.000 | 0.000 | 0.000 |
| TAEA | 1.323 | 1.418 | 1.256 | 1.217 | 0.943 | 1.295 | 1.188 | 1.308 | 1.216 |
| 1-TETA | 7.359 | 8.836 | 7.770 | 6.793 | 5.048 | 8.777 | 6.824 | 8.418 | 7.095 |
| DAEP | 0.163 | 0.347 | 0.300 | 0.112 | 0.071 | 0.485 | 0.130 | 0.370 | 0.143 |
| PEEDA | 0.160 | 0.417 | 0.373 | 0.120 | 0.076 | 0.528 | 0.145 | 0.432 | 0.153 |
| DPE | 0.046 | 0.069 | 0.061 | 0.042 | 0.025 | 0.114 | 0.046 | 0.034 | 0.050 |
| AE-TAEA | 1.015 | 1.431 | 1.257 | 0.863 | 0.494 | 1.551 | 0.865 | 1.450 | 0.923 |
| 1-TEPA | 2.990 | 4.899 | 4.463 | 2.563 | 1.436 | 5.428 | 2.725 | 4.968 | 2.853 |
| AE-DAEP | 0.242 | 0.305 | 0.326 | 0.045 | 0.074 | 0.345 | 0.060 | 0.264 | 0.065 |
| AE-PEEDA | 0.106 | 0.077 | 0.079 | 0.000 | 0.000 | 0.094 | 0.062 | 0.187 | 0.038 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.000 | 0.000 | 0.000 |
| BPEA | 0.031 | 0.052 | 0.046 | 0.123 | 0.080 | 0.273 | 0.127 | 0.070 | 0.049 |
| Others | 1.656 | 3.848 | 3.595 | 1.579 | 0.943 | 4.584 | 1.700 | 3.838 | 1.946 |
| MEA Conversion, % | 29.19 | 48.08 | 35.05 | 26.39 | 18.82 | 42.93 | 26.19 | 38.13 | 28.97 |
| DETA Conversion, % | 18.17 | 26.61 | 22.69 | 16.60 | 10.51 | 30.24 | 17.39 | 26.86 | 17.35 |
| Acyclic(N4), % | 95.92 | 92.50 | 92.49 | 96.69 | 97.20 | 89.50 | 96.15 | 92.08 | 96.01 |
| Acyclic(N5), % | 91.34 | 93.59 | 92.70 | 95.32 | 92.60 | 90.73 | 93.52 | 92.49 | 96.12 |
| Σ(N5)/Σ(N4), weight ratio | 0.48 | 0.61 | 0.63 | 0.43 | 0.34 | 0.68 | 0.46 | 0.66 | 0.45 |
| Acyclic(N4)/cyclic (<=N4), weight ratio | 4.64 | 3.05 | 3.61 | 4.87 | 10.96 | 2.33 | 4.56 | 2.78 | 4.48 |

TABLE XCIX

| Example No. | 951 | 952 | 953 | 954 | 955 | 956 | 957 | 958 | 959 |
|---|---|---|---|---|---|---|---|---|---|
| Catalyst Type | CCCCC | CCCCC | CCCCC | CCCCC | CCCCC | CCCCC | CCCCC | CCCCC | CCCCC |
| Catalyst weight, gm | 47.15 | 47.15 | 47.15 | 47.15 | 47.15 | 47.15 | 47.15 | 47.15 | 47.15 |
| Pressure, psig | 603 | 604 | 597 | 593 | 600 | 609 | 600 | 601 | 601 |

TABLE XCIX-continued

| Temperature, °C. | 270 | 281 | 258 | 272 | 280 | 273 | 281 | 272 | 272 |
|---|---|---|---|---|---|---|---|---|---|
| Time on organics, hrs. | 20.5 | 25.5 | 44.5 | 49.5 | 93.3 | 116.5 | 121.5 | 138.5 | 143.25 |
| Duration of run, hrs. | 2 | 2 | 2 | 2 | 1 | 2 | 2 | 2 | 2 |
| MEA SV, gmol/hr/kgcat | 5.62 | 5.50 | 6.38 | 5.77 | 5.23 | 4.89 | 6.12 | 5.90 | 6.45 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 4.112 | 6.049 | 3.022 | 3.411 | 5.550 | 3.212 | 4.820 | 3.441 | 2.793 |
| MEA | 3.993 | 1.805 | 8.392 | 5.992 | 2.263 | 7.178 | 3.892 | 6.533 | 8.131 |
| PIP | 2.090 | 2.764 | 1.493 | 1.835 | 2.928 | 1.697 | 2.331 | 1.856 | 1.521 |
| DETA | 26.200 | 19.797 | 30.716 | 29.072 | 19.595 | 30.928 | 25.883 | 27.399 | 32.697 |
| AEEA | 0.105 | 0.029 | 0.466 | 0.193 | 0.059 | 0.257 | 0.082 | 0.253 | 0.337 |
| AEP | 3.816 | 5.459 | 2.748 | 3.098 | 5.455 | 2.783 | 4.440 | 3.792 | 2.683 |
| HEP | 0.000 | 0.000 | 0.000 | 0.000 | 0.000 | 0.000 | 0.000 | 0.000 | 0.000 |
| TAEA | 3.246 | 1.816 | 3.371 | 3.690 | 1.636 | 3.637 | 1.211 | 3.154 | 3.657 |
| 1-TETA | 12.248 | 7.991 | 11.446 | 12.890 | 7.985 | 12.535 | 9.944 | 11.428 | 12.152 |
| DAEP | 2.327 | 3.836 | 1.908 | 1.821 | 3.625 | 1.607 | 2.852 | 2.506 | 1.457 |
| PEEDA | 1.147 | 2.001 | 1.029 | 0.933 | 1.998 | 0.854 | 1.534 | 1.473 | 0.870 |
| DPE | 0.205 | 0.259 | 0.072 | 0.159 | 0.343 | 0.212 | 0.287 | 0.292 | 0.199 |
| AE-TAEA | 5.841 | 3.653 | 5.224 | 6.189 | 3.051 | 6.144 | 4.652 | 4.999 | 5.566 |
| 1-TEPA | 9.617 | 6.279 | 8.218 | 9.146 | 4.846 | 8.976 | 8.411 | 7.886 | 8.254 |
| AE-DAEP | 1.138 | 2.226 | 1.270 | 0.744 | 0.976 | 0.196 | 0.637 | 0.703 | 0.282 |
| AE-PEEDA | 0.133 | 0.798 | 0.566 | 0.032 | 1.236 | 0.237 | 0.789 | 0.817 | 0.091 |
| iAE-PEEDA | 0.000 | 0.000 | 0.000 | 0.000 | 0.000 | 0.000 | 0.000 | 0.000 | 0.000 |
| AE-DPE | 0.198 | 0.335 | 0.262 | 0.062 | 0.124 | 0.064 | 0.176 | 0.106 | 0.138 |
| BPEA | 0.494 | 1.127 | 0.826 | 0.441 | 0.203 | 1.316 | 1.347 | 1.252 | 1.167 |
| Others | 13.100 | 17.605 | 11.271 | 10.063 | 19.810 | 9.418 | 16.332 | 12.551 | 9.604 |
| MEA Conversion, % | 89.29 | 94.88 | 77.77 | 83.74 | 93.38 | 80.79 | 89.55 | 82.50 | 78.25 |
| DETA Conversion, % | 58.24 | 66.61 | 51.64 | 53.13 | 65.93 | 50.81 | 58.69 | 56.38 | 48.01 |
| Acyclic(N4), % | 80.81 | 61.67 | 83.12 | 85.06 | 61.73 | 85.82 | 70.48 | 77.35 | 86.22 |
| Acyclic(N5), % | 88.73 | 68.89 | 82.14 | 92.30 | 75.68 | 89.29 | 81.59 | 81.74 | 89.16 |
| Σ(N5)/Σ(N4), weight ratio | 0.91 | 0.91 | 0.92 | 0.85 | 0.67 | 0.90 | 1.01 | 0.84 | 0.85 |
| Acyclic(N4)/cyclic (<=N4), weight ratio | 1.62 | 0.68 | 2.04 | 2.11 | 0.67 | 2.26 | 0.97 | 1.47 | 2.35 |

| Example No. | 960 | 961 | 962 | 963 | 964 | 965 | 966 | 967 | 968 |
|---|---|---|---|---|---|---|---|---|---|
| Catalyst Type | CCCCC | CCCCC | CCCCC | CCCCC | CCCCC | CCCCC | CCCCC | CCCCC | CCCCC |
| Catalyst weight, gm | 47.15 | 47.15 | 47.15 | 47.15 | 47.15 | 47.15 | 47.15 | 47.15 | 47.15 |
| Pressure, psig | 603 | 602 | 601 | 602 | 596 | 599 | 600 | 600 | 600 |
| Temperature, °C. | 270 | 280 | 260 | 269 | 259 | 269 | 269 | 279.6 | 268 |
| Time on organics, hrs. | 22.5 | 27.5 | 46.5 | 51.5 | 70.5 | 99.5 | 120 | 143 | 169.5 |
| Duration of run, hrs. | 2 | 2 | 2 | 2 | 2 | 2 | 2 | 2 | 2 |
| MEA SV, gmol/hr/kgcat | 4.97 | 4.30 | 3.85 | 2.94 | 0.75 | 5.31 | 5.03 | 4.80 | 3.32 |
| DETA/MEA mole ratio | 1.00 | 1.00 | 1.00 | 1.00 | 1.00 | 1.00 | 1.00 | 1.00 | 1.00 |
| $NH_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 2.967 | 4.366 | 4.440 | 2.967 | 4.460 | 1.952 | 3.142 | 4.055 | 2.453 |
| MEA | 9.344 | 4.942 | 4.115 | 7.299 | 4.769 | 11.879 | 10.054 | 6.454 | 12.691 |
| PIP | 1.511 | 2.037 | 2.043 | 1.452 | 2.132 | 1.272 | 1.700 | 2.182 | 1.366 |
| DETA | 31.637 | 26.975 | 25.016 | 30.734 | 25.564 | 38.106 | 32.444 | 26.800 | 38.319 |
| AEEA | 0.424 | 0.162 | 0.130 | 0.465 | 0.229 | 0.767 | 0.506 | 0.183 | 0.649 |
| AEP | 2.464 | 3.612 | 3.730 | 2.436 | 3.835 | 1.957 | 3.105 | 4.023 | 2.028 |
| HEP | 0.000 | 0.000 | 0.000 | 0.000 | 0.000 | 0.000 | 0.000 | 0.000 | 0.000 |
| TAEA | 3.232 | 3.170 | 3.039 | 4.030 | 3.514 | 3.588 | 2.814 | 2.467 | 3.544 |
| 1-TETA | 11.069 | 12.11 | 12.039 | 13.420 | 13.075 | 11.521 | 10.058 | 9.825 | 12.044 |
| DAEP | 1.231 | 2.138 | 2.332 | 1.243 | 2.045 | 0.861 | 1.515 | 2.269 | 0.889 |
| PEEDA | 0.679 | 1.195 | 1.326 | 0.704 | 1.131 | 0.508 | 0.922 | 1.458 | 0.524 |
| DPE | 0.187 | 0.300 | 0.338 | 0.255 | 0.476 | 0.141 | 0.254 | 0.309 | 0.124 |
| AE-TAEA | 5.103 | 5.422 | 5.331 | 6.126 | 5.933 | 4.797 | 4.017 | 4.146 | 4.610 |
| 1-TEPA | 7.681 | 9.105 | 9.262 | 8.935 | 9.548 | 6.845 | 6.630 | 7.426 | 6.884 |
| AE-DAEP | 0.028 | 0.438 | 0.477 | 0.260 | 0.377 | 0.367 | 0.846 | 1.348 | 0.370 |
| AE-PEEDA | 0.645 | 0.119 | 0.143 | 0.119 | 0.141 | 0.096 | 0.119 | 0.616 | 0.106 |
| iAE-PEEDA | 0.000 | 0.000 | 0.000 | 0.000 | 0.000 | 0.000 | 0.000 | 0.000 | 0.000 |
| AE-DPE | 0.437 | 0.190 | 0.276 | 0.126 | 0.050 | 0.048 | 0.028 | 0.092 | 0.029 |
| BPEA | 0.997 | 0.316 | 0.321 | 0.381 | 0.328 | 0.593 | 0.605 | 0.273 | 0.533 |
| Others | 6.554 | 13.105 | 14.254 | 9.326 | 11.795 | 5.441 | 9.162 | 13.636 | 4.287 |
| MEA Conversion, % | 73.30 | 86.63 | 88.77 | 80.18 | 87.07 | 67.40 | 71.78 | 82.09 | 65.35 |
| DETA Conversion, % | 46.27 | 56.62 | 59.43 | 50.41 | 58.82 | 37.84 | 45.87 | 55.81 | 37.82 |
| Acyclic(N4), % | 87.21 | 80.80 | 79.05 | 88.79 | 81.96 | 90.91 | 82.71 | 75.29 | 91.03 |
| Acyclic(N5), % | 85.85 | 93.18 | 92.31 | 94.44 | 94.53 | 91.34 | 86.95 | 83.25 | 91.71 |
| Σ(N5)/Σ(N4), weight ratio | 0.91 | 0.82 | 0.83 | 0.81 | 0.81 | 0.77 | 0.79 | 0.85 | 0.73 |
| Acyclic(N4)/cyclic (<=N4), weight ratio | 2.36 | 1.65 | 1.54 | 2.87 | 1.72 | 3.19 | 1.72 | 1.20 | 3.16 |

TABLE C

| Example No. | 969 | 970 | 971 | 972 | 973 |
|---|---|---|---|---|---|
| Catalyst Type | DDDDD | DDDDD | DDDDD | DDDDD | DDDDD |
| Catalyst weight, gm | 76.68 | 76.68 | 76.68 | 76.68 | 76.68 |
| Pressure, psig | 603 | 603 | 604 | 604 | 604 |

TABLE C-continued

| | | | | | |
|---|---|---|---|---|---|
| Temperature, °C. | 270 | 260 | 269 | 259 | 280 |
| Time on organics, hrs. | 22.5 | 46.5 | 51.5 | 70.5 | 75.5 |
| Duration of run, hrs. | 2 | 2 | 2 | 2 | 2 |
| MEA SV, gmol/hr/kgcat | 3.56 | 3.18 | 3.05 | 2.39 | 2.57 |
| DETA/MEA mole ratio | 1.00 | 1.00 | 1.00 | 1.00 | 1.00 |
| NH$_3$/MEA mole ratio | 5.97 | 5.97 | 5.97 | 5.97 | 5.97 |
| Crude product composition, wt. % | | | | | |
| EDA | 1.048 | 1.891 | 1.635 | 0.886 | 2.023 |
| MEA | 15.586 | 7.180 | 13.602 | 16.846 | 6.993 |
| PIP | 0.813 | 1.493 | 1.323 | 0.749 | 1.617 |
| DETA | 41.901 | 34.342 | 39.594 | 43.641 | 34.966 |
| AEEA | 1.865 | 0.611 | 1.010 | 2.381 | 0.717 |
| AEP | 0.823 | 1.517 | 1.156 | 0.704 | 1.562 |
| HEP | 0.000 | 0.000 | 0.000 | 0.000 | 0.000 |
| TAEA | 2.659 | 2.739 | 2.487 | 2.206 | 2.576 |
| 1-TETA | 11.989 | 13.676 | 12.245 | 10.267 | 13.010 |
| DAEP | 0.232 | 0.654 | 0.419 | 0.182 | 0.622 |
| PEEDA | 0.217 | 0.518 | 0.333 | 0.166 | 0.508 |
| DPE | 0.109 | 0.083 | 0.058 | 0.039 | 0.100 |
| AE-TAEA | 3.022 | 4.382 | 3.620 | 1.989 | 4.314 |
| 1-TEPA | 5.378 | 8.807 | 6.947 | 3.856 | 8.743 |
| AE-DAEP | 0.000 | 0.169 | 0.298 | 0.077 | 0.555 |
| AE-PEEDA | 0.213 | 0.106 | 0.056 | 0.030 | 0.119 |
| iAE-PEEDA | 0.000 | 0.000 | 0.000 | 0.000 | 0.000 |
| AE-DPE | 0.429 | 0.057 | 0.000 | 0.000 | 0.079 |
| BPEA | 0.423 | 0.255 | 0.529 | 0.212 | 0.715 |
| Others | 2.432 | 7.971 | 4.837 | 2.430 | 8.651 |
| MEA Conversion, % | 55.76 | 79.54 | 62.13 | 50.35 | 80.43 |
| DETA Conversion, % | 29.31 | 41.82 | 34.48 | 23.55 | 41.85 |
| Acyclic(N4), % | 96.35 | 92.90 | 94.78 | 96.99 | 92.69 |
| Acyclic(N5), % | 88.75 | 95.74 | 92.28 | 94.82 | 89.89 |
| Σ(N5)/Σ(N4), weight ratio | 0.62 | 0.78 | 0.74 | 0.48 | 0.86 |
| Acyclic(N4)/cyclic (<=N4), weight ratio | 6.67 | 3.85 | 4.48 | 6.78 | 3.54 |

| Example No. | 974 | 975 | 976 | 977 | 978 |
|---|---|---|---|---|---|
| Catalyst Type | DDDDD | DDDDD | DDDDD | DDDDD | DDDDD |
| Catalyst weight, gm | 76.68 | 76.68 | 76.68 | 76.68 | 76.68 |
| Pressure, psig | 604 | 602 | 600 | 600 | 603 |
| Temperature, °C. | 280 | 269 | 269 | 279.6 | 268 |
| Time on organics, hrs. | 94.5 | 99.5 | 120 | 143 | 169.5 |
| Duration of run, hrs. | 2 | 2 | 2 | 2 | 2 |
| MEA SV, gmol/hr/kgcat | 2.86 | 3.10 | 2.58 | 2.14 | 2.10 |
| DETA/MEA mole ratio | 1.00 | 1.00 | 1.00 | 1.00 | 1.00 |
| NH$_3$/MEA mole ratio | 5.97 | 5.97 | 5.97 | 5.97 | 5.97 |
| Crude product composition, wt. % | | | | | |
| EDA | 1.862 | 0.964 | 1.307 | 2.134 | 1.598 |
| MEA | 5.180 | 14.419 | 11.949 | 4.391 | 10.047 |
| PIP | 1.560 | 1.056 | 1.181 | 1.690 | 1.287 |
| DETA | 31.278 | 43.144 | 40.674 | 33.084 | 40.233 |
| AEEA | 0.512 | 2.061 | 1.865 | 0.489 | 1.972 |
| AEP | 1.651 | 0.963 | 1.108 | 1.845 | 1.344 |
| HEP | 0.000 | 0.000 | 0.000 | 0.000 | 0.000 |
| TAEA | 2.486 | 2.470 | 2.584 | 2.664 | 2.778 |
| 1-TETA | 12.812 | 11.950 | 12.589 | 14.102 | 14.021 |
| DAEP | 0.734 | 0.275 | 0.343 | 0.814 | 0.472 |
| PEEDA | 0.588 | 0.265 | 0.328 | 0.634 | 0.384 |
| DPE | 0.095 | 0.052 | 0.061 | 0.132 | 0.148 |
| AE-TAEA | 4.182 | 3.097 | 3.397 | 4.800 | 3.528 |
| 1-TEPA | 8.887 | 6.071 | 6.875 | 10.097 | 7.285 |
| AE-DAEP | 0.161 | 0.332 | 0.223 | 0.191 | 0.386 |
| AE-PEEDA | 0.104 | 0.049 | 0.039 | 0.121 | 0.860 |
| iAE-PEEDA | 0.000 | 0.000 | 0.000 | 0.000 | 0.000 |
| AE-DPE | 0.078 | 0.045 | 0.000 | 0.109 | 0.086 |
| BPEA | 0.986 | 0.407 | 0.447 | 1.153 | 0.657 |
| Others | 8.353 | 4.000 | 4.471 | 9.150 | 4.134 |
| MEA Conversion, % | 84.46 | 60.32 | 66.53 | 87.79 | 72.35 |
| DETA Conversion, % | 44.25 | 29.45 | 32.30 | 45.34 | 34.20 |
| Acyclic(N4), % | 91.52 | 96.06 | 95.40 | 91.39 | 94.36 |
| Acyclic(N5), % | 90.77 | 91.66 | 93.55 | 90.44 | 90.10 |
| Σ(N5)/Σ(N4), weight ratio | 0.86 | 0.67 | 0.69 | 0.90 | 0.67 |
| Acyclic(N4)/cyclic (<=N4), weight ratio | 3.31 | 5.53 | 5.02 | 3.28 | 4.62 |

TABLE CI

| Example No. | 979 | 980 | 981 | 982 | 983 | 984 | 985 | 986 | 987 | 988 |
|---|---|---|---|---|---|---|---|---|---|---|
| Catalyst Type | EEEEE | EEEEE | EEEEE | EEEEE | EEEEE | EEEEE | EEEEE | EEEEE | EEEEE | EEEEE |
| Catalyst weight, gm | 78.75 | 78.75 | 78.75 | 78.75 | 78.75 | 78.75 | 78.75 | 78.75 | 78.75 | 78.75 |
| Pressure, psig | 598 | 598 | 599 | 598 | 600 | 600 | 598 | 600 | 598 | 600 |

TABLE CI-continued

| Example No. | 979 | 980 | 981 | 982 | 983 | 984 | 985 | 986 | 987 | 988 |
|---|---|---|---|---|---|---|---|---|---|---|
| Temperature, °C. | 269 | 279 | 260 | 270 | 270 | 259.6 | 279 | 270 | 280 | 270 |
| Time on organics, hrs. | 21 | 28 | 49 | 54 | 73.5 | 97.5 | 116 | 121 | 139 | 144 |
| Duration of run, hrs. | 2 | 2 | 2 | 2 | 2 | 2 | 2 | 2 | 2 | 2 |
| MEA SV, gmol/hr/kgcat | 2.92 | 2.87 | 3.06 | 2.85 | 2.60 | 2.98 | 2.80 | 2.99 | 2.81 | 2.96 |
| DETA/MEA mole ratio | 1.00 | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 1.555 | 1.668 | 1.004 | 0.978 | 0.998 | 0.533 | 2.192 | 1.116 | 1.691 | 0.974 |
| MEA | 15.132 | 10.654 | 18.325 | 16.432 | 15.110 | 22.024 | 8.483 | 16.234 | 7.965 | 14.943 |
| PIP | 0.978 | 1.343 | 0.749 | 0.856 | 0.926 | 0.581 | 1.662 | 1.112 | 1.577 | 1.057 |
| DETA | 41.054 | 38.593 | 44.607 | 43.072 | 41.241 | 51.032 | 35.320 | 45.272 | 36.976 | 44.374 |
| AEEA | 1.683 | 0.873 | 1.751 | 1.997 | 1.834 | 2.629 | 0.512 | 1.883 | 0.650 | 1.955 |
| AEP | 1.101 | 1.347 | 0.771 | 0.821 | 0.835 | 0.570 | 1.905 | 0.982 | 1.561 | 1.000 |
| HEP | 0.000 | 0.000 | 0.000 | 0.000 | 0.000 | 0.000 | 0.000 | 0.000 | 0.000 | 0.000 |
| TAEA | 2.712 | 2.489 | 2.232 | 2.241 | 2.226 | 1.861 | 2.166 | 2.390 | 2.589 | 2.511 |
| 1-TETA | 11.777 | 11.906 | 10.383 | 10.387 | 10.429 | 8.845 | 11.724 | 11.589 | 13.232 | 12.136 |
| DAEP | 0.423 | 0.486 | 0.280 | 0.215 | 0.235 | 0.126 | 0.995 | 0.266 | 0.649 | 0.285 |
| PEEDA | 0.327 | 0.415 | 0.253 | 0.183 | 0.199 | 0.101 | 0.736 | 0.226 | 0.512 | 0.249 |
| DPE | 0.088 | 0.183 | 0.098 | 0.092 | 0.091 | 0.057 | 0.262 | 0.089 | 0.219 | 0.098 |
| AE-TAEA | 3.411 | 3.691 | 2.918 | 2.501 | 2.621 | 1.429 | 3.662 | 3.017 | 4.503 | 3.121 |
| 1-TEPA | 6.041 | 0.960 | 5.789 | 4.661 | 4.999 | 2.823 | 8.129 | 5.730 | 9.114 | 6.079 |
| AE-DAEP | 0.397 | 0.339 | 0.351 | 0.199 | 0.231 | 0.053 | 1.154 | 0.242 | 0.570 | 0.278 |
| AE-PEEDA | 0.058 | 0.077 | 0.059 | 0.052 | 0.032 | 0.000 | 0.223 | 0.032 | 0.163 | 0.042 |
| iAE-PEEDA | 0.000 | 0.000 | 0.000 | 0.000 | 0.000 | 0.000 | 0.000 | 0.000 | 0.000 | 0.000 |
| AE-DPE | 0.052 | 0.153 | 0.049 | 0.072 | 0.067 | 0.000 | 0.208 | 0.077 | 0.070 | 0.097 |
| BPEA | 0.695 | 0.772 | 0.603 | 0.425 | 0.457 | 0.177 | 0.094 | 0.547 | 0.803 | 0.556 |
| Others | 4.145 | 4.991 | 3.687 | 2.354 | 2.636 | 1.310 | 9.047 | 2.757 | 7.406 | 3.016 |
| MEA Conversion, % | 58.37 | 69.49 | 50.38 | 52.25 | 55.02 | 39.54 | 76.37 | 56.07 | 78.27 | 59.37 |
| DETA Conversion, % | 32.88 | 34.31 | 28.22 | 25.62 | 27.04 | 16.74 | 41.52 | 27.19 | 40.06 | 28.29 |
| Acyclic(N4), % | 94.53 | 92.99 | 95.23 | 96.26 | 96.01 | 97.42 | 87.46 | 96.01 | 91.98 | 95.86 |
| Acyclic(N5), % | 88.72 | 88.82 | 89.13 | 90.54 | 90.63 | 94.86 | 87.54 | 90.69 | 89.45 | 90.43 |
| Σ(N5)/Σ(N4), weight ratio | 0.70 | 0.77 | 0.74 | 0.60 | 0.64 | 0.41 | 0.85 | 0.66 | 0.88 | 0.67 |
| Acyclic(N4)/cyclic (<=N4), weight ratio | 4.97 | 3.81 | 5.86 | 5.83 | 5.53 | 7.46 | 2.50 | 5.23 | 3.50 | 5.45 |

TABLE CII

| Example No. | 989 | 990 | 991 | 992 | 993 | 994 | 995 | 996 | 997 | 998 |
|---|---|---|---|---|---|---|---|---|---|---|
| Catalyst Type | FFFFF | FFFFF | FFFFF | FFFFF | FFFFF | FFFFF | FFFFF | FFFFF | FFFFF | FFFFF |
| Catalyst weight, gm | 76.67 | 76.67 | 76.67 | 76.67 | 76.67 | 76.67 | 76.67 | 76.67 | 76.67 | 76.67 |
| Pressure, psig | 599 | 599 | 609 | 599 | 600 | 598 | 596 | 598 | 600 | 599 |
| Temperature, °C. | 270 | 280 | 260 | 269 | 259 | 280 | 280 | 269 | 269 | 268 |
| Time on organics, hrs. | 22.5 | 27.5 | 46.5 | 51.5 | 70.5 | 75.5 | 94.5 | 99.5 | 120 | 169.5 |
| Duration of run, hrs. | 2 | 2 | 2 | 2 | 2 | 2 | 2 | 2 | 2 | 2 |
| MEA SV, gmol/hr/kgcat | 3.05 | 3.06 | 2.79 | 3.10 | 3.07 | 3.13 | 3.03 | 3.01 | 3.05 | 3.15 |
| DETA/MEA mole ratio | 1.00 | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 1.520 | 2.437 | 2.447 | 1.228 | 1.029 | 2.414 | 2.547 | 1.320 | 1.437 | 1.242 |
| MEA | 14.652 | 8.505 | 6.424 | 13.718 | 18.262 | 7.632 | 6.416 | 14.174 | 12.516 | 13.988 |
| PIP | 1.110 | 1.615 | 1.625 | 1.089 | 0.811 | 1.685 | 1.788 | 1.154 | 1.228 | 1.100 |
| DETA | 39.856 | 33.953 | 30.620 | 42.604 | 44.433 | 34.076 | 32.533 | 40.980 | 39.040 | 42.773 |
| AEEA | 1.060 | 0.447 | 0.314 | 1.855 | 1.945 | 0.437 | 0.334 | 1.170 | 1.071 | 1.048 |
| AEP | 1.075 | 1.737 | 1.834 | 1.025 | 0.733 | 1.846 | 2.086 | 1.119 | 1.173 | 1.187 |
| HEP | 0.000 | 0.000 | 0.000 | 0.000 | 0.000 | 0.000 | 0.000 | 0.000 | 0.000 | 0.000 |
| TAEA | 2.436 | 2.526 | 2.311 | 2.830 | 2.495 | 2.424 | 2.285 | 2.594 | 2.614 | 2.592 |
| 1-TETA | 11.953 | 13.615 | 12.962 | 13.423 | 11.709 | 13.253 | 12.977 | 12.761 | 12.998 | 14.044 |
| DAEP | 0.316 | 0.845 | 0.960 | 0.297 | 0.197 | 0.863 | 1.049 | 0.408 | 0.461 | 0.325 |
| PEEDA | 0.271 | 0.647 | 0.738 | 0.284 | 0.177 | 0.663 | 0.796 | 0.337 | 0.392 | 0.267 |
| DPE | 0.114 | 0.099 | 0.099 | 0.049 | 0.040 | 0.099 | 0.102 | 0.071 | 0.074 | 0.052 |
| AE-TAEA | 3.524 | 4.505 | 4.333 | 3.359 | 2.704 | 4.359 | 4.387 | 3.710 | 3.897 | 3.401 |
| 1-TEPA | 6.384 | 9.138 | 9.198 | 6.628 | 5.017 | 9.080 | 9.494 | 6.780 | 7.415 | 6.586 |
| AE-DAEP | 0.000 | 0.248 | 0.279 | 0.314 | 0.207 | 0.679 | 0.267 | 0.307 | 0.269 | 0.300 |
| AE-PEEDA | 0.229 | 0.135 | 0.140 | 0.042 | 0.063 | 0.126 | 0.123 | 0.032 | 0.057 | 0.054 |
| iAE-PEEDA | 0.000 | 0.000 | 0.000 | 0.000 | 0.000 | 0.000 | 0.000 | 0.000 | 0.000 | 0.000 |
| AE-DPE | 0.553 | 0.191 | 0.210 | 0.000 | 0.000 | 0.052 | 0.093 | 0.000 | 0.033 | 0.000 |
| BPEA | 0.522 | 0.338 | 0.365 | 0.442 | 0.300 | 0.794 | 0.831 | 0.530 | 0.577 | 0.532 |
| Others | 3.075 | 9.229 | 10.383 | 4.003 | 2.618 | 9.258 | 10.540 | 4.653 | 5.267 | 2.788 |
| MEA Conversion, % | 58.39 | 76.75 | 81.53 | 63.00 | 49.80 | 79.10 | 82.29 | 61.34 | 65.43 | 61.89 |
| DETA Conversion, % | 32.73 | 44.85 | 47.68 | 31.70 | 27.42 | 44.55 | 46.62 | 33.56 | 35.92 | 30.74 |
| Acyclic(N4), % | 95.36 | 91.03 | 89.48 | 96.26 | 97.17 | 90.61 | 88.68 | 94.65 | 94.40 | 96.27 |
| Acyclic(N5), % | 88.37 | 93.73 | 93.16 | 92.61 | 93.12 | 89.06 | 91.35 | 92.35 | 92.35 | 91.85 |
| Σ(N5)/Σ(N4), weight ratio | 0.74 | 0.82 | 0.85 | 0.64 | 0.57 | 0.87 | 0.88 | 0.70 | 0.74 | 0.63 |
| Acyclic(N4)/cyclic (<=N4), weight ratio | 4.99 | 3.27 | 2.91 | 5.92 | 7.25 | 3.04 | 2.62 | 4.97 | 4.69 | 5.68 |

TABLE CIII

| Example No. | 999 | 1000 | 1001 | 1002 | 1003 | 1004 | 1005 | 1006 | 1007 |
|---|---|---|---|---|---|---|---|---|---|
| Catalyst Type | GGGGG | GGGGG | GGGGG | GGGGG | GGGGG | GGGGG | GGGGG | GGGGG | GGGGG |
| Catalyst weight, gm | 81.02 | 81.02 | 81.02 | 81.02 | 81.02 | 81.02 | 81.02 | 81.02 | 81.02 |
| Pressure, psig | 598 | 598 | 598 | 598 | 598 | 598 | 600 | 600 | 600 |
| Temperature, °C. | 258 | 270 | 259 | 278 | 269 | 278 | 279 | 270 | 270 |
| Time on organics, hrs. | 47 | 52 | 71 | 76 | 95 | 99 | 118.5 | 139.8 | 141.5 |
| Duration of run, hrs. | 2 | 2 | 2 | 2 | 2 | 2 | 2 | 1 | 1 |
| MEA SV, gmol/hr/kgcat | 2.59 | 2.69 | 2.76 | 2.69 | 2.62 | 2.89 | 2.50 | 2.61 | 2.85 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 1.431 | 1.466 | 0.836 | 2.026 | 1.389 | 1.898 | 3.937 | 1.319 | 1.270 |
| MEA | 20.803 | 15.928 | 21.573 | 8.455 | 13.153 | 5.684 | 3.430 | 11.218 | 12.033 |
| PIP | 0.619 | 0.793 | 0.421 | 1.275 | 0.987 | 1.265 | 2.108 | 1.046 | 0.955 |
| DETA | 41.470 | 40.511 | 47.612 | 36.072 | 40.931 | 31.699 | 26.932 | 37.630 | 37.696 |
| AEEA | 1.655 | 2.044 | 2.654 | 0.991 | 1.869 | 0.695 | 0.297 | 1.784 | 1.787 |
| AEP | 1.227 | 0.888 | 0.525 | 1.430 | 1.026 | 1.530 | 3.019 | 1.099 | 0.994 |
| HEP | 0.000 | 0.000 | 0.000 | 0.000 | 0.000 | 0.000 | 0.000 | 0.000 | 0.000 |
| TAEA | 1.792 | 2.202 | 1.893 | 2.343 | 2.432 | 2.392 | 1.670 | 2.598 | 2.308 |
| l-TETA | 9.207 | 11.790 | 9.627 | 13.461 | 13.115 | 13.772 | 11.582 | 14.083 | 12.425 |
| DAEP | 0.616 | 0.258 | 0.103 | 0.671 | 0.399 | 0.778 | 1.863 | 0.456 | 0.383 |
| PEEDA | 0.451 | 0.211 | 0.071 | 0.519 | 0.296 | 0.575 | 1.351 | 0.364 | 0.034 |
| DPE | 0.029 | 0.076 | 0.066 | 0.203 | 0.107 | 0.217 | 0.107 | 0.049 | 0.059 |
| AE-TAEA | 2.172 | 3.076 | 1.560 | 4.364 | 3.434 | 4.598 | 0.163 | 3.800 | 3.588 |
| l-TEPA | 4.520 | 5.662 | 2.989 | 9.213 | 7.036 | 9.871 | 9.389 | 7.945 | 7.481 |
| AE-DAEP | 0.421 | 0.185 | 0.102 | 0.530 | 0.226 | 6.503 | 0.543 | 0.066 | 0.134 |
| AE-PEEDA | 0.029 | 0.036 | 0.030 | 0.116 | 0.035 | 0.100 | 0.907 | 0.030 | 0.098 |
| iAE-PEEDA | 0.000 | 0.000 | 0.000 | 0.000 | 0.000 | 0.000 | 0.000 | 0.000 | 0.000 |
| AE-DPE | 0.023 | 0.000 | 0.000 | 0.223 | 0.050 | 0.264 | 0.161 | 0.068 | 0.138 |
| BPEA | 0.388 | 0.045 | 0.026 | 0.807 | 0.056 | 1.316 | 1.078 | 0.184 | 0.220 |
| Others | 3.269 | 3.950 | 1.862 | 7.511 | 4.907 | 4.583 | 16.344 | 5.932 | 7.028 |
| MEA Conversion, % | 40.86 | 54.65 | 39.37 | 76.88 | 63.86 | 84.34 | 90.23 | 68.77 | 66.03 |
| DETA Conversion, % | 29.93 | 31.45 | 20.47 | 41.38 | 33.16 | 48.10 | 54.39 | 37.75 | 36.75 |
| Acyclic(N4), % | 90.94 | 96.25 | 97.95 | 91.90 | 95.09 | 91.15 | 79.97 | 95.05 | 96.87 |
| Acyclic(N5), % | 88.61 | 97.05 | 96.63 | 89.01 | 96.62 | 63.88 | 78.03 | 97.13 | 94.95 |
| Σ(N5)/Σ(N4), weight ratio | 0.62 | 0.62 | 0.40 | 0.89 | 0.66 | 1.28 | 0.74 | 0.69 | 0.77 |
| Acyclic(N4)/cyclic (<=N4), weight ratio | 3.74 | 6.29 | 9.71 | 3.86 | 5.52 | 3.70 | 1.57 | 5.53 | 5.98 |

TABLE CIV

| Example No. | 1008 | 1009 | 1010 | 1011 | 1012 | 1013 | 1014 | 1015 | 1016 |
|---|---|---|---|---|---|---|---|---|---|
| Catalyst Type | HHHHH | HHHHH | HHHHH | HHHHH | HHHHH | HHHHH | HHHHH | HHHHH | HHHHH |
| Catalyst weight, gm | 68 | 68 | 68 | 68 | 68 | 68 | 68 | 68 | 68 |
| Pressure, psig | 606 | 599 | 602 | 606 | 593 | 593 | 601 | 600 | 600 |
| Temperature, °C. | 270 | 270 | 280 | 260 | 270 | 260 | 280 | 280 | 270 |
| Time on organics, hrs. | 7 | 26 | 30.5 | 50 | 55 | 74 | 79 | 98.8 | 123 |
| Duration of run, hrs. | 2 | 2 | 1 | 2 | 2 | 2 | 2 | 2 | 2 |
| MEA SV, gmol/hr/kgcat | 3.97 | 3.90 | 3.93 | 3.98 | 3.96 | 3.94 | 3.97 | 3.93 | 3.85 |
| DETA/MEA mole ratio | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.750 | 0.869 | 1.269 | 0.502 | 0.696 | 1.589 | 1.188 | 1.273 | 0.810 |
| MEA | 14.139 | 13.058 | 7.841 | 19.884 | 13.962 | 19.078 | 8.661 | 6.995 | 13.582 |
| PIP | 0.946 | 1.041 | 1.264 | 0.614 | 0.883 | 0.667 | 1.206 | 1.218 | 0.953 |
| DETA | 42.338 | 40.333 | 34.679 | 47.727 | 41.491 | 46.874 | 37.218 | 33.635 | 40.430 |
| AEEA | 1.641 | 1.480 | 0.679 | 2.213 | 1.609 | 2.241 | 0.609 | 0.617 | 1.541 |
| AEP | 0.987 | 1.041 | 1.527 | 0.599 | 0.913 | 0.603 | 1.467 | 1.500 | 0.961 |
| HEP | 0.000 | 0.000 | 0.000 | 0.000 | 0.000 | 0.000 | 0.000 | 0.000 | 0.000 |
| TAEA | 2.657 | 2.786 | 2.699 | 2.233 | 2.513 | 2.246 | 2.703 | 2.625 | 2.555 |
| l-TETA | 12.825 | 13.469 | 13.932 | 10.488 | 12.891 | 10.468 | 13.856 | 13.911 | 12.446 |
| DAEP | 0.340 | 0.387 | 0.763 | 0.170 | 0.305 | 0.165 | 0.693 | 0.770 | 0.335 |
| PEEDA | 0.302 | 0.336 | 0.601 | 0.150 | 0.227 | 0.146 | 0.549 | 0.605 | 0.284 |
| DPE | 0.132 | 0.150 | 0.301 | 0.094 | 0.099 | 0.099 | 0.088 | 0.118 | 0.077 |
| AE-TAEA | 3.574 | 3.998 | 4.830 | 2.253 | 3.538 | 2.309 | 4.432 | 4.606 | 3.500 |
| l-TEPA | 7.216 | 7.943 | 9.991 | 4.612 | 7.184 | 4.724 | 9.147 | 9.831 | 7.304 |
| AE-DAEP | 0.088 | 0.082 | 0.204 | 0.154 | 0.134 | 0.064 | 0.601 | 0.879 | 0.328 |

TABLE CIV-continued

| | | | | | | | | | |
|---|---|---|---|---|---|---|---|---|---|
| AE-PEEDA | 0.155 | 0.158 | 0.380 | 0.028 | 0.223 | 0.074 | 0.067 | 0.125 | 0.039 |
| iAE-PEEDA | 0.000 | 0.000 | 0.000 | 0.000 | 0.000 | 0.000 | 0.000 | 0.000 | 0.000 |
| AE-DPE | 0.038 | 0.067 | 0.403 | 0.056 | 0.248 | 0.075 | 0.078 | 0.313 | 0.048 |
| BPEA | 0.508 | 0.179 | 1.040 | 0.229 | 0.611 | 0.231 | 0.804 | 0.839 | 0.472 |
| Others | 5.025 | 5.875 | 9.178 | 2.946 | 5.812 | 3.348 | 7.734 | 8.939 | 4.826 |
| MEA conversion, % | 62.09 | 64.96 | 79.02 | 46.40 | 62.51 | 48.13 | 76.57 | 80.72 | 62.33 |
| DETA conversion, % | 32.54 | 35.67 | 44.85 | 23.54 | 33.79 | 24.26 | 40.15 | 44.90 | 33.36 |
| Acyclic(N4), wt. % | 95.24 | 94.91 | 90.90 | 96.85 | 95.77 | 96.87 | 92.56 | 91.71 | 95.57 |
| Acyclic(N5), wt. % | 93.19 | 96.09 | 87.98 | 93.64 | 89.81 | 94.07 | 89.76 | 87.00 | 92.42 |
| Σ(N5)/Σ(N4), weight ratio | 0.71 | 0.73 | 0.92 | 0.56 | 0.74 | 0.57 | 0.85 | 0.92 | 0.74 |
| Acyclic(N4)/cyclic(<=N4), weight ratio | 5.72 | 5.50 | 3.73 | 7.82 | 6.22 | 7.57 | 4.14 | 3.93 | 5.75 |

| Example No. | 1017 | 1018 | 1019 | 1020 | 1021 | 1022 | 1023 | 1024 | 1025 | 1026 |
|---|---|---|---|---|---|---|---|---|---|---|
| Catalyst Type | HHHHH | HHHHH | HHHHH | HHHHH | HHHHH | HHHHH | HHHHH | HHHHH | HHHHH | HHHHH |
| Catalyst weight, gm | 68 | 68 | 68 | 68 | 68 | 68 | 68 | 68 | 68 | 68 |
| Pressure, psig | 596 | 598 | 602 | 603 | 602 | 602 | 603 | 603 | 603 | 603 |
| Temperature, °C. | 271 | 282 | 260 | 270 | 260 | 281 | 272 | 280 | 272 | 271 |
| Time on organics, hrs. | 158 | 163 | 182 | 187 | 206 | 211 | 272 | 235 | 254 | 257.5 |
| Duration of run, hrs. | 2 | 2 | 2 | 2 | 83.7 | 2 | 2 | 2 | 2 | 2 |
| MEA SV, gmol/hr/kgcat | 3.92 | 3.89 | 3.99 | 3.83 | 0.09 | 3.85 | 3.80 | 3.88 | 3.86 | 4.03 |
| DETA/MEA mole ratio | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 1.086 | 1.518 | 0.564 | 0.960 | 0.630 | 1.769 | 1.921 | 2.220 | 1.641 | 1.650 |
| MEA | 13.203 | 6.960 | 18.056 | 12.558 | 17.829 | 6.838 | 12.002 | 5.827 | 11.663 | 13.072 |
| PIP | 1.186 | 1.446 | 0.765 | 1.101 | 0.770 | 1.362 | 1.263 | 1.380 | 1.178 | 1.205 |
| DETA | 40.181 | 35.494 | 45.781 | 40.874 | 44.267 | 34.368 | 39.115 | 30.652 | 38.907 | 40.441 |
| AEEA | 1.261 | 0.505 | 2.117 | 1.385 | 2.108 | 0.517 | 1.158 | 0.441 | 1.197 | 1.308 |
| AEP | 1.136 | 1.798 | 0.738 | 1.161 | 0.699 | 1.725 | 1.205 | 1.595 | 1.179 | 1.119 |
| HEP | 0.000 | 0.000 | 0.000 | 0.000 | 0.000 | 0.000 | 0.000 | 0.000 | 0.000 | 0.000 |
| TAEA | 2.661 | 2.671 | 2.384 | 2.732 | 2.320 | 2.531 | 2.548 | 2.402 | 2.575 | 2.513 |
| 1-TETA | 13.232 | 14.206 | 11.386 | 13.549 | 11.117 | 13.437 | 12.752 | 13.162 | 12.893 | 12.524 |
| DAEP | 0.452 | 0.939 | 0.225 | 0.438 | 0.196 | 0.889 | 0.485 | 0.981 | 0.469 | 0.410 |
| PEEDA | 0.372 | 0.692 | 0.187 | 0.361 | 0.175 | 0.670 | 0.383 | 0.728 | 0.375 | 0.335 |
| DPE | 0.076 | 0.107 | 0.056 | 0.091 | 0.033 | 0.111 | 0.077 | 0.133 | 0.082 | 0.076 |
| AE-TAEA | 4.013 | 4.667 | 2.669 | 3.990 | 2.705 | 4.603 | 4.023 | 4.890 | 3.878 | 3.770 |
| 1-TEPA | 8.152 | 9.680 | 5.588 | 8.225 | 5.696 | 9.840 | 8.145 | 10.433 | 8.054 | 7.706 |
| AE-DAEP | 0.401 | 0.783 | 0.156 | 0.382 | 0.201 | 0.171 | 0.377 | 0.235 | 0.379 | 0.324 |
| AE-PEEDA | 0.047 | 0.080 | 0.028 | 0.051 | 0.028 | 0.114 | 0.042 | 0.161 | 0.048 | 0.037 |
| iAE-PEEDA | 0.000 | 0.000 | 0.000 | 0.000 | 0.000 | 0.000 | 0.000 | 0.000 | 0.000 | 0.000 |
| AE-DPE | 0.057 | 0.105 | 0.046 | 0.043 | 0.036 | 0.053 | 0.049 | 0.706 | 0.047 | 0.046 |
| BPEA | 0.607 | 0.902 | 0.324 | 0.630 | 0.311 | 0.897 | 0.644 | 1.020 | 0.619 | 0.582 |
| Others | 5.537 | 8.116 | 3.310 | 5.711 | 3.339 | 10.005 | 5.502 | 13.484 | 5.564 | 5.184 |
| MEA conversion, % | 64.77 | 81.20 | 51.33 | 66.74 | 50.94 | 81.35 | 67.32 | 84.30 | 67.93 | 64.52 |
| DETA conversion, % | 36.28 | 43.03 | 26.65 | 35.67 | 27.60 | 44.30 | 36.70 | 50.93 | 36.43 | 34.77 |
| Acyclic(N4), wt. % | 94.64 | 90.67 | 96.72 | 94.81 | 97.08 | 90.53 | 94.19 | 89.41 | 94.35 | 94.83 |
| Acyclic(N5), wt. % | 91.63 | 88.47 | 93.7 | 91.70 | 93.58 | 92.12 | 91.63 | 87.84 | 91.61 | 92.07 |
| Σ(N5)/Σ(N4), weight ratio | 0.79 | 0.87 | 0.62 | 0.78 | 0.65 | 0.89 | 0.82 | 1.00 | 0.79 | 0.79 |
| Acyclic(N4)/cyclic(<=N4), weight ratio | 4.93 | 3.39 | 6.99 | 5.16 | 7.17 | 3.36 | 4.48 | 3.23 | 4.71 | 4.78 |

| Example No. | 1027 | 1028 | 1029 | 1030 | 1031 | 1032 | 1033 | 1034 | 1035 |
|---|---|---|---|---|---|---|---|---|---|
| Catalyst Type | HHHHH | HHHHH | HHHHH | HHHHH | HHHHH | HHHHH | HHHHH | HHHHH | HHHHH |
| Catalyst weight, gm | 67.2 | 67.2 | 67.2 | 67.2 | 67.2 | 67.2 | 67.2 | 67.2 | 67.2 |
| Pressure, psig | 600 | 600 | 600 | 600 | 600 | 600 | 600 | 600 | 600 |
| Temperature, °C. | 267.7 | 267.9 | 278 | 257.8 | 269.6 | 259.3 | 279.3 | 269.8 | 270.1 |
| Time on organics, hrs. | 4 | 6.5 | 28.5 | 47.5 | 52.5 | 71 | 76.5 | 96.5 | 99 |
| Duration of run, hrs. | 2 | 2 | 2 | 2 | 2 | 2 | 2 | 2 | 2 |
| MEA SV, gmol/hr/kgcat | 4.59 | 4.81 | 4.66 | 4.74 | 4.80 | 4.79 | 4.46 | 4.63 | 4.60 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.515 | 0.541 | 1.593 | 0.567 | 0.832 | 0.445 | 1.675 | 0.932 | 0.995 |
| MEA | 23.588 | 25.727 | 18.012 | 26.580 | 21.992 | 27.189 | 13.854 | 20.859 | 20.291 |
| PIP | 0.888 | 1.118 | 1.953 | 1.009 | 1.390 | 0.957 | 1.810 | 1.493 | 1.486 |
| DETA | 54.811 | 54.100 | 50.845 | 55.433 | 53.042 | 56.685 | 51.796 | 53.039 | 51.623 |
| AEEA | 0.344 | 0.802 | 0.233 | 0.360 | 0.208 | 0.377 | 0.150 | 0.478 | 0.210 |
| AEP | 0.883 | 0.858 | 1.884 | 0.856 | 1.352 | 0.775 | 2.177 | 1.423 | 1.423 |
| HEP | 0.000 | 0.000 | 0.000 | 0.000 | 0.000 | 0.000 | 0.000 | 0.000 | 0.000 |
| TAEA | 1.618 | 1.490 | 1.878 | 1.474 | 1.695 | 1.397 | 1.977 | 1.858 | 1.955 |
| 1-TETA | 7.964 | 7.269 | 9.198 | 6.586 | 8.327 | 6.490 | 9.962 | 8.880 | 10.270 |
| DAEP | 0.114 | 0.093 | 0.645 | 0.301 | 0.154 | 0.207 | 0.692 | 0.412 | 0.178 |
| PEEDA | 0.081 | 0.064 | 0.387 | 0.144 | 0.104 | 0.117 | 0.359 | 0.162 | 0.125 |
| DPE | 0.000 | 0.000 | 0.000 | 0.000 | 0.000 | 0.000 | 0.000 | 0.000 | 0.000 |
| AE-TAEA | 0.000 | 0.088 | 0.246 | 0.000 | 0.102 | 0.000 | 1.894 | 0.109 | 0.000 |
| 1-TEPA | 0.664 | 0.704 | 1.555 | 0.500 | 0.975 | 0.246 | 3.556 | 1.157 | 1.321 |
| AE-DAEP | 0.000 | 0.223 | 0.372 | 0.000 | 0.000 | 0.000 | 0.114 | 0.133 | 0.326 |
| AE-PEEDA | 0.000 | 0.000 | 0.099 | 0.000 | 0.175 | 0.000 | 0.075 | 0.000 | 0.069 |
| iAE-PEEDA | 0.000 | 0.000 | 0.000 | 0.000 | 0.000 | 0.000 | 0.000 | 0.000 | 0.000 |
| AE-DPE | 0.168 | 0.000 | 0.059 | 0.000 | 0.423 | 0.000 | 0.000 | 0.083 | 0.512 |

TABLE CIV-continued

| | | | | | | | | | |
|---|---|---|---|---|---|---|---|---|---|
| BPEA | 0.000 | 0.000 | 0.000 | 0.000 | 0.000 | 0.000 | 0.000 | 0.000 | 0.000 |
| Others | 1.532 | 0.963 | 2.990 | 1.492 | 2.047 | 0.994 | 0.880 | 1.861 | 2.579 |
| MEA conversion, % | 34.18 | 28.60 | 49.97 | 27.10 | 38.81 | 25.75 | 61.46 | 42.13 | 44.20 |
| DETA conversion, % | 9.11 | 10.77 | 16.06 | 9.64 | 12.29 | 7.99 | 14.37 | 12.55 | 15.64 |
| Acyclic(N4), wt. % | 98.01 | 98.23 | 91.48 | 94.77 | 97.49 | 96.05 | 91.91 | 94.93 | 97.59 |
| Acyclic(N5), wt. % | 79.79 | 78.07 | 77.26 | 100.00 | 64.30 | 100.00 | 96.64 | 85.40 | 59.30 |
| $\Sigma$(N5)/$\Sigma$(N4), weight ratio | 0.09 | 0.11 | 0.19 | 0.06 | 0.16 | 0.03 | 0.43 | 0.13 | 0.18 |
| Acyclic(N4)/cyclic($<$=N4), weight ratio | 4.87 | 4.11 | 2.27 | 3.49 | 3.34 | 3.83 | 2.37 | 3.08 | 3.81 |

TABLE CV

| Example No. | 1036 | 1037 | 1038 | 1039 | 1040 | 1041 | 1042 | 1043 | 1044 | 1045 | 1046 | 1047 |
|---|---|---|---|---|---|---|---|---|---|---|---|---|
| Catalyst Type | IIIII | IIIII | IIIII | IIIII | IIIII | IIIII | IIIII | IIIII | IIIII | IIIII | IIIII | IIIII |
| Catalyst weight, gm | 69.34 | 69.34 | 69.34 | 69.34 | 69.34 | 69.34 | 69.34 | 69.34 | 69.34 | 69.34 | 69.34 | 69.34 |
| Pressure, psig | 604 | 603 | 603 | 604 | 604 | 603 | 603 | 600 | 600 | 603 | 604 | 603 |
| Temperature, °C. | 270 | 270 | 280 | 260 | 270 | 260 | 280 | 280 | 270 | 271 | 282 | 260 |
| Time on organics, hrs. | 7 | 26 | 30.5 | 50 | 55 | 74 | 79 | 98.8 | 123 | 158 | 163 | 182 |
| Duration of run, hrs. | 2 | 2 | 1 | 2 | 2 | 2 | 2 | 2 | 2 | 2 | 2 | 2 |
| MEA SV, gmol/hr/kgcat | 4.33 | 4.26 | 4.21 | 4.20 | 4.33 | 4.20 | 4.17 | 4.26 | 4.16 | 4.01 | 4.31 | 4.28 |
| DETA/MEA mole ratio | 1.00 | 1.00 | 1.00 | 1.00 | 1.00 | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 | 5.97 | 5.97 | 5.97 | 5.97 | 5.97 |
| Crude product composition, wt. % | | | | | | | | | | | | |
| EDA | 0.805 | 1.034 | 1.662 | 0.510 | 0.908 | 0.544 | 1.363 | 2.077 | 0.963 | 1.212 | 1.778 | 0.757 |
| MEA | 14.316 | 13.747 | 10.093 | 20.646 | 15.418 | 19.410 | 8.991 | 9.550 | 15.047 | 12.554 | 9.298 | 20.034 |
| PIP | 0.832 | 0.927 | 1.260 | 0.542 | 0.841 | 0.555 | 1.085 | 1.325 | 0.906 | 1.009 | 1.387 | 0.734 |
| DETA | 41.647 | 40.641 | 36.709 | 48.819 | 43.537 | 47.902 | 35.150 | 32.997 | 41.105 | 37.117 | 36.552 | 46.016 |
| AEEA | 1.392 | 1.332 | 0.661 | 2.056 | 1.526 | 2.142 | 0.718 | 0.580 | 1.445 | 1.046 | 0.554 | 1.888 |
| AEP | 0.990 | 1.057 | 1.455 | 0.554 | 0.915 | 0.588 | 1.336 | 1.810 | 0.927 | 1.212 | 1.598 | 0.679 |
| HEP | 0.000 | 0.000 | 0.000 | 0.000 | 0.000 | 0.000 | 0.000 | 0.000 | 0.000 | 0.000 | 0.000 | 0.000 |
| TAEA | 2.980 | 2.906 | 2.683 | 2.272 | 2.709 | 2.329 | 2.593 | 1.994 | 2.443 | 2.311 | 2.549 | 2.223 |
| l-TETA | 13.276 | 13.074 | 12.859 | 9.750 | 12.028 | 10.013 | 12.850 | 10.946 | 11.547 | 11.703 | 13.076 | 10.211 |
| DAEP | 0.416 | 0.470 | 0.726 | 0.152 | 0.358 | 0.171 | 0.754 | 1.270 | 0.373 | 0.669 | 0.839 | 0.209 |
| PEEDA | 0.321 | 0.347 | 0.527 | 0.130 | 0.270 | 0.147 | 0.531 | 0.858 | 0.292 | 0.476 | 0.594 | 0.174 |
| DPE | 0.151 | 0.167 | 0.208 | 0.055 | 0.159 | 0.073 | 0.126 | 0.164 | 0.196 | 0.112 | 0.468 | 0.072 |
| AE-TAEA | 4.148 | 4.074 | 4.997 | 2.219 | 3.441 | 2.254 | 4.357 | 3.447 | 3.193 | 3.397 | 4.484 | 2.580 |
| 1-TEPA | 7.057 | 7.074 | 8.378 | 3.718 | 6.290 | 3.871 | 8.283 | 7.231 | 6.092 | 7.003 | 8.450 | 5.015 |
| AE-DAEP | 0.081 | 0.074 | 0.124 | 0.145 | 0.075 | 0.247 | 1.053 | 1.912 | 0.489 | 0.928 | 0.694 | 0.198 |
| AE-PEEDA | 0.148 | 0.141 | 0.238 | 0.027 | 0.117 | 0.067 | 0.154 | 0.294 | 0.065 | 0.153 | 0.085 | 0.045 |
| iAE-PEEDA | 0.000 | 0.000 | 0.000 | 0.000 | 0.000 | 0.000 | 0.000 | 0.000 | 0.000 | 0.000 | 0.000 | 0.000 |
| AE-DPE | 0.051 | 0.069 | 0.286 | 0.266 | 0.175 | 0.261 | 0.309 | 0.130 | 0.070 | 0.287 | 0.093 | 0.051 |
| BPEA | 0.582 | 0.570 | 0.800 | 0.207 | 0.479 | 0.205 | 0.737 | 0.613 | 0.415 | 0.510 | 0.761 | 0.054 |
| Others | 5.099 | 5.415 | 7.215 | 2.423 | 4.615 | 2.781 | 8.931 | 12.620 | 4.609 | 7.302 | 7.358 | 3.390 |
| MEA conversion, % | 61.90 | 63.00 | 72.52 | 43.91 | 58.43 | 46.90 | 75.19 | 73.83 | 57.94 | 64.82 | 74.69 | 45.65 |
| DETA conversion, % | 34.13 | 35.00 | 40.60 | 21.18 | 30.42 | 22.12 | 42.36 | 46.26 | 31.71 | 38.19 | 40.86 | 25.81 |
| Acyclic(N4), wt. % | 94.82 | 94.20 | 91.41 | 97.28 | 94.93 | 96.93 | 91.63 | 84.95 | 94.20 | 91.77 | 89.15 | 96.47 |
| Acyclic(N5), wt. % | 92.86 | 92.88 | 90.23 | 90.21 | 91.94 | 88.71 | 84.88 | 78.36 | 89.93 | 84.70 | 88.79 | 95.62 |
| $\Sigma$(N5)/$\Sigma$(N4), weight ratio | 0.70 | 0.71 | 0.87 | 0.53 | 0.68 | 0.54 | 0.88 | 0.89 | 0.70 | 0.80 | 0.83 | 0.62 |
| Acyclic(N4)/cyclic($<$=N4), weight ratio | 6.00 | 5.38 | 3.72 | 8.39 | 5.80 | 8.05 | 4.03 | 2.38 | 5.19 | 4.03 | 3.20 | 6.65 |

| Example No. | 1048 | 1049 | 1050 | 1051 | 1052 | 1053 | 1054 |
|---|---|---|---|---|---|---|---|
| Catalyst Type | IIIII | IIIII | IIIII | IIIII | IIIII | IIIII | IIIII |
| Catalyst weight, gm | 69.34 | 69.34 | 69.34 | 69.34 | 69.34 | 69.34 | 69.34 |
| Pressure, psig | 604 | 603 | 604 | 604 | 604 | 603 | 604 |
| Temperature, °C. | 270 | 260 | 281 | 272 | 280 | 272 | 271 |
| Time on organics, hrs. | 187 | 206 | 211 | 272 | 235 | 254 | 257.5 |
| Duration of run, hrs. | 2 | 2 | 2 | 2 | 2 | 2 | 2 |
| MEA SV, gmol/hr/kgcat | 4.05 | 4.11 | 4.41 | 4.13 | 4.11 | 4.22 | 4.43 |
| DETA/MEA mole ratio | 1.00 | 1.00 | 1.00 | 1.00 | 1.00 | 1.00 | 1.00 |
| NH$_3$/MEA mole ratio | 5.97 | 5.97 | 5.97 | 5.97 | 5.97 | 5.97 | 5.97 |
| Crude product composition, wt. % | | | | | | | |
| EDA | 0.980 | 0.861 | 2.156 | 1.946 | 2.350 | 1.794 | 1.594 |
| MEA | 13.105 | 18.882 | 8.720 | 12.941 | 7.170 | 13.118 | 13.362 |
| PIP | 0.962 | 0.794 | 1.385 | 1.150 | 1.343 | 1.147 | 1.045 |
| DETA | 38.892 | 44.565 | 34.824 | 39.610 | 33.663 | 39.912 | 39.851 |
| AEEA | 1.280 | 1.745 | 0.521 | 1.185 | 0.478 | 1.195 | 1.279 |
| AEP | 0.976 | 0.784 | 1.518 | 1.109 | 1.669 | 1.094 | 1.015 |
| HEP | 0.000 | 0.000 | 0.000 | 0.000 | 0.000 | 0.000 | 0.000 |
| TAEA | 2.513 | 2.187 | 2.296 | 2.546 | 2.452 | 2.458 | 2.496 |
| l-TETA | 11.973 | 10.178 | 12.160 | 12.466 | 13.106 | 12.081 | 12.149 |
| DAEP | 0.394 | 0.335 | 0.916 | 0.518 | 1.012 | 0.454 | 0.423 |
| PEEDA | 0.318 | 0.240 | 0.634 | 0.377 | 0.766 | 0.348 | 0.321 |
| DPE | 0.186 | 0.150 | 0.127 | 0.092 | 0.123 | 0.079 | 0.072 |
| AE-TAEA | 3.922 | 2.727 | 4.290 | 3.863 | 4.417 | 3.624 | 3.540 |
| 1-TEPA | 7.390 | 5.407 | 8.840 | 7.583 | 9.218 | 7.097 | 6.990 |
| AE-DAEP | 0.427 | 0.351 | 0.189 | 0.411 | 0.892 | 0.342 | 0.038 |
| AE-PEEDA | 0.079 | 0.059 | 0.132 | 0.052 | 0.135 | 0.036 | 0.038 |
| iAE-PEEDA | 0.000 | 0.000 | 0.000 | 0.000 | 0.000 | 0.000 | 0.000 |

TABLE CV-continued

| | | | | | | | |
|---|---|---|---|---|---|---|---|
| AE-DPE | 0.166 | 0.042 | 0.411 | 0.073 | 0.390 | 0.091 | 0.061 |
| BPEA | 0.563 | 0.330 | 0.822 | 0.597 | 0.843 | 0.577 | 0.535 |
| Others | 6.493 | 3.912 | 10.339 | 5.881 | 9.704 | 5.473 | 5.321 |
| MEA conversion, % | 63.83 | 48.59 | 76.20 | 64.94 | 80.41 | 63.82 | 62.91 |
| DETA conversion, % | 36.20 | 27.88 | 43.50 | 36.22 | 45.35 | 34.58 | 34.25 |
| Acyclic(N4), wt. % | 94.16 | 94.46 | 89.61 | 93.83 | 89.12 | 94.28 | 94.72 |
| Acyclic(N5), wt. % | 90.16 | 91.23 | 89.42 | 91.00 | 85.78 | 91.11 | 91.63 |
| Σ(N5)/Σ(N4), weight ratio | 0.82 | 0.68 | 0.91 | 0.79 | 0.91 | 0.76 | 0.74 |
| Acyclic(N4)/cyclic(<=N4), weight ratio | 5.11 | 5.37 | 3.16 | 4.63 | 3.17 | 4.66 | 5.00 |

TABLE CVI

| Example No. | 1055 | 1056 | 1057 | 1058 | 1059 | 1060 | 1061 | 1062 | 1063 |
|---|---|---|---|---|---|---|---|---|---|
| Catalyst Type | JJJJJ | JJJJJ | JJJJJ | JJJJJ | JJJJJ | JJJJJ | JJJJJ | JJJJJ | JJJJJ |
| Catalyst weight, gm | 70.6 | 70.6 | 70.6 | 70.6 | 70.6 | 70.6 | 70.6 | 70.6 | 70.6 |
| Pressure, psig | 600 | 600 | 600 | 600 | 600 | 600 | 600 | 600 | 600 |
| Temperature, °C. | 267.7 | 267.9 | 278 | 257.8 | 269.6 | 259.3 | 279.3 | 269.8 | 270.1 |
| Time on organics, hrs. | 4 | 6.5 | 30.5 | 49.5 | 54.5 | 73 | 78.5 | 98 | 101 |
| Duration of run, hrs. | 2 | 2 | 2 | 2 | 2 | 2 | 2 | 2 | 2 |
| MEA SV, gmol/hr/kgcat | 4.23 | 4.29 | 4.10 | 4.04 | 4.14 | 4.15 | 3.89 | 3.94 | 3.95 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.162 | 0.169 | 0.783 | 0.192 | 0.397 | 0.176 | 1.073 | 0.529 | 0.553 |
| MEA | 29.144 | 31.908 | 24.483 | 32.053 | 27.952 | 31.487 | 22.456 | 25.861 | 26.009 |
| PIP | 0.349 | 0.340 | 1.209 | 0.251 | 0.651 | 0.248 | 1.406 | 0.768 | 0.760 |
| DETA | 59.742 | 58.534 | 56.565 | 58.955 | 59.279 | 59.506 | 54.811 | 57.648 | 57.364 |
| AEEA | 0.310 | 0.929 | 0.200 | 0.321 | 0.342 | 0.351 | 0.776 | 0.366 | 0.370 |
| AEP | 0.544 | 0.498 | 1.287 | 0.436 | 0.711 | 0.471 | 1.454 | 0.793 | 0.801 |
| HEP | 0.000 | 0.000 | 0.000 | 0.000 | 0.000 | 0.000 | 0.000 | 0.000 | 0.000 |
| TAEA | 0.578 | 0.706 | 0.873 | 0.618 | 0.733 | 0.669 | 1.573 | 0.874 | 1.310 |
| 1-TETA | 4.153 | 2.968 | 6.200 | 2.623 | 4.926 | 2.835 | 6.907 | 5.628 | 5.841 |
| DAEP | 0.177 | 0.175 | 0.342 | 0.144 | 0.238 | 0.180 | 0.520 | 0.239 | 0.184 |
| PEEDA | 0.076 | 0.000 | 0.220 | 0.000 | 0.135 | 0.000 | 0.347 | 0.085 | 0.125 |
| DPE | 0.000 | 0.000 | 0.000 | 0.000 | 0.000 | 0.000 | 0.000 | 0.000 | 0.000 |
| AE-TAEA | 0.000 | 0.000 | 0.000 | 0.000 | 0.000 | 0.000 | 0.000 | 0.000 | 0.000 |
| 1-TEPA | 0.000 | 0.000 | 0.463 | 0.000 | 0.000 | 0.000 | 0.848 | 0.318 | 0.401 |
| AE-DAEP | 0.000 | 0.000 | 0.000 | 0.000 | 0.000 | 0.000 | 0.181 | 0.000 | 0.000 |
| AE-PEEDA | 0.000 | 0.000 | 0.000 | 0.000 | 0.000 | 0.000 | 0.000 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.279 | 0.000 | 0.000 |
| BPEA | 0.000 | 0.000 | 0.000 | 0.000 | 0.000 | 0.000 | 0.000 | 0.000 | 0.000 |
| Others | 0.976 | 0.215 | 1.483 | 1.078 | 1.416 | 1.247 | 1.734 | 1.491 | 2.212 |
| MEA conversion, % | 20.13 | 12.23 | 32.26 | 12.02 | 24.15 | 14.16 | 38.70 | 28.47 | 29.14 |
| DETA conversion, % | 2.69 | 4.31 | 6.99 | 3.83 | 4.40 | 3.59 | 11.07 | 5.24 | 7.12 |
| Acyclic(N4), wt. % | 94.94 | 95.46 | 92.64 | 95.76 | 93.82 | 95.11 | 90.14 | 95.25 | 95.85 |
| Acyclic(N5), wt. % | — | — | 100.00 | — | — | — | 70.20 | 100.00 | 100.00 |
| Σ(N5)/Σ(N4), weight ratio | 0.00 | 0.00 | 0.00 | 0.00 | 0.00 | 0.00 | 0.16 | 0.05 | 0.05 |
| Acyclic(N4)/cyclic(<=N4), weight ratio | 4.13 | 3.63 | 2.31 | 3.90 | 3.26 | 3.90 | 2.24 | 3.45 | 3.82 |

TABLE CVII

| Example No. | 1064 | 1065 | 1066 | 1067 | 1068 | 1069 | 1070 | 1071 | 1072 |
|---|---|---|---|---|---|---|---|---|---|
| Catalyst Type | KKKKK | KKKKK | KKKKK | KKKKK | KKKKK | KKKKK | KKKKK | KKKKK | KKKKK |
| Catalyst weight, gm | 67.5 | 67.5 | 67.5 | 67.5 | 67.5 | 67.5 | 67.5 | 67.5 | 67.5 |
| Pressure, psig | 598 | 597 | 597 | 598 | 598 | 598 | 598 | 600 | 600 |
| Temperature, °C. | 270 | 270 | 280 | 260 | 270 | 260 | 280 | 280 | 270 |
| Time on organics, hrs. | 7 | 26 | 30.5 | 50 | 55 | 74 | 79 | 98.8 | 123 |
| Duration of run, hrs. | 2 | 2 | 1 | 2 | 2 | 2 | 2 | 2 | 2 |
| MEA SV, gmol/hr/kgcat | 3.62 | 3.73 | 3.53 | 3.46 | 3.70 | 3.56 | 3.47 | 3.46 | 3.40 |
| DETA/MEA mole ratio | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 |
| Crude product composition, wt. % | | | | | | | | | |
| EDA | 0.294 | 0.424 | 0.706 | 0.273 | 0.506 | 0.342 | 0.979 | 1.001 | 0.624 |
| MEA | 25.314 | 22.475 | 18.589 | 26.092 | 22.747 | 25.743 | 18.317 | 16.142 | 21.635 |
| PIP | 0.421 | 0.496 | 0.707 | 0.266 | 0.485 | 0.297 | 0.712 | 0.692 | 0.469 |
| DETA | 54.036 | 51.203 | 48.723 | 54.115 | 52.329 | 54.167 | 48.580 | 42.653 | 47.745 |
| AEEA | 1.899 | 2.033 | 1.670 | 2.115 | 2.193 | 2.258 | 1.799 | 1.403 | 1.963 |
| AEP | 0.488 | 0.616 | 0.869 | 0.374 | 0.614 | 0.438 | 0.855 | 0.848 | 0.588 |
| HEP | 0.000 | 0.000 | 0.000 | 0.000 | 0.000 | 0.000 | 0.000 | 0.000 | 0.000 |
| TAEA | 1.340 | 1.728 | 1.888 | 1.215 | 1.590 | 1.290 | 1.768 | 1.764 | 1.551 |
| 1-TETA | 6.203 | 8.239 | 9.101 | 5.680 | 7.515 | 6.023 | 8.740 | 9.202 | 7.737 |
| DAEP | 0.091 | 0.205 | 0.282 | 0.096 | 0.157 | 0.110 | 0.267 | 0.415 | 0.216 |
| PEEDA | 0.093 | 0.162 | 0.229 | 0.076 | 0.133 | 0.090 | 0.209 | 0.313 | 0.172 |
| DPE | 0.048 | 0.111 | 0.178 | 0.076 | 0.126 | 0.084 | 0.220 | 0.387 | 0.232 |
| AE-TAEA | 1.230 | 1.884 | 2.347 | 1.338 | 1.704 | 1.006 | 1.902 | 2.806 | 1.832 |
| 1-TEPA | 2.363 | 3.385 | 4.197 | 1.841 | 2.798 | 1.882 | 3.504 | 5.099 | 3.159 |

TABLE CVII-continued

| | | | | | | | | | |
|---|---|---|---|---|---|---|---|---|---|
| AE-DAEP | 0.139 | 0.145 | 0.257 | 0.143 | 0.273 | 0.114 | 0.392 | 0.812 | 0.539 |
| AE-PEEDA | 0.066 | 0.034 | 0.101 | 0.042 | 0.061 | 0.024 | 0.100 | 0.168 | 0.078 |
| iAE-PEEDA | 0.000 | 0.000 | 0.000 | 0.000 | 0.000 | 0.000 | 0.000 | 0.000 | 0.000 |
| AE-DPE | 0.000 | 0.043 | 0.117 | 0.077 | 0.157 | 0.090 | 0.062 | 0.343 | 0.035 |
| BPEA | 0.110 | 0.211 | 0.290 | 0.056 | 0.110 | 0.069 | 0.063 | 0.209 | 0.048 |
| Others | 2.415 | 3.286 | 4.610 | 2.509 | 3.660 | 2.432 | 4.633 | 8.202 | 4.835 |
| MEA conversion, % | 31.77 | 40.08 | 50.03 | 29.37 | 39.57 | 30.42 | 49.72 | 55.92 | 40.42 |
| DETA conversion, % | 13.44 | 18.87 | 22.15 | 12.94 | 17.39 | 12.99 | 20.75 | 30.77 | 21.85 |
| Acyclic(N4), wt. % | 97.01 | 95.43 | 94.10 | 96.54 | 95.63 | 96.27 | 93.80 | 90.77 | 93.73 |
| Acyclic(N5), wt. % | 91.93 | 92.41 | 89.53 | 90.91 | 88.22 | 90.67 | 89.75 | 83.77 | 87.68 |
| $\Sigma$(N5)/$\Sigma$(N4), weight ratio | 0.50 | 0.55 | 0.63 | 0.49 | 0.54 | 0.42 | 0.54 | 0.78 | 0.57 |
| Acyclic(N4)/cyclic($<=$N4), weight ratio | 6.61 | 6.27 | 4.85 | 7.78 | 6.01 | 7.18 | 4.65 | 4.13 | 5.53 |

| Example No. | 1073 | 1074 | 1075 | 1076 | 1077 | 1078 | 1079 | 1080 | 1081 | 1082 |
|---|---|---|---|---|---|---|---|---|---|---|
| Catalyst Type | KKKKK | KKKKK | KKKKK | KKKKK | KKKKK | KKKKK | KKKKK | KKKKK | KKKKK | KKKKK |
| Catalyst weight, gm | 67.5 | 67.5 | 67.5 | 67.5 | 67.5 | 67.5 | 67.5 | 67.5 | 67.5 | 67.5 |
| Pressure, psig | 585 | 598 | 598 | 598 | 598 | 598 | 598 | 598 | 598 | 598 |
| Temperature, °C. | 271 | 282 | 260 | 270 | 260 | 281 | 272 | 280 | 272 | 271 |
| Time on organics, hrs. | 158 | 163 | 182 | 187 | 206 | 211 | 272 | 235 | 254 | 257.5 |
| Duration of run, hrs. | 2 | 2 | 2 | 2 | 2 | 2 | 2 | 2 | 2 | 2 |
| MEA SV, gmol/hr/kgcat | 2.97 | 3.69 | 3.58 | 3.41 | 3.41 | 3.54 | 3.99 | 3.53 | 3.50 | 3.70 |
| DETA/MEA mole ratio | 1.00 | 1.00 | 1.00 | 1.00 | 1.00 | 1.00 | 1.00 | 1.00 | 1.00 | 1.00 |
| NH3/MEA mole ratio | 5.97 | 5.97 | 5.97 | 5.97 | 5.97 | 5.97 | 5.97 | 5.97 | 5.97 | 5.97 |
| Crude product composition, wt. % | | | | | | | | | | |
| EDA | 0.764 | 1.129 | 0.479 | 0.786 | 0.509 | 1.756 | 1.803 | 1.993 | 1.749 | 1.597 |
| MEA | 20.571 | 16.885 | 25.262 | 21.504 | 25.342 | 18.397 | 20.631 | 15.100 | 20.996 | 22.350 |
| PIP | 0.531 | 0.826 | 0.351 | 0.538 | 0.352 | 0.865 | 0.634 | 0.781 | 0.638 | 0.567 |
| DETA | 47.941 | 46.768 | 52.656 | 48.687 | 51.138 | 47.357 | 46.647 | 42.162 | 46.440 | 48.370 |
| AEEA | 1.707 | 1.530 | 2.132 | 1.979 | 2.129 | 1.620 | 1.739 | 1.446 | 1.730 | 1.824 |
| AEP | 0.697 | 1.034 | 0.470 | 0.636 | 0.432 | 0.927 | 0.707 | 0.935 | 0.676 | 0.626 |
| HEP | 0.000 | 0.000 | 0.000 | 0.000 | 0.000 | 0.000 | 0.000 | 0.000 | 0.000 | 0.000 |
| TAEA | 1.641 | 1.964 | 1.408 | 1.541 | 1.337 | 1.743 | 1.648 | 1.942 | 1.596 | 1.530 |
| 1-TETA | 8.006 | 9.717 | 6.641 | 7.305 | 6.278 | 8.432 | 8.037 | 9.595 | 7.922 | 7.422 |
| DAEP | 0.239 | 0.408 | 0.135 | 0.174 | 0.125 | 0.291 | 0.359 | 0.442 | 0.295 | 0.232 |
| PEEDA | 0.186 | 0.297 | 0.101 | 0.138 | 0.094 | 0.224 | 0.234 | 0.314 | 0.215 | 0.169 |
| DPE | 0.211 | 0.069 | 0.110 | 0.183 | 0.114 | 0.089 | 0.099 | 0.103 | 0.182 | 0.107 |
| AE-TAEA | 1.858 | 2.661 | 1.266 | 1.659 | 1.462 | 2.013 | 2.165 | 2.975 | 2.063 | 1.905 |
| 1-TEPA | 3.247 | 5.154 | 2.314 | 2.935 | 2.396 | 3.688 | 3.984 | 5.395 | 3.860 | 3.394 |
| AE-DAEP | 0.401 | 0.342 | 0.130 | 0.223 | 0.173 | 0.261 | 0.335 | 0.507 | 0.256 | 0.234 |
| AE-PEEDA | 0.057 | 0.062 | 0.025 | 0.068 | 0.063 | 0.045 | 0.076 | 0.117 | 0.056 | 0.042 |
| iAE-PEEDA | 0.000 | 0.000 | 0.000 | 0.000 | 0.000 | 0.000 | 0.000 | 0.000 | 0.000 | 0.000 |
| AE-DPE | 0.053 | 0.067 | 0.086 | 0.211 | 0.083 | 0.034 | 0.229 | 0.080 | 0.055 | 0.040 |
| BPEA | 0.051 | 0.390 | 0.040 | 0.087 | 0.037 | 0.225 | 0.294 | 0.465 | 0.272 | 0.231 |
| Others | 4.459 | 5.997 | 2.874 | 5.176 | 3.565 | 5.035 | 6.480 | 8.307 | 5.107 | 4.381 |
| MEA conversion, % | 42.93 | 55.07 | 31.89 | 40.98 | 31.07 | 49.41 | 44.79 | 58.84 | 42.66 | 39.29 |
| DETA conversion, % | 20.95 | 26.04 | 15.63 | 20.58 | 17.33 | 22.60 | 25.81 | 31.71 | 24.63 | 31.91 |
| Acyclic(N4), wt. % | 93.81 | 93.79 | 95.88 | 94.70 | 95.80 | 94.40 | 93.33 | 93.06 | 93.21 | 94.64 |
| Acyclic(N5), wt. % | 90.08 | 90.08 | 92.72 | 88.64 | 91.56 | 90.98 | 86.82 | 87.74 | 90.25 | 90.67 |
| $\Sigma$(N5)/$\Sigma$(N4), weight ratio | 0.55 | 0.70 | 0.46 | 0.55 | 0.53 | 0.58 | 0.68 | 0.77 | 0.64 | 0.62 |
| Acyclic(N4)/cyclic ($<=$N4), weight ratio | 5.17 | 4.43 | 6.90 | 5.30 | 6.82 | 4.25 | 4.76 | 4.48 | 4.74 | 5.26 |

TABLE CVIII

| Example No. | 1083 | 1084 | 1085 | 1086 | 1087 | 1088 | 1089 | 1090 | 1091 | 1092 | 1093 |
|---|---|---|---|---|---|---|---|---|---|---|---|
| Catalyst Type | LLLLL | LLLLL | LLLLL | LLLLL | LLLLL | LLLLL | LLLLL | LLLLL | LLLLL | LLLLL | LLLLL |
| Catalyst weight, gm | 89.3 | 89.3 | 89.3 | 89.3 | 89.3 | 89.3 | 89.3 | 89.3 | 89.3 | 89.3 | 89.3 |
| Pressure, psig | 600 | 600 | 600 | 600 | 600 | 600 | 600 | 600 | 600 | 600 | 600 |
| Temperature, °C. | 270.4 | 271 | 280.8 | 260.7 | 270.6 | 260 | 280 | 251.2 | 260.9 | 246 | 256 |
| Time on organics, hrs. | 6 | 25 | 30 | 49 | 54 | 75 | 98 | 122 | 126 | 146 | 150 |
| Duration of run, hrs. | 2 | 2 | 2 | 2 | 2 | 2 | 2 | 2 | 2 | 2 | 2 |
| MEA SV, gmol/hr/kgcat | 2.58 | 3.38 | 3.44 | 3.51 | 3.60 | 3.57 | 3.24 | 3.36 | 3.38 | 3.39 | 3.40 |
| DETA/MEA mole ratio | 0.99 | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 | 5.98 |
| Crude product composition, wt. % | | | | | | | | | | | |
| EDA | 7.581 | 5.561 | 8.937 | 2.704 | 3.955 | 2.560 | 6.744 | 1.365 | 2.123 | 1.102 | 1.555 |
| MEA | 5.649 | 4.652 | 1.477 | 12.445 | 6.771 | 14.307 | 1.922 | 20.539 | 13.637 | 23.785 | 17.583 |
| PIP | 2.611 | 2.188 | 3.634 | 1.038 | 1.673 | 1.040 | 2.760 | 0.505 | 0.844 | 0.316 | 0.605 |
| DETA | 20.830 | 22.594 | 17.418 | 33.381 | 27.328 | 37.933 | 21.040 | 44.901 | 35.026 | 47.146 | 40.284 |

TABLE CVIII-continued

| Example No. | 1083 | 1084 | 1085 | 1086 | 1087 | 1088 | 1089 | 1090 | 1091 | 1092 | 1093 |
|---|---|---|---|---|---|---|---|---|---|---|---|
| AEEA | 0.277 | 0.720 | 0.119 | 1.862 | 1.082 | 2.151 | 0.214 | 2.495 | 2.047 | 2.268 | 2.300 |
| AEP | 4.086 | 3.847 | 6.035 | 1.539 | 2.846 | 1.511 | 4.978 | 0.671 | 1.240 | 0.438 | 0.841 |
| HEP | 0.000 | 0.000 | 0.000 | 0.000 | 0.000 | 0.000 | 0.000 | 0.000 | 0.000 | 0.000 | 0.000 |
| TAEA | 0.417 | 1.005 | 0.410 | 1.722 | 1.235 | 1.843 | 0.687 | 1.801 | 1.866 | 1.600 | 1.913 |
| 1-TETA | 6.468 | 10.968 | 6.099 | 13.376 | 11.500 | 13.551 | 8.038 | 12.034 | 13.031 | 10.358 | 13.283 |
| DAEP | 0.214 | 2.647 | 3.666 | 0.817 | 1.651 | 0.668 | 3.053 | 0.199 | 0.603 | 0.134 | 0.303 |
| PEEDA | 1.910 | 2.007 | 3.593 | 0.689 | 1.305 | 0.551 | 2.822 | 0.149 | 0.453 | 0.084 | 0.234 |
| DPE | 0.511 | 0.786 | 0.396 | 0.496 | 0.519 | 0.388 | 0.407 | 0.158 | 0.444 | 0.132 | 0.278 |
| AE-TAEA | 1.200 | 2.252 | 1.072 | 2.980 | 2.621 | 3.187 | 1.564 | 2.189 | 3.092 | 1.688 | 2.780 |
| 1-TEPA | 4.021 | 8.850 | 3.847 | 8.247 | 8.806 | 7.806 | 6.952 | 4.035 | 7.515 | 3.427 | 5.980 |
| AE-DAEP | 2.544 | 2.479 | 3.363 | 0.847 | 1.622 | 0.596 | 2.586 | 0.217 | 0.561 | 0.186 | 0.310 |
| AE-PEEDA | 1.209 | 1.148 | 1.857 | 0.301 | 0.275 | 0.127 | 0.657 | 0.082 | 0.144 | 0.229 | 0.085 |
| iAE-PEEDA | 0.000 | 0.000 | 0.000 | 0.000 | 0.000 | 0.000 | 0.000 | 0.000 | 0.000 | 0.000 | 0.000 |
| AE-DPE | 0.400 | 0.546 | 0.786 | 0.214 | 0.327 | 0.203 | 0.511 | 0.072 | 0.356 | 0.213 | 0.271 |
| BPEA | 0.426 | 0.441 | 0.406 | 0.579 | 0.417 | 0.504 | 0.538 | 0.049 | 0.256 | 0.087 | 0.212 |
| Others | 28.967 | 19.631 | 26.356 | 9.863 | 15.860 | 3.864 | 21.819 | 3.947 | 10.343 | 2.978 | 6.374 |
| MEA conversion, % | 84.58 | 87.85 | 96.06 | 66.71 | 81.58 | 61.26 | 94.72 | 44.71 | 63.52 | 35.97 | 53.12 |
| DETA conversion, % | 68.31 | 65.04 | 72.53 | 47.07 | 55.94 | 39.12 | 65.80 | 28.35 | 44.46 | 24.76 | 36.33 |
| Acyclic(N4), % | 72.31 | 68.75 | 45.95 | 88.28 | 78.55 | 90.54 | 58.43 | 96.46 | 90.84 | 97.14 | 94.89 |
| Acyclic(N5), % | 53.27 | 70.63 | 43.41 | 85.24 | 81.21 | 88.47 | 66.48 | 93.63 | 88.94 | 87.72 | 90.87 |
| $\Sigma(N5)/\Sigma(N4)$, weight ratio | 1.02 | 0.90 | 0.80 | 0.77 | 0.86 | 0.73 | 0.85 | 0.46 | 0.72 | 0.47 | 0.60 |
| Acyclic(N4)/cyclic($<=$N4), weight ratio | 0.73 | 1.04 | 0.37 | 3.29 | 1.59 | 3.70 | 0.62 | 8.20 | 4.15 | 10.80 | 6.71 |

TABLE CIX

| Example No. | 1094 | 1095 | 1096 | 1097 | 1098 | 1099 | 1100 | 1101 |
|---|---|---|---|---|---|---|---|---|
| Catalyst Type | MMMMM | MMMMM | MMMMM | MMMMM | MMMMM | MMMMM | MMMMM | MMMMM |
| Catalyst weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 249.9 | 259.9 | 270 | 265 | 275 | 280.7 | 245.4 | 255.6 |
| Time on organics, hrs. | 23 | 27 | 48 | 53 | 71 | 96 | 119 | 143 |
| Duration of run, hrs. | 2 | 2 | 2 | 2 | 2 | 2 | 2 | 2 |
| MEA SV, gmol/hr/kgcat | 3.68 | 3.83 | 3.55 | 3.76 | 3.33 | 3.79 | 3.95 | 3.85 |
| DETA/MEA mole ratio | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 |
| Crude product composition, wt. % | | | | | | | | |
| EDA | 1.576 | 2.613 | 3.978 | 3.156 | 5.524 | 6.509 | 0.996 | 1.499 |
| MEA | 17.638 | 11.313 | 5.763 | 9.706 | 3.516 | 3.037 | 24.706 | 19.664 |
| PIP | 0.661 | 1.130 | 1.710 | 1.360 | 2.341 | 2.601 | 0.354 | 0.600 |
| DETA | 39.776 | 31.481 | 24.483 | 30.274 | 23.630 | 21.989 | 47.915 | 42.143 |
| AEEA | 2.240 | 1.704 | 1.039 | 1.469 | 0.510 | 0.312 | 1.910 | 2.051 |
| AEP | 0.977 | 1.950 | 3.062 | 2.204 | 4.152 | 4.514 | 0.487 | 0.818 |
| HEP | 0.000 | 0.000 | 0.000 | 0.000 | 0.000 | 0.000 | 0.000 | 0.000 |
| TAEA | 1.670 | 1.413 | 1.130 | 1.389 | 0.831 | 0.617 | 1.418 | 1.634 |
| 1-TETA | 13.251 | 13.353 | 12.483 | 13.317 | 11.047 | 9.109 | 9.280 | 11.618 |
| DAEP | 0.478 | 1.311 | 2.314 | 1.454 | 2.807 | 3.039 | 0.151 | 0.330 |
| PEEDA | 0.351 | 0.887 | 1.565 | 0.988 | 2.444 | 2.697 | 0.112 | 0.237 |
| DPE | 0.312 | 0.494 | 0.685 | 0.566 | 0.162 | 0.218 | 0.143 | 0.272 |
| AE-TAEA | 2.637 | 2.967 | 2.606 | 2.999 | 0.260 | 0.286 | 1.553 | 2.328 |
| 1-TEPA | 6.180 | 8.339 | 9.381 | 8.829 | 8.372 | 6.929 | 2.536 | 4.917 |
| AE-DAEP | 0.385 | 1.116 | 1.890 | 1.178 | 2.735 | 0.320 | 0.103 | 0.269 |
| AE-PEEDA | 0.094 | 0.460 | 0.627 | 0.505 | 0.663 | 0.684 | 0.051 | 0.063 |
| iAE-PEEDA | 0.000 | 0.000 | 0.000 | 0.000 | 0.000 | 0.000 | 0.000 | 0.000 |
| AE-DPE | 0.203 | 0.336 | 0.071 | 0.097 | 0.053 | 0.192 | 0.186 | 0.135 |
| BPEA | 0.099 | 0.280 | 0.687 | 0.358 | 0.583 | 0.477 | 0.063 | 0.072 |
| Others | 6.086 | 11.972 | 16.987 | 14.062 | 19.743 | 24.147 | 2.010 | 4.512 |
| MEA conversion, % | 52.70 | 69.92 | 84.56 | 74.53 | 90.51 | 91.63 | 31.61 | 45.99 |
| DETA conversion, % | 36.77 | 50.39 | 61.12 | 52.92 | 62.23 | 64.10 | 21.37 | 31.38 |
| Acyclic(N4), % | 92.89 | 84.57 | 74.88 | 83.01 | 68.69 | 62.02 | 96.33 | 94.03 |
| Acyclic(N5), % | 91.85 | 83.74 | 78.54 | 84.68 | 68.15 | 81.17 | 91.02 | 93.05 |
| $\Sigma(N5)/\Sigma(N4)$, weight ratio | 0.59 | 0.77 | 0.84 | 0.78 | 0.73 | 0.56 | 0.40 | 0.55 |
| Acyclic(N4)/cyclic($<=$N4), weight ratio | 5.36 | 2.55 | 1.45 | 2.23 | 0.99 | 0.74 | 8.56 | 5.86 |

TABLE CX

| Example No. | 1102 | 1103 | 1104 | 1105 | 1106 | 1107 | 1108 | 1109 |
|---|---|---|---|---|---|---|---|---|
| Catalyst Type | NNNNN | NNNNN | NNNNN | NNNNN | NNNNN | NNNNN | NNNNN | NNNNN |
| Catalyst weight, gm | 50 | 50 | 50 | 50 | 50 | 50 | 50 | 50 |
| Pressure, psig | 600 | 600 | 600 | 600 | 600 | 600 | 600 | 600 |

TABLE CX-continued

| Example No. | 1102 | 1103 | 1104 | 1105 | 1106 | 1107 | 1108 | 1109 |
|---|---|---|---|---|---|---|---|---|
| Temperature, °C. | 249.9 | 259.9 | 270 | 265 | 275 | 280.7 | 245.4 | 255.6 |
| Time on organics, hrs. | 23 | 27 | 48 | 53 | 71 | 96 | 119 | 143 |
| Duration of run, hrs. | 2 | 2 | 2 | 2 | 2 | 2 | 2 | 2 |
| MEA SV, gmol/hr/kgcat | 4.13 | 4.06 | 3.61 | 3.95 | 3.59 | 3.73 | 3.92 | 3.85 |
| DETA/MEA mole ratio | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 1.549 | 2.657 | 3.816 | 2.918 | 4.945 | 5.969 | 0.647 | 1.041 |
| MEA | 26.153 | 22.877 | 17.520 | 20.205 | 16.087 | 14.680 | 30.721 | 27.460 |
| PIP | 1.065 | 1.698 | 3.017 | 2.402 | 3.952 | 4.620 | 0.575 | 0.919 |
| DETA | 45.023 | 38.851 | 29.155 | 34.030 | 27.311 | 23.227 | 52.572 | 47.799 |
| AEEA | 1.218 | 0.982 | 0.837 | 1.081 | 0.676 | 0.509 | 1.117 | 1.247 |
| AEP | 1.053 | 1.832 | 3.443 | 2.575 | 4.691 | 5.337 | 0.059 | 0.880 |
| HEP | 0.000 | 0.000 | 0.000 | 0.000 | 0.000 | 0.000 | 0.000 | 0.000 |
| TAEA | 0.900 | 0.792 | 0.594 | 0.766 | 0.491 | 0.319 | 0.738 | 0.840 |
| 1-TETA | 5.944 | 6.306 | 6.128 | 6.849 | 5.723 | 4.369 | 4.214 | 5.237 |
| DAEP | 0.360 | 0.709 | 1.430 | 1.052 | 2.070 | 2.354 | 0.120 | 0.254 |
| PEEDA | 0.397 | 0.866 | 2.099 | 1.325 | 2.733 | 3.018 | 0.131 | 0.289 |
| DPE | 0.253 | 0.301 | 0.310 | 0.288 | 0.386 | 0.613 | 0.086 | 0.156 |
| AE-TAEA | 0.991 | 0.999 | 0.917 | 1.079 | 0.819 | 0.226 | 0.604 | 0.915 |
| 1-TEPA | 4.013 | 4.927 | 5.460 | 5.824 | 4.414 | 3.018 | 2.018 | 2.952 |
| AE-DAEP | 0.401 | 0.835 | 1.545 | 1.161 | 2.224 | 2.681 | 0.112 | 0.278 |
| AE-PEEDA | 0.400 | 0.554 | 0.512 | 0.489 | 0.511 | 0.542 | 0.121 | 0.220 |
| iAE-PEEDA | 0.000 | 0.000 | 0.000 | 0.000 | 0.000 | 0.000 | 0.000 | 0.000 |
| AE-DPE | 0.324 | 0.318 | 0.392 | 0.318 | 0.632 | 0.239 | 0.000 | 0.089 |
| BPEA | 0.176 | 0.309 | 0.369 | 0.281 | 0.202 | 0.202 | 0.054 | 0.073 |
| Others | 7.341 | 11.517 | 13.927 | 12.910 | 15.843 | 20.589 | 2.521 | 3.702 |
| MEA conversion, % | 30.67 | 40.03 | 52.14 | 46.63 | 57.49 | 60.93 | 15.90 | 24.03 |
| DETA conversion, % | 29.24 | 39.62 | 52.78 | 46.72 | 57.22 | 63.35 | 14.68 | 21.60 |
| Acyclic(N4), % | 87.11 | 79.08 | 63.63 | 74.06 | 54.49 | 43.92 | 93.59 | 89.67 |
| Acyclic(N5), % | 79.35 | 74.60 | 69.34 | 75.42 | 59.44 | 46.96 | 90.10 | 85.38 |
| Σ(N5)/Σ(N4), weight ratio | 0.80 | 0.88 | 0.87 | 0.89 | 0.77 | 0.64 | 0.55 | 0.66 |
| Acyclic(N4)/cyclic(<=N4), weight ratio | 2.19 | 1.31 | 0.65 | 0.99 | 0.44 | 0.29 | 5.08 | 2.43 |

TABLE CXI

| Example No. | 1110 | 1111 | 1112 | 1113 | 1114 | 1115 | 1116 | 1117 | 1118 | 1119 |
|---|---|---|---|---|---|---|---|---|---|---|
| Catalyst Type | OOOOO | OOOOO | OOOOO | OOOOO | OOOOO | OOOOO | OOOOO | OOOOO | OOOOO | OOOOO |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.9 | 259.9 | 270 | 265 | 275 | 280.7 | 245.4 | 255.6 | 250.7 | 249.7 |
| Time on organics, hrs. | 23 | 27 | 48 | 53 | 71 | 96 | 119 | 143 | 4 | 22.5 |
| Duration of run, hrs. | 2 | 2 | 2 | 2 | 2 | 2 | 2 | 2 | 2 | 2 |
| MEA SV, gmol/hr/kgcat | 3.91 | 3.98 | 3.24 | 3.97 | 3.68 | 3.71 | 3.62 | 3.79 | 5.16 | 4.70 |
| DETA/MEA mole ratio | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.813 | 1.260 | 2.398 | 1.598 | 2.314 | 2.549 | 0.484 | 0.749 | 1.094 | 0.827 |
| MEA | 21.532 | 15.622 | 10.867 | 13.317 | 7.792 | 5.589 | 27.925 | 23.876 | 20.059 | 23.108 |
| PIP | 0.251 | 0.421 | 0.882 | 0.590 | 0.731 | 0.778 | 0.097 | 0.183 | 0.327 | 0.225 |
| DETA | 47.006 | 39.567 | 32.817 | 35.817 | 32.340 | 29.857 | 52.926 | 48.757 | 43.271 | 47.311 |
| AEEA | 2.748 | 2.642 | 1.046 | 2.119 | 1.372 | 1.018 | 1.990 | 2.368 | 2.409 | 2.483 |
| AEP | 0.401 | 0.686 | 1.551 | 0.829 | 1.174 | 1.246 | 0.252 | 0.319 | 0.548 | 0.347 |
| HEP | 0.000 | 0.000 | 0.000 | 0.000 | 0.000 | 0.000 | 0.000 | 0.000 | 0.000 | 0.000 |
| TAEA | 1.801 | 1.987 | 1.375 | 1.958 | 2.017 | 1.874 | 1.232 | 1.615 | 1.501 | 1.592 |
| 1-TETA | 12.031 | 14.750 | 10.951 | 12.866 | 14.396 | 13.387 | 6.891 | 9.157 | 11.936 | 10.715 |
| DAEP | 0.111 | 0.253 | 1.051 | 0.455 | 0.782 | 0.853 | 0.046 | 0.075 | 0.225 | 0.098 |
| PEEDA | 0.080 | 0.230 | 0.708 | 0.335 | 0.543 | 0.599 | 0.043 | 0.066 | 0.181 | 0.076 |
| DPE | 0.112 | 0.173 | 0.437 | 0.453 | 0.539 | 0.630 | 0.067 | 0.139 | 0.174 | 0.137 |
| AE-TAEA | 1.968 | 2.920 | 2.711 | 3.016 | 4.316 | 4.170 | 0.874 | 1.511 | 2.199 | 1.958 |
| 1-TEPA | 4.549 | 6.175 | 7.240 | 6.904 | 8.891 | 9.110 | 1.270 | 2.338 | 4.246 | 3.296 |
| AE-DAEP | 0.057 | 0.500 | 1.079 | 0.522 | 0.775 | 0.951 | 0.060 | 0.082 | 0.326 | 0.147 |
| AE-PEEDA | 0.000 | 0.477 | 0.256 | 0.215 | 0.250 | 0.299 | 0.000 | 0.000 | 0.181 | 0.127 |
| iAE-PEEDA | 0.000 | 0.000 | 0.000 | 0.000 | 0.000 | 0.000 | 0.000 | 0.000 | 0.000 | 0.000 |
| AE-DPE | 0.058 | 0.314 | 0.301 | 0.358 | 0.368 | 0.496 | 0.053 | 0.099 | 0.286 | 0.112 |
| BPEA | 0.185 | 0.182 | 0.313 | 0.582 | 0.348 | 0.444 | 0.056 | 0.141 | 0.107 | 0.050 |
| Others | 2.088 | 7.250 | 12.439 | 11.787 | 13.042 | 15.672 | 1.167 | 1.829 | 5.810 | 3.174 |
| MEA conversion, % | 42.08 | 58.67 | 69.47 | 64.44 | 79.13 | 84.73 | 23.07 | 33.43 | 45.87 | 37.58 |
| DETA conversion, % | 25.04 | 37.95 | 45.35 | 43.31 | 48.67 | 51.65 | 13.57 | 19.42 | 30.78 | 24.24 |
| Acyclic(N4), % | 97.84 | 96.21 | 84.86 | 92.25 | 89.78 | 87.99 | 98.09 | 97.46 | 95.84 | 97.51 |
| Acyclic(N5), % | 95.56 | 86.04 | 83.61 | 85.52 | 88.33 | 85.83 | 92.64 | 92.25 | 87.72 | 92.30 |
| Σ(N5)/Σ(N4), weight ratio | 0.48 | 0.60 | 0.81 | 0.72 | 0.81 | 0.89 | 0.27 | 0.37 | 0.52 | 0.45 |
| Acyclic(N4)/cyclic (<=N4), weight ratio | 14.43 | 9.47 | 2.66 | 5.56 | 4.35 | 3.71 | 16.01 | 13.75 | 9.21 | 13.89 |
| Example No. | 1120 | 1121 | 1122 | 1123 | 1124 | 1125 | 1126 | 1127 | 1128 | 1129 |
| Catalyst Type | OOOOO | OOOOO | OOOOO | OOOOO | OOOOO | OOOOO | OOOOO | OOOOO | OOOOO | OOOOO |

TABLE CXI-continued

| | | | | | | | | | | |
|---|---|---|---|---|---|---|---|---|---|---|
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 260 | 255.5 | 265.5 | 260.5 | 270.1 | 250.6 | 250 | 265.2 | 275.2 | 270.3 |
| Time on organics, hrs. | 28 | 46.5 | 52 | 71.5 | 76 | 95.5 | 118 | 145 | 148 | 170 |
| Duration of run, hrs. | 2 | 2 | 2 | 2 | 2 | 2 | 2 | 2 | 2 | 2 |
| MEA SV, gmol/hr/kgcat | 5.01 | 4.40 | 4.64 | 4.92 | 4.88 | 4.87 | 4.45 | 4.02 | 3.87 | 3.87 |
| DETA/MEA mole ratio | 0.99 | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 1.292 | 1.045 | 1.658 | 1.287 | 1.756 | 0.653 | 0.658 | 1.445 | 2.153 | 1.729 |
| MEA | 16.448 | 21.025 | 15.267 | 18.822 | 12.662 | 24.836 | 24.781 | 17.208 | 11.166 | 13.488 |
| PIP | 0.399 | 0.287 | 0.516 | 0.337 | 0.537 | 0.161 | 0.156 | 0.414 | 0.698 | 0.492 |
| DETA | 39.380 | 43.930 | 37.874 | 42.302 | 36.372 | 48.917 | 49.188 | 40.090 | 34.966 | 37.519 |
| AEEA | 2.393 | 2.382 | 2.051 | 2.263 | 1.834 | 2.123 | 2.116 | 1.781 | 1.886 | 1.571 |
| AEP | 0.583 | 0.411 | 0.711 | 0.476 | 0.801 | 0.303 | 0.298 | 0.559 | 0.957 | 0.762 |
| HEP | 0.000 | 0.000 | 0.000 | 0.000 | 0.000 | 0.000 | 0.000 | 0.000 | 0.000 | 0.000 |
| TAEA | 1.770 | 1.662 | 1.767 | 1.798 | 1.909 | 1.483 | 1.480 | 1.667 | 1.789 | 1.659 |
| l-TETA | 13.854 | 11.854 | 12.904 | 12.705 | 13.617 | 9.174 | 9.069 | 11.193 | 12.877 | 11.276 |
| DAEP | 0.249 | 0.137 | 0.361 | 0.199 | 0.443 | 0.094 | 0.073 | 0.298 | 0.501 | 0.557 |
| PEEDA | 0.183 | 0.102 | 0.256 | 0.143 | 0.304 | 0.067 | 0.057 | 0.210 | 0.366 | 0.360 |
| DPE | 0.205 | 0.156 | 0.410 | 0.181 | 0.122 | 0.066 | 0.128 | 0.100 | 0.135 | 0.412 |
| AE-TAEA | 3.040 | 2.393 | 3.401 | 2.775 | 3.772 | 1.512 | 1.451 | 2.977 | 3.693 | 3.182 |
| l-TEPA | 5.724 | 4.313 | 6.650 | 4.894 | 6.982 | 2.416 | 2.266 | 5.519 | 7.108 | 5.762 |
| AE-DAEP | 0.392 | 0.289 | 0.446 | 0.324 | 0.477 | 0.105 | 0.070 | 0.367 | 0.112 | 0.680 |
| AE-PEEDA | 0.182 | 0.086 | 0.178 | 0.101 | 0.174 | 0.062 | 0.029 | 0.122 | 0.140 | 0.117 |
| iAE-PEEDA | 0.000 | 0.000 | 0.000 | 0.000 | 0.000 | 0.000 | 0.000 | 0.000 | 0.000 | 0.000 |
| AE-DPE | 0.279 | 0.133 | 0.078 | 0.141 | 0.077 | 0.044 | 0.046 | 0.058 | 0.278 | 0.193 |
| BPEA | 0.278 | 0.178 | 0.626 | 0.192 | 0.706 | 0.129 | 0.129 | 0.572 | 0.680 | 0.209 |
| Others | 7.869 | 5.310 | 8.286 | 5.602 | 9.166 | 2.965 | 2.416 | 7.580 | 9.685 | 10.183 |
| MEA conversion, % | 55.95 | 43.59 | 58.83 | 49.17 | 65.41 | 32.04 | 31.64 | 52.56 | 68.72 | 62.38 |
| DETA conversion, % | 37.48 | 30.13 | 39.45 | 32.28 | 41.11 | 20.65 | 19.56 | 34.48 | 41.95 | 37.97 |
| Acyclic(N4), % | 96.06 | 97.15 | 93.45 | 96.51 | 94.69 | 97.89 | 97.60 | 95.47 | 93.59 | 90.67 |
| Acyclic(N5), % | 88.54 | 90.71 | 88.30 | 90.98 | 88.22 | 92.00 | 93.08 | 88.34 | 89.91 | 88.16 |
| Σ(N5)/Σ(N4), weight ratio | 0.60 | 0.53 | 0.72 | 0.56 | 0.74 | 0.39 | 0.36 | 0.71 | 0.76 | 0.71 |
| Acyclic(N4)/cyclic (<=N4), weight ratio | 9.63 | 12.34 | 6.50 | 10.84 | 7.02 | 15.35 | 14.76 | 8.11 | 5.51 | 5.00 |

| Example No. | 1130 | 1131 | 1132 | 1133 | 1134 | 1135 | 1136 | 1137 | 1138 |
|---|---|---|---|---|---|---|---|---|---|
| Catalyst Type | OOOOO | OOOOO | OOOOO | OOOOO | OOOOO | OOOOO | OOOOO | OOOOO | OOOOO |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 280.7 | 250.7 | 265.7 | 259.9 | 270 | 250.4 | 265.5 | 250 | 250 |
| Time on organics, hrs. | 172 | 191 | 196 | 216 | 220 | 239 | 244 | 262 | 286 |
| Duration of run, hrs. | 2 | 2 | 2 | 2 | 2 | 2 | 2 | 2 | 2 |
| MEA SV, gmol/hr/kgcat | 3.95 | 4.44 | 4.42 | 4.32 | 4.52 | 4.32 | 4.59 | 4.28 | 3.96 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 2.487 | 0.562 | 1.308 | 0.998 | 1.594 | 0.620 | 1.133 | 0.494 | 0.560 |
| MEA | 8.016 | 26.365 | 19.043 | 21.551 | 14.399 | 26.157 | 17.426 | 24.474 | 23.986 |
| PIP | 0.837 | 0.141 | 0.371 | 0.259 | 0.462 | 0.139 | 0.304 | 0.127 | 0.146 |
| DETA | 31.719 | 51.019 | 41.915 | 45.886 | 37.620 | 49.403 | 39.117 | 47.899 | 48.509 |
| AEEA | 1.511 | 2.181 | 2.319 | 2.375 | 1.945 | 2.052 | 2.033 | 1.815 | 1.816 |
| AEP | 1.224 | 0.289 | 0.484 | 0.404 | 0.668 | 0.283 | 0.454 | 0.283 | 0.038 |
| HEP | 0.000 | 0.000 | 0.000 | 0.000 | 0.000 | 0.000 | 0.000 | 0.000 | 0.000 |
| TAEA | 1.853 | 1.399 | 1.786 | 1.788 | 1.875 | 1.377 | 1.723 | 1.389 | 1.454 |
| l-TETA | 13.608 | 8.273 | 11.292 | 10.921 | 12.338 | 7.973 | 10.608 | 7.992 | 8.498 |
| DAEP | 0.762 | 0.078 | 0.234 | 0.143 | 0.335 | 0.095 | 0.209 | 0.102 | 0.104 |
| PEEDA | 0.533 | 0.051 | 0.168 | 0.103 | 0.259 | 0.072 | 0.149 | 0.071 | 0.079 |
| DPE | 0.509 | 0.144 | 0.321 | 0.215 | 0.438 | 0.171 | 0.354 | 0.160 | 0.170 |
| AE-TAEA | 4.179 | 1.285 | 2.934 | 2.270 | 3.574 | 1.424 | 2.823 | 1.514 | 1.614 |
| l-TEPA | 8.123 | 2.016 | 4.826 | 3.679 | 6.077 | 2.067 | 4.493 | 2.110 | 2.426 |
| AE-DAEP | 0.938 | 0.067 | 0.268 | 0.108 | 0.461 | 0.171 | 0.264 | 0.267 | 0.166 |
| AE-PEEDA | 0.201 | 0.060 | 0.086 | 0.066 | 0.101 | 0.061 | 0.134 | 0.107 | 0.000 |
| iAE-PEEDA | 0.000 | 0.000 | 0.000 | 0.000 | 0.000 | 0.000 | 0.000 | 0.000 | 0.000 |
| AE-DPE | 0.098 | 0.084 | 0.239 | 0.087 | 0.138 | 0.112 | 0.246 | 0.120 | 0.053 |
| BPEA | 0.850 | 0.042 | 0.137 | 0.075 | 0.193 | 0.046 | 0.175 | 0.053 | 0.056 |
| Others | 12.032 | 2.444 | 6.821 | 4.133 | 9.534 | 2.987 | 7.006 | 3.146 | 3.176 |
| MEA conversion, % | 77.91 | 28.64 | 48.59 | 41.59 | 60.59 | 28.29 | 49.91 | 30.83 | 33.03 |
| DETA conversion, % | 48.20 | 18.14 | 32.92 | 26.27 | 38.96 | 19.71 | 33.35 | 19.75 | 19.71 |
| Acyclic(N4), % | 89.54 | 97.24 | 94.75 | 96.48 | 93.21 | 96.49 | 94.53 | 96.56 | 96.56 |
| Acyclic(N5), % | 85.48 | 92.81 | 91.37 | 94.61 | 91.34 | 89.90 | 89.90 | 86.86 | 93.58 |
| Σ(N5)/Σ(N4), weight ratio | 0.83 | 0.35 | 0.61 | 0.47 | 0.69 | 0.40 | 0.62 | 0.42 | 0.41 |
| Acyclic(N4)/cyclic (<=N4), weight ratio | 3.99 | 13.72 | 8.28 | 11.28 | 6.56 | 12.25 | 8.37 | 12.60 | 12.29 |
| | 4.60 | 17.25 | 10.39 | 13.95 | 8.23 | 15.79 | 11.03 | 16.06 | 15.57 |

TABLE CXII

| Example No. | 1139 | 1140 | 1141 | 1142 | 1143 | 1144 | 1145 | 1146 | 1147 |
|---|---|---|---|---|---|---|---|---|---|
| Catalyst Type | PPPPP | PPPPP | PPPPP | PPPPP | PPPPP | PPPPP | PPPPP | PPPPP | PPPPP |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 249.2 | 249.8 | 259.9 | 264.9 | 269.9 | 254.8 | 244.9 | 269.2 | 274.5 |
| Time on organics, hrs. | 3.5 | 22.5 | 27.5 | 46.5 | 51.6 | 70.6 | 95.5 | 118.5 | 122.5 |
| Duration of run, hrs. | 2 | 2 | 2 | 2 | 2 | 2 | 2 | 2 | 2 |
| MEA SV, gmol/hr/kgcat | 3.05 | 3.45 | 3.71 | 3.37 | 3.66 | 4.11 | 3.75 | 3.37 | 3.61 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.701 | 1.330 | 2.175 | 2.857 | 3.642 | 1.575 | 0.790 | 2.998 | 4.045 |
| MEA | 16.452 | 20.045 | 13.804 | 10.226 | 7.809 | 18.066 | 25.597 | 9.273 | 6.909 |
| PIP | 0.640 | 0.536 | 0.952 | 1.209 | 1.520 | 0.606 | 0.260 | 1.165 | 1.515 |
| DETA | 35.879 | 42.232 | 35.213 | 31.459 | 28.823 | 40.057 | 48.800 | 31.599 | 29.253 |
| AEEA | 1.848 | 2.310 | 2.025 | 1.615 | 1.216 | 2.188 | 2.179 | 1.469 | 1.067 |
| AEP | 0.845 | 0.661 | 1.314 | 1.822 | 2.394 | 0.806 | 0.375 | 1.797 | 2.395 |
| HEP | 0.000 | 0.000 | 0.000 | 0.000 | 0.000 | 0.000 | 0.000 | 0.000 | 0.000 |
| TAEA | 1.322 | 1.559 | 1.518 | 1.409 | 1.216 | 1.638 | 1.501 | 1.434 | 1.240 |
| l-TETA | 11.392 | 12.975 | 14.107 | 14.075 | 13.354 | 13.401 | 10.153 | 13.748 | 13.019 |
| DAEP | 0.426 | 0.224 | 0.652 | 1.052 | 1.477 | 0.312 | 0.097 | 1.047 | 1.571 |
| PEEDA | 0.338 | 0.171 | 0.491 | 0.777 | 1.119 | 0.227 | 0.067 | 0.783 | 1.163 |
| DPE | 0.378 | 0.162 | 0.370 | 0.148 | 0.166 | 0.178 | 0.103 | 0.153 | 0.172 |
| AE-TAEA | 2.369 | 2.370 | 3.157 | 3.316 | 3.106 | 2.829 | 1.535 | 3.212 | 3.251 |
| l-TEPA | 5.829 | 5.299 | 8.162 | 9.154 | 9.766 | 5.998 | 2.509 | 8.811 | 9.487 |
| AE-DAEP | 0.502 | 0.250 | 0.590 | 0.924 | 1.403 | 0.326 | 0.060 | 0.968 | 1.481 |
| AE-PEEDA | 0.347 | 0.087 | 0.124 | 0.292 | 0.486 | 0.090 | 0.044 | 0.282 | 0.455 |
| iAE-PEEDA | 0.000 | 0.000 | 0.000 | 0.000 | 0.000 | 0.000 | 0.000 | 0.000 | 0.000 |
| AE-DPE | 0.232 | 0.275 | 0.287 | 0.246 | 0.088 | 0.181 | 0.082 | 0.038 | 0.044 |
| BPEA | 0.378 | 0.316 | 0.172 | 0.212 | 0.728 | 0.108 | 0.026 | 0.237 | 0.689 |
| Others | 6.553 | 3.689 | 8.018 | 10.689 | 12.800 | 5.245 | 2.365 | 11.008 | 12.985 |
| MEA conversion, % | 52.34 | 45.74 | 62.87 | 72.31 | 78.98 | 51.01 | 30.96 | 74.50 | 81.34 |
| DETA conversion, % | 38.38 | 32.23 | 43.85 | 49.50 | 54.02 | 35.61 | 21.97 | 48.49 | 53.19 |
| Acyclic(N4), % | 91.74 | 96.30 | 91.16 | 88.66 | 84.05 | 95.43 | 97.74 | 88.44 | 83.06 |
| Acyclic(N5), % | 84.87 | 89.18 | 90.60 | 88.15 | 82.62 | 92.58 | 94.97 | 88.74 | 82.66 |
| Σ(N5)/Σ(N4), weight ratio | 0.69 | 0.56 | 0.72 | 0.80 | 0.89 | 0.60 | 0.35 | 0.78 | 0.89 |
| Acyclic(N4)/cyclic(<=N4), weight ratio | 4.83 | 8.27 | 4.13 | 3.09 | 2.18 | 7.05 | 12.88 | 3.06 | 2.09 |

TABLE CXIII

| Example No. | 1148 | 1149 | 1150 | 1151 | 1152 | 1153 | 1154 | 1155 | 1156 |
|---|---|---|---|---|---|---|---|---|---|
| Catalyst Type | QQQQQ | QQQQQ | QQQQQ | QQQQQ | QQQQQ | QQQQQ | QQQQQ | QQQQQ | QQQQQ |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 249.2 | 249.8 | 259.9 | 264.9 | 269.9 | 254.8 | 244.9 | 269.2 | 274.5 |
| Time on organics, hrs. | 3.5 | 22.5 | 27.5 | 46.5 | 51.6 | 70.6 | 95.5 | 118.5 | 122.5 |
| Duration of run, hrs. | 2 | 2 | 2 | 2 | 2 | 2 | 2 | 2 | 2 |
| MEA SV, gmol/hr/kgcat | 2.81 | 3.68 | 3.89 | 3.54 | 3.97 | 4.37 | 3.98 | 3.57 | 3.82 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.087 | 0.784 | 1.159 | 1.518 | 1.787 | 0.898 | 0.427 | 1.694 | 2.168 |
| MEA | 18.000 | 23.201 | 17.032 | 13.812 | 11.331 | 21.539 | 28.009 | 12.798 | 9.998 |
| PIP | 0.304 | 0.215 | 0.374 | 0.499 | 0.603 | 0.261 | 0.099 | 0.550 | 0.705 |
| DETA | 38.387 | 48.461 | 41.116 | 37.786 | 35.688 | 46.385 | 52.406 | 37.936 | 35.454 |
| AEEA | 1.924 | 2.613 | 2.539 | 2.224 | 1.893 | 2.489 | 2.034 | 2.026 | 1.642 |
| AEP | 0.449 | 0.342 | 0.517 | 0.696 | 0.879 | 0.393 | 0.244 | 0.797 | 1.019 |
| HEP | 0.000 | 0.000 | 0.000 | 0.000 | 0.000 | 0.000 | 0.000 | 0.000 | 0.000 |
| TAEA | 1.318 | 1.639 | 1.852 | 1.906 | 1.859 | 1.711 | 1.190 | 1.917 | 1.886 |
| l-TETA | 10.672 | 10.861 | 13.747 | 14.589 | 13.661 | 10.892 | 7.078 | 13.335 | 13.840 |
| DAEP | 0.198 | 0.087 | 0.200 | 0.337 | 0.533 | 0.121 | 0.037 | 0.403 | 0.653 |
| PEEDA | 0.174 | 0.066 | 0.178 | 0.212 | 0.342 | 0.087 | 0.032 | 0.284 | 0.424 |
| DPE | 0.179 | 0.118 | 0.179 | 0.221 | 0.417 | 0.120 | 0.055 | 0.352 | 0.139 |
| AE-TAEA | 2.140 | 1.768 | 3.096 | 3.996 | 4.461 | 2.295 | 1.015 | 3.949 | 4.557 |
| l-TEPA | 4.234 | 2.982 | 5.888 | 7.317 | 8.157 | 3.420 | 1.361 | 7.182 | 8.348 |
| AE-DAEP | 0.296 | 0.057 | 0.409 | 0.400 | 0.522 | 0.133 | 0.088 | 0.409 | 0.588 |
| AE-PEEDA | 0.088 | 0.000 | 0.334 | 0.106 | 0.146 | 0.036 | 0.000 | 0.096 | 0.134 |
| iAE-PEEDA | 0.000 | 0.000 | 0.000 | 0.000 | 0.000 | 0.000 | 0.000 | 0.000 | 0.000 |
| AE-DPE | 0.160 | 0.104 | 0.269 | 0.268 | 0.263 | 0.116 | 0.063 | 0.216 | 0.185 |
| BPEA | 0.267 | 0.172 | 0.142 | 0.179 | 0.194 | 0.048 | 0.026 | 0.155 | 0.204 |
| Others | 4.394 | 1.773 | 5.061 | 7.143 | 9.034 | 3.187 | 4.556 | 7.761 | 10.098 |
| MEA conversion, % | 45.31 | 36.86 | 54.05 | 62.75 | 69.21 | 40.96 | 23.12 | 65.04 | 72.98 |
| DETA conversion, % | 30.85 | 21.83 | 34.25 | 39.59 | 42.51 | 24.63 | 14.72 | 38.57 | 43.21 |
| Acyclic(N4), % | 95.59 | 97.86 | 96.54 | 95.52 | 92.30 | 97.45 | 98.50 | 93.60 | 92.81 |
| Acyclic(N5), % | 88.69 | 93.42 | 88.59 | 92.21 | 91.80 | 94.45 | 93.00 | 92.68 | 92.06 |
| Σ(N5)/Σ(N4), weight ratio | 0.57 | 0.39 | 0.62 | 0.71 | 0.81 | 0.46 | 0.30 | 0.73 | 0.82 |
| Acyclic(N4)/cyclic(<=N4), | 9.17 | 15.04 | 10.75 | 8.38 | 5.58 | 12.79 | 17.59 | 6.38 | 5.34 |

TABLE CXIII-continued

| Example No. | 1148 | 1149 | 1150 | 1151 | 1152 | 1153 | 1154 | 1155 | 1156 |
|---|---|---|---|---|---|---|---|---|---|
| weight ratio | | | | | | | | | |

TABLE CXIV

| Example No. | 1157 | 1158 | 1159 | 1160 | 1161 | 1162 | 1163 | 1164 | 1165 |
|---|---|---|---|---|---|---|---|---|---|
| Catalyst Type | RRRRR | RRRRR | RRRRR | RRRRR | RRRRR | RRRRR | RRRRR | RRRRR | RRRRR |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 248.2 | 249.8 | 259.9 | 264.9 | 269.9 | 254.8 | 244.8 | 269.2 | 274.5 |
| Time on organics, hrs. | 3.5 | 22.5 | 27.5 | 46.5 | 51.6 | 70.6 | 95.5 | 118.5 | 122.5 |
| Duration of run, hrs. | 2 | 2 | 2 | 2 | 2 | 2 | 2 | 2 | 2 |
| MEA SV, gmol/hr/kgcat | 2.81 | 3.53 | 3.71 | 3.46 | 3.59 | 3.87 | 2.57 | 2.86 | 3.23 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.256 | 0.898 | 1.478 | 1.884 | 2.373 | 1.036 | 0.465 | 1.816 | 2.297 |
| MEA | 25.808 | 27.657 | 23.849 | 20.875 | 18.992 | 27.163 | 30.642 | 19.820 | 18.074 |
| PIP | 0.741 | 0.635 | 1.097 | 1.449 | 1.776 | 0.782 | 0.318 | 1.333 | 1.650 |
| DETA | 46.166 | 50.830 | 44.501 | 41.541 | 37.635 | 48.978 | 54.604 | 40.543 | 39.246 |
| AEEA | 1.262 | 1.412 | 1.399 | 1.264 | 1.114 | 1.392 | 1.370 | 1.307 | 1.228 |
| AEP | 0.698 | 0.614 | 1.115 | 1.609 | 2.034 | 0.761 | 0.370 | 1.447 | 1.897 |
| HEP | 0.000 | 0.000 | 0.000 | 0.000 | 0.000 | 0.000 | 0.000 | 0.000 | 0.000 |
| TAEA | 1.061 | 1.182 | 1.300 | 1.247 | 1.133 | 1.126 | 0.903 | 1.223 | 1.288 |
| 1-TETA | 6.765 | 6.611 | 7.971 | 8.544 | 8.553 | 6.512 | 4.641 | 8.127 | 8.926 |
| DAEP | 0.208 | 0.157 | 0.077 | 0.663 | 0.883 | 0.231 | 0.068 | 0.527 | 0.791 |
| PEEDA | 0.205 | 0.143 | 0.366 | 0.645 | 0.886 | 0.213 | 0.055 | 0.541 | 0.782 |
| DPE | 0.113 | 0.071 | 0.219 | 0.258 | 0.341 | 0.119 | 0.033 | 0.233 | 0.284 |
| AE-TAEA | 1.055 | 1.082 | 1.616 | 1.535 | 1.657 | 1.234 | 0.646 | 1.783 | 1.929 |
| 1-TEPA | 2.631 | 2.675 | 4.495 | 5.280 | 5.850 | 2.897 | 0.093 | 4.793 | 5.840 |
| AE-DAEP | 0.282 | 0.121 | 0.395 | 0.609 | 0.911 | 0.196 | 0.144 | 0.532 | 0.763 |
| AE-PEEDA | 0.292 | 0.151 | 0.092 | 0.119 | 0.165 | 0.038 | 0.053 | 0.122 | 0.135 |
| iAE-PEEDA | 0.000 | 0.000 | 0.000 | 0.000 | 0.000 | 0.000 | 0.000 | 0.000 | 0.000 |
| AE-DPE | 0.145 | 0.056 | 0.248 | 0.182 | 0.222 | 0.075 | 0.051 | 0.226 | 0.172 |
| BPEA | 0.092 | 0.102 | 0.103 | 0.126 | 0.126 | 0.045 | 0.017 | 0.125 | 0.148 |
| Others | 4.080 | 2.114 | 6.330 | 7.633 | 9.871 | 3.590 | 2.398 | 7.053 | 7.859 |
| MEA Conversion, % | 27.62 | 25.05 | 36.44 | 44.22 | 49.24 | 26.50 | 16.41 | 44.75 | 50.95 |
| DETA Conversion, % | 23.25 | 18.34 | 29.70 | 34.20 | 40.37 | 21.43 | 11.69 | 33.00 | 36.86 |
| Acyclic(N4), % | 93.68 | 95.43 | 93.13 | 86.19 | 82.11 | 93.10 | 97.23 | 87.77 | 84.60 |
| Acyclic(N5), % | 81.93 | 89.70 | 87.91 | 86.79 | 82.82 | 92.02 | 73.46 | 86.72 | 86.42 |
| $\Sigma(N5)/\Sigma(N4)$, weight ratio | 0.53 | 0.51 | 0.69 | 0.69 | 0.76 | 0.54 | 0.17 | 0.71 | 0.74 |
| Acyclic(N4)/cyclic (<=N4), weight ratio | 3.97 | 4.80 | 3.20 | 2.11 | 1.63 | 3.62 | 6.55 | 2.28 | 1.88 |

TABLE CXV

| Example No. | 1166 | 1167 | 1168 | 1169 | 1170 | 1171 | 1172 | 1173 | 1174 | 1175 |
|---|---|---|---|---|---|---|---|---|---|---|
| Catalyst Type | SSSSS | SSSSS | SSSSS | SSSSS | SSSSS | SSSSS | SSSSS | SSSSS | SSSSS | SSSSS |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.5 | 259.7 | 254.4 | 264.2 | 269.3 | 279.6 | 249.3 | 259.5 | 260 | 250 |
| Time on organics, hrs. | 19.5 | 24.5 | 43.5 | 48.5 | 69 | 73 | 92 | 97 | 116.3 | 138 |
| Duration of run, hrs. | 2 | 2 | 2 | 2 | 2 | 2 | 2 | 2 | 2 | 2 |
| MEA SV, gmol/hr/kgcat | 5.34 | 5.65 | 6.24 | 6.38 | 8.47 | 6.90 | 6.07 | 5.74 | 6.46 | 5.51 |
| DETA/MEA mole ratio | 0.99 | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.699 | 0.991 | 0.581 | 0.845 | 0.904 | 1.637 | 0.332 | 0.557 | 0.575 | 0.259 |
| MEA | 30.881 | 26.979 | 30.239 | 25.449 | 23.586 | 17.207 | 30.424 | 27.661 | 28.796 | 31.430 |
| PIP | 0.175 | 0.376 | 0.190 | 0.382 | 0.461 | 0.971 | 0.111 | 0.252 | 0.248 | 0.099 |
| DETA | 54.402 | 53.966 | 56.223 | 52.550 | 52.679 | 47.929 | 58.899 | 56.255 | 55.809 | 58.323 |
| AEEA | 2.275 | 3.020 | 2.563 | 2.952 | 3.082 | 2.508 | 2.232 | 2.891 | 2.746 | 2.097 |
| AEP | 0.295 | 0.411 | 0.323 | 0.398 | 0.511 | 0.939 | 0.287 | 0.368 | 0.336 | 0.287 |
| HEP | 0.000 | 0.000 | 0.000 | 0.000 | 0.000 | 0.000 | 0.000 | 0.000 | 0.000 | 0.000 |
| TAEA | 0.544 | 0.915 | 0.601 | 0.901 | 1.106 | 1.536 | 0.566 | 0.803 | 0.731 | 0.444 |
| 1-TETA | 3.185 | 5.582 | 3.529 | 5.218 | 6.542 | 9.101 | 3.328 | 4.694 | 4.368 | 2.706 |
| DAEP | 0.103 | 0.030 | 0.056 | 0.111 | 0.131 | 0.332 | 0.046 | 0.086 | 0.060 | 0.023 |
| PEEDA | 0.033 | 0.040 | 0.046 | 0.025 | 0.026 | 0.319 | 0.036 | 0.039 | 0.032 | 0.026 |
| DPE | 0.079 | 0.078 | 0.059 | 0.071 | 0.094 | 0.191 | 0.047 | 0.059 | 0.058 | 0.000 |
| AE-TAEA | 0.120 | 0.479 | 0.160 | 0.566 | 0.782 | 1.819 | 0.164 | 0.345 | 0.340 | 0.110 |
| 1-TEPA | 0.223 | 1.046 | 0.335 | 1.448 | 1.933 | 4.344 | 0.305 | 0.748 | 0.777 | 0.175 |
| AE-DAEP | 0.054 | 0.000 | 0.000 | 0.035 | 0.058 | 0.101 | 0.000 | 0.000 | 0.000 | 0.000 |
| AE-PEEDA | 0.000 | 0.043 | 0.000 | 0.037 | 0.000 | 0.047 | 0.062 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.085 | 0.000 | 0.053 | 0.000 | 0.000 | 0.108 | 0.000 | 0.000 | 0.000 | 0.098 |
| BPEA | 0.000 | 0.060 | 0.000 | 0.078 | 0.052 | 0.141 | 0.000 | 0.000 | 0.000 | 0.000 |
| Others | 1.439 | 1.936 | 1.433 | 2.104 | 2.736 | 5.251 | 1.312 | 1.757 | 1.538 | 0.936 |

TABLE CXV-continued

| | | | | | | | | | | |
|---|---|---|---|---|---|---|---|---|---|---|
| MEA Conversion, % | 13.32 | 26.12 | 16.89 | 28.40 | 35.09 | 53.51 | 17.91 | 24.54 | 21.17 | 13.94 |
| DETA Conversion, % | 9.48 | 12.39 | 8.40 | 12.35 | 14.06 | 23.24 | 5.79 | 9.02 | 9.43 | 5.33 |
| Acyclic(N4), % | 94.50 | 97.75 | 96.19 | 96.70 | 96.80 | 92.65 | 96.76 | 96.72 | 97.11 | 98.43 |
| Acyclic(N5), % | 71.06 | 93.57 | 90.33 | 92.98 | 96.07 | 93.91 | 88.20 | 100 | 100 | 74.27 |
| $\Sigma$(N5)/$\Sigma$(N4), weight ratio | 0.12 | 0.24 | 0.12 | 0.34 | 0.35 | 0.57 | 0.13 | 0.19 | 0.21 | 0.12 |
| Acyclic(N4)/cyclic ($<=$N4), weight ratio | 5.42 | 6.93 | 6.10 | 6.18 | 6.23 | 3.86 | 7.36 | 6.81 | 6.91 | 7.21 |

| Example No. | 1176 | 1177 | 1178 | 1179 | 1180 | 1181 | 1182 | 1183 | 1184 | 1185 |
|---|---|---|---|---|---|---|---|---|---|---|
| Catalyst Type | SSSSS | SSSSS | SSSSS | SSSSS | SSSSS | SSSSS | SSSSS | SSSSS | SSSSS | SSSS |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.9 | 259.7 | 254.4 | 264.4 | 269.3 | 279.6 | 249.3 | 259.5 | 260 | 250 |
| Time on organics, hrs. | 19.5 | 24.5 | 43.5 | 48.5 | 69 | 73 | 92 | 97 | 116.3 | 138 |
| Duration of run, hrs. | 2 | 2 | 2 | 2 | 2 | 2 | 2 | 2 | 2 | 2 |
| MEA SV, gmol/hr/kgcat | 5.31 | 5.47 | 5.77 | 6.00 | 6.06 | 6.55 | 5.78 | 5.50 | 5.21 | 5.66 |
| DETA/MEA mole ratio | 0.99 | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.745 | 0.944 | 0.594 | 0.847 | 1.030 | 1.615 | 0.327 | 0.590 | 0.591 | 0.329 |
| MEA | 30.660 | 27.781 | 30.325 | 25.425 | 24.014 | 17.349 | 31.104 | 27.787 | 28.697 | 31.814 |
| PIP | 0.148 | 0.317 | 0.168 | 0.346 | 0.455 | 0.912 | 0.099 | 0.228 | 0.218 | 0.088 |
| DETA | 56.688 | 54.036 | 55.722 | 53.130 | 52.088 | 48.017 | 59.117 | 56.024 | 55.945 | 58.205 |
| AEEA | 2.475 | 3.096 | 2.580 | 3.089 | 3.100 | 2.630 | 2.204 | 2.899 | 2.826 | 2.086 |
| AEP | 0.299 | 0.420 | 0.298 | 0.379 | 0.470 | 0.914 | 0.261 | 0.367 | 0.346 | 0.274 |
| HEP | 0.000 | 0.000 | 0.000 | 0.000 | 0.000 | 0.000 | 0.000 | 0.000 | 0.000 | 0.000 |
| TAEA | 0.588 | 0.879 | 0.588 | 0.969 | 1.022 | 1.530 | 0.489 | 0.798 | 0.714 | 0.410 |
| 1-TETA | 3.553 | 5.158 | 3.445 | 5.562 | 5.935 | 8.838 | 2.904 | 4.702 | 4.162 | 2.520 |
| DAEP | 0.105 | 0.125 | 0.051 | 0.095 | 0.114 | 0.319 | 0.031 | 0.066 | 0.065 | 0.018 |
| PEEDA | 0.026 | 0.043 | 0.060 | 0.030 | 0.042 | 0.332 | 0.042 | 0.036 | 0.027 | 0.022 |
| DPE | 0.055 | 0.072 | 0.073 | 0.088 | 0.099 | 0.211 | 0.040 | 0.071 | 0.055 | 0.000 |
| AE-TAEA | 0.066 | 0.361 | 0.137 | 0.513 | 0.679 | 1.746 | 0.102 | 0.299 | 0.261 | 0.078 |
| 1-TEPA | 0.144 | 0.806 | 0.322 | 1.126 | 1.742 | 3.970 | 0.183 | 0.650 | 0.621 | 0.101 |
| AE-DAEP | 0.068 | 0.000 | 0.000 | 0.030 | 0.037 | 0.180 | 0.000 | 0.000 | 0.000 | 0.000 |
| AE-PEEDA | 0.000 | 0.000 | 0.000 | 0.000 | 0.056 | 0.080 | 0.164 | 0.030 | 0.092 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.000 | 0.058 | 0.000 | 0.000 | 0.000 | 0.000 | 0.000 | 0.000 | 0.154 |
| BPEA | 0.000 | 0.000 | 0.000 | 0.056 | 0.046 | 0.093 | 0.000 | 0.000 | 0.000 | 0.000 |
| Others | 1.371 | 1.735 | 1.521 | 2.443 | 2.782 | 5.517 | 1.044 | 1.685 | 1.503 | 0.926 |
| MEA Conversion, % | 16.17 | 23.60 | 16.23 | 29.21 | 33.10 | 52.96 | 15.90 | 23.93 | 21.18 | 12.82 |
| DETA Conversion, % | 8.12 | 11.91 | 8.75 | 12.31 | 13.98 | 22.83 | 5.25 | 9.08 | 8.91 | 5.45 |
| Acyclic(N4), % | 95.65 | 96.13 | 95.62 | 96.81 | 96.43 | 92.31 | 96.73 | 96.92 | 97.05 | 98.63 |
| Acyclic(N5), % | 75.52 | 100.00 | 88.65 | 94.91 | 94.51 | 94.17 | 63.39 | 96.93 | 90.51 | 53.84 |
| $\Sigma$(N5)/$\Sigma$(N4), weight ratio | 0.06 | 0.18 | 0.12 | 0.25 | 0.35 | 0.54 | 0.12 | 0.17 | 0.19 | 0.11 |
| Acyclic(N4)/cyclic ($<=$N4), weight ratio | 6.50 | 6.15 | 6.19 | 6.93 | 5.88 | 3.85 | 7.13 | 7.13 | 6.83 | 7.26 |

TABLE CXVI

| Example No. | 1186 | 1187 | 1188 | 1189 | 1190 | 1191 | 1192 | 1193 | 1194 |
|---|---|---|---|---|---|---|---|---|---|
| Catalyst Type | TTTTT | TTTTT | TTTTT | TTTTT | TTTTT | TTTTT | TTTTT | TTTTT | TTTTT |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 250.1 | 259.9 | 270.4 | 250 | 250 | 265.4 | 274.9 | 270.4 | 280.5 |
| Time on organics, hrs. | 49 | 69 | 73 | 92 | 117 | 141 | 145 | 164 | 168 |
| Duration of run, hrs. | 2 | 2 | 2 | 2 | 2 | 2 | 2 | 2 | 2 |
| MEA SV, gmol/hr/kgcat | 6.27 | 5.79 | 6.32 | 6.13 | 5.94 | 5.89 | 5.95 | 6.07 | 6.15 |
| DETA/MEA mole ratio | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 0.646 | 0.996 | 1.453 | 0.520 | 0.455 | 1.300 | 2.007 | 1.580 | 2.469 |
| MEA | 26.654 | 23.680 | 16.639 | 28.140 | 28.547 | 22.094 | 15.810 | 19.303 | 11.900 |
| PIP | 0.159 | 0.228 | 0.386 | 0.099 | 0.087 | 0.283 | 0.468 | 0.350 | 0.631 |
| DETA | 51.837 | 47.809 | 41.131 | 53.445 | 54.624 | 47.199 | 40.533 | 44.569 | 38.430 |
| AEEA | 2.147 | 2.219 | 2.091 | 1.899 | 1.991 | 2.285 | 1.858 | 2.050 | 1.358 |
| AEP | 0.366 | 0.391 | 0.584 | 0.286 | 0.291 | 0.441 | 0.652 | 0.586 | 1.003 |
| HEP | 0.000 | 0.000 | 0.000 | 0.000 | 0.000 | 0.000 | 0.000 | 0.000 | 0.000 |
| TAEA | 1.404 | 1.960 | 2.022 | 1.297 | 1.245 | 1.889 | 1.973 | 1.833 | 2.102 |
| 1-TETA | 9.038 | 10.383 | 12.919 | 7.486 | 7.272 | 11.110 | 12.264 | 11.044 | 12.373 |
| DAEP | 0.091 | 0.136 | 0.267 | 0.047 | 0.050 | 0.144 | 0.296 | 0.227 | 0.594 |
| PEEDA | 0.049 | 0.069 | 0.074 | 0.030 | 0.025 | 0.066 | 0.089 | 0.070 | 0.162 |
| DPE | 0.102 | 0.194 | 0.327 | 0.078 | 0.085 | 0.208 | 0.379 | 0.309 | 0.460 |
| AE-TAEA | 1.004 | 1.822 | 3.107 | 0.781 | 0.689 | 1.905 | 3.070 | 2.472 | 3.435 |
| 1-TEPA | 1.515 | 2.906 | 5.194 | 1.189 | 1.007 | 2.936 | 5.147 | 4.012 | 5.957 |
| AE-DAEP | 0.043 | 0.106 | 0.253 | 0.000 | 0.000 | 0.051 | 0.422 | 0.311 | 0.280 |
| AE-PEEDA | 0.000 | 0.000 | 0.112 | 0.000 | 0.000 | 0.000 | 0.118 | 0.082 | 0.131 |
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.240 | 0.000 | 0.000 | 0.000 | 0.343 | 0.373 | 0.088 |

TABLE CXVI-continued

| | | | | | | | | | |
|---|---|---|---|---|---|---|---|---|---|
| BPEA | 0.085 | 0.242 | 0.492 | 0.078 | 0.000 | 0.281 | 0.275 | 0.212 | 0.296 |
| Others | 1.551 | 4.275 | 6.422 | 1.397 | 1.017 | 3.348 | 7.308 | 5.745 | 11.413 |
| MEA Conversion, % | 27.88 | 35.83 | 54.96 | 23.58 | 22.81 | 40.26 | 56.94 | 48.09 | 67.96 |
| DETA Conversion, % | 16.85 | 23.20 | 34.01 | 13.96 | 12.53 | 24.35 | 34.55 | 28.95 | 38.66 |
| Acyclic(N4), % | 97.71 | 96.35 | 95.71 | 98.25 | 98.13 | 96.87 | 94.89 | 95.49 | 92.24 |
| Acyclic(N5), % | 95.12 | 93.12 | 88.30 | 96.16 | 100.00 | 93.55 | 87.63 | 86.86 | 92.18 |
| Σ(N5)/Σ(N4), weight ratio | 0.24 | 0.46 | 0.60 | 0.22 | 0.19 | 0.38 | 0.62 | 0.55 | 0.64 |
| Acyclic(N4)/cyclic (<=N4), weight ratio | 13.55 | 10.36 | 9.11 | 16.20 | 15.74 | 11.35 | 7.54 | 8.33 | 5.07 |

| Example No. | 1195 | 1196 | 1197 | 1198 | 1199 | 1200 |
|---|---|---|---|---|---|---|
| Catalyst Type | TTTTT | TTTTT | TTTTT | TTTTT | TTTTT | TTTTT |
| Catalyst weight, gm | 50 | 50 | 50 | 50 | 50 | 50 |
| Pressure, psig | 600 | 600 | 600 | 600 | 600 | 600 |
| Temperature, °C. | 250.3 | 255.6 | 260.5 | 270.5 | 250.4 | 260.4 |
| Time on organics, hrs. | 187 | 192 | 212 | 216 | 235 | 240 |
| Duration of run, hrs. | 2 | 2 | 2 | 2 | 2 | 2 |
| MEA SV, gmol/hr/kgcat | 5.94 | 6.33 | 5.99 | 6.27 | 5.90 | 6.53 |
| DETA/MEA mole ratio | 0.99 | 0.99 | 0.99 | 0.99 | 0.99 | 0.99 |
| NH3/MEA mole ratio | 5.98 | 5.98 | 5.98 | 5.98 | 5.98 | 5.98 |
| Crude product composition, wt. % | | | | | | |
| EDA | 0.514 | 0.593 | 0.846 | 1.480 | 0.481 | 0.783 |
| MEA | 26.000 | 26.235 | 23.790 | 20.254 | 28.197 | 23.941 |
| PIP | 0.090 | 0.105 | 0.152 | 0.302 | 0.082 | 0.131 |
| DETA | 54.672 | 54.260 | 52.317 | 46.643 | 55.162 | 53.334 |
| AEEA | 1.820 | 1.991 | 2.249 | 2.223 | 1.878 | 2.190 |
| AEP | 0.502 | 0.388 | 0.389 | 0.514 | 0.325 | 0.363 |
| HEP | 0.000 | 0.000 | 0.000 | 0.000 | 0.000 | 0.000 |
| TAEA | 1.571 | 1.456 | 1.611 | 1.878 | 1.195 | 1.609 |
| 1-TETA | 7.704 | 7.909 | 9.027 | 10.859 | 6.705 | 8.957 |
| DAEP | 0.245 | 0.133 | 0.114 | 0.191 | 0.060 | 0.105 |
| PEEDA | 0.053 | 0.083 | 0.108 | 0.084 | 0.049 | 0.099 |
| DPE | 0.106 | 0.143 | 0.171 | 0.268 | 0.122 | 0.180 |
| AE-TAEA | 0.748 | 0.777 | 1.110 | 2.057 | 0.628 | 1.062 |
| 1-TEPA | 0.976 | 1.117 | 1.577 | 3.217 | 0.791 | 1.486 |
| AE-DAEP | 0.045 | 0.028 | 0.041 | 0.083 | 0.000 | 0.032 |
| AE-PEEDA | 0.151 | 0.102 | 0.121 | 0.043 | 0.195 | 0.055 |
| iAE-PEEDA | 0.000 | 0.000 | 0.000 | 0.000 | 0.000 | 0.000 |
| AE-DPE | 0.000 | 0.000 | 0.034 | 0.272 | 0.000 | 0.000 |
| BPEA | 0.000 | 0.000 | 0.052 | 0.156 | 0.000 | 0.047 |
| Others | 2.165 | 1.873 | 2.601 | 4.845 | 1.692 | 2.559 |
| MEA Conversion, % | 30.21 | 29.38 | 35.76 | 45.44 | 24.03 | 35.94 |
| DETA Conversion, % | 13.00 | 13.42 | 16.25 | 25.48 | 11.90 | 15.05 |
| Acyclic(N4), % | 95.80 | 96.29 | 96.42 | 95.89 | 97.14 | 96.48 |
| Acyclic(N5), % | 89.71 | 93.54 | 91.50 | 90.44 | 87.86 | 94.96 |
| Σ(N5)/Σ(N4), weight ratio | 0.19 | 0.20 | 0.26 | 0.43 | 0.19 | 0.24 |
| Acyclic(N4)/cyclic (<=N4), weight ratio | 9.28 | 10.96 | 11.35 | 9.35 | 12.35 | 12.00 |

TABLE CXVII

| Example No. | 1201 | 1202 | 1203 | 1204 | 1205 | 1206 | 1207 | 1208 | 1209 |
|---|---|---|---|---|---|---|---|---|---|
| Catalyst Type | UUUUU | UUUUU | UUUUU | UUUUU | UUUUU | UUUUU | UUUUU | UUUUU | UUUUU |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 250.1 | 259.9 | 270.4 | 250 | 250 | 285.4 | 274.9 | 270.4 | 280.5 |
| Time on organics, hrs. | 4 | 24 | 28 | 47 | 72 | 96 | 100 | 120 | 124 |
| Duration of run, hrs. | 2 | 2 | 2 | 2 | 2 | 2 | 2 | 2 | 2 |
| MEA SV, gmol/hr/kgcat | 6.18 | 2.34 | 5.82 | 5.84 | 5.69 | 5.51 | 5.75 | 5.84 | 5.73 |
| DETA/MEA mole ratio | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 0.917 | 1.897 | 2.108 | 0.590 | 0.434 | 1.245 | 2.140 | 1.671 | 2.735 |
| MEA | 25.662 | 20.472 | 16.778 | 28.012 | 27.367 | 22.431 | 16.450 | 20.118 | 12.411 |
| PIP | 0.380 | 0.881 | 1.077 | 0.268 | 0.212 | 0.674 | 1.189 | 0.858 | 1.490 |
| DETA | 50.521 | 43.321 | 39.423 | 52.720 | 54.768 | 47.275 | 40.189 | 45.395 | 37.922 |
| AEEA | 2.344 | 2.643 | 1.892 | 2.035 | 2.217 | 2.374 | 1.773 | 2.194 | 1.405 |
| AEP | 0.461 | 0.807 | 1.116 | 0.369 | 0.357 | 0.675 | 1.147 | 0.885 | 1.698 |
| HEP | 0.000 | 0.000 | 0.000 | 0.000 | 0.000 | 0.000 | 0.000 | 0.000 | 0.000 |
| TAEA | 1.220 | 1.437 | 1.468 | 1.065 | 1.114 | 1.421 | 1.395 | 1.422 | 1.542 |
| 1-TETA | 9.448 | 11.215 | 12.082 | 7.243 | 7.568 | 10.105 | 11.100 | 10.492 | 11.616 |
| DAEP | 0.115 | 0.274 | 0.481 | 0.069 | 0.062 | 0.210 | 0.438 | 0.310 | 0.808 |
| PEEDA | 0.063 | 0.175 | 0.071 | 0.039 | 0.033 | 0.056 | 0.067 | 0.060 | 0.135 |
| DPE | 0.116 | 0.171 | 0.245 | 0.071 | 0.076 | 0.182 | 0.299 | 0.250 | 0.107 |
| AE-TAEA | 1.057 | 1.803 | 2.308 | 0.672 | 0.602 | 1.534 | 2.154 | 1.795 | 2.349 |
| 1-TEPA | 2.317 | 4.207 | 5.775 | 1.422 | 1.227 | 3.460 | 5.412 | 4.306 | 6.191 |
| AE-DAEP | 0.039 | 0.195 | 0.407 | 0.000 | 0.029 | 0.142 | 0.610 | 0.314 | 0.399 |
| AE-PEEDA | 0.000 | 0.037 | 0.039 | 0.000 | 0.000 | 0.000 | 0.119 | 0.043 | 0.254 |

TABLE CXVII-continued

| | | | | | | | | | |
|---|---|---|---|---|---|---|---|---|---|
| iAE-PEEDA | 0.000 | 0.000 | 0.000 | 0.000 | 0.000 | 0.000 | 0.000 | 0.000 | 0.000 |
| AE-DPE | 0.000 | 0.000 | 0.042 | 0.000 | 0.000 | 0.000 | 0.184 | 0.112 | 0.044 |
| BPEA | 0.141 | 0.281 | 0.355 | 0.082 | 0.065 | 0.187 | 0.205 | 0.132 | 0.238 |
| Others | 1.669 | 3.555 | 5.886 | 1.375 | 1.291 | 3.662 | 7.822 | 4.954 | 11.756 |
| MEA Conversion, % | 30.62 | 43.66 | 53.48 | 23.36 | 26.31 | 39.42 | 55.00 | 45.87 | 66.59 |
| DETA Conversion, % | 19.04 | 29.32 | 35.21 | 14.49 | 12.58 | 24.32 | 34.91 | 27.60 | 39.49 |
| Acyclic(N4), % | 97.30 | 95.31 | 94.43 | 97.87 | 98.05 | 96.24 | 93.94 | 95.04 | 92.59 |
| Acyclic(N5), % | 94.89 | 92.10 | 90.54 | 96.19 | 95.07 | 93.80 | 87.10 | 90.99 | 90.10 |
| $\Sigma(N5)/\Sigma(N4)$, weight ratio | 0.32 | 0.49 | 0.62 | 0.25 | 0.21 | 0.44 | 0.65 | 0.53 | 0.66 |
| Acyclic(N4)/cyclic ($<=$N4), weight ratio | 9.37 | 5.47 | 4.52 | 10.14 | 11.70 | 6.40 | 3.97 | 5.03 | 3.10 |

| Example No. | 1210 | 1211 | 1212 | 1213 | 1214 | 1215 |
|---|---|---|---|---|---|---|
| Catalyst Type | UUUUU | UUUUU | UUUUU | UUUUU | UUUUU | UUUUU |
| Catalyst weight, gm | 50 | 50 | 50 | 50 | 50 | 50 |
| Pressure, psig | 600 | 600 | 600 | 600 | 600 | 600 |
| Temperature, °C. | 250.3 | 255.6 | 260.5 | 270.5 | 250.4 | 260.4 |
| Time on organics, hrs. | 143 | 148 | 168 | 172 | 191 | 196 |
| Duration of run, hrs. | 2 | 2 | 2 | 2 | 2 | 2 |
| MEA SV, gmol/hr/kgcat | 5.72 | 6.20 | 5.68 | 6.10 | 5.61 | 6.22 |
| DETA/MEA mole ratio | 0.99 | 0.99 | 0.99 | 0.99 | 0.99 | 0.99 |
| NH3/MEA mole ratio | 5.98 | 5.98 | 5.98 | 5.98 | 5.98 | 5.98 |
| Crude product composition, wt. % | | | | | | |
| EDA | 0.568 | 0.601 | 0.717 | 1.279 | 0.432 | 0.659 |
| MEA | 27.232 | 27.065 | 22.943 | 20.079 | 28.096 | 24.621 |
| PIP | 0.215 | 0.248 | 0.334 | 0.685 | 0.190 | 0.305 |
| DETA | 54.809 | 54.903 | 54.289 | 45.849 | 56.154 | 54.216 |
| AEEA | 1.865 | 2.067 | 2.397 | 2.218 | 1.939 | 2.262 |
| AEP | 0.495 | 0.410 | 0.506 | 0.739 | 0.377 | 0.454 |
| HEP | 0.000 | 0.000 | 0.000 | 0.000 | 0.000 | 0.000 |
| TAEA | 1.241 | 1.085 | 1.426 | 1.382 | 0.995 | 1.248 |
| 1-TETA | 7.018 | 6.914 | 8.559 | 9.775 | 6.269 | 7.933 |
| DAEP | 0.201 | 0.100 | 0.168 | 0.247 | 0.071 | 0.112 |
| PEEDA | 0.041 | 0.070 | 0.067 | 0.081 | 0.058 | 0.082 |
| DPE | 0.098 | 0.111 | 0.138 | 0.256 | 0.116 | 0.155 |
| AE-TAEA | 0.572 | 0.555 | 0.788 | 1.643 | 0.476 | 0.783 |
| 1-TEPA | 0.960 | 1.063 | 1.605 | 3.662 | 0.771 | 1.561 |
| AE-DAEP | 0.051 | 0.032 | 0.048 | 0.231 | 0.000 | 0.049 |
| AE-PEEDA | 0.060 | 0.172 | 0.043 | 0.121 | 0.267 | 0.041 |
| iAE-PEEDA | 0.000 | 0.000 | 0.000 | 0.000 | 0.000 | 0.000 |
| AE-DPE | 0.000 | 0.000 | 0.000 | 0.398 | 0.000 | 0.000 |
| BPEA | 0.000 | 0.000 | 0.093 | 0.146 | 0.000 | 0.100 |
| Others | 2.205 | 1.668 | 2.622 | 6.639 | 1.610 | 2.481 |
| MEA Conversion, % | 26.89 | 26.88 | 38.41 | 46.08 | 24.52 | 33.90 |
| DETA Conversion, % | 12.77 | 12.07 | 13.61 | 27.01 | 10.57 | 13.72 |
| Acyclic(N4), % | 96.03 | 96.59 | 96.39 | 95.01 | 96.71 | 96.32 |
| Acyclic(N5), % | 93.16 | 88.76 | 92.80 | 85.52 | 82.30 | 92.41 |
| $\Sigma(N5)/\Sigma(N4)$, weight ratio | 0.19 | 0.22 | 0.24 | 0.52 | 0.20 | 0.26 |
| Acyclic(N4)/cyclic ($<=$N4), weight ratio | 7.85 | 8.50 | 8.21 | 5.55 | 8.91 | 8.26 |

TABLE CXVIII

| Example No. | 1216 | 1217 | 1218 | 1219 | 1220 | 1221 | 1222 | 1223 | 1224 |
|---|---|---|---|---|---|---|---|---|---|
| Catalyst Type | VVVVV | VVVVV | VVVVV | VVVVV | VVVVV | VVVVV | VVVVV | VVVVV | VVVVV |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 250.1 | 259.9 | 270.4 | 250 | 250 | 285.4 | 274.9 | 270.4 | 280.5 |
| Time on organics, hrs. | 4 | 24 | 28 | 47 | 72 | 96 | 100 | 120 | 124 |
| Duration of run, hrs. | 2 | 2 | 2 | 2 | 2 | 2 | 2 | 2 | 2 |
| MEA SV, gmol/hr/kgcat | 5.91 | 5.22 | 5.79 | 5.68 | 5.01 | 4.83 | 3.20 | 4.69 | 4.67 |
| DETA/MEA mole ratio | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 1.242 | 1.425 | 2.314 | 0.692 | 0.693 | 1.556 | 2.532 | 2.046 | 2.610 |
| MEA | 24.360 | 19.503 | 13.469 | 26.303 | 26.975 | 19.666 | 10.987 | 15.532 | 8.187 |
| PIP | 0.265 | 0.346 | 0.627 | 0.143 | 0.124 | 0.340 | 0.644 | 0.486 | 0.714 |
| DETA | 47.368 | 41.906 | 36.625 | 50.994 | 52.751 | 43.552 | 35.351 | 40.568 | 37.477 |
| AEEA | 2.338 | 2.228 | 1.775 | 2.093 | 2.109 | 2.236 | 1.595 | 2.030 | 1.250 |
| AEP | 0.444 | 0.513 | 0.933 | 0.336 | 0.320 | 0.511 | 0.884 | 0.729 | 1.333 |
| HEP | 0.000 | 0.000 | 0.000 | 0.000 | 0.000 | 0.000 | 0.000 | 0.000 | 0.000 |
| TAEA | 1.585 | 1.779 | 1.946 | 1.465 | 1.421 | 1.853 | 1.907 | 1.979 | 2.217 |
| 1-TETA | 10.818 | 11.971 | 13.853 | 8.981 | 8.541 | 11.616 | 12.837 | 13.039 | 13.746 |
| DAEP | 0.137 | 0.201 | 0.508 | 0.073 | 0.066 | 0.184 | 0.434 | 0.315 | 0.805 |
| PEEDA | 0.048 | 0.063 | 0.083 | 0.041 | 0.045 | 0.070 | 0.105 | 0.089 | 0.181 |
| DPE | 0.147 | 0.053 | 0.357 | 0.113 | 0.106 | 0.275 | 0.379 | 0.354 | 0.142 |
| AE-TAEA | 1.536 | 2.197 | 3.601 | 1.105 | 0.931 | 2.462 | 3.448 | 3.044 | 3.487 |
| 1-TEPA | 2.585 | 3.750 | 6.842 | 1.710 | 1.407 | 4.084 | 6.236 | 5.278 | 6.468 |

TABLE CXVIII-continued

| | | | | | | | | | |
|---|---|---|---|---|---|---|---|---|---|
| AE-DAEP | 0.039 | 0.075 | 0.609 | 0.000 | 0.000 | 0.281 | 0.507 | 0.443 | 0.547 |
| AE-PEEDA | 0.000 | 0.041 | 0.143 | 0.000 | 0.040 | 0.099 | 0.122 | 0.116 | 0.102 |
| iAE-PEEDA | 0.000 | 0.000 | 0.000 | 0.000 | 0.000 | 0.000 | 0.000 | 0.000 | 0.000 |
| AE-DPE | 0.000 | 0.108 | 0.388 | 0.000 | 0.000 | 0.319 | 0.127 | 0.215 | 0.099 |
| BPEA | 0.201 | 0.347 | 0.305 | 0.127 | 0.079 | 0.340 | 0.272 | 0.259 | 0.272 |
| Others | 2.750 | 3.474 | 9.064 | 1.636 | 1.564 | 5.577 | 8.946 | 7.208 | 12.055 |
| MEA Conversion, % | 33.99 | 44.31 | 63.83 | 28.21 | 27.29 | 47.03 | 68.48 | 58.05 | 77.82 |
| DETA Conversion, % | 23.91 | 29.07 | 41.70 | 17.49 | 15.71 | 30.46 | 39.88 | 35.04 | 39.81 |
| Acyclic(N4), % | 97.38 | 97.73 | 94.33 | 97.86 | 97.84 | 96.20 | 94.12 | 95.18 | 93.39 |
| Acyclic(N5), % | 94.47 | 91.20 | 87.83 | 95.68 | 95.12 | 86.28 | 90.39 | 88.94 | 90.68 |
| Σ(N5)/Σ(N4), weight ratio | 0.34 | 0.46 | 0.70 | 0.27 | 0.24 | 0.54 | 0.68 | 0.59 | 0.64 |
| Acyclic(N4)/cyclic (<=N4), weight ratio | 11.89 | 11.66 | 6.29 | 14.74 | 15.00 | 9.73 | 6.02 | 7.59 | 5.02 |

| Example No. | 1225 | 1226 | 1227 | 1228 | 1229 | 1230 |
|---|---|---|---|---|---|---|
| Catalyst Type | VVVVV | VVVVV | VVVVV | VVVVV | VVVVV | VVVVV |
| Catalyst weight, gm | 50 | 50 | 50 | 50 | 50 | 50 |
| Pressure, psig | 600 | 600 | 600 | 600 | 600 | 600 |
| Temperature, °C. | 250.3 | 255.6 | 260.5 | 270.5 | 250.4 | 260.4 |
| Time on organics, hrs. | 143 | 148 | 168 | 172 | 191 | 196 |
| Duration of run, hrs. | 2 | 2 | 2 | 2 | 2 | 2 |
| MEA SV, gmol/hr/kgcat | 4.55 | 4.85 | 5.47 | 5.78 | 5.58 | 5.91 |
| DETA/MEA mole ratio | 0.99 | 0.99 | 0.99 | 0.99 | 0.99 | 0.99 |
| NH3/MEA mole ratio | 5.98 | 5.98 | 5.98 | 5.98 | 5.98 | 5.98 |
| Crude product composition, wt. % | | | | | | |
| EDA | 0.781 | 0.770 | 0.851 | 1.497 | 0.588 | 1.026 |
| MEA | 25.538 | 22.350 | 20.873 | 16.503 | 25.282 | 24.673 |
| PIP | 0.126 | 0.140 | 0.170 | 0.328 | 0.089 | 0.177 |
| DETA | 52.133 | 52.645 | 51.089 | 44.349 | 55.299 | 51.223 |
| AEEA | 2.040 | 2.312 | 2.326 | 2.193 | 2.078 | 2.224 |
| AEP | 0.426 | 0.428 | 0.436 | 0.591 | 0.356 | 0.443 |
| HEP | 0.000 | 0.000 | 0.000 | 0.000 | 0.000 | 0.000 |
| TAEA | 1.593 | 1.735 | 1.861 | 1.981 | 1.469 | 1.571 |
| 1-TETA | 8.770 | 9.724 | 10.271 | 11.974 | 8.218 | 9.145 |
| DAEP | 0.153 | 0.159 | 0.161 | 0.253 | 0.106 | 0.115 |
| PEEDA | 0.049 | 0.112 | 0.117 | 0.133 | 0.097 | 0.112 |
| DPE | 0.140 | 0.171 | 0.192 | 0.320 | 0.142 | 0.165 |
| AE-TAEA | 1.025 | 1.128 | 1.380 | 2.468 | 0.743 | 1.139 |
| 1-TEPA | 1.452 | 1.623 | 2.028 | 4.244 | 0.949 | 1.722 |
| AE-DAEP | 0.053 | 0.044 | 0.047 | 0.312 | 0.000 | 0.000 |
| AE-PEEDA | 0.079 | 0.041 | 0.037 | 0.094 | 0.106 | 0.000 |
| iAE-PEEDA | 0.000 | 0.000 | 0.000 | 0.000 | 0.000 | 0.000 |
| AE-DPE | 0.000 | 0.000 | 0.000 | 0.050 | 0.000 | 0.000 |
| BPEA | 0.000 | 0.100 | 0.106 | 0.197 | 0.000 | 0.030 |
| Others | 2.433 | 2.776 | 3.266 | 6.788 | 1.812 | 2.887 |
| MEA Conversion, % | 31.14 | 39.18 | 43.37 | 55.46 | 32.14 | 33.50 |
| DETA Conversion, % | 16.67 | 15.95 | 17.84 | 29.04 | 12.01 | 18.16 |
| Acyclic(N4), % | 96.78 | 96.26 | 96.26 | 95.17 | 96.54 | 96.46 |
| Acyclic(N5), % | 94.89 | 93.64 | 94.69 | 91.17 | 94.09 | 98.95 |
| Σ(N5)/Σ(N4), weight ratio | 0.24 | 0.24 | 0.28 | 0.50 | 0.17 | 0.26 |
| Acyclic(N4)/cyclic (<=N4), weight ratio | 11.55 | 11.30 | 11.24 | 8.57 | 12.22 | 10.56 |

TABLE CXIX

| Example No. | 1231 | 1232 | 1233 | 1234 | 1235 | 1236 | 1237 |
|---|---|---|---|---|---|---|---|
| Catalyst Type | WWWWW | WWWWW | WWWWW | WWWWW | WWWWW | WWWWW | WWWWW |
| Catalyst weight, gm | 50 | 50 | 50 | 50 | 50 | 50 | 50 |
| Pressure, psig | 600 | 600 | 600 | 600 | 600 | 600 | 600 |
| Temperature, °C. | 249.3 | 259.6 | 270.3 | 264.7 | 274.8 | 280.3 | 285.1 |
| Time on organics, hrs. | 4 | 24 | 28 | 48 | 52 | 72 | 76 |
| Duration of run, hrs. | 2 | 2 | 2 | 2 | 2 | 2 | 2 |
| MEA SV, gmol/hr/kgcat | 6.40 | 6.33 | 6.28 | 5.72 | 6.02 | 5.58 | 5.65 |
| DETA/MEA mole ratio | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 |
| Crude product composition, wt. % | | | | | | | |
| EDA | 0.770 | 0.980 | 1.583 | 1.111 | 1.832 | 2.142 | 3.301 |
| MEA | 25.827 | 23.440 | 17.219 | 22.571 | 16.310 | 16.564 | 10.045 |
| PIP | 0.276 | 0.393 | 0.662 | 0.422 | 0.751 | 0.950 | 1.442 |
| DETA | 51.636 | 48.836 | 42.304 | 48.278 | 40.898 | 42.099 | 35.503 |
| AEEA | 2.334 | 2.504 | 2.372 | 2.475 | 2.126 | 1.936 | 1.055 |
| AEP | 0.412 | 0.494 | 0.383 | 0.522 | 0.865 | 0.963 | 1.612 |
| HEP | 0.000 | 0.000 | 0.000 | 0.000 | 0.000 | 0.000 | 0.000 |
| TAEA | 1.110 | 1.332 | 1.599 | 1.416 | 1.525 | 1.379 | 1.308 |
| 1-TETA | 8.696 | 10.460 | 12.736 | 10.690 | 12.202 | 11.061 | 11.624 |
| DAEP | 0.101 | 0.165 | 0.378 | 0.173 | 0.369 | 0.370 | 0.792 |
| PEEDA | 0.489 | 0.055 | 0.252 | 0.693 | 0.263 | 0.286 | 0.651 |
| DPE | 0.112 | 0.134 | 0.073 | 0.039 | 0.086 | 0.085 | 0.110 |

TABLE CXIX-continued

| | | | | | | | |
|---|---|---|---|---|---|---|---|
| AE-TAEA | 0.841 | 1.303 | 2.375 | 1.359 | 2.466 | 2.153 | 2.771 |
| 1-TEPA | 1.854 | 3.003 | 5.582 | 3.165 | 5.909 | 5.377 | 7.397 |
| AE-DAEP | 0.000 | 0.051 | 0.359 | 0.070 | 0.646 | 0.658 | 0.827 |
| AE-PEEDA | 0.000 | 0.000 | 0.040 | 0.031 | 0.109 | 0.115 | 0.423 |
| iAE-PEEDA | 0.000 | 0.000 | 0.000 | 0.000 | 0.000 | 0.000 | 0.000 |
| AE-DPE | 0.000 | 0.112 | 0.049 | 0.000 | 0.057 | 0.476 | 0.079 |
| BPEA | 0.093 | 0.263 | 0.619 | 0.150 | 0.427 | 0.359 | 0.296 |
| Others | 1.692 | 2.457 | 4.961 | 2.959 | 6.639 | 6.450 | 12.385 |
| MEA Conversion, % | 29.54 | 36.72 | 53.44 | 38.82 | 55.78 | 55.02 | 72.73 |
| DETA Conversion, % | 16.50 | 21.84 | 32.20 | 22.43 | 34.26 | 32.23 | 42.86 |
| Acyclic(N4), % | 97.38 | 97.07 | 95.31 | 97.77 | 95.01 | 94.37 | 89.26 |
| Acyclic(N5), % | 96.65 | 90.95 | 88.16 | 94.71 | 87.09 | 82.38 | 86.19 |
| Σ(N5)/Σ(N4), weight ratio | 0.27 | 0.38 | 0.60 | 0.38 | 0.66 | 0.69 | 0.81 |
| Acyclic(N4)/cyclic (<=N4), weight ratio | 10.30 | 9.49 | 6.49 | 9.91 | 5.87 | 4.68 | 2.80 |

| Example No. | 1238 | 1239 | 1240 | 1241 |
|---|---|---|---|---|
| Catalyst Type | wwwww | wwwww | wwwww | wwwww |
| Catalyst weight, gm | 50 | 50 | 50 | 50 |
| Pressure, psig | 600 | 600 | 600 | 600 |
| Temperature, °C. | 260.4 | 270.3 | 250.7 | 250.8 |
| Time on organics, hrs. | 86 | 100 | 119.7 | 144.5 |
| Duration of run, hrs. | 2 | 2 | 2 | 2 |
| MEA SV, gmol/hr/kgcat | 6.24 | 6.17 | 6.94 | 5.93 |
| DETA/MEA mole ratio | 0.99 | 0.99 | 0.99 | 0.99 |
| NH3/MEA mole ratio | 5.98 | 5.98 | 5.98 | 5.98 |
| Crude product composition, wt. % | | | | |
| EDA | 0.774 | 1.198 | 0.345 | 0.350 |
| MEA | 27.643 | 21.820 | 30.552 | 30.853 |
| PIP | 0.265 | 0.454 | 0.111 | 0.096 |
| DETA | 52.572 | 47.132 | 55.797 | 55.617 |
| AEEA | 2.172 | 2.317 | 1.696 | 1.611 |
| AEP | 0.359 | 0.551 | 0.258 | 0.247 |
| HEP | 0.000 | 0.000 | 0.000 | 0.000 |
| TAEA | 1.011 | 1.348 | 0.717 | 0.639 |
| 1-TETA | 7.027 | 9.767 | 4.893 | 4.363 |
| DAEP | 0.081 | 0.178 | 0.044 | 0.039 |
| PEEDA | 0.025 | 0.122 | 0.023 | 0.032 |
| DPE | 0.079 | 0.180 | 0.004 | 0.052 |
| AE-TAEA | 0.689 | 1.489 | 0.308 | 0.099 |
| 1-TEPA | 1.584 | 3.350 | 0.591 | 0.239 |
| AE-DAEP | 0.000 | 0.171 | 0.000 | 0.342 |
| AE-PEEDA | 0.032 | 0.042 | 0.000 | 0.000 |
| iAE-PEEDA | 0.000 | 0.000 | 0.000 | 0.000 |
| AE-DPE | 0.000 | 0.000 | 0.000 | 0.045 |
| BPEA | 0.036 | 0.063 | 0.000 | 0.000 |
| Others | 2.004 | 3.510 | 1.034 | 0.830 |
| MEA Conversion, % | 24.68 | 39.81 | 16.04 | 14.31 |
| DETA Conversion, % | 15.08 | 22.93 | 9.10 | 8.43 |
| Acyclic(N4), % | 97.73 | 95.84 | 98.71 | 97.58 |
| Acyclic(N5), % | 97.08 | 94.57 | 100.00 | 46.54 |
| Σ(N5)/Σ(N4), weight ratio | 0.28 | 0.44 | 0.15 | 0.14 |
| Acyclic(N4)/cyclic (<=N4), weight ratio | 9.90 | 7.47 | 12.67 | 10.70 |

TABLE CXX

| Example No. | 1242 | 1243 | 1244 | 1245 | 1246 | 1247 | 1248 | 1249 | 1250 | 1251 |
|---|---|---|---|---|---|---|---|---|---|---|
| Catalyst Type | XXXXX | XXXXX | XXXXX | XXXXX | XXXXX | XXXXX | XXXXX | XXXXX | XXXXX | XXXXX |
| Catalyst weight, gm | 50 | 50 | 50 | 50 | 50 | 50 | 50 | 50 | 50 | 50 |
| Pressure, psig | 600 | 600 | 600 | 400 | 600 | 600 | 600 | 600 | 600 | 600 |
| Temperature, °C. | 249.3 | 259.6 | 270.3 | 264.7 | 274.8 | 280.3 | 285.1 | 270.3 | 250.7 | 250.8 |
| Time on organics, hrs. | 4 | 24 | 28 | 48 | 52 | 72 | 76 | 100 | 119.7 | 144.5 |
| Duration of run, hrs. | 2 | 2 | 2 | 2 | 2 | 2 | 2 | 2 | 2 | 2 |
| MEA SV, gmol/hr/kgcat | 6.17 | 5.95 | 5.82 | 5.54 | 5.88 | 4.57 | 6.15 | 6.07 | 7.05 | 5.82 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.893 | 1.185 | 1.874 | 1.443 | 2.387 | 2.639 | 3.678 | 1.556 | 0.481 | 0.515 |
| MEA | 23.997 | 21.165 | 15.053 | 20.703 | 14.059 | 13.349 | 8.387 | 18.730 | 28.844 | 29.482 |
| PIP | 0.250 | 0.368 | 0.597 | 0.409 | 0.727 | 0.812 | 1.108 | 0.435 | 0.112 | 0.093 |
| DETA | 50.182 | 46.524 | 39.414 | 45.397 | 38.993 | 39.116 | 35.238 | 42.781 | 53.913 | 53.627 |
| AEEA | 2.411 | 2.498 | 2.085 | 2.340 | 1.699 | 1.499 | 0.681 | 2.101 | 1.876 | 1.810 |
| AEP | 0.422 | 0.510 | 0.810 | 0.527 | 0.904 | 1.012 | 1.488 | 0.535 | 0.274 | 0.244 |
| HEP | 0.000 | 0.000 | 0.000 | 0.000 | 0.000 | 0.000 | 0.000 | 0.000 | 0.000 | 0.000 |
| TAEA | 1.425 | 1.775 | 1.846 | 1.795 | 1.800 | 1.721 | 1.514 | 1.777 | 1.179 | 1.018 |
| 1-TETA | 10.191 | 11.986 | 13.100 | 11.628 | 12.524 | 12.091 | 11.574 | 10.990 | 6.600 | 5.769 |

TABLE CXX-continued

| Example No. | 1242 | 1243 | 1244 | 1245 | 1246 | 1247 | 1248 | 1249 | 1250 | 1251 |
|---|---|---|---|---|---|---|---|---|---|---|
| DAEP | 0.109 | 0.185 | 0.375 | 0.187 | 0.419 | 0.473 | 0.929 | 0.206 | 0.053 | 0.044 |
| PEEDA | 0.063 | 0.051 | 0.228 | 0.118 | 0.266 | 0.306 | 0.601 | 0.128 | 0.026 | 0.066 |
| DPE | 0.125 | 0.171 | 0.107 | 0.060 | 0.110 | 0.107 | 0.462 | 0.286 | 0.080 | 0.066 |
| AE-TAEA | 1.294 | 2.017 | 3.232 | 2.258 | 3.432 | 3.203 | 3.391 | 2.731 | 0.694 | 0.490 |
| 1-TEPA | 2.267 | 3.609 | 6.173 | 3.897 | 6.441 | 6.147 | 7.234 | 4.636 | 1.042 | 0.691 |
| AE-DAEP | 0.031 | 0.048 | 0.524 | 0.080 | 0.621 | 0.625 | 0.927 | 0.399 | 0.000 | 0.000 |
| AE-PEEDA | 0.000 | 0.033 | 0.108 | 0.047 | 0.094 | 0.111 | 0.467 | 0.157 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.000 | 0.000 | 0.236 | 0.000 | 0.224 | 0.275 | 0.049 | 0.299 | 0.000 | 0.000 |
| BPEA | 0.045 | 0.106 | 0.552 | 0.282 | 0.617 | 0.594 | 0.195 | 0.235 | 0.000 | 0.000 |
| Others | 1.906 | 3.042 | 6.857 | 3.249 | 7.904 | 8.181 | 13.108 | 5.468 | 1.100 | 0.978 |
| MEA Conversion, % | 34.77 | 42.76 | 59.22 | 43.57 | 62.03 | 63.61 | 77.16 | 48.81 | 21.06 | 17.89 |
| DETA Conversion, % | 19.07 | 25.41 | 36.70 | 26.65 | 37.57 | 36.79 | 43.13 | 30.69 | 12.53 | 11.46 |
| Acyclic(N4), % | 97.49 | 97.11 | 95.45 | 97.33 | 94.73 | 93.96 | 86.78 | 95.35 | 97.98 | 97.44 |
| Acyclic(N5), % | 97.89 | 96.76 | 86.87 | 93.75 | 86.37 | 85.33 | 86.62 | 87.08 | 100.00 | 100.00 |
| Σ(N5)/Σ(N4), weight ratio | 0.30 | 0.41 | 0.69 | 0.47 | 0.75 | 0.74 | 0.81 | 0.63 | 0.21 | 0.16 |
| Acyclic(N4)/cyclic (<=N4), weight ratio | 11.96 | 10.68 | 7.04 | 10.28 | 5.89 | 5.09 | 2.85 | 8.01 | 14.23 | 13.14 |

TABLE CXXI

| Comparative Example No. | 1252 | 1253 | 1254 | 1255 | 1256 | 1257 | 1258 | 1259 | 1260 |
|---|---|---|---|---|---|---|---|---|---|
| Catalyst Type | YYYYY | YYYYY | YYYYY | YYYYY | YYYYY | YYYYY | YYYYY | YYYYY | YYYYY |
| Catalyst weight, gm | 50 | 50 | 50 | 50 | 50 | 50 | 50 | 50 | 50 |
| Pressure, psig | 600 | 600 | 600 | 600 | 600 | 600 | 600 | 600 | 600 |
| Temperature, °C. | 251 | 250.5 | 260.7 | 265.6 | 270.4 | 275.8 | 280.5 | 255.8 | 245.6 |
| Time on organics, hrs. | 4 | 23.5 | 27.5 | 46.5 | 51.5 | 70.5 | 75.5 | 95.5 | 119.5 |
| Duration of run, hrs. | 2 | 2 | 2 | 2 | 2 | 2 | 2 | 2 | 2 |
| MEA SV, gmol/hr/kgcat | 3.47 | 3.80 | 3.91 | 3.78 | 4.01 | 3.87 | 4.12 | 3.34 | 3.15 |
| DETA/MEA mole ratio | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 2.846 | 1.526 | 2.032 | 1.886 | 2.080 | 2.055 | 2.349 | 0.725 | 0.430 |
| MEA | 20.117 | 22.677 | 18.757 | 16.307 | 13.974 | 13.175 | 11.612 | 25.948 | 29.403 |
| PIP | 0.388 | 0.256 | 0.499 | 0.640 | 0.773 | 0.847 | 0.969 | 0.218 | 0.102 |
| DETA | 38.752 | 46.030 | 41.118 | 41.094 | 35.948 | 37.509 | 34.665 | 52.792 | 56.722 |
| AEEA | 2.423 | 3.036 | 3.076 | 3.058 | 2.464 | 2.253 | 1.745 | 3.079 | 2.412 |
| AEP | 0.532 | 0.351 | 0.611 | 0.804 | 0.961 | 1.106 | 1.326 | 0.327 | 0.250 |
| HEP | 0.000 | 0.000 | 0.000 | 0.000 | 0.000 | 0.000 | 0.000 | 0.000 | 0.000 |
| TAEA | 0.913 | 0.960 | 1.193 | 1.429 | 1.379 | 1.405 | 1.366 | 0.793 | 0.480 |
| 1-TETA | 6.883 | 7.323 | 9.136 | 10.360 | 9.961 | 9.612 | 9.046 | 5.680 | 3.493 |
| DAEP | 0.130 | 0.038 | 0.254 | 0.343 | 0.479 | 0.517 | 0.769 | 0.100 | 0.049 |
| PEEDA | 0.188 | 0.076 | 0.217 | 0.124 | 0.154 | 0.084 | 0.662 | 0.074 | 0.036 |
| DPE | 0.150 | 0.132 | 0.325 | 0.319 | 0.397 | 0.361 | 0.120 | 0.153 | 0.089 |
| AE-TAEA | 0.216 | 0.137 | 1.821 | 0.185 | 0.244 | 0.207 | 2.472 | 0.625 | 0.349 |
| 1-TEPA | 0.296 | 2.808 | 4.728 | 6.414 | 7.260 | 6.994 | 7.086 | 2.162 | 0.887 |
| AE-DAEP | 0.731 | 0.413 | 0.156 | 0.157 | 0.197 | 0.176 | 1.016 | 0.226 | 0.078 |
| AE-PEEDA | 0.175 | 0.237 | 0.215 | 0.263 | 0.406 | 0.407 | 0.313 | 0.082 | 0.031 |
| iAE-PEEDA | 0.000 | 0.000 | 0.000 | 0.000 | 0.000 | 0.000 | 0.000 | 0.000 | 0.000 |
| AE-DPE | 0.291 | 0.147 | 0.259 | 0.254 | 0.453 | 0.383 | 0.175 | 0.036 | 0.138 |
| BPEA | 0.199 | 0.113 | 0.345 | 0.433 | 0.745 | 0.091 | 0.611 | 0.033 | 0.000 |
| Others | 16.400 | 7.123 | 10.349 | 11.322 | 15.766 | 15.360 | 16.327 | 3.878 | 2.051 |
| MEA Conversion, % | 43.51 | 37.03 | 49.65 | 56.66 | 62.55 | 64.22 | 68.78 | 30.04 | 19.95 |
| DETA Conversion, % | 35.49 | 24.23 | 34.57 | 35.26 | 42.89 | 39.62 | 44.75 | 15.62 | 8.46 |
| Acyclic(N4), % | 94.31 | 97.10 | 92.83 | 93.73 | 91.66 | 91.95 | 87.02 | 95.16 | 95.77 |
| Acyclic(N5), % | 26.85 | 76.39 | 87.03 | 85.62 | 80.62 | 87.19 | 81.87 | 88.03 | 83.29 |
| Σ(N5)/Σ(N4), weight ratio | 0.23 | 0.45 | 0.67 | 0.61 | 0.75 | 0.68 | 0.97 | 0.46 | 0.35 |
| Acyclic(N4)/cyclic (<=N4), weight ratio | 5.60 | 9.69 | 5.41 | 5.27 | 4.09 | 3.77 | 2.70 | 7.39 | 7.51 |

TABLE CXXII

| Example No. | 1261 | 1262 | 1263 | 1264 | 1265 | 1266 | 1267 | 1268 | 1269 | 1270 |
|---|---|---|---|---|---|---|---|---|---|---|
| Catalyst Type | ZZZZZ | ZZZZZ | ZZZZZ | ZZZZZ | ZZZZZ | ZZZZZ | ZZZZZ | ZZZZZ | ZZZZZ | ZZZZZ |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.5 | 259.7 | 254.4 | 264.4 | 269.3 | 279.6 | 249.3 | 259.5 | 260 | 250 |
| Time on organics, hrs. | 19.5 | 24.5 | 43.5 | 48.5 | 69 | 73 | 72 | 97 | 116.3 | 138 |
| Duration of run, hrs. | 2 | 2 | 2 | 2 | 2 | 2 | 2 | 2 | 2 | 2 |
| MEA SV, gmol/hr/kgcat | 5.54 | 5.44 | 6.26 | 6.35 | 6.68 | 6.95 | 6.07 | 5.74 | 6.22 | 5.52 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |

TABLE CXXII-continued

| Example No. | 1261 | 1262 | 1263 | 1264 | 1265 | 1266 | 1267 | 1268 | 1269 | 1270 |
|---|---|---|---|---|---|---|---|---|---|---|
| EDA | 0.557 | 0.797 | 0.461 | 0.645 | 0.777 | 1.221 | 0.258 | 0.400 | 0.408 | 0.214 |
| MEA | 32.336 | 29.295 | 31.431 | 27.011 | 27.058 | 20.206 | 31.252 | 29.183 | 29.037 | 32.707 |
| PIP | 0.147 | 0.336 | 0.159 | 0.315 | 0.434 | 0.832 | 0.093 | 0.216 | 0.197 | 0.088 |
| DETA | 56.556 | 55.334 | 57.257 | 55.289 | 54.631 | 50.585 | 59.566 | 57.321 | 57.294 | 59.411 |
| AEEA | 2.101 | 2.829 | 2.340 | 2.851 | 2.944 | 2.743 | 2.003 | 2.673 | 2.620 | 1.871 |
| AEP | 0.307 | 0.366 | 0.271 | 0.435 | 0.440 | 0.778 | 0.285 | 0.332 | 0.318 | 0.272 |
| HEP | 0.000 | 0.000 | 0.000 | 0.000 | 0.000 | 0.000 | 0.000 | 0.000 | 0.000 | 0.000 |
| TAEA | 0.432 | 0.692 | 0.443 | 0.736 | 0.748 | 1.212 | 0.436 | 0.516 | 0.547 | 0.280 |
| 1-TETA | 2.629 | 4.380 | 2.617 | 4.340 | 4.427 | 7.328 | 2.476 | 3.221 | 3.344 | 1.831 |
| DAEP | 0.162 | 0.122 | 0.053 | 0.087 | 0.088 | 0.243 | 0.039 | 0.054 | 0.055 | 0.074 |
| PEEDA | 0.052 | 0.024 | 0.046 | 0.028 | 0.021 | 0.247 | 0.029 | 0.027 | 0.030 | 0.025 |
| DPE | 0.000 | 0.064 | 0.078 | 0.068 | 0.075 | 0.145 | 0.031 | 0.045 | 0.039 | 0.000 |
| AE-TAEA | 0.082 | 0.270 | 0.095 | 0.335 | 0.461 | 1.255 | 0.092 | 0.152 | 0.245 | 0.060 |
| 1-TEPA | 0.033 | 0.668 | 0.303 | 0.856 | 1.340 | 3.408 | 0.229 | 0.413 | 0.661 | 0.085 |
| AE-DAEP | 0.083 | 0.027 | 0.000 | 0.020 | 0.058 | 0.215 | 0.000 | 0.000 | 0.000 | 0.000 |
| AE-PEEDA | 0.055 | 0.000 | 0.000 | 0.000 | 0.000 | 0.025 | 0.075 | 0.161 | 0.184 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.106 | 0.000 | 0.000 | 0.000 | 0.000 | 0.087 | 0.000 | 0.000 | 0.000 | 0.118 |
| BPEA | 0.000 | 0.000 | 0.000 | 0.000 | 0.036 | 0.100 | 0.000 | 0.000 | 0.000 | 0.000 |
| Others | 1.554 | 1.558 | 1.509 | 1.685 | 2.059 | 3.632 | 1.368 | 1.728 | 1.572 | 0.679 |
| MEA Conversion, % | 11.54 | 20.03 | 14.00 | 24.93 | 25.58 | 44.77 | 15.58 | 20.02 | 20.56 | 10.86 |
| DETA Conversion, % | 8.29 | 10.46 | 7.13 | 8.91 | 10.93 | 18.03 | 4.61 | 6.87 | 7.07 | 4.01 |
| Acyclic(N4), % | 93.44 | 95.99 | 94.48 | 96.48 | 96.52 | 93.06 | 96.66 | 96.71 | 96.87 | 95.47 |
| Acyclic(N5), % | 32.06 | 97.13 | 100.00 | 98.26 | 94.89 | 91.56 | 80.95 | 77.80 | 83.06 | 55.28 |
| Σ(N5)/Σ(N4), weight ratio | 0.11 | 0.18 | 0.12 | 0.23 | 0.34 | 0.55 | 0.13 | 0.18 | 0.27 | 0.11 |
| Acyclic(N4)/cyclic (<=N4), weight ratio | 4.57 | 5.54 | 5.02 | 5.42 | 4.87 | 3.80 | 6.08 | 5.53 | 6.06 | 4.58 |

TABLE CXXIII

| Comparative Example No. | 1271 | 1272 | 1273 | 1274 | 1275 | 1276 | 1277 | 1278 | 1279 |
|---|---|---|---|---|---|---|---|---|---|
| Catalyst Type | AAAAAA | AAAAAA | AAAAAA | AAAAAA | AAAAAA | AAAAAA | AAAAAA | AAAAAA | AAAAAA |
| Catalyst weight, gm | 50 | 50 | 50 | 50 | 50 | 50 | 50 | 50 | 50 |
| Pressure, psig | 600 | 600 | 600 | 400 | 600 | 600 | 600 | 600 | 600 |
| Temperature, °C. | 251 | 250.5 | 260.7 | 265.6 | 270.4 | 275.8 | 280.5 | 255.8 | 245.5 |
| Time on organics, hrs. | 4 | 23.5 | 27.5 | 46.5 | 51.5 | 70.5 | 75.5 | 95.5 | 119.5 |
| Duration of run, hrs. | 2 | 2 | 2 | 2 | 2 | 2 | 2 | 2 | 2 |
| MEA SV, gmol/hr/kgcat | 3.46 | 3.96 | 3.89 | 3.66 | 3.88 | 3.96 | 4.00 | 3.97 | 4.04 |
| DETA/MEA mole ratio | 0.99 | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 0.569 | 0.369 | 0.606 | 0.790 | 0.904 | 1.370 | 1.436 | 0.353 | 0.165 |
| MEA | 22.906 | 25.594 | 20.285 | 17.926 | 14.593 | 14.303 | 12.427 | 26.475 | 30.271 |
| PIP | 0.366 | 0.218 | 0.401 | 0.561 | 0.667 | 1.037 | 1.090 | 0.220 | 0.079 |
| DETA | 50.355 | 54.133 | 48.370 | 47.753 | 41.854 | 42.262 | 40.213 | 53.453 | 59.022 |
| AEEA | 2.955 | 3.393 | 3.649 | 3.648 | 2.988 | 2.426 | 1.989 | 2.794 | 2.193 |
| AEP | 0.473 | 0.305 | 0.456 | 0.607 | 0.722 | 1.086 | 1.211 | 0.306 | 0.236 |
| HEP | 0.000 | 0.000 | 0.000 | 0.000 | 0.000 | 0.000 | 0.000 | 0.000 | 0.000 |
| TAEA | 1.254 | 1.114 | 1.436 | 1.582 | 1.518 | 1.586 | 1.556 | 0.732 | 0.447 |
| 1-TETA | 7.783 | 6.913 | 9.002 | 9.975 | 9.612 | 10.518 | 10.362 | 4.586 | 2.655 |
| DAEP | 0.122 | 0.065 | 0.137 | 0.196 | 0.312 | 0.449 | 0.543 | 0.081 | 0.040 |
| PEEDA | 0.065 | 0.039 | 0.117 | 0.171 | 0.130 | 0.064 | 0.515 | 0.067 | 0.029 |
| DPE | 0.063 | 0.049 | 0.181 | 0.170 | 0.302 | 0.281 | 0.115 | 0.161 | 0.062 |
| AE-TAEA | 0.161 | 0.112 | 1.712 | 1.846 | 2.488 | 0.152 | 2.426 | 0.607 | 0.179 |
| 1-TEPA | 2.457 | 1.842 | 3.712 | 4.439 | 5.404 | 6.285 | 6.578 | 1.410 | 0.198 |
| AE-DAEP | 0.059 | 0.063 | 0.165 | 0.212 | 0.623 | 0.154 | 0.685 | 0.248 | 0.065 |
| AE-PEEDA | 0.059 | 0.025 | 0.138 | 0.103 | 0.359 | 0.325 | 0.207 | 0.152 | 0.036 |
| iAE-PEEDA | 0.000 | 0.000 | 0.000 | 0.000 | 0.000 | 0.000 | 0.000 | 0.000 | 0.000 |
| AE-DPE | 0.044 | 0.028 | 0.236 | 0.276 | 0.341 | 0.169 | 0.351 | 0.184 | 0.138 |
| BPEA | 0.025 | 0.049 | 0.166 | 0.271 | 0.792 | 0.439 | 0.423 | 0.121 | 0.000 |
| Others | 3.746 | 2.581 | 5.592 | 4.546 | 10.542 | 10.867 | 9.666 | 4.479 | 1.866 |
| MEA Conversion, % | 36.31 | 30.93 | 45.92 | 51.83 | 60.98 | 61.53 | 66.10 | 28.20 | 17.97 |
| DETA Conversion, % | 17.00 | 13.40 | 23.56 | 23.94 | 33.65 | 32.63 | 34.97 | 14.06 | 5.18 |
| Acyclic(N4), % | 97.29 | 98.10 | 95.97 | 95.54 | 93.72 | 93.83 | 91.02 | 94.48 | 95.88 |
| Acyclic(N5), % | 93.26 | 92.16 | 88.46 | 87.92 | 78.84 | 85.42 | 84.36 | 74.04 | 61.21 |
| Σ(N5)/Σ(N4), weight ratio | 0.30 | 0.25 | 0.56 | 0.59 | 0.84 | 0.58 | 0.81 | 0.48 | 0.19 |

TABLE CXXIII-continued

| Comparative Example No. | 1271 | 1272 | 1273 | 1274 | 1275 | 1276 | 1277 | 1278 | 1279 |
|---|---|---|---|---|---|---|---|---|---|
| Acyclic(N4)/cyclic (<=N4), weight ratio | 8.28 | 11.82 | 8.06 | 6.76 | 5.21 | 4.14 | 3.42 | 6.35 | 6.89 |

TABLE CXXIV

| Comparative Example No. | 1280 | 1281 | 1282 | 1283 | 1284 | 1285 | 1286 | 1287 | 1288 |
|---|---|---|---|---|---|---|---|---|---|
| Catalyst Type | BBBBBB | BBBBBB | BBBBBB | BBBBBB | BBBBBB | BBBBBB | BBBBBB | BBBBBB | BBBBBB |
| Catalyst weight, gm | 50 | 50 | 50 | 50 | 50 | 50 | 50 | 50 | 50 |
| Pressure, psig | 600 | 600 | 600 | 400 | 600 | 600 | 600 | 600 | 600 |
| Temperature, °C. | 251 | 250.5 | 260.7 | 265.6 | 270.4 | 275.8 | 280.5 | 255.8 | 245.5 |
| Time on organics, hrs. | 4 | 23.5 | 27.5 | 46.5 | 51.5 | 70.5 | 75.5 | 95.5 | 119.5 |
| Duration of run, hrs. | 2 | 2 | 2 | 2 | 2 | 2 | 2 | 2 | 2 |
| MEA SV, gmol/hr/kgcat | 4.35 | 4.44 | 4.56 | 3.97 | 4.31 | 4.29 | 4.42 | 3.99 | 4.38 |
| DETA/MEA mole ratio | 0.99 | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 | 5.98 |
| Crude product composition, wt. % | | | | | | | | | |
| EDA | 0.129 | 0.034 | 0.081 | 0.130 | 0.184 | 0.319 | 0.432 | 0.086 | 0.044 |
| MEA | 31.011 | 33.961 | 32.995 | 30.431 | 29.013 | 27.475 | 26.166 | 30.793 | 34.503 |
| PIP | 0.136 | 0.085 | 0.172 | 0.302 | 0.423 | 0.645 | 0.863 | 0.155 | 0.069 |
| DETA | 59.305 | 59.998 | 58.455 | 58.206 | 56.825 | 54.579 | 51.202 | 55.790 | 59.775 |
| AEEA | 1.084 | 1.095 | 1.515 | 1.846 | 1.989 | 2.043 | 1.872 | 1.338 | 0.780 |
| AEP | 0.308 | 0.219 | 0.266 | 0.335 | 0.419 | 0.580 | 0.708 | 0.282 | 0.209 |
| HEP | 0.000 | 0.000 | 0.000 | 0.000 | 0.000 | 0.000 | 0.000 | 0.000 | 0.000 |
| TAEA | 0.432 | 0.292 | 0.389 | 0.566 | 0.673 | 0.798 | 0.785 | 0.390 | 0.223 |
| 1-TETA | 2.508 | 1.580 | 1.972 | 2.905 | 3.532 | 4.375 | 4.754 | 2.170 | 1.109 |
| DAEP | 0.065 | 0.025 | 0.043 | 0.060 | 0.080 | 0.127 | 0.290 | 0.149 | 0.046 |
| PEEDA | 0.047 | 0.029 | 0.037 | 0.051 | 0.085 | 0.146 | 0.239 | 0.084 | 0.027 |
| DPE | 0.022 | 0.038 | 0.057 | 0.072 | 0.080 | 0.101 | 0.100 | 0.221 | 0.018 |
| AE-TAEA | 0.305 | 0.284 | 0.525 | 0.127 | 0.137 | 1.094 | 0.823 | 0.664 | 0.107 |
| 1-TEPA | 0.579 | 0.428 | 0.478 | 1.062 | 1.431 | 1.985 | 2.525 | 1.037 | 0.075 |
| AE-DAEP | 0.063 | 0.194 | 0.053 | 0.066 | 0.116 | 0.232 | 0.666 | 0.600 | 0.000 |
| AE-PEEDA | 0.000 | 0.000 | 0.050 | 0.039 | 0.034 | 0.106 | 0.169 | 0.000 | 0.000 |
| iAE-PEEDA | 0.000 | 0.000 | 0.000 | 0.000 | 0.000 | 0.000 | 0.000 | 0.000 | 0.000 |
| AE-DPE | 0.053 | 0.078 | 0.027 | 0.063 | 0.028 | 0.045 | 0.037 | 0.417 | 0.201 |
| BPEA | 0.035 | 0.000 | 0.000 | 0.021 | 0.040 | 0.046 | 0.045 | 0.037 | 0.000 |
| Others | 1.348 | 0.783 | 1.767 | 2.309 | 2.800 | 3.375 | 4.038 | 3.468 | 0.757 |
| MEA Conversion, % | 15.65 | 8.73 | 11.34 | 18.47 | 22.00 | 26.74 | 28.82 | 16.92 | 5.92 |
| DETA Conversion, % | 4.38 | 4.41 | 6.89 | 7.56 | 9.44 | 13.72 | 17.43 | 10.77 | 3.38 |
| Acyclic(N4), % | 95.58 | 95.25 | 94.45 | 94.94 | 94.46 | 93.24 | 89.79 | 84.87 | 93.55 |
| Acyclic(N5), % | 85.28 | 72.27 | 88.43 | 86.18 | 87.68 | 87.70 | 78.48 | 61.69 | 47.55 |
| Σ(N5)/Σ(N4), weight ratio | 0.33 | 0.50 | 0.45 | 0.37 | 0.40 | 0.63 | 0.69 | 0.91 | 0.26 |
| Acyclic(N4)/cyclic (<=N4), weight ratio | 5.06 | 4.70 | 4.08 | 4.22 | 3.85 | 3.23 | 2.51 | 2.86 | 3.60 |

TABLE CXXV

| Example No. | 1289 | 1290 | 1291 | 1292 | 1293 | 1294 | 1295 |
|---|---|---|---|---|---|---|---|
| Catalyst Type | CCCCCC | CCCCCC | CCCCCC | CCCCCC | CCCCCC | CCCCCC | CCCCCC |
| Catalyst weight, gm | 50 | 50 | 50 | 50 | 50 | 50 | 50 |
| Pressure, psig | 600 | 600 | 600 | 600 | 600 | 600 | 600 |
| Temperature, °C. | 249.4 | 250.2 | 260.0 | 264.8 | 274.3 | 269.7 | 279.6 |
| Time on organics, hrs. | 3.5 | 22.5 | 27.0 | 46.5 | 50.5 | 70.5 | 74.5 |
| Duration of run, hrs. | 2 | 2 | 2 | 2 | 2 | 2 | 2 |
| MEA SV, gmol/hr/kgcat | 4.87 | 5.72 | 6.05 | 6.00 | 6.02 | 5.98 | 5.04 |
| DETA/MEA mole ratio | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 |
| Crude product composition, wt. % | | | | | | | |
| EDA | 1.519 | 0.694 | 1.216 | 1.280 | 2.428 | 1.153 | 2.115 |
| MEA | 31.506 | 32.042 | 30.354 | 30.605 | 27.717 | 30.601 | 23.296 |
| PIP | 0.817 | 0.572 | 1.053 | 1.075 | 1.986 | 0.958 | 1.628 |
| DETA | 49.429 | 53.921 | 50.152 | 49.725 | 43.594 | 50.450 | 38.887 |
| AEEA | 0.896 | 0.966 | 1.015 | 0.991 | 0.957 | 1.013 | 0.855 |
| AEP | 0.642 | 0.422 | 0.770 | 0.803 | 1.591 | 0.760 | 1.481 |
| HEP | 0.000 | 0.000 | 0.000 | 0.000 | 0.000 | 0.000 | 0.000 |
| TAEA | 0.734 | 0.732 | 0.884 | 0.820 | 0.779 | 0.837 | 0.758 |
| 1-TETA | 4.465 | 4.271 | 5.695 | 5.262 | 5.911 | 5.274 | 5.499 |
| DAEP | 0.173 | 0.090 | 0.194 | 0.193 | 0.476 | 0.176 | 0.452 |
| PEEDA | 0.153 | 0.064 | 0.187 | 0.199 | 0.589 | 0.178 | 0.544 |
| DPE | 0.059 | 0.026 | 0.052 | 0.062 | 0.131 | 0.056 | 0.168 |
| AE-TAEA | 0.538 | 0.468 | 0.781 | 0.769 | 0.931 | 0.682 | 0.987 |
| 1-TEPA | 1.798 | 1.534 | 2.851 | 2.784 | 3.990 | 2.531 | 3.812 |
| AE-DAEP | 0.111 | 0.079 | 0.177 | 0.165 | 0.389 | 0.088 | 0.463 |
| AE-PEEDA | 0.165 | 0.051 | 0.105 | 0.092 | 0.193 | 0.074 | 0.275 |

TABLE CXXV-continued

| | | | | | | | |
|---|---|---|---|---|---|---|---|
| iAE-PEEDA | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.105 |
| BPEA | 0.000 | 0.000 | 0.090 | 0.098 | 0.188 | 0.085 | 0.308 |
| Others | 2.487 | 1.092 | 2.264 | 2.409 | 4.492 | 2.276 | 5.439 |
| MEA Conversion, % | 12.79 | 12.53 | 18.53 | 17.36 | 25.28 | 17.17 | 30.93 |
| DETA Conversion, % | 18.89 | 12.74 | 20.21 | 20.40 | 30.33 | 19.05 | 31.65 |
| Acyclic(N4), % | 93.08 | 96.49 | 93.79 | 93.03 | 84.81 | 93.68 | 84.30 |
| Acyclic(N5), % | 89.40 | 93.87 | 90.65 | 90.87 | 86.46 | 92.82 | 80.64 |
| Σ(N5)/Σ(N4), weight ratio | 0.46 | 0.41 | 0.57 | 0.59 | 0.72 | 0.53 | 0.80 |
| Acyclic(N4)/cyclic (<=N4), weight ratio | 2.81 | 4.25 | 2.91 | 2.60 | 1.40 | 2.86 | 1.46 |

| Example No. | 1296 | 1297 | 1298 | 1299 |
|---|---|---|---|---|
| Catalyst Type | CCCCCC | CCCCCC | CCCCCC | CCCCCC |
| Catalyst weight, gm | 50 | 50 | 50 | 50 |
| Pressure, psig | 600 | 600 | 600 | 600 |
| Temperature, °C. | 254.9 | 265.5 | 250.0 | 250.0 |
| Time on organics, hrs. | 94.5 | 98.5 | 118.0 | 142.0 |
| Duration of run, hrs. | 2 | 2 | 2 | 2 |
| MEA SV, gmol/hr/kgcat | 5.89 | 5.99 | 5.66 | 5.83 |
| DETA/MEA mole ratio | 0.99 | 0.99 | 0.99 | 0.99 |
| NH3/MEA mole ratio | 5.98 | 5.98 | 5.98 | 5.98 |
| Crude product composition, wt. % | | | | |
| EDA | 0.252 | 0.488 | 0.120 | 0.078 |
| MEA | 33.872 | 32.164 | 35.051 | 35.546 |
| PIP | 0.224 | 0.444 | 0.105 | 0.071 |
| DETA | 57.536 | 55.374 | 59.521 | 60.251 |
| AEEA | 0.774 | 1.009 | 0.339 | 0.338 |
| AEP | 0.293 | 0.430 | 0.243 | 0.206 |
| HEP | 0.000 | 0.000 | 0.000 | 0.000 |
| TAEA | 0.520 | 0.767 | 0.322 | 0.235 |
| 1-TETA | 2.760 | 4.241 | 1.727 | 1.284 |
| DAEP | 0.039 | 0.095 | 0.000 | 0.000 |
| PEEDA | 0.025 | 0.099 | 0.000 | 0.000 |
| DPE | 0.000 | 0.044 | 0.000 | 0.000 |
| AE-TAEA | 0.185 | 0.411 | 0.000 | 0.000 |
| 1-TEPA | 0.440 | 1.232 | 0.000 | 0.000 |
| AE-DAEP | 0.000 | 0.000 | 0.000 | 0.000 |
| AE-PEEDA | 0.000 | 0.000 | 0.000 | 0.000 |
| iAE-PEEDA | 0.000 | 0.000 | 0.000 | 0.000 |
| AE-DPE | 0.000 | 0.000 | 0.000 | 0.000 |
| BPEA | 0.000 | 0.000 | 0.000 | 0.000 |
| Others | 0.924 | 1.213 | 0.418 | 0.337 |
| MEA Conversion, % | 7.75 | 13.08 | 4.17 | 3.21 |
| DETA Conversion, % | 7.11 | 11.29 | 3.53 | 2.74 |
| Acyclic(N4), % | 98.06 | 95.42 | 100.00 | 100.00 |
| Acyclic(N5), % | 100.00 | 100.00 | 0.00 | 0.00 |
| Σ(N5)/Σ(N4), weight ratio | 0.18 | 0.31 | 0.00 | 0.00 |
| Acyclic(N4)/cyclic (<=N4), weight ratio | 5.63 | 4.49 | 5.88 | 5.47 |

TABLE CXXVI

| Example No. | 1300 | 1301 | 1302 | 1303 | 1304 |
|---|---|---|---|---|---|
| Catalyst Type | DDDDDD | DDDDDD | DDDDDD | DDDDDD | DDDDDD |
| Catalyst weight, gm | 50 | 50 | 50 | 50 | 50 |
| Pressure, psig | 600 | 600 | 600 | 600 | 600 |
| Temperature, °C. | 249.4 | 260.0 | 264.8 | 274.3 | 269.7 |
| Time on organics, hrs. | 3.5 | 27.0 | 46.5 | 50.5 | 70.5 |
| Duration of run, hrs. | 2 | 2 | 2 | 2 | 2 |
| MEA SV, gmol/hr/kgcat | 5.19 | 6.09 | 7.07 | 6.15 | 6.06 |
| DETA/MEA mole ratio | 0.99 | 0.99 | 0.99 | 0.99 | 0.99 |
| NH3/MEA mole ratio | 5.98 | 5.98 | 5.98 | 5.98 | 5.98 |
| Crude product composition, wt. % | | | | | |
| EDA | 2.846 | 2.162 | 2.521 | 3.371 | 2.410 |
| MEA | 28.451 | 28.405 | 27.689 | 22.373 | 26.870 |
| PIP | 0.292 | 0.311 | 0.356 | 0.675 | 0.375 |
| DETA | 47.215 | 49.052 | 48.027 | 42.085 | 47.503 |
| AEEA | 1.527 | 1.477 | 1.552 | 1.306 | 1.542 |
| AEP | 0.394 | 0.489 | 0.563 | 0.836 | 0.604 |
| HEP | 0.000 | 0.000 | 0.000 | 0.000 | 0.000 |
| TAEA | 0.805 | 0.950 | 0.969 | 1.115 | 1.032 |
| 1-TETA | 6.223 | 6.861 | 7.071 | 8.458 | 7.313 |
| DAEP | 0.139 | 0.130 | 0.150 | 0.290 | 0.155 |
| PEEDA | 0.054 | 0.065 | 0.083 | 0.181 | 0.089 |
| DPE | 0.186 | 0.172 | 0.213 | 0.359 | 0.226 |
| AE-TAEA | 0.595 | 0.826 | 0.906 | 1.543 | 0.942 |
| 1-TEPA | 1.190 | 1.632 | 1.751 | 3.174 | 1.795 |

TABLE CXXVI-continued

| | | | | | |
|---|---|---|---|---|---|
| AE-DAEP | 0.075 | 0.104 | 0.098 | 0.253 | 0.091 |
| AE-PEEDA | 0.356 | 0.187 | 0.182 | 0.431 | 0.151 |
| iAE-PEEDA | 0.000 | 0.000 | 0.000 | 0.000 | 0.000 |
| AE-DPE | 0.079 | 0.083 | 0.070 | 0.063 | 0.065 |
| BPEA | 0.000 | 0.062 | 0.081 | 0.053 | 0.103 |
| Others | 4.635 | 4.013 | 4.427 | 8.254 | 4.444 |
| MEA Conversion, % | 21.20 | 23.10 | 24.95 | 39.09 | 26.53 |
| DETA Conversion, % | 22.48 | 21.28 | 22.83 | 32.08 | 23.00 |
| Acyclic(N4), % | 94.87 | 95.49 | 94.72 | 92.01 | 94.64 |
| Acyclic(N5), % | 77.74 | 84.86 | 85.97 | 85.46 | 86.94 |
| $\Sigma(N5)/\Sigma(N4)$, weight ratio | 0.31 | 0.35 | 0.36 | 0.53 | 0.35 |
| Acyclic(N4)/cyclic ($<=$N4), weight ratio | 6.58 | 6.67 | 5.87 | 4.08 | 5.74 |

| Example No. | 1305 | 1306 | 1307 | 1308 | 1309 |
|---|---|---|---|---|---|
| Catalyst Type | DDDDDD | DDDDDD | DDDDDD | DDDDDD | DDDDDD |
| Catalyst weight, gm | 50 | 50 | 50 | 50 | 50 |
| Pressure, psig | 600 | 600 | 600 | 600 | 600 |
| Temperature, °C. | 279.6 | 250.0 | 265.5 | 250.0 | 250.0 |
| Time on organics, hrs. | 74.5 | 94.5 | 98.5 | 118.0 | 142.0 |
| Duration of run, hrs. | 2 | 2 | 2 | 2 | 2 |
| MEA SV, gmol/hr/kgcat | 5.36 | 5.94 | 6.02 | 5.71 | 6.05 |
| DETA/MEA mole ratio | 0.99 | 0.99 | 0.99 | 0.99 | 0.99 |
| NH3/MEA mole ratio | 5.98 | 5.98 | 5.98 | 5.98 | 5.98 |
| Crude product composition, wt. % | | | | | |
| EDA | 3.708 | 0.958 | 1.667 | 0.727 | 0.656 |
| MEA | 19.491 | 30.997 | 27.854 | 33.177 | 33.332 |
| PIP | 0.711 | 0.117 | 0.226 | 0.073 | 0.061 |
| DETA | 38.192 | 54.844 | 50.639 | 55.737 | 56.938 |
| AEEA | 1.289 | 1.199 | 1.503 | 0.934 | 0.936 |
| AEP | 0.971 | 0.390 | 0.530 | 0.340 | 0.348 |
| HEP | 0.000 | 0.000 | 0.000 | 0.000 | 0.000 |
| TAEA | 1.206 | 0.726 | 1.030 | 0.478 | 0.461 |
| 1-TETA | 8.977 | 4.883 | 6.759 | 3.252 | 3.068 |
| DAEP | 0.368 | 0.054 | 0.112 | 0.000 | 0.000 |
| PEEDA | 0.248 | 0.048 | 0.059 | 0.046 | 0.037 |
| DPE | 0.502 | 0.080 | 0.180 | 0.036 | 0.025 |
| AE-TAEA | 1.789 | 0.306 | 0.113 | 0.129 | 0.072 |
| 1-TEPA | 3.752 | 0.447 | 1.274 | 0.082 | 0.419 |
| AE-DAEP | 0.309 | 0.000 | 0.036 | 0.000 | 0.000 |
| AE-PEEDA | 0.490 | 0.000 | 0.085 | 0.000 | 0.000 |
| iAE-PEEDA | 0.000 | 0.000 | 0.000 | 0.000 | 0.000 |
| AE-DPE | 0.158 | 0.101 | 0.121 | 0.309 | 0.000 |
| BPEA | 0.135 | 0.034 | 0.144 | 0.000 | 0.000 |
| Others | 10.424 | 2.167 | 4.231 | 1.493 | 1.571 |
| MEA Conversion, % | 46.19 | 15.71 | 24.30 | 8.77 | 9.35 |
| DETA Conversion, % | 37.50 | 11.59 | 18.42 | 9.14 | 8.20 |
| Acyclic(N4), % | 90.09 | 96.84 | 95.68 | 97.81 | 98.24 |
| Acyclic(N5), % | 83.49 | 84.65 | 78.19 | 40.69 | 100.00 |
| $\Sigma(N5)/\Sigma(N4)$, weight ratio | 0.58 | 0.15 | 0.21 | 0.13 | 0.13 |
| Acyclic(N4)/cyclic ($<=$N4), weight ratio | 3.63 | 8.11 | 7.02 | 7.50 | 7.46 |

TABLE CXXVII

| Example No. | 1310 | 1311 | 1312 | 1313 | 1314 | 1315 | 1316 |
|---|---|---|---|---|---|---|---|
| Catalyst Type | EEEEEE | EEEEEE | EEEEEE | EEEEEE | EEEEEE | EEEEEE | EEEEEE |
| Catalyst weight, gm | 50 | 50 | 50 | 50 | 50 | 50 | 50 |
| Pressure, psig | 600 | 600 | 600 | 600 | 600 | 600 | 600 |
| Temperature, °C. | 249.4 | 250.2 | 260.0 | 264.8 | 274.3 | 269.7 | 279.6 |
| Time on organics, hrs. | 3.5 | 22.5 | 27.0 | 46.5 | 50.5 | 70.5 | 74.5 |
| Duration of run, hrs. | 2 | 2 | 2 | 2 | 2 | 2 | 2 |
| MEA SV, gmol/hr/kgcat | 4.96 | 5.31 | 5.56 | 5.64 | 5.56 | 5.51 | 5.09 |
| DETA/MEA mole ratio | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 |
| Crude product composition, wt. % | | | | | | | |
| EDA | 0.654 | 0.449 | 0.757 | 0.960 | 1.686 | 1.190 | 2.015 |
| MEA | 27.386 | 29.344 | 25.472 | 23.704 | 17.028 | 22.148 | 12.850 |
| PIP | 0.229 | 0.158 | 0.318 | 0.417 | 0.765 | 0.526 | 0.925 |
| DETA | 53.639 | 55.586 | 52.752 | 50.945 | 45.979 | 49.847 | 40.504 |
| AEEA | 2.419 | 2.339 | 2.764 | 2.728 | 2.360 | 2.672 | 1.772 |
| AEP | 0.319 | 0.268 | 0.391 | 0.468 | 0.851 | 0.568 | 1.059 |
| HEP | 0.000 | 0.000 | 0.000 | 0.000 | 0.000 | 0.000 | 0.000 |
| TAEA | 1.067 | 0.826 | 1.226 | 1.323 | 1.677 | 1.416 | 1.728 |
| 1-TETA | 6.467 | 4.920 | 7.114 | 7.589 | 9.995 | 8.115 | 10.503 |
| DAEP | 0.088 | 0.062 | 0.117 | 0.137 | 0.317 | 0.176 | 0.437 |
| PEEDA | 0.054 | 0.044 | 0.081 | 0.083 | 0.227 | 0.154 | 0.396 |
| DPE | 0.045 | 0.029 | 0.068 | 0.096 | 0.188 | 0.128 | 0.297 |

TABLE CXXVII-continued

| | | | | | | | |
|---|---|---|---|---|---|---|---|
| AE-TAEA | 0.685 | 0.395 | 1.040 | 1.239 | 2.283 | 1.495 | 2.774 |
| 1-TEPA | 1.252 | 0.683 | 2.067 | 2.357 | 4.522 | 2.895 | 5.506 |
| AE-DAEP | 0.000 | 0.000 | 0.099 | 0.104 | 0.276 | 0.134 | 0.596 |
| AE-PEEDA | 0.031 | 0.000 | 0.000 | 0.034 | 0.087 | 0.038 | 0.220 |
| iAE-PEEDA | 0.000 | 0.000 | 0.000 | 0.000 | 0.000 | 0.000 | 0.000 |
| AE-DPE | 0.000 | 0.000 | 0.000 | 0.000 | 0.089 | 0.000 | 0.165 |
| BPEA | 0.098 | 0.000 | 0.136 | 0.132 | 0.363 | 0.186 | 0.107 |
| Others | 1.308 | 1.020 | 1.910 | 2.415 | 4.738 | 3.325 | 7.889 |
| MEA Conversion, % | 24.85 | 19.33 | 30.93 | 34.91 | 53.54 | 39.67 | 63.95 |
| DETA Conversion, % | 12.74 | 9.41 | 15.20 | 17.07 | 25.63 | 19.50 | 32.65 |
| Acyclic(N4), % | 97.56 | 97.67 | 96.88 | 96.55 | 94.09 | 95.39 | 91.54 |
| Acyclic(N5), % | 93.71 | 100.00 | 92.95 | 92.97 | 89.29 | 92.45 | 88.36 |
| Σ(N5)/Σ(N4), weight ratio | 0.26 | 0.18 | 0.38 | 0.41 | 0.61 | 0.47 | 0.70 |
| Acyclic(N4)/cyclic (<=N4), weight ratio | 10.21 | 10.19 | 8.53 | 7.40 | 4.96 | 6.13 | 3.92 |

| Example No. | 1317 | 1318 | 1319 | 1320 |
|---|---|---|---|---|
| Catalyst Type | EEEEEE | EEEEEE | EEEEEE | EEEEEE |
| Catalyst weight, gm | 50 | 50 | 50 | 50 |
| Pressure, psig | 600 | 600 | 600 | 600 |
| Temperature, °C | 254.9 | 265.5 | 250.0 | 250.0 |
| Time on organics, hrs. | 94.5 | 98.5 | 118.0 | 142.0 |
| Duration of run, hrs. | 2 | 2 | 2 | 2 |
| MEA SV, gmol/hr/kgcat | 5.43 | 5.54 | 5.23 | 5.37 |
| DETA/MEA mole ratio | 0.99 | 0.99 | 0.99 | 0.99 |
| NH3/MEA mole ratio | 5.98 | 5.98 | 5.98 | 5.98 |
| Crude product composition, wt. % | | | | |
| EDA | 0.476 | 0.898 | 0.343 | 0.351 |
| MEA | 28.641 | 23.935 | 30.296 | 30.702 |
| PIP | 0.165 | 0.377 | 0.111 | 0.109 |
| DETA | 56.024 | 51.376 | 57.092 | 57.637 |
| AEEA | 2.377 | 2.731 | 2.066 | 2.049 |
| AEP | 0.297 | 0.452 | 0.262 | 0.268 |
| HEP | 0.000 | 0.000 | 0.000 | 0.000 |
| TAEA | 0.900 | 1.406 | 0.710 | 0.675 |
| 1-TETA | 4.990 | 7.814 | 3.954 | 3.695 |
| DAEP | 0.057 | 0.137 | 0.044 | 0.052 |
| PEEDA | 0.040 | 0.081 | 0.029 | 0.052 |
| DPE | 0.045 | 0.106 | 0.037 | 0.032 |
| AE-TAEA | 0.419 | 1.182 | 0.238 | 0.195 |
| 1-TEPA | 0.703 | 2.253 | 0.393 | 0.295 |
| AE-DAEP | 0.000 | 0.079 | 0.000 | 0.000 |
| AE-PEEDA | 0.000 | 0.000 | 0.000 | 0.000 |
| iAE-PEEDA | 0.000 | 0.000 | 0.000 | 0.000 |
| AE-DPE | 0.000 | 0.000 | 0.525 | 0.202 |
| BPEA | 0.000 | 0.130 | 0.000 | 0.000 |
| Others | 1.257 | 2.793 | 1.201 | 1.290 |
| MEA Conversion, % | 21.61 | 34.98 | 17.69 | 16.70 |
| DETA Conversion, % | 9.10 | 17.26 | 8.05 | 7.29 |
| Acyclic(N4), % | 97.62 | 96.58 | 97.64 | 96.94 |
| Acyclic(N5), % | 100.00 | 94.22 | 54.59 | 70.75 |
| Σ(N5)/Σ(N4), weight ratio | 0.18 | 0.38 | 0.24 | 0.15 |
| Acyclic(N4)/cyclic (<=N4), weight ratio | 9.70 | 7.96 | 9.58 | 8.47 |

TABLE CXXVIII

| Example No. | 1321 | 1322 | 1323 | 1324 | 1325 | 1326 | 1327 | 1328 | 1329 | 1330 |
|---|---|---|---|---|---|---|---|---|---|---|
| Catalyst Type | FFFFFF | FFFFFF | FFFFFF | FFFFFF | FFFFFF | FFFFFF | FFFFFF | FFFFFF | FFFFFF | FFFFFF |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C | 250.7 | 260.9 | 265.9 | 275.6 | 270.7 | 280.7 | 255.9 | 266.0 | 250.0 | 250.0 |
| Time on organics, hrs. | 24 | 28 | 48 | 52 | 72 | 76 | 96 | 100 | 119 | 143 |
| Duration of run, hrs. | 2 | 2 | 2 | 2 | 2 | 2 | 2 | 2 | 2 | 2 |
| MEA SV, gmol/hr/kgcat | 5.63 | 5.74 | 3.32 | 5.65 | 5.42 | 5.49 | 5.53 | 5.57 | 5.89 | 5.93 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.903 | 1.402 | 1.768 | 2.544 | 1.835 | 3.073 | 0.888 | 1.294 | 0.515 | 0.506 |
| MEA | 25.752 | 20.894 | 16.605 | 12.576 | 17.830 | 10.281 | 26.167 | 20.923 | 27.453 | 29.003 |
| PIP | 0.219 | 0.362 | 0.507 | 0.711 | 0.498 | 0.901 | 0.187 | 0.353 | 0.106 | 0.103 |
| DETA | 50.036 | 46.155 | 42.553 | 38.126 | 43.798 | 37.053 | 51.456 | 47.042 | 54.880 | 54.395 |
| AEEA | 1.893 | 2.170 | 2.124 | 1.446 | 1.873 | 1.003 | 2.038 | 2.036 | 1.893 | 1.661 |
| AEP | 0.352 | 0.501 | 0.668 | 0.969 | 0.662 | 1.189 | 0.334 | 0.490 | 0.278 | 0.267 |
| HEP | 0.000 | 0.000 | 0.000 | 0.000 | 0.000 | 0.000 | 0.000 | 0.000 | 0.000 | 0.000 |
| TAEA | 1.345 | 1.686 | 1.782 | 1.715 | 1.776 | 1.699 | 1.361 | 1.719 | 1.214 | 1.039 |
| 1-TETA | 9.150 | 11.543 | 12.441 | 12.696 | 11.873 | 12.762 | 8.128 | 10.831 | 7.041 | 5.981 |

TABLE CXXVIII-continued

| Example No. | 1321 | 1322 | 1323 | 1324 | 1325 | 1326 | 1327 | 1328 | 1329 | 1330 |
|---|---|---|---|---|---|---|---|---|---|---|
| DAEP | 0.123 | 0.212 | 0.297 | 0.536 | 0.298 | 0.703 | 0.088 | 0.187 | 0.057 | 0.051 |
| PEEDA | 0.063 | 0.115 | 0.173 | 0.315 | 0.175 | 0.078 | 0.051 | 0.100 | 0.035 | 0.035 |
| DPE | 0.076 | 0.135 | 0.211 | 0.313 | 0.079 | 0.133 | 0.082 | 0.072 | 0.048 | 0.060 |
| AE-TAEA | 1.447 | 2.123 | 2.635 | 3.323 | 2.723 | 3.556 | 1.164 | 2.237 | 0.691 | 0.565 |
| 1-TEPA | 2.439 | 3.738 | 4.737 | 6.407 | 4.814 | 6.968 | 1.786 | 3.880 | 0.956 | 0.711 |
| AE-DAEP | 0.033 | 0.115 | 0.343 | 0.446 | 0.192 | 0.758 | 0.000 | 0.081 | 0.000 | 0.000 |
| AE-PEEDA | 0.000 | 0.048 | 0.132 | 0.326 | 0.068 | 0.357 | 0.000 | 0.045 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.062 | 0.077 | 0.106 | 0.119 | 0.091 | 0.112 | 0.000 | 0.000 | 0.000 | 0.000 |
| BPEA | 0.198 | 0.376 | 0.163 | 0.712 | 0.593 | 0.257 | 0.112 | 0.102 | 0.000 | 0.000 |
| Others | 1.859 | 3.207 | 5.566 | 8.060 | 4.576 | 10.826 | 1.993 | 3.228 | 1.156 | 1.187 |
| MEA Conversion, % | 30.00 | 43.32 | 54.48 | 65.46 | 51.49 | 72.02 | 28.58 | 43.01 | 25.09 | 19.91 |
| DETA Conversion, % | 19.37 | 25.78 | 30.84 | 37.92 | 29.36 | 40.22 | 16.74 | 24.04 | 11.23 | 10.95 |
| Acyclic(N4), % | 97.54 | 96.61 | 95.41 | 92.51 | 96.10 | 94.03 | 97.71 | 97.19 | 98.32 | 97.94 |
| Acyclic(N5), % | 92.96 | 90.47 | 90.82 | 85.91 | 88.84 | 87.63 | 96.33 | 96.38 | 100.00 | 100.00 |
| $\Sigma(N5)/\Sigma(N4)$, weight ratio | 0.38 | 0.47 | 0.54 | 0.72 | 0.59 | 0.78 | 0.31 | 0.49 | 0.19 | 0.17 |
| Acyclic(N4)/cyclic ($<=N4$), weight ratio | 12.56 | 9.96 | 7.65 | 5.06 | 7.95 | 4.80 | 12.76 | 10.41 | 15.69 | 13.56 |

TABLE CXXIX

| Example No. | 1331 | 1332 | 1333 | 1334 | 1335 |
|---|---|---|---|---|---|
| Catalyst Type | GGGGGG | GGGGGG | GGGGGG | GGGGGG | GGGGGG |
| Catalyst weight, gm | 50 | 50 | 50 | 50 | 50 |
| Pressure, psig | 600 | 600 | 600 | 600 | 600 |
| Temperature, °C. | 250.9 | 260.9 | 265.9 | 275.6 | 270.7 |
| Time on organics, hrs. | 24 | 28 | 48 | 52 | 72 |
| Duration of run, hrs. | 2 | 2 | 2 | 2 | 2 |
| MEA SV, gmol/hr/kgcat | 5.32 | 5.25 | 5.18 | 5.19 | 5.09 |
| DETA/MEA mole ratio | 0.99 | 0.99 | 0.99 | 0.99 | 0.99 |
| NH$_3$/MEA mole ratio | 5.98 | 5.98 | 5.98 | 5.98 | 5.98 |
| Crude product composition, wt. % | | | | | |
| EDA | 0.592 | 1.050 | 1.170 | 2.045 | 1.486 |
| MEA | 27.184 | 23.113 | 22.344 | 15.162 | 21.294 |
| PIP | 0.127 | 0.270 | 0.291 | 0.551 | 0.372 |
| DETA | 53.615 | 49.172 | 48.478 | 41.150 | 47.716 |
| AEEA | 2.106 | 2.326 | 2.191 | 1.866 | 2.144 |
| AEP | 0.280 | 0.388 | 0.415 | 0.715 | 0.489 |
| HEP | 0.000 | 0.000 | 0.000 | 0.000 | 0.000 |
| TAEA | 1.264 | 1.608 | 1.571 | 1.888 | 1.686 |
| 1-TETA | 7.794 | 10.144 | 9.823 | 12.185 | 10.176 |
| DAEP | 0.076 | 0.137 | 0.147 | 0.347 | 0.166 |
| PEEDA | 0.034 | 0.074 | 0.089 | 0.211 | 0.099 |
| DPE | 0.045 | 0.094 | 0.134 | 0.118 | 0.156 |
| AE-TAEA | 0.814 | 0.589 | 1.649 | 2.952 | 1.965 |
| 1-TEPA | 1.274 | 2.726 | 2.848 | 5.423 | 3.349 |
| AE-DAEP | 0.000 | 0.000 | 0.086 | 0.479 | 0.108 |
| AE-PEEDA | 0.000 | 0.000 | 0.029 | 0.188 | 0.035 |
| iAE-PEEDA | 0.000 | 0.000 | 0.000 | 0.000 | 0.000 |
| AE-DPE | 0.000 | 0.073 | 0.100 | 0.119 | 0.079 |
| BPEA | 0.000 | 0.199 | 0.189 | 0.565 | 0.277 |
| Others | 1.237 | 2.368 | 2.867 | 7.018 | 3.114 |
| MEA Conversion, % | 26.02 | 37.12 | 38.74 | 58.74 | 41.99 |
| DETA Conversion, % | 13.50 | 20.70 | 21.21 | 33.62 | 22.94 |
| Acyclic(N4), % | 98.30 | 97.45 | 96.84 | 95.40 | 96.55 |
| Acyclic(N5), % | 100.00 | 94.05 | 91.70 | 86.09 | 91.37 |
| $\Sigma(N5)/\Sigma(N4)$, weight ratio | 0.22 | 0.38 | 0.41 | 0.65 | 0.47 |
| Acyclic(N4)/cyclic ($<=N4$), weight ratio | 16.04 | 12.16 | 10.56 | 7.23 | 9.23 |

| Example No. | 1336 | 1337 | 1338 | 1339 | 1340 |
|---|---|---|---|---|---|
| Catalyst Type | GGGGGG | GGGGGG | GGGGGG | GGGGGG | GGGGGG |
| Catalyst weight, gm | 50 | 50 | 50 | 50 | 50 |
| Pressure, psig | 600 | 600 | 600 | 600 | 600 |
| Temperature, °C. | 280.7 | 255.9 | 266.0 | 250.0 | 250.0 |
| Time on organics, hrs. | 76 | 96 | 100 | 119 | 143 |
| Duration of run, hrs. | 2 | 2 | 2 | 2 | 2 |
| MEA SV, gmol/hr/kgcat | 5.20 | 5.18 | 5.12 | 5.39 | 5.47 |
| DETA/MEA mole ratio | 0.99 | 0.99 | 0.99 | 0.99 | 0.99 |
| NH$_3$/MEA mole ratio | 5.98 | 5.98 | 5.98 | 5.98 | 5.98 |
| Crude product composition, wt. % | | | | | |
| EDA | 2.547 | 0.696 | 1.188 | 0.456 | 0.452 |
| MEA | 13.368 | 28.286 | 24.782 | 31.286 | 31.867 |
| PIP | 0.660 | 0.135 | 0.269 | 0.080 | 0.076 |
| DETA | 39.980 | 54.059 | 50.590 | 55.663 | 57.022 |
| AEEA | 1.559 | 1.968 | 2.123 | 1.530 | 1.495 |
| AEP | 0.840 | 0.283 | 0.381 | 0.235 | 0.239 |

TABLE CXXIX-continued

| | | | | | |
|---|---|---|---|---|---|
| HEP | 0.000 | 0.000 | 0.000 | 0.000 | 0.000 |
| TAEA | 1.837 | 1.171 | 1.430 | 0.801 | 0.757 |
| 1-TETA | 11.968 | 6.606 | 8.234 | 4.501 | 4.245 |
| DAEP | 0.413 | 0.062 | 0.105 | 0.035 | 0.000 |
| PEEDA | 0.086 | 0.039 | 0.063 | 0.029 | 0.000 |
| DPE | 0.130 | 0.066 | 0.108 | 0.000 | 0.000 |
| AE-TAEA | 3.233 | 0.758 | 1.349 | 0.372 | 0.000 |
| 1-TEPA | 5.930 | 1.123 | 2.132 | 0.504 | 0.000 |
| AE-DAEP | 0.545 | 0.000 | 0.031 | 0.000 | 0.000 |
| AE-PEEDA | 0.201 | 0.000 | 0.000 | 0.000 | 0.000 |
| iAE-PEEDA | 0.000 | 0.000 | 0.000 | 0.000 | 0.000 |
| AE-DPE | 0.126 | 0.000 | 0.070 | 0.000 | 0.000 |
| BPEA | 0.243 | 0.000 | 0.169 | 0.000 | 0.000 |
| Others | 8.624 | 1.140 | 2.109 | 1.021 | 1.114 |
| MEA Conversion, % | 63.48 | 22.75 | 32.08 | 14.00 | 12.93 |
| DETA Conversion, % | 35.25 | 12.48 | 17.80 | 9.30 | 7.64 |
| Acyclic(N4), % | 95.63 | 97.87 | 97.21 | 98.79 | 100.00 |
| Acyclic(N5), % | 89.13 | 100.00 | 92.76 | 100.00 | 0.000 |
| Σ(N5)/Σ(N4), weight ratio | 0.71 | 0.23 | 0.37 | 0.16 | 0.000 |
| Acyclic(N4)/cyclic (<=N4), weight ratio | 6.47 | 13.22 | 10.42 | 12.02 | 15.87 |

TABLE CXXX

| Example No. | 1341 | 1342 | 1343 | 1344 | 1345 |
|---|---|---|---|---|---|
| Catalyst Type | HHHHHH | HHHHHH | HHHHHH | HHHHHH | HHHHHH |
| Catalyst weight, gm | 50 | 50 | 50 | 50 | 50 |
| Pressure, psig | 600 | 600 | 600 | 600 | 600 |
| Temperature, °C. | 249.8 | 249.5 | 259.9 | 264.3 | 274.1 |
| Time on organics, hrs. | 4 | 24 | 28 | 48 | 52 |
| Duration of run, hrs. | 2 | 2 | 2 | 2 | 2 |
| MEA SV, gmol/hr/kgcat | 6.01 | 5.76 | 6.31 | 6.08 | 6.51 |
| DETA/MEA mole ratio | 0.99 | 0.99 | 0.99 | 0.99 | 0.99 |
| $NH_3$/MEA mole ratio | 5.98 | 5.98 | 5.98 | 5.98 | 5.98 |
| Crude product composition, wt. % | | | | | |
| EDA | 0.761 | 0.624 | 1.038 | 1.221 | 1.948 |
| MEA | 25.622 | 26.514 | 24.098 | 23.576 | 16.694 |
| PIP | 0.313 | 0.180 | 0.319 | 0.354 | 0.596 |
| DETA | 51.757 | 52.135 | 49.333 | 49.050 | 42.503 |
| AEEA | 2.271 | 2.049 | 2.327 | 2.321 | 1.938 |
| AEP | 0.469 | 0.304 | 0.391 | 0.428 | 0.713 |
| HEP | 0.000 | 0.000 | 0.000 | 0.000 | 0.000 |
| TAEA | 1.249 | 1.216 | 1.449 | 1.478 | 1.706 |
| 1-TETA | 8.948 | 8.159 | 9.767 | 9.512 | 11.779 |
| DAEP | 0.121 | 0.097 | 0.148 | 0.142 | 0.316 |
| PEEDA | 0.067 | 0.063 | 0.086 | 0.097 | 0.232 |
| DPE | 0.039 | 0.054 | 0.073 | 0.086 | 0.203 |
| AE-TAEA | 1.082 | 1.193 | 1.621 | 1.608 | 2.838 |
| 1-TEPA | 2.014 | 2.188 | 2.900 | 2.766 | 5.279 |
| AE-DAEP | 0.000 | 0.000 | 0.066 | 0.041 | 0.429 |
| AE-PEEDA | 0.000 | 0.000 | 0.000 | 0.000 | 0.162 |
| iAE-PEEDA | 0.000 | 0.000 | 0.000 | 0.000 | 0.000 |
| AE-DPE | 0.000 | 0.083 | 0.071 | 0.078 | 0.546 |
| BPEA | 0.000 | 0.140 | 0.190 | 0.225 | 0.601 |
| Others | 1.401 | 1.373 | 1.963 | 2.198 | 5.197 |
| MEA Conversion, % | 30.38 | 28.05 | 34.69 | 35.69 | 54.79 |
| DETA Conversion, % | 16.63 | 16.13 | 20.74 | 20.69 | 31.77 |
| Acyclic(N4), % | 97.81 | 97.75 | 97.31 | 97.11 | 94.71 |
| Acyclic(N5), % | 100.00 | 93.80 | 93.22 | 92.68 | 82.34 |
| Σ(N5)/Σ(N4), weight ratio | 0.29 | 0.37 | 0.42 | 0.41 | 0.69 |
| Acyclic(N4)/cyclic (<=N4), weight ratio | 10.08 | 13.38 | 10.99 | 9.89 | 6.53 |

| Example No. | 1346 | 1347 | 1348 | 1349 | 1350 |
|---|---|---|---|---|---|
| Catalyst Type | HHHHHH | HHHHHH | HHHHHH | HHHHHH | HHHHHH |
| Catalyst weight, gm | 50 | 50 | 50 | 50 | 50 |
| Pressure, psig | 600 | 600 | 600 | 600 | 600 |
| Temperature, °C. | 270.2 | 279.2 | 254.5 | 264.3 | 251.7 |
| Time on organics, hrs. | 72 | 72 | 96 | 100 | 120 |
| Duration of run, hrs. | 2 | 2 | 2 | 2 | 2 |
| MEA SV, gmol/hr/kgcat | 6.27 | 6.51 | 6.20 | 6.03 | 6.22 |
| DETA/MEA mole ratio | 0.99 | 0.99 | 0.99 | 0.99 | 0.99 |
| $NH_3$/MEA mole ratio | 5.98 | 5.98 | 5.98 | 5.98 | 5.98 |
| Crude product composition, wt. % | | | | | |
| EDA | 1.583 | 2.362 | 0.611 | 1.025 | 0.465 |
| MEA | 20.651 | 13.560 | 28.634 | 23.574 | 29.808 |
| PIP | 0.466 | 0.712 | 0.136 | 0.289 | 0.092 |
| DETA | 46.442 | 40.240 | 54.507 | 48.715 | 53.735 |

TABLE CXXX-continued

| | | | | | |
|---|---|---|---|---|---|
| AEEA | 2.152 | 1.499 | 1.953 | 2.175 | 1.635 |
| AEP | 0.549 | 0.914 | 0.271 | 0.386 | 0.235 |
| HEP | 0.000 | 0.000 | 0.000 | 0.000 | 0.000 |
| TAEA | 1.601 | 1.752 | 1.109 | 1.439 | 0.776 |
| l-TETA | 10.430 | 12.550 | 6.599 | 9.395 | 4.640 |
| DAEP | 0.196 | 0.455 | 0.057 | 0.152 | 0.074 |
| PEEDA | 0.028 | 0.325 | 0.033 | 0.091 | 0.000 |
| DPE | 0.141 | 0.249 | 0.054 | 0.069 | 0.000 |
| AE-TAEA | 2.237 | 3.225 | 0.711 | 1.419 | 0.310 |
| 1-TEPA | 3.962 | 6.363 | 1.162 | 2.409 | 0.421 |
| AE-DAEP | 0.137 | 0.501 | 0.000 | 0.000 | 0.000 |
| AE-PEEDA | 0.052 | 0.290 | 0.000 | 0.000 | 0.000 |
| iAE-PEEDA | 0.000 | 0.000 | 0.000 | 0.000 | 0.000 |
| AE-DPE | 0.099 | 0.570 | 0.264 | 0.111 | 0.000 |
| BPEA | 0.329 | 0.696 | 0.000 | 0.132 | 0.000 |
| Others | 3.367 | 6.347 | 1.172 | 1.892 | 0.943 |
| MEA Conversion, % | 43.71 | 63.20 | 22.55 | 34.28 | 15.16 |
| DETA Conversion, % | 24.95 | 35.27 | 12.60 | 19.49 | 9.33 |
| Acyclic(N4), % | 97.04 | 93.27 | 98.14 | 97.18 | 98.64 |
| Acyclic(N5), % | 90.92 | 82.32 | 87.61 | 93.99 | 100.00 |
| Σ(N5)/Σ(N4), weight ratio | 0.54 | 0.75 | 0.27 | 0.36 | 0.13 |
| Acyclic(N4)/cyclic (<=N4), weight ratio | 8.70 | 5.38 | 13.91 | 10.95 | 13.46 |

TABLE CXXXI

| Example No. | 1351 | 1352 | 1353 | 1354 |
|---|---|---|---|---|
| Catalyst Type | IIIIII | IIIIII | IIIIII | IIIIII |
| Catalyst weight, gm | 50 | 50 | 50 | 50 |
| Pressure, psig | 600 | 600 | 600 | 600 |
| Temperature, °C. | 249.8 | 264.3 | 274.1 | 270.2 |
| Time on organics, hrs. | 4 | 37 | 40 | 61 |
| Duration of run, hrs. | 2 | 2 | 2 | 2 |
| MEA SV, gmol/hr/kgcat | 5.86 | 5.73 | 5.94 | 5.40 |
| DETA/MEA mole ratio | 0.99 | 0.99 | 0.99 | 0.99 |
| NH3/MEA mole ratio | 5.98 | 5.98 | 5.98 | 5.98 |
| Crude product composition, wt. % | | | | |
| EDA | 1.024 | 1.195 | 2.071 | 1.604 |
| MEA | 26.663 | 25.244 | 19.405 | 22.346 |
| PIP | 0.296 | 0.293 | 0.530 | 0.392 |
| DETA | 50.089 | 49.881 | 43.746 | 46.459 |
| AEEA | 1.810 | 1.985 | 1.764 | 1.910 |
| AEP | 0.383 | 0.382 | 0.629 | 0.466 |
| HEP | 0.000 | 0.000 | 0.000 | 0.000 |
| TAEA | 1.335 | 1.526 | 1.657 | 1.567 |
| 1-TETA | 7.810 | 8.794 | 10.168 | 9.213 |
| DAEP | 0.119 | 0.111 | 0.244 | 0.145 |
| PEEDA | 0.083 | 0.063 | 0.147 | 0.090 |
| DPE | 0.049 | 0.091 | 0.211 | 0.141 |
| AE-TAEA | 1.264 | 1.525 | 2.605 | 1.943 |
| 1-TEPA | 2.012 | 2.274 | 4.356 | 3.093 |
| AE-DAEP | 0.000 | 0.000 | 0.377 | 0.094 |
| AE-PEEDA | 0.057 | 0.000 | 0.155 | 0.035 |
| iAE-PEEDA | 0.000 | 0.000 | 0.000 | 0.000 |
| AE-DPE | 0.076 | 0.077 | 0.546 | 0.097 |
| BPEA | 0.038 | 0.166 | 0.533 | 0.257 |
| Others | 1.245 | 2.056 | 5.068 | 3.030 |
| MEA Conversion, % | 25.98 | 31.20 | 47.33 | 37.71 |
| DETA Conversion, % | 17.56 | 19.41 | 29.62 | 23.22 |
| Acyclic(N4), % | 97.31 | 97.48 | 95.14 | 96.61 |
| Acyclic(N5), % | 95.00 | 93.96 | 81.20 | 91.22 |
| Σ(N5)/Σ(N4), weight ratio | 0.36 | 0.38 | 0.68 | 0.49 |
| Acyclic(N4)/cyclic (<=N4), weight ratio | 9.81 | 10.94 | 6.70 | 8.72 |

TABLE CXXXII

| Example No. | 1355 | 1356 | 1357 | 1358 | 1359 | 1360 | 1361 | 1362 | 1363 | 1364 |
|---|---|---|---|---|---|---|---|---|---|---|
| Catalyst Type | JJJJJJ | JJJJJJ | JJJJJJ | JJJJJJ | JJJJJJ | JJJJJJ | JJJJJJ | JJJJJJ | JJJJJJ | JJJJJJ |
| Catalyst weight, gm | 50 | 50 | 50 | 50 | 50 | 50 | 50 | 50 | 50 | 50 |
| Pressure, psig | 600 | 600 | 600 | 600 | 600 | 600 | 600 | 600 | 600 | 600 |
| Temperature, °C. | 249.8 | 249.5 | 259.9 | 264.3 | 274.1 | 270.2 | 279.2 | 254.5 | 264.3 | 251.7 |
| Time on organics, hrs. | 4 | 24 | 28 | 48 | 52 | 72 | 72 | 96 | 100 | 120 |
| Duration of run, hrs. | 2 | 2 | 2 | 2 | 2 | 2 | 2 | 2 | 2 | 2 |
| MEA SV, gmol/hr/kgcat | 5.10 | 4.90 | 5.23 | 5.17 | 5.39 | 5.13 | 5.44 | 5.16 | 5.11 | 5.35 |
| DETA/MEA mole ratio | 0.99 | 0.99 | 0.99 | 0.99 | 0.99 | 0.99 | 0.99 | 0.99 | 0.99 | 0.99 |
| NH3/MEA mole ratio | 5.98 | 5.98 | 5.98 | 5.98 | 5.98 | 5.98 | 5.98 | 5.98 | 5.98 | 5.98 |
| Crude product composition, wt. % | | | | | | | | | | |
| EDA | 0.960 | 0.781 | 1.286 | 1.404 | 2.490 | 1.935 | 2.792 | 0.714 | 1.281 | 0.493 |
| MEA | 25.276 | 26.501 | 22.272 | 21.316 | 14.838 | 19.716 | 11.330 | 27.403 | 22.785 | 27.477 |
| PIP | 0.268 | 0.204 | 0.383 | 0.358 | 0.742 | 0.540 | 0.837 | 0.168 | 0.348 | 0.103 |
| DETA | 50.594 | 51.409 | 47.463 | 45.857 | 40.344 | 44.583 | 37.401 | 53.232 | 47.558 | 54.912 |
| AEEA | 2.227 | 2.171 | 2.322 | 2.246 | 1.783 | 2.068 | 1.362 | 2.040 | 2.125 | 1.779 |
| AEP | 0.365 | 0.314 | 0.469 | 0.481 | 0.878 | 0.612 | 1.085 | 0.294 | 0.441 | 0.273 |
| HEP | 0.000 | 0.000 | 0.000 | 0.000 | 0.000 | 0.000 | 0.000 | 0.000 | 0.000 | 0.000 |
| TAEA | 1.233 | 1.224 | 1.587 | 1.506 | 1.615 | 1.578 | 1.689 | 1.266 | 1.424 | 1.095 |
| 1-TETA | 9.272 | 8.238 | 10.975 | 10.156 | 11.821 | 10.601 | 12.728 | 7.741 | 9.232 | 6.746 |
| DAEP | 0.116 | 0.088 | 0.175 | 0.175 | 0.394 | 0.229 | 0.599 | 0.075 | 0.153 | 0.071 |
| PEEDA | 0.072 | 0.059 | 0.117 | 0.170 | 0.031 | 0.173 | 0.376 | 0.041 | 0.100 | 0.028 |
| DPE | 0.061 | 0.053 | 0.092 | 0.124 | 0.233 | 0.160 | 0.305 | 0.047 | 0.090 | 0.000 |
| AE-TAEA | 1.263 | 1.061 | 1.872 | 2.256 | 3.087 | 2.494 | 3.494 | 0.922 | 1.714 | 0.435 |
| 1-TEPA | 2.381 | 1.850 | 3.306 | 4.088 | 5.984 | 4.457 | 6.930 | 1.552 | 2.925 | 0.540 |
| AE-DAEP | 0.000 | 0.000 | 0.049 | 0.183 | 0.533 | 0.160 | 0.701 | 0.000 | 0.039 | 0.000 |
| AE-PEEDA | 0.000 | 0.000 | 0.000 | 0.202 | 0.312 | 0.063 | 0.374 | 0.000 | 0.000 | 0.000 |
| iAE-PEEDA | 0.000 | 0.000 | 0.000 | 0.000 | 0.000 | 0.000 | 0.000 | 0.000 | 0.000 | 0.000 |
| AE-DPE | 0.076 | 0.000 | 0.077 | 0.648 | 0.544 | 0.112 | 0.581 | 0.000 | 0.112 | 0.000 |

TABLE CXXXII-continued

| Example No. | 1355 | 1356 | 1357 | 1358 | 1359 | 1360 | 1361 | 1362 | 1363 | 1364 |
|---|---|---|---|---|---|---|---|---|---|---|
| BPEA | 0.118 | 0.075 | 0.262 | 0.540 | 0.639 | 0.399 | 0.995 | 0.049 | 0.240 | 0.000 |
| Others | 1.481 | 1.265 | 2.484 | 2.761 | 6.684 | 3.550 | 7.622 | 1.247 | 2.245 | 1.490 |
| MEA Conversion, % | 31.15 | 27.16 | 39.53 | 42.00 | 59.71 | 45.84 | 69.02 | 25.71 | 36.32 | 24.24 |
| DETA Conversion, % | 18.31 | 16.23 | 23.60 | 26.03 | 35.07 | 27.41 | 39.37 | 14.45 | 21.21 | 10.25 |
| Acyclic(N4), % | 97.67 | 97.91 | 97.01 | 96.12 | 95.31 | 95.57 | 91.83 | 98.20 | 96.87 | 98.74 |
| Acyclic(N5), % | 94.93 | 97.48 | 93.01 | 80.11 | 81.72 | 90.42 | 79.71 | 98.02 | 92.20 | 100.00 |
| Σ(N5)/Σ(N4), weight ratio | 0.35 | 0.30 | 0.43 | 0.65 | 0.78 | 0.60 | 0.83 | 0.27 | 0.45 | 0.12 |
| Acyclic(N4)/cyclic (<=N4), weight ratio | 11.88 | 13.13 | 10.13 | 8.90 | 5.89 | 7.09 | 4.49 | 14.33 | 9.39 | 16.44 |

TABLE CXXXIII

| Example No. | 1365 | 1366 | 1367 | 1368 | 1369 | 1370 | 1371 | 1372 |
|---|---|---|---|---|---|---|---|---|
| Catalyst Type | KKKKKK | KKKKKK | KKKKKK | KKKKKK | KKKKKK | KKKKKK | KKKKKK | KKKKKK |
| Catalyst weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.9 | 251.1 | 261.2 | 265.8 | 275.6 | 270.6 | 280.1 | 286.3 |
| Time on organics, hrs. | 4 | 23 | 28 | 48 | 52 | 72 | 76 | 96 |
| Duration of run, hrs. | 2 | 2 | 2 | 2 | 2 | 2 | 2 | 2 |
| MEA SV, gmol/hr/kgcat | 5.47 | 5.89 | 6.03 | 6.26 | 6.37 | 6.13 | 6.30 | 5.74 |
| DETA/MEA mole ratio | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 0.720 | 0.471 | 0.905 | 1.039 | 1.480 | 1.147 | 1.920 | 2.426 |
| MEA | 22.009 | 25.260 | 20.953 | 20.030 | 12.865 | 18.327 | 11.062 | 10.395 |
| PIP | 0.236 | 0.148 | 0.320 | 0.360 | 0.596 | 0.411 | 0.716 | 0.888 |
| DETA | 49.471 | 53.904 | 50.021 | 50.155 | 43.606 | 48.889 | 42.722 | 43.690 |
| AEEA | 2.596 | 2.713 | 2.960 | 3.007 | 2.400 | 2.930 | 1.997 | 1.666 |
| AEP | 0.369 | 0.293 | 0.450 | 0.511 | 0.832 | 0.592 | 1.018 | 1.209 |
| HEP | 0.000 | 0.000 | 0.000 | 0.000 | 0.000 | 0.000 | 0.000 | 0.000 |
| TAEA | 1.431 | 1.225 | 1.593 | 1.658 | 1.845 | 1.669 | 1.892 | 1.745 |
| 1-TETA | 9.494 | 7.564 | 9.777 | 9.875 | 11.583 | 9.862 | 11.226 | 10.431 |
| DAEP | 0.148 | 0.096 | 0.184 | 0.198 | 0.402 | 0.207 | 0.439 | 0.480 |
| PEEDA | 0.122 | 0.090 | 0.106 | 0.123 | 0.320 | 0.113 | 0.034 | 0.294 |
| DPE | 0.066 | 0.055 | 0.069 | 0.086 | 0.155 | 0.046 | 0.133 | 0.167 |
| AE-TAEA | 1.452 | 0.810 | 1.783 | 1.741 | 3.025 | 1.768 | 3.034 | 2.823 |
| 1-TEPA | 2.655 | 1.402 | 3.149 | 3.152 | 5.660 | 3.141 | 5.502 | 5.191 |
| AE-DAEP | 0.000 | 0.000 | 0.000 | 0.048 | 0.304 | 0.056 | 0.503 | 0.535 |
| AE-PEEDA | 0.000 | 0.000 | 0.000 | 0.000 | 0.217 | 0.036 | 0.192 | 0.219 |
| iAE-PEEDA | 0.000 | 0.000 | 0.000 | 0.000 | 0.000 | 0.000 | 0.000 | 0.000 |
| AE-DPE | 0.085 | 0.000 | 0.106 | 0.088 | 0.532 | 0.055 | 0.161 | 0.144 |
| BPEA | 0.089 | 0.000 | 0.224 | 0.200 | 0.722 | 0.287 | 0.763 | 0.720 |
| Others | 1.049 | 1.041 | 2.233 | 2.823 | 5.516 | 3.315 | 7.516 | 7.487 |
| MEA Conversion, % | 37.93 | 30.47 | 42.95 | 45.73 | 64.84 | 49.30 | 69.45 | 71.21 |
| DETA Conversion, % | 17.29 | 12.04 | 19.27 | 19.45 | 29.37 | 19.83 | 30.06 | 28.28 |
| Acyclic(N4), % | 97.00 | 97.30 | 96.93 | 96.58 | 93.85 | 96.91 | 95.57 | 92.81 |
| Acyclic(N5), % | 95.91 | 100.00 | 93.70 | 93.55 | 83.01 | 91.86 | 84.03 | 83.18 |
| Σ(N5)/Σ(N4), weight ratio | 0.38 | 0.24 | 0.44 | 0.43 | 0.73 | 0.44 | 0.74 | 0.73 |
| Acyclic(N4)/cyclic (<=N4), weight ratio | 11.57 | 12.82 | 10.05 | 9.01 | 5.82 | 8.40 | 5.59 | 4.00 |

TABLE CXXXIV

| Example No. | 1373 | 1374 | 1375 | 1376 | 1377 | 1378 | 1379 | 1380 |
|---|---|---|---|---|---|---|---|---|
| Catalyst Type | LLLLLL | LLLLLL | LLLLLL | LLLLLL | LLLLLL | LLLLLL | LLLLLL | LLLLLL |
| Catalyst weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.9 | 251.1 | 261.2 | 265.8 | 275.6 | 270.6 | 280.1 | 286.3 |
| Time on organics, hrs. | 4 | 23 | 28 | 48 | 52 | 72 | 76 | 96 |
| Duration of run, hrs. | 2 | 2 | 2 | 2 | 2 | 2 | 2 | 2 |
| MEA SV, gmol/hr/kgcat | 6.04 | 5.42 | 5.91 | 6.40 | 6.54 | 6.13 | 6.74 | 5.98 |
| DETA/MEA mole ratio | 0.99 | 0.99 | 0.99 | 0.99 | 0.99 | 0.99 | 0.99 | 0.99 |
| NH$_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 1.243 | 0.400 | 0.619 | 0.453 | 0.613 | 0.354 | 0.525 | 0.580 |
| MEA | 29.356 | 33.017 | 31.776 | 32.605 | 30.780 | 32.217 | 30.493 | 31.003 |
| PIP | 0.484 | 0.185 | 0.304 | 0.266 | 0.441 | 0.244 | 0.428 | 0.540 |
| DETA | 54.083 | 59.592 | 58.373 | 59.235 | 57.284 | 58.765 | 57.084 | 56.943 |
| AEEA | 1.249 | 0.742 | 1.272 | 1.184 | 1.363 | 1.159 | 1.500 | 1.300 |
| AEP | 0.395 | 0.262 | 0.352 | 0.330 | 0.422 | 0.301 | 0.428 | 0.482 |
| HEP | 0.000 | 0.000 | 0.000 | 0.000 | 0.000 | 0.000 | 0.000 | 0.000 |
| TAEA | 0.704 | 0.276 | 0.427 | 0.390 | 0.510 | 0.276 | 0.503 | 0.480 |
| 1-TETA | 3.680 | 1.530 | 2.245 | 1.887 | 2.609 | 1.462 | 2.595 | 2.425 |
| DAEP | 0.102 | 0.032 | 0.065 | 0.120 | 0.082 | 0.000 | 0.088 | 0.070 |

TABLE CXXXIV-continued

| Example No. | 1373 | 1374 | 1375 | 1376 | 1377 | 1378 | 1379 | 1380 |
|---|---|---|---|---|---|---|---|---|
| PEEDA | 0.057 | 0.000 | 0.034 | 0.066 | 0.054 | 0.000 | 0.087 | 0.097 |
| DPE | 0.044 | 0.000 | 0.026 | 0.000 | 0.026 | 0.000 | 0.035 | 0.000 |
| AE-TAEA | 0.259 | 0.000 | 0.096 | 0.057 | 0.153 | 0.000 | 0.230 | 0.182 |
| 1-TEPA | 0.507 | 0.000 | 0.236 | 0.106 | 0.469 | 0.000 | 0.673 | 0.501 |
| AE-DAEP | 0.000 | 0.000 | 0.000 | 0.000 | 0.000 | 0.000 | 0.000 | 0.000 |
| AE-PEEDA | 0.133 | 0.000 | 0.000 | 0.000 | 0.000 | 0.000 | 0.067 | 0.000 |
| iAE-PEEDA | 0.000 | 0.000 | 0.000 | 0.000 | 0.000 | 0.000 | 0.000 | 0.000 |
| AE-DPE | 0.000 | 0.000 | 0.000 | 0.000 | 0.000 | 0.000 | 0.299 | 0.000 |
| BPEA | 0.000 | 0.000 | 0.000 | 0.000 | 0.000 | 0.000 | 0.000 | 0.000 |
| Others | 2.796 | 1.200 | 1.868 | 1.546 | 1.758 | 1.067 | 1.606 | 1.461 |
| MEA Conversion, % | 18.40 | 9.46 | 13.61 | 11.72 | 15.52 | 8.49 | 16.54 | 14.42 |
| DETA Conversion, % | 10.89 | 3.12 | 5.92 | 4.92 | 6.79 | 4.03 | 7.37 | 6.82 |
| Acyclic(N4), % | 95.54 | 98.24 | 95.49 | 92.41 | 95.03 | 100.00 | 93.59 | 94.56 |
| Acyclic(N5), % | 85.20 | 0.00 | 100.00 | 100.00 | 100.00 | 0.00 | 71.12 | 100.00 |
| Σ(N5)/Σ(N4), weight ratio | 0.19 | 0.00 | 0.11 | 0.06 | 0.18 | 0.00 | 0.38 | 0.22 |
| Acyclic(N4)/cyclic (<=N4), weight ratio | 4.04 | 3.76 | 3.41 | 2.90 | 3.03 | 3.18 | 2.89 | 2.44 |

TABLE CXXXV

| Example No. | 1381 | 1382 | 1383 | 1384 | 1385 | 1386 | 1387 | 1388 |
|---|---|---|---|---|---|---|---|---|
| Catalyst Type | MMMMMM | MMMMMM | MMMMMM | MMMMMM | MMMMMM | MMMMMM | MMMMMM | MMMMMM |
| Catalyst weight, gm | 50 | 50 | 50 | 50 | 50 | 50 | 50 | 50 |
| Pressure, psig | 600 | 600 | 600 | 600 | 600 | 600 | 600 | 600 |
| Temperature, °C. | 250.9 | 251.1 | 261.2 | 265.8 | 275.6 | 270.6 | 280.1 | 286.3 |
| Time on organics, hrs. | 4 | 23 | 28 | 48 | 52 | 72 | 76 | 96 |
| Duration of run, hrs. | 2 | 2 | 2 | 2 | 2 | 2 | 2 | 2 |
| MEA SV, gmol/hr/kgcat | 4.89 | 4.52 | 5.00 | 4.97 | 5.03 | 4.67 | 5.18 | 4.59 |
| DETA/MEA mole ratio | 0.99 | 0.99 | 0.99 | 0.99 | 0.99 | 0.99 | 0.99 | 0.99 |
| $NH_3$/MEA mole ratio | 5.98 | 5.98 | 5.98 | 5.98 | 5.98 | 5.98 | 5.98 | 5.98 |
| Crude product composition, wt. % | | | | | | | | |
| EDA | 0.361 | 0.219 | 0.411 | 0.545 | 0.946 | 0.691 | 1.268 | 1.591 |
| MEA | 30.065 | 31.539 | 30.198 | 28.886 | 25.101 | 27.183 | 22.856 | 21.265 |
| PIP | 0.191 | 0.101 | 0.235 | 0.344 | 0.686 | 0.468 | 0.951 | 1.183 |
| DETA | 57.915 | 60.816 | 59.141 | 58.453 | 55.105 | 56.245 | 52.509 | 52.661 |
| AEEA | 1.844 | 1.669 | 2.173 | 2.351 | 2.319 | 2.307 | 2.115 | 1.849 |
| AEP | 0.299 | 0.245 | 0.312 | 0.391 | 0.627 | 0.461 | 0.842 | 1.032 |
| HEP | 0.000 | 0.000 | 0.000 | 0.000 | 0.000 | 0.000 | 0.000 | 0.000 |
| TAEA | 0.476 | 0.214 | 0.406 | 0.515 | 0.745 | 0.564 | 0.870 | 0.894 |
| 1-TETA | 2.817 | 1.483 | 2.555 | 3.157 | 4.703 | 3.517 | 5.428 | 5.629 |
| DAEP | 0.066 | 0.000 | 0.066 | 0.077 | 0.144 | 0.104 | 0.191 | 0.220 |
| PEEDA | 0.077 | 0.000 | 0.030 | 0.063 | 0.138 | 0.033 | 0.212 | 0.248 |
| DPE | 0.000 | 0.000 | 0.000 | 0.033 | 0.039 | 0.000 | 0.060 | 0.066 |
| AE-TAEA | 0.102 | 0.000 | 0.108 | 0.157 | 0.411 | 0.199 | 0.708 | 0.582 |
| 1-TEPA | 0.142 | 0.000 | 0.113 | 0.379 | 1.210 | 0.590 | 2.108 | 1.711 |
| AE-DAEP | 0.000 | 0.000 | 0.000 | 0.000 | 0.041 | 0.000 | 0.126 | 0.089 |
| AE-PEEDA | 0.000 | 0.000 | 0.000 | 0.000 | 0.037 | 0.000 | 0.098 | 0.085 |
| iAE-PEEDA | 0.000 | 0.000 | 0.000 | 0.000 | 0.000 | 0.000 | 0.000 | 0.000 |
| AE-DPE | 0.000 | 0.000 | 0.311 | 0.284 | 0.170 | 0.250 | 0.050 | 0.078 |
| BPEA | 0.000 | 0.000 | 0.000 | 0.000 | 0.000 | 0.000 | 0.101 | 0.096 |
| Others | 0.939 | 0.839 | 1.295 | 1.748 | 2.458 | 1.973 | 3.578 | 3.552 |
| MEA Conversion, % | 16.32 | 13.59 | 17.86 | 21.73 | 30.80 | 24.34 | 36.90 | 40.66 |
| DETA Conversion, % | 4.44 | 1.22 | 4.64 | 6.11 | 9.94 | 7.19 | 14.06 | 12.88 |
| Acyclic(N4), % | 95.83 | 100.00 | 96.82 | 95.45 | 94.40 | 96.74 | 93.13 | 92.40 |
| Acyclic(N5), % | 100.00 | 0.00 | 41.61 | 65.36 | 86.70 | 75.90 | 88.18 | 86.75 |
| Σ(N5)/Σ(N4), weight ratio | 0.07 | 0.00 | 0.17 | 0.21 | 0.32 | 0.24 | 0.47 | 0.37 |
| Acyclic(N4)/cyclic (<=N4), weight ratio | 5.19 | 4.88 | 4.59 | 4.03 | 3.32 | 3.82 | 2.78 | 2.37 |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process of making polyalkylene polyamines which comprises condensing, in the absence of hydrogen as a reactant,
   (i) an alkanolamine with an alkyleneamine,
   (ii) an alkanolamine with itself or another alkanolamine, or
   (iii) an alkylene glycol with an alkyleneamine,
optionally in the presence of ammonia, under condensation conditions including the presence of a condensation catalyst consisting essentially of a metatungstate and a condensation catalyst promoter free of phosphorus-containing compounds, wherein said condensation catalyst promoter differs from said condensation catalyst and is present in an amount sufficient to promote the condensation catalyst.

2. The process of claim 1 wherein the condensation catalyst has a surface area greater than about 70 m²/gm.

3. The process of claim 1 wherein the condensation catalyst promoter comprises one or more metal oxides.

4. The process of claim 3 wherein the condensation catalyst promoter comprises one or more Group IA metal oxides, Group IIA metal oxides, Group IIB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides, Group VIA metal oxides, Group IVB metal oxides or mixtures thereof.

5. The process of claim 4 wherein the condensation catalyst promoter comprises one or more oxides of scandium, yttrium, lanthanum, cerium, gadolinium, lutetium, ytterbium, niobium, tantalum, chromium, molybdenum, tungsten, titanium, zirconium, ion, cobalt, nickel, zinc, cadmium, boron, aluminum, gallium, indium, silicon, germanium, tin, lead, arsenic, antimony and bismuth.

6. The process of claim 1 wherein the condensation catalyst promoter comprises a Group VIB metal-containing substance.

7. The process of claim 6 wherein the condensation catalyst promoter comprises one or more oxides of tungsten, chromium and/or molybdenum.

8. The process of claim 1 wherein the condensation catalyst is associated with a support material.

9. The process of claim 8 wherein the support comprises an alumina material or an alumina-silica material.

10. The process of claim 8 wherein the support comprises a silica material or a silica-alumina material.

11. The process of claim 8 wherein the support comprises from about 2 to about 50 percent by weight of the condensation catalyst.

12. The process of claim 1 wherein the amines product has a TETA+TAEA to PIP+AEP+PEEDA+DAEP+DPE weight ratio of greater than about 0.5 and a TETA to TAEA weight ratio of greater than about 2.0.

13. The process of claim 1 in which the amines product comprises, based on 100 percent of the weight of the product and exclusive of any water and/or ammonia present,
   a) greater than about 3.0 weight percent of the combination of TETA and TEPA,
   b) greater than about 0.1 weight percent of TEPA,
   c) greater than about 3.0 weight percent of TETA,
   d) less than about 90.0 weight percent of DETA and/or EDA,
   e) less than about 90.0 weight percent of MEA and/or AEEA,
   f) less than about 12.5 weight percent of the combination of PIP and AEP,
   g) less than about 15.0 weight percent of other polyalkylene polyamines,
   h) a TETA+TAEA to PIP+AEP+PEEDA+DAEP+DPE weight ratio of greater than about 0.5,
   i) a TEPA+AETAEA to PIP+AEP+PEEDA+DAEP+DPE+AEPEEDA+iAEPEEDA+AEDAEP+AEDPE+BPEA weight ratio of greater than about 0.5,
   j) a TETA to TAEA weight ratio of greater than about 2.0, and
   k) a TEPA to AETAEA weight ratio of greater than about 1.0.

14. The process of claim 1 which is effected in the liquid phase, vapor phase, supercritical liquid phase or mixtures thereof.

15. The process of claim 1 wherein the metatungstate is associated with a Group IVB metal oxide.

16. The process of claim 15 wherein the Group IVB metal oxide comprises a high surface area titanium oxide.

17. A process of making alkylamines which comprises condensing, in the absence of hydrogen as a reactant, an alcohol and at least one of a primary amine, a secondary amine or a tertiary amine in the presence of a condensation catalyst consisting essentially of a metatungstate and a condensation catalyst promoter free of phosphorus-containing compounds, wherein said condensation catalyst promoter differs from said condensation catalyst and is present in an amount sufficient to promote the condensation catalyst.

18. The process of claim 1 wherein the condensation reaction is of said alkanolamine and alkyleneamine reactants (i).

19. The process of claim 18 wherein the alkanolamine is monoethanolamine.

20. The process of claim 18 wherein the alkanolamine is aminoethylethanolamine.

21. The process of claim 18 wherein the alkyleneamine is ethylenediamine.

22. The process of claim 187 wherein the alkyleneamine is diethylenetriamine.

23. The process of claim 18 wherein the alkanolamine is monoethanolamine and the alkyleneamine is ethylenediamine.

24. The process of claim 23 wherein the process is effected in the presence of ammonia.

25. The process of claim 18 wherein the alkanolamine is monoethanolamine and the alkyleneamine is diethylenetriamine.

26. The process of claim 25 wherein the process is effected in the presence of ammonia.

27. The process of claim 18 wherein the alkanolamine is aminoethylethanolamine and the alkyleneamine is ethylenediamine.

28. The process of claim 27 wherein the process is effected in the presence of ammonia.

29. The process of claim 18 wherein the alkanolamine is aminoethylenethanolamine and the alkyleneamine is diethylenetriamine.

30. The process of claim 29 wherein the process is effected in the presence of ammonia.

31. The process of claim 18 wherein the alkanolamine is diethanolamine and the alkyleneamine is ethylenediamine or diethylenetriamine.

32. The process of claim 19 wherein the alkanolamine is dihydroxyethylenethylenediamine and the alkyleneamine is ethylenediamine or diethylenetriamine.

33. The process of claim 18 wherein the alkanolamine is hydroxyethyldiethylenetriamine and the alkyleneamine is ethylenediamine or diethylenetriamine.

34. The process of claim 18 wherein the alkanolamine is hydroxyethyltriethylenetetramine and the alkyleneamine is ethylenediamine or diethylenetriamine.

35. The process of claim 1 wherein the condensation reaction is of said alkanolamine reactant (ii) with itself.

36. The process of claim 35 wherein said alkanolamine is monoethanolamine.

37. The process of claim 1 wherein the condensation reaction is of said alkylene glycol and alkyleneamine reactants (iii).

38. The process of claim 37 wherein the alkylene glycol is ethylene glycol and the alkyleneamine is ethylenediamine or diethylenetriamine.

39. The process of claim 17 further comprising ammonia as a reactant.

* * * * *

UNITED STATES PATENT AND TRADEMARK OFFICE
CERTIFICATE OF CORRECTION

PATENT NO. : 5,210,306
DATED : May 11, 1993
INVENTOR(S) : Arthur R. Doumaux, Jr., Stephen W. King, George A. Skoler It is certified that error appears in the above-indentified patent and that said Letters Patent is hereby corrected as shown below:

Col. 211, line 30, "Group IIB" should read --Group IIIB--.

Col. 212, line 51, "187" should read --18--.

Signed and Sealed this

Thirty-first Day of May, 1994

Attest:

BRUCE LEHMAN

Attesting Officer  Commissioner of Patents and Trademarks